(12) United States Patent
McBrayer et al.

(10) Patent No.: US 12,234,493 B2
(45) Date of Patent: **\*Feb. 25, 2025**

(54) COMPOSITIONS FOR SACCHARIFICATION OF CELLULOSIC MATERIAL

(71) Applicant: Novozymes, Inc., Davis, CA (US)

(72) Inventors: Brett McBrayer, Sacramento, CA (US); Elena Vlasenko, Davis, CA (US); Tarana Shaghasi, Guerneville, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/333,776

(22) Filed: Jun. 13, 2023

(65) Prior Publication Data

US 2024/0018560 A1 Jan. 18, 2024

Related U.S. Application Data

(60) Continuation of application No. 17/372,667, filed on Jul. 12, 2021, now Pat. No. 11,713,476, which is a continuation of application No. 16/840,012, filed on Apr. 3, 2020, now Pat. No. 11,091,785, which is a division of application No. 16/115,930, filed on Aug. 29, 2018, now Pat. No. 10,648,009, which is a division of application No. 15/422,245, filed on Feb. 1, 2017, now Pat. No. 10,072,280, which is a division of application No. 14/885,555, filed on Oct. 16, 2015, now Pat. No. 9,587,262, which is a division of application No. 14/052,360, filed on Oct. 11, 2013, now Pat. No. 9,175,277, which is a division of application No. 12/940,952, filed on Nov. 5, 2010, now Pat. No. 8,580,536.

(60) Provisional application No. 61/259,014, filed on Nov. 6, 2009.

(51) Int. Cl.
| | | |
|---|---|---|
| C12P 19/14 | (2006.01) | |
| C12N 1/22 | (2006.01) | |
| C12N 9/24 | (2006.01) | |
| C12N 9/42 | (2006.01) | |
| C12P 19/02 | (2006.01) | |
| C12P 19/12 | (2006.01) | |
| C12P 21/02 | (2006.01) | |

(52) U.S. Cl.
CPC .............. *C12P 19/14* (2013.01); *C12N 1/22* (2013.01); *C12N 9/2402* (2013.01); *C12N 9/2437* (2013.01); *C12N 9/2445* (2013.01); *C12N 9/248* (2013.01); *C12P 19/02* (2013.01); *C12P 19/12* (2013.01); *C12P 21/02* (2013.01); *C12Y 302/01* (2013.01); *C12Y 302/01004* (2013.01); *C12Y 302/01008* (2013.01); *C12Y 302/01021* (2013.01); *C12Y 302/01091* (2013.01); *C12P 2203/00* (2013.01); *C12Y 302/01037* (2013.01); *Y02P 20/52* (2015.11)

(58) Field of Classification Search
CPC .......... C12P 19/14; C12P 19/02; C12P 19/12; C12P 21/02; C12P 2203/00; C12N 1/22; C12N 9/2402; C12N 9/2437; C12N 9/2445; C12N 9/248; C12Y 302/01; C12Y 302/01004; C12Y 302/01008; C12Y 302/01091; C12Y 302/01037; Y02P 20/52; Y02E 50/10
See application file for complete search history.

(56) References Cited

U.S. PATENT DOCUMENTS

| | | | |
|---|---|---|---|
| 7,244,605 B2 | 7/2007 | Harris et al. | |
| 7,271,244 B2 | 9/2007 | Dotson et al. | |
| 7,960,160 B2 | 6/2011 | Yaver et al. | |
| 8,148,103 B2 | 4/2012 | Tang et al. | |
| 8,211,665 B2 | 7/2012 | Tang et al. | |
| 8,541,651 B2 | 9/2013 | Wogulis | |
| 8,546,106 B2 * | 10/2013 | Merino | C12P 21/02 435/71.1 |
| 8,580,536 B2 | 11/2013 | McBrayer et al. | |
| 9,115,368 B2 | 8/2015 | Abad et al. | |
| 9,175,277 B2 | 11/2015 | McBrayer et al. | |
| 10,072,280 B2 * | 9/2018 | McBrayer | C12N 9/248 |
| 11,091,785 B2 | 8/2021 | McBrayer et al. | |
| 11,713,476 B2 * | 8/2023 | McBrayer | C12Y 302/01004 435/99 |
| 2005/0210548 A1 | 9/2005 | Yaver et al. | |
| 2009/0123979 A1 | 5/2009 | Xu | |
| 2009/0130707 A1 | 5/2009 | Xu | |

FOREIGN PATENT DOCUMENTS

| | | |
|---|---|---|
| WO | 2003000941 | 1/2003 |
| WO | 2007071818 | 6/2007 |
| WO | 2008025165 | 3/2008 |
| WO | 2008095033 A2 | 8/2008 |
| WO | 2008140749 A2 | 11/2008 |
| WO | 2008151079 A2 | 12/2008 |

(Continued)

OTHER PUBLICATIONS

Pauly et al., A xyloglucan-specific endo-B-1.4-glucanase from *Aspergillus aculeatus*: expression cloning yeast, purification and characterization of the recombinant enzymes, Glycobiology, vol. 9, No. 1, pp. 93-100, 1999.
Zhou et al., Optimization of cellulose mixture for efficient hydrolysis of steam-exploded corn stover by statistically designed experiments, Bioresource Technology, 100, pp. 819-825, 2009.
Dashtban et al., Fungal Bioconversion of Lignocellulosic Residues; Opportunities & Perspectives, International Journal of Biological Sciences, pp. 578-595, 2009.
Rosgaard et al., Efficiency of New Fungal Cellulase Systems in Boosting Enzymatic Degradation of Barley Straw Lignocellulose, Biotechnol. Prog, 22, pp. 493-498, 2006.

(Continued)

*Primary Examiner* — Ganapathirama Raghu
(74) *Attorney, Agent, or Firm* — Kelly K. Reynolds

(57) ABSTRACT

The present invention relates to enzyme compositions for high temperature saccharification of cellulosic material and to uses thereof.

55 Claims, 42 Drawing Sheets
Specification includes a Sequence Listing.

(56) References Cited

FOREIGN PATENT DOCUMENTS

| WO | 2009018537 | A2 | 2/2009 |
|---|---|---|---|
| WO | 2009059175 | | 5/2009 |
| WO | 2009059234 | A2 | 5/2009 |
| WO | 2009085868 | A1 | 7/2009 |
| WO | 2009085935 | | 7/2009 |
| WO | 2009108941 | A2 | 9/2009 |

OTHER PUBLICATIONS

Merino et al., Progress and Challenges in Enzyme Development for Biomass Utilization, Adv. Biochem Engin/ Biotechnol, 108, pp. 95-120, 2007.

Vikari et al., Thermostable Enzymes in Lignocellulase Hydrolysis, Adv. Biochem Engin/Biotechnol, 108, pp. 121-145, 2007.

Wood et al., The mechanism of fungal cellulose action; Synergism between enzyme components of Penicillium pinophilum cellulose in solubilizing hydrogen bond-ordered cellulose, Biochem, J., 260, pp. 37-43, 1989.

Zhang et al., Toward an Aggregated Understanding of Enzymatic Hydrolysis of Cellulose: Noncomplexed Cellulase Systems, Biotechnology and Bioengineering, vol. 88, No. 7, pp. 797-824, 2004.

Broun et al, 1998, Science 282, 1315-1317.
Chica et al, 2005, Curr Opi Biotechnol 16, 378-384.
Devos et al, 2000, Proteins Stru, Fun, and Gene 41, 98-107.
Sen et al, 2007, Appl Biochem Biotechnol 143, 212-223.
Whisstock et al, 2003, Q Rev Biophysics 36(3), 307-340.
Wishart et al, 1995, J Biol Chem 270(45), 26782-26785.
Witkowski et al, 1999, Biochem J 38, 11643-11650.
Nierman et al, NCBI Access No. XP_748511.
Hong et al, 2003—EMBL Access No. AAL88714.
Birren et al, 2008—NCBI Access No. XP_001217291.
Kawaguchi et al, 1996—Uniprot Access No. P48825.
WO 2001-047944 A2—Geneseq Access No. AAL33603.
Rasmussen et al, 2006, Biotechnol Bioeng 94(5), 869-876.
WO 2009-108941 A2—EBI Accession No. AXR38839.
WO 2009-108941 A2—EBI Accession No. AXR38993.
WO 2009-108941 A2—EBI Accession No. AXR38839, , Univ Cent Florida Res Found Inc., Jan. 21, 2010.
WO 2009-108941 A2—EBI Accession No. AXR38993, Univ Cent Florida Res Found Inc., Jan. 21, 2010.
WO 2001-047944 A2—Geneseq Access No. AAL33603, Curagen Corp., Jan. 24, 2002.
Nierman et al, NCBI Access No. XP_748511, Feb. 19, 2008.

* cited by examiner

SEQUENCE LISTING

```
Sequence total quantity: 305
SEQ ID NO: 1            moltype = DNA  length = 1590
FEATURE                 Location/Qualifiers
source                  1..1590
                        mol_type = genomic DNA
                        organism = Chaetomium thermophilum
SEQUENCE: 1
atgatgtaca agaagttcgc cgctctcgcc gccctcgtgg ctggcgccgc cgcccagcag  60
gcttgctccc tcaccactga gacccacccc agactcactt ggaagcgctg cacctctggc 120
ggcaactgct cgaccgtgaa cggcgccgtc accatcgatg ccaactggcg ctggactcac 180
accgtttccg gctcgaccaa ctgctacacc ggcaacgagt gggatacctc catctgctct 240
gatggcaaga gctgcgccca gacctgctgc gtcgacgggc ctgactactc ttcgacctat 300
ggtatcacca ccagcggtga ctccctgaac ctcaagttcg tcaccaagca ccagtacggc 360
accaatgtcg gctctcgtgt ctacctgatg gagaacgaca ccaagtacca gatgttcgag 420
ctcctcggca acgagttcac cttcgatgtc gatgtctcta acctgggctg cggtctcaac 480
ggtgccctct acttcgtctc catggacgct gatggtggta tgagcaagta ctctggcaac 540
aaggctggcg ccaagtacgg gacggggtac tgtgatgctc agtgcccgcg cgaccttaag 600
ttcatcaacg gcgaggccaa cattgagaac tggacccctt cgaccaatga tgccaacgcc 660
ggtttcggcc gctatggcag ctgctgctct gagatggata tctgggaggc caacaacatg 720
gctactgcct tcactcctca cccttgcacc attatcggcc agagccgctg cgagggcaac 780
```

-continued

```
agctgcggtg gcacctacag ctctgagcgc tatgctggtg tttgcgatcc tgatggctgc    840
gacttcaacg cctaccgcca gggcgacaag accttctacg caagggcat gaccgtcgac     900
accaccaaga agatgaccgt cgtcacccag ttccacaaga actcggctgg cgtcctcagc    960
gagatcaagc gcttctacgt tcaggacggc aaggtcattg ccaacgccga gtccaagatc   1020
cccggcaacc ccggcaactc catcacccag gagtggtgga tgcccagaa ggtcgccttc    1080
ggtgacatcg atgacttcaa ccgcaagggc ggtatggctc agatgagcaa ggccctcgaa   1140
ggccctatgg tcctggtcat gtccgtctgg gatgaccact acgccaacat gctctggctc   1200
gactcgacct accccatcga caaggccggc accccggcg ccgagcgcgg tgcttgcccg    1260
accacctccg gtgtccctgc cgagattgca gcccaggtcc caacagcaa cgtcatcttc    1320
tccaacatcc gcttcggccc catcggtcg accgtccctg gcctgacgg cagcactccc    1380
agcaacccga ccgccaccgt tgctcctccc acttctacca ccagcgtgag aagcagcact   1440
actcagattt ccaccccgac tagccagccc ggcggctgca ccacccagaa gtggggccag   1500
tgcggtggta tcggctacac cggctgcact aactgcgttg ctggcactac ctgcactgag   1560
ctcaacccct ggtacagcca gtgcctgtaa                                     1590

SEQ ID NO: 2           moltype = AA  length = 529
FEATURE                Location/Qualifiers
source                 1..529
                       mol_type = protein
                       organism = Chaetomium thermophilum
SEQUENCE: 2
MMYKKFAALA ALVAGAAAQQ ACSLTTETHP RLTWKRCTSG GNCSTVNGAV TIDANWRWTH     60
TVSGSTNCYT GNEWDTSICS DGKSCAQTCC VDGADYSSTY GITTSGDSLN LKFVTKHQYG    120
TNVGSRVYLM ENDTKYQMFE LLGNEFTFDV DVSNLGCGLN GALYFVSMDA DGGMSKYSGN    180
KAGAKYGTGY CDAQCPRDLK FINGEANIEN WTPSTNDANA GFGRYGSCCS EMDIWEANNM    240
ATAFTPHPCT IIGQSRCEGN SCGGTYSSER YAGVCDPDGC DFNAYRQGDK TFYGKGMTVD    300
TTKKMTVVTQ FHKNSAGVLS EIKRFYVQDG KVIANAESKI PGNPGNSITQ EWCDAQKVAF    360
GDIDDFNRKG GMAQMSKALE GPMVLVMSVW DDHYANMLWL DSTYPIDKAG TPGAERGACP    420
TTSGVPAEIE AQVPNSNVIF SNIRFGPIGS TVPGLDGSTP SNPTATVAPP TSTTSVRSST    480
TQISTPTSQP GGCTTQKWGQ CGGIGYTGCT NCVAGTTCTE LNPWYSQCL                529

SEQ ID NO: 3           moltype = DNA  length = 1353
FEATURE                Location/Qualifiers
source                 1..1353
                       mol_type = genomic DNA
                       organism = Myceliophthora thermophila
SEQUENCE: 3
atgaagcagt acctccagta cctcgcggcg accctgcccc tggtgggcct ggccacggcc     60
cagcaggcgg gtaacctgca gaccgagact cacccccagg ctcacttggtc caagtgcacg   120
gccccgggat cctgccaaca ggtcaacggc gaggtcgtca tcgactccaa ctggcgctgg    180
gtgcacgacg agaacgcgca gaactgctac gacggcaacc agtggaccaa cgcttgcagc    240
tctgccaccg actgcgccga gaattgcgcg ctcgagggtg ccgactacca gggcacctat    300
ggcgcctcga gcaggggcaa tgccctgacg ctcaccttcg tcactaagca cgagtacggc    360
accaacattg gctcgcgcct ctacctcatg aacggcgcga acaagtacca gatgttcacc    420
ctcaagggca acgagctggc cttcgacgtc gacctctcgg ccgtcgagtg cggcctcaac    480
agcgccctct acttcgtggc catggaggag gatggcggtg tgtcgagcta cccgaccaac    540
acggccgggt ctaagttcgg cactgggtac tgcgacgccc aatgcgcacg cgacctcaag    600
ttcgtcggcg gcaagggcaa catcgagggc tggaagccgt ccaccaacga tgccaatgcc    660
ggtgtcggtc cttatggcgg tgctgcgct gagatcgacg tctgggagtc gaacaagtat    720
gctttcgctt tcaccccgca cggttgcgag aaccctaaat accacgtctg cgagaccacc    780
aactgcgggtg gcacctactc cgaggaccgc ttcgctggtg actgcgatgc caacggctgc    840
gactacaacc cctaccgcat gggcaaccag gacttctacg gtcccggctt gacggtcgat    900
accagcaaga agttcaccgt cgtcagccag ttcgaggaga acaagctcac ccagttcttc    960
gtccaggacg gcaagaagat tgagatcccc ggccccaagg tcgagggcat cgatgcggac   1020
agcgccgcta tcacccctga gctgtgcagt gccctgttca aggccttcga tgaccgtgac   1080
cgcttctcgg aggttggcgg cttcgatgcc atcaacacgg ccctcagcac tccatggtc    1140
ctcgtcatgt ccatctggga tgatcactac gccaatatgc tctggctcga ctcgagctac   1200
cccctgaga aggctggcca gcctggcggt gaccgtggcc cgtgtcctca ggactctggc    1260
gtcccggccg acgttgaggc tcagtaccct aatgccaagg tcatctggtc caacatccgc   1320
ttcggccca tcggctcgac tgtcaacgtc taa                                  1353

SEQ ID NO: 4           moltype = AA  length = 450
FEATURE                Location/Qualifiers
source                 1..450
                       mol_type = protein
                       organism = Myceliophthora thermophila
SEQUENCE: 4
MKQYLQYLAA TLPLVGLATA QQAGNLQTET HPRLTWSKCT APGSCQQVNG EVVIDSNWRW     60
VHDENAQNCY DGNQWTNACS SATDCAENCA LEGADYQGTY GASTSGNALT LTFVTKHEYG    120
TNIGSRLYLM NGANKYQMFT LKGNELAFDV DLSAVECGLN SALYFVAMEE DGGVSSYPTN    180
TAGAKFGTGY CDAQCARDLK FVGGKGNIEG WKPSTNDANA GVGPYGGCCA EIDVWESNKY    240
AFAFTPHGCE NPKYHVCETT NCGGTYSEDR FAGDCDANGC DYNPYRMGNQ DFYGPGLTVD    300
TSKKFTVVSQ FEENKLTQFF VQDGKKIEIP GPKVEGIDAD SAAITPELCS ALFKAFDDRD    360
RFSEVGGFDA INTALSTPMV LVMSIWDDHY ANMLWLDSSY PPEKAGQPGG DRGPCPQDSG    420
VPADVEAQYP NAKVIWSNIR FGPIGSTVNV                                     450

SEQ ID NO: 5           moltype = DNA  length = 1599
FEATURE                Location/Qualifiers
source                 1..1599
```

```
                        mol_type = genomic DNA
                        organism = Aspergillus fumigatus
SEQUENCE: 5
atgctggcct ccaccttctc ctaccgcatg tacaagaccg cgctcatcct ggccgccctt   60
ctgggctctg gccaggctca gcaggtcggt acttcccagg cggaagtgca tccgtccatg  120
acctggcaga gctgcacggc tggcggcagc tgcaccacca caacggcaa ggtggtcatc   180
gacgcgaact ggcgttgggt gcacaaagtc ggcgactaca ccaactgcta caccggcaac  240
acctgggaca cgactatctg ccctgacgat gcgacctgcg catccaactg cgcccttgag  300
ggtgccaact acgaatccac ctatgtcgtg accgccagcg gcaattccct ccgcctcaac  360
ttcgtcacca ccagccagca gaagaacatt ggctcgcgtc tgtacatgat gaaggacgac  420
tcgacctacg agatgtttaa gctgctgaac caggagttca ccttcgatgt cgatgtctcc  480
aacctcccct gcggtctcaa cggtgctctg tactttgtcg ccatggacgc cgacggtggc  540
atgtccaagt acccaaccaa caaggccggt gccaagtacg gtactggata ctgtgactcg  600
cagtgccctc gcgacctcaa gttcatcaac ggtcaggcca acgtcgaagg gtggcagccc  660
tcctccaacg atgccaatgc gggtaccggc aaccacgggt cctgctgcgc ggagatggat  720
atctgggagg ccaacagcat ctccacggcc ttcacccccc atccgtgcga cacgcccggc  780
caggtgatgt gcaccggtga tgcctgcggt ggcacctaca gctccgaccg ctacggcggc  840
acctgcgacc ccgacggatg tgatttcaac tccttccgcc agggcaacaa gaccttctac  900
ggccctggca tgaccgtcga caccaagagc aagtttaccg tcgtcaccca gttcatcacc  960
gacgacggca cctccagcgg caccctcaag gagatcaagc gcttctacgt gcagaacggc 1020
aaggtgatcc ccaactcgga gtcgacctgg accggcgtca gcggcaactc catcaccacc 1080
gagtactgca ccgcccagaa gagcctgttc caggaccaga acgtcttcga aaagcacggc 1140
ggcctcgagg gcatgggtgc tgccctcgcc cagggtatgg ttctcgtcat gtccctgtgg 1200
gatgatcact cggccaacat gctctggctc gacagcaact acccgaccac tgcctcttcc 1260
accactcccg gcgtcgcccg tggtacctgc gacatctcct ccggcgtccc tgcggatgtc 1320
gaggcgaacc accccgacgc ctacgtcgtc tactccaaca tcaaggtcgg ccccatcggc 1380
tcgaccttca cagcggtgg ctcgaacccc ggtggcggaa ccaccacgaa aactaccacc 1440
cagcctacta ccaccacgac cacggctgga aaccctggcg gcaccggagt cgcacagcac 1500
tatgccagtg tggtggaat cggatggacc ggacccacaa cctgtgccag cccttatacc 1560
tgccagaagc tgaatgatta ttactctcag tgcctgtag                        1599

SEQ ID NO: 6              moltype = AA  length = 532
FEATURE                   Location/Qualifiers
source                    1..532
                          mol_type = protein
                          organism = Aspergillus fumigatus
SEQUENCE: 6
MLASTFSYRM YKTALILAAL LGSGQAQQVG TSQAEVHPSM TWQSCTAGGS CTTNNGKVVI   60
DANWRWVHKV GDYTNCYTGN TWDTTICPDD ATCASNCALE GANYESTYGV TASGNSLRLN  120
FVTTSQQKNI GSRLYMMKDD STYEMFKLLN QEFTFDVDVS NLPCGLNGAL YFVAMDADGG  180
MSKYPTNKAG AKYGTGYCDS QCPRDLKFIN GQANVEGWQP SSNDANAGTG NHGSCCAEMD  240
IWEANSISTA FTPHPCDTPG QVMCTGDACG GTYSSDRYGG TCDPDGCDFN SFRQGNKTFY  300
GPGMTVDTKS KFTVVTQFIT DDGTSSGTLK EIKRFYVQNG KVIPNSESTW TGVSGNSITT  360
EYCTAQKSLF QDQNVFEKHG GLEGMGAALA QGMVLVMSLW DDHSANMLWL DSNYPTTASS  420
TTPGVARGTC DISSGVPADV EANHPDAYVV YSNIKVGPIG STFNSGGSNP GGGTTTTTTT  480
QPTTTTTTAG NPGGTGVAQH YGQCGGIGWT GPTTCASPYT CQKLNDYYSQ CL          532

SEQ ID NO: 7              moltype = DNA  length = 1374
FEATURE                   Location/Qualifiers
source                    1..1374
                          mol_type = genomic DNA
                          organism = Thermoascus aurantiacus
SEQUENCE: 7
atgtatcagc gcgctcttct cttctctttc ttcctctccg ccgccgcgc gcagcaggcc   60
ggtaccctaa ccgcagagaa tcacccttcc ctgacctggc agcaatgctc cagcggcggt  120
agttgtacca cgcagaatgg aaaagtcgtt atcgatgcga actggcgttg gtccatacc   180
acctctggat acaccaactg ctacacgggc aatacgtggg acaccagtat ctgtcccgac  240
gacgtgacct gcgctcagaa ttgtgccttg gatggagcgg attacagtgg cacctatggt  300
gttacgacca gtggcaacgc cctgagactg aactttgtca cccaaagctc agggaagaac  360
attggctcgc gcctgtacct gctgcaggac gacaccactt atcagatctt caagctgctg  420
ggtcaggagt taccttcga tgtcgacgtc tccaatctcc cttgcgggct gaacggcgcc  480
ctctacttg tggccatgga cgccgacggc ggattgtcca ataccctgg caacaaggca  540
ggcgctaagt atggcactgg ttactgcgac tctcagtgcc ctcgggatct caagttcatc  600
aacggtcagg ccaacgttga aggctggcag ccgtctgcca acgacccaac tgccgcggt  660
ggtaaccacg ttcctgctg cgctgagatg gatgtctcgg aagccaacag catctctact  720
gcggtgacgc ctcaccatg cgacacccc ggcagacca tgtgccaggg acgactgt  780
ggtggaacct actcctccac tcgatatgct ggtacctgcg accctgatgg ctgcgacttc  840
aatccttacc gccagggcaa ccactcgttc tacggccccg ggaagatcgt cgacactagc  900
tccaaattca cgtcgtcac ccagttcatc accgacgacg ggaccccctc cggcaccctc  960
acggagatca aacgcttcta cgtccagaac ggcaaggtga tccccagtc ggagtcgacg 1020
atcagcggcg tcaccggcaa ctcaatcacc accgagtatt gcacgccca aaggccgcc  1080
ttcggcgaca caccggctt cttcacgcac ggcgggcttc agaagatcag tcaggctctg 1140
gctcagggca tggtcctcgt catgagcctg tgggacgatc acgccgccaa catgctctgg 1200
ctgacacga cctaccgac tgatgcggac ccggacaccg tcgtcg cgcggtacc  1260
tgccccacga cctccggcgt cccgccgac gttgagtcgc agaacccaa ttcatatgtt 1320
atctactcca acatcaaggt cggacccatc aactcgacct tcaccgccaa ctaa        1374

SEQ ID NO: 8              moltype = AA  length = 420
FEATURE                   Location/Qualifiers
```

```
source              1..420
                    mol_type = protein
                    organism = Thermoascus aurantiacus
SEQUENCE: 8
MYQRALLFSF FLSAARAQQA GTLTAENHPS LTWQQCSSGG SCTTQNGKVV IDANWRWVHT    60
TSGYTNCYTG NTWDTSICPD DVTCAQNCAL DGADYSGTYG VTTSGNALRL NFVTQSSGKN   120
IGSRLYLLQD DTTYQIFKLL GQEFTFDVDV SNLPCGLNGA LYFVAMDADG GLSKYPGNKA   180
GAKYGTGYCD SQCPRDLKFI NGQANVEGWQ PSANDPNAGV GNHGSCCAEM DVWEANSIST   240
AVTPHPCDTP GQTMCQGDDC GGTYSSTRYA GTCDPDGCDF NPYRQGNHSF YGPGKIVDTS   300
SKFTVVTQFI TDDGTPSGTL TEIKRFYVQN GKVIPQSEST ISGVTGNSIT TEYCTAQKAA   360
FGDNTGFFTH GGLQKISQAL AQGMVLVMSL WDDHAANMLW LDSTYPTDAD PDTPGVARGT   420

SEQ ID NO: 9        moltype = DNA  length = 1802
FEATURE             Location/Qualifiers
source              1..1802
                    mol_type = genomic DNA
                    organism = Myceliophthora thermophila
SEQUENCE: 9
atggccaaga agcttttcat caccgccgcg cttgcggctg ccgtgttggc ggccccgtc     60
attgaggagc gccagaactg cggcgctgtg tggtaagaaa gcccggtccg agtctcccat   120
gattttctcg tcgagtaatg gcataaggc cacccccttcg actgaccgtg agaatcgatc   180
aaatccagga ctcaatgcgg cggtaacggg tggcaaggtc ccacatgctg cgcctcgggc   240
tcgacctgcg ttgcgcagaa cgagtggtac tctcagtgcc tgcccaacag ccaggtgacg   300
agttccacca ctccgtcgtc gacttccacc tcgcagcgca gcaccagcac tccagcagc    360
accaccagga gcggcagctc ctcctcctcc tccaccacgc cccgcccgt ctccagcccc    420
gtgaccagca ttcccggcgg tgcgacctcc acggcgagct actctggcaa ccccttcctg   480
ggcgtccggc tcttgccaa cgactactac aggtccgagg tccacaatct cgccattcct   540
agcatgactg gtactctggc ggccaaggct tccgccgtcg ccgaagtccc tagctttccag   600
tggctcgacc ggaacgtcac catcgacacc ctgatggtcc agactctgtc ccaggtccgg   660
gctctcaata aggccggtgc caatcctccc tatgctggtg agttacatgg cgacttgcct   720
tctcgtcccc tacctttcct gacgggatcg gttacctgac ctggaggcaa acaacaaca    780
gcccaactcg tcgtctacga cctccccgac cgtgactgtg ccgccgctgc gtccaacggc   840
gagttttcga ttgcaaacgg cggcgccgcc aactacagga gctacatcga cgctatccgc   900
aagcacatca ttgagtactc ggacatccgg atcatcctgg ttatcgagcc cgactcgatg   960
gccaacatgg tgaccaacat gaacgtggcc aagtgcagca acggccgcgtc gacgtaccac  1020
gagttgaccg tgtacgcgct caagcagctg aacctgccca acgtcgccat gtatctcgac  1080
gccgccacg ccggctggct cggctggccc gccaacatcc agcccgccgc cgagctgttt   1140
gccggcatct acaatgatgc cggcaagccg gctgccgtcc gcggcctggc cactaacgtc   1200
gccaactaca acgcctggag catcgcttcg gccccgtccta taaccctaac              1260
tacgacgaga agcactacat cgaggccttc agcccgctct tgaactcggc cggcttcccc   1320
gcacgcttca ttgtcgacac ctggcgcaac ggcaaacaac ctaccggtat gttttttttt   1380
cttttgtctc tgtcccccccc ttttctcccc cttcagttgg cgtccacaag gtctcttagt   1440
cctgcttcat ctgtgaccaa cctccccccc cccggcactg cccaaccg tttgactcta     1500
tactcttggg aatgggcgcc gaaactgacc gttccacagg ccaacaacag tggggtgact   1560
ggtgcaatgt caagggcacc ggctttgcg tgcgcccgac ggcaacacg ggccacgagc     1620
tggtcgatgc ctttgtctgg gtcaagcccg cggcgagtc cgacggcaca agcgaccaca   1680
gcgccgcccg ctacgactac cactcgcggcc tgtccgatgc cctgcagcct gccccgagg   1740
ctggacagtg gttccaggcc tacttcgagc agctgctcac caacgccaac ccgccttct   1800
aa                                                                   1802

SEQ ID NO: 10       moltype = AA   length = 481
FEATURE             Location/Qualifiers
source              1..481
                    mol_type = protein
                    organism = Myceliophthora thermophila
SEQUENCE: 10
MAKKLFITAA LAAAVLAAPV IEERQNCGAV WTQCGGNGWQ GPTCCASGST CVAQNEWYSQ    60
CLPNSQVTSS TTPSSTSTSQ RSTSTSSSTT RSGSSSSSST TPPPVSSPVT SIPGGATSTA   120
SYSGNPFSGV RLFANDYYRS EVHNLAIPSM TGTLAAKASA VAEVPSFQWL DRNVTIDTLM   180
VQTLSQVRAL NKAGANPPYA AQLVVYDLPD RDCAAAASNG EFSIANGGAA NYRSYIDAIR   240
KHIIEYSDIR IILVIEPDSM ANMVTNMNVA KCSNAASTYH ELTVYALKQL NLPNVAMYLD   300
AGHAGWLGWP ANIQPAAELF AGIYNDAGKP AAVRGLATNV ANYNAWSIAS APSYTSPNPN   360
YDEKHYIEAF SPLLNSAGFP ARFIVDTGRN GKQPTGQQQW GDWCNVKGTG FGVRPTANTG   420
HELVDAFVWV KPGGESDGTS DTSAARYDYH CGLSDALQPA PEAGQWFQAY FEQLLTNANP   480
P                                                                    481

SEQ ID NO: 11       moltype = DNA  length = 1812
FEATURE             Location/Qualifiers
source              1..1812
                    mol_type = genomic DNA
                    organism = Myceliophthora thermophila
SEQUENCE: 11
atggccaaga agcttttcat caccgccgcc cttgcggctg ccgtgttggc ggccccgtc     60
attgaggagc gccagaactg cggcgctgtg tggtaagaaa gcccggtccg agtttcccat   120
gactttctca tcgagtaatg gcataaggcc cacccccttcg actgactgtg agaatcgatc   180
aaatccagga ctcaatgcgg cggcaacggg tggcagggtc ccacatgctg cgcctcgggc   240
tcgacctgcg ttgcgcagaa cgagtggtac tctcagtgcc tgcccaacaa tcaggtgacg   300
agttccacca ctccgtcgtc gacttccacc tcgcagcgca gcagcagcac tccagcagc    360
agcaccagga gcggcagctc ctcctcctcc accaccacgc cccctccgt ctccagcccc    420
```

```
gtgactagca ttcccggcgg tgcgaccacc acggcgagct actctggcaa cccttctcg    480
ggcgtccggc tcttcgccaa cgactactac aggtccgagg tccacaatct cgccattcct    540
agcatgaccg gtactctggc ggccaaggct tccgccgtcg ccgaagtccc tagcttccag    600
tggctcgacc ggaacgtcac catcgacacc ctgatggtcc agactctgtc ccagatccgg    660
gctgccaata atgccggtgc caatcctccc tatgctgtg agttacatgg cggcgacttg    720
ccttctcgtc ccccaccttt cttgacggga tcggttacct gacctggagg caaaacaaaa    780
ccagcccaac ttgtcgtcta cgacctcccc gaccgtgact gcgccgccgc tgcgtccaac    840
ggcgagtttt cgattgcaaa cggcggcgcc gccaactaca ggagctacat cgacgctatc    900
cgcaagcaca tcattgagta tcggatcatc tggttatcga gcccgactcg                960
atggccaaca tggtgaccaa catgaacgtg gccaagtgca gcaacgccgc gtcgacgtac   1020
cacgagttga ccgtgtacgc gctcaagcag ctgaacctgc ccaacgtcgc catgtatctc   1080
gacgccggcc acgccggctg gctcggctgg cccgccaaca tccagccgc cgccgacctg   1140
tttgccggca tctacaatga cgccggcaag ccggctgccg tccgcggcct ggccactaac   1200
gtcgccaact acaacgcctg gagtatcgct tcggccccgc cgtacacgtc ccctaaccct   1260
aactacgacg agaagcacta catcgaggcc ttcagcccgc tcctgaacgc ggccggcttc   1320
cccgcacgct tcattgtcga cactggccgc aacggcaaac aacctaccgg tatggttttt   1380
ttctttttt ttctctgttc ccctcccct tcccttcag ttggcgtcca caaggtctct      1440
tagtcttgct tcttctcgga ccaaccttcc cccacccca aaacgcaccg ccacaaccg      1500
ttcgactcta tactcttggg aatgggcgcc gaaactgacc gttcgacagg ccaacaacag   1560
tggggtgact ggtgcaatgt caagggcact ggctttggcg tgcgcccgac ggccaacacg   1620
ggccacgacc tggtcgatgc ctttgtctgg gtcaagcccg gcggcgagtc cgacggcaca   1680
agcgacacca gcgccgcccg ctacgactac cactgcggcc tgtccgatgc cctgcagcct   1740
gctccggagg ctggacagtg gttccaggcc tacttcgagc agctgctcac caacgccaac   1800
ccgcccttct aa                                                        1812

SEQ ID NO: 12          moltype = AA   length = 482
FEATURE                Location/Qualifiers
source                 1..482
                       mol_type = protein
                       organism = Myceliophthora thermophila
SEQUENCE: 12
MAKKLFITAA LAAAVLAAPV IEERQNCGAV WTQCGGNGWQ GPTCCASGST CVAQNEWYSQ    60
CLPNNQVTSS NTPSSTSTSQ RSSSTSSSST RSGSSSSSTT TPPPVSSPVT SIPGGATTTA   120
SYSGNPFSGV RLFANDYYRS EVHNLAIPSM TGTLAAKASA VAEVPSFQWL DRNVTIDTLM   180
VQTLSQIRAA NNAGANPPYA AQLVVYDLPD RDCAAAASNG EFSIANGGAA NYRSYIDAIR   240
KHIIEYSDIR IILVIEPDSM ANMVTNMNVA KCSNAASTYH ELTVYALKQL NLPNVAMYLD   300
AGHAGWLGWP ANIQPAADLF AGIYNDAGKP AAVRGLATNV ANYNAWSIAS APSYTSPNPN   360
YDEKHYIEAF SPLLNAAGFP ARFIVDTGRN GKQPTGQQQW GDWCNVKGTG FGVRPTANTG   420
HDLVDAFVWV KPGGESDGTS DTSAARYDYH CGLSDALQPA PEAGQWFQAY FEQLLTNANP   480
PF                                                                   482

SEQ ID NO: 13          moltype = DNA   length = 1446
FEATURE                Location/Qualifiers
source                 1..1446
                       mol_type = genomic DNA
                       organism = Thielavia terrestris
SEQUENCE: 13
atggctcaga agctccttct cgccgccgcc cttgcggcca gcgccctcgc tgctcccgtc     60
gtcgaggagc gccagaactg cggttccgtc tggagccaat gcgcggcat ggctggtcc     120
ggcgcgacct gctgcgcttc gggcaatacc tgcgttgagc tgaacccgta ctactcgcag   180
tgcctgccca cagccaggt gactacctcg accagcaaga ccacctccac caccaccagg   240
agcagcacca ccagccacag cagcgtccc accagcaca ccaccaccac caccagcagt   300
cccgtggtca ctaccccgcc gagtacctcc atccccggcg gtgcctcgtc aacggccagc   360
tggtccggca acccgttctc gggcgtgcag atgtgggcca acgactacta cgcctccgag   420
gtctcgtcgc tggccatccc cagcatgacg ggcgccatgg ccaccaaggc ggccgaggtg   480
gccaaggtgc ccagcttcca gtggcttgac cgcaacgtca ccatcgacac gctgttcgcc   540
cacacgctgt cgcagatccg cgcggccaac cagaaaggcg ccaacccgcc ctacgccgtg   600
atcttcgtgg tctacgacct tccggaccgc gactgcgccg ccgccgcgtc caacggcgag   660
ttctccatcg cgaacaacgg ggcggccaac tacaagacgt acatcgacgc gatccggagc   720
ctcgtcatcc agtactcaga catccgcatc atcttcgtca tcgagcccga ctcgctggcc   780
aacatggtga ccaacctgaa cgtggccaag tgcgccaacg ccgagtcgac ctacaaggag   840
ttgaccgtct acgcgctgca gcagctgaac ctgcccaacg tggccatgta cctgacgcc   900
ggccacgccg gctggctcgg ctggcccgcc aacatccagc cggccgccaa cctcttcgcg    960
gagatctaca gcgaccggcg caagccggcc gccgtgcgcg gcctcgccac caacgtggcc   1020
aactacaacg cctggagcct ggccacgccg cctcgtaca cccagggcga ccccaactac   1080
gacgagagcc actacgtcca ggccctcgcc ccgctgctca ccgccaacgg cttcccgcc   1140
cacttcatca cggacacccg gccgaacggc aagcagccga ccggacaacg gcaatgggga   1200
gactggtgca acgttatcgg aactggcttc ggcgtgcgcc cgacgacaaa cacggcctc   1260
gacatcgagg acgccttcgt ctgggtcaag cccggcggcg agtgcgacgg cacgagcaac   1320
acgacctctc cccgctacga ctaccactgc ggcctgtcgg acgcgctgca gctgctccg    1380
gaggccggca cttggttcca ggcctacttc agcagctcc tgaccaacgc caacccgccc   1440
tttttaa                                                             1446

SEQ ID NO: 14          moltype = AA   length = 481
FEATURE                Location/Qualifiers
source                 1..481
                       mol_type = protein
                       organism = Thielavia terrestris
```

```
SEQUENCE: 14
MAQKLLLAAA LAASALAAPV VEERQNCGSV WSQCGGIGWS GATCCASGNT CVELNPYYSQ    60
CLPNSQVTTS TSKTTSTTTR SSTTSHSSGP TSTSTTTTSS PVVTTPPSTS IPGGASSTAS   120
WSGNPFSGVQ MWANDYYASE VSSLAIPSMT GAMATKAAEV AKVPSFQWLD RNVTIDTLFA   180
HTLSQIRAAN QKGANPPYAG IFVVYDLPDR DCAAAASNGE FSIANNGAAN YKTYIDAIRS   240
LVIQYSDIRI IFVIEPDSLA NMVTNLNVAK CANAESTYKE LTVYALQQLN LPNVAMYLDA   300
GHAGWLGWPA NIQPAANLFA EIYTSAGKPA AVRGLATNVA NYNGWSLATP PSYTQGDPNY   360
DESHYVQALA PLLTANGFPA HFITDTGRNG KQPTGQRQWG DWCNVIGTGF GVRPTTNTGL   420
DIEDAFVWVK PGGECDGTSN TTSPRYDYHC GLSDALQPAP EAGTWFQAYF EQLLTNANPP   480
F                                                                   481

SEQ ID NO: 15           moltype = DNA   length = 1543
FEATURE                 Location/Qualifiers
source                  1..1543
                        mol_type = genomic DNA
                        organism = Trichophaea saccata
SEQUENCE: 15
ggcacgaggg ctgccagcgt attcgcagca gatcgatcga ctcgaggacc acatcgcatc    60
atgaagaact tccttctggc gtccgcgctg atcgcggttg ccgcagctca gcagagtgct   120
tggggacagt gcggtggaat tggctggact ggcgcgacga cttgtatctc tggctacacg   180
tgctcaaaga tcaacgacta ctattcccag tgcattccgg gtacggcttc aaccaccact   240
caaggcggcg gcaatggcgg aggaaacggc ggtacaacga ctactcccac taccactcca   300
gcggccagta acaccaacaa cccgttctcc ggcaagaccc aatgggcgaa cccttactac   360
gcttccgagg tctcgagcat cgccatcccg tccctcgttg ccgccggaaa cacgcgcctg   420
gcttccgccg cggccaaggt tgcccaggtc ccctccttca cctggttgga caccgcgcc   480
aaagttccga gcgtgcgcac ctaccttcaa tccatcaaga acgccggcac caagaacgtg   540
atcgtcccga tcgtggtcta cgatctcccg gaacgagact gtgcagcggc cgcctccaac   600
ggagagctct cgctcgccaa caacggtacc gcaatttaca aggcagacta catcgaccag   660
atctacaaca tcctcgccga cttcccgaca attcccgtcg cgctgattat cgagccggat   720
tccctcgcta acttggttac gaacttgaat gtggccaagt gttcgaacgc tgagtccgcg   780
tataagacgc tcatcgctta tgcggtgcag aagtttggta ccctgtcgaa tgtggtcag   840
tatctcgacg gcgccacgg tggatggctc ggatggcccg cgaatcttcc gcctgctgcg   900
cagctgttcg cccagatccg gcagagcgct ggaagtccgg cgaatctgag gggttggct   960
actaacgttg ctaactacaa cgcttggtcc attgctacct ccccatctta cactcccc   1020
aaccctaact cgcacgagaa acgatacata gccgctatgt cctccgcact cgccgcccag  1080
ggctggtcca acacccacta catcgtcgac caaggccgca gcggcaagca gccgaccggc  1140
cagctccagc agggcgattg tgcaacgcc ctgggaaccg gctttggaat tcgtcctgat  1200
acaacccgg atgatcccaa ccttgatgct ttcgtgtggg ttaagccggg tggtgaatcg  1260
gatggtacca gcaatacttc ctcgacccgc tatgattatc attgtggaca gagcgatgcg  1320
ctacaaccgg ccccgaggc gggaacgtgg ttccaggcgt attttgtgca gttgctgcag  1380
aatgctaatc ctagcttcac gtaagcttgg gagcgtgggg gttggaagat gtgtattgta  1440
tgtgtagata gagaaaaact gttggcctat tcaggactaa gtttgggcgt ctgggttctg  1500
tttcttcgcg taggtagacg tgaacttgat gaacttgagc gtg                    1543

SEQ ID NO: 16           moltype = AA   length = 447
FEATURE                 Location/Qualifiers
source                  1..447
                        mol_type = protein
                        organism = Trichophaea saccata
SEQUENCE: 16
MKNFLLASAL IAVAAAQQSA WGQCGGIGWT GATTCISGYT CSKINDYYSQ CIPGTASTTT    60
QGGGNGGGNG GTTTTPTTTP AASNTNNPFS GKTQWANPYY ASEVSSIAIP SLVAAGNTAL   120
ASAAAKVAQV PSFTWLDTRA KVPSVRTYLQ SIKDAGTKNV IVPIVVYDLP ERDCAAAASN   180
GELSLANNGT AIYKADYIDQ IYNILADFPT IPVALIIEPD SLANLVTNLN VAKCSNAESA   240
YKTLIAYAVQ KFGTLSNVVQ YLDGGHGGWL GWPANLPPAA QLFAQIRQSA GSPANLRGLA   300
TNVANYNAWS IATCPSYTSP NPNCDEKRYI AAMSSALAAQ GWSNTHYIVD QGRSGKQPTG   360
QLQQGDWCNA LGTGFGIRPD TTPDDPNLDA FVWVKPGGES DGTSNTSSTR YDYHCGQSDA   420
LQPAPEAGTW FQAYFVQLLQ NANPSFT                                       447

SEQ ID NO: 17           moltype = DNA   length = 1713
FEATURE                 Location/Qualifiers
source                  1..1713
                        mol_type = genomic DNA
                        organism = Aspergillus fumigatus
SEQUENCE: 17
atgaagcacc ttgcatcttc catcgcattg actctactgt tgcctgccgt gcaggcccag    60
cagaccgtat ggggccaatg tatgttctgg ctgtcactgg aataagactg tatcaactgc   120
tgatatgctt ctaggtggcg gccaaggctg gtctggcccg acgagctgtg ttgccggcgc   180
agcctgtagc acactgaatc cctgtatgtt agatatcgct ctgagtggag acttatactg   240
acttccttag actacgctca gtgtatcccg ggagccaccg cgacgtccac cacccctcacg   300
acgacgacgg cggcgacgac gacatcccag accaccacca aacctaccac gactggtcca   360
actacatccg cacccaccgt gaccgcatcc ggtaaccctt tcagcggcta ccagctgtat   420
gccaaccct actactcctc cgaggtccat atctctgcca tgccttctct gcccagtcg   480
ctgcagccca aggctagtgc tgttgctgaa gtgccctcat ttgtttggct gtaagtggcc   540
ttatcccaat actgagacca actctctgac agtcgtagcg acgttgccgc caaggtgccc   600
actatgggaa cctacctggc cgacattcag gccaagaaca aggccggcgc caaccctcct   660
atcgctggta tcttcgtggt ctacgacttg ccggaccgtg actgcgccgc tctgccagt   720
aatgcgagt actcaattgc caacaacggt gtggccaact acaaggcgta cattgacgcc   780
atccgtgctc agctggtgaa gtactctgac gttcacacca tcctcgtcat cggtaggccg   840
```

```
tacacctccg ttgcgcgccg cctttctctg acatcttgca gaaccccgaca gcttggccaa    900
cctggtgacc aacctcaacg tcgccaaatg cgccaatgcg cagagcgcct acctggagtg    960
tgtcgactat gctctgaagc agctcaacct gcccaacgtc gccatgtacc tcgacgcagg   1020
tatgcctcac ttcccgcatt ctgtatccct tccagacact aactcatcag gccatgcggg   1080
ctggctcgga tggcccgcca acttgggccc cgccgcaaca ctcttcgcca aagtctacac   1140
cgacgcgggt tcccccgcgg ctgttcgtgg cctggccacc aacgtcgcca actacaacgc   1200
ctggtcgctc agtacctgcc cctcctacac ccagggagac cccaactgcg acgagaagaa   1260
gtacatcaac gccatggcgc ctcttctcaa ggaagccggc ttcgatgccc acttcatcat   1320
ggatacctgt aagtgcttat tccaatcgcc gatgtgtgac gactaatcaa tgtttcagcc   1380
cggaatggcg tccagcccac gaagcaaaac gcctgggtg actggtgcaa cgtcatcggc    1440
accggcttcg gtgttcgccc tcgactaac accggcgatc cgctccagga tgcctttgtg    1500
tggatcaagc ccggtggaga gagtgatggc acgtccaact cgacttcccc ccggtatgac   1560
gcgcactgcg gatatagtga tgctctgcag cctgctcctg aggctggtac ttggttccag   1620
gtatgtcatc cattagccag atgagggata agtgactgac ggacctaggc ctactttgag   1680
cagcttctga ccaacgctaa cccgtccttt taa                                1713

SEQ ID NO: 18           moltype = AA  length = 454
FEATURE                 Location/Qualifiers
source                  1..454
                        mol_type = protein
                        organism = Aspergillus fumigatus
SEQUENCE: 18
MKHLASSIAL TLLLPAVQAQ QTVWGQCGGQ GWSGPTSCVA GAACSTLNPY YAQCIPGATA     60
TSTTLTTTTA ATTTSQTTTK PTTTGPTTSA PTVTASGNPF SGYQLYANPY YSSEVHTLAM    120
PSLPSSLQPK ASAVAEVPSF VWLDVAAKVP TMGTYLADIQ AKNKAGANPP IAGIFVVYDL    180
PDRDCAALAS NGEYSIANNG VANYKAYIDA IRAQLVKYSD VHTILVIEPD SLANLVTNLN    240
VAKCANAQSA YLECVDYALK QLNLPNVAMY LDAGHAGWLG WPANLGPAAT LFAKVYTDAG    300
SPAAVRGLAT NVANYNAWSL STCPSYTQGD PNCDEKKYIN AMAPLLKEAG FDAHFIMDTS    360
RNGVQPTKQN AWGDWCNVIG TGFGVRPSTN TGDPLQDAFV WIKPGGESDG TSNSTSPRYD    420
AHCGYSDALQ PAPEAGTWFQ AYFEQLLTNA NPSF                                454

SEQ ID NO: 19           moltype = DNA  length = 1502
FEATURE                 Location/Qualifiers
source                  1..1502
                        mol_type = genomic DNA
                        organism = Aspergillus terreus
SEQUENCE: 19
ccatgaattc tcttacaaaa agcatcatcg ccgcagggct ggtcttccac ccacttgtcc     60
aggccccaaca accttcctcg tcttctccag gaaaccccttc tcttggcaacg tggaaatgca    120
cttctggcgg gggttgtgtg cagcaggata catcagtcgt cctagattgg ggtttccact    180
ggatccacac cagcagttct caatcctgca ccacctcctc cggtgtcaac tcggccctct    240
gccccgatga agcgacctgt gctaagaact gcgtgatcga tccggcaaac tacgtaacag    300
ctggcgtctc cacctcggga gacactttga cgatgcacca gtactaccaa aacaacggag    360
tcaccaccaa tgcgtcaccg cgtctctatc tcctgggctc agacggcaac tatgtcatgc    420
tgaagctcct cggccaggaa cttagtttta atgtggattt gtcaacgctt ccgtgtggcg    480
agaacggtgc cttgtatctg tcagagatga cgcccaccgg tggaagaaac gaatacaaca    540
caggaggcgc ccaggtattg agattctgat cgtttcctta gacaacaccg tgtatgctga    600
caaatttcaa gtatggttct ggttactgtg acgcacaatc gccagtcatg gcatggagaa    660
acggcacccct caacaccagt ggccaggggtt ttggctgcaa cgaaatggat atcctcgaag    720
ccaactcccg tgcaaactcc ttcacccctc accctgcaa cggcaatgat tgcgataaag    780
gggggtgtgg attcaatccc tacgctctcg gccagcaaca ctactgggcc ccaggcgggga    840
cggtcgacac gtccaagccg ttcactatca ccacgcagtt tatcaccgac gacggtacca    900
caactggggac tctgaaagag atcgccgtc aatacatcca aaacggtaag atcatcgcca    960
atgcgaagtc atcggctggg gtcgactcca tcaccgagcc atggtgcgaa tcagttacg    1020
gcgctgctgc tacctacggt ggtctgaaga gaatggggta ggcccctcgc cggggaatgg   1080
ttctgatttt cagcatctgg aacgacgcag gcggcttcat gaactggctg gatagcggca   1140
gcgccggacc ctgcagtagc acggaaggaa atccgtcatt gattcaatct gcccatccgg   1200
atactcacgt ggtgtttttcc aacatccgct ggggcgacat cggatcaacc tataccaatc   1260
cgggtggctc tggttctagt tccagctcta ctaggaccac aaccaagact acctccacca   1320
ctaccactac gaaaattacc actaccaccct ccgcaggtgg tgctaccag ccccactgga   1380
gccagtgtgg aggacaagga tggactgggc ctaccgcgtg tgcatcgccg tacacttgcc   1440
agaagcagaa tgagtggtac tctcagtgct tgtgaatagg tgcgtaacac atgcagactg   1500
cg                                                                 1502

SEQ ID NO: 20           moltype = AA  length = 471
FEATURE                 Location/Qualifiers
source                  1..471
                        mol_type = protein
                        organism = Aspergillus terreus
SEQUENCE: 20
MNSLTKSIIA AGLVFHPLVQ AQQPSSSSPG NPSLATWKCT SGGGCVQQDT SVVLDWGFHW     60
IHTSSSQSCT TSSGVNSALC PDEATCAKNC VIDPANYVTA GVSTSGDTLT MHQYYQNNGV    120
TTNASPRLYL LGSDGNYVML KLLGQELSFN VDLSTLPCGE NGALYLSEMS ATGGRNEYNT    180
GGAQYGSGYC DAQSPVMAWR NGTLNTSGQG FGCNEMDILE ANSRANSFTP HPCNGNDCDK    240
GGCGFNPYAL GQQNYWGPGG TVDTSKPFTI TTQFITDDGT TTGTLKEIRR QYIQNGKIIA    300
NAKSSAGVDS ITEPWCESVD GAAATYGGLK RMGEALGRGM VLIFSIWNDA GGFMNWLDSG    360
SAGPCSSTEG NPSLIQSAHP DTHVVFSNIR WGDIGSTYTN PGGSGSSSSS TRTTTKTTST    420
TTTTKITTTT SAGGATQTHW GQCGGQGWTG PTACASPYTC QKNEWYSQC L              471
```

```
SEQ ID NO: 21           moltype = DNA  length = 1849
FEATURE                 Location/Qualifiers
source                  1..1849
                        mol_type = genomic DNA
                        organism = Trichoderma reesei
SEQUENCE: 21
tgccatttct gacctggata ggttttccta tggtcattcc tataagagac acgctctttc    60
gtcggcccgt agatatcaga ttggtattca gtcgcacaga cgaaggtgag ttgatcctcc   120
aacatgagtt ctatgagccc ccccccttgcc cccccccgtt caccttgacc tgcaatgaga   180
atcccacctt ttacaagagc atcaagaagt attaatgcg ctgaatagcc tctgctcgat    240
aatatctccc cgtcatcgac aatgaacaag tccgtggctc cattgctgct tgcagcgtcc   300
atactatatg gcggcgccgt cgcacagcag actgtctggg gccagtgtgg aggtattggt   360
tggagcggac ctacgaattg tgctcctggc tcagcttgtt cgaccctcaa tccttattat   420
gcgcaatgta ttccgggagc cactactatc accacttcga cccggccacc atccggtcca   480
accaccacca ccagggctac ctcaacaagc tcatcaactc cacccacacg ctctgggtc    540
cgatttgccg gcgttaacat cgcgggtttt gactttggct gtaccacaga gtgagtaccc   600
ttgtttcctg gtgttgctgg ctggttgggc gggtatacag cgaagcggac gcaagaacac   660
cgccggtccg ccaccatcaa gatgtgggtg gtaagcggcg gtgtttgta caactacctg    720
acagctcact caggaaatga gaattaatgg aagtcttgtt acagtggcac ttgcgttacc   780
tcgaaggttt atcctccgtt gaagaacttc accggctcaa acaactaccc cgatggcatc   840
ggccagatgc agcacttcgt caacgaggac gggatgacta ttttccgctt acctgtcgga   900
tggcagtacc tcgtcaacaa caatttgggc ggcaatcttg attccacgag catttccaag   960
tatgatcagc ttgttcaggg gtgcctgtct ctgggcgcat actgcatcgt cgacatccac  1020
aattatgctc gatggaacgg tggaatcatt ggtcagggcg ccctactaa tgctcaattc   1080
acgagccttt ggtcgcagtt ggcatcaaag tacgcatctc agtcgagggt gtggttcggc  1140
atcatgaatg agccccacga cgtgaacatc aacacctggg ctgccaaggt ccaagaggtt  1200
gtaaccgcaa tccgcaacgc tggtgctacg tcgcaattca tctctttgcc tggaaatgat  1260
tggcaatctg ctgggctttt catatccgat ggcagtgcag ccgccctgtc tcaagtcacg   1320
aacccggatg ggtcaacaac gaatctgatt tttgacgtgc acaaatactt ggactcagac  1380
aactccggta ctcacgccga atgtactaca aataacattg ccggcgcctt ttctccgctt   1440
gccacttggc tccgacagaa caatcgccag gctatcctga cagaaaccgg tggtggcaac  1500
gttcagtcct gcatacaaga catgtgccag caaatccaat atctcaacca gaactcagat   1560
gtctatcttg gctatgttgg ttggggtgcc ggatcatttg atagcacgta tgtcctgacg  1620
gaaacacccga ctggcagtgg taactcatgg acggacacat cccttggtcag ctcgtgtctc  1680
gcaagaaagt agcactctga gctgaatgca gaagcctcgc caacgctttgt atctcgctat  1740
caaacatagt agctactcta tgaggctgtc tgttctcgat ttcagcttta tatagtttca  1800
tcaaacagta catattccct ctgtggccac gcaaaaaaaa aaaaaaaaa              1849

SEQ ID NO: 22           moltype = AA  length = 418
FEATURE                 Location/Qualifiers
source                  1..418
                        mol_type = protein
                        organism = Trichoderma reesei
SEQUENCE: 22
MNKSVAPLLL AASILYGGAV AQQTVWGQCG GIGWSGPTNC APGSACSTLN PYYAQCIPGA    60
TTITTSTRPP SGPTTTTRAT STSSSTPPTS SGVRFAGVNI AGFDFGCTTD GTCVTSKVYP   120
PLKNFTGSNN YPDGIGQMQH FVNEDGMTIF RLPVGWQYLV NNNLGGNLDS TSISKYDQLV   180
QGCLSLGAYC IVDIHNYARW NGGIIGQGGP TNAQFTSLWS QLASKYASQS RVWFGIMNEP   240
HDVNINTWAA TVQEVVTAIR NAGATSQFIS LPGNDWQSAG AFISDGSAAA LSQVTNPDGS   300
TTNLIFDVHK YLDSDNSGTH AECTTNNIDG AFSPLATWLR QNNRQAILTE TGGGNVQSCI   360
QDMCQQIQYL NQNSDVYLGY VGWGAGSFDS TYVLTETPTG SGNSWTDTSL VSSCLARK     418

SEQ ID NO: 23           moltype = DNA  length = 1188
FEATURE                 Location/Qualifiers
source                  1..1188
                        mol_type = genomic DNA
                        organism = Myceliophthora thermophila
SEQUENCE: 23
cgacttgaaa cgccccaaat gaagtcctcc atcctcgcca gcgtcttcgc cacgggcgcc     60
gtggctcaaa gtggtccgtg gcagcaatgt ggtggcatcg gatggcaagg atcgaccgac   120
tgtgtgtcgg gctaccactg cgtctaccag aacgattggt acagccagtg cgtgcctggc   180
gcggcgtcga caacgctgca gacatcgacc acgtccaggc ccaccgccac cagcaccgcc   240
cctccgtcgt ccaccacctc gcctagcaag ggcaagctga agtggctcgg cagcaacgag   300
tcgggcgccg agttcggga gggcaattac cccggcctct ggggcaagca cttcatcttc    360
ccgtcgactt cggcgattca gacgctcatc aatgatggat acaacatctt ccggatcgac   420
ttctcgatgg agcgtctggt gcccaaccag ttgacgtcgt ccttcgacca gggttacctc   480
cgcaacctga ccgaggtggt caacttcgtg acgaacgcgg gcaagtacgc cgtcctggac   540
ccgcacaact acgccggta ctacggcaac atcatcacgg acacgaacgc gttccggacc   600
ttctggacca acctggccaa gcagttcgcc tccaactgc tcgtcatctt cgacaccaac   660
aacgagtaca acacgatgga ccagaccctg tgctcaacc tcaaccaggc cgccatcgac    720
ggcatccggg ccgccggcgc gacctcgcag tacatcttcg tcgagggcaa cgcgtggagc   780
ggggcctgga gctggaacac gaccaacacc aacatggccg ccctgacgga cccgcagaac   840
aagatcgtgt acgagatgca ccagtacctc gactcggaca gctcgggcac ccacgccgag   900
tgcgtcagca gcaccatcgc gcccatcgc cgtctgggag tcgctggcg gtctccgccgc   960
aacggcaagc tcggcgtcct cggcgagttc gccggcggcg ccaacgccgt ctgcagcag   1020
gccgtcaccg gcctcctcga ccacctccag gacaacagcg acgtctggct gggtgccctc  1080
tggtgggccg ccgtccctg gtggggcgac tacatgtact cgttcgagcc tccttcgggc  1140
accggctatg tcaactacaa ctcgatcttg aagaagtact gccgtaa                1188
```

```
SEQ ID NO: 24              moltype = AA   length = 389
FEATURE                    Location/Qualifiers
source                     1..389
                           mol_type = protein
                           organism = Myceliophthora thermophila
SEQUENCE: 24
MKSSILASVF ATGAVAQSGP WQQCGGIGWQ GSTDCVSGYH CVYQNDWYSQ CVPGAASTTL        60
QTSTTSRPTA TSTAPPSSTT SPSKGKLKWL GSNESGAEFG EGNYPGLWGK HFIFPSTSAI       120
QTLINDGYNI FRIDFSMERL VPNQLTSSFD QGYLRNLTEV VNFVTNAGKY AVLDPHNYGR       180
YYGNIITDTN AFRTFWTNLA KQFASNSLVI FDTNNEYNTM DQTLVLNLNQ AAIDGIRAAG       240
ATSQYIFVEG NAWSGAWSWN TTNTNMAALT DPQNKIVYEM HQYLDSDSSG THAECVSSTI       300
GAQRVVGATQ WLRANGKLGV LGEFAGGANA VCQQAVTGLL DHLQDNSDVW LGALWWAAGP       360
WWGDYMYSFE PPSGTGYVNY NSILKKYLP                                         389

SEQ ID NO: 25              moltype = DNA   length = 1008
FEATURE                    Location/Qualifiers
source                     1..1008
                           mol_type = genomic DNA
                           organism = Thermoascus aurantiacus
SEQUENCE: 25
atgaagctcg gctctctcgt gctcgctctc agcgcagcta ggcttacact gtcggcccct        60
ctcgcagaca gaaagcagga gaccaagcgt gcgaaagtat tccaatggtt cggttcgaac       120
gagtccggtg ctgaattcgg aagccagaac cttccaggag tcgagggaaa ggattatata       180
tggcctgatc ccaacaccat tgacacattg atcagcaagg ggatgaacat ctttcgtgtc       240
cccttttatga tggagagatt ggttcccaac tcaatgaccg gctctccgga tccgaactac       300
ctggcagatc tcatagcgac tgtaaatgca atcacccaga aggtgccta cgccgtcgg        360
gatcctcata actacggcag atactacaat tctataatct cgagcccttc cgatttccag       420
accttctgga aacggtcgc ctcacagttt gcttcgaatc cactggtcat cttcgacact       480
aataacgaat accacgatat ggaccagacc ttagtcctca atctcaacca ggccgctatc       540
gacggcatcc gttccgccgg agccacttcc cagtacactc ttgtcgaggg caattcgtgg       600
accgggggcat ggacctggac gaacgtgaac gataacatga aaagcctgac cgacccatct       660
gacaagatca tatacgagat gcaccagtac ctggactctg acggatccgg acatcagcg       720
acctgcgtat cttcgaccat cggtcaagag cgaatcacca cgcaacgca gtggctcagg       780
gccaacggga agaagggcat catcggcgag tttgcgggcg gagccaacga cgtctgcgag       840
acggccatca cgggcatgct ggactacatg gcccagaaca cagacgtctg gactggcgcc       900
atctggtggg cggccgggcc gtggtgggga gactacatat tctccatgga gccggacaat       960
ggcatcgcgt atcagcagat acttcctatt ttgactccgt atctttga               1008

SEQ ID NO: 26              moltype = AA   length = 335
FEATURE                    Location/Qualifiers
source                     1..335
                           mol_type = protein
                           organism = Thermoascus aurantiacus
SEQUENCE: 26
MKLGSLVLAL SAARLTLSAP LADRKQETKR AKVFQWFGSN ESGAEFGSQN LPGVEGKDYI        60
WPDPNTIDTL ISKGMNIFRV PFMMERLVPN SMTGSPDPNY LADLIATVNA ITQKGAYAVV       120
DPHNYGRYYN SIISSPSDFQ TFWKTVASQF ASNPLVIFDT NNEYHDMDQT LVLNLNQAAI       180
DGIRSAGATS QYIFVEGNSW TGAWTWTNVN DNMKSLTDPS DKIIYEMHQY LDSDGSGTSA       240
TCVSSTIGQE RITSATQWLR ANGKKGIIGE FAGGANDVCE TAITGMLDYM AQNTDVWTGA       300
IWWAAGPWWG DYIFSMEPDN GIAYQQILPI LTPYL                                 335

SEQ ID NO: 27              moltype = DNA   length = 3060
FEATURE                    Location/Qualifiers
source                     1..3060
                           mol_type = genomic DNA
                           organism = Aspergillus fumigatus
SEQUENCE: 27
atgagattcg gttggctcga ggtggccgct ctgacggccg cttctgtagc caatgcccag        60
gtttgtgatg cttttcccgt cattgtttcgg atatagttga caatagtcat ggaaataatc       120
aggaattggc tttctctcca ccattctacc cttcgccttg ggctgatggc caggaggagt       180
gggcagatgc ccatcgacgc gccgtcgaga tcgtttctca gatgacactg gcggagaagg       240
ttaaccttac aacgggtact gggtggggttg cgactttttt gttgacagtg agctttcttc       300
actgaccatc tacacagatg ggaaatggac cgatgcgtcg gtcaaaccgg cagcgttccc       360
aggtaagctt gcaattctgc aacaacgtgc aagtgtagtc gctaaaacgc ggtggtgcag       420
acttggtatc aactgggtc tttgtggcca ggattcccct tgggtatcc gtttctgtga       480
gctatacccg cggagtcttt cagtccttgt attatgtgct gatgattgtc tctgtatagc       540
tgacctcaac tccgccttcc ctgctggtac taatgtcgcc gcgacatggg acaagacact       600
cgcctacctt cgtggcaagg ccatgggtga ggaattcaac gacaagggcg tggacattcg       660
gctggggcct gctgctggtc ctctcggcaa ataccggac ggcggcagaa tctgggaagg       720
cttctctcct gatccggttc tcactggtgt acttttcgcc gaaactatca agggtatcca       780
agacgcgggt gtgattgcta ctgccaagca ttacattctg aatgaacagg agcatttccg       840
acaggttggc gaggccagg gatatggtta caacatcacg gagacgatca gctccaacgt       900
ggatgacaag accatgcacg agttgtacct ttggtgagta gttgacactg caaatgagga       960
ccttgatga tttgactgac ctggaatgca ggccattcctg agatgctgtg gcggttaaga      1020
ttttccgtag acttgacctc gcgacgaaga aatcgctgac gaaccatcgt agctggcgtt      1080
ggcgctgtca tgtgttccta caatcaaatc aacaacagct acggttgtca aaacagtcaa      1140
actctcaaca agctcctcaa ggctgagctg ggcttcaag gcttcgtcat gagtgactgg      1200
agcgctcacc acagcggtgt cggcgctgcc ctcgctgggt tggatatgtc gatgcctgga      1260
gacatttcct tcgacgacgg actctccttc tgggggcacga acctaactgt cagtgttctt      1320
```

```
aacggcaccg ttccagcctg gcgtgtcgat gacatggctg ttcgtatcat gaccgcgtac  1380
tacaaggttg gtcgtgaccg tcttcgtatt cccctaact tcagctcctg acccgggat    1440
gagtacggct gggagcattc tgctgtctcc gagggagcct ggaccaaggt gaacgacttc  1500
gtcaatgtgc agcgcagtca ctctcagatc atccgtgaga ttggtgccgc tagtacagtg  1560
ctcttgaaga acacgggtgc tcttcctttg accggcaagg aggttaaagt gggtgttctc  1620
ggtgaagacg ctggttccaa cccgtggggt gctaacggct gccccgaccg cggctgtgat  1680
aacggcactc ttgctatggc ctgggtagt ggtactgcca acttcccta ccttgtcacc     1740
cccgagcagg ctatccagcg agaggtcatc agcaacggcg gcaatgtctt tgctgtgact  1800
gataacgggg ctctcagcca gatggcagat gttgcatctc aatccaggtg agtgcgggct  1860
cttagaaaaa gaacgttctc tgaatgaagt tttttaacca ttgcgaacag cgtgtctttg   1920
gtgtttgtca acgccgactc tggagagggt ttcatcagtg tcgacggcaa cgagggtgac   1980
cgcaaaaatc tcactctgtg gaagaacggc gaggccgtca ttgacactgt tgtcagccac   2040
tgcaacaaca cgattgtggt tattcacagt gttgggcccg tcttgatcga ccggtggtat  2100
gataacccca acgtcactgc catcatctgg gccggcttgc ccggtcagga gagtggcaac  2160
tccctggtcg acgtgctcta tggccgcgtc aaccccagcg ccaagacccc gttcacctgg   2220
ggcaagactc gggagtctta cggggctccc ttgctcaccg agcctaacaa tggcaatggt  2280
gctcccagg atgatttcaa cgagggcgtc ttcattgact accgtcactt tgacaagcgc   2340
aatgagaccc ccatttatga gtttggccat ggcttgagtc acaccacctt tggttactct  2400
caccttcggg ttcaggccct caatagttcg agttcggcat atgtcccgac tagcggagag  2460
accaagcctg cgccaaccta tggtgagatc ggtagtgccg ccgactacct gtatcccgag  2520
ggtctcaaaa gaattaccaa gtttatttac ccttggctca actcgaccga cctcgaggat  2580
tcttctgacg acccgaacta cggctgggag gactcggagt acatcccga aggcgctagg    2640
gatgggtctc ctcaaccct cctgaaggct ggcggcgctc tggtggtaa ccctaccctt    2700
tatcaggatc ttgttagggt gtcggccacc ataaccaaca ctggtaacgt cgccggttat  2760
gaagtccctc aattggtgag tgacccgcat gttccttgcg ttgcaatttg ctaactcgc   2820
ttctagtatg tttcactggg cggaccgaac gagcctcggg tcgttctgcg caagttcgac   2880
cgaatcttcc tggctcctgg ggagcaaaag gtttgacca cgactcttaa ccgtcgtgat    2940
ctcgccaatt gggatgtgga ggctcaggac tgggtcatca caaagtaccc caagaaagtg  3000
cacgtcggca gctcctcgcg taagctgcct ctgagagcgc ctctgccccg tgtctactag   3060

SEQ ID NO: 28            moltype = AA   length = 863
FEATURE                  Location/Qualifiers
source                   1..863
                         mol_type = protein
                         organism = Aspergillus fumigatus
SEQUENCE: 28
MRFGWLEVAA LTAASVANAQ ELAFSPPFYP SPWADGQGEW ADAHRRAVEI VSQMTLAEKV   60
NLTTGWEM   DRCVGQTGSV PRLGINWGLC GQDSPLGIRF SDLNSAFPAG TNVAATWDKT   120
LAYLRGKAMG EEFNDKGVDI LLGPAAGPLG KYPDGGRIWE GFSPDPVLTG VLFAETIKGI   180
QDAGVIATAK HYILNEQEHF RQVGEAQGYG YNITETISSN VDDKTMHELY LWPFADAVRA   240
GVGAVMCSYN QINNSYGCQN SQTLNKLLKA ELGFQGFVMS DWSAHHSGVG AALAGLDMSM   300
PGDISFDDGL SFWGTNLTVS VLNGTVPAWR VDDMAVRIMT AYYKVGRDRL RIPPNFSSWT   360
RDEYGWEHSA VSEGAWTKVN DFVNVQRSHS QIIREIGAAS TVLLKNTGAL PLTGKEVKVG   420
VLGEDAGSNP WGANGCPDRG CDNGTLAMAW GSGTANFPYL VTPEQAIQRE VISNGGNVFA   480
VTDNGALSQM ADVASQSSVS LVFVNADSGE GFISVDGNEG DRKNLTLWKN GEAVIDTVVS   540
HCNNTIVVIH SVGPVLIDRW YDNPNVTAII WAGLPGQESG NSLVDVLYGR VNPSAKTPFT   600
WGKTRESYGA PLLTEPNNGN GAPQDDFNEG VFIDYRHFDK RNETPIYEFG HGLSYTTFGY   660
SHLRVQALNS SSSAYVPTSG ETKPAPTYGE IGSAADYLYP EGLKRITKFI YPWLNSTDLE   720
DSSDDPNYGW EDSEYIPEGA RDGSPQPLLK AGGAPGGNPT LYQDLVRVSA TITNTGNVAG   780
YEVPQLYVSL GGPNEPRVVL RKFDRIFLAP GEQKVWTTTL NRRDLANWDV EAQDWVITKY   840
PKKVHVGSSS RKLPLRAPLP RVY                                         863

SEQ ID NO: 29            moltype = DNA   length = 2800
FEATURE                  Location/Qualifiers
source                   1..2800
                         mol_type = genomic DNA
                         organism = Penicillium brasilianum
SEQUENCE: 29
tgaaaatgca gggttctaca atctttctgg ctttcgcctc atgggcgagc caggttgctg   60
ccattgcgca gcccatacag aagcacgagg tttgttttat cttgctcatg acgtgctttt   120
gacttgacta attgttttac atacagcccg gatttctgca cgggcccaa gccatagaat   180
cgttctcaga accgttctac ccgtcgccct ggatgaatcc tcacgccgag ggctggggag   240
ccgcatatca gaaagctcaa gattttgtct cgcaactcac tatcttggag aaaataaatc   300
tgaccaccgg tgttgggtaa gtctctccga tgcttctgg gtcacggtgc gacgagccac   360
tgactttttg aagctgggaa atgggccgt gtgtaggaaa cactggatca attcctcgtc     420
tcggattcaa aggattttgt acccaggatt caccacaggg tgttcggttc gcagattatt   480
cctccgcttt cacatctagc caaatggccg ccgcaacatt tgaccgctca attctttatc   540
aacgaggcca agccatggca caggaacaca aggctaaggg tatcacaatt caattgggcc   600
tgttgccgg ccctcctcgg tgcatccccg agggcggcc caactggaa ggattctcaa     660
ctgatcctgt cttgactggt atagccatgg ctgagacaat taagggcatg caggatactg   720
gagtgattgc ttgcgctaaa cattatattg gaaacgagca ggagcacttc cgtcaagtgg   780
gtgaagctgc gggtcacgga tacactattt ccgatactat ttcatctaat attgacgacc   840
gtgctatgca tgagctatac ttgtggccat tgctgatgc cgttcgcgct ggtgtgggtt   900
ctttcatgtg actctcatat agatcaaca actcctacgg atgccaaaac agtcagaccc   960
tcaacaagct cctcaagagc gaattgggct tccaaggctt tgtcatgagc gattggggtg   1020
cccatcactc tggagtgtca tcggcgtag ctggacttga tatgagcatg ccgggtgata   1080
ccgaatttga ttctggcttg agcttctggg gctctaacct caccattgca attctgaacg   1140
gcacggttcc cgaatggcgc ctggatgaca tggcgatgcg aattatggct gcatacttca   1200
aagttggcct tactattgag gatcaaccag atgtcaactt caatgcctgg acccatgaca   1260
```

```
cctacggata taaatacgct tatagcaagg aagattacga gcaggtcaac tggcatgtcg   1320
atgttcgcag cgaccacaat aagctcattc gcgagactgc cgcgaagggt acagttctgc   1380
tgaagaacaa ctttcatgct ctccctctga agcagcccag gttcgtggcc gtcgttggtc   1440
aggatgccgg gccaaacccc aagggcccta acggctgcgc agaccgagga tgcgaccaag   1500
gcactctcgc aatgggatgg ggctcagggt ctaccgaatt cccttacctg gtcactcctg   1560
acactgctat tcagtcaaag gtcctcgaat acggggtcg atacgagagt attttttgata   1620
actatgacga caatgctatc ttgtcgcttg tctcacagcc tgatgcaacc tgtatcgttt   1680
ttgcaaatgc cgattccggt gaaggctaca tcactgtcga caacaactgg ggtgaccgca   1740
acaatctgac cctctggcaa aatgccgatc aagtgattag cactgtcagc tcgcgatgca   1800
acaacacaat cgttgttctc cactctgtcg gaccagtgtt gctaaatggt atatatgagc   1860
acccgaacat cacagctatt gtctgggcag ggatgccagg cgaagaatct ggcaatgctc   1920
tcgtggatat tctttgggc aatgttaacc ctgccggtcg cactccgttc acctgggcca   1980
aaagtcgaga ggactatggc actgatataa tgtacgagcc caacaacggc cagcgtgcgc   2040
ctcagcagga tttcaccgag agcatctacc tcgactaccg ccatttcgac aaagctggta   2100
tcgagccaat ttacgagttt ggattcggcc tctcctatac caccttcgaa tactctgacc   2160
tccgtgttgt gaagaagtat gttcaaccat acagtccac gaccggcacc ggtgctcaag   2220
cacctcccat cggacagcca cctagccaga acctggatac ctacaagttc cctgctacat   2280
acaagtacat caaaacttc atttatccct acctgaacag cactgtctcc ctccgcgctg   2340
cttccaagga tcccgaatac ggtcgtacga actttatccc accccacgcg cgtgatggct   2400
cccctcaacc tctcaacccc gctcgagacc cagtggccag tggtgaaaac aacatgctct   2460
acgacgaact ttacgaggtc actgcacaga tcaaaaacac tggcgacgtg gccggcgacg   2520
aagtcgtcca gctttacgta gatctcgggg gtgacaacct gctcgtcag ttgagaaact   2580
ttgacaggtt ttatctgctg cccggtcaga gctcaacatt ccgggctaca ttgacgcgcc   2640
gtgatttgag caactgggat attgaggcgc agaactggcg agttacgaa tcgcctaaga   2700
gagtgtatgt tggacggtcg agtcgggatt tgccgctgag ctcacaattg gagtaatgat   2760
catgtctacc aatagatgtt gaatgtctgg tgtggatatt                        2800
```

```
SEQ ID NO: 30              moltype = AA  length = 878
FEATURE                    Location/Qualifiers
source                     1..878
                           mol_type = protein
                           organism = Penicillium brasilianum
SEQUENCE: 30
MQGSTIFLAF ASWASQVAAI AQPIQKHEPG FLHGPQAIES FSEPFYPSPW MNPHAEGWEA    60
AYQKAQDFVS QLTILEKINL TTGVGWENGP CVGNTGSIPR LGFKGFCTQD SPQGVRFADY   120
SSAFTSSQMA AATFDRSILY QRGQAMAQEH KAKGITIQLG PVAGPLGRIP EGGRNWEGFS   180
PDPVLTGIAM AETIKGMQDT GVIACAKHYI GNEQEHFRQV GEAAGHGYTI SDTISSNIDD   240
RAMHELYLWP FADAVRAGVG SFMCSYSQIN NSYGCQNSQT LNKLLKSELG FQGFVMSDWG   300
AHHSGVSSAL AGLDMSMPGD TEFDSGLSFW GSNLTIAILN GTVPEWRLDD MAMRIMAAYF   360
KVGLTIEDQP DVNFNAWTHD TYGYKYAYSK EDYEQVNWHV DVRSDHNKLI RETAAKGTVL   420
LKNNFHALPL KQPRFVAVVG QDAGPNPKGP NGCADRGCDQ GTLAMGWGSG STEFPYLVTP   480
DTAIQSKVLE YGGRYESIFD NYDDNAILSL VSQPDATCIV FANADSGEGY ITVDNNWGDR   540
NNLTLWQNAD QVISTVSSRC NNTIVVLHSV GPVLLNGIYE HPNITAIVWA GMPGEESGNA   600
LVDILWGNVN PAGRTPFTWA KSREDYGTDI MYEPNNGQRA PQQDFTESIY LDYRHFDKAG   660
IEPIYEFGFG LSYTTFEYSD LRVVKKYVQP YSPTTGTGAQ APSIGQPPSQ NLDTYKFPAT   720
YKYIKTFIYP YLNSTVSLRA ASKDPEYGRT DFIPPHARDG SPQPLNPAGD PVASGGNNML   780
YDELYEVTAQ IKNTGDVAGD EVVQLYVDLG GDNPPRQLRN FDRFYLLPGQ SSTFRATLTR   840
RDLSNWDIEA QNWRVTESPK RVYVGRSSRD LPLSSQLE                          878

SEQ ID NO: 31              moltype = DNA  length = 2934
FEATURE                    Location/Qualifiers
source                     1..2934
                           mol_type = genomic DNA
                           organism = Aspergillus niger
SEQUENCE: 31
atgaggttca cttcgatcga ggcggtggct ctgactgccg tctcgctggc cagcgctgta    60
cgtgccgtta ctttgtcctg agaattgcaa ttgtgcttaa ctagattcat ttgtttgttt   120
catcatcgct gacaatggtc ttttcatagg atgaattggc ctactcccca ccgtattacc   180
catccccttg ggccaatggc cagggcaggt gggcgcagge ataccagcgc gctgttgata   240
ttgtctcgca aatgacattg gatgagaagg tcaatctgac cacaggaact gtgtagggct   300
tacatgcgc aatctgtatg ctccggctaa caacttctag atgggaattg gaactatgtg   360
ttggtcgac tggcggtgtt ccccggtagg tttgaaaata ttgtcgagac aggggacatt   420
tattgattaa cggtgacaga ttgggagttc cgggaatgtg tttacaggat agccctctgg   480
gcgttcgcga ctgtaagcca tctgctgttg ttaggccttg atgctctcac tgacacggcg   540
cagccgacta caactctgct ttccctgccg gcatgaactg ggctgcaacc tgggacaaga   600
atctggcata ccttcgcggc aaggctatgg gtcaggaatt tagtgacaag gtgccgata   660
tccaattggg tccagctgcc ggccctctcg gtagaagtcc cgacggtggt cgtaactggg   720
agggcttctc cccagaccct gccctaagtg gtgtgctctt tgccgagacc atcaagggta   780
tccaagatgc tggtgtggtt gcgacggcta agcactacat tgcttacgag caagagcatt   840
tccgtcaggc gcctgaagcc caaggttatg gatttaatat ttccgagagt ggaagtgcga   900
acctcgacga taagactatg cacgagctgt acctctggcc cttcgcggat gccatccgtg   960
caggtgctgg cgctgtgatg tgctcctaca ccagatcaa caacagttat ggctgccaga  1020
acagctcac tctgaacaag ctgctcaagg ccgagctggg cttccagggc tttgtcatga  1080
gtgattggg tgctcaccat gtcgtgtga ggcaggattg gatatgtcta                1140
tgccaggaga cgtcgactac gacagtggta cgtcttactg gggtacaaac ttgaccatta   1200
gcgtgctcaa cggaacggtg cccaatggcg tgtttgatga catggctgtc cgcatcatgg  1260
ccgcctacta caaggtcgga cgtgaccgtc tgtggactcc tccaacttc agctcatgga  1320
ccagagatga atacgctac aagtactact acgtgtcgga gggaccgtac gagaaggtca  1380
accagtacgt gaacgtgcaa cgcaaccaca gcgaactgat tcgccgcatt ggagcggaca  1440
```

-continued

```
gcacggtgct cctcaagaac gacggcgctc tgcctttgac tggtaaggag cgcctggtcg 1500
cgcttatcgg agaagatgcg ggctccaacc cttatggtgc caacggctgc agtgaccgtg 1560
gatgcgacaa tggaacattg gcgatgggct ggggaagtgg tactgccaac ttcccctact 1620
tggtgacccc cgagcaggcc atctcaaacg aggtgcttaa gcacaagaat ggtgtattca 1680
ccgccaccga taactgggct atcgatcaaa ttgaggcgct tgctaagacc gccaggtaag 1740
aagatctcca atttttttt cttgtactat ggatgctgac agcatgctag tgtctctctt 1800
gtctttgtca acgccgactc tggcgagggt tacatcaatg tggacggaaa cctgggtgac 1860
cgcaggaacc tgaccctgtg gaggaacggc gataatgtga tcaaggctgc tgctagcaac 1920
tgcaacaaca ccattgttgt cattcactct gtcggcccac tcttggttca cgaatggtac 1980
gacaaccca atgttaccgc tatcctctgg ggtggtctgc ccggtcagga gtctggcaac 2040
tctcttgccg acgtcctcta tggccgtgtc aaccccggtg ccaagtcgcc ctttacctgg 2100
ggcaagactc gtgaggccta ccaagactac ttggtcaccg agcccaacaa cggcaacgga 2160
gcccctcagg aagacttcgt cgagggcgtc ttcattgact accgtggatt tgacaagcgc 2220
aacgagaccc cgatctacga gttcggctat ggtttaagct acaccacttt caactactcg 2280
aaccttgagg tgcaggtgct gagcgcccct gcatacgagc ctgcttcggg tgagaccgag 2340
gcagcgccaa ccttcggaga ggttggaaat gcgtcggatt acctctaccc cagcggattg 2400
cagagaatta ccaagttcat ctacccctgg ctcaacggta ccgatctcga ggcatcttcc 2460
ggggatgcta gctacgggca ggactcctcg gactatcttc cagaggggac caccgatggc 2520
tctgcgcaac cgatcctgcc tgctggtggc ggtcctggcg gcaaccctcg cctgtacgac 2580
gagctcatcc gcgtgtcagt gaccatcaag aacaccggca aggttgctgg tgatgaagtt 2640
ccccaactgt aagtaaaca tgaggtccga acgaggttga acaaagctaa tcagtcgcag 2700
tatgtttcgc ttggcggtcc caacgagccc aaaatcgtcg tgcgtcaatt cgagcgcatc 2760
acgctgcagc cgtcggagga gacgaagtgg agcacgactc tgacgcgccg tgaccttgca 2820
aactggaatg ttgagaagca ggactgggag attacgtcgt atcccaagat ggtgtttgtc 2880
ggaagctcct cgcggaagct gccgctccgg cgtctctgc ctactgttca ctaa 2934
```

```
SEQ ID NO: 32           moltype = AA  length = 860
FEATURE                 Location/Qualifiers
source                  1..860
                        mol_type = protein
                        organism = Aspergillus niger
SEQUENCE: 32
MRFTSIEAVA LTAVSLASAD ELAYSPPYYP SPWANGQGDW AQAYQRAVDI VSQMTLDEKV   60
NLTTGTGWEL ELCVGQTGGV PRLGVPGMCL QDSPLGVRDS DYNSAFPDGM NVAATWDKNL  120
AYLRGKAMGQ EFSDKGADIQ LGPAAGPLGR SPDGGRNWEG FSPDPALSGV LFAETIKGIQ  180
DAGVVATAKH YIAYEQEHFR QAPEAQGYGF NISESGSANL DDKTMHELYL WPFADAIRAG  240
AGAVMCSYNQ INNSYGCQNS YTLNKLLKAE LGFQGFVMSD WAAHHAGVSG ALAGLDMSMP  300
GDVDYDSGTS YWGTNLTISV LNGTVPQWRV DDMAVRIMAA YYKVGRDRLW TPPNFSSWTR  360
DEYGYKYYYV SEGPYEKVNQ YVNVQRNHSE LIRRIGADST VLLKNDGALP LTGKERLVAL  420
IGEDAGSNPY GANGCSDRGC DNGTLAMGWG SGTANFPYLV TPEQAISNEV LKHKNGVFTA  480
TDNWAIDQIE ALAKTASVSL VFVNADSGEG YINVDGNLGD RRNLTLWRNG DNVIKAAASN  540
CNNTIVVIHS VGPVLNEWY DNPNVTAILW GGLPGQESGN SLADVLYGRV NPGAKSPFTW  600
GKTREAYQDY LVTEPNNGNG APQEDFVEGV FIDYRGFDKR NETPIYEFGY GLSYTTFNYS  660
NLEVQVLSAP AYEPASGETE AAPTFGEVGN ASDYLYPSGL QRITKFIYPW LNGTDLEASS  720
GDASYGQDSS DYLPEGATDG SAQPILPAGG GPGGNPRLYD ELIRVSVTIK NTGKVAGDEV  780
PQLYVSLGGP NEPKIVLRQF ERITLQPSEE TKWSTTLTRR DLANWNVEKQ DWEITSYPKM  840
VFVGSSSRKL PLRASLPTVH                                             860
```

```
SEQ ID NO: 33           moltype = DNA  length = 799
FEATURE                 Location/Qualifiers
source                  1..799
                        mol_type = genomic DNA
                        organism = Thermoascus aurantiacus
SEQUENCE: 33
atgtcctttt ccaagataat tgctactgcc ggcgttcttg cctctgcttc tctagtggct   60
ggccatggct tcgttcagaa catcgtgatt gatggtaaaa agtatgtcat tgcaagacgc  120
acataagcgg caacagctga caatcgacag ttatggcggg tatctagtga accagtatcc  180
atacatgtcc aatcctccag aggtcatcgc ctggtctact acggcaactg atcttggatt  240
tgtgacggt actggatacc aaaccccaga tatcatctgc catagggcg ccaagcctgg  300
agccctgact gctccagtct ctccaggagg aactgttgag cttcaatgga ctccatggcc  360
tgattctcac catggcccag ttatcaacta ccttgctccg tcaatggtg attgttccac  420
tgtggataag acccaattag aattcttcaa aattgccgag agcggtctca tcaatgatga  480
caatcctcct gggatctggg cttcagacaa tctgatagca gccaacaaca gctgactgt  540
caccattcca accacaattg cacctggaaa ctatgttctg aggcatgaga ttattgctct  600
tcactcagct cagaaccagg atggtgccca gaactatccc cagtgcatca atctgcaggt  660
cactggaggt ggttctgata cccctgctgg aactcttgga acggcactct accacgtac  720
cgatcctgga attctgatca acatctatca gaaactttcc agctatatca tccctggtcc  780
tcctctgtat actggttaa                                                799
```

```
SEQ ID NO: 34           moltype = AA  length = 250
FEATURE                 Location/Qualifiers
source                  1..250
                        mol_type = protein
                        organism = Thermoascus aurantiacus
SEQUENCE: 34
MSFSKIIATA GVLASASLVA GHGFVQNIVI DGKKYYGGYL VNQYPYMSNP PEVIAWSTTA   60
TDLGFVDGTG YQTPDIICHR GAKPGALTAP VSPGGTVELQ WTPWPDSHHG PVINYLAPCN  120
```

```
GDCSTVDKTQ LEFFKIAESG LINDDNPPGI WASDNLIAAN NSWTVTIPTT IAPGNYVLRH    180
EIIALHSAQN QDGAQNYPQC INLQVTGGGS DNPAGTLGTA LYHDTDPGIL INIYQKLSSY    240
IIPGPPLYTG                                                          250

SEQ ID NO: 35           moltype = DNA   length = 681
FEATURE                 Location/Qualifiers
source                  1..681
                        mol_type = genomic DNA
                        organism = Thielavia terrestris
SEQUENCE: 35
atgctcgcaa acggtgccat cgtcttcctg gccgccgccc tcggcgtcag tggccactac    60
acctggccac gggttaacga cggcgccgac tggcaacagg tccgtaaggc ggacaactgg   120
caggacaacg gctacgtcgg ggatgtcacg tcgccacaga tccgctgttt ccaggcgacc   180
ccgtccccgg ccccatccgt cctcaacacc acggccgacc cgaccgtgac ctactgggcg   240
aaccccgacg tctaccaccc cgggcctgtg cagttttaca tggcccgcgt gcccgatggc   300
gaggacatca actcgtggaa cggcgacggc gccgtgtggt tcaaggtgta cgaggaccat   360
cctacctttg gcgctcagct cacatggccc agcacgggca gagctcgtt cgcggttccc    420
atcccccgt gcatcaagtc cggctactac ctcctccggg ggagcaaat gcctgcac       480
gtcgcccaga gcgtaggcgg agcgcagttc tacatctcat gcgcccagct cagcgtcacc   540
ggcggcggca gcaccgagcc gccgaacaag gtggccttcc ccggcgctta cagtgcgacg   600
gacccgggca ttctgatcaa catctactac cctgttccca cgtcctacca gaaccccggc   660
ccggccgtct cagctgctg a                                              681

SEQ ID NO: 36           moltype = AA   length = 226
FEATURE                 Location/Qualifiers
source                  1..226
                        mol_type = protein
                        organism = Thielavia terrestris
SEQUENCE: 36
MLANGAIVFL AAALGVSGHY TWPRVNDGAD WQQVRKADNW QDNGYVGDVT SPQIRCFQAT     60
PSPAPSVLNT TAGSTVTYWA NPDVYHPGPV QFYMARVPDG EDINSWNGDG AVWFKVYEDH   120
PTFGAQLTWP STGKSSFAVP IPPCIKSGYY LLRAEQIGLH VAQSVGGAQF YISCAQLSVT   180
GGGSTEPPNK VAFPGAYSAT DPGILINIYY PVPTSYQNPG PAVFSC                  226

SEQ ID NO: 37           moltype = DNA   length = 862
FEATURE                 Location/Qualifiers
source                  1..862
                        mol_type = genomic DNA
                        organism = Aspergillus fumigatus
SEQUENCE: 37
atgactttgt ccaagatcac ttccattgct ggccttctgg cctcagcgtc tctcgtggct    60
ggccacggct ttgtttctgg cattgttgct gatgggaaat agtatgtgct gaaccacac   120
aaatgacagc tgcaacagct aacttctatt ccagttgcag agggtacctt gttaaccaat   180
accctacat gagcaaccct cccgacacca ttgcctggtc caccaccgcc accgacctcg    240
gctttgtgga cggcaccggc taccagtctc cggatattat ctgccacaga gacgcaaaga   300
atggcaagtt gaccgcaacc gttgcagccg gttcacagat cgaattccag tggacgacgt   360
ggccagagtc tcaccatgga ccggtacgac gccgaagaga agagaacata ttgtgaccag   420
ataggctaac atagcatagt tgattactta cctcgctcca tgcaacgcg actgtgccac    480
cgtggacaag accaccctga agtttgtcaa gatcgccgct caaggcttga tcgacggctc   540
caacccacct ggtgtttggg ctgatgatga aatgatcgcc aacaacaaca cggccacagt   600
gaccattcct gcctcctatg cccccggaaa ctacgtcctt cgccacgaga tcatcgccct   660
tcactctgcg ggtaacctga acggcgcgca gaactacccc cagtgtttca acatccaat   720
caccggtggc ggcagtgctc agggatctgg caccgctggc acgtccctgt acaagaatac   780
tgatcctggc atcaagtttg acatctactc ggatctgagc ggtggatacc ctattcctgg   840
tcctgcactg ttcaacgctt aa                                            862

SEQ ID NO: 38           moltype = AA   length = 250
FEATURE                 Location/Qualifiers
source                  1..250
                        mol_type = protein
                        organism = Aspergillus fumigatus
SEQUENCE: 38
MTLSKITSIA GLLASASLVA GHGFVSGIVA DGKYYGGYLV NQYPYMSNPP DTIAWSTTAT     60
DLGFVDGTGY QSPDIICHRD AKNGKLTATV AAGSQIEFQW TTWPESHHGP LITYLAPCNG   120
DCATVDKTTL KFVKIAAQGL IDGSNPPGVW ADDEMIANNN TATVTIPASY APGNYVLRHE   180
IIALHSAGNL NGAQNYPQCF NIQITGGGSA QGSGTAGTSL YKNTDPGIKF DIYSDLSGGY   240
PIPGPALFNA                                                          250

SEQ ID NO: 39           moltype = DNA   length = 969
FEATURE                 Location/Qualifiers
source                  1..969
                        mol_type = genomic DNA
                        organism = Penicillium pinophilum
SEQUENCE: 39
atgccttcta ctaaagtcgc tgcccttttct gctgttctag ctttggcctc cacggttgct    60
ggccatggtt ttgtgcaaaa catcgttatc gacggtaaat cttactctgg atacttgtg    120
aatcagttcc cctacgagtc caacccacca gctgttattg ggtgggcaac aactgcaacc   180
gacctggat tcgtcgctcc cagtgagtac accaatgcag acattatctg ccacaagaac    240
gccacacctg gcgcgctttc tgctccagtt gctgcagggg gcactgtcga gctccagtgg   300
```

```
actacatggc cgatagtca tcacggtcct gtcatcagct acctcgccaa ctgcaatggc  360
aattgttcta ccgtggataa gactaagcta gactttgtca agattgacca aggtggtttg  420
atcgacgata ctaccccccc gggtacatgg gcttccgaca aacttatcgc tgccaacaac  480
agctggactg taactatccc ctccaccatc gcgcctggaa actacgtttt gcgccacgaa  540
atcattgctc ttcactccgc tggaaacgca gacggtgccc aaaaactacc tcaatgcatc  600
aacttggaga tcaccggcag cggaaccgcc gctccctctg gtaccgctgg cgaaaagctc  660
tacacctcta ctgaccccgg tatcttggtc aatatctacc aatccttgtc gacctacgtt  720
attcccggac caactctgtg gagcggtgct gccaatggcg ctgttgccac tggttctgct  780
actgcggttg ctacgactgc cactgcttct gcgaccgcta ctcctaccac acttgttacc  840
tctgtcgctc cagcttcatc tacctttgcc actgctgttg tgaccactgt cgctcctgca  900
gtaactgatg tcgtgactgt caccgatgta gttaccgtga ccaccgtcat caccactact  960
gtcctttaa                                                           969

SEQ ID NO: 40        moltype = AA  length = 322
FEATURE              Location/Qualifiers
source               1..322
                     mol_type = protein
                     organism = Penicillium pinophilum
SEQUENCE: 40
MPSTKVAALS AVLALASTVA GHGFVQNIVI DGKSYSGYLV NQFPYESNPP AVIGWATTAT   60
DLGFVAPSEY TNADIICHKN ATPGALSAPV AAGGTVELQW TTWPDSHHGP VISYLANCNG  120
NCSTVDKTKL DFVKIDQGGL IDDTTPPGTW ASDKLIAANN SWTVTIPSTI APGNYVLRHE  180
IIALHSAGNA DGAQNYPQCI NLEITGSGTA APSGTAGEKL YTSTDPGILV NIYQSLSTYV  240
IPGPTLWSGA ANGAVATGSA TAVATTATAS ATATPTTLVT SVAPASSTFA TAVVTTVAPA  300
VTDVVTVTDV VTVTTVITTT VL                                           322

SEQ ID NO: 41        moltype = DNA  length = 835
FEATURE              Location/Qualifiers
source               1..835
                     mol_type = genomic DNA
                     organism = Penicillium sp.
SEQUENCE: 41
atgctgtctt cgacgactcg caccctcgcc tttacaggcc ttgcgggcct tctgtccgct   60
ccctggtca aggcccatgg ctttgtccag ggcattgtca tcggtgacca attgtaagtc  120
cctctcttgc agttctgtcg attaactgct ggactgcttg tcggtgactcc tgctgactcc  180
caacagctac agcgggtaca tcgtcaactc gttcccctac gaatccaacc cacccccgt   240
catcggctgg gccacgaccg ccaccgacct gggcttcgtc gacggcacag gataccaagg  300
cccggacatc atctgccacc ggaatgcgac gcccgcgccg ctgacagccc ccgtggccgc  360
cggcgtgacc gtcgagctgc agtggacgcc gtggccggac agccaccacg gacccgtcat  420
cacctacctg cgccgtgca acggcaactg ctcgaccgtc gacaagacga cgctggagtt  480
cttcaagatc gaccagcagg gcctgatcga cgacacgagc ccgccgggca cctgggcgtc  540
ggacaacctc atcgccaaca caatagctg accgtcacc attcccaaca gcgtcgcccc  600
cggcaactac gtcctgcgcc acgagatcat cgccctgcac tcggccaaca acaaggacgg  660
cgcccagaac taccccagt gcatcaacat cgaggtcacg ggcggcggct ccgacgcgcc  720
tgagggtact ctgggcgagg atctctacca tgacaccgac ccgggcattc tggtcgacat  780
ttacgagccc attgcgacgt ataccattcc ggggccgcct gagccgacgt tctag      835

SEQ ID NO: 42        moltype = AA  length = 253
FEATURE              Location/Qualifiers
source               1..253
                     mol_type = protein
                     organism = Penicillium sp.
SEQUENCE: 42
MLSSTTRTLA FTGLAGLLSA PLVKAHGFVQ GIVIGDQFYS GYIVNSFPYE SNPPPVIGWA   60
TTATDLGFVD GTGYQGPDII CHRNATPAPL TAPVAAGGTV ELQWTPWPDS HHGPVITYLA  120
PCNGNCSTVD KTTLEFFKID QQGLIDDTSP PGTWASDNLI ANNNSWTVTI PNSVAPGNYV  180
LRHEIIALHS ANNKDGAQNY PQCINIEVTG GGSDAPEGTL GEDLYHDTDP GILVDIYEPI  240
ATYTIPGPPE PTF                                                     253

SEQ ID NO: 43        moltype = DNA  length = 1107
FEATURE              Location/Qualifiers
source               1..1107
                     mol_type = genomic DNA
                     organism = Thielavia terrestris
SEQUENCE: 43
atgccttctt tcgcctccaa gactctcctt tccaccctgg cgggtgccgc atccgtggcc   60
gcccacgggc acgtgtcgaa catcgtcatc aacggggtct cgtaccaggg ttacgatccg  120
acctccttcc cttacatgca gaaccgcccc atcgtggtcg gctggactgc cgccgacaac  180
gacaacggct ttgttgcccc ggatgccttc gccagtggcg atatcatctg ccacaagaac  240
gccaccaacg ccaagggcca cgccgtggtc gccgcgggag acaagatctt catccagtgg  300
aacacatggc ccgagtccca ccacggcccc gtcatcgact cctcgccgag ctgcggcagc  360
gcgtcctgcg agaccgtcga caagaccaag ctcgagttct tcaagatcga cgaggtcggc  420
ctggtcgacg gcagctcggc gccggtgtgt ggggctccg accagctcat cgccaacaac  480
aactggactg tcgtcgagat cccgcccacc atgcgcgcag cgaactgcgc cctggcgtgc  540
gagatcatcg cgctgcacag cgccgaaaac gccgacgggc cccagaacta ccgcagtgc  600
ttcaacctgc agatcaccgg caccggcacc gccaccccct ccggcgtccc ggcacctcg  660
ctctacaccc cgaccgaccc gggcatcctc gtcaacatct acagcgcccc gatcacctac  720
accgtcccgg ggccggccct catctccggc gccgtcagca tcgcccagtc ctcctccgcc  780
atcaccgcct ccggcaccgc cctgaccggc tctgccaccg cacccgccgc cgccgctgct  840
```

```
accacaactt ccaccaccaa cgccgcggct gctgctacct ctgctgctgc tgctgctggt   900
acttccacaa ccaccaccag cgccgcggcc gtggtccaga cctcctcctc ctcctcctcc   960
gccccgtcct ctgccgccgc cgccgccacc accaccgcgg ctgccagcgc ccgcccgacc  1020
ggctgctcct ctgccgcctc caggaagcag ccgcgccgcc acgcgcggga tatggtggtt  1080
gcgcgagggg ctgaggaggc aaactga                                      1107
```

```
SEQ ID NO: 44           moltype = AA   length = 368
FEATURE                 Location/Qualifiers
source                  1..368
                        mol_type = protein
                        organism = Thielavia terrestris
SEQUENCE: 44
MPSFASKTLL STLAGAASVA AHGHVSNIVI NGVSYQGYDP TSFPYMQNPP IVVGWTAADT    60
DNGFVAPDAF ASGDIICHKN ATNAKGHAVV AAGDKIFIQW NTWPESHHGP VIDYLASCGS   120
ASCETVDKTK LEFFKIDEVG LVDGSSAPGV WGSDQLIANN NSWLVEIPPT IAPGNYVLRH   180
EIIALHSAEN ADGAQNYPQC FNLQITGTGT ATPSGVPGTS LYTPTDPGIL VNIYSAPITY   240
TVPGPALISG AVSIAQSSSA ITASGTALTG SATAPAAAAA TTTSTTNAAA AATSAAAAAG   300
TSTTTTSAAA VVQTSSSSSS APSSAAAAAT TTAAASARPT GCSSGRSRKQ PRRHARDMVV   360
ARGAEEAN                                                           368

SEQ ID NO: 45           moltype = DNA   length = 1327
FEATURE                 Location/Qualifiers
source                  1..1327
                        mol_type = genomic DNA
                        organism = Aspergillus aculeatus
SEQUENCE: 45
aaaatggtcg gactgctttc aatcaccgcg gcgcttgccg cgactgtgtt gccaaacatt    60
gtctctgccg ttggtctgga tcaggctgca gttgccaaag gacttcaata ctttggcaca   120
gctacggata atcccgagct cacgcagata ccatacgtta ctcagctgaa caacaccgcg   180
gactttggtc aaattacccc tggaaactcg atgaagtggg ctgaccagag accatctcag   240
ggcaccttca cgttcacgaa aggcgatgtc attgcagatc tggctgaggg taatggcaaa   300
tatctccgat gtcatactct ggtttggtat aatcagctac ctagctgggt gactagcgga   360
acttggacta tgctactcct caccgccgca ttgaagaacc acatcacgaa tgtggtgtcg   420
cactacaaag ggaaatgtct tcattgggac gtggtcaatg aggcgttgaa tgacgacggg   480
acctaccgca ccaacatctt ctacaccacc atcggcgaag cctacatccc cattgccttt   540
gccgcagcgg ctgcagccga cccggacgcg aagctgttct acaatgacta caacctcgaa   600
tacggcggcg ccaaagccgc cagcgcccgc gccattgtcc agctggtcaa gaatgcaggt   660
gccaagatcg acggggtagg gttgcaggcc catttcagcg tcggcaccgt gccgagtacg   720
agctcgctcg tctcggtgct gcaatctttc actgcgctcg gggtcgaggt cgcctacacg   780
gaggccgacg tgcgcattct cctgcccacc accgccacta ccctggccca acagtcgagc   840
gatttccagg ccctggtgca atcctgtgtg cagacaacgg gctgcgtcgg cttcactatc   900
tgggattgga cagataagta cagctgggtt cccagcacgt tctcgggcta tggggcggcg   960
ctaccctggg atgagaacct ggttaagaag cccgcgtaca atggcttgtt ggccggcatg  1020
ggggttacag ttaccactac gactaccacc accactgcta ctgccactgg taagactacg  1080
actaccacaa cgggtgccac gagcacgggg actacggctg cgcattgggg cagtgtgga   1140
gggctcaact ggagtggacc gacggcgtgt gccactgggt acacctgcac ttatgtcaat  1200
gactattact cgcagtgtct gtgaagtata gcccaaccta aacctgccgg cgtgcttgcc  1260
attcagtcag tgagatttat atatcacaat actcaaaatt cattgctcga cctctgaaaa  1320
aaaaaaa                                                            1327
```

```
SEQ ID NO: 46           moltype = AA   length = 407
FEATURE                 Location/Qualifiers
source                  1..407
                        mol_type = protein
                        organism = Aspergillus aculeatus
SEQUENCE: 46
KMVGLLSITA ALAATVLPNI VSAVGLDQAA VAKGLQYFGT ATDNPELTDI PYVTQLNNTA    60
DFGQITPGNS MKWDATEPSQ GTFTFTKGDV IADLAEGNGQ YLRCHTLVWY NQLPSWVTSG   120
TWTNATLTAA LKNHITNVVS HYKGKCLHWD VVNEALNDDG TYRTNIFYTT IGEAYIPIAF   180
AAAAADPDA KLFYNDYNLE YGGAKAASAR AIVQLVKNAG AKIDGVGLQA HFSVGTVPST   240
SSLVSVLQSF TALGVEVAYT EADVRILLPT TATTLAQQSS DFQALVQSCV QTTGCVGFTI   300
WDWTDKYSWV PSTFSGYGAA LPWDENLVKK PAYNGLLAGM GVTVTTTTTT TTATATGKTT   360
TTTTGATSTG TTAAHWGQCG GLNWSGPTAC ATGYTCTYVN DYYSQCL               407

SEQ ID NO: 47           moltype = DNA   length = 1415
FEATURE                 Location/Qualifiers
source                  1..1415
                        mol_type = genomic DNA
                        organism = Aspergillus fumigatus
SEQUENCE: 47
atggtccatc tatcttcatt ggcagcagcc ctggctgctc tgcctctgta tgtttaccca    60
ctcacgagag gaggaacagc tttgacattg ctatagtgta tatggagctg gcctgaacac   120
agcagccaaa gccaaaggac taaagtactt tggttccgcc acggacaatc agagctcac   180
ggactgtgcg tatgtcgcgc aactgagcaa caccgatgat tttggtcaaa tcacacccag   240
aaactccatg aaggtttgct tacgtctgcc tccctggagc attggcctcaa agctaattg   300
gttgttttgt ttggatagtg ggatgccacc gagccttctc agaattcttt ttcgttcgca   360
aatggagacg ccgtggtcaa tctgcgaac aagaatggcc agctgatgcg atgccatact   420
ctggtctggc acagtcagct accgaactgg ggtatgtaaa cgtcttgtct attctcaaat   480
actctctaac agttgacagt ctctagcggg tcatggacca atgcgaccct tttggcggcc   540
```

```
atgaagaatc atatcaccaa tgtggttact cactacaagg ggaagtgcta cgcctgggat    600
gttgtcaatg aaggtttgtt gctccatcta tcctcaatag ttcttttgaa actgacaagc    660
ctgtcaatct agccctgaac gaggacggta cttteegtaa ctctgtcttc taccagatca    720
tcggcccage atacattcet attgcgttcg ccacggctgc tgccgcagat cccgacgtga    780
aactctacta caacgactac aacattgaat actcaggcga caaagcgact gctgcgcaga    840
atatcgtcaa gatgatcaag gcctacggcg cgaagatcga cggcgtcggc ctccaggcac    900
actttatcgt cggcagcact ccgagtcaat cggatctgac gaccgtcttg aagggctaca    960
ctgctctcgg cgttgaggtg gcctataccg aacttgacat ccgcatgcag ctgccctcga   1020
ccgccgcaaa gctggcccag cagtccactg acttccaagg cgtggccgca gcatgcgtta   1080
gcaccactgg ctgcgtgggt gtcactatct gggactgaac cgacaagtac tcctgggtcc   1140
ccagcgtgtt ccaaggctac ggcgcccat tgccttggga tgagaactat gtgaagaagc   1200
cagcgtacga tggcctgatg gcgggtcttg gagcaagcgg ctccggcacc acaacgacca   1260
ctactactac ttctactacg acaggaggta cggaccctac tggagtcgct cagaaatggg   1320
gacagtgtgg cggtattggc tggaccgggc caacaacttg tgtcagtggt accacttgcc   1380
aaaagctgaa tgactggtac tcacagtgcc tgtaa                              1415

SEQ ID NO: 48           moltype = AA length = 397
FEATURE                 Location/Qualifiers
source                  1..397
                        mol_type = protein
                        organism = Aspergillus fumigatus
SEQUENCE: 48
MVHLSSLAAA LAALPLVYGA GLNTAAKAKG LKYFGSATDN PELTDSAYVA QLSNTDDFGQ    60
ITPGNSMKWD ATEPSQNSFS FANGDAVVNL ANKNGQLMRC HTLVWHSQLP NWVSSGSWTN   120
ATLLAAMKNH ITNVVTHYKG KCYAWDVVNE ALNEDGTFRN SVFYQIIGPA YIPIAFATAA   180
AADPDVKLYY NDYNIEYSGA KATAAQNIVK MIKAYGAKID GVGLQAHFIV GSTPSQSDLT   240
TVLKGYTALG VEVAYTELDI RMQLPSTAAK LAQQSTDFQG VAAACVSTTG CVGVTIWDWT   300
DKYSWVPSVF QGYGAPLPWD ENYVKKPAYD GLMAGLGASG SGTTTTTTTT STTTGGTDPT   360
GVAQKWGQCG GIGWTGPTTC VSGTTCQKLN DWYSQCL                            397

SEQ ID NO: 49           moltype = DNA length = 1197
FEATURE                 Location/Qualifiers
source                  1..1197
                        mol_type = genomic DNA
                        organism = Trichophaea saccata
SEQUENCE: 49
atgcgtacct tctcgtctct tctcggtgtt gcccttctct tgggtgcagc taatgcccag    60
gtcgcggttt ggggacagtg tggtggcatt ggttactctg gctcgacaac ctgcgctgcg   120
ggaacgactt gtgttaagct gaacgactac tactcccaat gccaaccegg cggtaccact   180
ttgacaacca ccaccaaacc cgccaccact accactacca ccacggcaac ttctccctca   240
tcttctcccg gattaaatgc cctggcacaa agagcggcc ggtacttegg tagtgcaact   300
gacaacccag agctctccga tgcggcatac attgccatce tgagcaacaa aaacgagttt   360
gggatcatca cgcctggaaa ctcgatgaaa tgggatgcta ctgaaccgtc ccgcgggagt   420
ttctcgttca ctggtggaca gcaaattgtt gattttgcgc agggcaatgg gcaggctatc   480
agaggccata ctcttgtctg gtactcccag ttgccgtcct gggttactag cggaaacttc   540
gataaagcta cattgacatc gatcatgcaa atcacatta caactcttgt cagccactgg   600
aagggccage tcgcctactg ggatgttgtc aacgaagcat tcaacgatga tggcactttc   660
cgtcaaaacg tgttctacac aaccattgga gaggactaca tccagctcgc cttcgaagcc   720
gccegtgccg ccgaccccgac cgcaaagctc tgcatcaacg actacaacat cgagggcact   780
ggagccaagt caacagccat gtacaatctc gtctcgaagc tgaaatccgc cggcgttccc   840
atcgactgta ttggtgttca gggacacctc atcgtcgtg aagttcccac caccatccaa   900
gcaaaccttg cccagtttgc gtctttgggt gtggatgtcg cgatcacgga gctagatatc   960
agaatgacgc tgccatctac gactgcattg ctccagcagc aggctaagga ttacgtctcg   1020
gttgttacag cctgcatgaa tgttcccagg tgtatcggta tcaccatctg ggactacact  1080
gataaatact cttgggtgcc acaaaccttc agccggcagg gcgatgcttg cccatgggat  1140
gccaacctgc agaagaagcc agcctactcc gctattgcgt ctgctcttgc ggcttga     1197

SEQ ID NO: 50           moltype = AA length = 398
FEATURE                 Location/Qualifiers
source                  1..398
                        mol_type = protein
                        organism = Trichophaea saccata
SEQUENCE: 50
MRTFSSLLGV ALLLGAANAQ VAVWGQCGGI GYSGSTTCAA GTTCVKLNDY YSQCQPGGTT    60
LTTTTKPATT TTTTTATSPS SSPGLNALAQ KSGRYFGSAT DNPELSDAAY IAILSNKNEF   120
GIITPGNSMK WDATEPSRGS FSFTGGQQIV DFAQGNGQAI RGHTLVWYSQ LPSWVTSGNF   180
DKATLTSIMQ NHITTLVSHW KGQLAYWDVV NEAFNDDGTF RQNVFYTTIG EDYIQLAFEA   240
ARAADPTAKL CINDYNIEGT GAKSTAMYNL VSKLKSAGVP IDCIGVQGHL IVGEVPTTIQ   300
ANLAQFASLG VDVAITELDI RMTLPSTTAL LQQQAKDYVS VVTACMNVPR CIGITIWDYT   360
DKYSWVPQTF SGQGDACPWD ANLQKKPAYS AIASALAA                           398

SEQ ID NO: 51           moltype = DNA length = 1440
FEATURE                 Location/Qualifiers
source                  1..1440
                        mol_type = genomic DNA
                        organism = Penicillium pinophilum
SEQUENCE: 51
atgactctag taaaggctat tctttttagcg cttgctgtgg ccacgttgc ccaggcccaa     60
ttgaacacgg ccgcaaaagc agctggtcta ttgtactttg gtactgcggt tgacaatcca   120
```

```
gacttgagcg actccaaata tattgcaaac cttgagactg cggatttcgg tcagatcacg    180
ccagcaaatg caatgaaagt cagtggccaa tcactactgt atacaaccag ctaagtgatg    240
acaatttagt ggcaacccac cgagccgtct caaggctctt atactttcac tcagggtgac    300
cagattgcga gcctggccaa gtctaataat gactacttga gatgccacaa tctggtctgg    360
tacaaccagt tgccatcata cggtaagcaa gcatacgacc tccatgaatt gtcatccaac    420
atccacgata gcaagctgat acggtatctg tctagttact tcgggttcat ggacaaacgc    480
aaccctatt gctgccttga aggagcatat caatggagtt gtcacgcatt acaagggaca    540
atgctacgcg tgggatgttg taaacgaagg tatgcgatat tatatacagg cccttttctct   600
gcatccttac atcttttta tctccattct acgtaatcgt gtcgagctaa gtgaagtatc    660
tagccttgaa cgaagacggc acctatcgtc aaaatgtttt ctaccaatat ataggcgagg    720
catacattcc aattgcgttt gctgccgctg cagccgcgga ccctaatgcc aagttgtact    780
acaacgacta caacatcgaa tacgctgggt caaaggcaac tggtgctcag cgcattgtaa    840
aattaattca agctgctggt ggtcgtatcg atggcgtggg tcttcagtct cacttcattg    900
tgggacaaac ccctagtctt gctactcaga aagcaaacat ggctgctttt actgctctcg    960
gtgttgatgt tgccattact gagcttgaca ttcgtatgac tctcccggat accagcgctc   1020
ttcaaactca gcagtccacc gactaccaga ccaccactac tgcctgcgtc cagactaaag   1080
gctgtgttgg tatcacgcta tgggattaca cagacaagta ctcatgggtt cccggtacct   1140
tctctggcca gggtgatgct tgtccatggg actcaaatta caacaagaag ccggcatact   1200
atggtatcct tgctggctta caatctggca ctggttcttc atcgtcaact tctagcacca   1260
ccctaacaac caccacaaca cccactaccg cttcaagtac tacgtcaacg actagcacaa   1320
gcgctaccct caggtgctgca cactgggac aatgcgagg cattggctgg tctggtccta    1380
ccatttgtgt ttcgccctac acttgtcaag tgttgaaccc atactactcc caatgtttgt    1440

SEQ ID NO: 52           moltype = AA  length = 407
FEATURE                 Location/Qualifiers
source                  1..407
                        mol_type = protein
                        organism = Penicillium pinophilum
SEQUENCE: 52
MTLVKAILLA LAVGHVAQAQ LNTAAKAAGL LYFGTAVDNP LSDSKYIAN LETADFGQIT    60
PANAMKWQPT EPSQGSYTFT QGDQIASLAK SNNDYLRCHN LVWYNQLPSY VTSGSWTNAT   120
LIAALKEHIN GVVTHYKGQC YAWDVVNEAL NEDGTYRQNV FYQYIGEAYI PIAFAAAAAA   180
DPNAKLYYND YNIEYAGSKA TGAQRIVKLI QAAGGRIDGV GLQSHFIVGQ TPSLATQKAN   240
MAAFTALGVD VAITELDIRM TLPDTSALQT QQSTDYQTTT TACVQTKGCV GITLWDYTDK   300
YSWVPGTFSG QGDACPWDSN YNKKPAYYGI LAGLQSGTGS SSSTSSTTLT TTTTPTTASS   360
TTSTTSTSAT SGAAHWGQCG GIGWSGPTIC VSPYTCQVLN PYYSQCL               407

SEQ ID NO: 53           moltype = DNA  length = 1188
FEATURE                 Location/Qualifiers
source                  1..1188
                        mol_type = genomic DNA
                        organism = Thielavia terrestris
SEQUENCE: 53
atggccctca aatcgctcct gttgacctcg ctggcaacgg ccggccttgt ggtcgccgat     60
ggcctcaacg tccgggctaa ggcgctgggc aagaagtatt ttggcactga gatcagcacg   120
accgtcatga cgacgcgaa cgccaacaac atcgccaaga actcgcagga cttcggccag   180
tacacatgcg agaacgagat gaagttcgac gcgctcgaga cgtcccgcgg caccttcaac   240
tacgccaatg cggaccggat agtggcccag gcgcaagcca acggcatgct catgcgctgc   300
cacaacctgc tctggcacaa ccaagtgccg tcgtgggtga ccaatggcca cttcgacaac   360
gcgacgctga tcagcatcat gaagaaccac atcgccaact ggtgggcca ctacaagggc   420
aagtgctacg cctgggatgt ggtcaacgag gccctgaacg aggacggcac gtaccgcacg   480
tcgggctccg tctggggctc gaccatcggc ccggcctaca tcccgatcgc cttcgcggcc   540
gcggcggagg ccgacccaga cgcgaagctc tactacaacg actacaactg cgaccgcgct   600
ggcgccaagg ccacgggcgc gcagaacctg atcaagatgg tcaagcagta cggcgcgccc   660
atccacggct tcggcatgca gggccacctg acgacggcag ggtgggctc ggcgtcgcag   720
tacgtgagca acatgcaggc gttcgcggcc ctcggcgtcg aggtggcctt cacggagctg   780
gacatcgcga cgccgtccag caaccccaac ttccagcagc aggcgaccga ctacgcgacc   840
atcgtgtcgg cgtgcaagca ggtcgacgcc tgcgtcggaa tcaccacctg ggcttcacc    900
gacaaataca cctggatcag caactccgac ccgctgccct gggactccaa cctgcagaag   960
aagccggcgt acaccgcgat cctgaacgcc tggggctcgt cgccgccgcc ttcgacgacg   1020
acgaccacgg ccgcgacgac cacaacgccg ccgagcgggg gtggcggcaa cggatgcacc   1080
gcgccgcact gggcccagtg cggtggcatc ggctactcgg gctgcaccac ctgcgaggct   1140
ccctacacgt gcaagtactc caacgactgg tactctcagt gcttgtaa                1188

SEQ ID NO: 54           moltype = AA  length = 395
FEATURE                 Location/Qualifiers
source                  1..395
                        mol_type = protein
                        organism = Thielavia terrestris
SEQUENCE: 54
MALKSLLLTS LATAGLVVAD GLNVRAKAAG KKYFGTEIST TVMNDANANN IAKNSQDFGQ    60
YTCENEMKFD ALEPSRGTFN YANADRIVAQ AQANGMLMRC HNLVWHNQVP SWVTNGHFDN   120
ATLISIMKNH IANVVGHYKG KCYAWDVVNE ALNEDGTYRT SGSVWGSTIG PAYIPIAFAA   180
AAEADPDAKL YYNDYNCDRA GAKATGAQNL IKMVKQYGAP IHGFGMQGHL TTGQVGSASQ   240
YVSNMQAFAA LGVEVAFTEL DIATPSSNPN FQQQATDYAT IVSACKQVDA CVGITTWGFT   300
DKYTWISNSD PLPWDSNLQK KPAYTAILNA WGSSPPPSTT TTAATTTTP PSGGGGNGCT   360
APHWAQCGGI GYSGCTTCEA PYTCKYSNDW YSQCL                             395

SEQ ID NO: 55           moltype = DNA  length = 1038
```

```
FEATURE              Location/Qualifiers
source               1..1038
                     mol_type = genomic DNA
                     organism = Thermobifida fusca
SEQUENCE: 55
atgaaccatg cccccgccag tctgaagagc cggagacgct tccggcccag actgctcatc    60
ggcaaggcgt tcgccgcggc actcgtcgcg gtcgtcacga tgatcccag tactgccgcc    120
cacgcggcc tgacctccaa ccagaccggg taccacgacg gtacttcta ctcgttctgg     180
accgacgcgc ccggaacggt tccatggag ctgggccctg gcgaaaacta cagcacctcc    240
tggcggaaca ccgggaactt cgtcgccggt aagggatggg ccaccggtgg ccgccggacc   300
gtgacctact ccgccagctt caacccgtcg ggtaacggca acctgaccct ctacgggtgg   360
acgcggaacc cgctcgtgga gtactacatc gtcgaaagct ggggcaccta ccggcccacc   420
ggtacctaca tgggcacggt gaccaccgac ggtggtacct acgacatcta caagaccacg   480
cggtacaacg cgccctccat cgaaggcacc cggaccttcg accagtactg gagcgtccgc   540
cagtccaagc ggaccagcgg taccatcacc gcggggaacc acttcgacgc gtgggccgc    600
cacggtatgc acctcggaac ccacgactac atgatcatgg cgactgaggg ctaccagagc   660
agcggatcct ccaacgtgac gttgggcacc agcggcggtg gcaacccgg tggggcaac    720
ccccccggtg gcggcaaccc cctggtggc ggtggctgca cggcgacgct gtccgcggca    780
cagcagtgga acgaccgcta caacctcaac gtcaacgtca gcggctccaa caactggacc   840
gtgaccgtga acgttccgtg gccgcgagg atcatcgcca cctggaacat ccacgccagc    900
tacccggact cccagacctt ggttgccgg cctaacggca acggcaacaa ctggggcatg    960
acgatcatgc acaacggcaa ctggacgtgg cccacgtgt cctgcagcgc caaccatcag   1020
caccaacacc agcattag                                                 1038

SEQ ID NO: 56        moltype = AA  length = 345
FEATURE              Location/Qualifiers
source               1..345
                     mol_type = protein
                     organism = Thermobifida fusca
SEQUENCE: 56
MNHAPASLKS RRRFRPRLLI GKAFAAALVA VVTMIPSTAA HAAVTSNQTG YHDGYFYSFW     60
TDAPGTVSME LGPGGNYSTS WRNTGNFVAG KGWATGGRRT VTYSASFNPS GNAYLTLYGW    120
TRNPLVEYYI VESWGTYRPT GTYMGTVTTD GGTYDIYKTT RYNAPSIEGT RTFDQYWSVR    180
QSKRTSGTIT AGNHFDAWAR HGMHLGTHDY MIMATEGYQS SGSSNVTLGT SGGGNPGGGN    240
PPGGGNPPGG GGCTATLSAG QQWNDRYNLN VNVSGSNNWT VTVNVPWPAR IIATWNIHAS    300
YPDSQTLVAR PNGNGNNWGM TIMHNGNWTW PTVSCSANHQ HQHQH                    345

SEQ ID NO: 57        moltype = DNA  length = 2394
FEATURE              Location/Qualifiers
source               1..2394
                     mol_type = genomic DNA
                     organism = Trichoderma reesei
SEQUENCE: 57
atggtgaata acgcagctct tctcgccgcc ctgtcggctc tcctgcccac ggccctggcg    60
cagaacaatc aaacatacgc caactactct gctcagggcc agcctgatct ctaccccgag   120
acacttgcca cgctcacact ctcgttcccc gactgcgaac atggcccct caagaacaat    180
ctcgtctgtg actcatcggc cggctatgta gagcgagcc aggccctcat ctcgctcttc    240
accctcgagg agctcattct caacacgcaa aactcgggcc ccggcgtgcc tgcctgggt    300
cttccgaact accaagtctg gaatgaggct ctgcacggct tggaccgcgc caacttcgcc   360
accaaggggc gccagttcga atgggcgacc tcgttcccca tgcccatcct cactacggcg    420
gccctcaacc gcacattgat ccaccagatt gccgacatca tctcgaccca agctcgacga   480
ttcagcaaca gcggccgtta cggtctcgac gtctatgcgc caaacgtcaa tggcttccga   540
agccccctct ggggccgtgg ccaggagacg cccggcgaag acgcttttt cctcagctcc    600
gcctatactc acgagtacat cacgggcatc cagggtggcg tcgaccctga gcacctcaag   660
gttgccgcca cggtgaagca ctttgccgga tacgacctcg agaactggaa ccagcagtcc   720
cgtctcggtt tcgacgccat cataactcag caggacctct ccgaatacta cactcccag    780
ttcctcgctg cggcccgtta tgcaaagtca cgcagcttga tgtgcgcata caactccgtc   840
aacggcgtgc ccagctgtgc caacagcttc ttcctgcaga cgcttttgcg cgagagctgg   900
ggcttccccg aatggggata cgtctcgtcc gattcgatgc gtctctacaa cgttttcaac   960
cctcatgact acgccagcaa ccagtcgtca gccgccgcca gctcactgcg agccggcacc   1020
gatatcgact gcgtcagac ttaccgtgg cacctcaacg agtcctttgt ggccggcgaa   1080
gtctcccgcg gcagatcga gcggtccgtc accgtctgt acgccaacct cgtcgtctc    1140
ggatacttcg acaagaagaa ccagtaccgc tcgctcggtt ggaaggatgt cgtcaagact   1200
gatgcctgga acatccgta cgaggctgct gttgaaggac tcgtcctgct caagaacgat   1260
ggcactctcc ctctgtccaa gaaggtgcgc agcattgctc tgatcggacc atgggccaat   1320
gccacaaccc aaatgcaagg caactactat gggccgtgcc catacctcat cagccctctg   1380
gaagctgcta agaaggccgg ctatcacgtc aactttgaac tcggcacaga gatcgccggc   1440
aacagcacca tggctttgc caaggccatt gctgccgcca agaagtcgga tgccatcatc   1500
taccctcggtg gaattgacaa caccattgaa caggagggcg ctgaccgcac ggacattgct   1560
tggcccggta tcagctggga tctcatcaag cagctcagcg aggtcggcaa acccttgtc   1620
gtcctgcaaa tggcgtgg tcaggtagac tcatcctcgc tcaagagcaa caagaaggtc   1680
aactccctcg tctggggcgg atatcccggc cagtcgggag cgttgccct cttcgacatt   1740
ctctctggca gcgtgctcc tgccggccga ctggtcacca ctcagtaccc ggctgagtat   1800
gttcaccaat tcccccagaa tgacatgaac cggaaagtc aaaccctgga   1860
cagacttaca tctggtacac cggcaaaccc gtctacgagt ttggcagtgg tctcttctac   1920
accaccttca aggagactct cgccagccac ccaagagcc tcaagttcaa cacctcatcg   1980
atcctctctg ctcctcaccc cggatacact tacagcgagc agattccgt cttcaccttc   2040
gaggccaaca tcaagaactc gggcaagacg gagtcccat atacggccat gctgttgtt   2100
cgcacaagca acgctgggcc cagcccgtac ccgaacaagt ggctcgtcgg attcgaccga   2160
```

```
cttgccgaca tcaagcctgg tcactcttcc aagctcagca tccccatccc tgtcagtgct   2220
ctcgcccgtg ttgattctca cggaaaccgg attgtatacc ccggcaagta tgagctagcc   2280
ttgaacaccg acgagtctgt gaagcttgag tttgagttgg tgggagaaga ggtaacgatt   2340
gagaactggc cgttggagga gcaacagatc aaggatgcta cacctgacgc ataa         2394

SEQ ID NO: 58              moltype = AA    length = 797
FEATURE                    Location/Qualifiers
source                     1..797
                           mol_type = protein
                           organism = Trichoderma reesei
SEQUENCE: 58
MVNNAALLAA LSALLPTALA QNNQTYANYS AQGQPDLYPE TLATLTLSFP DCEHGPLKNN    60
LVCDSSAGYV ERAQALISLF TLEELILNTQ NSGPGVPRLG LPNYQVWNEA LHGLDRANFA   120
TKGGQFEWAT SFPMPILTTA ALNRTLIHQI ADIISTQARA FSNSGRYGLD VYAPNVNGFR   180
SPLWGRGQET PGEDAFFLSS AYTYEYITGI QGGVDPEHLK VAATVKHFAG YDLENWNNQS   240
RLGFDAIITQ QDLSEYYTPQ FLAAARYAKS RSLMCAYNSV NGVPSCANSF FLQTLLRESW   300
GFPEWGYVSS DCDAVYNVFN PHDYASNQSS AAASSLRAGT DIDCGQTYPW HLNESFVAGE   360
VSRGEIERSV TRLYANLVRL GYFDKKNQYR SLGWKDVVKT DAWNISYEAA VEGIVLLKND   420
GTLPLSKKVR SIALIGPWAN ATTQMQGNYY GPAPYLISPL EAAKKAGYHV NFELGTEIAG   480
NSTTGFAKAI AAAKKSDAII YLGGIDNTIE QEGADRTDIA WPGNQLDLIK QLSEVGKPLV   540
VLQMGGGQVD SSSLKSNKKV NSLVWGGYPG QSGGVALFDI LSGKRAPAGR LVTTQYPAEY   600
VHQFPQNDMN LRPDGKSNPG QTYIWYTGKP VYEFGSGLFY TTFKETLASH PKSLKFNTSS   660
ILSAPHPGYT YSEQIPVFTF EANIKNSGKT ESPYTAMLFV RTSNAGPAPY PNKWLVGFDR   720
LADIKPGHSS KLSIPIPVSA LARVDSHGNR IVYPGKYELA LNTDESVKLE FELVGEEVTI   780
ENWPLEEQQI KDATPDA                                                  797

SEQ ID NO: 59              moltype = DNA    length = 2388
FEATURE                    Location/Qualifiers
source                     1..2388
                           mol_type = genomic DNA
                           organism = Talaromyces emersonii
SEQUENCE: 59
atgatgactc ccacggcgat tctcaccgca gtggcggcgc tcctgcccac cgcgacatgg     60
gcacaggata accaaaccta tgccaattac tcgtcgcagt ctcagccgga cctgtttccc    120
cggaccgtcg cgaccatcga cctgtccttc cccgactgtg agaatggccc gctcagcacg    180
aacctggtgt gcaacaaatc ggccgatccc tgggcccgag ctgaggccct catctcgctc    240
tttaccctcg aagagctgat taacaacacc cagaacaccg ctcctggcgt gccccgtttg    300
ggtctgcccc agtatcaggt gtggaatgaa gctctgcacg gactggaccg cgccaatttc    360
tcccattcgg gcgaatacag ctgggccacg tccttcccca tgcccatcct gtcgatggcg    420
tccttcaacc ggaccctcat caaccagatt gcctccatca ttgcaacgca agcccgtgcc    480
ttcaacaacg ccggccgtta cggccttgac agctatgcgc ccaacatcaa tggcttccgc    540
agtcccctct ggggccgtgg acaggagacg cctggtgagg atgcgttctt cttgagttcc    600
acctatgcgt acgagtacat cacaggcctg cagggcgtg tgaccccaga gcatgtcaag    660
atcgtcgcga cggcgaagca cttcgccggc tatgatctgg agaactgggg caacgtctct    720
cggctggggt tcaatgctat catcacgcag caggatctct ccgagtacta caccccctcag   780
ttcctggcgt ctgctcgata cgccaagacg cgcagcatca tgtgctccta caatgcagtg    840
aatggagtcc caagctgtgc caactccttc ttcctccaga cgcttctccg agaaaacttt    900
gacttcgttg acgacgggta cgtctcgtcg gattgcgacg ccgtctacaa cgtcttcaac    960
ccacacggtt acgcccttaa ccagtcggga gccgctgcgg actcgctcct agcaggtacc   1020
gatatcgact gtggtcagac cttgccgtgg cacctgaatg agtccttcgt agaaggatac   1080
gtctcccgcg gtgagatcga gaaatccctc accgtctct actcaaacct ggtgcgtctc   1140
ggctactttg acggcaacaa cagcgagtac cgcaacctca actgaacga cgtcgtgact   1200
acggacgcct ggaacatctc gtacgaggcc gcggtggaag gtatcaccct gctcaagaac   1260
gacgaacgc tgccgctgtc caagaaggtc cgcagcattg cgtcatcgg tccttgggcc   1320
aatgccacgg tgcagatgca gggtaactac tatggaacgc caccgtatct gatcagtccg   1380
ctggaagccg ccaaggccag tgggttcacg gtcaactatg cattcggtac caacatctcg   1440
accgattcta cccagtggtt cgcggaagcc atcgcggcag actgaaagtc ggacgtgatg   1500
atctacgccg gtggtattga caacacgatc gaggcagagg gacaggaccg cacggatctc   1560
aagtggccgg ggaaccagct ggatctgatc gagcagctca gccaggtggg caagcccttg   1620
gtcgtcctgc agatgggcgg tggccaggtg gattcgtcgt cactcaaggc caacaagaat   1680
gtcaacgctc tggtgtgggg tggctatccc ggacagtcgg gtggtgcggc cctgtttgac   1740
atccttacgg gcaagcgtgc gccggccgct cgtctggtga gcacgcagta cccggccaag   1800
tatgcgacgc agttcccggc caacgacatg aacctggtc cgaacggcag caacccggga   1860
cagacataca tctggtacac gggcacgccc gtgtatgagt tcggccacgg tctgttctac   1920
acggagttcc aggagtcggc tgcggcgggc acgaacaaga cgtcgacttt cgacattctg   1980
gacctttctc ccaccctca tccgggatac gagtacatcg agcaggttcc gttcatcaac   2040
gtgactgtgg acgtgaagaa cgtcggccac acgccatcgc cgtacgcggg tctgttgttc   2100
gcgaacacga cagccggccc caagccgtac ccgaacaaat gctcgtcg gttcgactgg   2160
ctgccgacga tccagccggg cgagactgcc aagttgacga tcccggtgcc gttgggcgcg   2220
attgcgtggg cggacgagaa cggcaacaag gtggtcttcc cggcaacta cgaattggca   2280
ctgaacaatg agcgatcggt agtggtgtcg ttcacgctga cgggcgatgc ggcgactcta   2340
gagaaatggc ctttgtggga gcaggcggtt ccggggggtgc tgcagcaa              2388

SEQ ID NO: 60              moltype = AA    length = 796
FEATURE                    Location/Qualifiers
source                     1..796
                           mol_type = protein
                           organism = Talaromyces emersonii
```

```
SEQUENCE: 60
MMTPTAILTA VAALLPTATW AQDNQTYANY SSQSQPDLFP RTVATIDLSF PDCENGPLST    60
NLVCNKSADP WARAEALISL FTLEELINNT QNTAPGVPRL GLPQYQVWNE ALHGLDRANF   120
SHSGEYSWAT SFPMPILSMA SFNRTLINQI ASIIATQARA FNNAGRYGLD SYAPNINGFR   180
SPLWGRGQET PGEDAFFLSS TYAYEYITGL QGGVDPEHVK IVATAKHFAG YDLENWGNVS   240
RLGFNAIITQ QDLSEYYTPQ FLASARYAKT RSIMCSYNAV NGVPSCANSF FLQTLLRENF   300
DFVDDGYVSS DCDAVYNVFN PHGYALNQSG AAADSLLAGT DIDCGQTLPW HLNESFVEGY   360
VSRGDIEKSL TRLYSNLVRL GYFDNNSEY RNLNWNDVVT TDAWNISYEA AVEGITLLKN    420
DGTLPLSKKV RSIALIGPWA NATVQMQGNY YGTPPYLISP LEAAKASGFT VNYAFGTNIS   480
TDSTQWFAEA IAAAKKSDVI IYAGGIDNTI EAEGQDRTDL KWPGNQLDLI EQLSQVGKPL   540
VVLQMGGGQV DSSSLKANKN VNALVWGGYP GQSSGGAALFD ILTGKRAPAG RLVSTQYPAE  600
YATQFPANDM NLRPNGSNPG QTYIWYTGTP VYEFGHGLFY TEFQESAAAG TNKTSTFDIL   660
DLFSTPHPGY EYIEQVPFIN VTVDVKNVGH TPSPYTGLLF ANTTAGPKPY PNKWLVGFDW   720
LPTIQPGETA KLTIPVPLGA IAWADENGNK VVFPGNYELA LNNERSVVVS FTLTGDAATL   780
EKWPLWEQAV PGVLQQ                                                  796

SEQ ID NO: 61           moltype = DNA  length = 1380
FEATURE                 Location/Qualifiers
source                  1..1380
                        mol_type = genomic DNA
                        organism = Trichoderma reesei
SEQUENCE: 61
atggcgccct cagttacact gccgttgacc acggccatcc tggccattgc ccggctcgtc    60
gccgccagc aacgggtac cagcaccccc gaggtccatc ccaagttgac aacctacaag    120
tgtacaaagt ccgggggtg cgtggcccag gacacctcgg tggtccttga ctggaactac   180
cgctggatgc acgacgcaaa ctacaactcg tgcaccgtca acggcggcgt caacaccacg   240
ctctgccctg acgaggcgac ctgtggcaag aactgcttca tcgagggcgt cgactacgcg   300
gcctcgggcg tcacgacctc gggcagcagc ctcaccatga accagtacat gcccagcagc   360
tctggcggct acagcagcgt ctcctccgg ctgtatctcc tggactctga cggtgagtac    420
gtgatgctga agctcaacgg ccaggagctg agcttcgacg tcgacctctc tgctctgccg   480
tgtggagaga acggctcgct ctacctgtct cagatggacg agaacgggg cgccaaccag    540
tataacacgg ccggtgccaa ctacgggagc ggctactgcg atgctcagtg ccccgtccag   600
acatggagga acggcaccct caacactagc accagggct tctgctgcaa cgagatggat    660
atcctggagg gcaactcgag ggcgaatgcc ttgaccctc actcttgcac ggccacggcc   720
tgcgactctg ccggttgcgg cttcaacccc tatggcagcg gctacaaaag ctactacggc   780
cccggagata ccgttgacac ctccaagacc ttcaccatca tcacccagtt caacacggac   840
aacggctcgc cctcgggcaa ccttgtgagc atcacccgca agtaccagca aacggcgtc    900
gacatcccca gcgcccagcc cggcggcgac accatctcgt cctgcccgtc cgcctcagcc   960
tacggcggc tcgccaccat gggcaaggcc ctgagcagcg gcatggtgct cgtgttcagc   1020
atttggaacg acaacagcca gtacatgaac tggctcgaca gcggcaacgc cggcccctgc  1080
agcagcaccg agggcaaccc atccaacatc ctggccaaca accccaacac gcacgtcgtc  1140
ttctccaaca tccgctgggg agacattggg tctactacga actcgactgc gccccgccc   1200
ccgcctgcgt ccagcacgac gttttcgact acacggagga gctcgaacgc ttcgagcagc  1260
ccgagctgca cgcagactca ctgggggcag tgcggtggca ttgggtacag cgggtgcaag  1320
acgtgcacgt cgggcactac gtgccagtat agcaacgact actactcgca atgcctttag  1380

SEQ ID NO: 62           moltype = AA  length = 459
FEATURE                 Location/Qualifiers
source                  1..459
                        mol_type = protein
                        organism = Trichoderma reesei
SEQUENCE: 62
MAPSVTLPLT TAILAIARLV AAQQPGTSTP EVHPKLTTYK CTKSGGCVAQ DTSVVLDWNY    60
RWMHDANYNS CTVNGGVNTT LCPDEATCGK NCFIEGVDYA ASGVTTSGSS LTMNQYMPSS   120
SGGYSSVSPR LYLLDSDGEY VMLKLNGQEL SFDVDLSALP CGENGSLYLS QMDENGGANQ   180
YNTAGANYGS GYCDAQCPVQ TWRNGTLNTS HQGFCCNEMD ILEGNSRANA LTPHSCTATA   240
CDSAGCGFNP YGSGYKSYYG PGDTVDTSKT FTIITQFNTD NGSPSGNLVS ITRKYQQNGV   300
DIPSAQPGGD TISSCPSASA YGGLATMGKA LSSGMVLVFS IWNDNSQYMN WLDSGNAGPC   360
SSTEGNPSNI LANNPNTHVV FSNIRWGDIG STTNSTAPPP PPASSTTFST TRRSSTTSSS   420
PSCTQTHWGQ CGGIGYSGCK TCTSGTTCQY SNDYYSQCL                         459

SEQ ID NO: 63           moltype = DNA  length = 1545
FEATURE                 Location/Qualifiers
source                  1..1545
                        mol_type = genomic DNA
                        organism = Trichoderma reesei
SEQUENCE: 63
atgtatcgga agttggccgt catctcggcc ttcttggcca cagctcgtgc tcagtcggcc    60
tgcactctcc aatcggagac tcacccgcct ctgacatggc agaaatgctc gtctggtggc   120
acgtgcactc aacagacagg ctccgtggtc atcgacgcca actggcgctg gactcacgct   180
acgaacagca gcacgaactg ctacgatggc aacacttgga gctcgaccct atgtcctgac   240
aacgagacct gcgcgaagaa ctgctgtctg acggtgccg cctacgcgtc cacgtacgga   300
gttaccacga gcggtaacag cctctccatt ggctttgtca cccagtctgc gcagaagaac   360
gttggcgtc gcctttacct tatggcgagc gacacgacct accaggaatt caccccgctt   420
ggcaacgagt tctcctttcga tgttgatgtt tcgcagctgc cgtcgcggctt gaacggagct   480
ctctacttcg tgtccatgga cgcggatggt ggcgtgagca agtatcccac caacaccgct   540
ggcgccaagt acggcacggg gtactgtgac agccagtgtc ccgcgatctc gaagttcatc   600
aatggccagg ccaacgttga gggctgggag ccgtcatcca caacgcgaa cacgggcatt   660
ggaggacacg gaagctgctg ctctgagatg gatatctggg aggccaactc catctccgag   720
```

-continued

```
gctcttaccc cccaccttg cacgactgtc ggccaggaga tctgcgaggg tgatgggtgc  780
ggcggaactt actccgataa cagatatggc ggcacttgcg atcccgatgg ctgcgactgg  840
aacccatacc gcctgggcaa caccagcttc tacggccctg gctcaagctt taccctcgat  900
accaccaaga aattgaccgt tgtcacccag ttcgagacgt cgggtgccat caaccgatac  960
tatgtccaga atggcgtcac tttccagcag cccaacgcag agcttggtag ttactctgga 1020
aacgagctca acgatgatta ctgcacagct gaggaggcag aattcggcgg atcctctttc 1080
tcagacaagg gcggcctgac tcagttcaag aaggctacct tggcggcat ggttctggtc 1140
atgagtctgt gggatgatta ctacgccaac atgctgtggc tggactccac ctacccgaca 1200
aacgagacct cctccacacc cggtgccgtg cgcggaagct gctccaccag ctccggtgtc 1260
cctgctcagg tcgaatctca gtctcccaac gccaaggtca ccttctccaa catcaagttc 1320
ggacccattg gcagcaccgg caaccctagc ggcggcaacc ctcccggcgg aaacccgcct 1380
ggcaccacca ccaccgccg cccagccact accactggaa gctctcccgg acctacccag 1440
tctcactacg gccagtgcgg cggtattggc tacagcggcc cacggtctg cgccagcggc 1500
acaacttgcc aggtcctgaa cccttactac tctcagtgcc tgtaa         1545

SEQ ID NO: 64              moltype = AA  length = 514
FEATURE                    Location/Qualifiers
source                     1..514
                           mol_type = protein
                           organism = Trichoderma reesei
SEQUENCE: 64
MYRKLAVISA FLATARAQSA CTLQSETHPP LTWQKCSSGG TCTQQTGSVV IDANWRWTHA   60
TNSSTNCYDG NTWSSTLCPD NETCAKNCCL DGAAYASTYG VTTSGNSLSI GFVTQSAQKN  120
VGARLYLMAS DTTYQEFTLL GNEFSFDVDV SQLPCGLNGA LYFVSMDADG GVSKYPTNTA  180
GAKYGTGYCD SQCPRDLKFI NGQANVEGWE PSSNNANTGI GGHGSCCSEM DIWEANSISE  240
ALTPHPCTTV GQEICEGDGC GGTYSDNRYG GTCDPDGCDW NPYRLGNTSF YGPGSSFTLD  300
TTKKLTVVTQ FETSGAINRY YVQNGVTFQQ PNAELGSYSG NELNDDYCTA EEAEFGGSSF  360
SDKGGLTQFK KATSGGMVLV MSLWDDYYAN MLWLDSTYPT NETSSTPGAV RGSCSTSSGV  420
PAQVESQSPN AKVTFSNIKF GPIGSTGNPS GGNPPGGNPP GTTTTRRPAT TTGSSPGPTQ  480
SHYGQCGGIG YSGPTVCASG TTCQVLNPYY SQCL                              514

SEQ ID NO: 65              moltype = DNA  length = 1611
FEATURE                    Location/Qualifiers
source                     1..1611
                           mol_type = genomic DNA
                           organism = Trichoderma reesei
SEQUENCE: 65
atgattgtcg gcattctcac cacgctggct acgctggcca cactcgcagc tagtgtgcct   60
ctagaggagc ggcaagcttg ctcaagcgtc tggtaattat gtgaaccctc tcaagagacc  120
caaatactga gatatgtcaa ggggccaatg tggtggccag aattggtcgg gtccgacttg  180
ctgtgcttcc ggaagcacat gcgtctactc aacgactat tactcccagt gtcttcccgg  240
cgctgcaagc tcaagctcgt ccacgcgcgc cgcgtcgacg acttctcgag tatccccac   300
aacatcccgg tcgagctccg cgacgcctcc acctggttct actactacca gagtacctcc  360
agtcggatcg ggaaccgcta cgtattcagg caacccttt gttggggtca ctccttgggc  420
caatgcatat tacgcctctg aagttagcag cctcgctatt cctagcttga ctggagccat  480
ggccactgct gcagcagctg tcgcaaaggt tccctctttt atgtggctgt aggtcctccc  540
ggaaccaagg caatctgtta ctgaaggctc atcattcaat gcagagatac tcttgacaag  600
accctctca tggagcaaac cttggccgac atccgcaccg ccaacaagaa tggcggtaac  660
tatgccggac agttttgtgg gtatgacttg ccggatcgcg attgcgctgc ccttgcctcg  720
aatgcgaat actctattgc cgatggtggc gtcgccaaat ataagaacta tatcgacacc  780
attcgtcaa ttgtcgtgga atattccgat atccggcacc tcctggttat tggtatgagt  840
ttaaacacct gcctcccccc cccccttcct tcctttcccg ccggcatctt gtcgttgtgc  900
taactattgt tccctcttcc agagcctgac tctcttgcca acctggtgac caacctcggt  960
actccaaagt gtgccaatgc tcagtcagcc taccttgagt gcatcaacta cgccgtcaca 1020
cagctgaacc ttcaaatgt tgcgatgtat ttggacgcgtg gccatgcagg atggcttgag 1080
tggccggcaa accaagaccc ggccgctcag ctatttgcaa atgtttacaa gaatgcatcg 1140
tctccgagag ctcttcgcgg attggcaacc aatgtcgcca actacaacgg tgaacattt  1200
accagccccc catcgtacac gcaaggcaac gctgtctaca acgagaagct gtacatccac 1260
gctattggac gtcttcttgc caatcacggc tggtccaacg ccttcttcat cactgatcaa 1320
ggtcgatcgg gaaagcagcc taccggacag caacagtggg gagactgtga caatgtgatc 1380
ggcaccggat ttggtattcg cccatccgca aacactgggg actcgttgct ggattcgttt 1440
gtctgggtca gccaggcgg cgagtgtgac ggcaccagcg acagcagtgc gccacgattt 1500
gactccact gtgcgctccc agatgccttg caaccggcgc ctcaagctgg tgcttggttc 1560
caagccact ttgtgcagct tctcacaaac gcaaacccat cgttcctgta a            1611

SEQ ID NO: 66              moltype = AA  length = 471
FEATURE                    Location/Qualifiers
source                     1..471
                           mol_type = protein
                           organism = Trichoderma reesei
SEQUENCE: 66
MIVGILTTLA TLATLAASVP LEERQACSSV WGQCGGQNWS GPTCCASGST CVYSNDYYSQ   60
CLPGAASSSS STRAASTTSR VSPTTSRSSS ATPPPGSTTT RVPPVGSGTA TYSGNPFVGV  120
TPWANAYYAS EVSSLAIPSL TGAMATAAAA VAKVPSFMWL DTLDKTPLME QTLADIRTAN  180
KNGGNYAGQF VVYDLPDRDC AALASNGEYS IADGGVAKYK NYIDTIRQIV VEYSDIRTLL  240
VIEPDSLANL VTNLGTPKCA NAQSAYLECI NYAVTQLNLP NVAMYLDAGH AGWLGWPANQ  300
DPAAQLFANV YKNASSPRAL RGLATNVANY NGWNITSPPS YTQGNAVYNE KLYIHAIGRL  360
LANHGWSNAF FITDQGRSGK QPTGQQQWGD WCNVIGTGFG IRPSANTGDS LLDSFVWVKP  420
GGECDGTSDS SAPRFDSHCA LPDALQPAPQ AGAWFQAYFV QLLTNANPSF L            471
```

```
SEQ ID NO: 67           moltype = DNA   length = 17
FEATURE                 Location/Qualifiers
misc_feature            3
                        note = N=A,C,G, OR T
misc_feature            6
                        note = N=A,C,G, OR T
misc_feature            9
                        note = N=A,C,G, OR T
source                  1..17
                        mol_type = other DNA
                        organism = Chaetomium thermophilum
SEQUENCE: 67
ggnacnggnt aytgyga                                                          17

SEQ ID NO: 68           moltype = DNA   length = 20
FEATURE                 Location/Qualifiers
source                  1..20
                        mol_type = other DNA
                        organism = Chaetomium thermophilum
SEQUENCE: 68
ggccacgcgt cgactagtac                                                       20

SEQ ID NO: 69           moltype = DNA   length = 19
FEATURE                 Location/Qualifiers
source                  1..19
                        mol_type = other DNA
                        organism = Chaetomium thermophilum
SEQUENCE: 69
agatatccat ctcagagca                                                        19

SEQ ID NO: 70           moltype = DNA   length = 17
FEATURE                 Location/Qualifiers
source                  1..17
                        mol_type = other DNA
                        organism = Chaetomium thermophilum
SEQUENCE: 70
gttggcatca ttggtcg                                                          17

SEQ ID NO: 71           moltype = DNA   length = 20
FEATURE                 Location/Qualifiers
source                  1..20
                        mol_type = other DNA
                        organism = Chaetomium thermophilum
SEQUENCE: 71
atcctctcct tccagttttc                                                       20

SEQ ID NO: 72           moltype = DNA   length = 20
FEATURE                 Location/Qualifiers
source                  1..20
                        mol_type = other DNA
                        organism = Chaetomium thermophilum
SEQUENCE: 72
tatccaagta gtccacaacc                                                       20

SEQ ID NO: 73           moltype = DNA   length = 24
FEATURE                 Location/Qualifiers
source                  1..24
                        mol_type = other DNA
                        organism = Chaetomium thermophilum
SEQUENCE: 73
tcatgatgta caagaagttc gccg                                                  24

SEQ ID NO: 74           moltype = DNA   length = 25
FEATURE                 Location/Qualifiers
source                  1..25
                        mol_type = other DNA
                        organism = Chaetomium thermophilum
SEQUENCE: 74
tcatgattac aggcactggc tgtac                                                 25

SEQ ID NO: 75           moltype = DNA   length = 18
FEATURE                 Location/Qualifiers
source                  1..18
                        mol_type = other DNA
                        organism = Myceliophthora thermophila
SEQUENCE: 75
ctcgcagtcg cagtcaag                                                         18
```

```
SEQ ID NO: 76          moltype = DNA   length = 19
FEATURE                Location/Qualifiers
source                 1..19
                       mol_type = other DNA
                       organism = Myceliophthora thermophila
SEQUENCE: 76
cggtcaggtt gcagtttag                                                        19

SEQ ID NO: 77          moltype = DNA   length = 22
FEATURE                Location/Qualifiers
source                 1..22
                       mol_type = other DNA
                       organism = Myceliophthora thermophila
SEQUENCE: 77
tcatgaagca gtacctccag ta                                                    22

SEQ ID NO: 78          moltype = DNA   length = 28
FEATURE                Location/Qualifiers
source                 1..28
                       mol_type = other DNA
                       organism = Myceliophthora thermophila
SEQUENCE: 78
ttaattaatt agacgttgac agtcgagc                                              28

SEQ ID NO: 79          moltype = DNA   length = 25
FEATURE                Location/Qualifiers
source                 1..25
                       mol_type = other DNA
                       organism = Aspergillus fumigatus
SEQUENCE: 79
gggcatgctg gcctccacct tctcc                                                 25

SEQ ID NO: 80          moltype = DNA   length = 30
FEATURE                Location/Qualifiers
source                 1..30
                       mol_type = other DNA
                       organism = Aspergillus fumigatus
SEQUENCE: 80
gggttaatta actacaggca ctgagagtaa                                            30

SEQ ID NO: 81          moltype = DNA   length = 17
FEATURE                Location/Qualifiers
misc_feature           3
                       note = N=A,C,G, OR T
misc_feature           6
                       note = N=A,C,G, OR T
misc_feature           9
                       note = N=A,C,G, OR T
source                 1..17
                       mol_type = other DNA
                       organism = Thermoascus aurantiacus
SEQUENCE: 81
ggnacnggnt aytgyga                                                          17

SEQ ID NO: 82          moltype = DNA   length = 17
FEATURE                Location/Qualifiers
misc_feature           3
                       note = N=A,C,G, OR T
misc_feature           9
                       note = N=A,C,G, OR T
source                 1..17
                       mol_type = other DNA
                       organism = Thermoascus aurantiacus
SEQUENCE: 82
tcnarccana rcatrtt                                                          17

SEQ ID NO: 83          moltype = DNA   length = 18
FEATURE                Location/Qualifiers
source                 1..18
                       mol_type = other DNA
                       organism = Thermoascus aurantiacus
SEQUENCE: 83
gtagagatgc tgttggct                                                         18

SEQ ID NO: 84          moltype = DNA   length = 21
FEATURE                Location/Qualifiers
source                 1..21
                       mol_type = other DNA
                       organism = Thermoascus aurantiacus
```

```
SEQUENCE: 84
tctcagcgca gcaggaaccg t                                                 21

SEQ ID NO: 85           moltype = DNA   length = 18
FEATURE                 Location/Qualifiers
source                  1..18
                        mol_type = other DNA
                        organism = Thermoascus aurantiacus
SEQUENCE: 85
agcgacagca ataacaat                                                     18

SEQ ID NO: 86           moltype = DNA   length = 23
FEATURE                 Location/Qualifiers
source                  1..23
                        mol_type = other DNA
                        organism = Thermoascus aurantiacus
SEQUENCE: 86
acatgtatca gcgcgctctt ctc                                               23

SEQ ID NO: 87           moltype = DNA   length = 28
FEATURE                 Location/Qualifiers
source                  1..28
                        mol_type = other DNA
                        organism = Thermoascus aurantiacus
SEQUENCE: 87
ttaattaatt agttggcggt gaaggtcg                                          28

SEQ ID NO: 88           moltype = DNA   length = 30
FEATURE                 Location/Qualifiers
source                  1..30
                        mol_type = other DNA
                        organism = Myceliophthora thermophila
SEQUENCE: 88
attggcagcc cggatctggg acagagtctg                                        30

SEQ ID NO: 89           moltype = DNA   length = 30
FEATURE                 Location/Qualifiers
source                  1..30
                        mol_type = other DNA
                        organism = Myceliophthora thermophila
SEQUENCE: 89
ccggtcatgc taggaatggc gagattgtgg                                        30

SEQ ID NO: 90           moltype = DNA   length = 24
FEATURE                 Location/Qualifiers
source                  1..24
                        mol_type = other DNA
                        organism = Myceliophthora thermophila
SEQUENCE: 90
gctgtaaact gcgaatgggt tcag                                              24

SEQ ID NO: 91           moltype = DNA   length = 20
FEATURE                 Location/Qualifiers
source                  1..20
                        mol_type = other DNA
                        organism = Myceliophthora thermophila
SEQUENCE: 91
gggtcccaca tgctgcgcct                                                   20

SEQ ID NO: 92           moltype = DNA   length = 20
FEATURE                 Location/Qualifiers
source                  1..20
                        mol_type = other DNA
                        organism = Myceliophthora thermophila
SEQUENCE: 92
aaaattcacg agacgccggg                                                   20

SEQ ID NO: 93           moltype = DNA   length = 36
FEATURE                 Location/Qualifiers
source                  1..36
                        mol_type = other DNA
                        organism = Myceliophthora thermophila
SEQUENCE: 93
actggattta ccatggccaa gaagcttttc atcacc                                 36

SEQ ID NO: 94           moltype = DNA   length = 38
FEATURE                 Location/Qualifiers
```

```
source                 1..38
                       mol_type = other DNA
                       organism = Myceliophthora thermophila
SEQUENCE: 94
tcacctctag ttaattaatt agaagggcgg gttggcgt                              38

SEQ ID NO: 95          moltype = DNA   length = 34
FEATURE                Location/Qualifiers
source                 1..34
                       mol_type = other DNA
                       organism = Trichophaea saccata
SEQUENCE: 95
tcgcgatccg ttttcgcatt tatcgtgaaa cgct                                  34

SEQ ID NO: 96          moltype = DNA   length = 33
FEATURE                Location/Qualifiers
source                 1..33
                       mol_type = other DNA
                       organism = Trichophaea saccata
SEQUENCE: 96
ccgcaaacgc tggtgaaagt aaagatgct gaa                                    33

SEQ ID NO: 97          moltype = DNA   length = 20
FEATURE                Location/Qualifiers
source                 1..20
                       mol_type = other DNA
                       organism = Trichophaea saccata
SEQUENCE: 97
agcgtttgcg gccgcgatcc                                                  20

SEQ ID NO: 98          moltype = DNA   length = 21
FEATURE                Location/Qualifiers
source                 1..21
                       mol_type = other DNA
                       organism = Trichophaea saccata
SEQUENCE: 98
ttattcggtc gaaaaggatc c                                                21

SEQ ID NO: 99          moltype = DNA   length = 40
FEATURE                Location/Qualifiers
source                 1..40
                       mol_type = other DNA
                       organism = Trichophaea saccata
SEQUENCE: 99
acacaactgg ggatcctcat catgaagaac ttccttctgg                            40

SEQ ID NO: 100         moltype = DNA   length = 40
FEATURE                Location/Qualifiers
source                 1..40
                       mol_type = other DNA
                       organism = Trichophaea saccata
SEQUENCE: 100
ccctctagat ctcgagttac gtgaagctag gattagcatt                            40

SEQ ID NO: 101         moltype = DNA   length = 37
FEATURE                Location/Qualifiers
source                 1..37
                       mol_type = other DNA
                       organism = Aspergillus fumigatus
SEQUENCE: 101
actggattta ccatgaagca ccttgcatct tccatcg                               37

SEQ ID NO: 102         moltype = DNA   length = 34
FEATURE                Location/Qualifiers
source                 1..34
                       mol_type = other DNA
                       organism = Aspergillus fumigatus
SEQUENCE: 102
tcacctctag ttaattaaaa ggacgggtta gcgt                                  34

SEQ ID NO: 103         moltype = DNA   length = 37
FEATURE                Location/Qualifiers
source                 1..37
                       mol_type = other DNA
                       organism = Aspergillus terreus
SEQUENCE: 103
taacaattgt caccatgaat tctcttacaa aaagcat                               37

SEQ ID NO: 104         moltype = DNA   length = 33
```

```
FEATURE                 Location/Qualifiers
source                  1..33
                        mol_type = other DNA
                        organism = Aspergillus terreus
SEQUENCE: 104
tatgcggccg cagtctgcat gtgttacgca cct                           33

SEQ ID NO: 105          moltype = DNA   length = 38
FEATURE                 Location/Qualifiers
source                  1..38
                        mol_type = other DNA
                        organism = Trichoderma reesei
SEQUENCE: 105
actggattta ccatgaacaa gtccgtggct ccattgct                      38

SEQ ID NO: 106          moltype = DNA   length = 38
FEATURE                 Location/Qualifiers
source                  1..38
                        mol_type = other DNA
                        organism = Trichoderma reesei
SEQUENCE: 106
tcacctctag ttaattaact actttcttgc gagacacg                      38

SEQ ID NO: 107          moltype = DNA   length = 20
FEATURE                 Location/Qualifiers
misc_feature            9
                        note = N=A,C,G OR T
misc_feature            12
                        note = N=A,C,G OR T
misc_feature            15
                        note = N=A,C,G OR T
source                  1..20
                        mol_type = other DNA
                        organism = Thermoascus aurantiacus
SEQUENCE: 107
aaygartcng gngcngaatt                                          20

SEQ ID NO: 108          moltype = DNA   length = 20
FEATURE                 Location/Qualifiers
misc_feature            9
                        note = N=A,C,G, OR T
misc_feature            12
                        note = N=A,C,G, OR T
misc_feature            15
                        note = N=A,C,G, OR T
source                  1..20
                        mol_type = other DNA
                        organism = Thermoascus aurantiacus
SEQUENCE: 108
aaygartcng gngcngagtt                                          20

SEQ ID NO: 109          moltype = DNA   length = 20
FEATURE                 Location/Qualifiers
misc_feature            12
                        note = N=A,C,G, OR T
misc_feature            15
                        note = N=A,C,G, OR T
source                  1..20
                        mol_type = other DNA
                        organism = Thermoascus aurantiacus
SEQUENCE: 109
aaygaragyg gngcngaatt                                          20

SEQ ID NO: 110          moltype = DNA   length = 20
FEATURE                 Location/Qualifiers
misc_feature            12
                        note = N=A,C,G, OR T
misc_feature            15
                        note = N=A,C,G, OR T
source                  1..20
                        mol_type = other DNA
                        organism = Thermoascus aurantiacus
SEQUENCE: 110
aaygaragyg gngcngagtt                                          20

SEQ ID NO: 111          moltype = DNA   length = 26
FEATURE                 Location/Qualifiers
```

```
source                    1..26
                          mol_type = other DNA
                          organism = Thermoascus aurantiacus
SEQUENCE: 111
gatctcatga agctcggctc tctcgt                                          26

SEQ ID NO: 112            moltype = DNA   length = 32
FEATURE                   Location/Qualifiers
source                    1..32
                          mol_type = other DNA
                          organism = Thermoascus aurantiacus
SEQUENCE: 112
ttaattaatc aaagatacgg agtcaaaata gg                                   32

SEQ ID NO: 113            moltype = DNA   length = 41
FEATURE                   Location/Qualifiers
source                    1..41
                          mol_type = other DNA
                          organism = Aspergillus niger
SEQUENCE: 113
acacaactgg ggatccacca tgaggttcac ttcgatcgag g                         41

SEQ ID NO: 114            moltype = DNA   length = 41
FEATURE                   Location/Qualifiers
source                    1..41
                          mol_type = other DNA
                          organism = Aspergillus niger
SEQUENCE: 114
agatctcgag aagcttagtg aacagtaggc agagacgccc g                         41

SEQ ID NO: 115            moltype = DNA   length = 37
FEATURE                   Location/Qualifiers
source                    1..37
                          mol_type = other DNA
                          organism = Aspergillus fumigatus
SEQUENCE: 115
actggattta ccatgacttt gtccaagatc acttcca                              37

SEQ ID NO: 116            moltype = DNA   length = 40
FEATURE                   Location/Qualifiers
source                    1..40
                          mol_type = other DNA
                          organism = Aspergillus fumigatus
SEQUENCE: 116
tcacctctag ttaattaagc gttgaacagt gcaggaccag                           40

SEQ ID NO: 117            moltype = DNA   length = 17
FEATURE                   Location/Qualifiers
source                    1..17
                          mol_type = other DNA
                          organism = Aspergillus fumigatus
SEQUENCE: 117
tgtcccttgt cgatgcg                                                    17

SEQ ID NO: 118            moltype = DNA   length = 17
FEATURE                   Location/Qualifiers
source                    1..17
                          mol_type = other DNA
                          organism = Aspergillus fumigatus
SEQUENCE: 118
cacatgactt ggcttcc                                                    17

SEQ ID NO: 119            moltype = DNA   length = 34
FEATURE                   Location/Qualifiers
source                    1..34
                          mol_type = other DNA
                          organism = Penicillium pinophilum
SEQUENCE: 119
tcgcgatccg ttttcgcatt tatcgtgaaa cgct                                 34

SEQ ID NO: 120            moltype = DNA   length = 33
FEATURE                   Location/Qualifiers
source                    1..33
                          mol_type = other DNA
                          organism = Penicillium pinophilum
SEQUENCE: 120
ccgcaaacgc tggtgaaagt aaaagatgct gaa                                  33

SEQ ID NO: 121            moltype = DNA   length = 20
```

```
FEATURE               Location/Qualifiers
source                1..20
                      mol_type = other DNA
                      organism = Penicillium pinophilum
SEQUENCE: 121
agcgtttgcg gccgcgatcc                                               20

SEQ ID NO: 122        moltype = DNA   length = 21
FEATURE               Location/Qualifiers
source                1..21
                      mol_type = other DNA
                      organism = Penicillium pinophilum
SEQUENCE: 122
ttattcggtc gaaaaggatc c                                             21

SEQ ID NO: 123        moltype = DNA   length = 48
FEATURE               Location/Qualifiers
source                1..48
                      mol_type = other DNA
                      organism = Penicillium pinophilum
SEQUENCE: 123
acacaactgg ggatccacca tgactctagt aaaggctatt cttttagc                48

SEQ ID NO: 124        moltype = DNA   length = 40
FEATURE               Location/Qualifiers
source                1..40
                      mol_type = other DNA
                      organism = Penicillium pinophilum
SEQUENCE: 124
gtcaccctct agatcttcac aaacattggg agtagtatgg                         40

SEQ ID NO: 125        moltype = DNA   length = 41
FEATURE               Location/Qualifiers
source                1..41
                      mol_type = other DNA
                      organism = Penicillium sp.
SEQUENCE: 125
acacaactgg ggatccacca tgctgtcttc gacgactcgc a                       41

SEQ ID NO: 126        moltype = DNA   length = 41
FEATURE               Location/Qualifiers
source                1..41
                      mol_type = other DNA
                      organism = Penicillium sp.
SEQUENCE: 126
gtcaccctct agatctcgac ttcttctaga acgtcggctc a                       41

SEQ ID NO: 127        moltype = DNA   length = 32
FEATURE               Location/Qualifiers
source                1..32
                      mol_type = other DNA
                      organism = Thielavia terrestris
SEQUENCE: 127
actggattta ccatgccttc tttcgcctcc aa                                 32

SEQ ID NO: 128        moltype = DNA   length = 38
FEATURE               Location/Qualifiers
source                1..38
                      mol_type = other DNA
                      organism = Thielavia terrestris
SEQUENCE: 128
tcacctctag ttaattaatc agtttgcctc ctcagccc                           38

SEQ ID NO: 129        moltype = DNA   length = 19
FEATURE               Location/Qualifiers
source                1..19
                      mol_type = other DNA
                      organism = Trichophaea saccata
SEQUENCE: 129
tgaaatggga tgctactga                                                19

SEQ ID NO: 130        moltype = DNA   length = 20
FEATURE               Location/Qualifiers
source                1..20
                      mol_type = other DNA
                      organism = Trichophaea saccata
SEQUENCE: 130
caacgactac aacatcgagg                                               20
```

```
SEQ ID NO: 131           moltype = DNA   length = 20
FEATURE                  Location/Qualifiers
source                   1..20
                         mol_type = other DNA
                         organism = Trichophaea saccata
SEQUENCE: 131
atttgctgtc caccagtgaa                                                 20

SEQ ID NO: 132           moltype = DNA   length = 34
FEATURE                  Location/Qualifiers
source                   1..34
                         mol_type = other DNA
                         organism = Penicillium pinophilum
SEQUENCE: 132
tcgcgatccg ttttcgcatt tatcgtgaaa cgct                                 34

SEQ ID NO: 133           moltype = DNA   length = 33
FEATURE                  Location/Qualifiers
source                   1..33
                         mol_type = other DNA
                         organism = Penicillium pinophilum
SEQUENCE: 133
ccgcaaacgc tggtgaaagt aaagatgct gaa                                   33

SEQ ID NO: 134           moltype = DNA   length = 20
FEATURE                  Location/Qualifiers
source                   1..20
                         mol_type = other DNA
                         organism = Penicillium pinophilum
SEQUENCE: 134
agcgtttgcg gccgcgatcc                                                 20

SEQ ID NO: 135           moltype = DNA   length = 21
FEATURE                  Location/Qualifiers
source                   1..21
                         mol_type = other DNA
                         organism = Penicillium pinophilum
SEQUENCE: 135
ttattcggtc gaaaaggatc c                                               21

SEQ ID NO: 136           moltype = DNA   length = 48
FEATURE                  Location/Qualifiers
source                   1..48
                         mol_type = other DNA
                         organism = Penicillium pinophilum
SEQUENCE: 136
acacaactgg ggatccacca tgactctagt aaaggctatt cttttagc                  48

SEQ ID NO: 137           moltype = DNA   length = 40
FEATURE                  Location/Qualifiers
source                   1..40
                         mol_type = other DNA
                         organism = Penicillium pinophilum
SEQUENCE: 137
gtcaccctct agatcttcac aaacattggg agtagtatgg                           40

SEQ ID NO: 138           moltype = DNA   length = 36
FEATURE                  Location/Qualifiers
source                   1..36
                         mol_type = other DNA
                         organism = Thielavia terrestris
SEQUENCE: 138
actggattta ccatggccct caaatcgctc ctgttg                               36

SEQ ID NO: 139           moltype = DNA   length = 36
FEATURE                  Location/Qualifiers
source                   1..36
                         mol_type = other DNA
                         organism = Thielavia terrestris
SEQUENCE: 139
tcacctctag ttaattaatt acaagcactg agagta                               36

SEQ ID NO: 140           moltype = DNA   length = 17
FEATURE                  Location/Qualifiers
source                   1..17
                         mol_type = other DNA
                         organism = Thielavia terrestris
SEQUENCE: 140
tgtcccttgt cgatgcg                                                    17
```

```
SEQ ID NO: 141         moltype = DNA  length = 17
FEATURE                Location/Qualifiers
source                 1..17
                       mol_type = other DNA
                       organism = Thielavia terrestris
SEQUENCE: 141
cacatgactt ggcttcc                                                    17

SEQ ID NO: 142         moltype = DNA  length = 43
FEATURE                Location/Qualifiers
source                 1..43
                       mol_type = other DNA
                       organism = Thermobifida fusca
SEQUENCE: 142
ctgaaaaaaa ggagaggata aagaatgaac catgcccccg cca                       43

SEQ ID NO: 143         moltype = DNA  length = 45
FEATURE                Location/Qualifiers
source                 1..45
                       mol_type = other DNA
                       organism = Thermobifida fusca
SEQUENCE: 143
ctaatgctgg tgttggtgct gatggttggc gctgcaggac accgt                     45

SEQ ID NO: 144         moltype = DNA  length = 42
FEATURE                Location/Qualifiers
source                 1..42
                       mol_type = other DNA
                       organism = Thermobifida fusca
SEQUENCE: 144
ctaatgctgg tgttggtgct gatggggggtt gtcaccgccg ct                       42

SEQ ID NO: 145         moltype = DNA  length = 21
FEATURE                Location/Qualifiers
source                 1..21
                       mol_type = other DNA
                       organism = Thermobifida fusca
SEQUENCE: 145
gagtatcgcc agtaaggggc g                                               21

SEQ ID NO: 146         moltype = DNA  length = 29
FEATURE                Location/Qualifiers
source                 1..29
                       mol_type = other DNA
                       organism = Thermobifida fusca
SEQUENCE: 146
tctttatcct ctccttttt tcagagctc                                        29

SEQ ID NO: 147         moltype = DNA  length = 50
FEATURE                Location/Qualifiers
source                 1..50
                       mol_type = other DNA
                       organism = Thermobifida fusca
SEQUENCE: 147
catcagcacc aacaccagca tccgtaatcg catgttcaat ccgctccata                50

SEQ ID NO: 148         moltype = DNA  length = 23
FEATURE                Location/Qualifiers
source                 1..23
                       mol_type = other DNA
                       organism = Thermobifida fusca
SEQUENCE: 148
gcagccctaa aatcgcataa agc                                             23

SEQ ID NO: 149         moltype = DNA  length = 22
FEATURE                Location/Qualifiers
source                 1..22
                       mol_type = other DNA
                       organism = Trichoderma reesei
SEQUENCE: 149
gtgaataacg cagctcttct cg                                              22

SEQ ID NO: 150         moltype = DNA  length = 25
FEATURE                Location/Qualifiers
source                 1..25
                       mol_type = other DNA
                       organism = Trichoderma reesei
```

```
SEQUENCE: 150
ccttaattaa ttatgcgtca ggtgt                                         25

SEQ ID NO: 151          moltype = DNA   length = 33
FEATURE                 Location/Qualifiers
source                  1..33
                        mol_type = other DNA
                        organism = Trichoderma reesei
SEQUENCE: 151
cggactgcgc accatggtga ataacgcagc tct                                33

SEQ ID NO: 152          moltype = DNA   length = 35
FEATURE                 Location/Qualifiers
source                  1..35
                        mol_type = other DNA
                        organism = Trichoderma reesei
SEQUENCE: 152
tcgccacgga gcttattatg cgtcaggtgt agcat                              35

SEQ ID NO: 153          moltype = DNA   length = 37
FEATURE                 Location/Qualifiers
source                  1..37
                        mol_type = other DNA
                        organism = Trichoderma reesei
SEQUENCE: 153
tcttggatcc accatggtcg gactgctttc aatcacc                            37

SEQ ID NO: 154          moltype = DNA   length = 34
FEATURE                 Location/Qualifiers
source                  1..34
                        mol_type = other DNA
                        organism = Trichoderma reesei
SEQUENCE: 154
ttaactcgag tcacagacac tgcgagtaat agtc                               34

SEQ ID NO: 155          moltype = DNA   length = 33
FEATURE                 Location/Qualifiers
source                  1..33
                        mol_type = other DNA
                        organism = Trichoderma reesei
SEQUENCE: 155
cggactgcgc accatggtcg gactgctttc aat                                33

SEQ ID NO: 156          moltype = DNA   length = 35
FEATURE                 Location/Qualifiers
source                  1..35
                        mol_type = other DNA
                        organism = Trichoderma reesei
SEQUENCE: 156
tcgccacgga gcttatcaca gacactgcga gtaat                              35

SEQ ID NO: 157          moltype = DNA   length = 1467
FEATURE                 Location/Qualifiers
source                  1..1467
                        mol_type = genomic DNA
                        organism = Penicillium emersonii
SEQUENCE: 157
atgcttcgac gggctcttct tctatcctct tccgccatcc ttgctgtcaa ggcacagcag    60
gccggcacgg cgacggcaga gaaccacccg cccctgacat ggcaggaatg caccgcccct   120
gggagctgca ccacccagaa cggggcggtc gttcttgatg cgaactggcg ttgggtgcac   180
gatgtgaacg gatacaccaa ctgctacacg gcaataccct ggaacccac gtactgccct    240
gacgacgaaa cctgcgccca gaactgtgcg ctggacggcg cggattacga gggcacctac   300
ggcgtgactt cgtcgggcag ctccttgaag tcaatttcg tcaccgggtc gaacgtcgga    360
tcccgtctct acctgctgca ggacgactcg acctatcaga tcttcaagct tctgaaccgc   420
gagtttacct tgacgtcga tgtctccaat cttccgtgcg gattgaacgg cgctctgtac    480
tttgtcgcca tggacgccga cggcggcgtg tccaagtacc cgaacaacaa ggctggtgcc   540
aagtacggaa ccgggtattg cgactcccaa tgcccacggg acctcaagtt catcgacggc   600
gaggtatgtc cagtggtaaa atcgatcgtc tcgtgaactt ctgctgacag gttcgatcta   660
caggccaacg tcgagggctg gcagccgtct tcgaacaacg ccaacaccgg aattggcgac   720
catggctcct gctgtgcgga gatggatgtc tgggaagcca acagcatctc caatgcggtc   780
actccgcacc cgtgcgacac gccaggccag acgatgtgct ctggcgatga ctgcggtggc   840
acatactcta acgatcgcta cgcgggaacc tgcgatcctg acggctgtga cttcaaccct   900
taccgcatgg gcaacacttc tttctacggg cctggcaaga tcatcgatac caccaagcct   960
ttcactgtcg tgacgcagtt cctcactgat gatggtacgg atactggaac tctcagcgag  1020
atcaagcgct tctacgtcca gaacggcaac gtcattccgc agcccaactc ggacatcagt  1080
gtcgtgaccg gcaactcgat cacgacggag ttctgtactg ctcagaagca ggcctttggc  1140
gacacggacg acttctctca gcacggtggc ctggccaaga tgggagcggc catgcagcag  1200
ggtatggtc tggtgatgag tttgtgggac gactacgccg cgcagatgct gtggctggat   1260
tccgactacc cgacggatgc ggaccccacg accctggta ttgcccgtgg aacgtgtccg   1320
```

```
acggactcgg gcgtcccatc ggatgtcgag tcgcagagcc ccaactccta cgtgacctac   1380
tcgaacatca agtttggtcc gatcaactcg accttcaccg cttcgtgagt cttggttaca   1440
tgtgaagtag acggaagttg ctctgcg                                       1467

SEQ ID NO: 158          moltype = AA   length = 455
FEATURE                 Location/Qualifiers
source                  1..455
                        mol_type = protein
                        organism = Penicillium emersonii
SEQUENCE: 158
MLRRALLLSS SAILAVKAQQ AGTATAENHP PLTWQECTAP GSCTTQNGAV VLDANWRWVH    60
DVNGYTNCYT GNTWNPTYCP DDETCAQNCA LDGADYEGTY GVTSSGSSLK LNFVTGSNVG   120
SRLYLLQDDS TYQIFKLLNR EFTFDVDVSN LPCGLNGALY FVAMDADGGV SKYPNNKAGA   180
KYGTGYCDSQ CPRDLKFIDG EANVEGWQPS SNNANTGIGD HGSCCAEMDV WEANSISNAV   240
TPHPCDTPGQ TMCSGDDCGG TYSNDRYAGT CDPDGCDFNP YRMGNTSFYG PGKIIDTTKP   300
FTVVTQFLTD DGTDTGTLSE IKRFYVQNGN VIPQPNSDIS VVTGNSITTE FCTAQKQAFG   360
DTDDFSQHGG LAKMGAAMQQ GMVLVMSLWD DYAAQMLWLD SDYPTDADPT TPGIARGTCP   420
TDSGVPSDVE SQSPNSYVTY SNIKFGPINS TFTAS                              455

SEQ ID NO: 159          moltype = DNA   length = 1590
FEATURE                 Location/Qualifiers
source                  1..1590
                        mol_type = genomic DNA
                        organism = Penicillium pinophilum
SEQUENCE: 159
atgtctgcct tgaactcttt caatatgtac aagagcgccc tcatcttggg ctccttgctg    60
gcaacagctg gtgctcagca aattggtaca tataccgctg aaacccatcc ctctttgagc   120
tggtctactt gcaaatcggg tggtagctgc accacaaact ccggtgccat tacgttagat   180
gccaactggc gttgggtcca tggtgtcaat accagcacca actgctacac tgcaacact    240
tggaatagcg ccatctgcga cactgatgca tcctgtgcc aaggactgtgc tctcgatgtg   300
gctgactact ctggcacgta cggtatcact acctccggca actcactgcg cctgaacttc   360
gttaccggtt ccaacgtcgg atctgtaca tacctgatgg ccgataacac ccactaccaa   420
atcttcgact tgttgaacca ggagttcacc ttcaccgtcg atgtctccca cctcccttgc   480
ggtttgaacg gtgccctcta cttcgtgacc atggatgcag acggtggcgt ctccaagtac   540
cccaacaaca aggccggtgc tcagtacgg gttggatact gtgactctca atgcctcgt     600
gacttgaagt tcatcgctgg tcaggccaac gttgagggct ggacgccctc cgccaacaac   660
gccaacactg gaattggcaa tcacggagct tgctgcgcgg agcttgatat ctgggaggca   720
aacagcatct cagaggcctt gactcctcac ccttgcgaca cactcggtct atctgtttgc   780
actactagtg cctgcggtgg tacctacagc tctgatcgtt acgccggtac ctgcgaccct   840
gatggatgtg acttcaaccc ttaccgtctt ggtgtcactg acttctacgg ctccggcaag   900
accgttgaca ccaccaagcc ctttaccgtt gtgactcaat cgtcactaa cgacggtacc   960
tccaccggtt ccctctccga gatcagacgt tactacgttc agaacggcgt tgtcatcccc  1020
cagccttcct ccaagatctc cggaatcagc ggaaatgtca tcaactccga ctactgcgct  1080
gctgaaatct ccacctttgg cgggactgcc tccttcagca aacacggtgg cttgacaaac  1140
atggccgctg gtatggaagc tggtatggtc ttggtcatga gtttgtggga cgactactcc  1200
gtcaacatgc tctggctcga cagcacctac cctacaaacg cgactggtac ccccggtgcc  1260
gctcgtggta cctgcgctac cacttctggg gaccccaaga ccgttgaatc acaatccggc  1320
agctcctatg tcaccttctc tgacattcgg gttggtcctt tcaattctac gttcagcggt  1380
ggttctagca ccggtggcag cactactact accgctagcc gcaccaccac cacctcggcc  1440
tcttccacct ctacttccag cacctctact ggcactgagg tcgctggtca ctggggtcag  1500
tgtggtggcc agggctggac tggtcctacc acctgtgtta gtggaaccac atgcaccgtc  1560
gtgaacccct actactctca atgtttgtaa                                   1590

SEQ ID NO: 160          moltype = AA   length = 529
FEATURE                 Location/Qualifiers
source                  1..529
                        mol_type = protein
                        organism = Penicillium pinophilum
SEQUENCE: 160
MSALNSFNMY KSALILGSLL ATAGAQQIGT YTAETHPSLS WSTCKSGGSC TTNSGAITLD    60
ANWRWVHGVN TSTNCYTGNT WNSAICDTDA SCAQDCALDG ADYSGTYGIT TSGNSLRLNF   120
VTGSNVGSRT YLMADNTHYQ IFDLLNQEFT FTVDVSHLPC GLNGALYFVT MDADGGVSKY   180
PNNKAGAQYG VGYCDSQCPR DLKFIAGQAN VEGWTPSANN ANTGIGNHGA CCAELDIWEA   240
NSISEALTPH PCDTPGLSVC TTDACGGTYS SDRYAGTCDP DGCDFNPYRL GVTDFYGSGK   300
TVDTTKPFTV VTQFVTNDGT STGSLSEIRR YYVQNGVVIP QPSSKISGIS GNVINSDYCA   360
AEISTFGGTA SFSKHGGLTN MAAGMEAGMV LVMSLWDDYS VNMLWLDSTY PTNATGTPGA   420
ARGTCATTSG DPKTVESQSG SSYVTFSDIR VGPFNSTFSG GSSTGGSTTT TASRTTTTSA   480
SSTSTSSTST GTGVAGHWGQ CGGQGWTGPT TCVSGTTCTV VNPYYSQCL               529

SEQ ID NO: 161          moltype = DNA   length = 1678
FEATURE                 Location/Qualifiers
source                  1..1678
                        mol_type = genomic DNA
                        organism = Aspergillus terreus
SEQUENCE: 161
atgccttcca cctacgatat ctacaagaag ctcctcctgc tggccagctt cctgagtgcc    60
tctcaggccc agcaggtcgg cacctccaag gccgaagtcc atccttcctt gacttggcaa   120
acttgcacca cgcggcggtag ctgcaccacc gtcaacggca aggtcgtcgt tgacgccaac   180
tggcgctggg tccacaacgt cgacggctac aacaactgct atactggcaa tacctgggat   240
```

```
accactctct gccctgatga tgagacctgt gcctccaact gcgcctggaa aggtgcggac    300
tactctggca cgtatggtgt caccaccagc ggcaactccc tgcggttgaa ctttgtcacc    360
caggcttcgc aaaagaacat cggatcccgt ctgtacctca tggaggacga cagcacctac    420
aagatgttca agctgctgaa ccaggagttc acctttgacg tggatgtctc gaacctcccc    480
tgcggtctga acggcgccgt ttactttgtc tccatgacg ccgatggtgg catggccaag    540
tacccggcca acaaggcggg cgcaaaggtg agcattgtgc ctttccgtcg accataccgt    600
gtatgctgac agattttagt acggcaccgg ctactgtgac tcgcagtgcc cgcgcgactt    660
gaagttcatc aacggcatgg ccaacgtcga gggctgggag ccctctgcca tgacgccaa    720
cgccggcacc ggcaaccacg gctcctgctg cgctgagatg gacatctggg aggccaacag    780
catctccacc gcgtacaccc cgcatccctg gacacccc ggtcaagtca tgtgcacgag    840
cgactcctgc ggcggcactt acagcagcga ccggtatggc ggcacgtgcg atccggatgg    900
atgcgacttc aactcgtacc gccagggcaa caagaccttc tatggccccg gcatgacggt    960
cgacaccaaa agcaagatca cggtggtgac gcagttcctc accaacgacg gcaccgcgtc   1020
cggcacgctc tccgagaaca agcgcttcta cgtgcagaac ggcaaggtca tccccaactc   1080
ggagtcgacg tggtccggcg tgtcgggcaa ctcgatcacc accgcctact gcaacgcgca   1140
gaagacgctc ttcggcgaca cggatgtctt caccaagcac ggtggcatgg agggtatggg   1200
cgcggcgctg gccgagggca tggtgctcgt gctgagtctg tgggacgacc acaactccaa   1260
catgctctgg ctggacagca actacccac gacaagccc tcgacgacc ccggcgtgg    1320
ccgcggctcg tgcgacatct cctcgggcga cccgaaggac gtggaggcca acgacgccaa   1380
cgcgtatgtg gtgtactcga acatcaaggt gggtccatt ggctcgacct ttagcgggtc    1440
gactggcggc ggctccagct cgtccaccac cgccacctcc aagaccacca cgaccagcgc   1500
gaccaagacg acgaccacca ccaccaagac cactctgcct cgtccaccag    1560
caccggcgga gcgcagcact gggcccagtg cggcggtatt ggctggaccg gcccaaccac   1620
ctgtgtcgcg ccgtacacct gccagaagca gaacgactac tactcgcagt gcctgtag    1678

SEQ ID NO: 162          moltype = AA  length = 541
FEATURE                 Location/Qualifiers
source                  1..541
                        mol_type = protein
                        organism = Aspergillus terreus
SEQUENCE: 162
MPSTYDIYKK LLLLASFLSA SQAQQVGTSK AEVHPSLTWQ TCTSGGSCTT VNGKVVVDAN     60
WRWVHNVDGY NNCYTGNTWD TTLCPDDETC ASNCALEGAD YSGTYGVTTS GNSLRLNFVT    120
QASQKNIGSR LYLMEDDSTY KMFKLLNQEF TFDVDVSNLP CGLNGAVYFV SMDADGGMAK    180
YPANKAGAKY GTGYCDSQCP RDLKFINGMA NVEGWEPSAN DANAGTGNHG SCCAEMDIWE    240
ANSISTAYTP HPCDTPGQVM CTGDSCGGTY SSDRYGGTCD PDGCDFNSYR QGNKTFYGPG    300
MTVDTKSKIT VVTQFLTNDG TASGTLSEIK RFYVQNGKVI PNSESTWSGV SGNSITTAYC    360
NAQKTLFGDT DVFTKHGGME GMGAALAEGM VLVLSLWDDH NSNMLWLDSN YPTDKPSTTP    420
GVARGSCDIS SGDPKDVEAN DANAYVVYSN IKVGPIGSTF SGSTGGGSSS STTATSKTTT    480
TSATKTTTTT TKTTTTTSAS STSTGGAQHW AQCGGIGWTG PTTCVAPYTC QKQNDYYSQC    540
L                                                                  541

SEQ ID NO: 163          moltype = DNA  length = 1608
FEATURE                 Location/Qualifiers
source                  1..1608
                        mol_type = genomic DNA
                        organism = Neosartorya fischeri
SEQUENCE: 163
atggcatccg caatttcttt ccaagtctac aggagtgcat tgattctgtc tgccttcctg     60
ccgtctatta cgcaggcgca gcagatcggc acatacacca ctgagaccca tccatcgatg    120
acatgggaga cctgcactag cggtggaagt tgtgccacca accagggctc tgtcgttgtc    180
gatgcgaact ggcgatgggt gcaccaggtt ggcagcacca ccaactgcta tactggcaat    240
acttgggata cctccatctg cgataccgac gagacctgtg ccactgaatg tgcggttgac    300
ggagcagact acgaatcaac ctacggagtc accaccagcg gcagccagat ccgcctcaac    360
tttgtgacgc agaactcaaa tggtgccaat gtcggctcac gtcttacat gatgcggat    420
aatacacact accagatgtt caagctactg aaccaggagt tcacctttga cgtggtcgtg    480
tccaacctcc cctgtggctt gaacggggcc ctctactttg tgaccatgga tgaagatggc    540
ggtgtctcca ataccccaa taataaggct ggagcccaat acggcgtggg atattgcgat    600
tctcaatgtc cgcgcgatct taaatttatc caaggccagg caaatgtgga aggctggact    660
ccgtcgtcca acaacgaaaa cacgggactg gcaattatg gatcttgctg cgccgagctg    720
gacatctggg aatccaacag catctctcag gctctgacac ctcatccatg tgatactgcc    780
accaacacta tgtgcactgg tgatgcctgc ggcggacat atagcagtga tcggtatgct    840
ggcacttgcg acccggatgg ctgcgacttc aacccctacc gcatgggcaa taccacattc    900
tacggcccg ggaagacaat cgataccaac tcgcccttca ccgtggtgac gcagttcatt    960
acagatgacg gcaccgatac cggcaccttg tctgaaatcc gccgctacta tgtccagaac   1020
ggcgttacct acgccagcc tgactcagac atcagtggta ttaccggcaa cgccataaac   1080
gctgactact gcactgccga gaatactgtc tttgacgggc cgggtacatt tgccaagcac   1140
ggtggggtttt ccgccatgtc cgaggccatg tctaccggta tggtactggt catgtcgctc   1200
tgggacgatt actacggcga tgtcgctgg cttgacagca cctatcccac taatgcgtct   1260
tcgtcgaccc caggtgctgt ccgtggttcc tgctcgaccg actccggtgt ccccgccacc   1320
attgaatccg agagtcctga ttcgtatgtg acctattcga acatcaaagt tggtccgatc   1380
ggatcaacct tcagcagcgg ttctggctct ggaagctctg gctctggaag ttccggctcg   1440
gcttcgacct cgaccacctc caccaagacc acagctgcaa cgagccacctc gactgccgtg   1500
gcgcagcact ataggcagtg tggtggcagg gactggactg gcccgactac ttgtgtctct   1560
ccttatacct gccaagtgca gaacgcgtac tattctcagt gtctgtag              1608

SEQ ID NO: 164          moltype = AA  length = 535
FEATURE                 Location/Qualifiers
source                  1..535
```

```
                        mol_type = protein
                        organism = Neosartorya fischeri
SEQUENCE: 164
MASAISFQVY RSALILSAFL PSITQAQQIG TYTTETHPSM TWETCTSGGS CATNQGSVVM    60
DANWRWVHQV GSTTNCYTGN TWDTSICDTD ETCATECAVD GADYESTYGV TTSGSQIRLN   120
FVTQNSNGAN VGSRLYMMAD NTHYQMFKLL NQEFTFDVDV SNLPCGLNGA LYFVTMDEDG   180
GVSKYPNNKA GAQYGVGYCD SQCPRDLKFI QGQANVEGWT PSSNNENTGL GNYGSCCAEL   240
DIWESNSISQ ALTPHPCDTA TNTMCTGDAC GGTYSSDRYA GTCDPDGCDF NPYRMGNTTF   300
YGPGKTIDTN SPFTVVTQFI TDDGTDTGTL SEIRRYYVQN GVTYAQPDSD ISGITGNAIN   360
ADYCTAENTV FDGPGTFAKH GGFSAMSEAM STGMVLVMSL WDDYYADMLW LDSTYPTNAS   420
SSTPGAVRGS CSTDSGVPAT IESESPDSYV TYSNIKVGPI GSTFSSGSGS GSSGSGSSGS   480
ASTSTTSTKT TAATSTSTAV AQHYSQCGGQ DWTGPTTCVS PYTCQVQNAY YSQCL        535

SEQ ID NO: 165          moltype = DNA  length = 1581
FEATURE                 Location/Qualifiers
source                  1..1581
                        mol_type = genomic DNA
                        organism = Aspergillus nidulans
SEQUENCE: 165
atggcatctt cattccagtg gtacaaagct ctcctctttt tctcttctct gctttctgca    60
gtgcaagccc agaaggtcgg cactcagcaa gctgaagtgc accccggcct gacctggcag   120
acctgcacga gctccggcag ctgcaccacc gtcaacggcg aggtcactat tgacgcaaac   180
tggcgctggc tgcacaccgt caatgggtac accaactgct atactggcaa cgaatgggat   240
acctccatct gcaccagcaa cgaggtttgc gcggaacaat gcgctgtcga cggtgctaac   300
tatgcctcca catacggcat caccacatcc ggcagctcgc tgcgtctgaa cttcgtcacg   360
cagtcgcagc agaagaatat cggttccaga gtctatctca ttgatgacga agatacatac   420
accatgttct acctgctcaa caaggaattc acttttgacg tcgacgtctc cgagctcccc   480
tgcggtctca acggggcggt ctactttgtg tctatggacg ccgacggcgg caaatcccgc   540
tatgccacca cgaagccgg tgccaaatac ggcacgggga ctgcgactc tcagtgcccg   600
cgggacctca agttcatcaa cggcgtcgcc aacgtcgagg gctgggaatc ctccgatacg   660
aaccccaacg gcgcgcgtcgg caatcacggc tcctgctgcg cagagatgga tatctgggag   720
gcaaacagca tttccactgc tttcactccc catccctgcg ataccccggg ccagaccctc   780
tgcaccggtg actcatgcgg tgggacctat agcaacgacc gctacggcgg cacctgcgac   840
cccgatggct gcgactttaa ctcctaccgt caggggacca agaccttcta cgggcaggc   900
ctgacagtcg acacgaacag cccggtcaca gtggtgacc agttcctgac agacgacag   960
acggacacag gcaccctctc ggaaatcaaa cgcttctatg tccagaacgg cgtcgtcatc  1020
cccaactccg agtcgaccta ccccgctaat ccgggtaact cgatcacaac ggagttctgc  1080
gagtcgcaaa aggaactctt cggcgacgtc gatgtttct ccgcccacgg cggcatggcg  1140
ggcatgggcg ccgcgttgga acaaggcatg gtccttgtac tgtccctgtg ggacgacaac  1200
tactcaaaca tgctctggct cgactcgaat taccccacgg acgcggaccc gactcaacca  1260
ggtatcgcgc gcgggacgtg cccgacggac tcgggcgttc cgtctggagt cgaggcccaa  1320
tatccgaatg cgtatgtcgt gtactcgaac atcaagtttg gtcctattgg aagtaccttt  1380
ggcaacggtg gaggctcagg gccaacaaca acggtgacga cgattaccgc tactagtaca  1440
actagctcgg cgacgtcgac ggctaccggt caggcgcagc actgggagca gtgtggtggg  1500
aatggctgga ctggtccgac ggtctgcgct agccctggg cttgcacagt ggtgaactca  1560
tggtactcgc agtgtctgta a                                            1581

SEQ ID NO: 166          moltype = AA  length = 526
FEATURE                 Location/Qualifiers
source                  1..526
                        mol_type = protein
                        organism = Aspergillus nidulans
SEQUENCE: 166
MASSFQWYKA LLFFSSLLSA VQAQKVGTQQ AEVHPGLTWQ TCTSSGSCTT VNGEVTIDAN    60
WRWLHTVNGY TNCYTGNEWD TSICTSNEVC AEQCAVDGAN YASTYGITTS GSSLRLNFVT   120
QSQQKNIGSR VYLMDDEDTY TMFYLLNKEF TFDVDVSELP CGLNGAVYFV SMDADGGKSR   180
YATNEAGAKY GTGYCDSQCP RDLKFINGVA NVEGWESSDT NPNGGVGNHG SCCAEMDIWE   240
ANSISTAFTP HPCDTPGQTL CTGDSCGGTY SNDRYGGTCD PDGCDFNSYR QGNKTFYGPG   300
LTVDTNSPVT VVTQFLTDDN TDTGTLSEIK RFYVQNGVVI PNSESTYPAN PGNSITTEFC   360
ESQKELFGDV DVFSAHGGMA GMGAALEQGM VLVLSLWDDN YSNMLWLDSN YPTDADPTQP   420
GIARGTCPTD SGVPSGVEAQ YPNAYVVYSN IKFGPIGSTF GNGGGSGPTT TVTTSTATST   480
TSSATSTATG QAQHWEQCGG NGWTGPTVCA SPWACTVVNS WYSQCL                 526

SEQ ID NO: 167          moltype = DNA  length = 1752
FEATURE                 Location/Qualifiers
source                  1..1752
                        mol_type = genomic DNA
                        organism = Fennellia nivea
SEQUENCE: 167
atgggacggg ttctttctct tgcgcttgcc cttctgcttc ctgctgtgca ggcccagcag    60
accctctggg gtcaatgtac gattccttct tgttgcggat atacgccttt actgactggg   120
gacaggcggt ggcattggat ggacaggagc aaccaactgt gtcgctggtg ctgcttgtag   180
cacgcagaat ccttgtatgg ttcatgccgt ctcttcagct agacatctac tgaccgttta   240
gactatcgcc agtgcctccc tgcgacgggc accacctcca ccacctgac caccgacc    300
aggtctacca ctaccacgac ggcaacgtcc accacgtctc agggctcatc ttcaagctct   360
tctacgacta cgacaaagtc gacgagcacc accaccggct cttctaccac catcacctct   420
gcgccgtccg gcaacccgtt cagtggatat caactctatg ccaaccctta ctattcttcc   480
gaggtccaca ccctcgccat gccctccctt gctagctccc ttctgccggc tgccagtgct   540
gccgccaagg ttccctcgtt cacctggctg tatgtattct tcgtgatttg tatcatttcc   600
```

```
atctgaccac cgcagggaca ccgctgccaa agtgccgacc atgggcacct acctggcgga    660
catcaaggcc aagaacgccg ctggtgccaa cccgcccatt gctgcccagt tcgtcgtcta    720
cgatcttccc gatcgtgact gtgctgccct ggctagcaat ggcgagtact cgattgcgaa    780
caacggtgtt gccaactaca aggcgtacat tgactccatc cgggcccagt tggtgaaata    840
cccggacgtc cacaccatcc ttgttatcgg tacgctcgtg cccatggttg ttctcaatct    900
atttacaata ctaactctca acagagcccg atagccttgg caacctggtc accaacctga    960
acgtggccaa atgcgccaac gcccagagcg cgtatctgga gtcgtcaac  tacgcccctga  1020
tcaacctgaa cctgcccaac gttgccatgt acatcgacgc tggtacgcat accacgcact   1080
ccccgttat accctcgctc acatttcttt aggacacgcc ggctggctcg gatggcccgc    1140
caacatcggc cccgcgcca ccctcttcgc cggggtgtac aatgacgccg gctctcccgc     1200
tgcactgcgc ggcctcgcga ccaacgtcgc caactacaac gccttcagca tcagcacctg    1260
cccgtcctac acgtcgggcg acgccaactg cgacgaaaac cgctacatca cgccttggc    1320
ccctctcttg aaatcggctg gcttcgatgc gcatttatc gttgatactg gttcgtatta     1380
tcttcccagc gagttgacag gttctgcag acgcaggtcg caacggtgtc cagcctacta    1440
agcagcaggc ttggggcgat tggtgcaacg tcatcggcac tggattcggt gtccggccga    1500
ccactaacac tggcaattcg ctggttgatg cgtttgtctg ggtaagcct ggcggcgaga      1560
gcgatggcac ctccaactct agctctccgc ggtacgatgc gcactgtgga tacagtgatg   1620
cgctccagcc tgctcctgag gccggaacct ggttccaggt gagttctttt ctggtgtagt    1680
gggactcggg tagctgacaa tatgcaggcg tactttgagc agcttctgac caacgctaac   1740
cctgcgttct ga                                                         1752

SEQ ID NO: 168        moltype = AA  length = 469
FEATURE               Location/Qualifiers
source                1..469
                      mol_type = protein
                      organism = Fennellia nivea
SEQUENCE: 168
MGRVSSLALA LLLPAVQAQQ TLWGQCGGIG WTGATNCVAG AACSTQNPYY AQCLPATATT     60
STTLTTTTRS TTTTTATSTT SQGSSSSSST TTTKSTSTTT GSSTTITSAP SGNPFSGYQL   120
YANPYYSSEV HTLAMPSLAS SLLPAASAAA KVPSFTWLDT AAKVPTMGTY LADIKAKNAA   180
GANPPIAAQF VVYDLPDRDC AALASNGEYS IANNGVANYK AYIDSIRAQL VKYPDVHTIL   240
VIEPDSLANL VTNLNVAKCA NAQSAYLECV NYALINLNLP NVAMYIDAGH AGWLGWPANI   300
GPAATLFAGV YNDAGSPAAL RGLATNVANY NAFSISTCPS YTSGDANCDE NRYINALAPL   360
LKSAGFDAHF IVDTGRNGVQ PTKQQAWGDW CNVIGTGFGV RPTTNTGNSL VDAFVWVKPG   420
GESDGTSNSS SPRYDAHCGY SDALQPAPEA GTWFQAYFEQ LLTNANPAF               469

SEQ ID NO: 169        moltype = DNA  length = 1744
FEATURE               Location/Qualifiers
source                1..1744
                      mol_type = genomic DNA
                      organism = Penicillium emersonii
SEQUENCE: 169
atgcggaatc ttcttgctct tgcaccggcc gcgctgcttg tcggcgcagc ggaagcgcag     60
caatccctct ggggacaatg tgagtagctc ctaaacgtct cttgaggga ttatgtctga     120
ctgctcaggc ggcgggagtt cgtggactgg cgcaacgagc tgtgctgctg gagcgacgtg   180
cagcacgatc aatccttgta cgtctgctaa cgataattc tgcattgttg acttgctaac    240
tgcgtagact acgcacaatg cgtccctgca acggccactc cgaccacgct gacgacaacg   300
acaaaaccaa cgtccaccgg cggcgctgct ccaacgactc ctcctccgac aacgactgga   360
acaacgacat cgcccgtcgt caccaggccc gcgtctgcct ccggcaaccc gttcgaaggc   420
taccagctct acgccaatcc gtactatgcg tcggaggtga ttagtttggc aattccctcg   480
ctgagcagcg agctggttcc caaggcgagc gaggtggcca aggtgccgtc tttcgtctgg   540
ctgtaagtaa attcccccag gctgtcattt cccttactg atcttgtcca gcgaccaagt   600
cgccaaggtg cccagcatgg gtgactatct gaaagacatc cagtcgcaga acgcagccgg   660
cgcagacccc ccgattgcag gcatctttgt cgtctacgac ctgcctgacc gtgactgcgc   720
ggctgcagcag agcaatggcg agttctccat cgccaacaac ggcgtcgccc tgtacaagca   780
gtacatcgac tcgatccgcg agcagctgac gacctattca gatgtgcaca ccatcctggt   840
catcggtagt tccagtcctc ttctgtgatg ttgatgaaaa atactgactg actcccgcag   900
aacccgacag cctggccaac ctggtcacca acctgaacgt gccgaaatgc gcaaatgccc   960
aggacgccta tctcgaatgc atcaactacg ccatcaccca gctcgatctg cccaacgtgg  1020
ccatgtatct tgatgctggt gagtcctcac atacaagtga ataaaaataa aactgatgca  1080
gtgcaggaca cgccggatgg ctaggctggc aagccaacct cgcccccgcc gcccagctgt  1140
ttgcctcggt gtacaagaac gcctcctcgc cggcatccgt ccgcggtctc gccaccaacg  1200
tgccaactac caacgcctgg tcgatcagcg cgtgcccgtc gtacacgcag ggcgactcca  1260
actgcgacga ggaggactac gtgaatgccc tggggccgct gctccaggaa cagggattcc  1320
cggcgtactt tatcactgat acatgtaagc ttaccccag aaccccctcca tagaaggtca   1380
atctaacggt aatgtacagc cgcaatggc gtccaaccca ccaagcaaag ccaatggggc   1440
gactggtgca acgtcatcgg cacgggcttc ggcgtccggc ccacgaccga caccggcaat  1500
cctctcgagg acgccttcgt ctgggtcaag ccgggtggag acgcgatgg cacgtccaac  1560
acgacctctc gcggtacgca ctaccactga gggctgagcg atgcgctgca gccggcgccg  1620
gaggcgggga cttggttcca ggtatgatgc gccttcgtat tagcaattac gatacatgtg  1680
catgctgacc atgcgacagg cgtactttga gcagttgctc acgaatgcta acccgctgtt  1740
ctag                                                                1744

SEQ ID NO: 170        moltype = AA  length = 459
FEATURE               Location/Qualifiers
source                1..459
                      mol_type = protein
                      organism = Penicillium emersonii
```

SEQUENCE: 170
```
MRNLLALAPA ALLVGAAEAQ QSLWGQCGGS SWTGATSCAA GATCSTINPY YAQCVPATAT   60
PTTLTTTTKP TSTGGAAPTT PPPTTTGTTT SPVVTRPASA SGNPFEGYQL YANPYYASEV  120
ISLAIPSLSS ELVPKASEVA KVPSFVWLDQ AAKVPSMGDY LKDIQSQNAA GADPPIAGIF  180
VVYDLPDRDC AAAASNGEFS IANNGVALYK QYIDSIREQL TTYSDVHTIL VIEPDSLANL  240
VTNLNVPKCA NAQDAYLECI NYAITQLDLP NVAMYLDAGH AGWLGWQANL APAAQLFASV  300
YKNASSPASV RGLATNVANY NAWSISPCPS YTQGDSNCDE EDYVNALGPL LQEQGFPAYF  360
ITDTSRNGVQ PTKQSQWGDW CNVIGTGFGV RPTTDTGNPL EDAFVWVKPG GESDGTSNTT  420
SPRYDYHCGL SDALQPAPEA GTWFQAYFEQ LLTNANPLF                        459
```

```
SEQ ID NO: 171          moltype = DNA   length = 1701
FEATURE                 Location/Qualifiers
source                  1..1701
                        mol_type = genomic DNA
                        organism = Penicillium pinophilum
```
SEQUENCE: 171
```
atgttgcgat atctttccac cgttgccgcc acggcaattc tgaccggagt tgaagctcag    60
caatcagtct ggggacaatg taagaagtct cttgagaagc ttcaagttaa gaataatcca   120
cggttgttga caatcttgga aacatatagg tggcggccaa ggctggtctg gcgcgacttc   180
atgcgccgcc ggttctacgt gcagcactct aaacccttgt aaggtgccag ctgattagta   240
tgttggctct aattcctgac gccaattgtt cattagacta cgcacaatgt atccctggta   300
ccgctacttc aactacattg gtgaaaacaa cgtcttctac gacgtcgga acgacatcgc    360
cgccgacaac aaccacgacg aaagctagta ccactgctac taccactgcc gctgcatccg   420
gaaaccctttt ctctggttac cagctttatg ccaatccgta ctattcttca gaagtacaca   480
ctcttgccat cccatctttg actggctcgc tcgctgctgc tgctaccaaa gctgccgaga   540
tccctcatt tgtctggctg tgagtgttcc cgagaacatc cattgagtg atataaaatat    600
atgcatggag atttcctaaa cctctatagt gacacggcag ccaaagtgcc tacaatgggc   660
acctacttgg ccaacattga ggctgcaaac aaggctggcg ccagcccacc tattgccggt   720
atcttcgttt tctatgaccc tgcctgaccgt gactgtgcag ctgctgcaag taatggcgaa   780
tacactgtag caaacaacgg tgttgcaaac tacaaggctt acatcgacag cattgtgcca   840
cagttgaaag cttatcccga tgtgcacaca atccttatca ttggtacgtt ctctactatt   900
gggtcttgaa gaggtactct tgagagaaat ttgtgtctaa caaatcgccg atctacagag   960
cctgatagtc tcgccaacat ggtcaccaat ctgtctacag ccaagtgtgc tgaggctcaa  1020
tctgcatact atgagtgcgt caactacgca ttgatcaacc tcaacttggc caacgtggcc  1080
atgtacattg atgctggtca tgctggttgg ctcggatggt ctgcgaatct ttcaccagcc  1140
gctcaactct tcgcaacagt ctataagaat gcaagtgccc ctgcatctct tcgtggattg  1200
gccaccaacg ttgccaacta caacgcttgg tcgatcagca gcccaccctc atacacatct  1260
ggcgactcca actacgacga aaagctctac atcaacgctt gtctcctct cctgacatct   1320
aacggctggc ctaacgctca cttcatcatg gatacttgta agtgtttgc ggatgaatca   1380
agtgctcggt ttactaactg aacttcttta gcccgaaacg tgttcaacc gactaagcag  1440
caggcatggg gtgactggtg caatgtgatc ggaaccggct tcggtgttca accgacaaca  1500
aatactggta acccacttga ggatgccttt gtctgggtca agccaggtgg tgaaagtgat  1560
ggtacatcaa acagttcgc tactcgttac gatttccatt gcggctacag tgatgcactt  1620
caacccgccc cgaggctgg gacttggttc caagcatact ttgtccagct tttgacaaat  1680
gccaacccag ctttggtcta g                                            1701
```

```
SEQ ID NO: 172          moltype = AA   length = 457
FEATURE                 Location/Qualifiers
source                  1..457
                        mol_type = protein
                        organism = Penicillium pinophilum
```
SEQUENCE: 172
```
MLRYLSTVAA TAILTGVEAQ QSVWGQCGGQ GWSGATSCAA GSTCSTLNPY YAQCIPGTAT   60
STTLVKTTSS TSVGTTSPPT TTTTKASTTA TTTAAASGNP FSGYQLYANP YYSSEVHTLA  120
IPSLTGSLAA AATKAAEIPS FVWLDTAAKV PTMGTYLANI EAANKAGASP PIAGIFVVYD  180
LPDRDCAAAA SNGEYTVANN GVANYKAYID SIVAQLKAYP DVHTILIIEP DSLANMVTNL  240
STAKCAEAQS AYYECVNYAL INLNLANVAM YIDAGHAGWL GWSANLSPAA QLFATVYKNA  300
SAPASLRGLA TNVANYNAWS ISSPPSYTSG DSNYDEKLYI NALSPLLTSN GWPNAHFIMD  360
TSRNGVQPTK QQAWGDWCNV IGTGFGVQPT TNTGDPLEDA FVWVKPGGES DGTSNSSATR  420
YDFHCGYSDA LQPAPEAGTW FQAYFVQLLT NANPALV                           457
```

```
SEQ ID NO: 173          moltype = DNA   length = 1233
FEATURE                 Location/Qualifiers
source                  1..1233
                        mol_type = genomic DNA
                        organism = Aspergillus fumigatus
```
SEQUENCE: 173
```
atgaaattcg gtagcattgt gctcattgct gctgcggcag gcttcgcggt ggctgctcct    60
gcaaagagag cttcggtatt tcaatgttgg ttccctgtgg taaagttgga ttaaaaggac   120
actaacatac tgcagggttc ggaagcaatg agtctggagc agagtttggc gaaaatacca   180
ttcctggctc ttatgtatgt tgtgcatctg agagaagtat actgctgctg acaacatcaa   240
ggggaaagaa ttcatcttcc cggaccettc tacaatcagc acattgatcg ggaagggcat   300
gaacatcttc cggattcaat tcctcatgga gagactggtg ccaagctcta tgacaggctc   360
ctataacgag gagtacccttg ccaatctgac atcggtgga ttgagcagca gcatgttgga   420
ctgtatgagg ctgactcgac caggttgtgg acgctgtcac caaggcagga tcttatgcta   480
ttttggaccc acacaacttt ggcagatagt gagtaatgcc cggcatactg tggacttgtt   540
ctaacgccac tcagcaatgg tcagattatc tccagcaccg acgacttcaa gaccttctgg   600
cagaatctgc tggaaagtt caagtccaac aatctctca tctttgatac tagtatggct   660
aactcatttg gttctgatga gcttcactga ccccggatgt tagacaatga gatcacgac   720
```

```
atggaccaga cactggtact gaacctcaac caggccgcta tcaacggtat ccgcgctgca    780
ggagccacct cgcaatacat ctttgtggag ggcaactcct ggaccggcgc ctggacctgg    840
gccgacgtca atgacaacct gaaggctctg accgaccccc aggataagat cgtctacgag    900
atgcaccagt atctcgactc ggatggatcc ggcaccgcgg agagctgcgt gtctaccacg    960
attggtaagg agcgggtttc ggccgcaaca aagtggctca ataacgcaag gttggc       1020
atcattggtg agttcgctgg tggcgtcaat gatcagtgcc ggaccgctat ttcaggaatg   1080
ctggagtact tggctcagaa cacagacgtg tggaagggag ctctctggtg ggcggctggc   1140
ccctggtggg gaaactatat gttcaacatg gagcctccga gcggtgcagc ttatgtgggc   1200
atgttggaca tcttggagcc ctacctgggt tga                                1233

SEQ ID NO: 174          moltype = AA  length = 329
FEATURE                 Location/Qualifiers
source                  1..329
                        mol_type = protein
                        organism = Aspergillus fumigatus
SEQUENCE: 174
MKFGSIVLIA AAAGFAVAAP AKRASVFQWF GSNESGAEFG ENTIPGSYGK EFIFPDPSTI     60
STLIGKGMNI FRIQFLMERL VPSSMTGSYN EEYLANLTSV VDAVTKAGSY AILDPHNFGR    120
YNGQIISSTD DFKTFWQNLA GKFKSNNLVI FDTNNEYHDM DQTLVLNLNQ AAINGIRAAG    180
ATSQYIFVEG NSWTGAWTWA DVNDNLKALT DPQDKIVYEM HQYLDSDGSG TAESCVSTTI    240
GKERVSAATK WLKDNGKVGI IGEFAGGVND QCRTAISGML EYLAQNTDVW KGALWWAAGP    300
WWGNYMFNME PPSGAAYVGM LDILEPYLG                                      329

SEQ ID NO: 175          moltype = DNA  length = 1381
FEATURE                 Location/Qualifiers
source                  1..1381
                        mol_type = genomic DNA
                        organism = Neosartorya fischeri
SEQUENCE: 175
atgaaggctt cgactattat ctgtgcactt ctccccttg ctttggcggt gccgaatgcg      60
aggcggggctt ctgggtttgt ttgtatgttt ccctttcttc tcttcatcgc agaagctgac   120
ggtgagatag ggtttggaag taacgagtct ggcgccgagt ttggagagac caagctcccg    180
ggcgtgctgg ggacggatta tatctggccc gatgcgtcga ctatcaagac tctgcatgat    240
gccgggatga acatcttccg tgttgcgttc cggatggaga ggcttatccc ggataagtga    300
acgggggactc cagatgcgac gtacatgaat gatctcaagg cggttggtct gctgatctgg    360
gtgttgaggc gtcgctgacg aggatagact gtcaatgcga ttacgagtct gggggcgtat    420
gcggtgattg atccccataa ctatggaaga tagtgagttt gttgctgcct tgcttctgat    480
gtgagacagt gctgacggca cagctacggg aacatcatct cgtcgactga cgactttgct    540
ggttctggaa agaccgtggc tgcccagttt gcgtccaatg accatgtcat ttttgacacc    600
agtatgtttc catcagtttt gaaatgaagg acaagctgac ggaacagaca atgagtacca    660
tgatatggac cagacgctcg ttctcaacct caaccaggct gccatcaacg ccatccgtgc    720
tgcaggcgcc acctcgcagt acattttgt cgagggcaac tcgtggtccg cgcgtggac     780
ctggaccaac gtcaacgaca acctcaaggc cctcaccgac cctcaggata agatcgtcta    840
cgagatgcac cagtatctcg actcagacgg gtccggcacg tcggccacct cgtgagctc    900
caccatcggc caggagcgcg tgcagtccgg cacacagtgg ttgaagacca atggtaagaa    960
aggtatcata ggcgagttcg ctggaggccc aacagcgtg tgccagtccg ctgtcacagg   1020
catgcttgac tactgtctg ccaactcgga tgtgtggatg ggcgcagcat ggtgggccgc   1080
tggtccctgg tggcagatt atatgttcag catggagccg ccgtctggca ctggctatca   1140
gaactatctc tcgttgttga agccgtattt cgtcggtggt tcgggtggta accctccaac   1200
gaccaccacg acaactacca gcaagcctac tacgaccact accacggctg gaaccctggg   1260
cggcaccggg gtcgcacagc actggggcca gtgtggtgga attggatgga agggtccgac   1320
tgcctgcgcc acgccatata cctgccagaa gctgaacgac tactactctc aatgcctgta   1380
g                                                                   1381

SEQ ID NO: 176          moltype = AA  length = 412
FEATURE                 Location/Qualifiers
source                  1..412
                        mol_type = protein
                        organism = Neosartorya fischeri
SEQUENCE: 176
MKASTIICAL LPLALAVPNA RRASGFVCMF PFLLFIAEAD GEIGFGSNES GAEFGETKLP     60
GVLGTDYIWP DASTIKTLHD AGMNIFRVAF RMERLIPDKM TGTPDATYMN DLKATVNAIT    120
SLGAYAVIDP HNYGRYYGNI ISSTDDFAAF WKTVAAQFAS NDHVIFDTNN EYHDMDQTLV    180
LNLNQAAINA IRAAGATSQY IFVEGNSWSG AWTWTNVNDN LKALTDPQDK IVYEMHQYLD    240
SDGSGTSATC VSSTIGQERV QSATQWLKTN GKKGIIGEFA GGPNSVCQSA VTGMLDYLSA    300
NSDVWMGAAW WAAGPWWADY MFSMEPPSGT GYQNYLSLLK PYFVGGSSGN PPTTTTTTS    360
KPTTTTTTAG NPGGTGVAQH WGQCGGIGWK GPTACATPYT CQKLNDYYSQ CL            412

SEQ ID NO: 177          moltype = DNA  length = 2940
FEATURE                 Location/Qualifiers
source                  1..2940
                        mol_type = genomic DNA
                        organism = Aspergillus aculeatus
SEQUENCE: 177
atgaagctca gttggcttga ggcggctgcc ttgacggctg cttcagtcgt cagcgctgta     60
tgttggctttt ttttgaccctc ctcgctgctt ctagatattt ggtgtgaggc tgacaattcg   120
tgctctacag gatgaactgg cgttctctcc tcctttctac cctctccgt gggccaatgg    180
ccagggagag tgggcggaag cctaccacgc tgcagtggcc attgtatccc agatgactct    240
ggatgagaag gtcaacctga ccaccggaac tgggtaatga cactacagct gctgcgagat    300
```

```
gaatcgcctg ctaacgagct tctagatggg agctggagaa gtgcgtcggt cagactggtg    360
gtgtcccaag gtaggacccc cggataaaaa catgtgttca gttggctaac cgacgatcgc    420
tgtctagact gaacatcggt ggcatgtgtc ttcaggacag tcccttggga attcgtgata    480
gtaagtcttg atacaactgg agctcggccg ttgacactct tgctcacaat gtgttctgca    540
ggtgactaca attcggcttt ccctgctggt gtcaacgttg ctgcgacatg ggacaagaac    600
cttgcttatc tacgtggtca ggctatgggt caagagttca gtgacaaagg aattgatgtt    660
caattgggac cggccgcggg tccctcggc aggagccctg atggaggtcg caactgggaa    720
ggtttctctc cagacccggc tcttactggt gtgctctttg cggagacgat taagggtatt    780
caagacgctg gtgtcgtggc gacagccaag cattacattc tcaatgagca agagcatttc    840
cgccaggtcg cagaggctgg gggctacgga ttcaatatct ccgacacgat cagctctaac    900
gttgatgaca agaccattca tgaaatgtac ctctggccct cgcggatgc cgttcgcgcc    960
ggcgttggcg ccatcatgtg ttcctacaac cagatcaaca acagctacgg ttgccagaac   1020
agttacactc tgaacaagct tctgaaggcc gagctcggct ccagggcttt gtgatgtct   1080
gactggggtg ctcaccacag tggtgttggt tctgcttttgg ccggcttgga tatgtcaatg   1140
cctggcgata tcaccttcga ttctgccact agtttctggg gtaccaacct gaccattgct   1200
gtgctcaacg gtaccgtccc gcagtggcgc gttgacgaca tggctgtccg tatcatggct   1260
gcctactaca aggttggccg cgaccgcctg taccagccgc ctaacttcag ctcctggact   1320
cgcgatgaat acggcttcaa gtatttctac ccccaggaag gcccctatga gaaggtcaat   1380
cactttgtca atgtgcagcg caaccacagc gaggttattc gcaagttggg agcagacagt   1440
actgttctac tgaagaacaa caatgccctg ccgctgaccg gaaaggagcg caaagttgcg   1500
atcctgggtg aagatgctgg atccaactcg tacggtgcca atggctgctc tgaccgtggc   1560
tgtgacaacg gtactccttgc tatggcttgg ggtagcgcca gtgccgaatt cccatatctc   1620
gtgacccctg agcaggctat tcaagccgag gtgctcaagc ataagggcag cgtctacgcc   1680
atcacggaca actgggcgct gagccaggtg gagaccctcg ctaaacaagc caggtaagtt   1740
ctgtcgtcca tacattggag gtatatgttt tcagtgaact gacaagtgtc tccgtagtgt   1800
ctctcttgta tttgtcaact cggacgcggg agagggctat atctccgtgg acggaaacga   1860
gggcgaccgc aacaacctca ccctctgaa gaacggcgca aacctcatca aggctgctgc   1920
aaacaactgc aacaacacca tcgttgtcat ccactccgtt ggacctgttt tggttgacga   1980
gtggtatgac caccccaacg ttactgccat cctctgggcg ggcttgccag gccaggagtc   2040
tggcaactcc ttggctgacg tgctctacgg ccgcgtcaac ccgggcgcca aatctccatt   2100
cacctggggc aagacgaggg aggcgtacgg ggattacctt gtccgtgagc tcaacaacgg   2160
caacggagct cccaagatg atttctcgga aggtgttttc attgactacc gcggattcga   2220
caagcgcaat gagacccga tctacgagtt cggacatggt ctgagctaca ccactttcaa   2280
ctactctggc cttcacatcc aggttctcaa cgcttcctcc aacgctcaag tagccactgg   2340
gactggccgc gctccacct tcggacaagt cggcaatgcc tctgactacg tgtaccctga   2400
gggattgacc agaatcagca agttcatcta tccctggctt aattcacag acctgaaggc   2460
ctcatctggc gacccgtact atggagtcga caccgcggag cacgtgcccg agggtgctac   2520
tgatggctct ccgcagcccg ttctgcctgc cggtggtggc ttcggtggta acccgcgcct   2580
ctacgatgag ttgatccgtg tttcggtgac agtcaagaac actggtcgtg ttgccggtga   2640
tgctgtgcct caattggtaa ttagatcctc gtgcagtatt ggttccagat gctaaccgct   2700
tgctagtatg tttcccttgg tggacccaat gagcccaagg ttgtgttgcg caaattcgac   2760
cgcctcaccc tcaagccctc cgaggagacg gtgtggacga ctaccctgac ccgccgcgat   2820
ctgtctaact gggacgttgc ggctcaggac tgggtcatca cttcttccc gaagaaggtc   2880
catgttggta gctcttcgcg tcagctgccc cttcacgcgc cgctcccgaa ggtgcaataa   2940

SEQ ID NO: 178          moltype = AA  length = 860
FEATURE                 Location/Qualifiers
source                  1..860
                        mol_type = protein
                        organism = Aspergillus aculeatus
SEQUENCE: 178
MKLSWLEAAA LTAASVVSAD ELAFSPPFYP SPWANGQGEW AEAYQRAVAI VSQMTLDEKV    60
NLTTGTGWEL EKCVGQTGGV PRLNIGGMCL QDSPLGIRDS DYNSAFPAGV NVAATWDKNL   120
AYLRGQAMGQ EFSDKGIDVQ LGPAAGPLGR SPDGGRNWEG FSPDPALTGV LFAETIKGIQ   180
DAGVVATAKH YILNEQEHFR QVAEAAGYGF NISDTISSNV DDKTIHEMYL WPFADAVRAG   240
VGAIMCSYNQ INNSYGCQNS YTLNKLLKAE LGFQGFVMSD WGAHHSGVGS ALAGLDMSMP   300
GDITFDSATS FWGTNLTIAV LNGTVPQWRV DDMAVRIMAA YYKVGRDRLY QPPNFSSWTR   360
DEYGFKYFYP QEGPYEKVNH FVNVQRNHSE VIRKLGADST VLLKNNNALP LTGKERKVAI   420
LGEDAGSNSY GANGCSDRGC DNGTLAMAWG SGTAEFPYLV TPEQAIQAEV LKHKGSVYAI   480
TDNWALSQVE TLAKQASVSL VFVNSDAGEG YISVDGNEGD RNNLTLWKNG DNLIKAAANN   540
CNNTIVVIHS VGPVLVDEWY DHPNVTAILW AGLPGQESGN SLADVLYGRV NPGAKSPFTW   600
GKTREAYGDY LVRELNNGNG APQDDFSEGV FIDYRGFDKR NETPIYEFGH GLSYTTFNYS   660
GLHIQVLNAS SNAQVATETG AAPTFGQVGN ASDYVYPEGL TRISKFIYPW LNSTDLKASS   720
GDPYYGVDTA EHVPEGATDG SPQPVLPAGG GFGGNPRLYD ELIRVSVTVK NTGRVAGDAV   780
PQLYVSLGGP NEPKVVLRKF DRLTKPSEE TVWTTTLTRR DLSNWDVAAQ DWVITSYPKK   840
VHVGSSSRQL PLHAALPKVQ                                               860

SEQ ID NO: 179          moltype = DNA  length = 2935
FEATURE                 Location/Qualifiers
source                  1..2935
                        mol_type = genomic DNA
                        organism = Aspergillus kawachii
SEQUENCE: 179
atgaggttca ctttgattga ggcggtggct ctcactgctg tctcgctggc cagcgctgta    60
cgtgccgttc ctttgtcctg tgaattgcaa ttgtgctcaa ttagattcac ttgtttgtac   120
catcatcgct gacaatggtc tattcatagg atgaattggc ttactcccca ccgtattacc   180
catcccttg ggccaatggc cagggcgact gggcgcaggc ataccagcgc gctgttgata   240
ttgtctcgca gatgacattg gctgagaagg tcaatctgac cacaggaact gggtaggact   300
tacaaggcgc aatctgtatg ctccggctaa caacctctag atgggaattg gagctatgtg   360
```

```
ttggtcagac tggcggggtt ccccggtagg tttgaaaaga atgtcgagac agggggcatt    420
cattgattaa cggcgacaga ttgggagttc cggaatgtg tttacaggat agccctctgg     480
gcgttcgcga ctgtaagcca tctgctgttg ttaggctttg atgctcttac tgacacgtcg    540
cagccgacta caactctgct ttcccttccg gtatgaacgt ggctgcaacc tgggacaaga    600
atctggcata cctccgcggc aaggctatgg gtcaggaatt tagtgacaag ggtgccgata    660
tccaattggg tccagctgcc ggccctctcg gtagaagtcc cgacggtggt cgtaactgga    720
agggcttctc ccccgacccg gccctaagtg tgtgctctt tgcagagacc atcaagggta     780
tccaagatgc tggtgtggtc gcgacggcta agcactacat tgcctacgag caagagcatt    840
tccgtcaggc gcctgaagcc caaggttatg gatttaacat ttccgagagt ggaagcgcga    900
acctcgacga taagactatg cacgagctgt acctctggcc cttcgcggat gccatccgtg    960
cgggtgctgg cgctgtgatg tgctcctaca accagatcaa caacagctat ggctgccaga   1020
acagctacac tctgaacaag ctgctcaagg ccgagctggg tttccagggc tttgtcatga   1080
gtgattgggc ggctcaccat gctggtgtga gtggtgcttt ggcaggattg gatatgtcta   1140
tgccaggaga cgtcgactac gacagtggta cgtcttactg gggtacaaac ctgaccgtta   1200
gcgtgctcaa cggaacggtg ccccaatggc gtgttgatga catggctgtc cgcatcatgg   1260
ccgcctacta caaggtcggc cgtgaccgtc tgtggactcc tcccaacttc agctcatgga   1320
ccagagatga atacggctac aagtactact atgtgtcgga gggaccgtac gagaaggtca   1380
accactacgt gaacgtgcaa cgcaaccaca gcgaactgat ccgccgcatt ggagcggaca   1440
gcacggtgct cctcaagaac gacggcgctc tgccttttgac tggtaaggag cgcctggtcg   1500
cgcttatcgg agaagatgcg ggctccaacc cttatggtgc caacggctgc agtgaccgtg   1560
gatgcgacaa tggaacattg gcgatgggct ggggaagtgg tactgccaac ttcccatacc   1620
tggtgacccc cgagcaggcc atctcaaacg aggtgctcaa caagaat ggtgtattca      1680
ccgccaccga taactgggct atcgatcaga ttgaggcgct tgctaagacc gccaggtaag   1740
aagatctcca attcttttgt ttcttgtgca atggatgctg acaacgtgct agtgtctctc   1800
ttgtctttgt caacgccgac tctggcgagg ttacatcaa tgtcgacgga aacctgggtg    1860
accgcaggaa cctgaccctg tggaggaacg gcgataatgt gatcaaggct gctgctagca   1920
actgcaacaa caccattgtt atcattcact ctgtcggccc agtcttggtt aacgaatggt   1980
acgacaaccc caatgttacc gctattctct ggggtggtct gccccggtcag gagtctggca   2040
actctcttgc cgacgtcctc tatggccgtg tcaaccccgg tgccaagtcg cccttttacct   2100
ggggcaagac tcgtgaggcc taccaagatt acttggtcac cgagcccaac aacggcaatg   2160
gagccccca ggaagacttc gtcgagggcc tcttcattga ctaccgcgga ttcgacaagc    2220
gcaacgagac cccgatctac gagttcggct atggtctgag ctacaccact ttcaactact   2280
cgaaccttga ggtgcaggtt ctgagcgccc cgcgtacga gcctgcttcg ggtgagactg    2340
aggcagcgc aacttttgga gaggttggaa atgcgtcgaa ttacctctac cccgacggac    2400
tgcagaaaat caccaagttc atctaccct ggctcaacag taccgatctc gaggcatctt    2460
ctggggatgc tagctacgga caggactcct cggactatct tcccgaggga gccaccgatg    2520
gctctgcgca accgatcctg cctgctggtg cggtcctgg cggcaaccct cgcctgtacg    2580
acgagctcat ccgcgtgtcg gtgaccatca agaacaccgg caaggttgct ggtgatgaag    2640
ttccccaact ggtaagtaac agaagaaccg aacgatgtg aacaaagcta atcagtcgca     2700
gtatgttttcc cttggcggcc ccaacgagcc caagatcgtg ctgcgtcaat tcgagcgcat    2760
cacgctgcag ccgtcagagg agacgaagtg gagcacgact ctgacgcgcc gtgaccttgc    2820
aaactggaat gttgagaagc aggactggga gattacgtcg tatcccaaga tggtgtttgt    2880
cggaagctcc tcgcggaagc tgccgctccg ggcgtctctg cctactgttc actaa          2935

SEQ ID NO: 180       moltype = AA  length = 860
FEATURE              Location/Qualifiers
source               1..860
                     mol_type = protein
                     organism = Aspergillus kawachii
SEQUENCE: 180
MRFTLIEAVA LTAVSLASAD ELAYSPPYYP SPWANGQGDW AQAYQRAVDI VSQMTLAEKV     60
NLTTGTGWEL ELCVGQTGGV PRLGVPGMCL QDSPLGVRDS DYNSAFPSGM NVAATWDKNL   120
AYLRGKAMGQ EFSDKGADIQ LGPAAGPLGR SPDGGRNWEG FSPDPALSGV LFAETIKGIQ   180
DAGVVATAKH YIAYEQEHFR QAPEAQGYGF NISESGSANL DDKTMHELYL WPFADAIRAG   240
AGAVMCSYNQ INNSYGCQNS YTLNKLLKAE LGFQGFVMSD WAAHHAGVSG ALAGLDMSMP   300
GDVDYDSGTS YWGTNLTVSV LNGTVPQWRV DDMAVRIMAA YYKVGRDRLW TPPNFSSWTR   360
DEYGYKYYYV SEGPYEKVNH YVNVQRNHSE LIRRIGADST VLLKNDGALP LTGKERLVAL   420
IGEDAGSNPY GANGCSDRGC DNGTLAMGWG SGTANFPYLV TPEQAISNEV LKNKNGVFTA   480
TDNWAIDQIE ALAKTASVSL VFVNADSGEG YINVDGNLGD RRNLTLWRNG DNVIKAAASN   540
CNNTIVIIHS VGPVLVNEWY DNPNVTAILW GGLPGQESGN SLADVLYGRV NPGAKSPFTW   600
GKTREAYQDY LVTEPNNGNG APQEDFVEGV FIDYRGFDKR NETPIYEFGY GLSYTTFNYS   660
NLEVQVLSAP AYEPASGETE AAPTFGEVGN ASNYLYPDGL QKITKFIYPW LNSTDLEASS   720
GDASYGQDSS DYLPEGATDG SAQPILPAGG GPGGNPRLYD ELIRVSVTIK NTGKVAGDEV   780
PQLVSLGGP NEPKIVLRQF ERITLQPSEE TKWSTTLTRR DLANWNVEKQ DWEITSYPKM    840
VFVGSSSRKL PLRASLPTVH                                                860

SEQ ID NO: 181       moltype = DNA  length = 3062
FEATURE              Location/Qualifiers
source               1..3062
                     mol_type = genomic DNA
                     organism = Aspergillus clavatus
SEQUENCE: 181
atgaggttca gctggcttga ggtcgccgtg acggctgcct cattggccaa tgccaatgtt     60
tgtattcctc tgttcccttg gtatggtttg tgatccttgt tgaccatcgt atctgcatga    120
tcaggaatta gtctcttccc ctccatttta cccgtcgcct tggcaaatg gtcagggaga    180
atgggcggag gcgcatcaac gcgctgtcga gatcgtttct cagatgacac tcacagaaaa    240
agtcaacttg acaacgggca ctgggtacgt gatgcgaagg aatacttgga aaagatggt    300
tcaatacact gacactgtcc tccagttgga tgatggaaga atgcgttggt cagacaggca    360
gtgttcctcg tgagtttga tctacgtgcg atgtatcgta tctcttgacc gaacgctgag    420
```

```
acagtattgc agacttggta tcaactgggg tctttgcggt caagattccc ccctgggtat  480
ccgtttttgt aagctacgcc cccgatttct acccttcatt tgtgtccact ctgctaacgg  540
ttctgctatg cagccgacct caattcggct ttccctgctg gcatcaatgt tgcggcaaca  600
tgggataaga cgctcgcgta cctccgtggc aaggcaatgg gtgaagagtt caatgacaag  660
ggtatcgata tccaactggg cccggctgct ggtccccgtg ggaaatatcc cgatggtggt  720
cggatctggg aaggcttctc tcccgaccca gctcttactg gcgtgctttt cgcagagacc  780
atcaagggta ttcaggatgc tggcgtgatt gctactgcca agcattacat tctcaacgaa  840
caggagcagt tccgtcaggt tgcggaggcc cagggatacg gatataacat caccgagact  900
ctgagttcca atgtggatga taagactatg cacgaattgt atctctggtg agtagtgcag  960
cccatctttg gttgaaaacc aactgacttt ggagaaggcc attcgcagat gctgtgcgcg 1020
gtaagatctt ggaatatgcc ctggtccatc tcgtgttact aaccttcaca cagctggtgt 1080
gggcgctatc atgtgttcct acaaccgat caacaacagc tacggttgcc agaacagcca 1140
gactttgaac aagttgctga aggccgagct tggcttccag ggctttgtca tgagcgactg 1200
gagcgcccac cacagcggtg ttggcgctgc tctggctggc ttggacatgt cgatgcctgg 1260
cgacatttct tttgatgatg gtctctcttt ctggggtgcc aatatgacgg ttggtgtcct 1320
gaacgggacc atcccggcct ggcgcgtgga cgacatggct gtccgtatca tgacggctta 1380
ctacaaggtt ggacgcgatc gccttcgcgt tcccccaac ttcagctcgt ggactagaga 1440
cgaatacgga tacgagcatg ctgctgtttc cgagggagcc tggaaaaagg tcaatgatt  1500
tgtcaacgtg caacgcgacc atgcccagct gatccgcgag gttggctccg ctagcactgt 1560
gcttctcaag aacgttggtg cactcccgct aaccggcaaa gagcgtaaag tgggtatctt 1620
tggagaagat gctggctcga acccatgggg ccccaacggc tgcgaaaacc ggggctgcga 1680
caatgaacc cttgcgatgg cttggggtag cggtactgcc gagttccctt atctcgtgac 1740
accagagcag gcaatccaga gcgaggtcat caagaacggg ggcaatgtct tcccgtgac 1800
tcataacggc gcgctgaccc agatggcgaa tattgcctct caatcttcgt gagtgacctc 1860
tttcagatgc attccttctc agcttgaata ctaacggatc attggacagc gtctcgcttg 1920
tgtttgtcaa tgccgacgct ggagaaggat tcatcagtgt tgatggtaac attggtgacc 1980
gcaagaacct caccctttgg aagaatggcg aggaagtcat caagactgtg gctagccata 2040
gcaacaaac cgtcgttgtt atccacagtg tcggcccaat cctggtcgat gaatggcatg 2100
acaaccccaa catcacggct atcctctggg ccggcttgcc cggccaggag agcggcaact 2160
ccattgccga cgtgctttac ggccgtgtca accccagcgc caagaccct ttcacctggg 2220
gcaagacgcg cgaatcctac ggtgctcccc tggtcactaa gcctaacaat ggcaatggag 2280
ctccccagga tgatttcagc gaaggtgtct tcattgacta ccgttacttt gacaagcgta 2340
acgagacgcc ggtttatgaa ttcggcttcg gattgagcta cacctccttt ggctattctc 2400
accttcgcgt ccaacctctg aatggttcca ctttatgtcc ctgccaccggc acgactggac 2460
ctgcgccagc ttacggaagt atcggtagc ctgcggatta cttgttcccc gaggggctca 2520
agaggattac caagttcatc tatccatggc tgaactcgac cgacctcaag gcttcctctg 2580
cagacccgaa ctacggctgg gaggactccg agtacattcc cgaggctgct accgatggct 2640
ctcctcagcc tattctcaag gcgggcgtgt ctcctggtgg caatcccact ctttaccacg 2700
acttggtcaa ggtgtccgct accatcacca acacggtaac tgttgcgggc tacgaggttc 2760
ctcaactggt gagtgaccta gactactatt ccttgaggag aggcgcattt ccgctgacct 2820
gtatctagta tgtgtctctt ggtggaccca atgagcccg agtcgttctg cgcaagttcg 2880
accgcatcca cctcgcccc ggagagcaga aggtctggac cacaacgctg acgcgccgtg 2940
atctcgccaa ctgggacgtg aagcgcagg actgggtcat caccaagtat cccaagaggg 3000
tttacgtcgg aagctcctct cgaaagctcc cgctgagagc acctctgccc cgggtacagt 3060
aa                                                                3062

SEQ ID NO: 182         moltype = AA  length = 860
FEATURE                Location/Qualifiers
source                 1..860
                       mol_type = protein
                       organism = Aspergillus clavatus
SEQUENCE: 182
MRFSWLEVAV TAASLANANE LVSSPPFYPS PWANGQGEWA EAHQRAVEIV SQMTLTEKVN   60
LTTGTGWMME ECVGQTGSVP RLGINWGLCG QDSPLGIRFS DLNSAFPAGI NVAATWDKTL  120
AYLRGKAMGE EFNDKGIDIQ LGPAAGPLGK YPDGGRIWEG FSPDPALTGV LFAETIKGIQ  180
DAGVIATAKH YILNEQEQFR QVAEAQGYGY NITETLSSNV DDKTMHELYL WPFADAVRAG  240
VGAIMCSYNQ INNSYGCQNS QTLNKLLKAE LGFQGFVMSD WSAHHSGVGA ALAGLDMSMP  300
GDISFDDGLS FWGANMTVGV LNGTIPAWRV DDMAVRIMTA YYKVGRDRLR VPPNFSSWTR  360
DEYGYEHAAV SEGAWKKVND FVNVQRDHAQ LIREVGSAST VLLKNVGALP LTGKERKVGI  420
FGEDAGSNPW GPNGCENRGC DNGTLAMAWG SGTAEFPYLV TPEQAIQSEV IKNGGNVFPV  480
THNGALTQMA NIASQSSVSL VFVNADAGEG FISVDGNIGD RKNLTLWKNG EEVIKTVASH  540
SNNTVVIHS VGPILVDEWH DNPNITAILW AGLPGQESGN SIADVLYGRV NPSAKTPFTW  600
GKTRESYGAP LVTKPNNGNG APQDDFSEGV FIDYRYFDKR NETPVYEFGF GLSYTSFGYS  660
HLRVQPLNGS TYVPATGTTG PAPAYGSIGS AADYLFPEGL KRITKFIYPW LNSTDLKASS  720
ADPNYGWEDS EYIPEAATDG SPQPILKAGG APGGNPTLYH DLVKVSATIT NTGNVAGYEV  780
PQLYVSLGGP NEPRVVLRKF DRIHLAPGEQ KVWTTTLTRR DLANWDVEAQ DWVITKYPKR  840
VYVGSSSRKL PLRAPLPRVQ                                              860

SEQ ID NO: 183         moltype = DNA  length = 3032
FEATURE                Location/Qualifiers
source                 1..3032
                       mol_type = genomic DNA
                       organism = Thielavia terrestris
SEQUENCE: 183
atgaagcctg ccattgtgct ttccagcctg gcctgcagcg gtcttgctgc cgccagtgcg   60
gtcagctcgt cggacaaggt atggttaact tgcaggttcc gtcgcattcg tctcccctt  120
cattcccct ttttcccttc tcccgccgtt gcagcgaagg ctgcgagagt ccattcattg  180
gaccctcttg ttttatttc cgttccaagc atcgcccggg aagttcaccc gctgccaaga  240
ttcgctttag ccagattggc gagccgttg cgcgttgcaa cccgctcccg ccatgcggct  300
```

```
cagatctgcg gctcaatggc tcctcgtgct cccggcgaga agcagcggtc ttgctgacaa    360
aaactcccac cagccgcttg agaaaaggac actcgcaacg tcggaacctt tctacccgtc    420
gccatggatg aacccggacg ccgacggttg gaccgaggcc tatgcccgcg ctaaggagtt    480
cgtctcccgg atgacgctgc tggagaaggt caacctgacc acggggttg ggtaagtgcg     540
aaccgggcct gggaccgtcg aatgcgagct gtgctgatcg tcctgcagct gggaggcgga    600
gcagtgcgtc ggccaggtgg cgccattcc tcgcctgggc ctgcggagct tgtgcatgca     660
ggactctccg ctcggtgtcc gggggaccga cttcaactcc gggttcctt ccggccagac     720
ggcggccgcc accttcgatc gcggcctgat ctaccggcgc ggctatgcca tgggccagga    780
ggccagggc aagggagtca atgtcctgct cggacctgtt gccggcccc ttggacgtgg      840
ccctaccggc ggtcggaact gggaagggtt ctcccctgac cctgttctca ccggcgtggg    900
catgccgag tccatcaagg catccaaga cgccggcacg attgcttgtg cgaagcactt      960
tattggcaac gagcaaggtg agccgcgatt gcagtcccgg ggctttccga gaggaagaac   1020
gtgctaacag acgtgcagag cacttcaggc aagtggggga ggcgcaaggt tacggggttca  1080
acatcagcga ggcctgtcg tccaacattg acgacaagac cctgcacgag ctctacctct    1140
ggccgtttgc ggacgccgtg agggccggc tcggctccgt catgtgctcg taccagcagc    1200
tcaacaactc gtacagctgc cagaactcca agctcctgaa tggcctgctc aagggcgaac   1260
tcggttttcca gggcttcgtc atgagcgatt ggcaggccca gcacacgggc gccgcaagcg  1320
ctgttgccgg cctcgacatg accatgccgg gagacaccga gttcaacacg ggcgggagct   1380
actggggcgc caacctgacg ctcgcggtgc tcaacggcac cgtccccgcc taccgcatcg   1440
acgacatggc catgcgcatc atggccgcct tcttcaaggt caacaaggac atcaagctgg   1500
accccatcaa cttctccttc tggaccctgg acacgtacgg cccgattcac tgggcggcgc   1560
agacgggcta ccagcagatc aactaccacg tggatgtgcg agccgaccac ggcagccgtta  1620
tccgggagat cggcgccaag ggaaccgtgc tcctcaagaa caccggctct ctgcccttga   1680
agaagccgaa attcctggcc gtgattggcg aggacgccgg cccaacacc agcgggccga    1740
actcttgctc cgacagggga tgtgacaatg cactctcgc catgggctgg ggttccggca    1800
ccgccaactt cccgtacgtc gtcacgcccg atgccgcgt gcaggcgcag gcctccagg    1860
acggttcgcg ctacgagagc atcctgtcca actatgcgac atcgcaaata aaggctcttg   1920
tgtcacaagc caacgtgaca gcaatcgtct ttgtcaacgc cgactcgggc gagggctaca   1980
tcaatgtgga cggaaacatg ggcgaccgga gaaacctgac gctgtggaag gatggcgacg   2040
cgctggtcaa gaacgtggcc agctggtgct ccaacaccat cgtcgtgatc cattcccgg    2100
gcccggttct gctgaccgag tggtacaaca gccccaacgt taccgctatc ctctgggccg   2160
gtctccccgg ccaagagtcc ggcaactcga tcgccgacgt tctgtacggc agggtcaacc   2220
ctgccgcgcg gtcgccgttc acgtgggcc caacccgcga gagttacggg accgatgttc   2280
tctacacgcc gaacaacggc aacggcgcgc gcaggacga cttcaccgag ggcgtgttca   2340
tcgactaccg ctactttgac aagaccaact cgtccgtcat ttacgagttc ggccacggcc   2400
tcagctacac cacgtttgag tacagcaaca tccgggtaca gaagtcgaac gcgggcaagt   2460
acgagcccac gacgggcaag acctcgcccg cgccaccctt tggcaacttc tcgaccaacc   2520
tcaaagacta cgtgttcccg agccacgagt tcccttacgt ttacgagtac atctatcctt   2580
acctcaacac gaccgacccc aaggcgcct cggcgacg aactacggc cagacgccgg       2640
acaagttcct cccgccgcac gcgaccgact cgtcggccca gcctctgctg cgctcgtcgg   2700
gcaagttactc gccgggcggc aaccggcagt tgtacgacgt catgtacacg atcacggccg   2760
acatcaagaa cacgggctcg atcgtcggcg aggaggtgcc gcagctgtac gtcgcgctgg   2820
gcgggccgga cgacccccaag gtgcagctgc gcgactttga ccgcatccgc atcgacccgg   2880
gcaagacggc gcagttccgc ggcacgctga cccgcaggga cctgagcaac tgggatacga   2940
cgctgcagga ctgggtcatt agcaagtaca agaagacggc gtatgtgggg aggagcagcc   3000
ggaagctgga cttgagcatt gagttgccgt ga                                 3032
SEQ ID NO: 184          moltype = AA   length = 872
FEATURE                 Location/Qualifiers
source                  1..872
                        mol_type = protein
                        organism = Thielavia terrestris
SEQUENCE: 184
MKPAIVLSSL ACSGLAAASA VSSSDKPLEK RTLATSEPFY PSPWMNPDAD GWTEAYARAK    60
EFVSRMTLLE KVNLTTGVGW EAEQCVGQVG AIPRLGLRSL CMQDSPLGVR GTDFNSGFPS   120
GQTAAATFDR GLIYRRGYAM GQEARGKGVN VLLGPVAGPL GRAPTGGRNW EGFSPDPVLT   180
GVGMAESIKG IQDAGTIACA KHFIGNEQEH FRQVGEAQGY GFNISEALSS NIDDKTLHEL   240
YLWPFADAVR AGVGSVMCSY QQLNNSYSCQ NSKLLNGLLK GELGFQGFVM SDWQAHTGA    300
ASAVAGLDMT MPGDTEFNTG RSYWGANLTL AVLNGTVPAY RIDDMAMRIM AAFFKVNKDI   360
KLDPINFSFW TLDTYGPIHW AAQTGYQQIN YHVDVRADHG SLIREIGAKG TVLLKNTGSL   420
PLKKPKFLAV IGEDAGPNTS GPNSCSDRGC DNGTLAMGWG SGTANFPYVV TPDAALQAQA   480
LQDGSRYESI LSNYATSQIK ALVSQANVTA IVFVNADSGE GYINVDGNMG DRKNLTLWKD   540
GDALVKNVAS WCSNTIVVIH SPGPVLLTEW YNSPNVTAIL WAGLPGQESG NSIADVLYGR   600
VNPAARSPFT WGPTRESYGT DVLYTPNNGN GAPQDDFTEG VFIDYRYFDK TNSSVIYEFG   660
HGLSYTTFEY SNIRVQKSNA GKYEPTTGKT SPAPTFGNFS TNLKDYVFPS HEFPYVYEYI   720
YPYLNTTDPK AASGDANYGQ TADKFLPPHA TDSSAQPLLR SSGKNSPGGN RQLYDVMYTI   780
TADIKNTGSI VGEEVPQLYV ALGGPDDPKV QLRDFDRIRI DPGKTAQFRG TLTRRDLSNW   840
DTTLQDWVIS KYKKTAYVGR SSRKLDLSIE LP                                 872
SEQ ID NO: 185          moltype = DNA   length = 2793
FEATURE                 Location/Qualifiers
source                  1..2793
                        mol_type = genomic DNA
                        organism = Penicillium oxalicum
SEQUENCE: 185
atgaggagct caacgacggt tctggccttt gtgtcatacg ggagttttgg gattgcggca     60
gcgaagccca tacaagagca caaggtatga acgttttctt ttaagggaga acgcgagata   120
taacgattcg agagtaacgg gcactgacca tttttgttctc tcaaagcccg agcttctgaa   180
tagctttcac ggctttcaga ttgaagagcc gtattcgccg ccgttttatc cctcgccatg   240
```

-continued

```
gatgaatcct cgtgctgaag gctgggagga tgcgtatcag aaggcgcttg catttgtctc    300
tcaactgacg ttactcgaga aggtcaatct gacgacgggt gttgggtgag tgattgccct    360
tttcctctat gatctgtgcg acagtgggct gaacatgttc aaagttggga aaacggacca    420
tgtgtaggaa ataccggatc ggtccctcgc cttggcttca aggggctttg cttgcaagac    480
tctccctcaag gtgtgagatt tgccgactat gcatctgctt tcacgtccag tcagatggct    540
gctgccacat ttgacaagac ggttctttat gagcgtggtg ttgccatggc tcaagagcac    600
aagggcaagg gcatcacggt gcaactgggc ccgtcgctg gcctttggg ccgcgccct     660
gaaggaggcc gaaactggga aggattctcg cccgatccg tcctgaacgg cattgcgatg     720
gccgagacca tcaagggcat gcaagatacc ggagtcttgg cctgcgcgaa acattatgtt    780
ggaaacgaac aagagcactt ccgacaagca ggcgagtcgg ccgggcatgg atacaacatt    840
gctgaatcga tctcgtcgaa cattgacgat cgtactatgc atgaaatgta cttgtgcct     900
tttgctgatg ccgtacgtgc tggagtggca tcttttatgt gctcctacaa ccagatcaac    960
aactcgtacg gatgccaaaa cagtcacact ctaaacaaac tcctcaagag cgagttgggc   1020
ttccaagggt tcgtgatgag tgactggcaa gcacaacact ctggagtatc gtcggcgctg   1080
gccgggctcg atatgacaat gccaggagat actgaattcg acaccggact cagcttttgg   1140
ggatccaatc tcactattgc ggttctgaac ggcaccgtgc ccgagtggag gattgacgat   1200
atggcgatgc ggatcatggc cgcttatttc aaagtcggtc tgacaattga agatcagcct   1260
gacgtgaatt tcaactcatg gacctacgat acctatggt acaaatactt ttacagcgag   1320
gagggttacg agaaagtgaa ctggcatgtc gacgtgcgtg caaaccacgc ccaacagatt   1380
cgtgagacgg ccgcaagggg aactgtgctt ctcaaaaaca ccaatggtgc tcttccgctg   1440
aaacgacctt ccttcgtcgc cgttgttggc gaagatgcgg gtccaaatcc caagggtccg   1500
aatgggtgtc ctgatcgtgg ctgcgatgag ggaaccctgg cgatgggatg gggatctgga   1560
tcgacccagt tcccgttcct tgttactcca gactctgcga ttcaagccaa ggtcttggag   1620
tatggtggcc gatatgagag tatttttggac aactacgatg aaagtgccat ctccgcactg   1680
gtctcgcagc ctgatgctac ttgcatcgtc tttggcaact cggattctgg cgaagctttc   1740
atcaccgtcg acggcaactg gggggatcgg aataacctca ctctttggca aaatgccatc   1800
gcggtgatcc gcaatgtcag tgctctgtgc agcaacacca ttgtcgttct tcacactgtc   1860
ggccctgtgc tgttgaccga ttactatgag caccccaaca tcacagccat tgtctgggcc   1920
ggcctacctg gcgaagaatc agggaatgct cttgtcgata tcctctgggg cgatgtcaac   1980
ccagccggtc gcacgccatt cacatggggcc aagagccgtg aagactatgg cacagacgtg   2040
atgtatgtgc ccaacaacgg cgaacaggca ccccagcaat ccttctccga aggcatcttc   2100
cttgactacc ggcattttga ccaagctggc attgatccca tctacgagtt cggccacggt   2160
ctctcatata ccaatttctc atactctgac ctccgcatcg tcaccaaaca cgttcgtccc   2220
tatcgaccca cgacaggcat gaccacgcaa gcacctatca cgcaacccct ccccagccca   2280
aacctcaccg agtatcaatt ccctgctact ttcaaataca tccggccctt tatctatccc   2340
tacctcaaca gcacagagtc cctccgcgcc gcctcaaaag accctcacta cggcagcacc   2400
gcattcattc cccctcatgc cctcgacagc tccccacagc ctctcaaccc agcgggtgac   2460
cccatcgcct ccggcggtaa cagtatgctc tatcaggagc tctacgaaat caccgccaaa   2520
atcaccaaca ccggcaatct agccggtgac gaggttgtcc aactgtacgt caacctcggt   2580
ggcgacaatc ctcctcgaca gcttcgagga tttgaccgaa tccacctcct gcccggccag   2640
agtaaggtgt tccgagcgac gttgacacgt cgggacttga gtaattggga cgttgcggcg   2700
cagaattggc gcatcatcag gtccgccaag gaggtttatg tcggacgctc aagtcgagat   2760
ctgcccttga gcgcgcgatt ggagtcatgg taa                                 2793
```

```
SEQ ID NO: 186        moltype = AA  length = 872
FEATURE               Location/Qualifiers
source                1..872
                      mol_type = protein
                      organism = Penicillium oxalicum
SEQUENCE: 186
MRSSTTVLAF VSYGSFGIAA AKPIQEHKIE EPYSPPFYPS PWMNPRAEGW EDAYQKALAF     60
VSQLTLLEKV NLTTGVGWEN GPCVGNTGSV PRLGFKGLCL QDSPQGVRFA DYASAFTSSQ    120
MAAATFDKTV LYERGVAMAQ EHKGKGITVQ LGPVAGPLGR APEGGRNWEG FSPDPVLNGI    180
AMAETIKGMQ DTGVLACAKH YVGNEQEHFR QAGESAGHGY NIAESISSNI DDRTMHEMYL    240
WPFADAVRAG VASFMCSYNQ INNSYGCQNS HTLNKLLKSE LGFQGFVMSD WQAQHSGVSS    300
ALAGLDMTMP GDTEFDTGLS FWGSNLTIAV LNGTVPEWRI DDMAMRIMAA YFKVGLTIED    360
QPDVNFNSWT YDTYGYKYFY SKEGYEKVNW HVDVRANHAQ QIRETAAKGT VLLKNTNGAL    420
PLKRPSFVAV VGEDAGPNPK GPNGCPDRGC DEGTLAMGWG SGSTQFPFLV TPDSAIQAKV    480
LEYGGRYESI LDNYDESAIS ALVSQPDATC IVFGNSDSGE AFITVDGNWG DRNNLTLWQN    540
ADAVIRNVSA LCSNTIVVLH TVGPVLLTDY YEHPNITAIV WAGLPGEESG NALVDILWGD    600
VNPAGRTPFT WAKSREDYGT DVMYVPNNGE QAPQQSFSEG IFLDYRHFDQ AGIDPIYEFG    660
HGLSYTNFSY SDLRIVTKHV RPYRPTTGMT TQAPIIGPLP SPNLTEYQFP ATFKYIPAFI    720
YPYLNSTESL RAASKDPHYG STAFIPPHAL DSSPQPLNPA GDPIASGGNS MLYQELYEIT    780
AKITNTGNLA GDEVVQLYVN LGGDNPPRQL RGFDRIHLLP GQSKVFRATL TRRDLSNWDV    840
AAQNWRIIRS AKEVYVGRSS RDLPLSARLE SW                                  872
```

```
SEQ ID NO: 187        moltype = DNA  length = 2964
FEATURE               Location/Qualifiers
source                1..2964
                      mol_type = genomic DNA
                      organism = Penicillium oxalicum
SEQUENCE: 187
atgaagctcg agtggctgga agccacggtg cttgcggccg ccacggttgc tagtgcaaag     60
gtatgttgcc gaatgtaccc ccagttgact tgcgatgact cccaagttgt ttttctttgt    120
gtttactagt ggatctgaca caaatacttt tggtgatata ggatcttgcc tactctcccc    180
ccttctatcc ttctccatgg gcaaccggtg aaggtgaatg gccgaggcc tacaagaagg    240
ctgtggactt tgtttctggt ctgactcttg ccgagaaggt caacatcacg accggtgctg    300
ggtaggtcca tgcgctgaag atgattgctc tgtgtatgca cattgcggct gacaattgtg    360
tccagatggg aacaggagcg ttgtgtgggt gagaccggcg gtgtccctcg gtaagattgt    420
```

```
actctcatct aatatcctct tgggtccagc aaagggcaaa tcaaattgac atgcgaaccg    480
ttgaatcaga cttggaatgt ggggaatgtg catgcaagat tctcctctcg gcgttcgtaa    540
tggtgagaca aactctttct caaggatgat tcacttcacg cgaaagacta accaaccgaa    600
tgtagccgac tacagctctg ccttcccgc cggtgtgaat gtggctgcca cctgggaccg     660
acgactcgcg taccagcgtg gtacggccat gggcgaggag catcgcgaca agggtgtcga    720
cgtgcagctt ggccccgtcg ctggtccatt gggcaagaac cccgacggtg gtcgtgggctg   780
ggaaggcttt tctcccgatc cggttctgac cggtgttatg gtggccgaga caatcaaggg    840
tatccaagat gctggtgtca ttgcttgcgc aagcacttc atcatgaatg agcaggagca     900
cttccgccag gcgggtgaag cccagggata cggattcaat atttctcaga gtttgagcg     960
caacgtcgat gacaagacca tgcacgagct gtacttgtgg ccgtttgtcg attcggttcg    1020
ggccggtgtg ggtccgtca tgtgctctta caaccagatc aacaacagct acgggtgctc     1080
caacagctac acgctcaaca aattgctcaa gggcgagctc ggctttcagg gcttcgtcat    1140
gagcgactgg ggtgcgcacc acagcggtgt cggtgacgcc cttgccggtc tcgacatgtc    1200
tatgcccggt gatgtgattc ttggtagccc ctactcctgg tggggaacta acttgaccgt    1260
ctctgtgctg aacagcacca tccccgaatg gcgtctggat gacatggccg ttcgtatcat    1320
ggctgcctac tacaaggtcg gcagagatcg tcatcgcact cctcccaact tcagctcctg    1380
gacccgcgat gagtacggct acgagcactt tattgtccag gagaactatg tcaagctcaa    1440
cgagcgtgtc aatgttcaac gtgatcatgc caacgtcatc cgcaagattg gctccgacag    1500
tatcgtgatg ctcaagaaca acgggggtct gcctttgact catcaagagc gctctggtgc    1560
tatcttgggc gaggatgctg gttccaacgc ctacggcgcc aacggctgca gtgaccgagg    1620
ctgtgacaac ggtaccttgg ccatgggctg gggcagtgga acggccaact tcccctacct    1680
gatcactccc gagcaagcca ttcagaatga ggttctcaac tacggcaacg gtgacaccaa    1740
tgtctttgct gtcacagaca acggtgccct cagccaaatg gctgcccttg cttcaaccgc    1800
aagtgttgca ttggtgttcg tcaacgctga ttcgggcgag ggctacatca gtgtggacgg    1860
caacgagggc gatcgcaaga acatgaccct gtggaagaac ggcgaggagc tgatcaagac    1920
cgccactgcc aactgcaaca acaccatcgt catcatgcac accccaacgc ccgtcctcgt    1980
cgattcatgg tacgacaatg agaacatcac tgccattctg tgggctggta tgccggcca     2040
agagagtggt cgtagcttgg ttgatgttct ctacggccgc acgaaccctg gtggcaagac    2100
cccttcacc tgggtaagg agcgcaagga ttggggatct cctcttctga ctaaacccaa      2160
caacggccac ggtgctcctc aggatgactt caccgatgtt ctgattgact atcgccgttt    2220
cgacaaggac aacgtggagc ccatcttcga gttcggcttc ggtctgagct acaccaaatt    2280
tgagttctct gacatccagg tcaaggcgct gaatcacggc gagtacaacg ccaccgtggg    2340
caagaccaag cctgcccctt cgttgggcaa gcctggtaat gcctccgatc atctgttccc    2400
cagcaacatc aaccgtgtgc gacagtacct ttaccttac ctgaactcga ccgatctgaa    2460
ggcgtctgcc aacgaccctg actatgcat gaatgcatcg gcgtacattc ctccccatgc    2520
caccgacagc gacccacagg accttctccc cgccagcgga ccttccggtg caaccctgg    2580
tttgtttgag gaccttattg aggtgactgc tactgtcacc aacaccggct cagttactgg    2640
tgacgaggtt ccccagctgg taagttctcc cgaattccga ctccaagcgc tttgcgcgag   2700
attgaggttt ctgacaggaa tgttatatag tacgtttcgc ttggcggtgc cgatgacccc   2760
gttaaggtcc tccgtgcctt cgaccgtgtc acgatcgccc ctggtcagaa gctccggtgca  2820
acagcaaccc tcaaccgtcg tgatctgtcc aactgggatg tcccatcaca gaactggatc   2880
atctcagacg cccccaagaa ggtgtgggtg gcaactcgt cgcgcaagct gcctctttca    2940
gccgatctgc ccaaggtgca gtaa                                          2964

SEQ ID NO: 188         moltype = AA  length = 861
FEATURE                Location/Qualifiers
source                 1..861
                       mol_type = protein
                       organism = Penicillium oxalicum
SEQUENCE: 188
MKLEWLEATV LAAATVASAK DLAYSPPFYP SPWATGEGEW AEAYKKAVDF VSGLTLAEKV     60
NITTGAGWEQ ERCVGETGGV PRLGMWGMCM QDSPLGVRNA DYSSAFPGAV NVAATWDRRL   120
AYQRGTAMGE EHRDKGVDVQ LGPVAGPLGK NPDGGRGWEG FSPDPVLTGV MVAETIKGIQ   180
DAGVIACAKH FIMNEQEHFR QAGEAQGYGF NISQSLSSNV DDKTMHELYL WPFVDSVRAG   240
VGSVMCSYNQ INNSYGCSNS YTLNKLLKGE LGFQGFVMSD WGAHHSGVGD ALAGLDMSMP   300
GDVILGSPYS FWGTNLTVSV LNSTIPEWRL DDMAVRIMAA YYKVGRDRHR TPPNFSSWTR   360
DEYGYEHFIV QENYVKLNER VNVQRDHANV IRKIGSDSIV MLKNNGGLPL THQERLVAIL   420
GEDAGSNAYG ANGCSDRGCD NGTLAMGWGS GTANFPYLIT PEQAIQNEVL NYGNGDTNVF   480
AVTDNGALSQ MAALASTASV ALVFVNADSG EGYISVDGNE GDRKNMTLWK NGEELIKTAT   540
ANCNNTIVIM HTPNAVLVDS WYDNENITAI LWAGMPGQES GRSLVDVLYG RTNPGGKTPF   600
TWGKERKDWG SPLLTKPNNG HGAPQDDFTD VLIDYRRFDK DNVEPIFEFG FGLSYTKFEF   660
SDIQVKALNH GEYNATVGKT KPAPSLGKPG NASDHLFPSN INRVRQYLYP YLNSTDLKAS   720
ANDPDYGMNA SAYIPPHATD SDPQDLLPAS GPSGGNPGLF EDLIEVTATV TNTGSVTGDE   780
VPQLYVSLGG ADDPVKVLRA FDRVTIAPGQ KLRWTATLNR RDLSNWDVPS QNWIISDAPK   840
KVWVGNSSRK LPLSADLPKV Q                                             861

SEQ ID NO: 189         moltype = DNA  length = 2925
FEATURE                Location/Qualifiers
source                 1..2925
                       mol_type = genomic DNA
                       organism = Talaromyces emersonii
SEQUENCE: 189
atgaggaacg ggttgctcaa ggtcgccgcc cttgcggccg cgtccgccgt caatggcgag     60
gtacgtgcac tctacgcttt tgcatggaga attcgtcttt tctctaaccg tccacaatag   120
aacctggcgt attcacctcc cttctaccct tcgccgtggg ccaatggaca gggcgactgg   180
gcagaggcct accagaaggc cgtccagttt gtgtcccaac tcaccctggc cgagaaggtc   240
aacctgacca ccggaactgg gtacgttgac tgatgaaacc tttggatcca cgccatgttc   300
ggactgctga cattgtcaaa gttgggagca ggaccgatgt gtcggtcaag tgggtagcat   360
cccaaggtat gttgattcga gtccccgatc cggttcgctg tggatgctga ctggactgtc   420
```

```
aattaggctg gtttccctg gactttgcat gcaggactct ccgctgggcg ttcgagacag   480
tatgcttgtt catccccgca gtatctgag catgtgctaa tgcgtttccg caacagctga    540
ctacaactcg gccttccctg ccggtgtcaa tgtcgctgct acctgggacc ggaatctcgc   600
ctaccgtcgc ggcgtagcga tgggcgagga gcatcgcggc aaaggtgtcg acgtgcagct   660
gggccctgtg gccggcccgc tgggcaggtc tcccgatgcg ggcagaaact gggaaggttt   720
cgccccggat cccgtgctga ccggaaacat gatggcgtca accatccagg gtattcaaga   780
tgctggcgtc attgcttgcg ccaagcattt catcctctac gagcaggagc acttccgtca   840
aggcgctcag gacggctatg atatctccga cagtatcagt gccaacgctg acgacaagac   900
gatgcacgag ttgtacttgt ggcccttcgc cgatgctgtt cgcgcgggcg tcggttccgt   960
catgtgctcc tacaaccagg tgaacaacag ctatgcctgc tccaacagct acaccatgaa  1020
caagctgctc aagagcgaac tcggtttcca aggcttcgtc atgaccgact ggggtggcca  1080
ccacagtggt gtgggttccg ccctcgctgg tttggatatg tcgatgcccg agacattgc   1140
cttcgacagt ggcacttcct tctggggcac gaacctgacc gtcgccgtgc tcaatggcag  1200
tattcccgag tggcgtgttg atgacatggc tgtccgtatc atgtcggctt actacaaagt  1260
cggccgcgac cgctacagcg tccccatcaa ctttgactcg tggaccctgg ataccatgt   1320
tcctgagcac tatgcggtgg gccagggcca gaccaagatt aacgagcacg ttgatgtccg  1380
cggcaaccac gccgaaatca tccacgaaat cggtgctgcc agcgccgtcc ttcttaagaa  1440
caagggtggc cttcctttga cgggcaccga gcggttttgtc ggtgttttcg gagaggatgc  1500
cggatccaac ccctgggggtg tgaacggctg cagtgaccga gctgcgaca atggtacatt   1560
ggccatgggc tggggcagtg gtactgctaa cttcccctat ctggtgacgc cggagcaggc  1620
gatccagaga gaagtcttgt cccgaaacgg aaccttcacc gccatcacgg acaatggcgc  1680
tcttgctgag atggcggcag ccgcctctca ggccgagtaa gtatttccgc tgtcctcgag  1740
ctctctaaag gacgtgactg acccgttcat agtacttgtc tggtcttcgc caacgccgac  1800
tccggtgaag gttacatcac cgtcgacggc aatgagggtg accggaagaa tctgaccctg  1860
tggcaagggg cggatcaggt catccacaac gtctctgcca actgcaacaa caccgtcgtg  1920
gtgttgcaca ctgtcggccc cgttttgatc gatgattggt atgaccaacc caacgtcacg  1980
gccattctct gggctggtct tccgggccag gagagcggta actcgctcgt cgatgtcctc  2040
tacggccggg tcaaccctgg tggaaagact ccgttcactt ggggacgcgc ccgggacgat  2100
tacggtcgc ctttgatcgt caagccgaac aatggcaagg cgccccgca gcaggacttt    2160
actgagggta tcttcatcga ctacactcgg tttgacaagt acaacatcac ccccatctac  2220
gagttcggat tcggtctgag ctacactacc tttgagttct ctcagctcaa tgtgcagccg  2280
atcaatgcgc cgccgtacac tcctgcctcc ggcttcacca aggcagcgca gtcattcggc  2340
cagccttcca acgcttcgga caacctgtac cccagcgaca tcgagcgggt cccgttgtac  2400
atctacccat ggctcaactc caccgatttg aaggcgtccg ccaatgacc tgactatggg   2460
ttgcctacgg agaagtacgt tcctcccaac gccacgaacg gcgacccgcc gcccattgac  2520
ccggctggcg gtgctcctgg tggcaacccg agtctgtatg agcctgttgc tcgggtcacc  2580
accatcatca ccaacaccgg taaggttacg ggtgacgagg ttcctcaact ggtaagtgtc  2640
ccaacattgg ttgctggagg tcccttttac tgacttcaac tcaagtacgt ctctcttggc  2700
ggtcccgatg acgctcccaa ggttcttcgt ggcttcgaca gtatcaccct tgcgcctgct  2760
cagcagtact tgtggacgac caccctgacg aggcgcgacc tctcgaactg ggaccctgtc  2820
acccagaact gggtcgtgac caactatacc aagacgatta tgttggcaa ctcgtcccgc    2880
aacctgcctt tgcaggcgcc ccttaagcca taccctggaa tttaa                   2925

SEQ ID NO: 190         moltype = AA  length = 858
FEATURE                Location/Qualifiers
source                 1..858
                       mol_type = protein
                       organism = Talaromyces emersonii
SEQUENCE: 190
MRNGLLKVAA LAAASAVNGE NLAYSPPFYP SPWANGQGDW AEAYQKAVQF VSQLTLAEKV    60
NLTTGTGWEQ DRCVGQVGSI PRLGFPGLCM QDSPLGVRDT DYNSAFPAGV NVAATWDRNL   120
AYRRGVAMGE EHRGKGVDVQ LGPVAGPLGR SPDAGRNWEG FAPDPVLTGN MMASTIQGIQ   180
DAGVIACAKH FILYEQEHFR QGAQDGYDIS DSISANADDK TMHELYLWPF ADAVRAGVGS   240
VMCSYNQVNN SYACSNSYTM NKLLKSELGF QGFVMTDWGG HHSGVGSALA GLDMSMPGDI   300
AFDSGTSFWG TNLTVAVLNG SIPEWRVDDM AVRIMSAYYK VGRDRYSVPI NFDSWTLDTY   360
GPEHYAVGQG QTKINEHVDV RGNHAEIIHE IGAASAVLLK NKGGLPLTGT ERFVGVFGED   420
AGSNPWGVNG CSDRGCDNGT LAMGWGSGTA NFPYLVTPEQ AIQREVLSRN GTFTAITDNG   480
ALAEMAAAAS QADTCLVFAN ADSGEGYITV DGNEGDRKNL TLWQGADQVI HNVSANCNNT   540
VVVLHTVGPV LIDDWYDHPN VTAILWAGLP GQESGNSLVD VGRVNPGG KTPFTWGRAR     600
DDYGAPLIVK PNNGKGAPQQ DFTEGIFIDY RRFDKYNITP IYEFGFGLSY TTFEFSQLNV   660
QPINAPPYTP ASGFTKAAQS FGQPSNASDN LYPSDIERVP LYIYPWLNST DLKASANDPD   720
YGLPTEKYVP PNATNGDPQP IDPAGGAPGG NPSLYEPVAR VTTIITNTGK VTGDEVPQLY   780
VSLGGPDDAP KVLRGFDRIT LAPGQQYLWT TTLTRRDISN WDPVTQNWVV TNYTKTIYVG   840
NSSRNLPLQA PLKPYPGI                                                 858

SEQ ID NO: 191         moltype = DNA  length = 871
FEATURE                Location/Qualifiers
source                 1..871
                       mol_type = genomic DNA
                       organism = Thermoascus crustaceus
SEQUENCE: 191
atggcctttt cccagataat ggctattacc ggcgttttc ttgcctctgc ttccctggtg     60
gctggccatg gctttgttca gaatatcgtg attgatggta aaaggtacct aactaccac   120
cttactatct gatgtcattt acaagaaagg gcacagacac aagcggcaaa aaaaagaaag   180
aaagaaagaa agaaagaaag ctgacaaaaa ttcaacaagt tatgcgcggt acatcgtgaa   240
ccaatatcca tacatgtcag atcctccgga ggtcgtcggc tggtctacca ccgcaaccga   300
cctcggattc gtgacggta ccggataccca aggacctgat atcatctgcc acgggggcgc    360
caagcctgca gccctgactg cccagtggcc gccggagga ccgtcaagc tggaatggac    420
tccatggcct gattctcacc acggcccggt gatcaactac cttgctcctt gcaacggtga   480
```

```
ctgttccacc gtggacaaga cccaattgaa attcttcaag atcgcccagg ccggtctcat    540
cgatgacaac agtcctcctg gtatctgggc ctcagacaat ctgatagcgg ccaacaacag    600
ctggactgtc accatcccaa ccacaactgc acctggaaac tatgttctaa ggcatgagat    660
cattgctctc cactcagctg gaacaagga tggtgcgcag aactatcccc agtgcatcaa    720
cctgaaggtc actggaaatg gttctggcaa tcctcctgct ggtgctcttg aacggcact    780
ctacaaggat acagatccgg gaattctgat caatatctac cagaaacttt ccagctatgt    840
tattcctggt cctgctttgt acactggtta g                                    871

SEQ ID NO: 192         moltype = AA  length = 251
FEATURE                Location/Qualifiers
source                 1..251
                       mol_type = protein
                       organism = Thermoascus crustaceus
SEQUENCE: 192
MAFSQIMAIT GVFLASASLV AGHGFVQNIV IDGKSYGGYI VNQYPYMSDP PEVVGWSTTA     60
TDLGFVDGTG YQGPDIICHR GAKPAALTAQ VAAGGTVKLE WTPWPDSHHG PVINYLAPCN    120
GDCSTVDKTQ LKFFKIAQAG LIDDNSPPGI WASDNLIAAN NSWTVTIPTT TAPGNYVLRH    180
EIIALHSAGN KDGAQNYPQC INLKVTGNGS GNPPAGALGT ALYKDTDPGI LINIYQKLSS    240
YVIPGPALYT G                                                         251

SEQ ID NO: 193         moltype = DNA  length = 1386
FEATURE                Location/Qualifiers
source                 1..1386
                       mol_type = genomic DNA
                       organism = Talaromyces emersonii
SEQUENCE: 193
atggttcgcc tcagtccagt cctgctggca tcgatcgcag gctctggcct gcctctgtac     60
gcacaagcag ccggcctcaa caccgccgcc aaagccgtcg gcctgaaata cttcggcacg    120
gcgaccgaca accccgaact gagcgacacc gcgtacgaga cggagctgaa caacacgcag    180
gatttcgggc agttgacacc tgcgaattcg atgaaagtga gtctgacacc cccccccct    240
cctgggcgag tgagtgagtt cgacgctgat ggttttttgca gtgggacgca accgagcccc    300
agcaaaacac tttcacgttc agcggcggcg atcagatcgc taacctggcc aaggcgaatg    360
ccagatgtt gaggtgccat aatcttgttt ggtataatca gttgccgtcg tggggtatgt    420
atagtacctg cgtgcttgtt tgtaatgatt gtcttggctg atttgtgaag tcaccggtgg    480
atcctggacc aacgagacgc tgcttgctgc catgaagaat cacatcacaa acgtcgttac    540
ccattacaag ggccagtgct atgcatggga tgtcgtgaat gagggtgcgt ccatataatt    600
gctgttacta tcgagaggaa tcagctaatg acgacagccc tcaacgacga cggcacctac    660
cgcagcaacg tcttctacca gtatatcggg gaggcgtaca tccccatcgc cttcgcgacg    720
gccgccgccg acgcccccga cgccaagctg tactacaacg actacaacat cgagtacccc    780
ggcgtcaagg ccacggcggc gcagaacatc gtcaagctgg tgcagtcgta cggcgcgcgc    840
atcgacggcg tcggcctgca gtcgcacttc atcgtgggcc agacgccaag cacgagcgcc    900
cagcagcaga acatggctgc cttcaccgcg ctgggcgtcg aggtcgccat caccgagctc    960
gacatccgca tgcagctgcc cgagagctcc gcgcagctga cacagcaggc gaccgactac   1020
cagagcacgg tccaggcctg cgtcaacacc gacagctgcg tcggcatcac cctctggac   1080
tggaccgaca agtactcgtg ggtgcccagc accttctcag gctggggcga cgcctgtccc   1140
tgggacgaca actaccagaa gaagcccgcg tacaacggca tcctcactgc tctggaggc   1200
acgccctcct ccagtaccag ctacacccctc acgccggacga cgacctcgag cggcggcagt   1260
ggcagcccga ctgacgtggc tcagcattgg gagcagtgcg gtggcctggg ctggactggg   1320
ccgacggttt cgccagtggc cttcacttgc actgtcatca acgagtatta ctcgcagtgt   1380
ctgtaa                                                              1386

SEQ ID NO: 194         moltype = AA  length = 403
FEATURE                Location/Qualifiers
source                 1..403
                       mol_type = protein
                       organism = Talaromyces emersonii
SEQUENCE: 194
MVRLSPVLLA SIAGSGLPLY AQAAGLNTAA KAVGLKYFGT ATDNPELSDT AYETELNNTQ     60
DFGQLTPANS MKWDATEPQQ NTFTFSGGDQ IANLAKANGQ MLRCHNLVWY NQLPSWVTGG    120
SWTNETLLAA MKNHITNVVT HYKGQCYAWD VVNEALNDDG TYRSNVFYQY IGEAYIPIAF    180
ATAAAADPDA KLYYNDYNIE YPGVKATAAQ NIVKLVQSYG ARIDGVGLQS HFIVGQTPST    240
SAQQQNMAAF TALGVEVAIT ELDIRMQLPE TSAQLTQQAT DYQSTVQACV NTDSCVGITL    300
WDWTDKYSWV PSTFSGWGDA CPWDDNYQKK PAYNGILTAL GGTPSSSTSY TLTPTTTSSG    360
GSGSPTDVAQ HWEQCGGLGW TGPTVCASGF TCTVINEYYS QCL                      403

SEQ ID NO: 195         moltype = DNA  length = 1387
FEATURE                Location/Qualifiers
source                 1..1387
                       mol_type = genomic DNA
                       organism = Penicillium sp.
SEQUENCE: 195
atggttcgcc tcagtccagt cctgctggca tcgatcgcag gctctggcct gcctctgtac     60
gcacaagcag ccggcctcaa caccgccgcc aaagccatcg gcctgaaata cttcggcacg    120
gcgaccgaca accccgaact gagcgacacc gcgtacgaga cggagctgaa caacacgcag    180
gatttcgggc agttgacacc tgcgaattgc atgaaggtga gtctgacagc tccccccct    240
cctggggtga gtgagtgagt tcgacgctaa tggttttttgc agtgggacgc aaccgagccc    300
cagcaaaaca ctttcacgtt cagcggcggc gatcagatcg ctaacctggc caaggcgaat    360
ggccagatgt tgaggtgcca taatcttgtt tggtataatc agttgccgtc gtggggtatg    420
tatagtacct gcgtacttgt ttgtaatgat tgtcttggct gatttgtgaa gtcaccggtg    480
```

```
gatcctggac caacgagacg ctgcttgctg ccatgaagaa tcacatcacc aacgtcgtta    540
cccattacaa gggccagtgc tatgcatggg atgtcgtgaa tgagggtacg tccatataat    600
tgctgttact atcgagagga atcagctaat gacgacagcc ctcaacgacg acggcaccta    660
ccgcagcaac gtcttctacc agtatatcgg ggaggcgtac atccccatcg ccttcgcgac    720
ggccgccgcc gccgacccccg acgccaagct gtactacaac gactacaaca tcgagtaccc    780
cggcgccaag gccacggcgg cgcagaacat cgtcaagctg gtgcagtcgt acggggcgcg    840
catcgacggc gtcggcctgc agtcgcactt catcgtgggc cagacgccca gcacgagcgc    900
ccagcagcag aacatggccg ccttcaccgc gctgggcgtc gaggtcgcca tcaccgagct    960
cgacatccgc atgcagctgc ccgagacgtc cgcgcagctg acgcagcagg cgaccgacta   1020
ccagagcacg gtccaggcct gcgtcaacac cgacagctgc gtcggcatta ccctctggga   1080
ctggaccgac aagtactcgt gggtgcccag caccttctca ggctggggcg acgcctgtcc   1140
ctgggacgac aactaccaga agaaacccgc gtacaacggc atcctcactg ctctgggagg   1200
cacgccctcc tccagtacca gctacaccct cacgccgacg acgacctcaa gcggcggcag   1260
tggcagcccg actgacgtgg cccagcattg ggagcagtgc ggtggcctgg gctggactgg   1320
gccgacggtt tgcgccagtg gcttcacttg cactgtcatc aacgagtatt actcgcagtg   1380
tctgtaa                                                             1387

SEQ ID NO: 196          moltype = AA   length = 403
FEATURE                 Location/Qualifiers
source                  1..403
                        mol_type = protein
                        organism = Penicillium sp.
SEQUENCE: 196
MVRLSPVLLA SIAGSGLPLY AQAAGLNTAA KAIGLKYFGT ATDNPELSDT AYETELNNTQ    60
DFGQLTPANS MKWDATEPQQ NTFTFSGGDQ IANLAKANGQ MLRCHNLVWY NQLPSWVTGG   120
SWTNETLLAA MKNHITNVVT HYKGQCYAWD VVNEALNDDG TYRSNVFYQY IGEAYIPIAF   180
ATAAAADPDA KLYYNDYNIE YPGAKATAAQ NIVKLVQSYG ARIDGVGLQS HFIVGQTPST   240
SAQQQNMAAF TALGVEVAIT ELDIRMQLPE TSAQLTQQAT DYQSTVQACV NTDSCVGITL   300
WDWTDKYSWV PSTFSGWGDA CPWDDNYQKK PAYNGILTAL GGTPSSSTSY TLTPTTTSSG   360
GSGSPTDVAQ HWEQCGGLGW TGPTVCASGF TCTVINEYYS QCL                     403

SEQ ID NO: 197          moltype = DNA   length = 1191
FEATURE                 Location/Qualifiers
source                  1..1191
                        mol_type = genomic DNA
                        organism = Meripilus giganteus
SEQUENCE: 197
atgaagttct ccgcgacctt ctcagcactc gccgcgctga tccctacgc cctcgctcag     60
tccccagaat ggggccaatg cggcggcact ggctggacag cgccacgac ctgcgtgtcg    120
ggcaccgtgt gcacggtgat caatccgtat tactcgcaat gtctcccgg aagtgcgaca    180
tccgcaacgt ctagcgctcc cagctctacc actacgacag gctcatccgc acccagcgcg    240
agtggtctgc acacgctggc gaaggcggcg ggcaagctct acttcggcac agcgacggac    300
aatccagagt tgaccgacac cgcctacgtc acgaagctca cgataacaa ggagttcggc    360
cagatcaccc caggcaacag tatgaaatgg gacgctacgg agccgactcg cgggacgttc    420
acgttcacga acggagacgt agttgcgaac ctggcgaaga caacgggca gctgctgcgc    480
gggcacaact gcgtgtggca caaccagctc ccgagctggg tatccaatgg gcagttcacc    540
gcggcggacc tcacggacgt catccagacg cactgtggca cggtcgtagg acattacaag    600
ggccagattt attcttggga tgttgtgaac gagcctttca acgacgacgg cacctggcgc    660
acggatgttt tctataacac gctcggcacg tcctacgtcg ccatcgcgct caaagccgcg    720
cgcgctgccg accccgccgc caaactctac atcaacgact acaacatcga gcagacgggc    780
gccaagtcgg ccgcgatgct cgcgctcgtc aaggagctcc tcgcggacgg cgtgccccctc    840
gacggcgtcg gctttcagag ccacttcatc gtcggcgcgg tgccgggcag cctccagcag    900
acgctcgagc agttcaccgc gctcgggctc gaggtcgcga tcacggagct cgacatccgc    960
atgacgctcc ccgcgacgga cgcgctcctc gcgcagcagc agaaggacta cgaggcggtt   1020
gtgcaggcgt gcatgaatgt gaacggctgt gtgggcgtca cgatctggga ctggacggac   1080
aagtactcgt gggtgccgtc gaccttctct ggccaggggc ccgctctccc ttgggatgag   1140
aacttcaaca gaagcccgc gtacagcggt attacagcag cacttgcata a             1191

SEQ ID NO: 198          moltype = AA   length = 396
FEATURE                 Location/Qualifiers
source                  1..396
                        mol_type = protein
                        organism = Meripilus giganteus
SEQUENCE: 198
MKFSATFSAL AALIPYALAQ SPEWGQCGGT GWTGATTCVS GTVCTVINPY YSQCLPGSAT    60
SATSSAPSST TTTGSSAPSA SGLHTLAKAA GKLYFGTATD NPELTDTAYV TKLSDNKEFG   120
QITPGNSMKW DATEPTRGTF TFTNGDVVAN LAKNNGQLLR GHNCVWHNQL PSWVSNGQFT   180
AADLTDVIQT HCGTVVGHYK GQIYSWDVVN EPFNDDGTWR TDVFYNTLGT SYVAIALKAA   240
RAADPAAKLY INDYNIEQTG AKSAAMLALV KELLADGVPL DGVGFQSHFI VGAVPGSLQQ   300
TLEQFTALGL EVAITELDIR MTLPATDALL AQQQKDYEAV VQACMNVNGC VGVTIWDWTD   360
KYSWVPSTFS GQGAALPWDE NFNKKPAYSG ITAALA                             396

SEQ ID NO: 199          moltype = DNA   length = 1083
FEATURE                 Location/Qualifiers
source                  1..1083
                        mol_type = genomic DNA
                        organism = Dictyoglomus thermophilum
```

```
SEQUENCE: 199
atgtttctta aaaaacttag taagttgctc ttagtcgtac tacttgtcgc agtgtatacg    60
caagttaatg ctcaaacgtc tataacacta acaagtaatg caagcggtac ttttgatggc   120
tactactatg aactatggaa agatacaggg aatacaacca tgactgtata cacacaagga   180
aggtttagct gtcagtggag caatataaac aatgcattat tcagaacagg taagaagtac   240
aaccaaaact ggcagtcatt aggcactatt agaatcacct actcagccac atataatcct   300
aatggtaact cctactatgt tatccatggt tggtctacta atcctttagt agagttttac   360
attgtagaaa gttggggtaa ttggcgtcca ccaggtgcaa cctctcttgg acaggttact   420
atcgacggtg gtacctatga catttacaga actacccgtg taaatcagcc atctattgtc   480
ggtacagcta cttttgatca atattggagt gtaaggacat ctaagagaac aagtggaaca   540
gtcactgtaa cagatcactt tagggcatgg gcaaatagag gtttaaacct tggtactatt   600
gatcaaatta ctctttgtgt tgaaggatat caaagcagtg gttcggctaa tataacacaa   660
aatactttt ctcaaggtag cagtagtgga agtagtgggg cagtagtgg tagtacaaca   720
actactagaa tagaatgtga aaacatgtca ttaagtggac cctatgtatc aagaattaca   780
aatccattta atggtatagc tctttatgca aatggagata ctgcaagagc tacagtaaac   840
ttcccagcaa gtcgtaacta aatttcagg ttaagaggat gcggaaataa caataattta   900
gctcgggttg atttacgaat agatgggagg actgtaggta cgttctatta tcagggaaca   960
tatccttggg aggctcctat agacaatgta tacgtgagtg caggttctca tacagtggaa  1020
attacagtta cggctgataa tgggacatgg gatgtttatg cagattatct ggtgatacag  1080
taa                                                                1083

SEQ ID NO: 200          moltype = AA length = 360
FEATURE                 Location/Qualifiers
source                  1..360
                        mol_type = protein
                        organism = Dictyoglomus thermophilum
SEQUENCE: 200
MFLKKLSKLL LVVLLAVYT QVNAQTSITL TSNASGTFDG YYYELWKDTG NTTMTVYTQG     60
RFSCQWSNIN NALFRTGKKY NQNWQSLGTI RITYSATYNP NGNSYLCIYG WSTNPLVEFY   120
IVESWGNWRP PGATSLGQVT IDGGTYDIYR TTRVNQPSIV GTATFDQYWS VRTSKRTSGT   180
VTVTDHFRAW ANRGLNLGTI DQITLCVEGY QSSGSANITQ NTFSQGSSSG SSGGSSGSTT   240
TTRIECENMS LSGPYVSRIT NPFNGIALYA NGDTARATVN FPASRNYNFR LRGCGNNNNL   300
ARVDLRIDGR TVGTFYYQGT YPWEAPIDNV YVSAGSHTVE ITVTADNGTW DVYADYLVIQ   360

SEQ ID NO: 201          moltype = DNA length = 2412
FEATURE                 Location/Qualifiers
source                  1..2412
                        mol_type = genomic DNA
                        organism = Aspergillus aculeatus
SEQUENCE: 201
atggctgtgg cggctcttgc tctgctggcg cttttgcctc aagctctggc ccaacataac    60
agcagctacg tggattacaa cgtcgaggcc aacccggact gtttccgca atgtctggac   120
acaatctcct tgtccttccc cgactgccag agcggtcctc tgagcaagaa cctcgtctgc   180
gactcgaccg cctcgcccta tgaccgcgcc gcgccctga tctccctctt cacccctcag   240
gagctcattg ccaacactgg taacaccagc cccggtgtcc ctcgtctggg tctacctcca   300
taccaggtct ggagtgaggc cttgcatggc ctggaccgcg gcaatttcac cgacgagggg   360
gcttacagct gggcgacatc cttcccctcg cccattctcc ccgctgctgc cttcaatcgc   420
accctgatca accagatcgc atccattatc tcaactcagg ggcgcgcctt caataacgcg   480
ggccgctacg gtctcgatgt ctacgccccc aacatcaatg cctccgtca tcccgtctgg   540
gggcgcggac aggaaactcc gggcgaggat gcgtatactc tcacagccgc ctacgcctac   600
gaatacatca cgggtatcca gggtggcgtg gacccagcta atctgaagct gcagcgaca   660
gccaagcact ttgccggcta tgacatcgag aactgggaca ccactcccg gctggggaac   720
gatgtcaaca tcacgcagca agacctggca gagtactaca cgccgcagtt cctcgtggcc   780
acgcgcgatg cccgcgtcca cagcgtcatg tgctcgtaca acgccgtcaa cggcgtgccc   840
agctgctcca acaccttctt cctgcagacg tcctcgtaca acaccttctc cttcgttgac   900
cacggctacg tctccggcga ttgcggtgcc gtctacggcg ttttcaaccc ccacggctac   960
gcggccaacg agtccagcgc cgccgccgac tccatcctcg ccggcaccga catcgactgc  1020
ggcacctcct accaatacca cttcaacgag tccatcacca ccaggcggt cgcccgcgac  1080
gacatcgagc gcggcctcac ccggctatac gccaacctcc tccggctagg ctacttcgag  1140
ggcaacagca gcagcagcag cccgtaccgc agcctgagct ggtccgacgt ccagaagaca  1200
gacgcatgga acatttccta cgaagcggcc gtcgagggca tcgtcctcct gaagaacgac  1260
ggcgccctcc cgcttccctc ctcctcctcc tcgggcaaga taaatccat cgccctcatc  1320
ggcccctggg ccaacgccac cacccagctc cagggcaact actacggcgc ggcgccatac  1380
ctcatcagcc cggtcgagcc cttcacggcc gccggctaca cggtccacta cgccggctcc  1440
acggagatct ccacgaactc gacggcgaac ttcagcgccg cgctctccgc cgcgcgcgc   1500
gccgacacca tcgtattctt cggagggatc gacaacacca tcgaggcgga agcccaagac  1560
cgcagctcga tcgcctggcc cggcaaccaa ctcgagctga tctcgcaact ggccgcgcag  1620
aaatccgagt cccagcccct ggtggtgtac cagatgggcg gcgggcaggt cgactcctcc  1680
gccctgaaag cgaatccgaa ggtcaacgcc ctcctgtggg tcggcgctacc cggccaatcc  1740
ggcggcctcg ccctccgcga catcctcacg ggcgccgcg cccggcggg ccgcctcacc  1800
acgacccagt accccgccgc ctacgccgag agcttctcgg cgctcgacat gaacctgcgg  1860
cccaacacca ccaccaacaa cccaggccaa acctacatgt ggtacaccgg cgaacccgtc  1920
tacgaattcg gccacggcct cttctacacc ccttcaagg ctgcccccgc agcggcgaag  1980
aagtatacct tcaacatcac aggccccacc tcctccgccc tcggcgacac cacccgtc   2040
gcccaacgca ccctcttcaa cttcacggcg accatcacga actctgggc ccgggactcc  2100
gattacaccg ccctggtgtt cgccaacacc tcgagtgcgg gcccgtcccc gtacccgaac  2160
aaatggctcg tcgggttcga taggctcgct gctgtggcca aggagggggg cacgacggtg  2220
ttgaatgtgc ccgtggcggt ggatcggttg ccaggtggtg atgacaatgg gaattccgtg  2280
ctgtttccgg ggcggtatga ggtggccttg aataatgagc gcgaggtcgt ggttgaggtg  2340
```

```
gagttggtgg gggaggcggt ggtgttggtg aagtggccgg aggaggtgca gggggtgcag   2400
ggggatgagt ag                                                        2412

SEQ ID NO: 202         moltype = AA  length = 803
FEATURE                Location/Qualifiers
source                 1..803
                       mol_type = protein
                       organism = Aspergillus aculeatus
SEQUENCE: 202
MAVAALALLA LLPQALAQHN SSYVDYNVEA NPDLFPQCLD TISLSFPDCQ SGPLSKNLVC    60
DSTASPYDRA AALISLFTLE ELIANTGNTS PGVPRLGLPP YQVWSEALHG LDRGNFTDEG   120
AYSWATSFPS PILSAAAFNR TLINQIASII STQGRAFNNA GRYGLDVYAP NINAFRHPVW   180
GRGQETPGED AYTLTAAYAY EYITGIQGGV DPEHLKLAAT AKHFAGYDIE NWDNHSRLGN   240
DVNITQQDLA EYYTPQFLVA TRDARVHSVM CSYNAVNGVP SCSNTFFLQT LLRDTFSFVD   300
HGYVSGDCGA VYGVFNPHGY AANESSAAAD SILAGTDIDC GTSYQYHFNE SITTRAVARD   360
DIERGLTRLY ANLVRLGYFE GNSSSSSPYR SLSWSDVQKT DAWNISYEAA VEGIVLLKND   420
GALPLPSSSS SGKNKSIALI GPWANATTQL QGNYYGAAPY LISPVDAFTA AGYTVHYAPG   480
TEISTNSTAN FSAALSAARA ADTIVFFGGI DNTIEAEAQD RSSIAWPGNQ LELISQLAAQ   540
KSESQPLVVY QMGGGQVDSS ALKANPKVNA LLWGGYPGQS GGLALRDILT GARAPAGRLT   600
TTQYPAAYAE SFSALDMNLR PNTTTNNPGQ TYMWYTGEPV YEFGHGLFYT TFKAAPAAAK   660
KYTFNITDLT SSAHPDTTTV AQRTLFNFTA TITNSGARDS DYTALVFANT SSAGPSPYPN   720
KWLVGFDRLA AVAKEGGTTV LNVPVAVDRL ARVDDNGNSV LFPGRYEVAL NNEREVVVEV   780
ELVGEAVVLV KWPEEVQGVQ GDE                                           803

SEQ ID NO: 203         moltype = DNA  length = 2454
FEATURE                Location/Qualifiers
source                 1..2454
                       mol_type = genomic DNA
                       organism = Aspergillus aculeatus
SEQUENCE: 203
atggctgtgg cggctcttgc tctgctggcg ctgttgcccc aagctctggc ccaacataac    60
agcagctacg tggattacaa cgtcgaggcc aacccggact gtttccgca atgtctggat    120
acaatctcct tgtccttccc cgactgccag agcggtcctc tgagcaagaa cgtcgtctgc   180
gactcgaccg cctcgcccta tgaccgcgcc gcggccctga tctccctctt caccctcgag   240
gagctcatcg ccaacactgg taataccagc ccgggtgtcc cgctcgtagg tctgcctcca   300
taccaagtct ggagtgaggc ccttgcatgg ctggaccgcg gcaatttcac ggacgagggg   360
gcttacagct gggcgacatc cttccctcg cccattctct ccgctgctgc ctttaatcgc   420
accctgatca accagatcgc ctccattatc tcaactcagg gtcgcgcctt caacaacgcc   480
ggccgctacg gtctcgatgt ctacgccccc aacatcaatg ccttccgtca cccgtctgg   540
ggtcgcggac aggaaactcc gggcgaggat gcgtacactc tcacagccgc ctacgcctac   600
gaatacatca cgggtatcca gggtggcgtg gacccagagc atctgaagct cgcagcaaca   660
gccaagcact tgccggcta tgacatcgag aactgggaca ccactcccg gctggggaac    720
gatgtcaaca tcacgcagca agacctggca gagtactaca cgccgcagtt cctcgtggcc   780
acgcgcgatg cccgcgttca cagtgttatg tgctcctaca cgccgtcaa cggcgtgccc   840
agctgctcca acaccttctt cctgcagacc ctcctgcgcg acacctttc cttcgtcgac   900
cacggctacg tctccggcga ctgcggcgcc gtctacggcg tcttcaaccc ccacggctac   960
gcggccaacg agtccagtgc cgccgccgac tctatcctcg ctggcaccga catcgattgc  1020
ggcacctcct accagtacca cttcaatgag tccatcacca ccggggcggt cgcccgcgac  1080
gacatcgagc gcgggctcat ccggctgtac gccaacctcg tccggctggg ctacttcgac  1140
ggcaacagca gcagcagcag cccgtaccgc agcctgagct ggtccgacgt ccaaaagaca  1200
gacgcatgga acatctccta cgaagcggca gtcgaatggc tgttcctcct gaagaatgaa  1260
ggcgccctcc cgcttccctc ctcctcctcg gtaagaacaa aatccatcgc cctcatcggc  1320
ccctgggcca acgccaccac ccagctcag gcaactact acggcgcggc gccatacctc  1380
atcagcccag tcgacgcctt cacggccgcc ggctacacgg tccactacgc cgccggcacg  1440
gagatctcca cgaactcgac ggcgaacttc agcgccgcgc tctccgccgc gcgcgccgcc  1500
gacaccatcg tattcttcgg cgggatcgac aacaccatcg aggcggaagc ccaagaccgg  1560
agctcgatcg cctggcccgg caaccagctc gagctgatcg cgcaactggc cgcgcagaaa  1620
tccgagtccc agcccctggt ggtgtaccaa atgggcggcg gcaggtcga ctcgtccgcc   1680
ctgaaagcaa acccgaaggt caacgccctc tctggggcg gctacccggg ccaatccggc  1740
ggcctcgccc tccgcgacat cctcacgggc gcccgcgccc cggccggccg cctcaccacg  1800
acccagtacc ccgcctccta cgccgagagc ttctcggcgc tcgacatgaa cctgcggcct  1860
aacaccacca ccaacaaccc aggccaaacc tacatgtggt acaccggcga acccgtctac  1920
gaattcggcc acggctcttt ctacaccacc ttcaaggctt cctccctgcc ctcttccacc  1980
cagaacacga cctccgcagc agcagcggca gcagcgca agaagtatac attcaacatc  2040
acagacctca cctcctccgc cacccgac caccaccg tcgcccaaca cacctcttc    2100
aacttcacgg cgtccatcac gaattccggg gccagggact ccgattacac cgccctgctg  2160
tacgccaaca cctcgagtgc ggggcccgtcc ccgtacccga ataaatggct cgtcgggttc  2220
gataggctcg gtgccgtggc caaggagggg ggcacggcgg tgttgaatgt gcctgtggcg  2280
gtggatcggt tggcgagggt cgatgacgac gggaattccg tgctgtttcc ggggcgctat  2340
gaggtggcct tgaataatga gcgcgaggtc gtggtcgagg tcgagttggt gggggaggcg  2400
gtggtgttgg tgaagtggcc ggaggaggtg caggggggtg cggggatga gtaa          2454

SEQ ID NO: 204         moltype = AA  length = 817
FEATURE                Location/Qualifiers
source                 1..817
                       mol_type = protein
                       organism = Aspergillus aculeatus
```

```
SEQUENCE: 204
MAVAALALLA LLPQALAQHN SSYVDYNVEA NPDLFPQCLD TISLSFPDCQ SGPLSKNVVC    60
DSTASPYDRA AALISLFTLE ELIANTGNTS PGVPRLGLPP YQVWSEALHG LDRGNFTDEG   120
AYSWATSFPS PILSAAAFNR TLINQIASII STQGRAFNNA GRYGLDVYAP NINAFRHPVW   180
GRGQETPGED AYTLTAAYAY EYITGIQGGV DPEHLKLAAT AKHFAGYDIE NWDNHSRLGN   240
DVNITQQDLA EYYTPQFLVA TRDARVHSVM CSYNAVNGVP SCSNTFFLQT LLRDTFSFVD   300
HGYVSGDCGA VYGVFNPHGY AANESSAAAD SILAGTDIDC GTSYQYHFNE SITTGAVARD   360
DIERGLIRLY ANLVRLGYFD GNSSSSSPYR SLSWSDVQKT DAWNISYEAA VEGIVLLKND   420
GALPLPSSSS GKNKSIALIG PWANATTQLQ GNYYGAAPYL ISPVDAFTAA GYTVHYAAGT   480
EISTNSTANF SAALSAARAA DTIVFFGGID NTIEAEAQDR SSIAWPGNQL ELIAQLAAQK   540
SESQPLVVYQ MGGGQVDSSA LKANPKVNAL LWGGYPGQSG GLALRDILTG ARAPAGRLTT   600
TQYPASYAES FSALDMNLRP NTTTNNPGQT YMWYTGEPVY EFGHGLFYTT FKASSLPSST   660
QNTTSAAAAA AAAKKYTFNI TDLTSSAHPD TTTVAQHTLF NFTASITNSG ARDSDYTALL   720
YANTSSAGPS PYPNKWLVGF DRLGAVAKEG GTAVLNVPVA VDRLARVDDD GNSVLFPGRY   780
EVALNNEREV VVEVELVGEA VVLVKWPEEV QGVAGDE                            817

SEQ ID NO: 205          moltype = DNA   length = 2376
FEATURE                 Location/Qualifiers
source                  1..2376
                        mol_type = genomic DNA
                        organism = Aspergillus fumigatus
SEQUENCE: 205
atggcggttg ccaaatctat tgctgccgtg ctggtagcac tgttgcctgg tgcgcttgct    60
caggcgaata caagctatgt tgattacaat gtggaggcga atccggatct cacccctcag   120
tcggtcgcta cgattgacct gtcctttccc gactgcgaga atggaccgct cagcaagact   180
ctcgtttgcg acacgtcggc tcggccgcat gaccgagctg ctgccctgtc ttccatgttc   240
accttcgagg agctggtgaa caacacaggc aacactagcc ctggtgttcc aagacttggt   300
ctccctccgt accaagtatg gagcgaggct ctccatggac ttgaccgcgc caacttcaca   360
aacgagggag agtacagctg ggccacctcg ttccccatgc ctatcctgac aatgtcggcc   420
ttgaaccgaa ccctgatcaa ccagatcgcg accatcatcg caactcaagg acagagcttc   480
aataacgttg gcggtatgg gctggacgtg tacgccccga atataaatgc attcagatcg   540
gctatgtggg gaagaggtca agagaccccc ggagaagacg cttactgcct ggcatcggcg   600
tatgcgtacg agtatatcac tggcatccag ggtggtgttg atccggaaca cctcaagttg   660
gtggccactg ccaaacacta tgcgggctac gatcttgaga actgggacgg tcactccgt    720
ttgggcaacg atatgaacat tacacagcag gaacttccg aatactacac ccctcagttc    780
cttgttgcag ccagagacgc caagtgcac agtgtcatgt gctcctacaa cgcggtaaat    840
ggggtgccca gctgcgcaaa ctcgttcttc ctccagaccc tcctccgtga cacattcggc   900
ttcgtcgagg atggttatgt atccagcgac tgcgactcgg cgtacaatgt ctggaacccg   960
cacgagtttg cggccaacat cacgggggcc gctgcagact ctatccggcg ggggacggac  1020
attgattgcg gcactactta tcaatactat ttcggcgaag cctttgacga gcaagaggtc  1080
acccgtgcag aaatcgaaag aggtgtgatc cgcctgtaca gcaacttggt gcgtctcggc  1140
tatttcgatg gcaatggaag cgtgtatcgg gacctgacgt ggaatgatgt cgtgaccacg  1200
gatgcctgga atatctcata cgaagccgct gtagaaggca ttgtcctact gaagaacgat  1260
ggaaccttgc ctctcgccaa gtcggtccgc agtgttgcat tgattgggcc ctggatgaat  1320
gtgacgactc agcttcaggg caactacttt ggaccggcgc cttatctgat tagtccgttg  1380
aatgccttcc agaattctga cttcgacgtg aactacgctt tcggcacgaa catttcatcc  1440
cactccacag atgggttttc cgaggcgttg tctgctgcga agaaatcgaa cgtcatcata  1500
ttcgcgggcg ggattgacaa cactttggaa gcagaagcca tggatcgcat gaatatcaca  1560
tggcccggca atcagctaca gctcatcgac cagttgagcc aactcggcaa accgctgatc  1620
gtcctccaga tgggcggcgg ccaagtcgac tcctcctcgc tcaagtccaa caagaatgtc  1680
aactccctga tctgggtgg atacccggga caatccggcg ggcaggctct cctagacatc  1740
atcaccggca agcgcgcccc cgccggccga ctcgtggtca cgcagtaccc ggccgaatac  1800
gcaacccagt tccccgccac cgacatgagc ctgcggcctc acggcaataa tcccggccag  1860
acctacatgt ggtacaccgg caccccgtc tacgagtttg gccacgggct cttctacacg   1920
accttccaag cctccctccc tggcaccggc aaggacaaga cctccttcaa catccaagac  1980
ctcctcacgc agccgcatcc gggcttcgca aacgtcgagc aaatgccttt gctcaacttc  2040
accgtgacga tcaccaatac cggcaaggtc gcttccgact cactgctat gctcttcgcg   2100
aacaccaccg cgggacctgc tccataccgg aacaagtggc tcgtcggctt cgaccggctg  2160
gcgagcctgg aaccgcacag gtcgcagact atgaccatcc ccgtgactat cgacagcgtg  2220
gtctcgtacg gatgaggccgg caatcggtt tctcacccgg gaaagtacga gttggccctg   2280
aacaatgagc ggtcggttgt ccttcagttt gtgctgacag gccgagaggc tgtgattttc   2340
aagtggcctg tagagcagca gcagatttcg tctgcg                             2376

SEQ ID NO: 206          moltype = AA    length = 792
FEATURE                 Location/Qualifiers
source                  1..792
                        mol_type = protein
                        organism = Aspergillus fumigatus
SEQUENCE: 206
MAVAKSIAAV LVALLPGALA QANTSYVDYN VEANPDLTPQ SVATIDLSFP DCENGPLSKT    60
LVCDTSARPH DRAAALVSMF TFEELVNNTG NTSPGVPRLG LPPYQVWSEA LHGLDRANFT   120
NEGEYSWATS FPMPILTMSA LNRTLINQIA TIIATQGRAF NNVGRYGLDV YAPNINAFRS   180
AMWGRGQETP GEDAYCLASA YAYEYITGIQ GGVDPEHLKL VATAKHYAGY DLENWDGHSR   240
LGNDMNITQQ ELSEYYTPQF LVAARDAKVH SVMCSYNAVN GVPSCANSFF LQTLLRDTFG   300
FVEDGYVSSD CDSAYNVWNP HEFAANITGA AADSIRAGTD IDCGTTYQYY FGEAFDEQEV   360
TRAEIERGVI RLYSNLVRLG YFDGNSVYR DLTWNDVVTT DAWNISYEAA VEGIVLLKND    420
GTLPLAKSVR SVALIGPWMN VTTQLQGNYF GPAPYLISPL NAFQNSDFDV NYAFGTNISS   480
HSTDGFSEAL SAAKKSDVII FAGGIDNTLE AEAMDRMNIT WPGNQLQLID QLSQLGKPLI   540
VLQMGGGQVD SSSLKSNKNV NSLIWGGYPG QSGGQALLDI ITGKRAPAGR LVVTQYPAEY   600
```

```
ATQFPATDMS LRPHGNNPGQ TYMWYTGTPV YEFGHGLFYT TFHASLPGTG KDKTSFNIQD    660
LLTQPHPGFA NVEQMPLLNF TVTITNTGKV ASDYTAMLFA NTTAGPAPYP NKWLVGFDRL    720
ASLEPHRSQT MTIPVTIDSV ARTDEAGNRV LYPGKYELAL NNERSVVLQF VLTGREAVIF    780
KWPVEQQQIS SA                                                       792

SEQ ID NO: 207          moltype = DNA   length = 38
FEATURE                 Location/Qualifiers
source                  1..38
                        mol_type = other DNA
                        organism = Penicillium emersonii
SEQUENCE: 207
acacaactgg ggatccacca tgcttcgacg ggctcttc                            38

SEQ ID NO: 208          moltype = DNA   length = 40
FEATURE                 Location/Qualifiers
source                  1..40
                        mol_type = other DNA
                        organism = Penicillium emersonii
SEQUENCE: 208
gtcaccctct agatctcgca gagcaacttc cgtctacttc                          40

SEQ ID NO: 209          moltype = DNA   length = 40
FEATURE                 Location/Qualifiers
source                  1..40
                        mol_type = other DNA
                        organism = Penicillium pinophilum
SEQUENCE: 209
acacaactgg ggatccacca tgtctgcctt gaactctttc                          40

SEQ ID NO: 210          moltype = DNA   length = 43
FEATURE                 Location/Qualifiers
source                  1..43
                        mol_type = other DNA
                        organism = Penicillium pinophilum
SEQUENCE: 210
gtcaccctct agatcttcac aaacattgag agtagtaagg gtt                      43

SEQ ID NO: 211          moltype = DNA   length = 29
FEATURE                 Location/Qualifiers
source                  1..29
                        mol_type = other DNA
                        organism = Aspergillus terreus
SEQUENCE: 211
taagaattca ccatgccttc cacctacga                                      29

SEQ ID NO: 212          moltype = DNA   length = 32
FEATURE                 Location/Qualifiers
source                  1..32
                        mol_type = other DNA
                        organism = Aspergillus terreus
SEQUENCE: 212
tatgcggccg cattctccta gacaccccgc at                                  32

SEQ ID NO: 213          moltype = DNA   length = 29
FEATURE                 Location/Qualifiers
source                  1..29
                        mol_type = other DNA
                        organism = Neosartorya fischeri
SEQUENCE: 213
taagaattca ccatgccttc cacctacga                                      29

SEQ ID NO: 214          moltype = DNA   length = 32
FEATURE                 Location/Qualifiers
source                  1..32
                        mol_type = other DNA
                        organism = Neosartorya fischeri
SEQUENCE: 214
tatgcggccg cattctccta gacaccccgc at                                  32

SEQ ID NO: 215          moltype = DNA   length = 35
FEATURE                 Location/Qualifiers
source                  1..35
                        mol_type = other DNA
                        organism = Aspergillus nidulans
SEQUENCE: 215
taacaattga ccatggcatc ttcattccag ttgta                               35

SEQ ID NO: 216          moltype = DNA   length = 33
FEATURE                 Location/Qualifiers
```

```
source                  1..33
                        mol_type = other DNA
                        organism = Aspergillus nidulans
SEQUENCE: 216
tatgcggccg cgtctcccat ttacgaccca cca                               33

SEQ ID NO: 217          moltype = DNA  length = 41
FEATURE                 Location/Qualifiers
source                  1..41
                        mol_type = other DNA
                        organism = Fennellia nivea
SEQUENCE: 217
acacaactgg ggatccacca tgggacgggt ttcttctctt g                      41

SEQ ID NO: 218          moltype = DNA  length = 39
FEATURE                 Location/Qualifiers
source                  1..39
                        mol_type = other DNA
                        organism = Fennellia nivea
SEQUENCE: 218
gtcaccctct agatctaaga acaccccgca aagaaagtc                         39

SEQ ID NO: 219          moltype = DNA  length = 42
FEATURE                 Location/Qualifiers
source                  1..42
                        mol_type = other DNA
                        organism = Penicillium emersonii
SEQUENCE: 219
acacaactgg ggatccacca tgcggaatct tcttgctctt gc                     42

SEQ ID NO: 220          moltype = DNA  length = 41
FEATURE                 Location/Qualifiers
source                  1..41
                        mol_type = other DNA
                        organism = Penicillium emersonii
SEQUENCE: 220
gtcaccctct agatctctag aacagcgggt tagcattcgt g                      41

SEQ ID NO: 221          moltype = DNA  length = 40
FEATURE                 Location/Qualifiers
source                  1..40
                        mol_type = other DNA
                        organism = Penicillium pinophilum
SEQUENCE: 221
acacaactgg ggatccacca tgttgcgata tctttccacc                        40

SEQ ID NO: 222          moltype = DNA  length = 39
FEATURE                 Location/Qualifiers
source                  1..39
                        mol_type = other DNA
                        organism = Penicillium pinophilum
SEQUENCE: 222
gtcaccctct agatcttcat ctagaccaaa gctgggttg                         39

SEQ ID NO: 223          moltype = DNA  length = 36
FEATURE                 Location/Qualifiers
source                  1..36
                        mol_type = other DNA
                        organism = Aspergillus fumigatus
SEQUENCE: 223
actggattta ccatgaaatt cggtagcatt gtgctc                            36

SEQ ID NO: 224          moltype = DNA  length = 43
FEATURE                 Location/Qualifiers
source                  1..43
                        mol_type = other DNA
                        organism = Aspergillus fumigatus
SEQUENCE: 224
tcacctctag ttaattaatc aacccaggta gggctccaag atg                    43

SEQ ID NO: 225          moltype = DNA  length = 39
FEATURE                 Location/Qualifiers
source                  1..39
                        mol_type = other DNA
                        organism = Neosartorya fischeri
SEQUENCE: 225
taagaattca ccatgaaggc ttcgactatt atctgtgca                         39

SEQ ID NO: 226          moltype = DNA  length = 32
```

```
FEATURE                 Location/Qualifiers
source                  1..32
                        mol_type = other DNA
                        organism = Neosartorya fischeri
SEQUENCE: 226
tatgcggccg cacggcaatc caagtcattc aa                                32

SEQ ID NO: 227          moltype = DNA   length = 44
FEATURE                 Location/Qualifiers
source                  1..44
                        mol_type = other DNA
                        organism = Aspergillus aculeatus
SEQUENCE: 227
acacaactgg ggatccacca tgaagctcag ttggcttgag gcgg                   44

SEQ ID NO: 228          moltype = DNA   length = 44
FEATURE                 Location/Qualifiers
source                  1..44
                        mol_type = other DNA
                        organism = Aspergillus aculeatus
SEQUENCE: 228
agatctcgag aagcttattg caccttcggg agcgccgcgt gaag                   44

SEQ ID NO: 229          moltype = DNA   length = 44
FEATURE                 Location/Qualifiers
source                  1..44
                        mol_type = other DNA
                        organism = Aspergillus kawachii
SEQUENCE: 229
acacaactgg ggatccacca tgaggttcac tttgattgag gcgg                   44

SEQ ID NO: 230          moltype = DNA   length = 45
FEATURE                 Location/Qualifiers
source                  1..45
                        mol_type = other DNA
                        organism = Aspergillus kawachii
SEQUENCE: 230
agatctcgag aagcttagtg aacagtaggc agagacgccc ggagc                  45

SEQ ID NO: 231          moltype = DNA   length = 44
FEATURE                 Location/Qualifiers
source                  1..44
                        mol_type = other DNA
                        organism = Aspergillus clavatus
SEQUENCE: 231
acacaactgg ggatccacca tgaggttcag ctggcttgag gtcg                   44

SEQ ID NO: 232          moltype = DNA   length = 42
FEATURE                 Location/Qualifiers
source                  1..42
                        mol_type = other DNA
                        organism = Aspergillus clavatus
SEQUENCE: 232
agatctcgag aagcttactg tacccggggc agaggtgctc tc                     42

SEQ ID NO: 233          moltype = DNA   length = 46
FEATURE                 Location/Qualifiers
misc_feature            45
                        note = V=A, C, OR G
misc_feature            46
                        note = N=A, C, G, OR T
source                  1..46
                        mol_type = other DNA
                        organism = Thielavia terrestris
SEQUENCE: 233
gactagttct agatcgcgag cggccgccct tttttttttt ttttvn                 46

SEQ ID NO: 234          moltype = DNA   length = 16
FEATURE                 Location/Qualifiers
source                  1..16
                        mol_type = other DNA
                        organism = Thielavia terrestris
SEQUENCE: 234
tcgacccacg cgtccg                                                  16

SEQ ID NO: 235          moltype = DNA   length = 12
FEATURE                 Location/Qualifiers
```

```
source                      1..12
                            mol_type = other DNA
                            organism = Thielavia terrestris
SEQUENCE: 235
cggacgcgtg gg                                                               12

SEQ ID NO: 236              moltype = DNA   length = 17
FEATURE                     Location/Qualifiers
source                      1..17
                            mol_type = other DNA
                            organism = Thielavia terrestris
SEQUENCE: 236
gtaaaacgac ggccagt                                                          17

SEQ ID NO: 237              moltype = DNA   length = 19
FEATURE                     Location/Qualifiers
source                      1..19
                            mol_type = other DNA
                            organism = Thielavia terrestris
SEQUENCE: 237
aggaaacagc tatgaccat                                                        19

SEQ ID NO: 238              moltype = DNA   length = 20
FEATURE                     Location/Qualifiers
source                      1..20
                            mol_type = other DNA
                            organism = Thielavia terrestris
SEQUENCE: 238
atttaggtga cactatagaa                                                       20

SEQ ID NO: 239              moltype = DNA   length = 20
FEATURE                     Location/Qualifiers
source                      1..20
                            mol_type = other DNA
                            organism = Thielavia terrestris
SEQUENCE: 239
taatacgact cactataggg                                                       20

SEQ ID NO: 240              moltype = DNA   length = 32
FEATURE                     Location/Qualifiers
source                      1..32
                            mol_type = other DNA
                            organism = Thielavia terrestris
SEQUENCE: 240
actggattta ccatgaagcc tgccattgtg ct                                         32

SEQ ID NO: 241              moltype = DNA   length = 38
FEATURE                     Location/Qualifiers
source                      1..38
                            mol_type = other DNA
                            organism = Thielavia terrestris
SEQUENCE: 241
tcacctctag ttaattaatc acggcaactc aatgctca                                   38

SEQ ID NO: 242              moltype = DNA   length = 35
FEATURE                     Location/Qualifiers
misc_feature                25
                            note = Y= C OR T
misc_feature                27
                            note = N= A, C, G, OR T
misc_feature                30
                            note = N= A, C, G, OR T
misc_feature                33
                            note = N= A, C, G, OR T
source                      1..35
                            mol_type = other DNA
                            organism = Penicillium oxalicum
SEQUENCE: 242
atgaccctgg ccgaaaaagt caacytnacn acngg                                      35

SEQ ID NO: 243              moltype = DNA   length = 35
FEATURE                     Location/Qualifiers
misc_feature                26
                            note = S= C OR G
misc_feature                27
                            note = N= A, C, G, OR T
misc_feature                30
                            note = N= A, C, G, OR T
```

```
misc_feature           33
                       note = Y= C OR T
source                 1..35
                       mol_type = other DNA
                       organism = Penicillium oxalicum
SEQUENCE: 243
ggtggccgga actgggaagg cttctsnccn gaycc                           35

SEQ ID NO: 244         moltype = DNA  length = 36
FEATURE                Location/Qualifiers
misc_feature           24
                       note = N= A,C, G, OR T
misc_feature           28
                       note = W= A OR T
misc_feature           29
                       note = S= C OR G
misc_feature           30
                       note = N= A, C, G, OR T
misc_feature           33
                       note = Y= C OR T
source                 1..36
                       mol_type = other DNA
                       organism = Penicillium oxalicum
SEQUENCE: 244
gagctgggct tccagggctt tgtnatgwsn gaytgg                          36

SEQ ID NO: 245         moltype = DNA  length = 32
FEATURE                Location/Qualifiers
misc_feature           21
                       note = Y=C OR T
misc_feature           25
                       note = W= A OR T
misc_feature           26
                       note = S= C OR G
misc_feature           27
                       note = N= A, C, G, OR T
source                 1..32
                       mol_type = other DNA
                       organism = Penicillium oxalicum
SEQUENCE: 245
agcgctttgg ccggcctcga yatgwsnatg cc                              32

SEQ ID NO: 246         moltype = DNA  length = 27
FEATURE                Location/Qualifiers
misc_feature           21
                       note = K= G OR T
misc_feature           22
                       note = N= A,C, G, OR T
misc_feature           24
                       note = K= G OR T
misc_feature           25
                       note = N= A, C, G, OR T
source                 1..27
                       mol_type = other DNA
                       organism = Penicillium oxalicum
SEQUENCE: 246
atcccagttg ctcaggtccc knckngt                                    27

SEQ ID NO: 247         moltype = DNA  length = 33
FEATURE                Location/Qualifiers
misc_feature           19
                       note = N= A,C ,G, OR T
misc_feature           22
                       note = R= A OR G
misc_feature           25
                       note = N= A,C ,G, OR T
misc_feature           28
                       note = R= A OR G
misc_feature           31
                       note = Y = C OR T
source                 1..33
                       mol_type = other DNA
                       organism = Penicillium oxalicum
SEQUENCE: 247
aaaggttgtg tagctcagnc crtgnccraa ytc                             33

SEQ ID NO: 248         moltype = DNA  length = 33
FEATURE                Location/Qualifiers
```

```
misc_feature            22
                        note = R= A OR G
misc_feature            25
                        note = N= A, C, G, OR T
misc_feature            28
                        note = N= A, C, G, OR T
misc_feature            31
                        note = Y= C OR T
source                  1..33
                        mol_type = other DNA
                        organism = Penicillium oxalicum
SEQUENCE: 248
gtcaaagtgg cggtagtcga traanacncc ytc                                     33

SEQ ID NO: 249          moltype = DNA   length = 39
FEATURE                 Location/Qualifiers
misc_feature            34
                        note = R= A OR G
misc_feature            37
                        note = N= A,C, G, OR T
misc_feature            39
                        note = R= A OR G
source                  1..39
                        mol_type = other DNA
                        organism = Penicillium oxalicum
SEQUENCE: 249
ggtgggcgag ttgccgacgg ggttgactct gccrtanar                               39

SEQ ID NO: 250          moltype = DNA   length = 39
FEATURE                 Location/Qualifiers
misc_feature            28
                        note = N= A,C, G, OR T
misc_feature            31
                        note = N= A,C, G, OR T
misc_feature            34
                        note = R= A OR G
misc_feature            37
                        note = N= A, C ,G, OR T
source                  1..39
                        mol_type = other DNA
                        organism = Penicillium oxalicum
SEQUENCE: 250
gccgggcaga ccggcccaga ggatggcngt nacrttngg                               39

SEQ ID NO: 251          moltype = DNA   length = 39
FEATURE                 Location/Qualifiers
misc_feature            28
                        note = N= A, C, G, OR T
misc_feature            31
                        note = D= A, G, OR T
misc_feature            34
                        note = N= A, C, G, OR T
misc_feature            37
                        note = R= A OR G
source                  1..39
                        mol_type = other DNA
                        organism = Penicillium oxalicum
SEQUENCE: 251
caggacgggg ccaaccgagt gaatgacnac datngtrtt                               39

SEQ ID NO: 252          moltype = DNA   length = 21
FEATURE                 Location/Qualifiers
source                  1..21
                        mol_type = other DNA
                        organism = Penicillium oxalicum
SEQUENCE: 252
caccaacacc ggcaatctag c                                                  21

SEQ ID NO: 253          moltype = DNA   length = 25
FEATURE                 Location/Qualifiers
source                  1..25
                        mol_type = other DNA
                        organism = Penicillium oxalicum
SEQUENCE: 253
ggtgacgagg ttgtccaact gtacg                                              25

SEQ ID NO: 254          moltype = DNA   length = 18
FEATURE                 Location/Qualifiers
```

```
source                  1..18
                        mol_type = other DNA
                        organism = Penicillium oxalicum
SEQUENCE: 254
cttgaagcca aggcgagg                                                      18

SEQ ID NO: 255          moltype = DNA  length = 24
FEATURE                 Location/Qualifiers
source                  1..24
                        mol_type = other DNA
                        organism = Penicillium oxalicum
SEQUENCE: 255
tccggtattt cctacacatg gtcc                                               24

SEQ ID NO: 256          moltype = DNA  length = 43
FEATURE                 Location/Qualifiers
source                  1..43
                        mol_type = other DNA
                        organism = Penicillium oxalicum
SEQUENCE: 256
agatctcgag aagcttacca tgactccaat cgcgcgctca agg                          43

SEQ ID NO: 257          moltype = DNA  length = 46
FEATURE                 Location/Qualifiers
source                  1..46
                        mol_type = other DNA
                        organism = Penicillium oxalicum
SEQUENCE: 257
acacaactgg ggatccacca tgaggagctc aacgacggtt ctggcc                       46

SEQ ID NO: 258          moltype = DNA  length = 35
FEATURE                 Location/Qualifiers
misc_feature            25
                        note = Y= C OR T
misc_feature            27
                        note = N= A, C, G, OR T
misc_feature            30
                        note = N= A, C, G, OR T
misc_feature            33
                        note = N= A, C, G, OR T
source                  1..35
                        mol_type = other DNA
                        organism = Penicillium oxalicum
SEQUENCE: 258
atgaccctgg ccgaaaaagt caacytnacn acngg                                   35

SEQ ID NO: 259          moltype = DNA  length = 35
FEATURE                 Location/Qualifiers
misc_feature            26
                        note = S= C OR G
misc_feature            27
                        note = N= A, C, G, OR T
misc_feature            30
                        note = N= A, C, G, OR T
misc_feature            33
                        note = Y= C OR T
source                  1..35
                        mol_type = other DNA
                        organism = Penicillium oxalicum
SEQUENCE: 259
ggtggccgga actgggaagg cttctsnccn gaycc                                   35

SEQ ID NO: 260          moltype = DNA  length = 36
FEATURE                 Location/Qualifiers
misc_feature            24
                        note = N= A, C, G, OR T
misc_feature            28
                        note = W= A OR T
misc_feature            29
                        note = S= C OR G
misc_feature            30
                        note = N= A, C, G, OR T
misc_feature            33
                        note = Y= C OR T
source                  1..36
                        mol_type = other DNA
                        organism = Penicillium oxalicum
SEQUENCE: 260
gagctgggct tccagggctt tgtnatgwsn gaytgg                                  36
```

```
SEQ ID NO: 261          moltype = DNA  length = 32
FEATURE                 Location/Qualifiers
misc_feature            21
                        note = Y= C OR T
misc_feature            25
                        note = W= A OR T
misc_feature            26
                        note = S= C OR G
misc_feature            27
                        note = N= A, C, G, OR T
source                  1..32
                        mol_type = other DNA
                        organism = Penicillium oxalicum
SEQUENCE: 261
agcgctttgg ccggcctcga yatgwsnatg cc                                    32

SEQ ID NO: 262          moltype = DNA  length = 27
FEATURE                 Location/Qualifiers
misc_feature            21
                        note = K= G OR T
misc_feature            22
                        note = N= A, C, G, OR T
misc_feature            24
                        note = K= G OR T
misc_feature            25
                        note = N= A, C, G, OR T
source                  1..27
                        mol_type = other DNA
                        organism = Penicillium oxalicum
SEQUENCE: 262
atcccagttg ctcaggtccc knckngt                                          27

SEQ ID NO: 263          moltype = DNA  length = 33
FEATURE                 Location/Qualifiers
misc_feature            19
                        note = N= A,C ,G, OR T
misc_feature            22
                        note = R= A OR G
misc_feature            25
                        note = N= A, C, G, OR T
misc_feature            28
                        note = R= A OR G
misc_feature            31
                        note = Y= C OR T
source                  1..33
                        mol_type = other DNA
                        organism = Penicillium oxalicum
SEQUENCE: 263
aaaggttgtg tagctcagnc crtgnccraa ytc                                   33

SEQ ID NO: 264          moltype = DNA  length = 33
FEATURE                 Location/Qualifiers
misc_feature            22
                        note = R= A OR G
misc_feature            25
                        note = N= A, C, G, OR T
misc_feature            28
                        note = N= A, C, G, OR T
misc_feature            31
                        note = Y= C OR T
source                  1..33
                        mol_type = other DNA
                        organism = Penicillium oxalicum
SEQUENCE: 264
gtcaaagtgg cggtagtcga traanacncc ytc                                   33

SEQ ID NO: 265          moltype = DNA  length = 39
FEATURE                 Location/Qualifiers
misc_feature            34
                        note = R= A OR G
misc_feature            37
                        note = N= A, C, G, OR T
misc_feature            39
                        note = R= A OR G
source                  1..39
                        mol_type = other DNA
                        organism = Penicillium oxalicum
```

| | | |
|---|---|---|
| SEQUENCE: 265 | | |
| ggtgggcgag ttgccgacgg ggttgactct gccrtanar | | 39 |
| | | |
| SEQ ID NO: 266 | moltype = DNA  length = 39 | |
| FEATURE | Location/Qualifiers | |
| misc_feature | 28 | |
| | note = N= A, C, G, OR T | |
| misc_feature | 31 | |
| | note = N= A, C, G, OR T | |
| misc_feature | 34 | |
| | note = R= A OR G | |
| misc_feature | 37 | |
| | note = N= A, C, G, OR T | |
| source | 1..39 | |
| | mol_type = other DNA | |
| | organism = Penicillium oxalicum | |
| SEQUENCE: 266 | | |
| gccgggcaga ccggcccaga ggatggcngt nacrttngg | | 39 |
| | | |
| SEQ ID NO: 267 | moltype = DNA  length = 39 | |
| FEATURE | Location/Qualifiers | |
| misc_feature | 28 | |
| | note = N= A, C, G, OR T | |
| misc_feature | 31 | |
| | note = D= A, G, OR T | |
| misc_feature | 34 | |
| | note = N= A, C, G, OR T | |
| misc_feature | 37 | |
| | note = R= A OR G | |
| source | 1..39 | |
| | mol_type = other DNA | |
| | organism = Penicillium oxalicum | |
| SEQUENCE: 267 | | |
| caggacgggg ccaaccgagt gaatgacnac datngtrtt | | 39 |
| | | |
| SEQ ID NO: 268 | moltype = DNA  length = 42 | |
| FEATURE | Location/Qualifiers | |
| source | 1..42 | |
| | mol_type = other DNA | |
| | organism = Penicillium oxalicum | |
| SEQUENCE: 268 | | |
| acacaactgg ggatccacca tgaagctcga gtggctggaa gc | | 42 |
| | | |
| SEQ ID NO: 269 | moltype = DNA  length = 40 | |
| FEATURE | Location/Qualifiers | |
| source | 1..40 | |
| | mol_type = other DNA | |
| | organism = Penicillium oxalicum | |
| SEQUENCE: 269 | | |
| agatctcgag aagcttactg caccttgggc agatcggctg | | 40 |
| | | |
| SEQ ID NO: 270 | moltype = DNA  length = 44 | |
| FEATURE | Location/Qualifiers | |
| source | 1..44 | |
| | mol_type = other DNA | |
| | organism = Talaromyces emersonii | |
| SEQUENCE: 270 | | |
| acacaactgg ggatccacca tgaggaacgg gttgctcaag gtcg | | 44 |
| | | |
| SEQ ID NO: 271 | moltype = DNA  length = 42 | |
| FEATURE | Location/Qualifiers | |
| source | 1..42 | |
| | mol_type = other DNA | |
| | organism = Talaromyces emersonii | |
| SEQUENCE: 271 | | |
| agatctcgag aagcttaaat tccagggtat ggcttaaggg gc | | 42 |
| | | |
| SEQ ID NO: 272 | moltype = DNA  length = 19 | |
| FEATURE | Location/Qualifiers | |
| misc_feature | 3 | |
| | note = N= A, C, G, OR T | |
| misc_feature | 6 | |
| | note = N= A, C, G, OR T | |
| misc_feature | 9 | |
| | note = Y= C OR T | |
| misc_feature | 12 | |
| | note = N= A, C, G, OR T | |
| misc_feature | 15 | |
| | note = N= A, C, G, OR T | |

| | | |
|---|---|---|
| source | 1..19 | |
| | mol_type = other DNA | |
| | organism = Thermoascus crustaceus | |
| SEQUENCE: 272 | | |
| gcnacngayc tnggntttg | | 19 |
| | | |
| SEQ ID NO: 273 | moltype = DNA length = 19 | |
| FEATURE | Location/Qualifiers | |
| misc_feature | 3 | |
| | note = N= A, C, G, OR T | |
| misc_feature | 6 | |
| | note = N= A, C, G, OR T | |
| misc_feature | 9 | |
| | note = Y= C OR T | |
| misc_feature | 12 | |
| | note = N= A, C, G, OR T | |
| misc_feature | 15 | |
| | note = N= A, C, G, OR T | |
| source | 1..19 | |
| | mol_type = other DNA | |
| | organism = Thermoascus crustaceus | |
| SEQUENCE: 273 | | |
| gcnacngayc tnggnttcg | | 19 |
| | | |
| SEQ ID NO: 274 | moltype = DNA length = 19 | |
| FEATURE | Location/Qualifiers | |
| misc_feature | 3 | |
| | note = N= A, C, G, OR T | |
| misc_feature | 6 | |
| | note = N= A, C, G, OR T | |
| misc_feature | 9 | |
| | note = Y= C OR T | |
| misc_feature | 12 | |
| | note = R= A OR G | |
| misc_feature | 15 | |
| | note = N= A, C, G, OR T | |
| misc_feature | 18 | |
| | note = Y= C OR T | |
| misc_feature | 18 | |
| | note = Y= C OR T | |
| source | 1..19 | |
| | mol_type = other DNA | |
| | organism = Thermoascus crustaceus | |
| SEQUENCE: 274 | | |
| gcnacngayt trggnttyg | | 19 |
| | | |
| SEQ ID NO: 275 | moltype = DNA length = 20 | |
| FEATURE | Location/Qualifiers | |
| misc_feature | 3 | |
| | note = Y= C OR T | |
| misc_feature | 6 | |
| | note = N= A, C, G, OR T | |
| misc_feature | 9 | |
| | note = R= A OR G | |
| misc_feature | 12 | |
| | note = R= A OR G | |
| misc_feature | 15 | |
| | note = Y= C OR T | |
| misc_feature | 18 | |
| | note = N= A, C, G, OR T | |
| source | 1..20 | |
| | mol_type = other DNA | |
| | organism = Thermoascus crustaceus | |
| SEQUENCE: 275 | | |
| caytgnggrt arttytgngc | | 20 |
| | | |
| SEQ ID NO: 276 | moltype = DNA length = 21 | |
| FEATURE | Location/Qualifiers | |
| source | 1..21 | |
| | mol_type = other DNA | |
| | organism = Thermoascus crustaceus | |
| SEQUENCE: 276 | | |
| tgcaaggagc aaggtagttg a | | 21 |
| | | |
| SEQ ID NO: 277 | moltype = DNA length = 22 | |
| FEATURE | Location/Qualifiers | |
| source | 1..22 | |
| | mol_type = other DNA | |
| | organism = Thermoascus crustaceus | |

-continued

```
SEQUENCE: 277
gagtccattc cagcttgacg gt                                              22

SEQ ID NO: 278          moltype = DNA   length = 20
FEATURE                 Location/Qualifiers
source                  1..20
                        mol_type = other DNA
                        organism = Thermoascus crustaceus
SEQUENCE: 278
tcagacaatc tgatagcggc                                                 20

SEQ ID NO: 279          moltype = DNA   length = 21
FEATURE                 Location/Qualifiers
source                  1..21
                        mol_type = other DNA
                        organism = Thermoascus crustaceus
SEQUENCE: 279
atcccaacca caactgcacc t                                               21

SEQ ID NO: 280          moltype = DNA   length = 44
FEATURE                 Location/Qualifiers
source                  1..44
                        mol_type = other DNA
                        organism = Thermoascus crustaceus
SEQUENCE: 280
acacaactgg ggatccacca tggccttttc ccagataatg gcta                      44

SEQ ID NO: 281          moltype = DNA   length = 36
FEATURE                 Location/Qualifiers
source                  1..36
                        mol_type = other DNA
                        organism = Thermoascus crustaceus
SEQUENCE: 281
gtcaccctct agatctggat cgcaggagcg ttcaga                               36

SEQ ID NO: 282          moltype = DNA   length = 38
FEATURE                 Location/Qualifiers
source                  1..38
                        mol_type = other DNA
                        organism = Talaromyces emersonii
SEQUENCE: 282
acacaactgg ggatccacca tggttcgcct cagtccag                             38

SEQ ID NO: 283          moltype = DNA   length = 44
FEATURE                 Location/Qualifiers
source                  1..44
                        mol_type = other DNA
                        organism = Talaromyces emersonii
SEQUENCE: 283
gtcaccctct agatctttac agacactgcg agtaatactc attg                      44

SEQ ID NO: 284          moltype = DNA   length = 25
FEATURE                 Location/Qualifiers
source                  1..25
                        mol_type = other DNA
                        organism = Dictyoglomus thermophilum
SEQUENCE: 284
ggatccatta tgtagggcgt aaagc                                           25

SEQ ID NO: 285          moltype = DNA   length = 31
FEATURE                 Location/Qualifiers
source                  1..31
                        mol_type = other DNA
                        organism = Dictyoglomus thermophilum
SEQUENCE: 285
ttagcaagct taatcacttt aatgccctca g                                    31

SEQ ID NO: 286          moltype = DNA   length = 31
FEATURE                 Location/Qualifiers
source                  1..31
                        mol_type = other DNA
                        organism = Dictyoglomus thermophilum
SEQUENCE: 286
tgattaagct tgctaatccg caggacactt c                                    31

SEQ ID NO: 287          moltype = DNA   length = 26
FEATURE                 Location/Qualifiers
```

```
source                    1..26
                          mol_type = other DNA
                          organism = Dictyoglomus thermophilum
SEQUENCE: 287
ggtaccaaca ctgcctctct catctc                                          26

SEQ ID NO: 288            moltype = DNA   length = 48
FEATURE                   Location/Qualifiers
source                    1..48
                          mol_type = other DNA
                          organism = Dictyoglomus thermophilum
SEQUENCE: 288
cttttagttc atcgatcgca tcggctgctc agacatcaat cacactta                  48

SEQ ID NO: 289            moltype = DNA   length = 49
FEATURE                   Location/Qualifiers
source                    1..49
                          mol_type = other DNA
                          organism = Dictyoglomus thermophilum
SEQUENCE: 289
ctagggttga tgctggtgtt ggtgctgatg gctgccctga gagaaagtg                 49

SEQ ID NO: 290            moltype = DNA   length = 21
FEATURE                   Location/Qualifiers
source                    1..21
                          mol_type = other DNA
                          organism = Dictyoglomus thermophilum
SEQUENCE: 290
gagtatcgcc agtaaggggc g                                               21

SEQ ID NO: 291            moltype = DNA   length = 22
FEATURE                   Location/Qualifiers
source                    1..22
                          mol_type = other DNA
                          organism = Dictyoglomus thermophilum
SEQUENCE: 291
agccgatgcg atcgatgaac ta                                              22

SEQ ID NO: 292            moltype = DNA   length = 53
FEATURE                   Location/Qualifiers
source                    1..53
                          mol_type = other DNA
                          organism = Dictyoglomus thermophilum
SEQUENCE: 292
catcagcacc aacaccagca ccagccataa tcgcatgttc aatccgctcc ata            53

SEQ ID NO: 293            moltype = DNA   length = 23
FEATURE                   Location/Qualifiers
source                    1..23
                          mol_type = other DNA
                          organism = Dictyoglomus thermophilum
SEQUENCE: 293
gcagccctaa aatcgcataa agc                                             23

SEQ ID NO: 294            moltype = DNA   length = 40
FEATURE                   Location/Qualifiers
source                    1..40
                          mol_type = other DNA
                          organism = Dictyoglomus thermophilum
SEQUENCE: 294
gagctctata aaaatgagga gggaaccgaa tgaagaaacc                           40

SEQ ID NO: 295            moltype = DNA   length = 28
FEATURE                   Location/Qualifiers
source                    1..28
                          mol_type = other DNA
                          organism = Dictyoglomus thermophilum
SEQUENCE: 295
acgcgtttag ctgccctgag agaaagtg                                        28

SEQ ID NO: 296            moltype = DNA   length = 20
FEATURE                   Location/Qualifiers
source                    1..20
                          mol_type = other DNA
                          organism = Dictyoglomus thermophilum
SEQUENCE: 296
ccgttgggga aaattgtcgc                                                 20

SEQ ID NO: 297            moltype = DNA   length = 20
```

```
FEATURE              Location/Qualifiers
source               1..20
                     mol_type = other DNA
                     organism = Dictyoglomus thermophilum
SEQUENCE: 297
gcgacaattt tccccaacgg                                               20

SEQ ID NO: 298       moltype = DNA   length = 37
FEATURE              Location/Qualifiers
source               1..37
                     mol_type = other DNA
                     organism = Aspergillus aculeatus
SEQUENCE: 298
acacaactgg ggatccacca tggctgtggc ggctctt                            37

SEQ ID NO: 299       moltype = DNA   length = 35
FEATURE              Location/Qualifiers
source               1..35
                     mol_type = other DNA
                     organism = Aspergillus aculeatus
SEQUENCE: 299
agatctcgag aagcttacta ctcatccccc tgcac                              35

SEQ ID NO: 300       moltype = DNA   length = 47
FEATURE              Location/Qualifiers
source               1..47
                     mol_type = other DNA
                     organism = Aspergillus aculeatus
SEQUENCE: 300
acacaactgg ggatccacca tggctgtggc ggctcttgct ctgctgg                 47

SEQ ID NO: 301       moltype = DNA   length = 45
FEATURE              Location/Qualifiers
source               1..45
                     mol_type = other DNA
                     organism = Aspergillus aculeatus
SEQUENCE: 301
agatctcgag aagcttactc atccccgcc accccctgca cctcc                    45

SEQ ID NO: 302       moltype = DNA   length = 36
FEATURE              Location/Qualifiers
source               1..36
                     mol_type = other DNA
                     organism = Aspergillus fumigatus
SEQUENCE: 302
actggattta ccatggcggt tgccaaatct attgct                             36

SEQ ID NO: 303       moltype = DNA   length = 38
FEATURE              Location/Qualifiers
source               1..38
                     mol_type = other DNA
                     organism = Aspergillus fumigatus
SEQUENCE: 303
tcacctctag ttaattaatc acgcagacga aatctgct                           38

SEQ ID NO: 304       moltype = DNA   length = 696
FEATURE              Location/Qualifiers
source               1..696
                     mol_type = other DNA
                     organism = Dictyoglomus thermophilum
SEQUENCE: 304
atgaagaaac cgttgggaa aattgtcgca agcaccgcac tactcattc tgttgctttt     60
agttcatcga tcgcatcggc tgctcagaca tcaatcacac ttcatctaa cgcatcaggc   120
acattcgacg gctattacta cgagcttttgg aaggacacag gcaacacgac tatgactgta  180
tacactcaag gtcgcttctc atgccagtgg tctaacatca caacgcgct tttccgcacg   240
ggcaagaagt acaaccagaa ctggcaatct cttggcacta ccgcatcac ttattctgcg   300
acatacaacc cgaacggcaa ctcttacctt tgtatctacg gctggtctac gaacccgctt  360
gttgagttct acatcgtaga gtcttgggc aactggcgtc ctcctggcgc aacatctctt   420
ggccaggtta caatcgatgg tggcacatat gacatctcac cgactactcg cgttaaccag  480
cctagcatcg ttggcacagc tactttcgac caatactgga gcgttcgcac tagcaagcgc  540
acatctggca cagttacggt tacggaccac tttcgcgcat gggcaaatcg tggccttaac  600
cttggcacaa tcgaccaaat cacactttgt gttgagggct accagtcttc tggcagcgca  660
aacatcactc aaaaacacttt ctctcagggc agctaa                            696

SEQ ID NO: 305       moltype = AA   length = 231
FEATURE              Location/Qualifiers
source               1..231
                     mol_type = protein
                     organism = Dictyoglomus thermophilum
```

```
SEQUENCE: 305
MKKPLGKIVA STALLISVAF SSSIASAAQT SITLTSNASG TFDGYYYELW KDTGNTTMTV   60
YTQGRFSCQW SNINNALFRT GKKYNQNWQS LGTIRITYSA TYNPNGNSYL CIYGWSTNPL  120
VEFYIVESWG NWRPPGATSL GQVTIDGGTY DIYRTTRVNQ PSIVGTATFD QYWSVRTSKR  180
TSGTVTVTDH FRAWANRGLN LGTIDQITLC VEGYQSSGSA NITQNTFSQG S           231
```

COMPOSITIONS FOR SACCHARIFICATION OF CELLULOSIC MATERIAL

CROSS-REFERENCE TO RELATED APPLICATION

This application is a continuation of U.S. application Ser. No. 17/372,667 filed Jul. 12, 2020, which is a continuation of U.S. application Ser. No. 16/840,012 filed Apr. 3, 2020, now U.S. Pat. No. 11,091,785, which is a divisional of U.S. patent application Ser. No. 16/115,930, filed Aug. 29, 2018, now U.S. patent Ser. No. 16/840,012, which is a divisional of U.S. patent application Ser. No. 15/422,245 filed Feb. 1, 2017, now U.S. Pat. No. 10,072,280, which is a divisional of U.S. patent application Ser. No. 14/885,555 filed Oct. 16, 2015, now U.S. Pat. No. 9,587,262, which is a divisional of U.S. patent application Ser. No. 14/052,360 filed Oct. 11, 2013, now U.S. Pat. No. 9,175,277, which is a divisional of U.S. patent application Ser. No. 12/940,952 filed Nov. 5, 2010, now U.S. Pat. No. 8,580,536, which claims the benefit of U.S. Provisional Application Ser. No. 61/259,014 filed Nov. 6, 2009, which are incorporated herein by reference.

STATEMENT AS TO RIGHTS TO INVENTIONS MADE UNDER FEDERALLY SPONSORED RESEARCH AND DEVELOPMENT

This invention was made in part with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form. The contents of the electronic sequence listing created on Jun. 13, 2023, named SQ_ST26.xlm and 439 KB in size, is hereby incorporated by reference in its entirety.
Reference to Deposits of Biological Material
This application contains a reference to deposits of biological material, which deposits are incorporated herein by reference.

BACKGROUND OF THE INVENTION

Field of the Invention

The present invention relates to enzyme compositions for high temperature saccharification of cellulosic material and to uses thereof.

Description of the Related Art

Cellulose is a polymer of the simple sugar glucose linked by beta-1,4 bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

There is a need in the art for new enzyme compositions to increase efficiency and to provide cost-effective enzyme solutions for high temperature saccharification of cellulosic material.

The present invention provides compositions for high temperature saccharification of cellulosic material and to uses thereof

SUMMARY OF THE INVENTION

The present invention relates to enzyme compositions, comprising two or more (several) components selected from the group consisting of:
 (I) a polypeptide having cellobiohydrolase I activity selected from the group consisting of:
  (A) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 2; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 1, (ii) the genomic DNA sequence of the mature polypeptide coding sequence of SEQ ID NO: 1, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 1;
  (B) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 4; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 3, (ii) the genomic DNA sequence of the mature polypeptide coding sequence of SEQ ID NO: 3, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 3;
  (C) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 6; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 5, (ii) the cDNA sequence of the mature polypeptide coding sequence of SEQ ID NO: 5, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 5;

(D) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 8; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 7, (ii) the genomic DNA sequence of the mature polypeptide coding sequence of SEQ ID NO: 7, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 7;

(E) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 158; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 157, (ii) the genomic DNA sequence of the mature polypeptide coding sequence of SEQ ID NO: 157, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 157;

(F) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 160; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 159, (ii) the genomic DNA sequence of the mature polypeptide coding sequence of SEQ ID NO: 159, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 159;

(G) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 162; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 161, (ii) the genomic DNA sequence of the mature polypeptide coding sequence of SEQ ID NO: 161, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 161;

(H) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 164; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 163, (ii) the genomic DNA sequence of the mature polypeptide coding sequence of SEQ ID NO: 163, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 163; and (I) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 166; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 165, (ii) the genomic DNA sequence of the mature polypeptide coding sequence of SEQ ID NO: 165, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 165;

(II) a polypeptide having cellobiohydrolase II activity selected from the group consisting of:

(A) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 10; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 9, (ii) the cDNA sequence of the mature polypeptide coding sequence of SEQ ID NO: 9, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 9;

(B) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 12; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 11, (ii) the cDNA sequence of the mature polypeptide coding sequence of SEQ ID NO: 11, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 11;

(C) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 14; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 13, (ii) the genomic DNA sequence of the mature polypeptide coding sequence of SEQ ID NO: 13, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 13;

(D) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 16; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 15, (ii) the genomic DNA sequence of the mature polypeptide coding sequence of SEQ ID NO: 15, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 15;

(E) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 18; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 17, (ii) the cDNA sequence of the mature polypeptide coding sequence of SEQ ID NO: 17, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 17;

(F) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 168; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 167, (ii) the cDNA sequence of the mature polypeptide coding sequence of SEQ ID NO: 167, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 167;

(G) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 170; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 169, (ii) the cDNA sequence of the mature polypeptide coding sequence of SEQ ID NO: 169, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 169; and (H) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 172; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 172, (ii) the cDNA sequence of the mature polypeptide coding sequence of SEQ ID NO: 172, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 172;

(III) a polypeptide having endoglucanase I activity selected from the group consisting of: (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 20; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 19, (ii) the cDNA sequence of the mature polypeptide coding sequence of SEQ ID NO: 19, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 19;

(IV) a polypeptide having endoglucanase II activity selected from the group consisting of:

(A) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 22; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 21, (ii) the genomic DNA sequence of the mature polypeptide coding sequence of SEQ ID NO: 21, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 21;

(B) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 24; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 23, (ii) the cDNA sequence of the mature polypeptide coding sequence of SEQ ID NO: 23, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 23;

(C) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 26; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 25, (ii) the genomic DNA sequence of the mature polypeptide coding sequence of SEQ ID NO: 25, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 25;

(D) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 174; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 173, (ii) the genomic DNA sequence of the mature polypeptide coding sequence of SEQ ID NO: 173, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 173; and (E) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 176; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 175, (ii) the genomic DNA sequence of the mature polypeptide coding sequence of SEQ ID NO: 175, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 175; and (V) a polypeptide having beta-glucosidase activity selected from the group consisting of:

(A) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 28; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 27, (ii) the cDNA sequence of the mature polypeptide coding sequence of SEQ ID NO: 27, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 27;

(B) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 30; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 29, (ii) the cDNA sequence of the mature polypeptide coding sequence of SEQ ID NO: 29, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 29;

(C) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 32; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 31, (ii) the cDNA sequence of the mature polypeptide coding sequence of SEQ ID NO: 31, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 31;

(D) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 178; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 177, (ii) the cDNA sequence of the mature polypeptide coding sequence of SEQ ID NO: 177, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 177;

(E) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 180; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 179, (ii) the cDNA sequence of the mature polypeptide coding sequence of SEQ ID NO: 179, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 179;

(F) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 182; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 181, (ii) the cDNA sequence of the mature polypeptide coding sequence of SEQ ID NO: 181, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 181;

(G) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 184; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 183, (ii) the cDNA sequence of the mature polypeptide coding sequence of SEQ ID NO: 183, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 183;

(H) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 186; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 185, (ii) the cDNA sequence of the mature polypeptide coding sequence of SEQ ID NO: 185, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 185;

(I) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 188; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 187, (ii) the cDNA sequence of the mature polypeptide coding sequence of SEQ ID NO: 187, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 187; and (J) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 190; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 189, (ii) the cDNA sequence of the mature polypeptide coding sequence of SEQ ID NO: 189, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 189.

The present invention also relates to host cells encoding such an enzyme composition and methods of producing such an enzyme composition.

The present invention also relates to methods for degrading or converting a cellulosic material, comprising: treating the cellulosic material with such an enzyme composition.

The present invention also relates to methods for producing a fermentation product, comprising:
(a) saccharifying a cellulosic material with such an enzyme composition;
(b) fermenting the saccharified cellulosic material with one or more (several) fermenting microorganisms to produce the fermentation product; and
(c) recovering the fermentation product from the fermentation.

The present invention also relates to methods of fermenting a cellulosic material, comprising: fermenting the cellulosic material with one or more (several) fermenting microorganisms, wherein the cellulosic material is saccharified with such an enzyme composition.

GH61E GH61 polypeptides having cellulolytic enhancing activity and their binary 1:1 composition on PCS-hydrolyzing activity of a high-temperature enzyme composition at 60° C.

Figure 6:
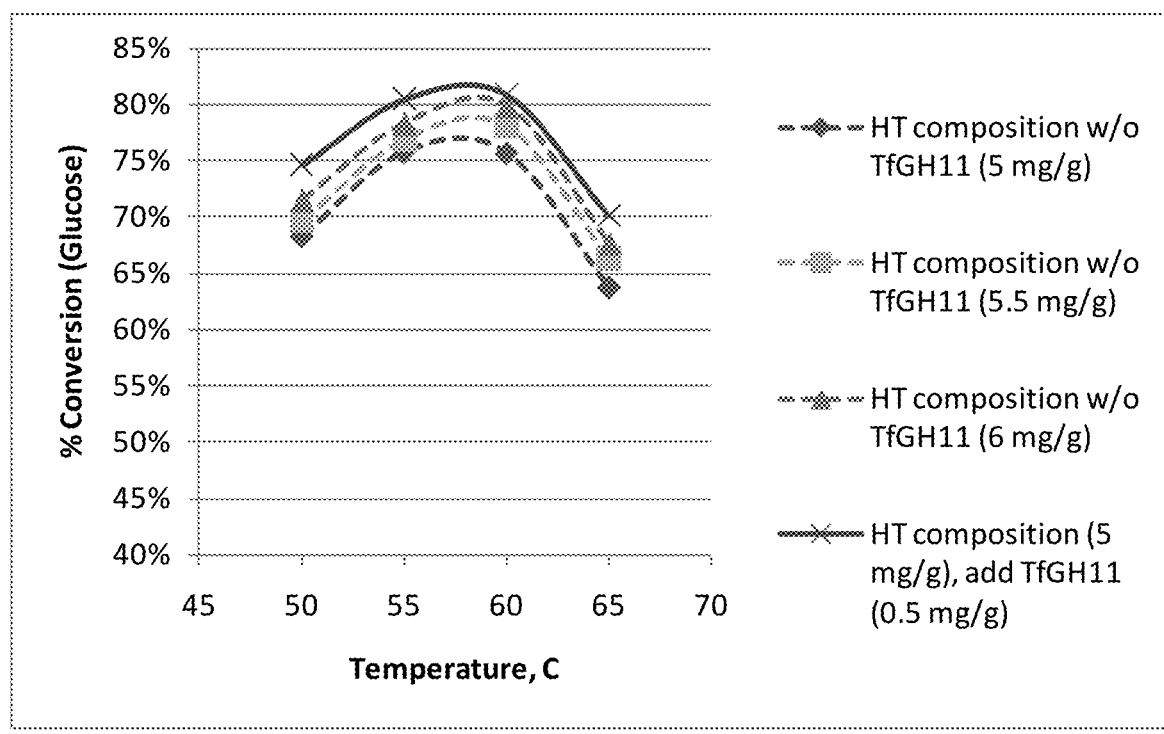

FIG. 6 shows the effect of a *Thermobifida fusca* GH11 xylanase on hydrolysis of milled washed PCS by a high-temperature enzyme composition at 50-65° C.

Figure 7:
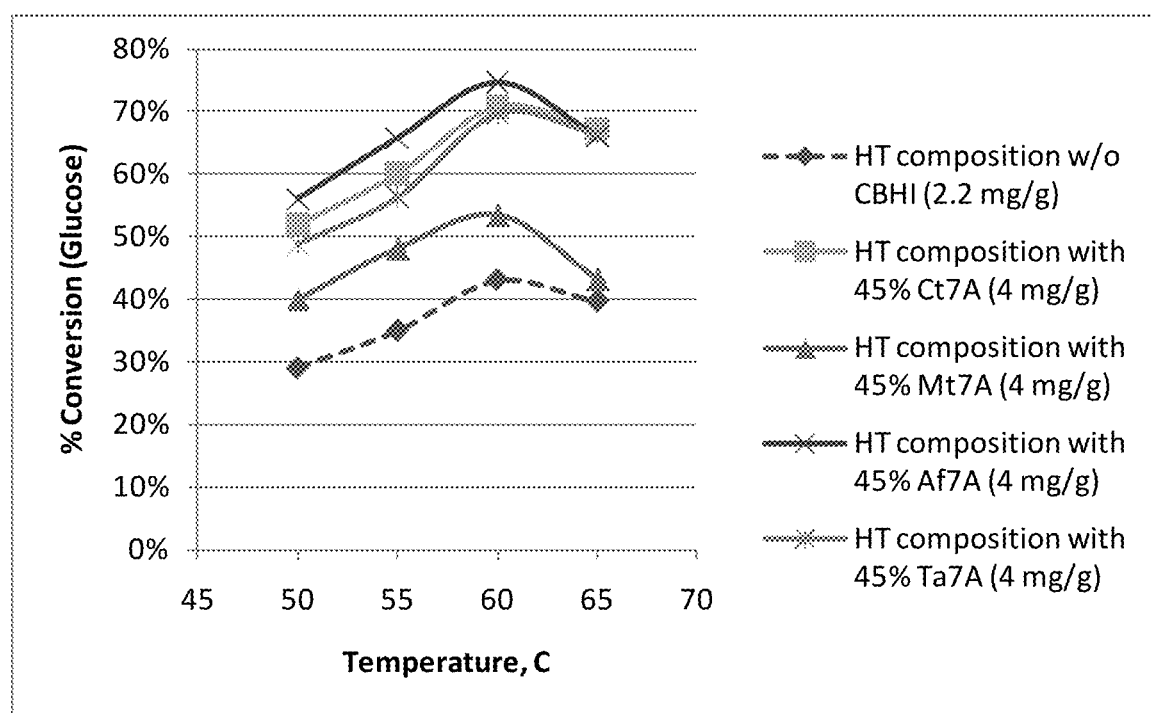

FIG. 7 shows the effect of replacing *Chaetomium thermophilum* Cel7A cellobiohydrolase I in a high-temperature enzyme composition with various thermostable cellobiohydrolase I proteins on hydrolysis of milled washed PCS at 50-65° C.

Figure 8:
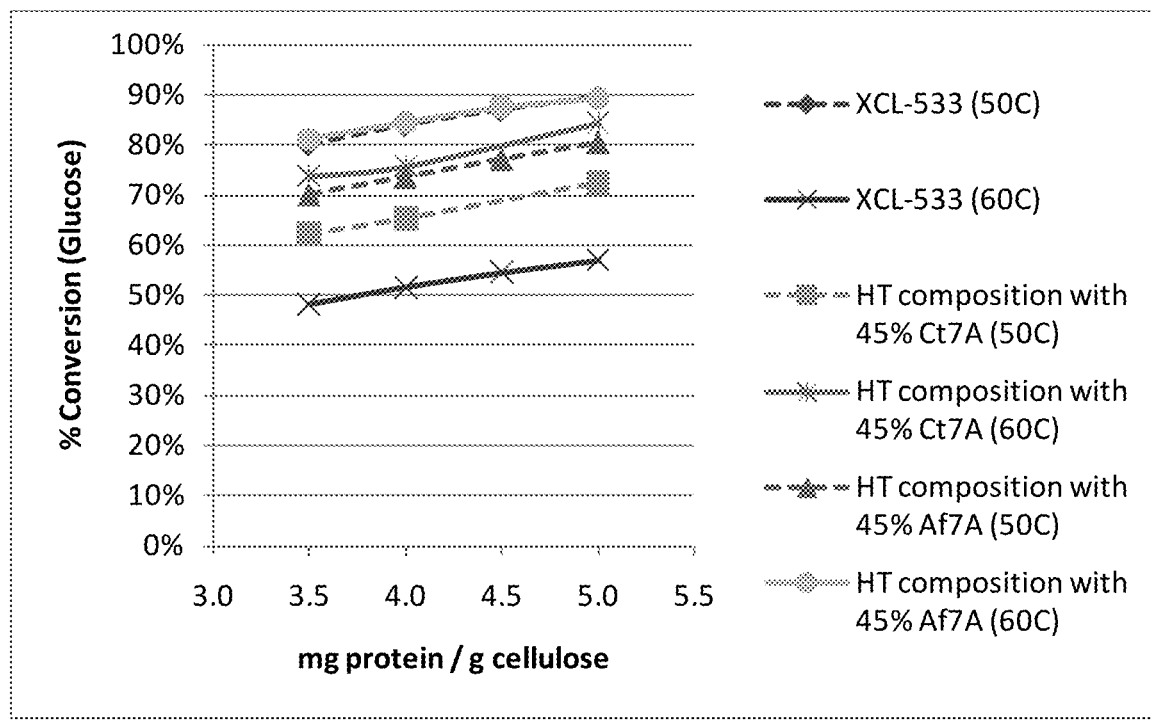

FIG. 8 shows a comparison of *Aspergillus fumigatus* Cel7A- and *Chaetomium thermophilum* Cel7A-based high-temperature enzyme compositions with *Trichoderma reesei*-based cellulase XCL-533 at 50° C. and 60° C. in hydrolysis of milled washed PCS.

Figure 9:
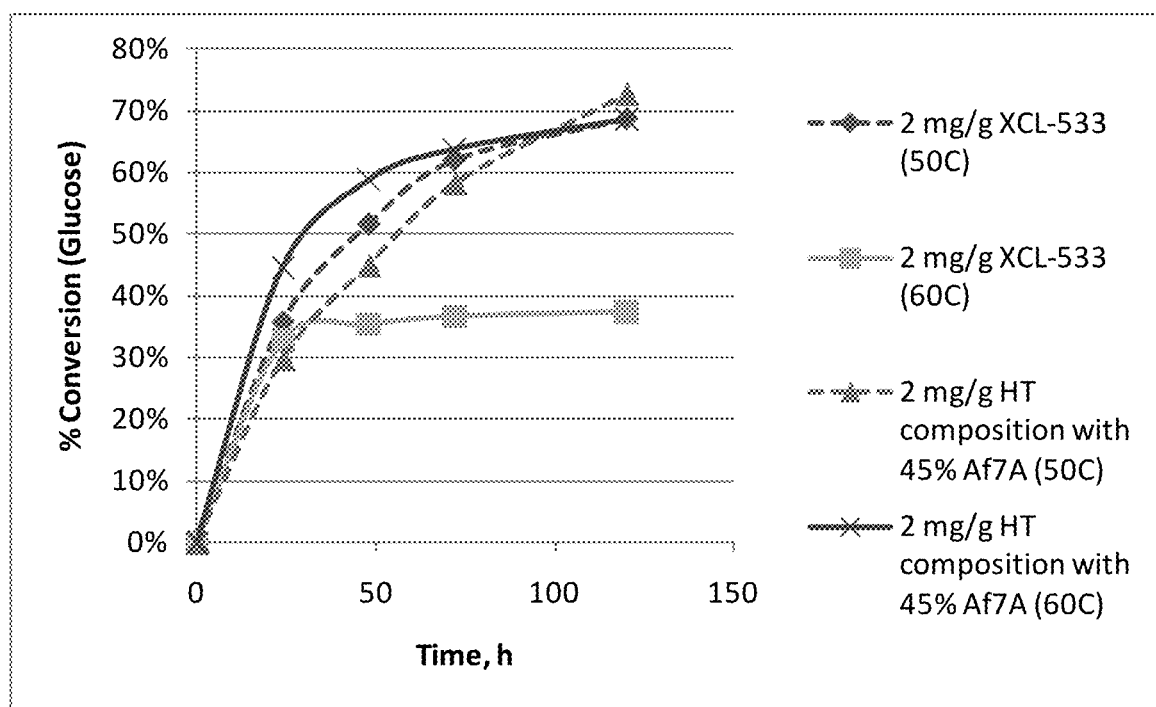

FIG. 9 shows the hydrolysis time-course for *Aspergillus fumigatus* Cel7A-based high-temperature enzyme composition in comparison with *Trichoderma reesei*-based cellulase XCL-533 at 50° C. and 60° C. (2 mg protein/g cellulose).

Figure 10:
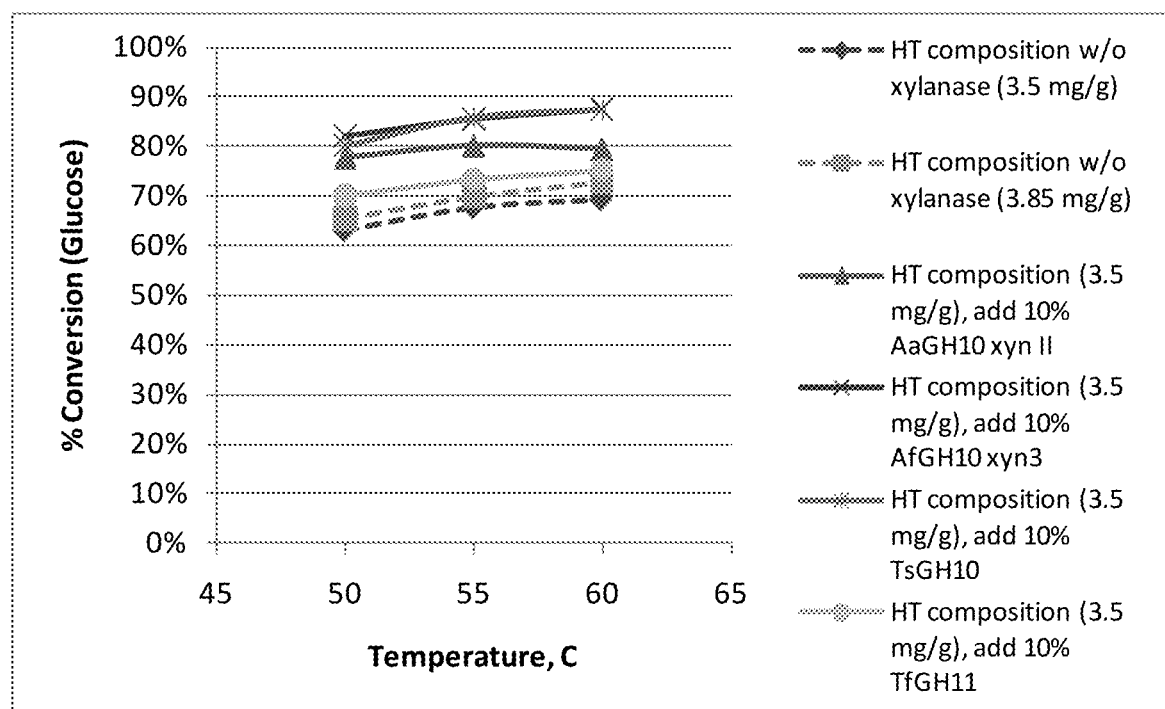

FIG. 10 shows an evaluation of *Aspergillus aculeatus* GH10 xylanase II, *Aspergillus fumigatus* GH10 xyn3 xylanase, *Trichophaea saccata* GH10 xylanase, and *Thermobifida fusca* GH11 xylanase at 10% addition (0.35 mg protein/g cellulose) to a high-temperature enzyme composition (3.5 mg protein/g cellulose) in hydrolysis of milled washed PCS at 50° C., 55° C., and 60° C.

Figure 11:
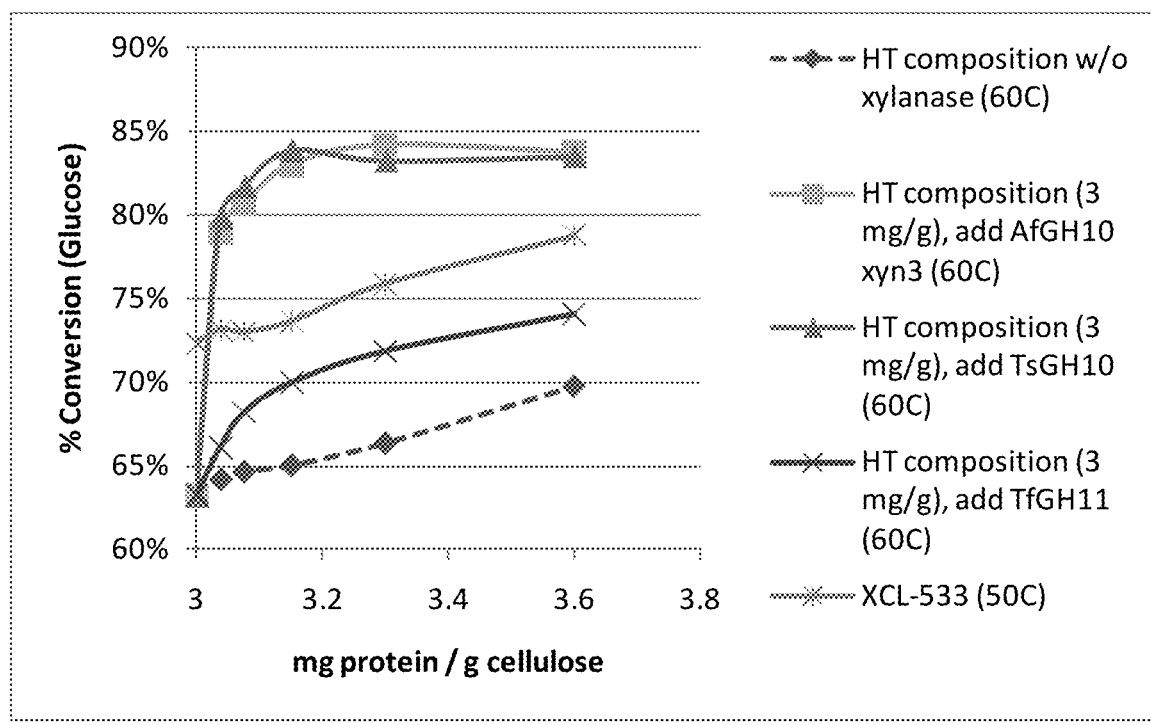

FIG. 11 shows an evaluation of *Aspergillus fumigatus* GH10 xyn3 xylanase, *Trichophaea saccata* GH10 xylanase, and *Thermobifida fusca* GH11 xylanase for synergy with a high-temperature enzyme composition in hydrolysis of milled washed PCS at 50° C., 55° C., and 60° C. Each xylanase was added at different levels (1.25%, 2.5%, 5%, 10%, and 20%) to a constant loading of the high-temperature enzyme composition (3 mg protein per g cellulose).

Figure 12:
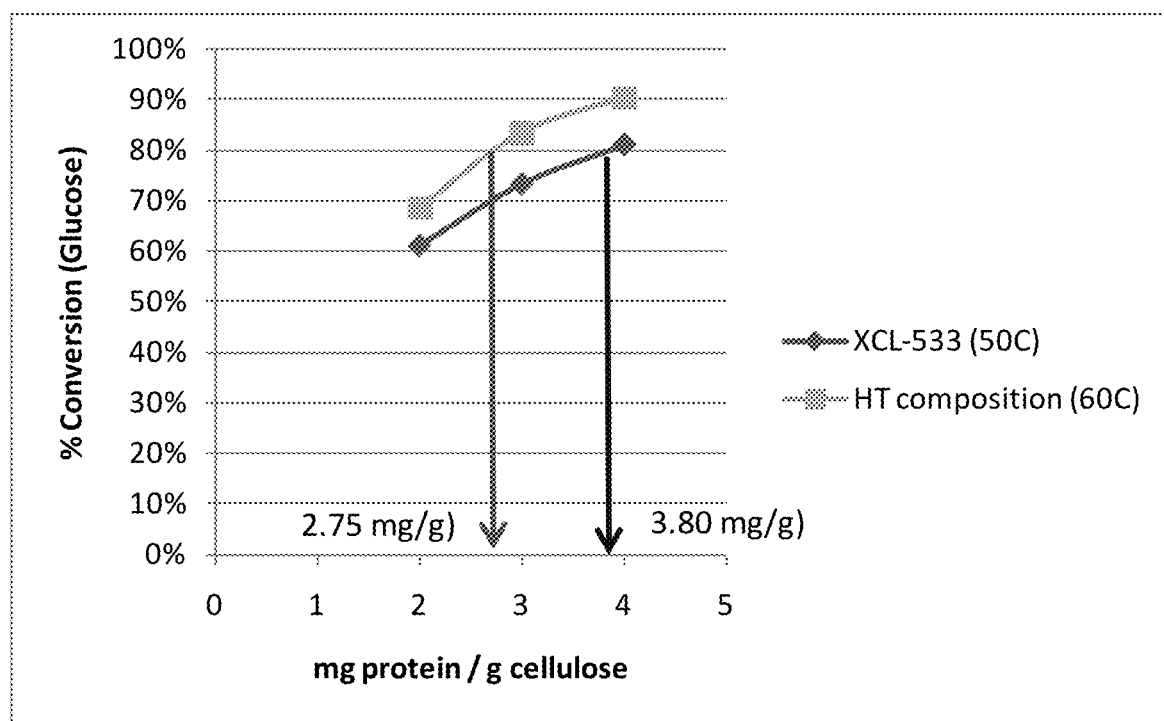

FIG. 12 shows a comparison of an improved high-temperature enzyme composition containing *Aspergillus fumigatus* GH10 xyn3 xylanase at 60° C. with *Trichoderma reesei*-based cellulase XCL-533 at 50° C. in hydrolysis of milled washed PCS.

Figures 13A, 13B:
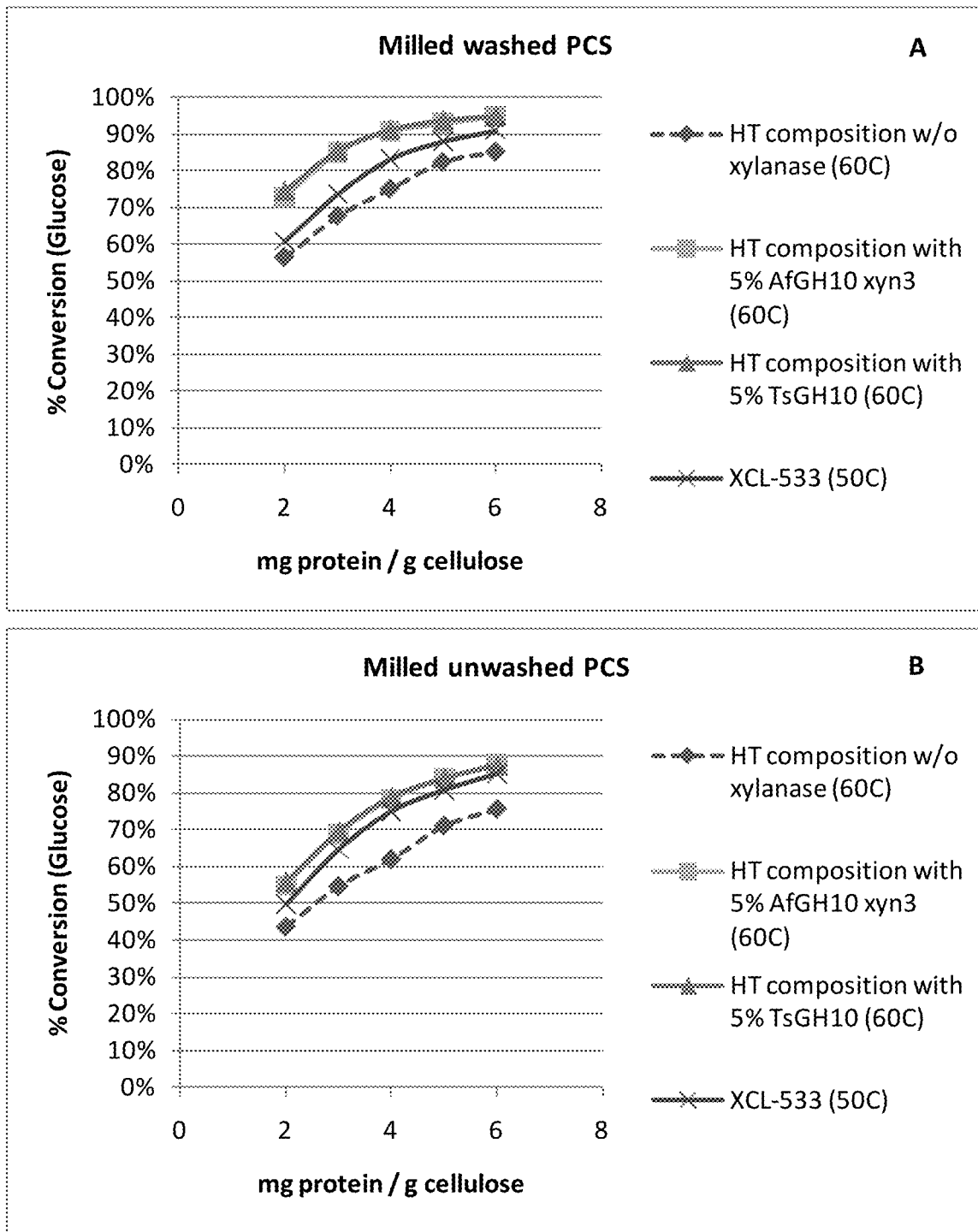

FIGS. 13A and 13B show a comparison of improved high-temperature enzyme compositions containing *Aspergillus fumigatus* GH10 xyn3 xylanase or *Trichophaea saccata* GH10 xylanase (60° C.) with *Trichoderma reesei*-based cellulase XCL-533 (50° C.) in hydrolysis of washed (A) and unwashed (B) PCS.

Figures 14A, 14B:
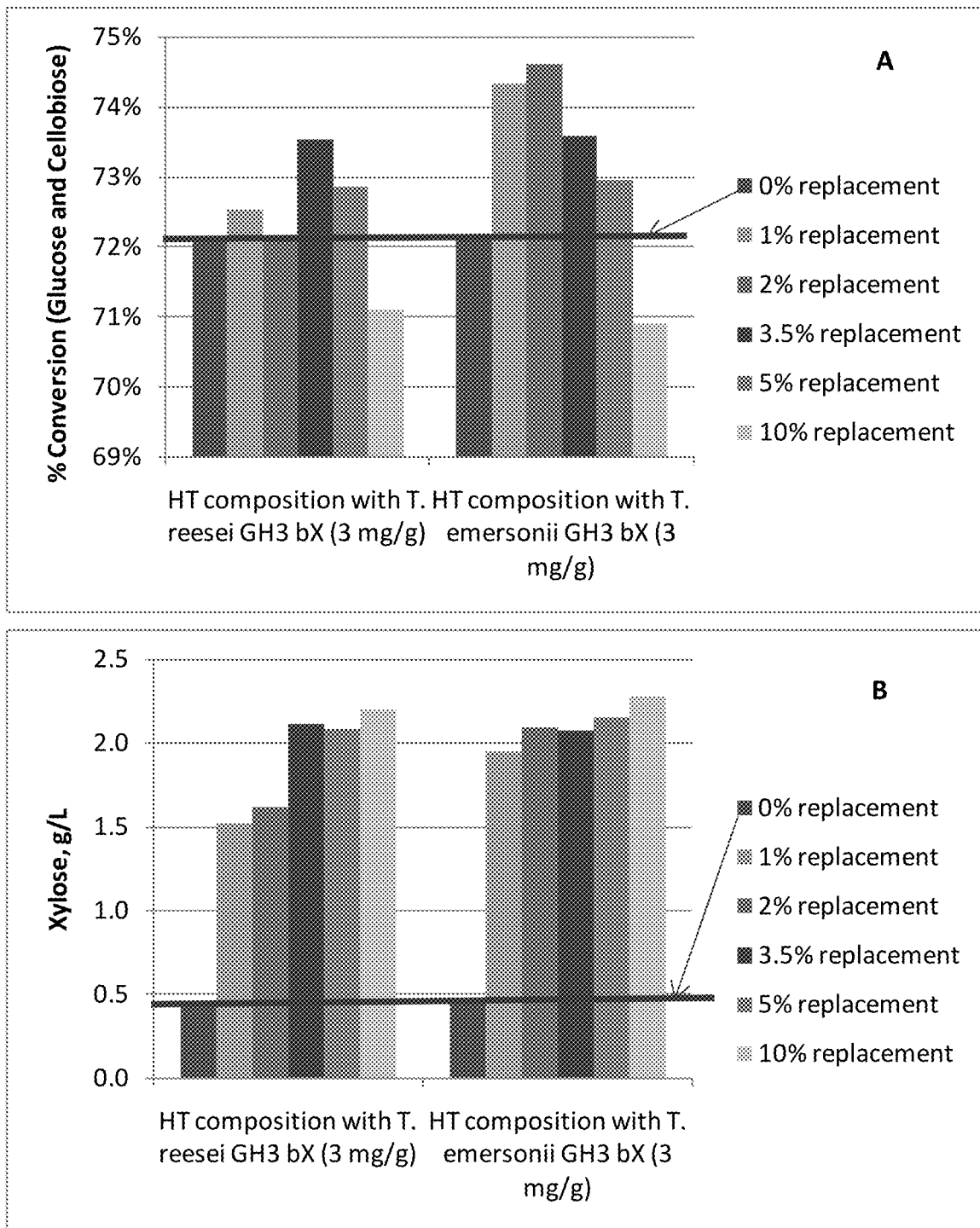

FIGS. 14A and 14B show the effect of replacement of protein in a high-temperature enzyme composition (3 mg protein per g cellulose) with GH3 beta-xylosidases from *Trichoderma reesei* and *Talaromyces emersonii* at 60° C.

Figure 15:
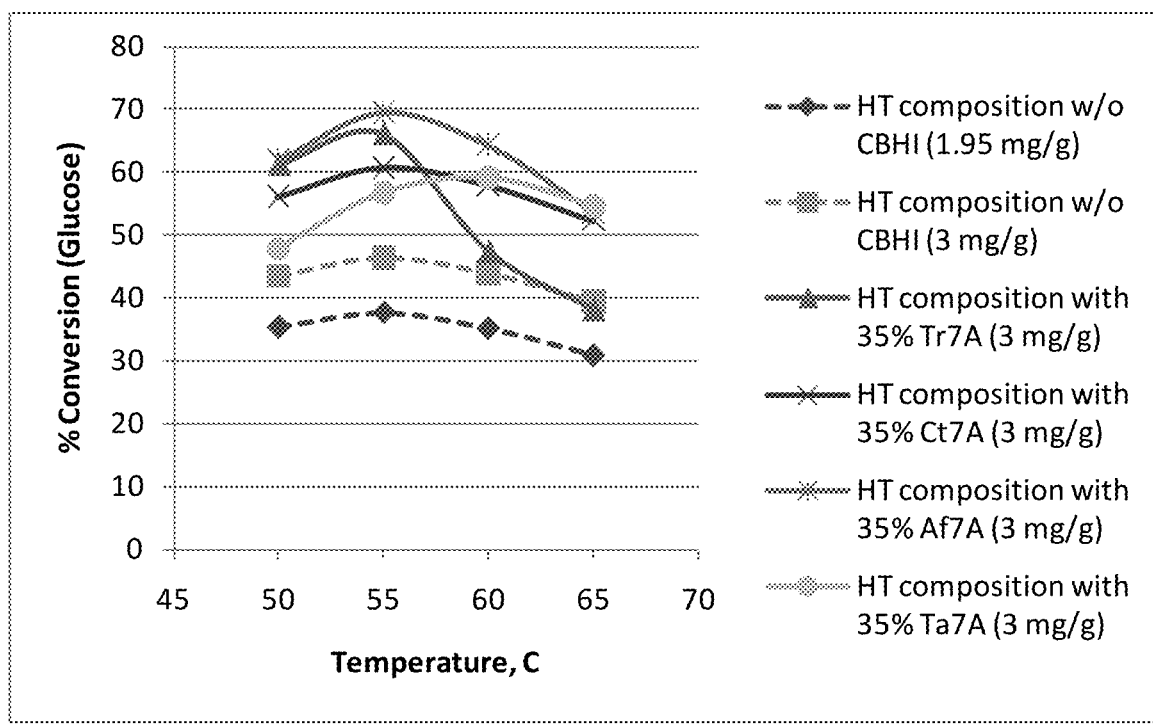

FIG. 15 shows a comparison of *Trichoderma reesei* Cel7A CBHI, *Chaetomium thermophilum* Cel7A CBHI, *Aspergillus fumigatus* Cel7A CBHI, and *Thermoascus aurantiacus* Cel7A CBHI replacing a CBHI component in a high-temperature enzyme composition in hydrolysis of milled unwashed PCS at 50-65° C.

Figure 16:
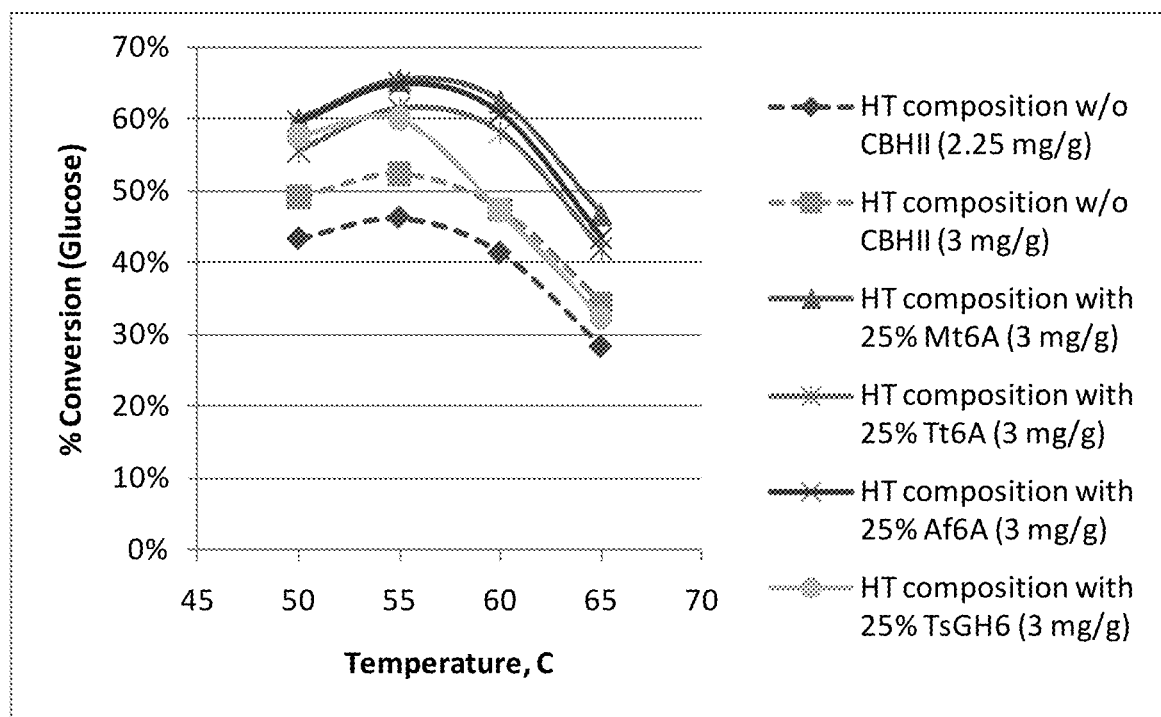

FIG. 16 shows a comparison of *Myceliophthora thermophila* Cel6A CBHII, *Thielavia terrestris* Cel6A CBHII, *Aspergillus fumigatus* Cel6A CBHII, and *Trichophaea saccata* Cel6A CBHII replacing a CBHII component in a high-temperature enzyme composition in hydrolysis of milled washed PCS at 50-65° C.

Figure 17:
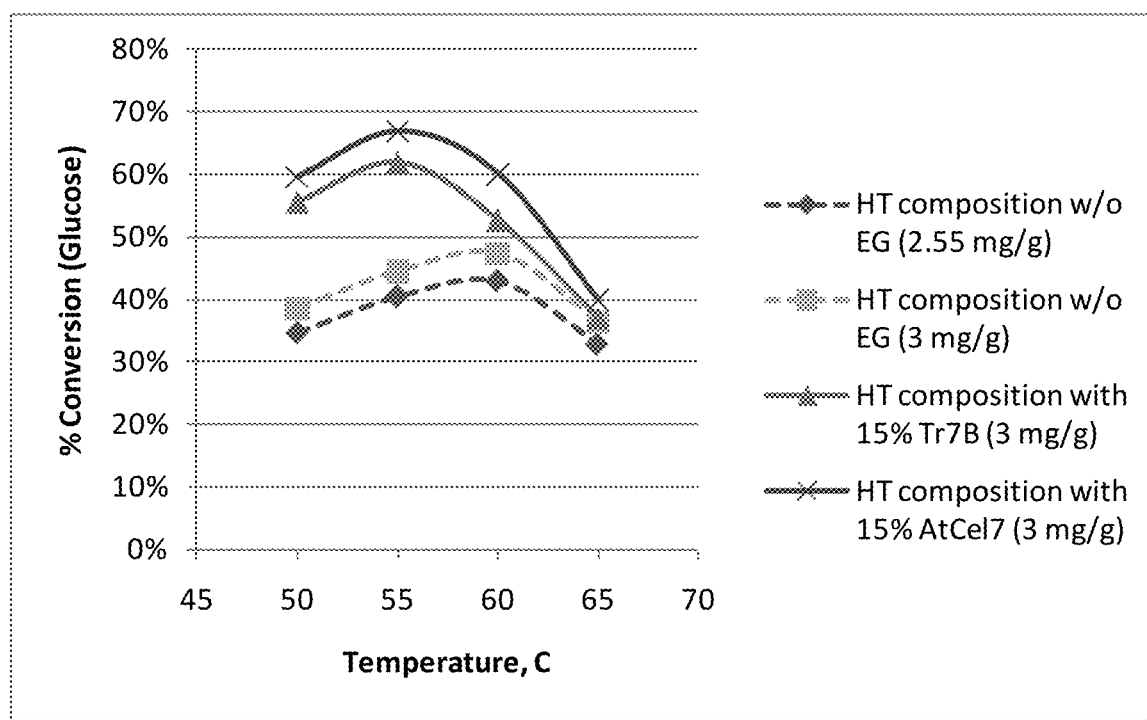

FIG. 17 shows a comparison of *Trichoderma reesei* Cel7B EGI and *Aspergillus terreus* Cel7 EGI replacing an endoglucanase component in a high-temperature enzyme composition in hydrolysis of milled unwashed PCS at 50-65° C.

Figure 18:
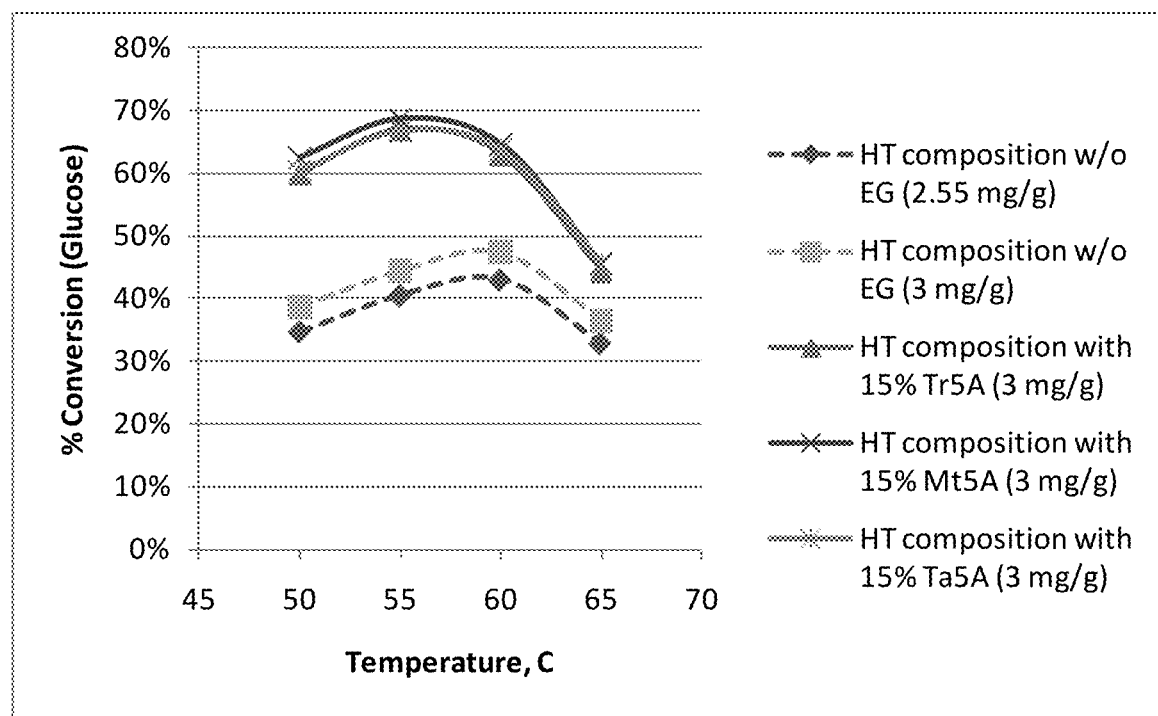

FIG. 18 shows a comparison of *Trichoderma reesei* Cel5A EGII, *Myceliophthora thermophila* Cel5A EGII, and *Thermoascus aurantiacus* Cel5A EGII replacing an endoglucanase component in a high-temperature enzyme composition in hydrolysis of milled unwashed PCS at 50-65° C.

Figure 19:
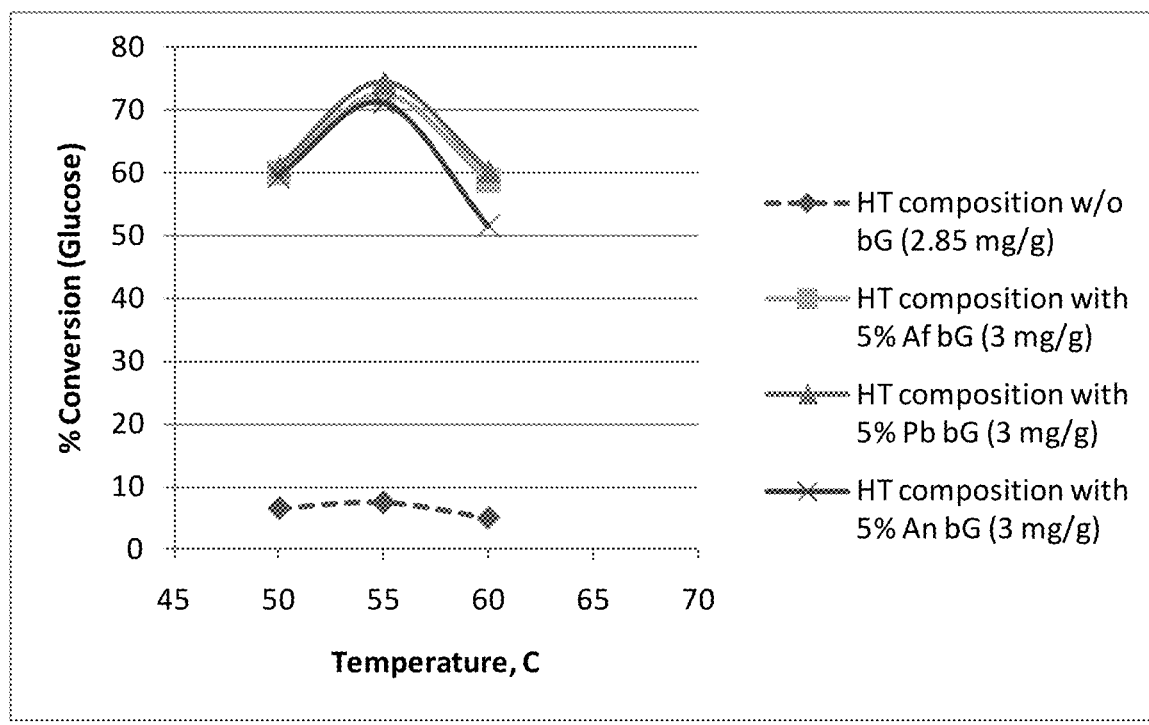

FIG. 19 shows a comparison of *Aspergillus fumigatus* Cel3A beta-glucosidase, *Penicillium brasilianum* Cel3A beta-glucosidase, and *Aspergillus niger* Cel3 beta-glucosidase in a high-temperature enzyme composition at 50-60° C. using milled unwashed PCS.

Figure 20:
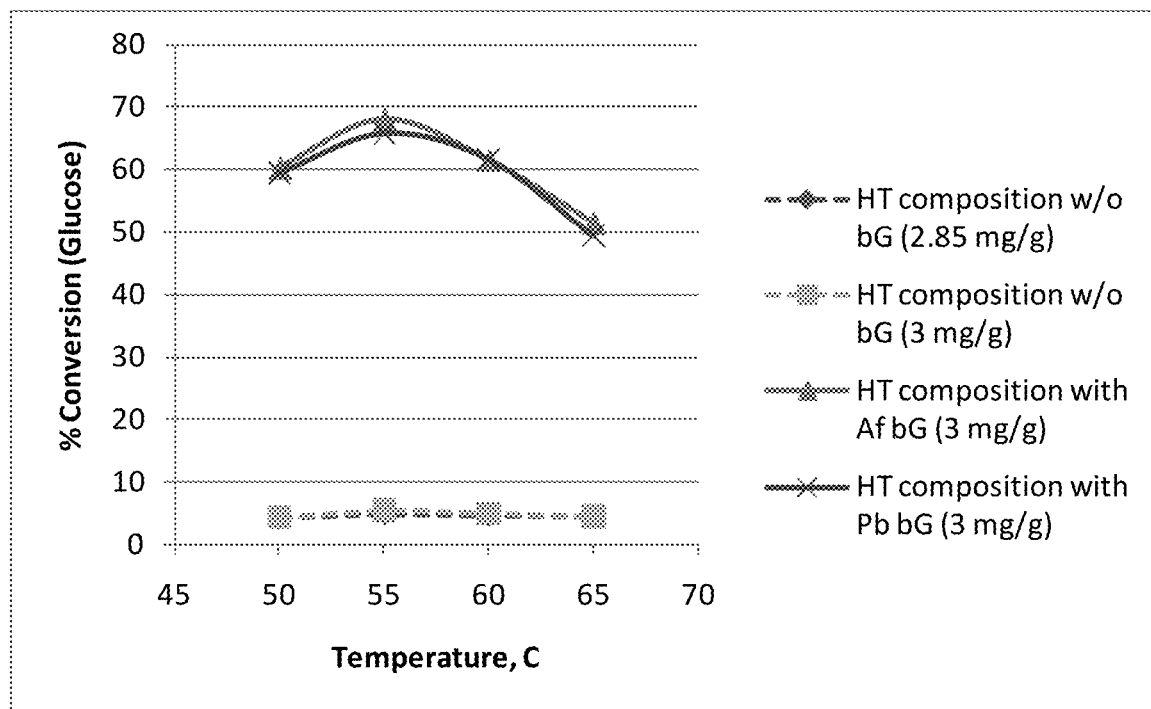

FIG. 20 shows a comparison of *Aspergillus fumigatus* Cel3A beta-glucosidase, *Penicillium brasilianum* Cel3A beta-glucosidase, and *Aspergillus niger* Cel3 beta-glucosidase in a high-temperature enzyme composition at 50-65° C. using milled unwashed PCS.

Figure 21:
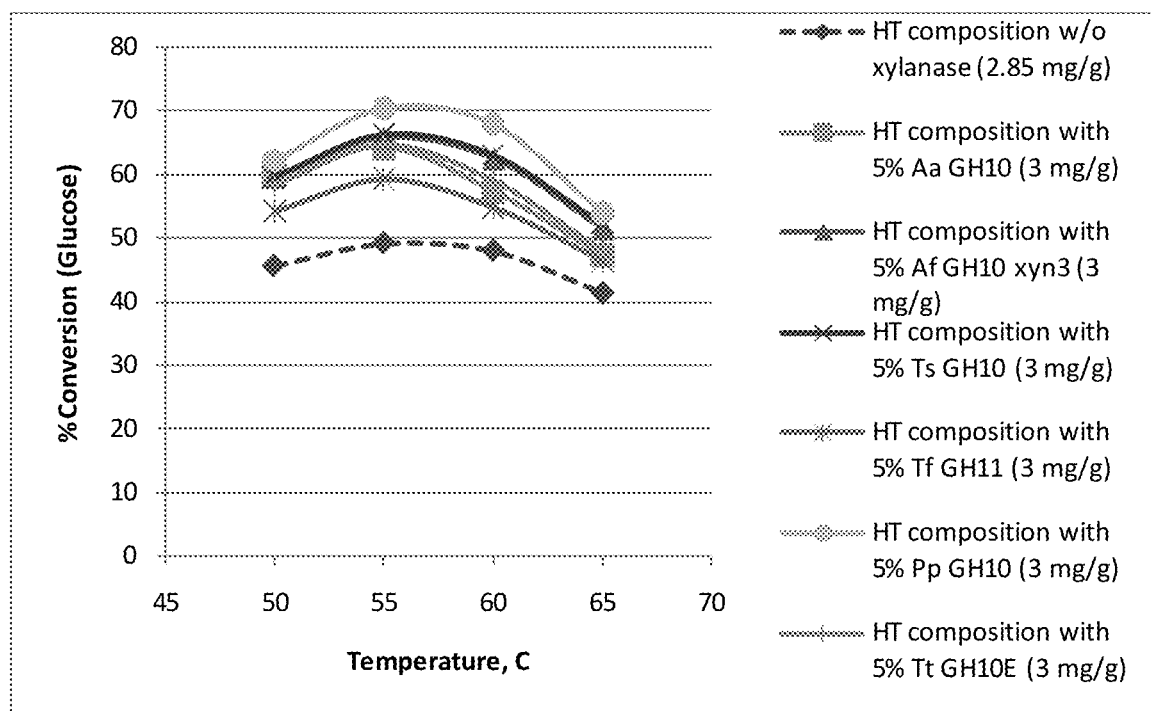

FIG. 21 shows a comparison of *Aspergillus aculeatus* GH10 xyn II xylanase, *Aspergillus fumigatus* GH10 xyn3, *Trichophaea saccata* GH10 xylanase, *Thermobifida fusca* GH11 xylanase, *Penicillium pinophilum* GH10 xylanase, and *Thielavia terrestris* GH10E xylanase replacing a xylanase component in a high-temperature enzyme composition in hydrolysis of milled unwashed PCS at 50-65° C.

Figure 22:
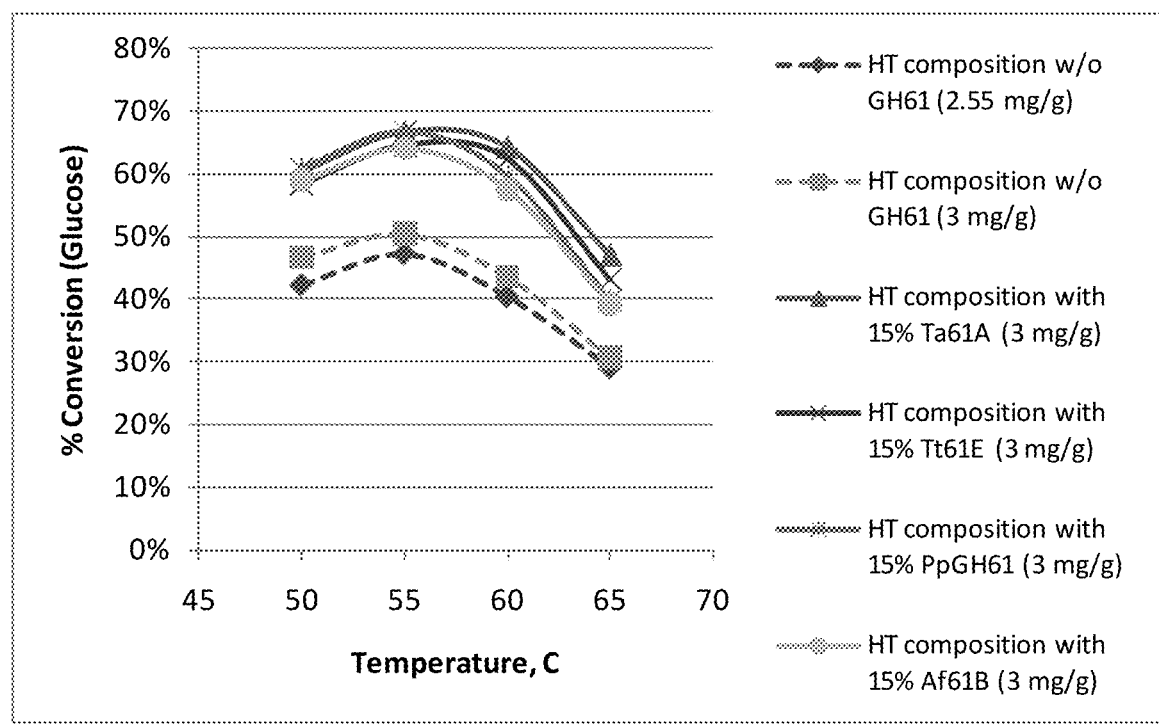

FIG. 22 shows a comparison of the cellulase-enhancing activity of *Thermoascus aurantiacus* GH61A, *Thielavia terrestris* GH61E, *Penicillium pinophilum* GH61, and *Aspergillus fumigatus* GH61B polypeptides replacing a GH61 component in a high-temperature enzyme composition in hydrolysis of milled unwashed PCS at 50-65° C.

Figure 23:
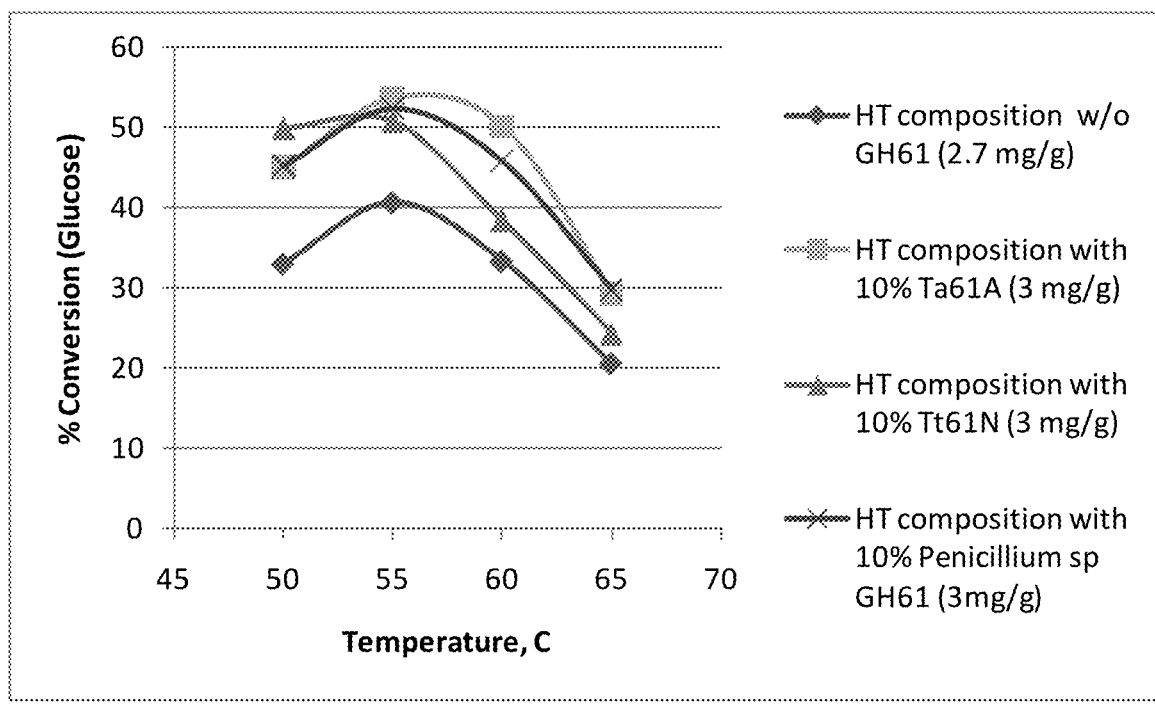

FIG. 23 shows a comparison of the cellulase-enhancing activity of *Thermoascus aurantiacus* GH61A, *Thielavia terrestris* GH61N, and *Penicillium* sp GH61A polypeptides replacing a GH61 component in a high-temperature enzyme composition in hydrolysis of milled unwashed PCS at 50-65° C.

Figure 24:
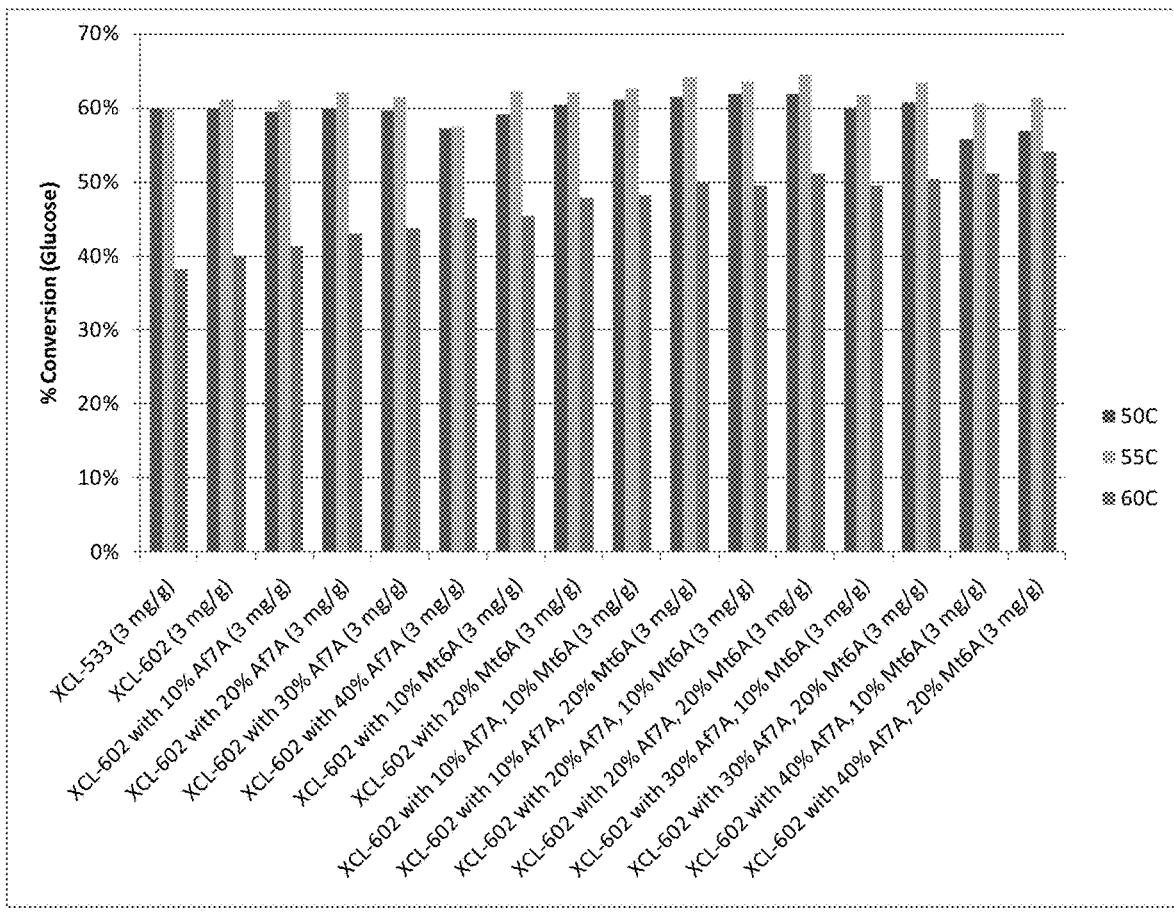

FIG. 24 shows the effect of *Trichoderma reesei*-based XCL-602 cellulase replacement by *Aspergillus fumigatus* Cel7A cellobiohydrolase I and/or *Myceliophthora thermophila* Cel6A cellobiohydrolase II on saccharification of milled unwashed PCS at 50-60° C.

Figures 25A, 25B:
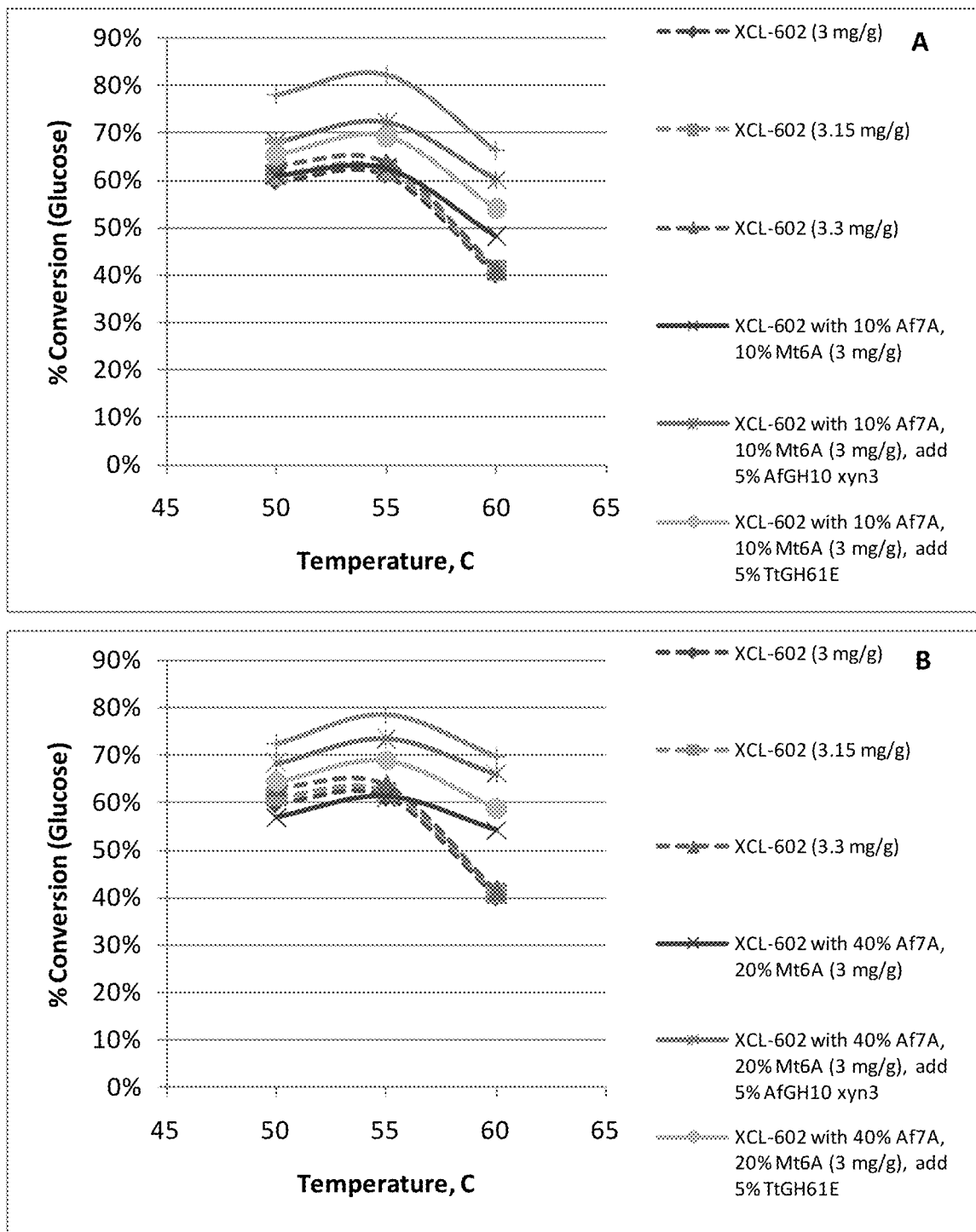

FIGS. 25A and 25B show the hydrolysis of milled unwashed PCS by *Trichoderma reesei*-based XCL-602 cellulase compositions containing *Aspergillus fumigatus* Cel7A cellobiohydrolase I and *Myceliophthora thermophila* Cel6A cellobiohydrolase II (3 mg total protein per g cellulose) and additionally supplemented by 5% *Aspergillus fumigatus* GH10 xyn 3 and/or 5% *Thielavia terrestris* GH61E at 50-60° C.

Figure 26:
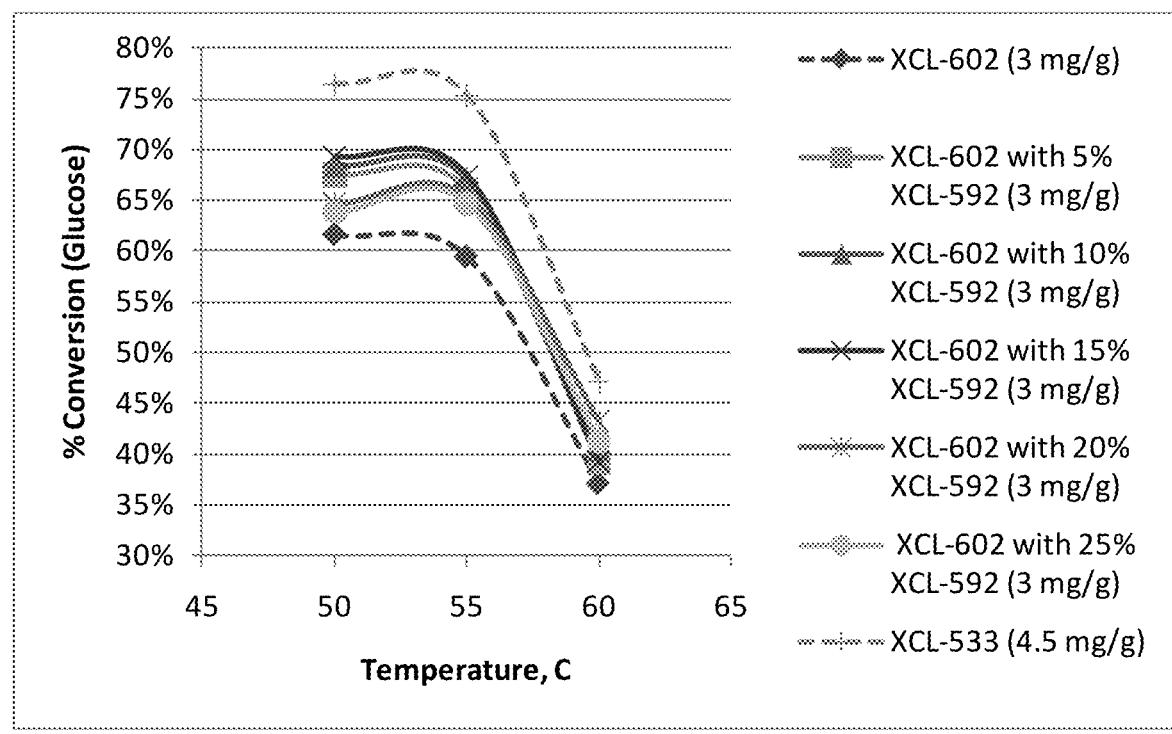

FIG. 26 shows the hydrolysis of milled unwashed PCS by *Trichoderma reesei*-based XCL-602 compositions containing different replacement levels of *Trichoderma reesei*-based XCL-592 cellulase at 50-60° C.

Figures 27A, 27B:
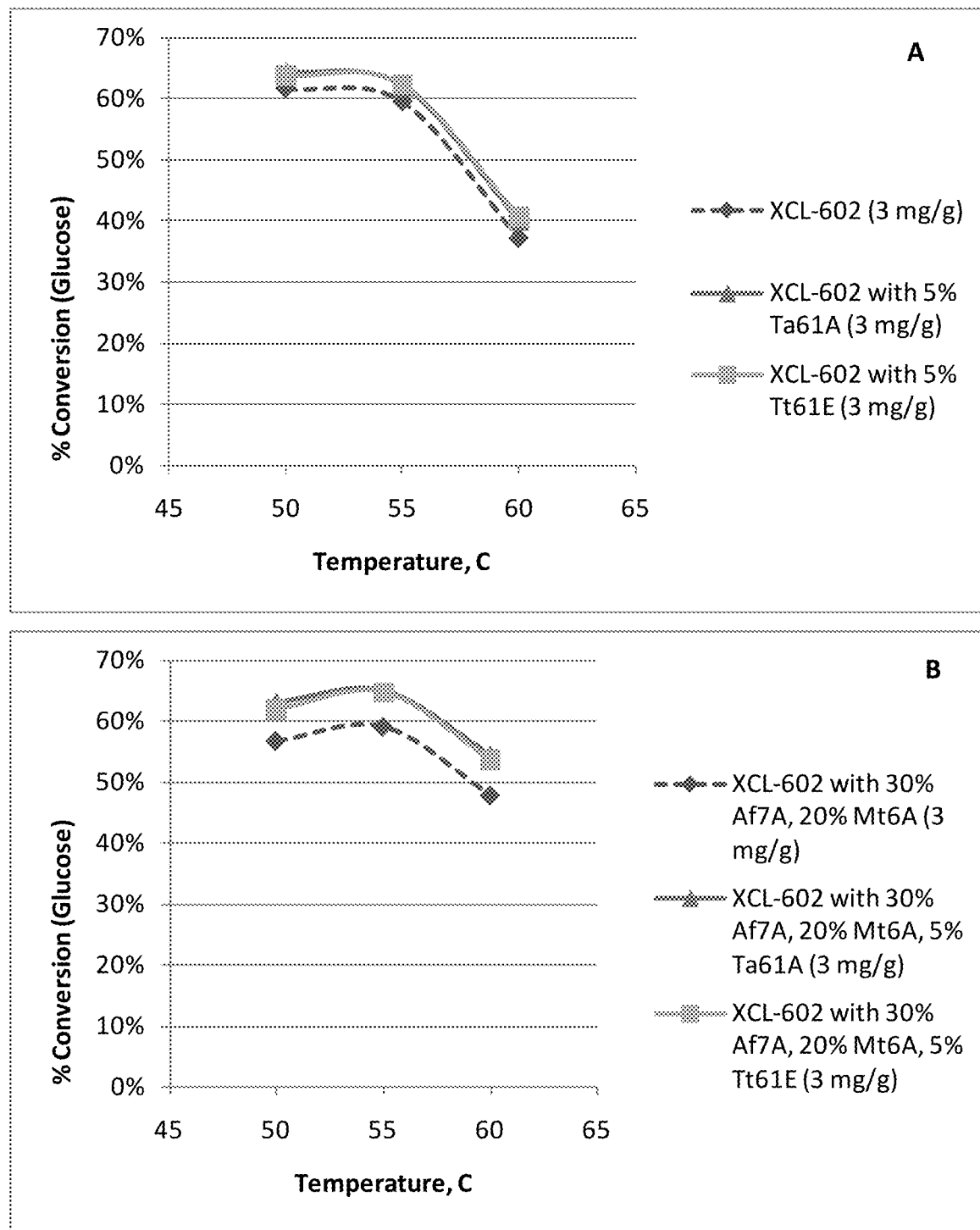

FIGS. 27A and 27B show a comparison of *Thermoascus aurantiacus* GH61A and *Thielavia terrestris* GH61E polypeptides replacing 5% of protein in *Trichoderma reesei*-based XCL-602 cellulase or XCL-602-based enzyme composition in hydrolysis of milled unwashed PCS at 50-60° C.

Figures 28A, 28B:
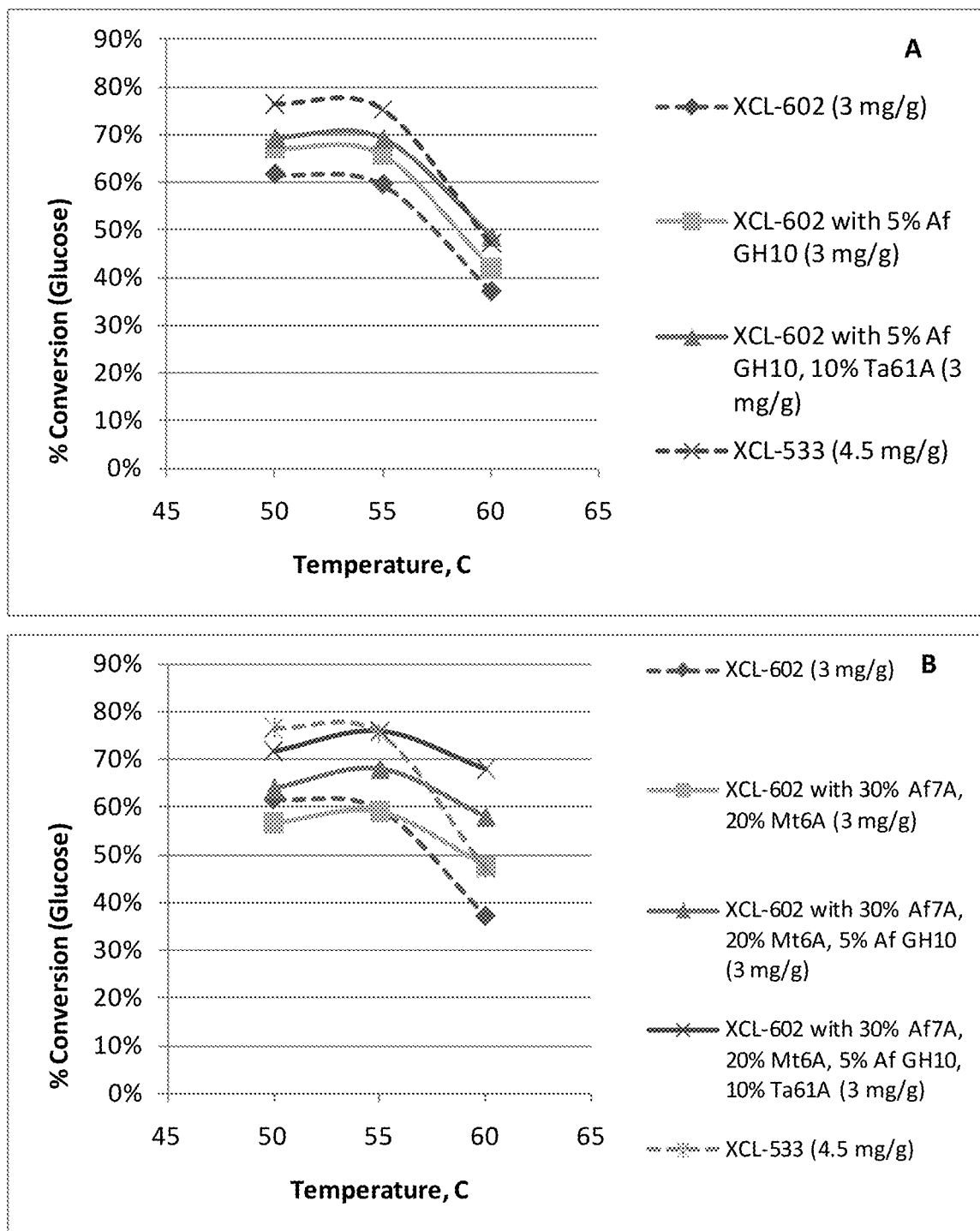

FIGS. 28A and 28B show the hydrolysis of milled unwashed PCS by non-replaced *Trichoderma reesei*-based XCL-602 cellulase and various XCL-602-based enzyme compositions (3 mg protein per g cellulose) in comparison with *Trichoderma reesei*-based XCL-533 cellulase (4.5 mg protein per g cellulose) at 50-60° C.

Figure 29:
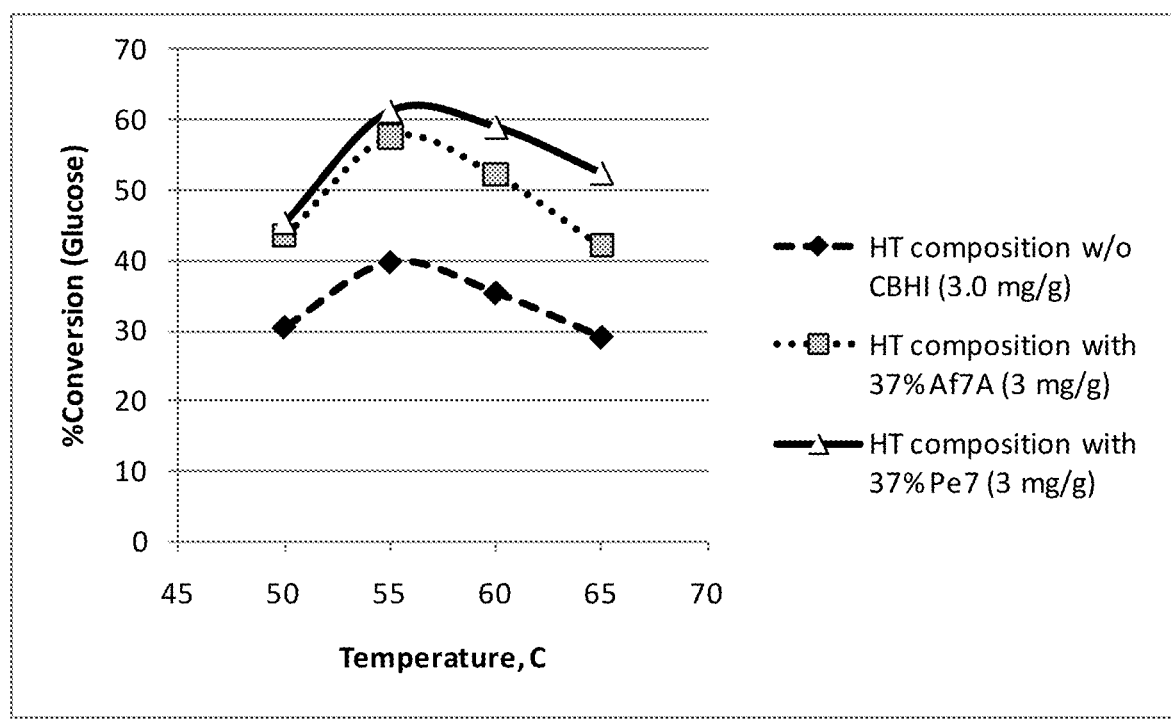

FIG. 29 shows a comparison of *Aspergillus fumigatus* Cel7A CBHI and *Penicillium emersonii* Cel7 CBHI in a high-temperature enzyme composition in hydrolysis of milled unwashed PCS at 50-65° C.

Figure 30:
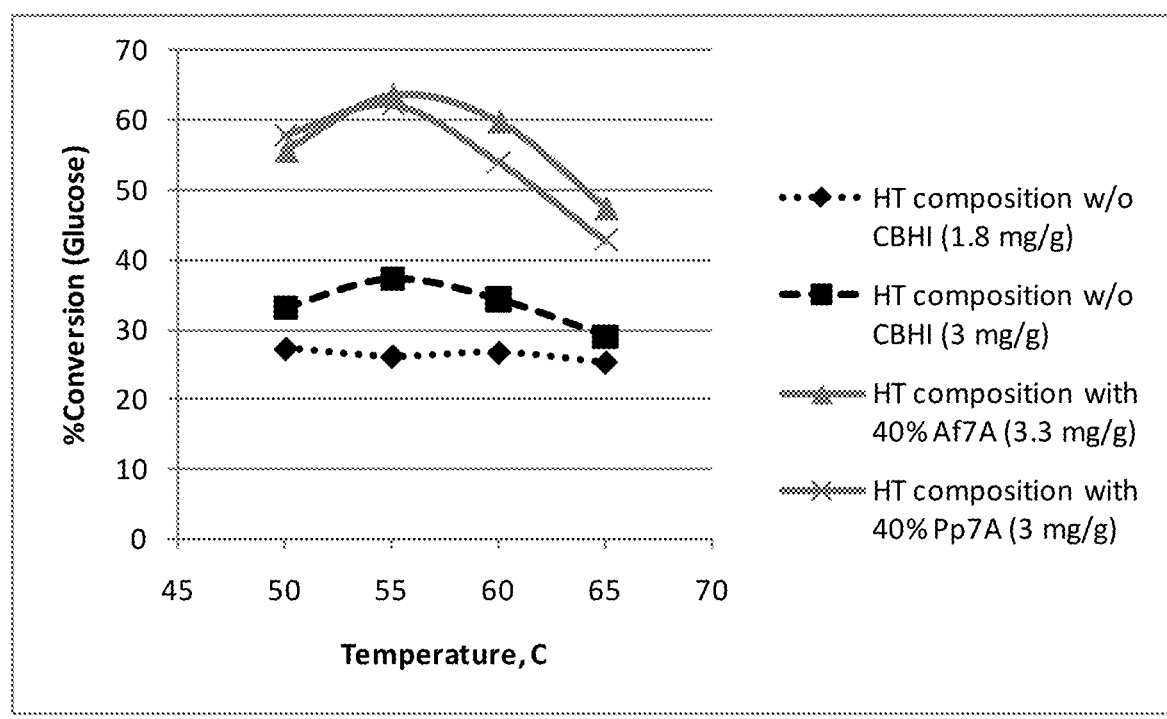

FIG. 30 shows an evaluation of *Aspergillus fumigatus* Cel7A CBHI and *Penicillium pinophilum* Cel7A CBHI in a high-temperature enzyme composition in hydrolysis of milled unwashed PCS at 50-65° C.

Figure 31:
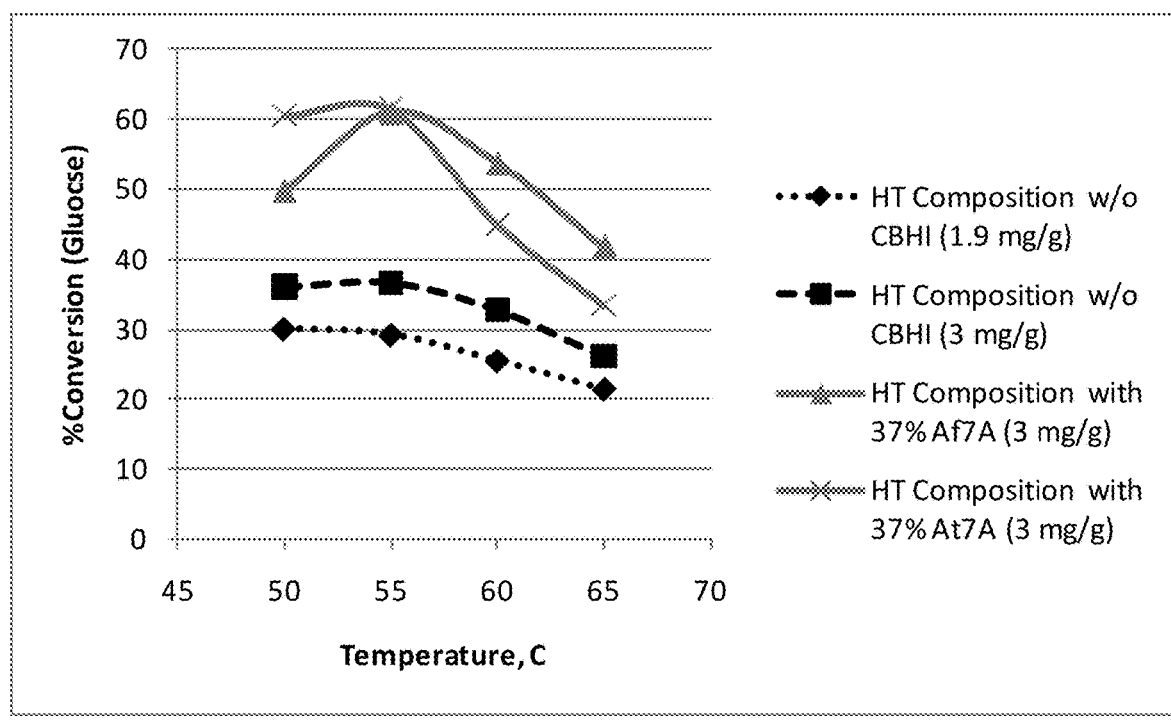

FIG. 31 shows an evaluation of *Aspergillus fumigatus* Cel7A CBHI and *Aspergillus terreus* Cel7A CBHI in a high-temperature enzyme composition in hydrolysis of milled unwashed PCS at 50-65° C.

Figure 32:
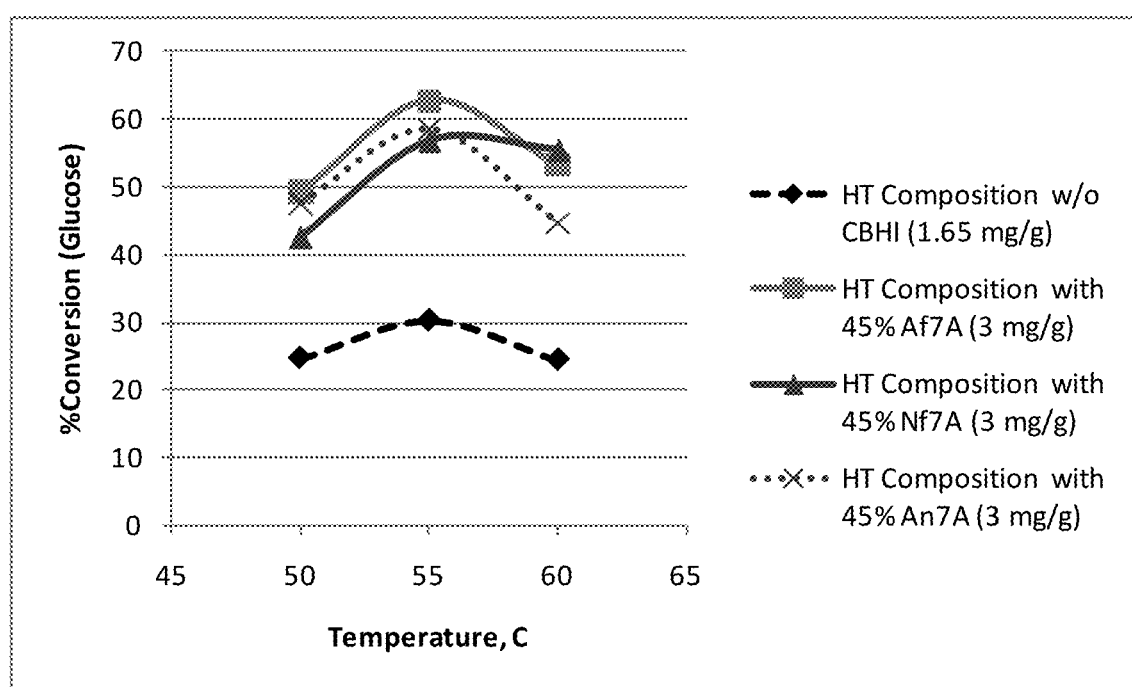

FIG. 32 shows an evaluation of *Aspergillus fumigatus* Cel7A CBHI, Neosartorya *fischeri* Cel7A CBHI, and *Aspergillus nidulans* Cel7A CBHI in a high-temperature enzyme composition in hydrolysis of milled unwashed PCS at 50-60° C.

Figure 33:
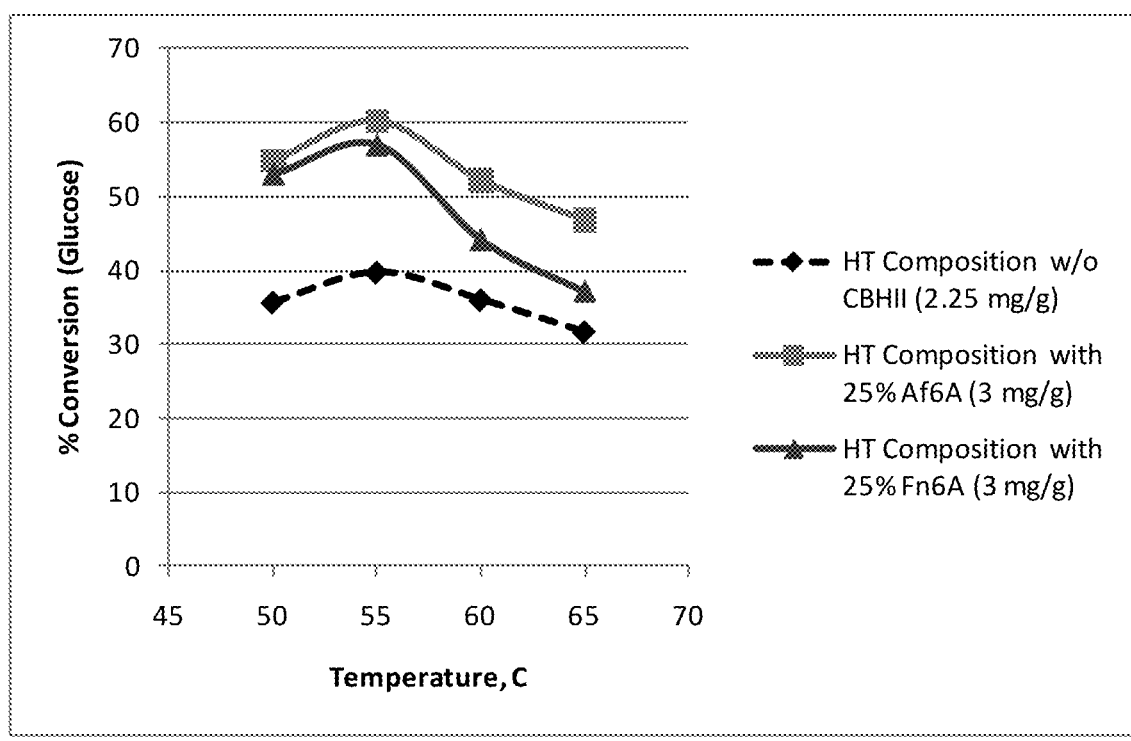

FIG. 33 shows an evaluation of *Aspergillus fumigatus* Cel6A CBHII and *Finnellia nivea* Cel6A CBHII in a high-temperature enzyme composition in hydrolysis of milled unwashed PCS at 50-65° C.

Figure 34:
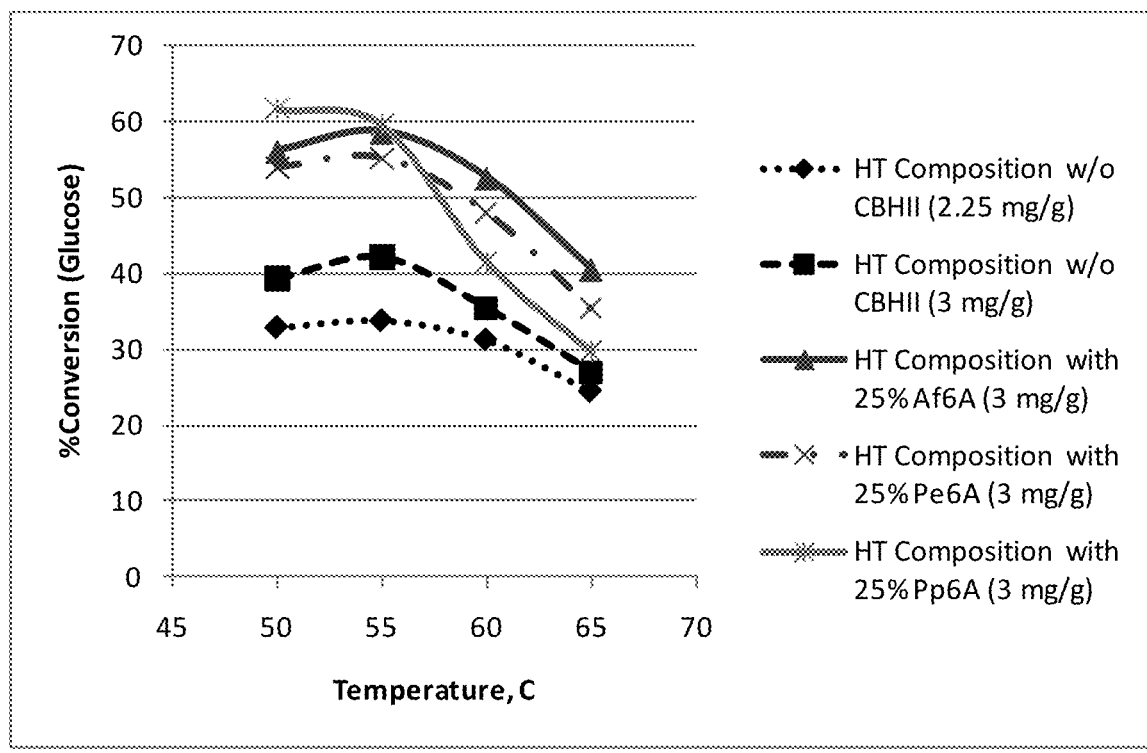

FIG. 34 shows an evaluation of *Aspergillus fumigatus* Cel6A CBHII, *Penicillium emersonii* Cel6A CBHII, and *Penicillium pinophilum* Cel6A CBHII proteins replacing a CBHII component in a high-temperature enzyme composition in hydrolysis of milled unwashed PCS at 50-65° C.

Figure 35:
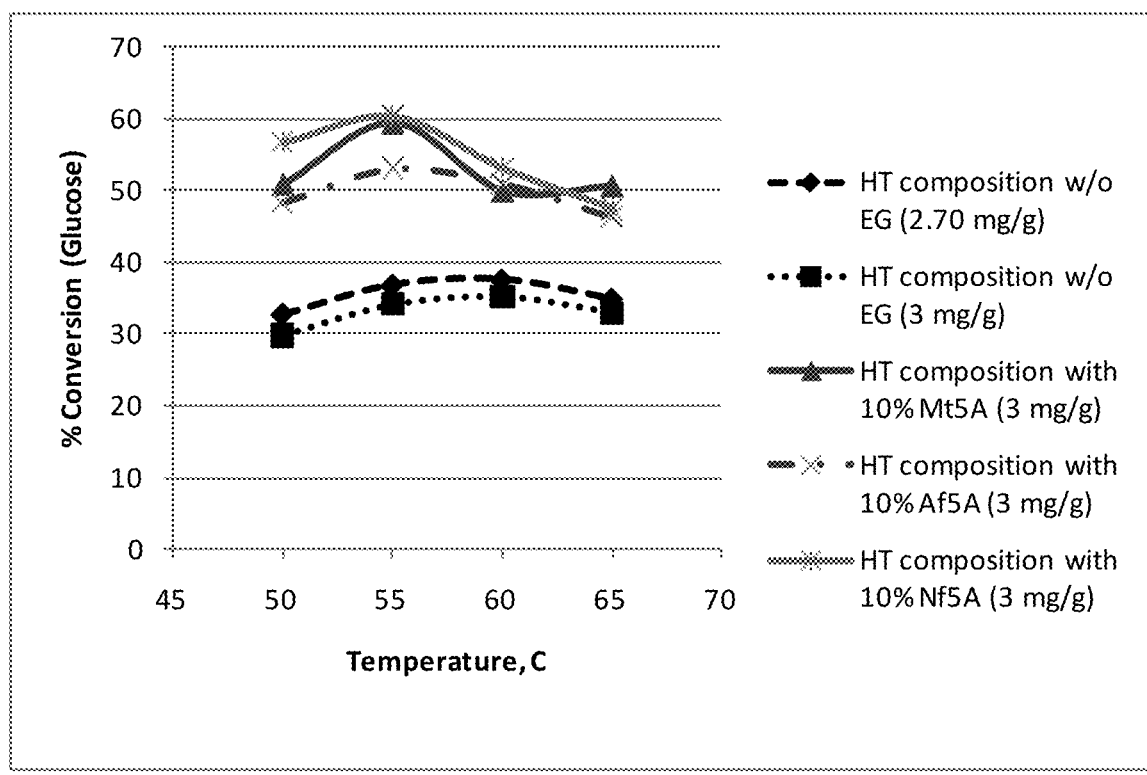

FIG. 35 shows an evaluation of *Aspergillus fumigatus* Cel5A EGII, Neosartorya *fischeri* Cel5A EGII, and *Myceliophthora thermophila* Cel5A EGII proteins replacing a EG component in a high-temperature enzyme composition in hydrolysis of milled unwashed PCS at 50-65° C.

Figure 36:
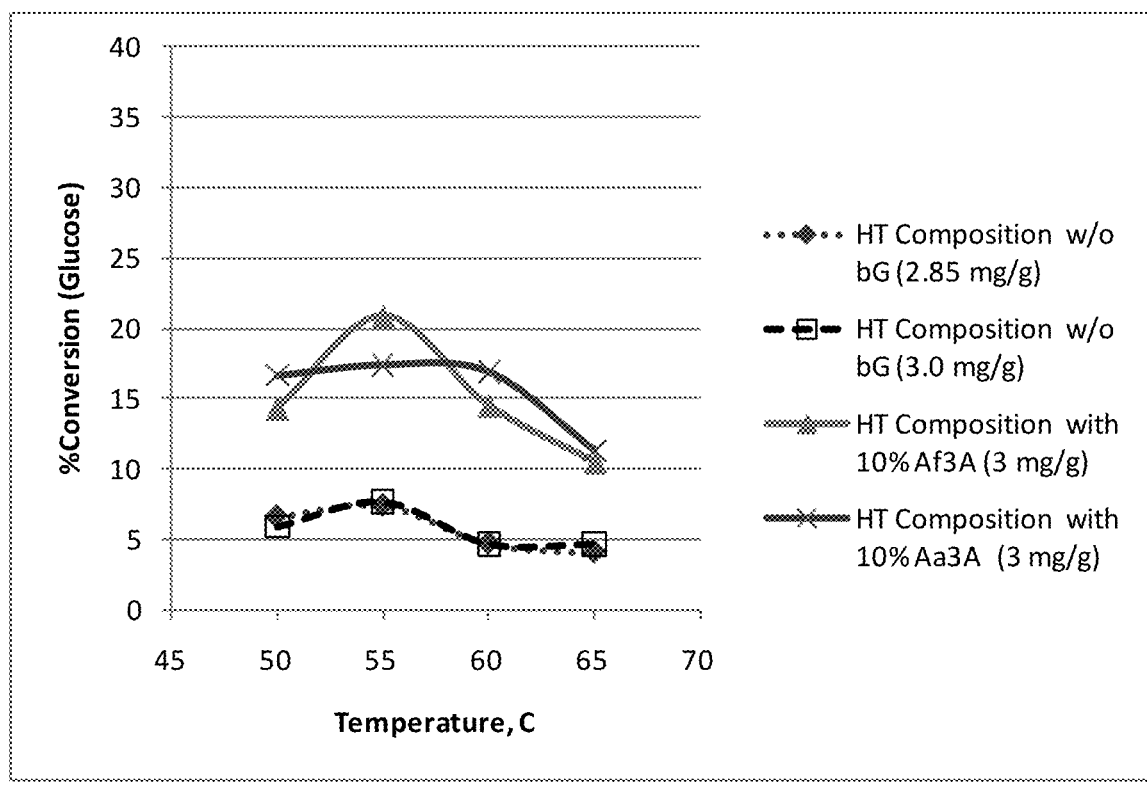

FIG. 36 shows an evaluation of *Aspergillus fumigatus* Cel3A beta-glucosidase and *Aspergillus aculeatus* beta-glucosidase in a high-temperature enzyme composition in hydrolysis of milled unwashed PCS at 50-65° C.

Figure 37:
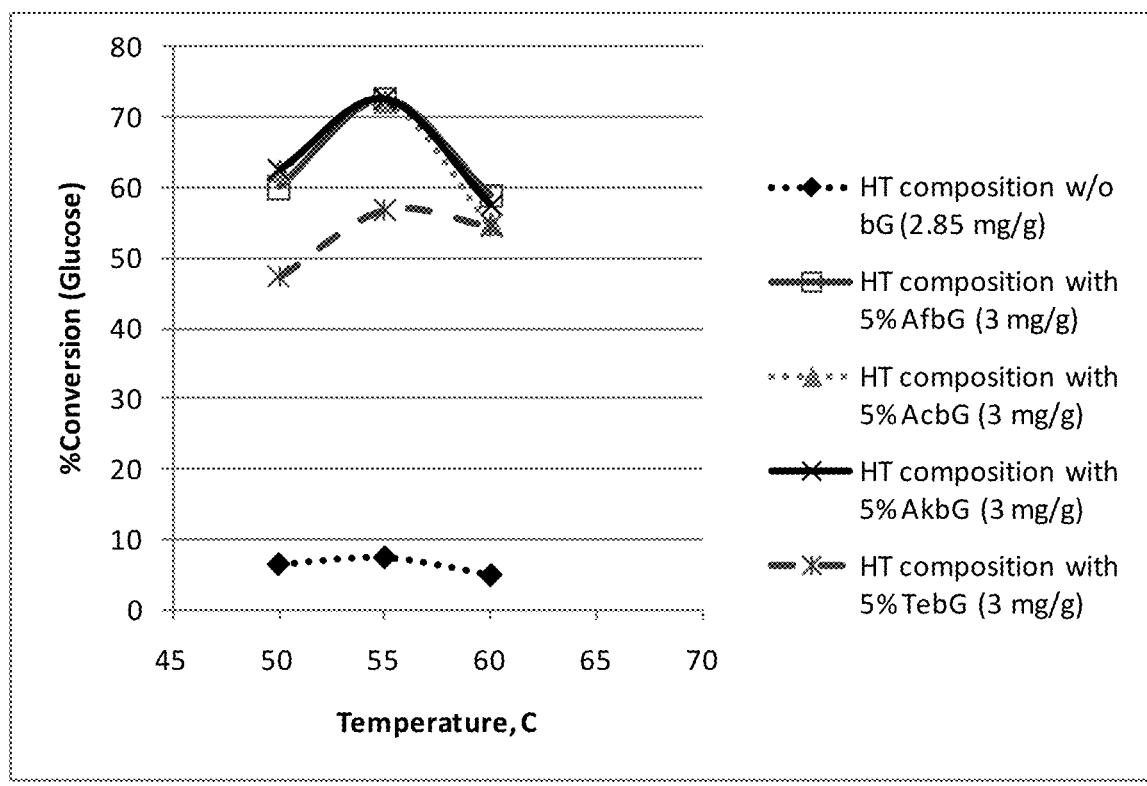

FIG. 37 shows an evaluation of *Aspergillus fumigatus* Cel3A beta-glucosidase, *Aspergillus kawashii* Cel3A beta-glucosidase, *Aspergillus clavatus* Cel3 beta-glucosidase, and *Talaromyces emersonii* Cel3A beta-glucosidase in a high-temperature enzyme composition in hydrolysis of milled unwashed PCS at 50-60° C.

Figure 38:
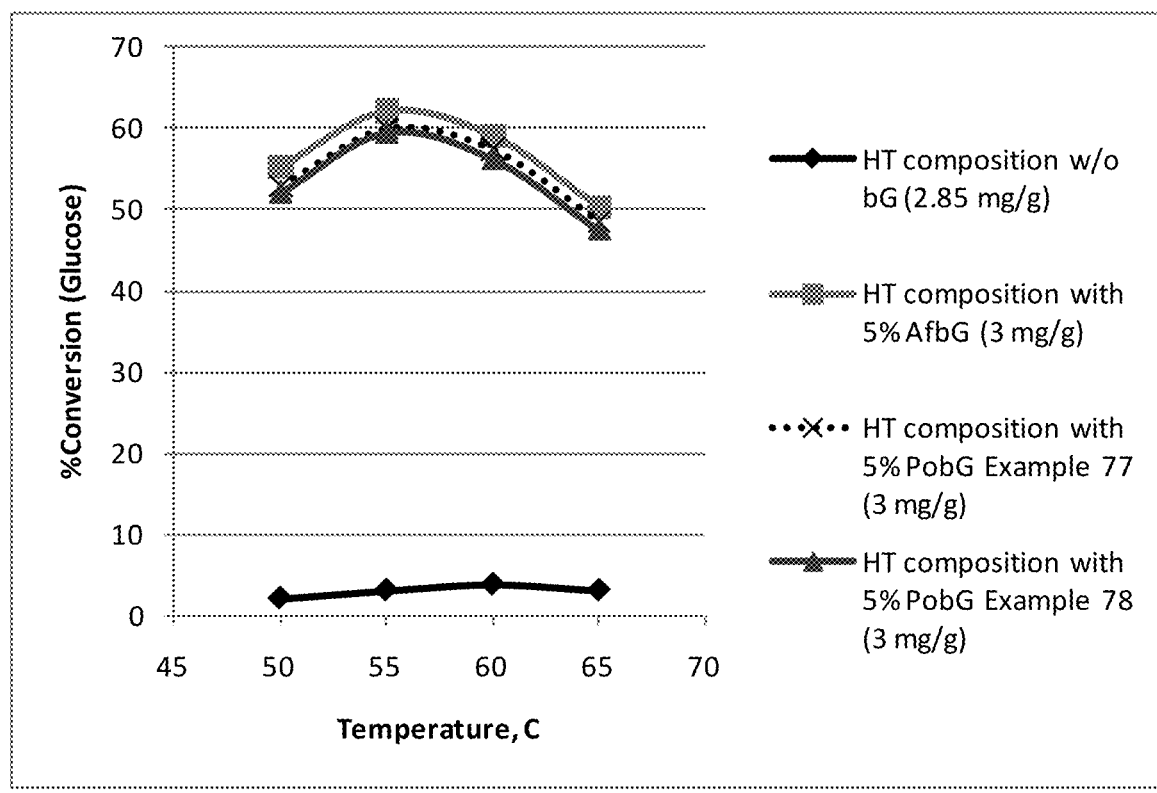

FIG. 38 shows an evaluation of *Aspergillus fumigatus* Cel3A beta-glucosidase, *Penicillium oxalicum* Cel3A beta-glucosidase (Example 77) and *Penicillium oxalicum* Cel3A beta-glucosidase (Example 78) in a high-temperature enzyme composition in hydrolysis of milled unwashed PCS at 50-65° C.

Figure 39:
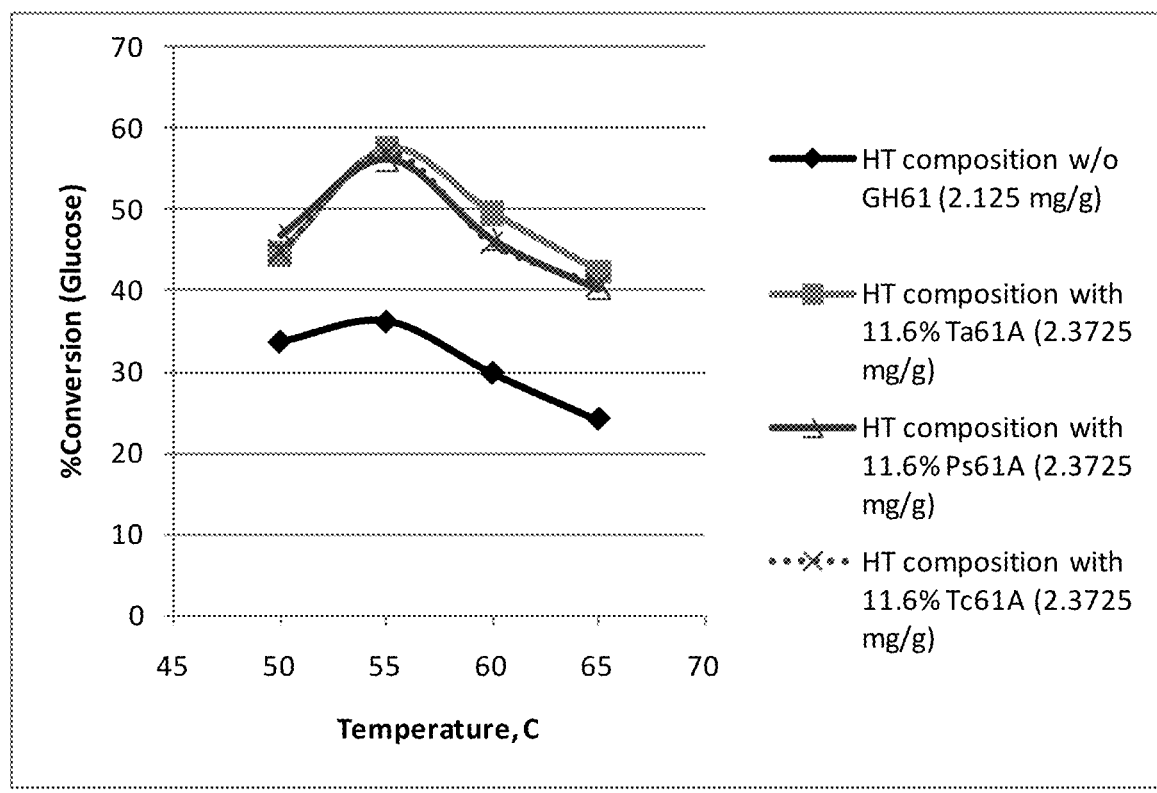

FIG. 39 shows an evaluation of three GH61 polypeptides having cellulolytic enhancing activity in a high-temperature enzyme composition in hydrolysis of milled washed PCS at 50-65° C.

Figure 40:
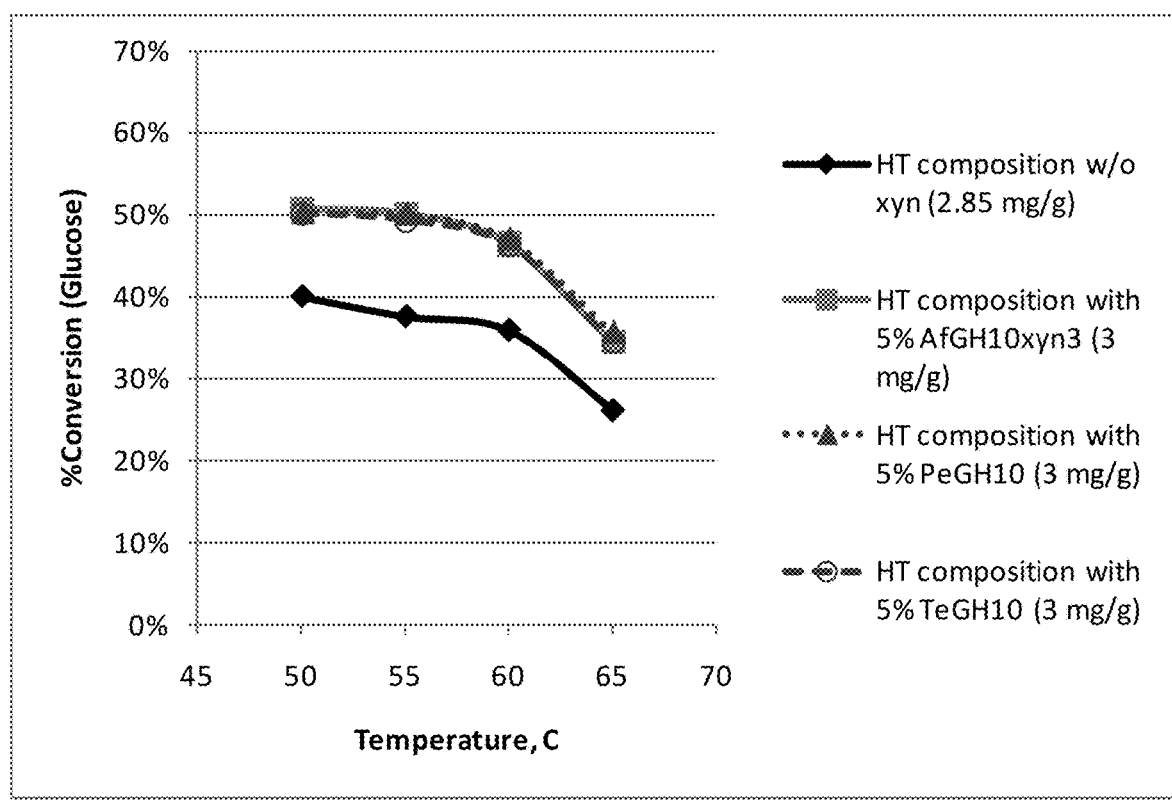

FIG. 40 shows an evaluation of three xylanases in a high-temperature enzyme composition in hydrolysis of milled unwashed PCS at 50-65° C.

Figure 41:
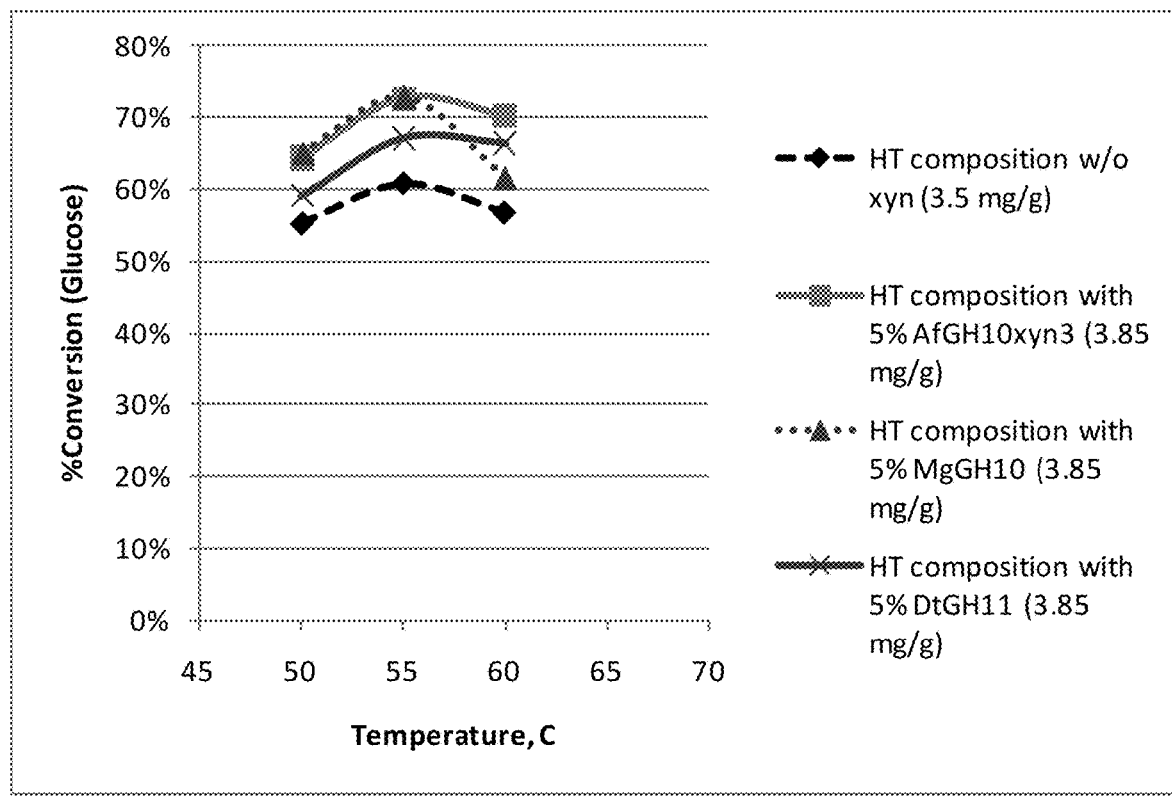

FIG. 41 shows an evaluation of three xylanases in a high-temperature enzyme composition in hydrolysis of milled unwashed PCS at 50-65° C.

Figure 42:
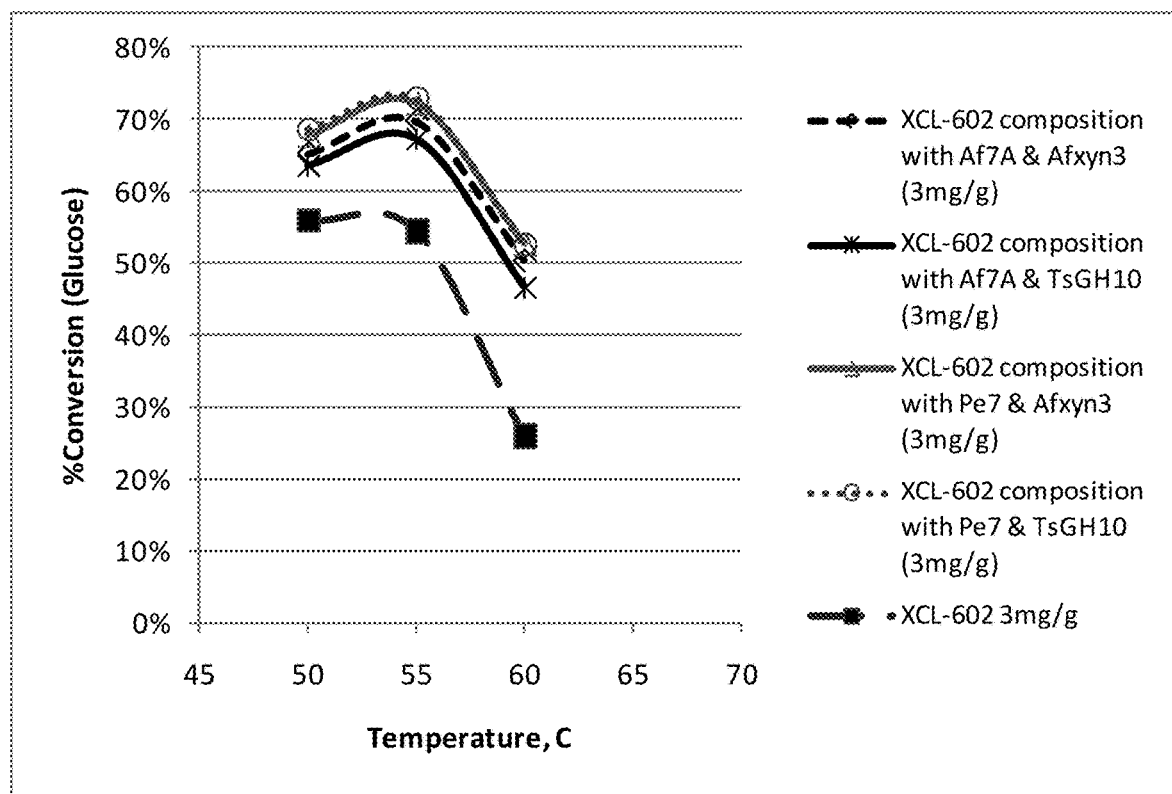

FIG. 42 shows the hydrolysis of milled unwashed PCS by non-replaced *Trichoderma reesei*-based XCL-602 cellulase and various XCL-602-based enzyme compositions containing different cellobiohydrolases and xylanases (3 mg protein per g cellulose) at 50-60° C.

DEFINITIONS

Cellulolytic enzyme or cellulase: The term "cellulolytic enzyme" or "cellulase" means one or more (several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman N°1 filter paper, microcrystalline cellulose, bacterial cellulose, algal cellulose, cotton, pretreated lignocellulose, etc. The most common total cellulolytic activity assay is the filter paper assay using Whatman N°1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-20 mg of cellulolytic enzyme protein/g of cellulose in PCS for 3-7 days at 50° C. compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 72 hours, sugar analysis by AMINEX® HPX-87H column (Bio-Rad Laboratories, Inc., Hercules, CA, USA).

Endoglucanase: The term "endoglucanase" means an endo-1,4-(1,3;1,4)-beta-D-glucan 4-glucanohydrolase (E.C. 3.2.1.4), which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Cellobiohydrolase: The term "cellobiohydrolase" means a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). For purposes of the present invention, cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters*, 187: 283-288; and Tomme et al., 1988, *Eur. J. Biochem.* 170: 575-581. In the present invention, the Lever et al. method can be employed to assess hydrolysis of cellulose in corn stover, while the methods of van Tilbeurgh et al. and Tomme et al. can be used to determine the cellobiohydrolase activity on a fluorescent disaccharide derivative, 4-methylumbelliferyl-β-D-lactoside.

Beta-glucosidase: The term "beta-glucosidase" means a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at pH 4.8 from 1 mM p-nitrophenyl-beta-D-glucopyranoside as substrate in 50 mM sodium citrate containing 0.01% TWEEN® 20.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at 50° C. compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsvaerd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-fold, more preferably at least 4-fold, more preferably at least 5-fold, even more preferably at least 10-fold, and most preferably at least 20-fold.

Hemicellulolytic enzyme or hemicellulase: The term "hemicellulolytic enzyme" or "hemicellulase" means one or more (several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetyxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families marked by numbers. Some families, with overall similar fold, can be further grouped into clans, marked alphabetically (e.g., GH-A). A most informative and updated classification of these and other carbohydrate active enzymes is available on the Carbohydrate-Active Enzymes (CAZy) database. Hemicellulolytic enzyme activities can be measured according to Ghose and Bisaria, 1987, *Pure & Appl. Chem.* 59: 1739-1752.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% Triton X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, MO, USA) by xylan-degrading enzyme(s) under the following typical conditions: 1 ml reactions, mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in Triton X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides, to remove successive D-xylose residues from the non-reducing termini. For purposes of the present invention, one unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

Acetylxylan esterase: The term "acetylxylan esterase" means a carboxylesterase (EC 3.1.1.72) that catalyses the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20. One unit of acetylxylan esterase is defined as the amount of enzyme capable of releasing 1 µmole of p-nitrophenolate anion per minute at pH 5, 25° C.

Feruloyl esterase: The term "feruloyl esterase" means a 4-hydroxy-3-methoxycinnamoyl-sugar hydrolase (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 µmole of p-nitrophenolate anion per minute at pH 5, 25° C.

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 µmole of glucuronic or 4-O-methylglucuronic acid per minute at pH 5, 40° C.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, CA, USA).

Family 3, 5, 6, 7, 10, 11, or 61, or GH3, GH5, GH6, GH7, GH10, GH11, or GH61, or Cel3, Cel5, Cel6 or Cel7: The terms "Family 3", "Family 5", "Family 6", "Family 7", "Family 10", "Family 11", "Family 61", "GH3", "GH5", "GH6", "GH7", "GH10", "GH11", "GH61", "Cel3", "Cel5", "Cel6", or "Cel7" are defined herein as a polypeptide falling into the glycoside hydrolase Families 3, 5, 6, 7, 10, 11, and 61 according to Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696.

Cellulosic material: The cellulosic material can be any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is lignocellulose.

In one aspect, the cellulosic material is herbaceous material. In another aspect, the cellulosic material is agricultural residue. In another aspect, the cellulosic material is forestry residue. In another aspect, the cellulosic material is municipal solid waste. In another aspect, the cellulosic material is waste paper. In another aspect, the cellulosic material is pulp and paper mill residue.

In another aspect, the cellulosic material is corn stover. In another aspect, the cellulosic material is corn fiber. In another aspect, the cellulosic material is corn cob. In another aspect, the cellulosic material is orange peel. In another aspect, the cellulosic material is rice straw. In another aspect, the cellulosic material is wheat straw. In another aspect, the cellulosic material is switch grass. In another aspect, the cellulosic material is miscanthus. In another aspect, the cellulosic material is bagasse. In another aspect, the cellulosic material is softwood. In another aspect, the cellulosic material is hardwood.

In another aspect, the cellulosic material is microcrystalline cellulose. In another aspect, the cellulosic material is bacterial cellulose. In another aspect, the cellulosic material is algal cellulose. In another aspect, the cellulosic material is cotton linter. In another aspect, the cellulosic material is amorphous phosphoric-acid treated cellulose. In another aspect, the cellulosic material is filter paper.

The cellulosic material may be used as is or may be subjected to pretreatment, using conventional methods known in the art, as described herein. In a preferred aspect, the cellulosic material is pretreated.

Pretreated corn stover: The term "PCS" or "Pretreated Corn Stover" means a cellulosic material derived from corn stover by treatment with heat and dilute sulfuric acid.

Isolated or purified: The term "isolated" or "purified" means a polypeptide or polynucleotide that is removed from at least one component with which it is naturally associated. For example, a polypeptide may be at least 1% pure, e.g., at least 5% pure, at least 10% pure, at least 20% pure, at least 40% pure, at least 60% pure, at least 80% pure, at least 90% pure, or at least 95% pure, as determined by SDS-PAGE, and a polynucleotide may be at least 1% pure, e.g., at least 5% pure, at least 10% pure, at least 20% pure, at least 40% pure, at least 60% pure, at least 80% pure, at least 90% pure, or at least 95% pure, as determined by agarose electrophoresis.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. The mature polypeptide can be predicted using the SignalP program (Nielsen et al., 1997, *Protein Engineering* 10: 1-6).

Mature polypeptide coding sequence: The term "mature polypeptide coding sequence" is defined herein as a nucleotide sequence that encodes a mature polypeptide having biological activity. The mature polypeptide coding sequence can be predicted using the SignalP program (Nielsen et al., 1997, supra).

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Polypeptide fragment: The term "fragment" means a polypeptide having one or more (several) amino acids deleted from the amino and/or carboxyl terminus of a mature polypeptide; wherein the fragment has biological activity.

Subsequence: The term "subsequence" means a polynucleotide having one or more (several) nucleotides deleted from the 5' and/or 3' end of a mature polypeptide coding sequence; wherein the subsequence encodes a fragment having biological activity.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a polypeptide. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

DETAILED DESCRIPTION OF THE INVENTION

Enzyme Compositions

The present invention relates to enzyme compositions, comprising two or more (several) components selected from the group consisting of:
(I) a polypeptide having cellobiohydrolase I activity selected from the group consisting of:
(A) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 2; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 1, (ii) the genomic DNA sequence of the mature polypeptide coding sequence of SEQ ID NO: 1, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 1;
(B) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 4; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 3, (ii) the genomic DNA sequence of the mature polypeptide coding sequence of SEQ ID NO: 3, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 3;
(C) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 6; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 5, (ii) the cDNA sequence of the mature polypeptide coding sequence of SEQ ID NO: 5, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 5;
(D) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 8; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 7, (ii) the genomic DNA sequence of the mature polypeptide coding sequence of SEQ ID NO: 7, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 7;
(E) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 158; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 157, (ii) the genomic DNA sequence of the mature polypeptide coding sequence of SEQ ID NO: 157, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 157;
(F) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 160; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 159, (ii) the genomic DNA sequence of the mature polypeptide coding sequence of SEQ ID NO: 159, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 159;

(G) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 162; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 161, (ii) the genomic DNA sequence of the mature polypeptide coding sequence of SEQ ID NO: 161, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 161;

(H) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 164; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 163, (ii) the genomic DNA sequence of the mature polypeptide coding sequence of SEQ ID NO: 163, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 163; and (I) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 166; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 165, (ii) the genomic DNA sequence of the mature polypeptide coding sequence of SEQ ID NO: 165, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 165;

(II) a polypeptide having cellobiohydrolase II activity selected from the group consisting of:

(A) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 10; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 9, (ii) the cDNA sequence of the mature polypeptide coding sequence of SEQ ID NO: 9, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 9;

(B) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 12; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 11, (ii) the cDNA sequence of the mature polypeptide coding sequence of SEQ ID NO: 11, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 11;

(C) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 14; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 13, (ii) the genomic DNA sequence of the mature polypeptide coding sequence of SEQ ID NO: 13, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 13;

(D) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 16; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 15, (ii) the genomic DNA sequence of the mature polypeptide coding sequence of SEQ ID NO: 15, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 15;

(E) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 18; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 17, (ii) the cDNA sequence of the mature polypeptide coding sequence of SEQ ID NO: 17, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 17;

(F) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 168; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 167, (ii) the cDNA sequence of the mature polypeptide coding sequence of SEQ ID NO: 167, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 167;

(G) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 170; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 169, (ii) the cDNA sequence of the mature polypeptide coding sequence of SEQ ID NO: 169, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 169; and (H) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 172; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 172, (ii) the cDNA sequence of the mature polypeptide coding sequence of SEQ ID NO: 172, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 172;

(III) a polypeptide having endoglucanase I activity selected from the group consisting of: (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 20; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 19, (ii) the cDNA sequence of the mature polypeptide coding sequence of SEQ ID NO: 19, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 19;

(IV) a polypeptide having endoglucanase II activity selected from the group consisting of:

(A) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 22; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 21, (ii) the genomic DNA sequence of the mature polypeptide coding sequence of SEQ ID NO: 21, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 21;

(B) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 24; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 23, (ii) the cDNA sequence of the mature polypeptide coding sequence of SEQ ID NO: 23, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 23;

(C) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 26; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 25, (ii) the genomic DNA sequence of the mature polypeptide coding sequence of SEQ ID NO: 25, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 25;

(D) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 174; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 173, (ii) the genomic DNA sequence of the mature polypeptide coding sequence of SEQ ID NO: 173, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 173; and (E) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 176; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 175, (ii) the genomic DNA sequence of the mature polypeptide coding sequence of SEQ ID NO: 175, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 175; and (V) a polypeptide having beta-glucosidase activity selected from the group consisting of:

(A) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 28; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 27, (ii) the cDNA sequence of the mature polypeptide coding sequence of SEQ ID NO: 27, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 27;

(B) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 30; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 29, (ii) the cDNA sequence of the mature polypeptide coding sequence of SEQ ID NO: 29, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 29;

(C) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 32; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 31, (ii) the cDNA sequence of the mature polypeptide coding sequence of SEQ ID NO: 31, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 31;

(D) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 178; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 177, (ii) the cDNA sequence of the mature polypeptide coding sequence of SEQ ID NO: 177, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 177;

(E) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 180; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 179, (ii) the cDNA sequence of the mature polypeptide coding sequence of SEQ ID NO: 179, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 179;

(F) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 182; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 181, (ii) the cDNA sequence of the mature polypeptide coding sequence of SEQ ID NO: 181, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 181;

(G) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 184; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 183, (ii) the cDNA sequence of the mature polypeptide coding sequence of SEQ ID NO: 183, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 183;

(H) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 186; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 185, (ii) the cDNA sequence of the mature polypeptide coding sequence of SEQ ID NO: 185, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 185;

(I) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 188; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 187, (ii) the cDNA sequence of the mature polypeptide coding sequence of SEQ ID NO: 187, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 187; and (J) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 190; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 189, (ii) the cDNA sequence of the mature polypeptide coding sequence of SEQ ID NO: 189, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 189.

In a preferred aspect, the polypeptide having cellobiohydrolase I activity is a *Chaetomium thermophilum* Cel7A cellobiohydrolase I of the mature polypeptide of SEQ ID NO: 2. In another aspect, the *Chaetomium thermophilum* Cel7A cellobiohydrolase I is encoded by the mature polypeptide coding sequence of SEQ ID NO: 1.

In another aspect, the polypeptide having cellobiohydrolase I activity is a *Myceliophthora thermophila* Cel7A cellobiohydrolase I of the mature polypeptide of SEQ ID NO: 4. In another aspect, the *Myceliophthora thermophila* Cel7A cellobiohydrolase I is encoded by the mature polypeptide coding sequence of SEQ ID NO: 3.

In another aspect, the polypeptide having cellobiohydrolase I activity is a *Aspergillus fumigatus* Cel7A cellobiohydrolase I of the mature polypeptide of SEQ ID NO: 6. In another aspect, the *Aspergillus fumigatus* Cel7A cellobiohydrolase I is encoded by the mature polypeptide coding sequence of SEQ ID NO: 5.

In another aspect, the polypeptide having cellobiohydrolase I activity is a *Thermoascus aurantiacus* Cel7A cellobiohydrolase I of the mature polypeptide of SEQ ID NO: 8. In another aspect, the *Thermoascus aurantiacus* Cel7A cellobiohydrolase I is encoded by the mature polypeptide coding sequence of SEQ ID NO: 7.

In another aspect, the polypeptide having cellobiohydrolase I activity is a *Penicillium emersonii* Cel7 cellobiohydrolase I of the mature polypeptide of SEQ ID NO: 158. In another aspect, the *Penicillium emersonii* Cel7 cellobiohydrolase 1 is encoded by the mature polypeptide coding sequence of SEQ ID NO: 157.

In another aspect, the polypeptide having cellobiohydrolase I activity is a *Penicillium pinophilum* Cel7 cellobiohydrolase I of the mature polypeptide of SEQ ID NO: 160. In another aspect, the *Penicillium pinophilum* Cel7A cellobiohydrolase I is encoded by the mature polypeptide coding sequence of SEQ ID NO: 159.

In another aspect, the polypeptide having cellobiohydrolase I activity is an *Aspergillus terreus* Cel7 cellobiohydrolase I of the mature polypeptide of SEQ ID NO: 162. In another aspect, the *Aspergillus terreus* Cel7 cellobiohydrolase I is encoded by the mature polypeptide coding sequence of SEQ ID NO: 161.

In another aspect, the polypeptide having cellobiohydrolase I activity is a *Neosartorya fischeri* Cel7 cellobiohydrolase I of the mature polypeptide of SEQ ID NO: 164. In another aspect, the *Neosartorya fischeri* Cel7 cellobiohydrolase I is encoded by the mature polypeptide coding sequence of SEQ ID NO: 163.

In another aspect, the polypeptide having cellobiohydrolase I activity is an *Aspergillus nidulans* Cel7 cellobiohydrolase I of the mature polypeptide of SEQ ID NO: 166. In another aspect, the *Aspergillus nidulans* Cel7 cellobiohydrolase I is encoded by the mature polypeptide coding sequence of SEQ ID NO: 165.

In another aspect, the polypeptide having cellobiohydrolase II activity is a *Myceliophthora thermophila* Cel6A cellobiohydrolase II of the mature polypeptide of SEQ ID NO: In another aspect, the *Myceliophthora thermophila* Cel6A cellobiohydrolase II is encoded by the mature polypeptide coding sequence of SEQ ID NO: 9.

In another aspect, the polypeptide having cellobiohydrolase II activity is a *Myceliophthora thermophila* Cel6B cellobiohydrolase II of the mature polypeptide of SEQ ID NO: 12. In another aspect, the *Myceliophthora thermophila* Cel6B cellobiohydrolase II is encoded by the mature polypeptide coding sequence of SEQ ID NO: 11.

In another aspect, the polypeptide having cellobiohydrolase II activity is a *Thielavia terrestris* Cel6A cellobiohydrolase II of the mature polypeptide of SEQ ID NO: 14. In another aspect, the *Thielavia terrestris* Cel6A cellobiohydrolase II is encoded by the mature polypeptide coding sequence of SEQ ID NO: 13.

In another aspect, the polypeptide having cellobiohydrolase II activity is a *Trichophaea saccata* CBS 804.70 Cel6A cellobiohydrolase II of the mature polypeptide of SEQ ID NO: 16. In another aspect, the *Trichophaea saccata* Cel6A cellobiohydrolase II is encoded by the mature polypeptide coding sequence of SEQ ID NO: 15.

In another aspect, the polypeptide having cellobiohydrolase II activity is an *Aspergillus fumigatus* Cel6A cellobiohydrolase II of the mature polypeptide of SEQ ID NO: 18. In another aspect, the *Aspergillus fumigatus* Cel6A cellobiohydrolase II is encoded by the mature polypeptide coding sequence of SEQ ID NO: 17.

In another aspect, the polypeptide having cellobiohydrolase II activity is a *Fennellia nivea* Cel6 cellobiohydrolase II of the mature polypeptide of SEQ ID NO: 168. In another aspect, the *Fennellia nivea* Cel6 cellobiohydrolase II is encoded by the mature polypeptide coding sequence of SEQ ID NO: 167.

In another aspect, the polypeptide having cellobiohydrolase II activity is a *Penicillium emersonii* Cel6A cellobiohydrolase II of the mature polypeptide of SEQ ID NO: 170. In another aspect, the *Penicillium emersonii* Cel6A cellobiohydrolase II is encoded by the mature polypeptide coding sequence of SEQ ID NO: 169.

In another aspect, the polypeptide having cellobiohydrolase II activity is a *Penicillium pinophilum* Cel6A cellobiohydrolase II of the mature polypeptide of SEQ ID NO: 172. In another aspect, the *Penicillium pinophilum* Cel6A cellobiohydrolase II is encoded by the mature polypeptide coding sequence of SEQ ID NO: 171.

In another aspect, the polypeptide having endoglucanase I activity is a *Aspergillus terreus* Cel7A endoglucanase I of the mature polypeptide of SEQ ID NO: 20. In another aspect, the *Aspergillus terreus* Cel7A endoglucanase I is encoded by the mature polypeptide coding sequence of SEQ ID NO: 19.

In another aspect, the polypeptide having endoglucanase II activity is a *Trichoderma reesei* Cel5A endoglucanase II of the mature polypeptide of SEQ ID NO: 22. In another aspect, the *Trichoderma reesei* Cel5A endoglucanase II is encoded by the mature polypeptide coding sequence of SEQ ID NO: 21.

In another aspect, the polypeptide having endoglucanase II activity is a *Myceliophthora thermophila* Cel5A endoglucanase II of the mature polypeptide of SEQ ID NO: 24. In another aspect, the *Myceliophthora thermophila* Cel5A endoglucanase II is encoded by the mature polypeptide coding sequence of SEQ ID NO: 23.

In another aspect, the polypeptide having endoglucanase II activity is a *Thermoascus aurantiacus* Cel5A endoglucanase II of the mature polypeptide of SEQ ID NO: 26. In another aspect, the *Thermoascus aurantiacus* Cel5A endoglucanase II is encoded by the mature polypeptide coding sequence of SEQ ID NO: 25.

In another aspect, the polypeptide having endoglucanase II activity is an *Aspergillus fumigatus* Cel5 endoglucanase II of the mature polypeptide of SEQ ID NO: 174. In another aspect, the *Aspergillus fumigatus* Cel5 endoglucanase II is encoded by the mature polypeptide coding sequence of SEQ ID NO: 173.

In another aspect, the polypeptide having endoglucanase II activity is a Neosartorya *fischeri* Cel5 endoglucanase II of the mature polypeptide of SEQ ID NO: 176. In another aspect, the Neosartorya *fischeri* Cel5 endoglucanase II is encoded by the mature polypeptide coding sequence of SEQ ID NO: 175.

In another aspect, the polypeptide having beta-glucosidase activity is a *Aspergillus fumigatus* beta-glucosidase of the mature polypeptide of SEQ ID NO: 28. In another aspect, the *Aspergillus fumigatus* beta-glucosidase is encoded by the mature polypeptide coding sequence of SEQ ID NO: 27.

In another aspect, the polypeptide having beta-glucosidase activity is a *Penicillium brasilianum* beta-glucosidase of the mature polypeptide of SEQ ID NO: 30. In another aspect, the *Penicillium brasilianum* beta-glucosidase is encoded by the mature polypeptide coding sequence of SEQ ID NO: 29.

In another aspect, the polypeptide having beta-glucosidase activity is a *Aspergillus niger* beta-glucosidase of the mature polypeptide of SEQ ID NO: 32. In another aspect, the *Aspergillus niger* beta-glucosidase is encoded by the mature polypeptide coding sequence of SEQ ID NO: 31.

In another aspect, the polypeptide having beta-glucosidase activity is an *Aspergillus aculeatus* Cel3 beta-glucosidase of the mature polypeptide of SEQ ID NO: 178. In another aspect, the *Aspergillus aculeatus* Cel3 beta-glucosidase is encoded by the mature polypeptide coding sequence of SEQ ID NO: 177.

In another aspect, the polypeptide having beta-glucosidase activity is an *Aspergillus kawashii* Cel3 beta-glucosidase of the mature polypeptide of SEQ ID NO: 180. In another aspect, the *Aspergillus kawashii* Cel3 beta-glucosidase is encoded by the mature polypeptide coding sequence of SEQ ID NO: 179.

In another aspect, the polypeptide having beta-glucosidase activity is an *Aspergillus clavatus* Cel3 beta-glucosidase of the mature polypeptide of SEQ ID NO: 182. In another aspect, the *Aspergillus clavatus* Cel3 beta-glucosidase is encoded by the mature polypeptide coding sequence of SEQ ID NO: 181.

In another aspect, the polypeptide having beta-glucosidase activity is a *Thielavia terrestris* NRRL 8126 Cel3 beta-glucosidase of the mature polypeptide of SEQ ID NO: 184. In another aspect, the *Thielavia terrestris* NRRL 8126 Cel3 beta-glucosidase is encoded by the mature polypeptide coding sequence of SEQ ID NO: 183.

In another aspect, the polypeptide having beta-glucosidase activity is a *Penicillium oxalicum* Cel3 beta-glucosidase of the mature polypeptide of SEQ ID NO: 186. In another aspect, the *Penicillium oxalicum* Cel3 beta-glucosidase is encoded by the mature polypeptide coding sequence of SEQ ID NO: 185.

In another aspect, the polypeptide having beta-glucosidase activity is a *Penicillium oxalicum* Cel3 beta-glucosidase of the mature polypeptide of SEQ ID NO: 188. In another aspect, the *Penicillium oxalicum* Cel3 beta-glucosidase is encoded by the mature polypeptide coding sequence of SEQ ID NO: 187.

In another aspect, the polypeptide having beta-glucosidase activity is a *Talaromyces emersonii* Cel3 beta-glucosidase of the mature polypeptide of SEQ ID NO: 190. In another aspect, the *Talaromyces emersonii* Cel3 beta-glucosidase is encoded by the mature polypeptide coding sequence of SEQ ID NO: 189.

In one aspect, the enzyme composition further comprises or even further comprises a polypeptide having cellulolytic enhancing activity selected from the group consisting of:

(I) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 34; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 33, (ii) the cDNA sequence of the mature polypeptide coding sequence of SEQ ID NO: 33, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 33;

(II) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 36; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 35, (ii) the genomic DNA sequence of the mature polypeptide coding sequence of SEQ ID NO: 35, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 35;

(III) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 38; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 37, (ii) the cDNA sequence of the mature polypeptide coding sequence of SEQ ID NO: 37, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 37;

(IV) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 40; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 39, (ii) the cDNA sequence of the mature polypeptide coding sequence of SEQ ID NO: 39, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 39;

(V) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 42; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 41, (ii) the cDNA sequence of the mature polypeptide coding sequence of SEQ ID NO: 41, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 41;

(VI) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 44; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 43, (ii) the cDNA sequence of the mature polypeptide coding sequence of SEQ ID NO: 43, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 43;

(VII) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 192; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 191, (ii) the cDNA sequence of the mature polypeptide coding sequence of SEQ ID NO: 191, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 191; and (VIII) a combination of any of I, II, III, IV, V, VI, and VII.

In a preferred aspect, the polypeptide having cellulolytic enhancing activity is a *Thermoascus aurantiacus* GH61A polypeptide having cellulolytic enhancing activity of the mature polypeptide of SEQ ID NO: 34. In another aspect, the *Thermoascus aurantiacus* GH61A polypeptide having cellulolytic enhancing activity is encoded by the mature polypeptide coding sequence of SEQ ID NO: 33.

In another aspect, the polypeptide having cellulolytic enhancing activity is a *Thielavia terrestris* GH61E polypeptide having cellulolytic enhancing activity of the mature polypeptide of SEQ ID NO: 36. In another aspect, the *Thielavia terrestris* GH61E polypeptide having cellulolytic enhancing activity is encoded by the mature polypeptide coding sequence of SEQ ID NO: 35.

In another aspect, the polypeptide having cellulolytic enhancing activity is a *Aspergillus fumigatus* GH61B polypeptide having cellulolytic enhancing activity of the mature polypeptide of SEQ ID NO: 38. In another aspect, the *Aspergillus fumigatus* GH61B polypeptide having cellulolytic enhancing activity is encoded by the mature polypeptide coding sequence of SEQ ID NO: 37.

In another aspect, the polypeptide having cellulolytic enhancing activity is a *Penicillium pinophilum* GH61 polypeptide having cellulolytic enhancing activity of the mature polypeptide of SEQ ID NO: 40. In another aspect, the *Penicillium pinophilum* GH61A polypeptide having cellulolytic enhancing activity is encoded by the mature polypeptide coding sequence of SEQ ID NO: 39.

In another aspect, the polypeptide having cellulolytic enhancing activity is a *Penicillium* sp. GH61A polypeptide having cellulolytic enhancing activity of the mature polypeptide of SEQ ID NO: 42. In another aspect, the *Penicillium* sp. GH61 polypeptide having cellulolytic enhancing activity is encoded by the mature polypeptide coding sequence of SEQ ID NO: 41.

In another aspect, the polypeptide having cellulolytic enhancing activity is a *Thielavia terrestris* GH61N polypeptide having cellulolytic enhancing activity of the mature polypeptide of SEQ ID NO: 44. In another aspect, the *Thielavia terrestris* GH61N polypeptide having cellulolytic enhancing activity is encoded by the mature polypeptide coding sequence of SEQ ID NO: 43.

In another aspect, the polypeptide having cellulolytic enhancing activity is a *Thermoascus crustaceus* GH61A polypeptide having cellulolytic enhancing activity of the mature polypeptide of SEQ ID NO: 192. In another aspect, the *Thermoascus crustaceus* GH61A polypeptide having cellulolytic enhancing activity is encoded by the mature polypeptide coding sequence of SEQ ID NO: 191.

In another aspect, the enzyme composition further comprises or even further comprises a polypeptide having xylanase activity. In a preferred aspect, the polypeptide having xylanase activity is a Family 10 polypeptide having xylanase activity. In another aspect, the polypeptide having xylanase activity is a Family 11 polypeptide having xylanase activity.

In a more preferred aspect, the Family 10 polypeptide having xylanase activity is selected from the group consisting of:

(I) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 46; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 45, (ii) the genomic DNA sequence of the mature polypeptide coding sequence of SEQ ID NO: 45, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 45;

(II) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 48; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 47, (ii) the cDNA sequence of the mature polypeptide coding sequence of SEQ ID NO: 47, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 47;

(III) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 50; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 49, (ii) the genomic DNA sequence of the mature polypeptide coding sequence of SEQ ID NO: 49, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 49;

(IV) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 52; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 51, (ii) the cDNA sequence of the mature polypeptide coding sequence of SEQ ID NO: 51, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 51;

(V) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 54; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 53, (ii) the genomic DNA sequence of the mature polypeptide coding sequence of SEQ ID NO: 53, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 53;

(VI) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 194; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 193, (ii) the genomic DNA sequence of the mature polypeptide coding sequence of SEQ ID NO: 193, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 193;

(VII) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 196; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 195, (ii) the genomic DNA sequence of the mature polypeptide coding sequence of SEQ ID NO: 195, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 195; and (VIII) (a) a polypeptide comprising an amino acid sequence having preferably at least 80%, more preferably at least 85%, even more preferably at least 90%, even more preferably at least 95% identity, and most preferably at least 97% identity to the mature polypeptide of SEQ ID NO: 198; (b) a polypeptide encoded by a polynucleotide that hybridizes under preferably at least medium-high stringency conditions, more preferably at least high stringency conditions, and most preferably very high stringency conditions with (i) the mature polypeptide coding sequence of SEQ ID NO: 197, (ii) the genomic DNA sequence of the mature polypeptide coding sequence of SEQ ID NO: 197, or (iii) a full-length complementary strand of (i) or (ii); and (c) a polypeptide encoded by a polynucleotide comprising a nucleotide sequence having preferably at least 80%, more preferably at least 85%, even more preferably at least 90%, even more preferably at least 95% identity, and most preferably at least 97% identity to the mature polypeptide coding sequence of SEQ ID NO: 197.

In one aspect, the enzyme compositions comprise *Aspergillus fumigatus* Cel 7A CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus fumigatus* GH3A beta-glucosidase, *Aspergillus fumigatus* GH100 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus fumigatus* GH3A beta-glucosidase, *Aspergillus fumigatus* GH100 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Penicillium* sp GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus aculeatus* GH3 beta-glucosidase, *Aspergillus fumigatus* GH10C xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus aculeatus* GH3 beta-glucosidase, *Aspergillus fumigatus* GH10C xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus fumigatus* GH3A beta-glucosidase, *Aspergillus fumigatus* GH100 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Penicillium* sp GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus aculeatus* GH3 beta-glucosidase, *Aspergillus fumigatus* GH10O xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Aspergillus fumigatus* GH61B GH61 polypeptides having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Aspergillus fumigatus* GH61B polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise the enzyme compositions comprise *Aspergillus fumigatus* Cel 7A CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus aculeatus* GH3 beta-glucosidase, *Aspergillus fumigatus* GH10O xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus fumigatus* GH3A beta-glucosidase, *Aspergillus fumigatus* GH10O xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus aculeatus* GH3 beta-glucosidase, *Aspergillus fumigatus* GH10O xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus aculeatus* GH3 beta-glucosidase, *Aspergillus fumigatus* GH10C xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Aspergillus fumigatus* GH61B polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus fumigatus* GH3A beta-glucosidase, *Aspergillus fumigatus* GH10O xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus aculeatus* GH3 beta-glucosidase, *Aspergillus fumigatus* GH10C xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus aculeatus* GH3 beta-glucosidase, *Aspergillus fumigatus* GH10O xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus fumigatus* GH3A beta-glucosidase, *Aspergillus fumigatus* GH10O xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus aculeatus* GH3 beta-glucosidase, *Aspergillus fumigatus* GH10C xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Thermoascus aurantiacus* Cel5A EGII, *Thermoascus aurantiacus* GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus aculeatus* GH3 beta-glucosidase, *Aspergillus fumigatus* GH10O xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Aspergillus fumigatus* Cel 7A CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus aculeatus* GH3 beta-glucosidase, *Aspergillus fumigatus* GH10O xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Penicillium emersonii* Cel 7 CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus fumigatus* GH3A beta-glucosidase, *Aspergillus fumigatus* GH10C xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus aculeatus* GH3 beta-glucosidase, *Aspergillus fumigatus* GH100 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus fumigatus* GH3A beta-glucosidase, *Trichophaea saccata* GH10 xylanase, and *Talaromyces emersonii* GH3 beta-xylosidase.

In another aspect, the enzyme compositions comprise *Thermoascus aurantiacus* Cel 7A CBHI, *Aspergillus fumigatus* Cel 6A CBHII, *Aspergillus fumigatus* Cel5A EGII, *Thermoascus aurantiacus* GH61A polypeptide having cellulolytic enhancing activity, *Aspergillus aculeatus* GH3 beta-glucosidase, *Trichophaea saccata* GH10 xylanase, and *Talaromyces emersonii* GH3 beta-xylosidase.

Enzyme Composition Components and Polynucleotides Thereof

In first aspect, the isolated polypeptides having cellobiohydrolase I activity comprise amino acid sequences having a degree of identity to the mature polypeptide of SEQ ID NO: 2 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter "homologous polypeptides"). In a preferred aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 2.

In one aspect, a polypeptide having cellobiohydrolase I activity comprises or consists of the amino acid sequence of SEQ ID NO: 2 or an allelic variant thereof; or a fragment thereof having cellobiohydrolase I activity. In another aspect, the polypeptide comprises or consists of the amino acid sequence of SEQ ID NO: 2. In another aspect, the polypeptide comprises or consists of the mature polypeptide of SEQ ID NO: 2. In another aspect, the polypeptide comprises or consists of amino acids 19 to 530 of SEQ ID NO: 2, or an allelic variant thereof; or a fragment thereof having cellobiohydrolase I activity. In another aspect, the polypeptide comprises or consists of amino acids 19 to 530 of SEQ ID NO: 2.

In another first aspect, the isolated polypeptides having cellobiohydrolase I activity comprise amino acid sequences having a degree of identity to the mature polypeptide of SEQ ID NO: 4 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter "homologous polypeptides"). In one aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 4.

In one aspect, a polypeptide having cellobiohydrolase I activity comprises or consists of the amino acid sequence of SEQ ID NO: 4 or an allelic variant thereof; or a fragment thereof having cellobiohydrolase I activity. In another aspect, the polypeptide comprises or consists of the amino acid sequence of SEQ ID NO: 4. In another aspect, the polypeptide comprises or consists of the mature polypeptide of SEQ ID NO: 4. In another aspect, the polypeptide comprises or consists of amino acids 21 to 450 of SEQ ID NO: 4, or an allelic variant thereof; or a fragment thereof having cellobiohydrolase I activity. In another aspect, the polypeptide comprises or consists of amino acids 21 to 450 of SEQ ID NO: 4.

In another first aspect, the isolated polypeptides having cellobiohydrolase I activity comprise amino acid sequences having a degree of identity to the mature polypeptide of SEQ ID NO: 6 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 6.

In one aspect, a polypeptide having cellobiohydrolase I activity comprises or consists of the amino acid sequence of SEQ ID NO: 6 or an allelic variant thereof; or a fragment thereof having cellobiohydrolase I activity. In another aspect, the polypeptide comprises or consists of the amino acid sequence of SEQ ID NO: 6. In another aspect, the polypeptide comprises or consists of the mature polypeptide of SEQ ID NO: 6. In another aspect, the polypeptide comprises or consists of amino acids 27 to 532 of SEQ ID NO: 6, or an allelic variant thereof; or a fragment thereof having cellobiohydrolase I activity. In another aspect, the polypeptide comprises or consists of amino acids 27 to 532 of SEQ ID NO: 6.

In another first aspect, the isolated polypeptides having cellobiohydrolase I activity comprise amino acid sequences having a degree of identity to the mature polypeptide of SEQ ID NO: 8 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 8.

In one aspect, a polypeptide having cellobiohydrolase I activity comprises or consists of the amino acid sequence of SEQ ID NO: 8 or an allelic variant thereof; or a fragment thereof having cellobiohydrolase I activity. In another aspect, the polypeptide comprises or consists of the amino acid sequence of SEQ ID NO: 8. In another aspect, the polypeptide comprises or consists of the mature polypeptide of SEQ ID NO: 8. In another aspect, the polypeptide comprises or consists of amino acids 18 to 457 of SEQ ID NO: 8, or an allelic variant thereof; or a fragment thereof having cellobiohydrolase I activity. In another aspect, the polypeptide comprises or consists of amino acids 18 to 457 of SEQ ID NO: 8.

In another first aspect, the isolated polypeptides having cellobiohydrolase I activity comprise amino acid sequences having a degree of identity to the mature polypeptide of SEQ ID NO: 158 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 158.

In one aspect, a polypeptide having cellobiohydrolase I activity comprises or consists of or consists of the amino acid sequence of SEQ ID NO: 158 or an allelic variant thereof; or a fragment thereof having cellobiohydrolase I activity. In another aspect, the polypeptide comprises or consists of or consists of the amino acid sequence of SEQ ID NO: 158. In another aspect, the polypeptide comprises or consists of or consists of the mature polypeptide of SEQ ID NO: 158. In another aspect, the polypeptide comprises or consists of or consists of amino acids 19 to 455 of SEQ ID NO: 158, or an allelic variant thereof; or a fragment thereof having cellobiohydrolase I activity. In another aspect, the polypeptide comprises or consists of or consists of amino acids 19 to 455 of SEQ ID NO: 158.

In another first aspect, the isolated polypeptides having cellobiohydrolase I activity comprise amino acid sequences having a degree of identity to the mature polypeptide of SEQ ID NO: 160 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 160.

In one aspect, a polypeptide having cellobiohydrolase I activity comprises or consists of the amino acid sequence of SEQ ID NO: 160 or an allelic variant thereof; or a fragment thereof having cellobiohydrolase I activity. In another aspect, the polypeptide comprises or consists of the amino acid sequence of SEQ ID NO: 160. In another aspect, the polypeptide comprises or consists of the mature polypeptide of SEQ ID NO: 160. In another aspect, the polypeptide comprises or consists of amino acids 26 to 529 of SEQ ID NO: 160, or an allelic variant thereof; or a fragment thereof having cellobiohydrolase I activity. In another aspect, the polypeptide comprises or consists of amino acids 26 to 529 of SEQ ID NO: 160.

In another first aspect, the isolated polypeptides having cellobiohydrolase I activity comprise amino acid sequences having a degree of identity to the mature polypeptide of SEQ ID NO: 162 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 162.

In one aspect, a polypeptide having cellobiohydrolase I activity comprises or consists of the amino acid sequence of SEQ ID NO: 162 or an allelic variant thereof; or a fragment thereof having cellobiohydrolase I activity. In another aspect, the polypeptide comprises or consists of the amino acid sequence of SEQ ID NO: 162. In another aspect, the polypeptide comprises or consists of the mature polypeptide of SEQ ID NO: 162. In another aspect, the polypeptide comprises or consists of amino acids 24 to 541 of SEQ ID NO: 162, or an allelic variant thereof; or a fragment thereof having cellobiohydrolase I activity. In another aspect, the polypeptide comprises or consists of amino acids 24 to 541 of SEQ ID NO: 162.

In another first aspect, the isolated polypeptides having cellobiohydrolase I activity comprise amino acid sequences having a degree of identity to the mature polypeptide of SEQ ID NO: 164 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 164.

In one aspect, a polypeptide having cellobiohydrolase I activity comprises or consists of the amino acid sequence of SEQ ID NO: 164 or an allelic variant thereof; or a fragment thereof having cellobiohydrolase I activity. In another aspect, the polypeptide comprises or consists of the amino acid sequence of SEQ ID NO: 164. In another aspect, the polypeptide comprises or consists of the mature polypeptide of SEQ ID NO: 164. In another aspect, the polypeptide comprises or consists of amino acids 27 to 535 of SEQ ID NO: 164, or an allelic variant thereof; or a fragment thereof having cellobiohydrolase I activity. In another aspect, the polypeptide comprises or consists of amino acids 27 to 535 of SEQ ID NO: 164.

In another first aspect, the isolated polypeptides having cellobiohydrolase I activity comprise amino acid sequences having a degree of identity to the mature polypeptide of SEQ ID NO: 166 of preferably at least 80%, more preferably at least 85%, even more preferably at least 90%, most preferably at least 95%, and even most preferably at least 96%, at least 97%, at least 98%, or at least 99%, which have cellobiohydrolase I activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 166.

In one aspect, a polypeptide having cellobiohydrolase I activity comprises or consists of the amino acid sequence of SEQ ID NO: 166 or an allelic variant thereof; or a fragment thereof having cellobiohydrolase I activity. In another aspect, the polypeptide comprises or consists of the amino acid sequence of SEQ ID NO: 166. In another aspect, the polypeptide comprises or consists of the mature polypeptide of SEQ ID NO: 166. In another aspect, the polypeptide comprises or consists of amino acids 24 to 526 of SEQ ID NO: 166, or an allelic variant thereof; or a fragment thereof having cellobiohydrolase I activity. In another aspect, the polypeptide comprises or consists of amino acids 24 to 526 of SEQ ID NO: 166.

In another first aspect, the isolated polypeptides having cellobiohydrolase II activity comprise amino acid sequences having a degree of identity to the mature polypeptide of SEQ ID NO: 10 of preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO:

In one aspect, a polypeptide having cellobiohydrolase II activity comprises or consists of the amino acid sequence of SEQ ID NO: 10 or an allelic variant thereof; or a fragment thereof having cellobiohydrolase II activity. In another aspect, the polypeptide comprises or consists of the amino acid sequence of SEQ ID NO: 10. In another aspect, the polypeptide comprises or consists of the mature polypeptide of SEQ ID NO: 10. In another aspect, the polypeptide comprises or consists of amino acids 18 to 482 of SEQ ID NO: 10, or an allelic variant thereof; or a fragment thereof having cellobiohydrolase II activity. In another aspect, the polypeptide comprises or consists of amino acids 18 to 482 of SEQ ID NO: 10.

In another first aspect, the isolated polypeptides having cellobiohydrolase II activity comprise amino acid sequences having a degree of identity to the mature polypeptide of SEQ ID NO: 12 of preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 12.

In one aspect, a polypeptide having cellobiohydrolase II activity comprises or consists of the amino acid sequence of SEQ ID NO: 12 or an allelic variant thereof; or a fragment thereof having cellobiohydrolase II activity. In another aspect, the polypeptide comprises or consists of the amino acid sequence of SEQ ID NO: 12. In another aspect, the polypeptide comprises or consists of the mature polypeptide of SEQ ID NO: 12. In another aspect, the polypeptide comprises or consists of amino acids 18 to 482 of SEQ ID NO: 12, or an allelic variant thereof; or a fragment thereof having cellobiohydrolase II activity. In another aspect, the polypeptide comprises or consists of amino acids 18 to 482 of SEQ ID NO: 12.

In another first aspect, the isolated polypeptides having cellobiohydrolase II activity comprise amino acid sequences having a degree of identity to the mature polypeptide of SEQ ID NO: 14 of preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 14.

In one aspect, a polypeptide having cellobiohydrolase II activity comprises or consists of the amino acid sequence of SEQ ID NO: 14 or an allelic variant thereof; or a fragment thereof having cellobiohydrolase II activity. In another aspect, the polypeptide comprises or consists of the amino acid sequence of SEQ ID NO: 14. In another aspect, the polypeptide comprises or consists of the mature polypeptide of SEQ ID NO: 14. In another aspect, the polypeptide comprises or consists of amino acids 18 to 481 of SEQ ID NO: 14, or an allelic variant thereof; or a fragment thereof having cellobiohydrolase II activity. In another aspect, the polypeptide comprises or consists of amino acids 18 to 481 of SEQ ID NO: 14.

In another first aspect, the isolated polypeptides having cellobiohydrolase II activity comprise amino acid sequences having a degree of identity to the mature polypeptide of SEQ ID NO: 16 of preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 16.

In one aspect, a polypeptide having cellobiohydrolase II activity comprises or consists of the amino acid sequence of SEQ ID NO: 16 or an allelic variant thereof; or a fragment thereof having cellobiohydrolase II activity. In another aspect, the polypeptide comprises or consists of the amino acid sequence of SEQ ID NO: 16. In another aspect, the polypeptide comprises or consists of the mature polypeptide of SEQ ID NO: 16. In another aspect, the polypeptide comprises or consists of amino acids 17 to 447 of SEQ ID NO: 16, or an allelic variant thereof; or a fragment thereof having cellobiohydrolase II activity. In another aspect, the polypeptide comprises or consists of amino acids 17 to 447 of SEQ ID NO: 16.

In another first aspect, the isolated polypeptides having cellobiohydrolase II activity comprise amino acid sequences having a degree of identity to the mature polypeptide of SEQ ID NO: 18 of preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 18.

In one aspect, a polypeptide having cellobiohydrolase II activity comprises or consists of the amino acid sequence of SEQ ID NO: 18 or an allelic variant thereof; or a fragment thereof having cellobiohydrolase II activity. In another aspect, the polypeptide comprises or consists of the amino acid sequence of SEQ ID NO: 18. In another aspect, the polypeptide comprises or consists of the mature polypeptide of SEQ ID NO: 18. In another aspect, the polypeptide comprises or consists of amino acids 20 to 454 of SEQ ID NO: 18, or an allelic variant thereof; or a fragment thereof having cellobiohydrolase II activity. In another aspect, the polypeptide comprises or consists of amino acids 20 to 454 of SEQ ID NO: 18.

In another first aspect, the isolated polypeptides having cellobiohydrolase II activity comprise amino acid sequences having a degree of identity to the mature polypeptide of SEQ ID NO: 168 of preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 168.

In one aspect, a polypeptide having cellobiohydrolase II activity comprises or consists of the amino acid sequence of SEQ ID NO: 168 or an allelic variant thereof; or a fragment thereof having cellobiohydrolase II activity. In another aspect, the polypeptide comprises or consists of the amino acid sequence of SEQ ID NO: 168. In another aspect, the polypeptide comprises or consists of the mature polypeptide of SEQ ID NO: 168. In another aspect, the polypeptide comprises or consists of amino acids 19 to 469 of SEQ ID NO: 168, or an allelic variant thereof; or a fragment thereof having cellobiohydrolase II activity. In another aspect, the polypeptide comprises or consists of amino acids 19 to 469 of SEQ ID NO: 168.

In another first aspect, the isolated polypeptides having cellobiohydrolase II activity comprise amino acid sequences having a degree of identity to the mature polypeptide of SEQ ID NO: 170 of preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 170.

In one aspect, a polypeptide having cellobiohydrolase II activity comprises or consists of the amino acid sequence of SEQ ID NO: 170 or an allelic variant thereof; or a fragment thereof having cellobiohydrolase II activity. In another aspect, the polypeptide comprises or consists of the amino acid sequence of SEQ ID NO: 170. In another aspect, the polypeptide comprises or consists of the mature polypeptide of SEQ ID NO: 170. In another aspect, the polypeptide comprises or consists of amino acids 20 to 459 of SEQ ID NO: 170, or an allelic variant thereof; or a fragment thereof having cellobiohydrolase II activity. In another aspect, the polypeptide comprises or consists of amino acids 20 to 459 of SEQ ID NO: 170.

In another first aspect, the isolated polypeptides having cellobiohydrolase II activity comprise amino acid sequences having a degree of identity to the mature polypeptide of SEQ ID NO: 172 of preferably at least 80%, more preferably at least 85%, even more preferably at least 90%, most preferably at least 95%, and even most preferably at least 96%, at least 97%, at least 98%, or at least 99%, which have cellobiohydrolase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 172.

In one aspect, a polypeptide having cellobiohydrolase II activity comprises or consists of the amino acid sequence of SEQ ID NO: 172 or an allelic variant thereof; or a fragment thereof having cellobiohydrolase II activity. In another aspect, the polypeptide comprises or consists of the amino acid sequence of SEQ ID NO: 172. In another aspect, the polypeptide comprises or consists of the mature polypeptide of SEQ ID NO: 172. In another aspect, the polypeptide comprises or consists of amino acids 20 to 457 of SEQ ID NO: 172, or an allelic variant thereof; or a fragment thereof having cellobiohydrolase II activity. In another aspect, the polypeptide comprises or consists of amino acids 20 to 457 of SEQ ID NO: 172.

In another first aspect, the isolated polypeptides having endoglucanase I activity comprise amino acid sequences having a degree of identity to the mature polypeptide of SEQ ID NO: 20 of preferably at least 80%, more preferably at least 85%, even more preferably at least 90%, most preferably at least 95%, and even most preferably at least 96%, at least 97%, at least 98%, or at least 99%, which have endoglucanase I activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO:

In one aspect, a polypeptide having endoglucanase I activity comprises or consists of the amino acid sequence of SEQ ID NO: 20 or an allelic variant thereof; or a fragment thereof having endoglucanase I activity. In another aspect, the polypeptide comprises or consists of the amino acid sequence of SEQ ID NO: 20. In another aspect, the polypeptide comprises or consists of the mature polypeptide of SEQ ID NO: 20. In another aspect, the polypeptide comprises or consists of amino acids 22 to 471 of SEQ ID NO: 20, or an allelic variant thereof; or a fragment thereof having endoglucanase I activity. In another aspect, the polypeptide comprises or consists of amino acids 22 to 471 of SEQ ID NO: 20.

In another first aspect, the isolated polypeptides having endoglucanase II activity comprise amino acid sequences having a degree of identity to the mature polypeptide of SEQ ID NO: 22 of preferably at least 80%, more preferably at least 85%, even more preferably at least 90%, most preferably at least 95%, and even most preferably at least 96%, at least 97%, at least 98%, or at least 99%, which have endoglucanase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 22.

In one aspect, a polypeptide having endoglucanase II activity comprises or consists of the amino acid sequence of SEQ ID NO: 22 or an allelic variant thereof; or a fragment thereof having endoglucanase II activity. In another aspect, the polypeptide comprises or consists of the amino acid sequence of SEQ ID NO: 22. In another aspect, the polypeptide comprises or consists of the mature polypeptide of SEQ ID NO: 22. In another aspect, the polypeptide comprises or consists of amino acids 22 to 418 of SEQ ID NO: 22, or an allelic variant thereof; or a fragment thereof having endoglucanase II activity. In another aspect, the polypeptide comprises or consists of amino acids 22 to 418 of SEQ ID NO: 22.

In another first aspect, the isolated polypeptides having endoglucanase II activity comprise amino acid sequences having a degree of identity to the mature polypeptide of SEQ ID NO: 24 of preferably at least 80%, more preferably at least 85%, even more preferably at least 90%, most preferably at least 95%, and even most preferably at least 96%, at least 97%, at least 98%, or at least 99%, which have endoglucanase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 24.

In one aspect, a polypeptide having endoglucanase II activity comprises or consists of the amino acid sequence of SEQ ID NO: 24 or an allelic variant thereof; or a fragment thereof having endoglucanase II activity. In another aspect, the polypeptide comprises or consists of the amino acid sequence of SEQ ID NO: 24. In another aspect, the polypeptide comprises or consists of the mature polypeptide of SEQ ID NO: 24. In another aspect, the polypeptide comprises or consists of amino acids 17 to 389 of SEQ ID NO: 24, or an allelic variant thereof; or a fragment thereof having endoglucanase II activity. In another aspect, the polypeptide comprises or consists of amino acids 17 to 389 of SEQ ID NO: 24.

In another first aspect, the isolated polypeptides having endoglucanase II activity comprise amino acid sequences having a degree of identity to the mature polypeptide of SEQ ID NO: 26 of preferably at least 80%, more preferably at least 85%, even more preferably at least 90%, most preferably at least 95%, and even most preferably at least 96%, at least 97%, at least 98%, or at least 99%, which have endoglucanase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 26.

In another first aspect, the isolated polypeptides having endoglucanase II activity comprise amino acid sequences having a degree of identity to the mature polypeptide of SEQ ID NO: 174 of preferably at least 80%, more preferably at least 85%, even more preferably at least 90%, most preferably at least 95%, and even most preferably at least 96%, at least 97%, at least 98%, or at least 99%, which have endoglucanase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 174.

In one aspect, a polypeptide having endoglucanase II activity comprises or consists of the amino acid sequence of SEQ ID NO: 174 or an allelic variant thereof; or a fragment thereof having endoglucanase II activity. In another aspect, the polypeptide comprises or consists of the amino acid sequence of SEQ ID NO: 174. In another aspect, the polypeptide comprises or consists of the mature polypeptide of SEQ ID NO: 174. In another aspect, the polypeptide comprises or consists of amino acids 19 to 329 of SEQ ID NO: 174, or an allelic variant thereof; or a fragment thereof having endoglucanase II activity. In another aspect, the polypeptide comprises or consists of amino acids 19 to 329 of SEQ ID NO: 174.

In another first aspect, the isolated polypeptides having endoglucanase II activity comprise amino acid sequences having a degree of identity to the mature polypeptide of SEQ ID NO: 176 of preferably at least 80%, more preferably at least 85%, even more preferably at least 90%, most preferably at least 95%, and even most preferably at least 96%, at least 97%, at least 98%, or at least 99%, which have endoglucanase II activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 176.

In one aspect, a polypeptide having endoglucanase II activity comprises or consists of the amino acid sequence of SEQ ID NO: 176 or an allelic variant thereof; or a fragment thereof having endoglucanase II activity. In another aspect, the polypeptide comprises or consists of the amino acid sequence of SEQ ID NO: 176. In another aspect, the polypeptide comprises or consists of the mature polypeptide of SEQ ID NO: 176. In another aspect, the polypeptide comprises or consists of amino acids 17 to 412 of SEQ ID NO: 176, or an allelic variant thereof; or a fragment thereof having endoglucanase II activity. In another aspect, the polypeptide comprises or consists of amino acids 17 to 412 of SEQ ID NO: 176.

In one aspect, a polypeptide having endoglucanase II activity comprises or consists of the amino acid sequence of SEQ ID NO: 26 or an allelic variant thereof; or a fragment thereof having endoglucanase II activity. In another aspect, the polypeptide comprises or consists of the amino acid sequence of SEQ ID NO: 26. In another aspect, the polypeptide comprises or consists of the mature polypeptide of SEQ ID NO: 26. In another aspect, the polypeptide comprises or consists of amino acids 31 to 335 of SEQ ID NO: 26, or an allelic variant thereof; or a fragment thereof having endoglucanase II activity. In another aspect, the polypeptide comprises or consists of amino acids 31 to 335 of SEQ ID NO: 26.

In another first aspect, the isolated polypeptides having beta-glucosidase activity comprise amino acid sequences having a degree of identity to the mature polypeptide of SEQ ID NO: 28 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 28.

In one aspect, a polypeptide having beta-glucosidase activity comprises or consists of the amino acid sequence of SEQ ID NO: 28 or an allelic variant thereof; or a fragment thereof having beta-glucosidase activity. In another aspect, the polypeptide comprises or consists of the amino acid sequence of SEQ ID NO: 28. In another aspect, the polypeptide comprises or consists of the mature polypeptide of SEQ ID NO: 28. In another aspect, the polypeptide comprises or consists of amino acids 20 to 863 of SEQ ID NO: 28, or an allelic variant thereof; or a fragment thereof having beta-glucosidase activity. In another aspect, the polypeptide comprises or consists of amino acids 20 to 863 of SEQ ID NO: 28.

In another first aspect, the isolated polypeptides having beta-glucosidase activity comprise amino acid sequences having a degree of identity to the mature polypeptide of SEQ ID NO: 30 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 30.

In one aspect, a polypeptide having beta-glucosidase activity comprises or consists of the amino acid sequence of SEQ ID NO: 30 or an allelic variant thereof; or a fragment thereof having beta-glucosidase activity. In another aspect, the polypeptide comprises or consists of the amino acid sequence of SEQ ID NO: 30. In another aspect, the polypeptide comprises or consists of the mature polypeptide of SEQ ID NO: 30. In another aspect, the polypeptide comprises or consists of amino acids 37 to 878 of SEQ ID NO: 30, or an allelic variant thereof; or a fragment thereof having beta-glucosidase activity. In another aspect, the polypeptide comprises or consists of amino acids 37 to 878 of SEQ ID NO: 30.

In another first aspect, the isolated polypeptides having beta-glucosidase activity comprise amino acid sequences having a degree of identity to the mature polypeptide of SEQ ID NO: 32 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 32.

In one aspect, a polypeptide having beta-glucosidase activity comprises or consists of the amino acid sequence of SEQ ID NO: 32 or an allelic variant thereof; or a fragment thereof having beta-glucosidase activity. In another aspect, the polypeptide comprises or consists of the amino acid sequence of SEQ ID NO: 32. In another aspect, the polypeptide comprises or consists of the mature polypeptide of SEQ ID NO: 32. In another aspect, the polypeptide comprises or consists of amino acids 20 to 860 of SEQ ID NO: 32, or an allelic variant thereof; or a fragment thereof having beta-glucosidase activity. In another aspect, the polypeptide comprises or consists of amino acids 20 to 860 of SEQ ID NO: 32.

In another first aspect, the isolated polypeptides having beta-glucosidase activity comprise amino acid sequences having a degree of identity to the mature polypeptide of SEQ ID NO: 178 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 178.

In one aspect, a polypeptide having beta-glucosidase activity comprises or consists of the amino acid sequence of SEQ ID NO: 178 or an allelic variant thereof; or a fragment thereof having beta-glucosidase activity. In another aspect, the polypeptide comprises or consists of the amino acid sequence of SEQ ID NO: 178. In another aspect, the polypeptide comprises or consists of the mature polypeptide of SEQ ID NO: 178. In another aspect, the polypeptide comprises or consists of amino acids 20 to 680 of SEQ ID NO: 178, or an allelic variant thereof; or a fragment thereof having beta-glucosidase activity. In another aspect, the polypeptide comprises or consists of amino acids 20 to 680 of SEQ ID NO: 178.

In another first aspect, the isolated polypeptides having beta-glucosidase activity comprise amino acid sequences having a degree of identity to the mature polypeptide of SEQ ID NO: 180 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 180.

In one aspect, a polypeptide having beta-glucosidase activity comprises or consists of the amino acid sequence of SEQ ID NO: 180 or an allelic variant thereof; or a fragment thereof having beta-glucosidase activity. In another aspect, the polypeptide comprises or consists of the amino acid sequence of SEQ ID NO: 180. In another aspect, the polypeptide comprises or consists of the mature polypeptide of SEQ ID NO: 180. In another aspect, the polypeptide comprises or consists of amino acids 20 to 860 of SEQ ID NO: 180, or an allelic variant thereof; or a fragment thereof having beta-glucosidase activity. In another aspect, the polypeptide comprises or consists of amino acids 20 to 860 of SEQ ID NO: 180.

In another first aspect, the isolated polypeptides having beta-glucosidase activity comprise amino acid sequences having a degree of identity to the mature polypeptide of SEQ ID NO: 182 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 182.

In one aspect, a polypeptide having beta-glucosidase activity comprises or consists of the amino acid sequence of SEQ ID NO: 182 or an allelic variant thereof; or a fragment thereof having beta-glucosidase activity. In another aspect, the polypeptide comprises or consists of the amino acid sequence of SEQ ID NO: 182. In another aspect, the polypeptide comprises or consists of the mature polypeptide of SEQ ID NO: 182. In another aspect, the polypeptide comprises or consists of amino acids 19 to 860 of SEQ ID NO: 182, or an allelic variant thereof; or a fragment thereof having beta-glucosidase activity. In another aspect, the polypeptide comprises or consists of amino acids 19 to 860 of SEQ ID NO: 182.

In another first aspect, the isolated polypeptides having beta-glucosidase activity comprise amino acid sequences having a degree of identity to the mature polypeptide of SEQ ID NO: 184 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 184.

In one aspect, a polypeptide having beta-glucosidase activity comprises or consists of the amino acid sequence of SEQ ID NO: 184 or an allelic variant thereof; or a fragment thereof having beta-glucosidase activity. In another aspect, the polypeptide comprises or consists of the amino acid sequence of SEQ ID NO: 184. In another aspect, the polypeptide comprises or consists of the mature polypeptide of SEQ ID NO: 184. In another aspect, the polypeptide comprises or consists of amino acids 19 to 872 of SEQ ID NO: 184, or an allelic variant thereof; or a fragment thereof having beta-glucosidase activity. In another aspect, the polypeptide comprises or consists of amino acids 19 to 872 of SEQ ID NO: 184.

In another first aspect, the isolated polypeptides having beta-glucosidase activity comprise amino acid sequences having a degree of identity to the mature polypeptide of SEQ ID NO: 186 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 186.

In one aspect, a polypeptide having beta-glucosidase activity comprises or consists of the amino acid sequence of SEQ ID NO: 186 or an allelic variant thereof; or a fragment thereof having beta-glucosidase activity. In another aspect, the polypeptide comprises or consists of the amino acid sequence of SEQ ID NO: 186. In another aspect, the polypeptide comprises or consists of the mature polypeptide of SEQ ID NO: 186. In another aspect, the polypeptide comprises or consists of amino acids 22 to 883 of SEQ ID NO: 186, or an allelic variant thereof; or a fragment thereof having beta-glucosidase activity. In another aspect, the polypeptide comprises or consists of amino acids 22 to 883 of SEQ ID NO: 186.

In another first aspect, the isolated polypeptides having beta-glucosidase activity comprise amino acid sequences having a degree of identity to the mature polypeptide of SEQ ID NO: 188 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 188.

In one aspect, a polypeptide having beta-glucosidase activity comprises or consists of the amino acid sequence of SEQ ID NO: 188 or an allelic variant thereof; or a fragment thereof having beta-glucosidase activity. In another aspect, the polypeptide comprises or consists of the amino acid sequence of SEQ ID NO: 188. In another aspect, the polypeptide comprises or consists of the mature polypeptide of SEQ ID NO: 188. In another aspect, the polypeptide comprises or consists of amino acids 22 to 861 of SEQ ID NO: 188, or an allelic variant thereof; or a fragment thereof having beta-glucosidase activity. In another aspect, the polypeptide comprises or consists of amino acids 22 to 861 of SEQ ID NO: 188.

In another first aspect, the isolated polypeptides having beta-glucosidase activity comprise amino acid sequences having a degree of identity to the mature polypeptide of SEQ ID NO: 190 of preferably at least 80%, more preferably at least 85%, even more preferably at least 90%, most preferably at least 95%, and even most preferably at least 96%, at least 97%, at least 98%, or at least 99%, which have beta-glucosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 190.

In one aspect, a polypeptide having beta-glucosidase activity comprises or consists of the amino acid sequence of SEQ ID NO: 190 or an allelic variant thereof; or a fragment thereof having beta-glucosidase activity. In another aspect, the polypeptide comprises or consists of the amino acid sequence of SEQ ID NO: 190. In another aspect, the polypeptide comprises or consists of the mature polypeptide of SEQ ID NO: 190. In another aspect, the polypeptide comprises or consists of amino acids 22 to 861 of SEQ ID NO: 190, or an allelic variant thereof; or a fragment thereof having beta-glucosidase activity. In another aspect, the polypeptide comprises or consists of amino acids 22 to 861 of SEQ ID NO: 190.

In another first aspect, the isolated GH61 polypeptides having cellulolytic enhancing activity comprise amino acid sequences having a degree of identity to the mature polypeptide of SEQ ID NO: 34 of preferably at least 80%, more preferably at least 85%, even more preferably at least 90%, most preferably at least 95%, and even most preferably at least 96%, at least 97%, at least 98%, or at least 99%, which have cellulolytic enhancing activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 34.

In one aspect, a polypeptide having cellulolytic enhancing activity comprises or consists of the amino acid sequence of SEQ ID NO: 34 or an allelic variant thereof; or a fragment thereof having cellulolytic enhancing activity. In another aspect, the polypeptide comprises or consists of the amino acid sequence of SEQ ID NO: 34. In another aspect, the polypeptide comprises or consists of the mature polypeptide of SEQ ID NO: 34. In another aspect, the polypeptide comprises or consists of amino acids 23 to 250 of SEQ ID NO: 34, or an allelic variant thereof; or a fragment thereof having cellulolytic enhancing activity. In another aspect, the polypeptide comprises or consists of amino acids 23 to 250 of SEQ ID NO: 34.

In another first aspect, the isolated GH61 polypeptides having cellulolytic enhancing activity comprise amino acid sequences having a degree of identity to the mature polypeptide of SEQ ID NO: 36 of preferably at least 80%, more preferably at least 85%, even more preferably at least 90%, most preferably at least 95%, and even most preferably at least 96%, at least 97%, at least 98%, or at least 99%, which have cellulolytic enhancing activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 36.

In one aspect, a polypeptide having cellulolytic enhancing activity comprises or consists of the amino acid sequence of SEQ ID NO: 36 or an allelic variant thereof; or a fragment thereof having cellulolytic enhancing activity. In another aspect, the polypeptide comprises or consists of the amino acid sequence of SEQ ID NO: 36. In another aspect, the polypeptide comprises or consists of the mature polypeptide of SEQ ID NO: 36. In another aspect, the polypeptide comprises or consists of amino acids 20 to 258 of SEQ ID NO: 36, or an allelic variant thereof; or a fragment thereof having cellulolytic enhancing activity. In another aspect, the polypeptide comprises or consists of amino acids 20 to 258 of SEQ ID NO: 36.

In another first aspect, the isolated GH61 polypeptides having cellulolytic enhancing activity comprise amino acid sequences having a degree of identity to the mature polypeptide of SEQ ID NO: 38 of preferably at least 80%, more preferably at least 85%, even more preferably at least 90%, most preferably at least 95%, and even most preferably at least 96%, at least 97%, at least 98%, or at least 99%, which have cellulolytic enhancing activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 38.

In one aspect, a polypeptide having cellulolytic enhancing activity comprises or consists of the amino acid sequence of SEQ ID NO: 38 or an allelic variant thereof; or a fragment thereof having cellulolytic enhancing activity. In another aspect, the polypeptide comprises or consists of the amino acid sequence of SEQ ID NO: 38. In another aspect, the polypeptide comprises or consists of the mature polypeptide of SEQ ID NO: 38. In another aspect, the polypeptide comprises or consists of amino acids 22 to 250 of SEQ ID NO: 38, or an allelic variant thereof; or a fragment thereof having cellulolytic enhancing activity. In another aspect, the polypeptide comprises or consists of amino acids 22 to 250 of SEQ ID NO: 38.

In another first aspect, the isolated GH61 polypeptides having cellulolytic enhancing activity comprise amino acid sequences having a degree of identity to the mature polypeptide of SEQ ID NO: 40 of preferably at least 80%, more preferably at least 85%, even more preferably at least 90%, most preferably at least 95%, and even most preferably at least 96%, at least 97%, at least 98%, or at least 99%, which have cellulolytic enhancing activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO:

In one aspect, a polypeptide having cellulolytic enhancing activity comprises or consists of the amino acid sequence of SEQ ID NO: 40 or an allelic variant thereof; or a fragment thereof having cellulolytic enhancing activity. In another aspect, the polypeptide comprises or consists of the amino acid sequence of SEQ ID NO: 40. In another aspect, the polypeptide comprises or consists of the mature polypeptide of SEQ ID NO: 40. In another aspect, the polypeptide comprises or consists of amino acids 22 to 322 of SEQ ID NO: 40, or an allelic variant thereof; or a fragment thereof having cellulolytic enhancing activity. In another aspect, the polypeptide comprises or consists of amino acids 22 to 322 of SEQ ID NO: 40.

In another first aspect, the isolated GH61 polypeptides having cellulolytic enhancing activity comprise amino acid sequences having a degree of identity to the mature polypeptide of SEQ ID NO: 42 of preferably at least 80%, more preferably at least 85%, even more preferably at least 90%, most preferably at least 95%, and even most preferably at least 96%, at least 97%, at least 98%, or at least 99%, which have cellulolytic enhancing activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 42.

In one aspect, a polypeptide having cellulolytic enhancing activity comprises or consists of the amino acid sequence of SEQ ID NO: 42 or an allelic variant thereof; or a fragment thereof having cellulolytic enhancing activity. In another aspect, the polypeptide comprises or consists of the amino acid sequence of SEQ ID NO: 42. In another aspect, the polypeptide comprises or consists of the mature polypeptide of SEQ ID NO: 42. In another aspect, the polypeptide comprises or consists of amino acids 26 to 253 of SEQ ID NO: 42, or an allelic variant thereof; or a fragment thereof having cellulolytic enhancing activity. In another aspect, the polypeptide comprises or consists of amino acids 26 to 253 of SEQ ID NO: 42.

In another first aspect, the isolated GH61 polypeptides having cellulolytic enhancing activity comprise amino acid sequences having a degree of identity to the mature polypeptide of SEQ ID NO: 44 of preferably at least 80%, more preferably at least 85%, even more preferably at least 90%, most preferably at least 95%, and even most preferably at least 96%, at least 97%, at least 98%, or at least 99%, which have cellulolytic enhancing activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 44.

In one aspect, a polypeptide having cellulolytic enhancing activity comprises or consists of the amino acid sequence of SEQ ID NO: 44 or an allelic variant thereof; or a fragment thereof having cellulolytic enhancing activity. In another aspect, the polypeptide comprises or consists of the amino acid sequence of SEQ ID NO: 44. In another aspect, the polypeptide comprises or consists of the mature polypeptide of SEQ ID NO: 44. In another aspect, the polypeptide comprises or consists of amino acids 22 to 368 of SEQ ID NO: 44, or an allelic variant thereof; or a fragment thereof having cellulolytic enhancing activity. In another aspect, the polypeptide comprises or consists of amino acids 22 to 368 of SEQ ID NO: 44.

In another first aspect, the isolated GH61 polypeptides having cellulolytic enhancing activity comprise amino acid sequences having a degree of identity to the mature polypeptide of SEQ ID NO: 192 of preferably at least 80%, more preferably at least 85%, even more preferably at least 90%, most preferably at least 95%, and even most preferably at least 96%, at least 97%, at least 98%, or at least 99%, which have cellulolytic enhancing activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 192.

In one aspect, a polypeptide having cellulolytic enhancing activity comprises or consists of the amino acid sequence of SEQ ID NO: 192 or an allelic variant thereof; or a fragment thereof having cellulolytic enhancing activity. In another aspect, the polypeptide comprises or consists of the amino acid sequence of SEQ ID NO: 192. In another aspect, the polypeptide comprises or consists of the mature polypeptide of SEQ ID NO: 192. In another aspect, the polypeptide comprises or consists of amino acids 23 to 251 of SEQ ID NO: 186, or an allelic variant thereof; or a fragment thereof having cellulolytic enhancing activity. In another aspect, the polypeptide comprises or consists of amino acids 23 to 251 of SEQ ID NO: 186.

In another first aspect, the isolated GH10 polypeptides having xylanase activity comprise amino acid sequences having a degree of identity to the mature polypeptide of SEQ ID NO: 46, of at preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 46.

In one aspect, a GH10 polypeptide having xylanase activity comprises or consists of the amino acid sequence of SEQ ID NO: 46 or an allelic variant thereof; or a fragment thereof that has xylanase activity. In another aspect, the polypeptide comprises or consists of the amino acid sequence of SEQ ID NO: 46. In another aspect, the polypeptide comprises or consists of the mature polypeptide of SEQ ID NO: 46. In another aspect, the polypeptide comprises or consists of amino acids 23 to 406 of SEQ ID NO: 46, or an allelic variant thereof; or a fragment thereof that has xylanase activity. In another aspect, the polypeptide comprises or consists of amino acids 23 to 406 of SEQ ID NO: 46.

In another first aspect, the isolated GH10 polypeptides having xylanase activity comprise amino acid sequences having a degree of identity to the mature polypeptide of SEQ ID NO: 48, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 48.

In one aspect, a GH10 polypeptide having xylanase activity comprises or consists of the amino acid sequence of SEQ ID NO: 48 or an allelic variant thereof; or a fragment thereof that has xylanase activity. In another aspect, the polypeptide comprises or consists of the amino acid sequence of SEQ ID NO: 48. In another aspect, the polypeptide comprises or consists of the mature polypeptide of SEQ ID NO: 48. In another aspect, the polypeptide comprises or consists of amino acids 20 to 397 of SEQ ID NO:

48, or an allelic variant thereof; or a fragment thereof that has xylanase activity. In another aspect, the polypeptide comprises or consists of amino acids 20 to 397 of SEQ ID NO: 48.

In another first aspect, the isolated GH10 polypeptides having xylanase activity comprise amino acid sequences having a degree of identity to the mature polypeptide of SEQ ID NO: 50, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 50.

In one aspect, a GH10 polypeptide having xylanase activity comprises or consists of the amino acid sequence of SEQ ID NO: 50 or an allelic variant thereof; or a fragment thereof that has xylanase activity. In another aspect, the polypeptide comprises or consists of the amino acid sequence of SEQ ID NO: 50. In another aspect, the polypeptide comprises or consists of the mature polypeptide of SEQ ID NO: 50. In another aspect, the polypeptide comprises or consists of amino acids 20 to 398 of SEQ ID NO: 50, or an allelic variant thereof; or a fragment thereof that has xylanase activity. In another aspect, the polypeptide comprises or consists of amino acids 20 to 398 of SEQ ID NO: 50.

In another first aspect, the isolated GH10 polypeptides having xylanase activity comprise amino acid sequences having a degree of identity to the mature polypeptide of SEQ ID NO: 52, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 52.

In one aspect, a GH10 polypeptide having xylanase activity comprises or consists of the amino acid sequence of SEQ ID NO: 50 or an allelic variant thereof; or a fragment thereof that has xylanase activity. In another aspect, the polypeptide comprises or consists of the amino acid sequence of SEQ ID NO: 52. In another aspect, the polypeptide comprises or consists of the mature polypeptide of SEQ ID NO: 52. In another aspect, the polypeptide comprises or consists of amino acids 20 to 407 of SEQ ID NO: 52, or an allelic variant thereof; or a fragment thereof that has xylanase activity. In another aspect, the polypeptide comprises or consists of amino acids 20 to 407 of SEQ ID NO: 52.

In another first aspect, the isolated GH10 polypeptides having xylanase activity comprise amino acid sequences having a degree of identity to the mature polypeptide of SEQ ID NO: 54, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 54.

In one aspect, a GH10 polypeptide having xylanase activity comprises or consists of the amino acid sequence of SEQ ID NO: 50 or an allelic variant thereof; or a fragment thereof that has xylanase activity. In another aspect, the polypeptide comprises or consists of the amino acid sequence of SEQ ID NO: 54. In another aspect, the polypeptide comprises or consists of the mature polypeptide of SEQ ID NO: 54. In another aspect, the polypeptide comprises or consists of amino acids 20 to 395 of SEQ ID NO: 54, or an allelic variant thereof; or a fragment thereof that has xylanase activity. In another aspect, the polypeptide comprises or consists of amino acids 20 to 395 of SEQ ID NO: 54.

In another first aspect, the isolated GH10 polypeptides having xylanase activity comprise amino acid sequences having a degree of identity to the mature polypeptide of SEQ ID NO: 194, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 194.

A GH10 polypeptide having xylanase activity comprises or consists of the amino acid sequence of SEQ ID NO: 194 or an allelic variant thereof; or a fragment thereof that has xylanase activity. In another aspect, the polypeptide comprises or consists of the amino acid sequence of SEQ ID NO: 194. In another aspect, the polypeptide comprises or consists of the mature polypeptide of SEQ ID NO: 194. In another aspect, the polypeptide comprises or consists of amino acids 24 to 403 of SEQ ID NO: 194, or an allelic variant thereof; or a fragment thereof that has xylanase activity. In another aspect, the polypeptide comprises or consists of amino acids 24 to 403 of SEQ ID NO: 194.

In another first aspect, the isolated GH10 polypeptides having xylanase activity comprise amino acid sequences having a degree of identity to the mature polypeptide of SEQ ID NO: 196, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 196.

A GH10 polypeptide having xylanase activity comprises or consists of the amino acid sequence of SEQ ID NO: 194 or an allelic variant thereof; or a fragment thereof that has xylanase activity. In another aspect, the polypeptide comprises or consists of the amino acid sequence of SEQ ID NO: 196. In another aspect, the polypeptide comprises or consists of the mature polypeptide of SEQ ID NO: 196. In another aspect, the polypeptide comprises or consists of amino acids 24 to 403 of SEQ ID NO: 196, or an allelic variant thereof; or a fragment thereof that has xylanase activity. In another aspect, the polypeptide comprises or consists of amino acids 24 to 403 of SEQ ID NO: 196.

In another first aspect, the isolated GH10 polypeptides having xylanase activity comprise amino acid sequences having a degree of identity to the mature polypeptide of SEQ ID NO: 198, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 198.

A GH10 polypeptide having xylanase activity comprises or consists of the amino acid sequence of SEQ ID NO: 194 or an allelic variant thereof; or a fragment thereof that has xylanase activity. In another aspect, the polypeptide comprises or consists of the amino acid sequence of SEQ ID NO: 198. In another aspect, the polypeptide comprises or consists of the mature polypeptide of SEQ ID NO: 198. In another aspect, the polypeptide comprises or consists of amino acids 20 to 396 of SEQ ID NO: 198, or an allelic variant thereof; or a fragment thereof that has xylanase activity. In another aspect, the polypeptide comprises or consists of amino acids 20 to 396 of SEQ ID NO: 198.

In another first aspect, the isolated GH11 polypeptides having xylanase activity comprise amino acid sequences having a degree of identity to the mature polypeptide of SEQ ID NO: 56, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 56.

In one aspect, a GH11 polypeptide having xylanase activity comprises or consists of the amino acid sequence of SEQ ID NO: 56 or an allelic variant thereof; or a fragment thereof that has xylanase activity. In another aspect, the polypeptide comprises or consists of the amino acid sequence of SEQ ID NO: 56. In another aspect, the polypeptide comprises or consists of the mature polypeptide of SEQ ID NO: 56. In another aspect, the polypeptide comprises or consists of amino acids 43 to 338 of SEQ ID NO: 56, or an allelic variant thereof; or a fragment thereof that has xylanase activity. In another aspect, the polypeptide comprises or consists of amino acids 43 to 338 of SEQ ID NO: 56. In another aspect, the polypeptide comprises or consists of amino acids 43 to 338 of SEQ ID NO: 56. In another aspect, the polypeptide consists of the amino acid sequence of SEQ ID NO: 56 or an allelic variant thereof; or a fragment thereof that has xylanase activity.

In another first aspect, the isolated GH11 polypeptides having xylanase activity comprise amino acid sequences having a degree of identity to the mature polypeptide of SEQ ID NO: 200 or SEQ ID NO: 305, of preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 200 or SEQ ID NO: 305.

A GH11 polypeptide having xylanase activity comprises or consists of the amino acid sequence of SEQ ID NO: 200, or an allelic variant thereof; or a fragment thereof that has xylanase activity, or SEQ ID NO: 305 or a fragment thereof that has xylanase activity. In another aspect, the polypeptide comprises or consists of the amino acid sequence of SEQ ID NO: 200 or SEQ ID NO: 305. In another aspect, the polypeptide comprises or consists of the mature polypeptide of SEQ ID NO: 200 or SEQ ID NO: 305. In another aspect, the polypeptide comprises or consists of amino acids 25 to 360 of SEQ ID NO: 200, or an allelic variant thereof; or a fragment thereof that has xylanase activity, or amino acids 29 to 231 of SEQ ID NO: 305 or a fragment thereof that has xylanase activity. In another aspect, the polypeptide comprises or consists of amino acids 25 to 360 of SEQ ID NO: 200 or amino acids 29 to 231 of SEQ ID NO: 305. In another aspect, the polypeptide comprises or consists of amino acids 25 to 360 of SEQ ID NO: 200 or amino acids 29 to 231 of SEQ ID NO: 305.

In another first aspect, the isolated polypeptides having beta-xylosidase activity comprise amino acid sequences having a degree of identity to the mature polypeptide of SEQ ID NO: 58, of preferably at least 80%, more preferably at least 85%, even more preferably at least 90%, most preferably at least 95%, and even most preferably at least 96%, at least 97%, at least 98%, or at least 99%, which have beta-xylosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 58.

In one aspect, a polypeptide having beta-xylosidase activity comprises or consists of the amino acid sequence of SEQ ID NO: 58 or an allelic variant thereof; or a fragment thereof that has beta-xylosidase activity. In another aspect, the polypeptide comprises or consists of the amino acid sequence of SEQ ID NO: 58. In another aspect, the polypeptide comprises or consists of the mature polypeptide of SEQ ID NO: 58. In another aspect, the polypeptide comprises or consists of amino acids 21 to 797 of SEQ ID NO: 58, or an allelic variant thereof; or a fragment thereof that has beta-xylosidase activity. In another aspect, the polypeptide comprises or consists of amino acids 21 to 797 of SEQ ID NO: 58.

In another first aspect, the isolated polypeptides having beta-xylosidase activity comprise amino acid sequences having a degree of identity to the mature polypeptide of SEQ ID NO: 60, of preferably at least 80%, more preferably at least 85%, even more preferably at least 90%, most preferably at least 95%, and even most preferably at least 96%, at least 97%, at least 98%, or at least 99%, which have beta-xylosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 60.

In one aspect, a polypeptide having beta-xylosidase activity comprises or consists of the amino acid sequence of SEQ ID NO: 60 or an allelic variant thereof; or a fragment thereof that has beta-xylosidase activity. In another aspect, the polypeptide comprises or consists of the amino acid sequence of SEQ ID NO: 60. In another aspect, the polypeptide comprises or consists of the mature polypeptide of SEQ ID NO: 60. In another aspect, the polypeptide comprises or consists of amino acids 22 to 795 of SEQ ID NO: 60, or an allelic variant thereof; or a fragment thereof that has beta-xylosidase activity. In another aspect, the polypeptide comprises or consists of amino acids 22 to 795 of SEQ ID NO: 60.

In another first aspect, the isolated polypeptides having beta-xylosidase activity comprise amino acid sequences having a degree of identity to the mature polypeptide of SEQ ID NO: 202, of preferably at least 80%, more preferably at least 85%, even more preferably at least 90%, most preferably at least 95%, and even most preferably at least 96%, at least 97%, at least 98%, or at least 99%, which have beta-xylosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 202.

In one aspect, a polypeptide having beta-xylosidase activity comprises or consists of the amino acid sequence of SEQ ID NO: 202 or an allelic variant thereof; or a fragment thereof that has beta-xylosidase activity. In another aspect, the polypeptide comprises or consists of the amino acid sequence of SEQ ID NO: 202. In another aspect, the polypeptide comprises or consists of the mature polypeptide of SEQ ID NO: 202. In another aspect, the polypeptide comprises or consists of amino acids 18 to 803 of SEQ ID NO: 202, or an allelic variant thereof; or a fragment thereof that has beta-xylosidase activity. In another aspect, the polypeptide comprises or consists of amino acids 18 to 803 of SEQ ID NO: 202.

In one aspect, a polypeptide having beta-xylosidase activity comprises or consists of the amino acid sequence of SEQ ID NO: 204 or an allelic variant thereof; or a fragment thereof that has beta-xylosidase activity. In another aspect, the polypeptide comprises or consists of the amino acid sequence of SEQ ID NO: 204. In another aspect, the polypeptide comprises or consists of the mature polypeptide of SEQ ID NO: 204. In another aspect, the polypeptide comprises or consists of amino acids 18 to 817 of SEQ ID NO: 204, or an allelic variant thereof; or a fragment thereof that has beta-xylosidase activity. In another aspect, the polypeptide comprises or consists of amino acids 18 to 817 of SEQ ID NO: 204.

In another first aspect, the isolated polypeptides having beta-xylosidase activity comprise amino acid sequences having a degree of identity to the mature polypeptide of SEQ ID NO: 206, of preferably at least 80%, more preferably at least 85%, even more preferably at least 90%, most preferably at least 95%, and even most preferably at least 96%, at least 97%, at least 98%, or at least 99%, which have beta-xylosidase activity (hereinafter "homologous polypeptides"). In another aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 206.

In one aspect, a polypeptide having beta-xylosidase activity comprises or consists of the amino acid sequence of SEQ ID NO: 206 or an allelic variant thereof; or a fragment thereof that has beta-xylosidase activity. In another aspect, the polypeptide comprises or consists of the amino acid sequence of SEQ ID NO: 206. In another aspect, the polypeptide comprises or consists of the mature polypeptide of SEQ ID NO: 206. In another aspect, the polypeptide comprises or consists of amino acids 21 to 792 of SEQ ID NO: 206, or an allelic variant thereof; or a fragment thereof that has beta-xylosidase activity. In another aspect, the polypeptide comprises or consists of amino acids 21 to 792 of SEQ ID NO: 206.

In a second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 1, (ii) the genomic DNA sequence of the mature polypeptide coding sequence of SEQ ID NO: 1, or (iii) a full-length complementary strand of (i) or (ii) (J. Sambrook, E. F. Fritsch, and T. Maniatis, 1989, supra).

In another second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 3, (ii) the genomic DNA sequence of the mature polypeptide coding sequence of SEQ ID NO: 3, or (iii) a full-length complementary strand of (i) or (ii).

In another second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 5, (ii) the cDNA sequence of the mature polypeptide coding sequence of SEQ ID NO: 5, or (iii) a full-length complementary strand of (i) or (ii).

In another second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 7, (ii) the genomic DNA sequence of the mature polypeptide coding sequence of SEQ ID NO: 7, or (iii) a full-length complementary strand of (i) or (ii).

In another second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 157, (ii) the cDNA sequence of the mature polypeptide coding sequence of SEQ ID NO: 157, or (iii) a full-length complementary strand of (i) or (ii).

In another second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 159, (ii) the cDNA sequence of the mature polypeptide coding sequence of SEQ ID NO: 159, or (iii) a full-length complementary strand of (i) or (ii).

In another second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 161, (ii) the cDNA sequence of the mature polypeptide coding sequence of SEQ ID NO: 161, or (iii) a full-length complementary strand of (i) or (ii).

In another second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 163, (ii) the cDNA sequence of the mature polypeptide coding sequence of SEQ ID NO: 163, or (iii) a full-length complementary strand of (i) or (ii).

In another second aspect, the isolated polypeptides having cellobiohydrolase I activity are encoded by polynucleotides that hybridize under preferably medium-high stringency conditions, more preferably high stringency conditions, and most preferably very high stringency conditions with (i) the mature polypeptide coding sequence of SEQ ID NO: 165, (ii) the cDNA sequence of the mature polypeptide coding sequence of SEQ ID NO: 165, or (iii) a full-length complementary strand of (i) or (ii).

In another second aspect, the isolated polypeptides having cellobiohydrolase II activity are encoded by polynucleotides that hybridize under preferably medium-high stringency conditions, more preferably high stringency conditions, and most preferably very high stringency conditions with (i) the mature polypeptide coding sequence of SEQ ID NO: 9, (ii) the cDNA sequence of the mature polypeptide coding sequence of SEQ ID NO: 9, or (iii) a full-length complementary strand of (i) or (ii).

In another second aspect, the isolated polypeptides having cellobiohydrolase II activity are encoded by polynucleotides that hybridize under preferably medium-high stringency conditions, more preferably high stringency conditions, and most preferably very high stringency conditions with (i) the mature polypeptide coding sequence of SEQ ID NO: 11, (ii) the cDNA sequence of the mature polypeptide coding sequence of SEQ ID NO: 11, or (iii) a full-length complementary strand of (i) or (ii).

In another second aspect, the isolated polypeptides having cellobiohydrolase II activity are encoded by polynucleotides that hybridize under preferably medium-high stringency conditions, more preferably high stringency conditions, and most preferably very high stringency conditions with (i) the mature polypeptide coding sequence of SEQ ID NO: 13, (ii) the genomic DNA sequence of the mature polypeptide coding sequence of SEQ ID NO: 13, or (iii) a full-length complementary strand of (i) or (ii).

In another second aspect, the isolated polypeptides having cellobiohydrolase II activity are encoded by polynucleotides that hybridize under preferably medium-high stringency conditions, more preferably high stringency conditions, and most preferably very high stringency conditions with (i) the mature polypeptide coding sequence of SEQ ID NO: 15, (ii) the genomic DNA sequence of the mature polypeptide coding sequence of SEQ ID NO: 15, or (iii) a full-length complementary strand of (i) or (ii).

In another second aspect, the isolated polypeptides having cellobiohydrolase II activity are encoded by polynucleotides that hybridize under preferably medium-high stringency conditions, more preferably high stringency conditions, and most preferably very high stringency conditions with (i) the mature polypeptide coding sequence of SEQ ID NO: 17, (ii) the cDNA sequence of the mature polypeptide coding sequence of SEQ ID NO: 17, or (iii) a full-length complementary strand of (i) or (ii).

In another second aspect, the isolated polypeptides having cellobiohydrolase II activity are encoded by polynucleotides that hybridize under preferably medium-high stringency conditions, more preferably high stringency conditions, and most preferably very high stringency conditions with (i) the mature polypeptide coding sequence of SEQ ID NO: 167, (ii) the cDNA sequence of the mature polypeptide coding sequence of SEQ ID NO: 167, or (iii) a full-length complementary strand of (i) or (ii).

In another second aspect, the isolated polypeptides having cellobiohydrolase II activity are encoded by polynucleotides that hybridize under preferably medium-high stringency conditions, more preferably high stringency conditions, and most preferably very high stringency conditions with (i) the mature polypeptide coding sequence of SEQ ID NO: 169, (ii) the cDNA sequence of the mature polypeptide coding sequence of SEQ ID NO: 169, or (iii) a full-length complementary strand of (i) or (ii).

In another second aspect, the isolated polypeptides having cellobiohydrolase II activity are encoded by polynucleotides that hybridize under preferably medium-high stringency conditions, more preferably high stringency conditions, and most preferably very high stringency conditions with (i) the mature polypeptide coding sequence of SEQ ID NO: 171, (ii) the cDNA sequence of the mature polypeptide coding sequence of SEQ ID NO: 171, or (iii) a full-length complementary strand of (i) or (ii).

In another second aspect, the isolated polypeptides having endoglucanase I activity are encoded by polynucleotides that hybridize under preferably medium-high stringency conditions, more preferably high stringency conditions, and most preferably very high stringency conditions with (i) the mature polypeptide coding sequence of SEQ ID NO: 19, (ii) the cDNA sequence of the mature polypeptide coding sequence of SEQ ID NO: 19, or (iii) a full-length complementary strand of (i) or (ii).

In another second aspect, the isolated polypeptides having endoglucanase II activity are encoded by polynucleotides that hybridize under preferably medium-high stringency conditions, more preferably high stringency conditions, and most preferably very high stringency conditions with (i) the mature polypeptide coding sequence of SEQ ID NO: 21, (ii) the genomic DNA sequence of the mature polypeptide coding sequence of SEQ ID NO: 21, or (iii) a full-length complementary strand of (i) or (ii).

In another second aspect, the isolated polypeptides having endoglucanase II activity are encoded by polynucleotides that hybridize under preferably medium-high stringency conditions, more preferably high stringency conditions, and most preferably very high stringency conditions with (i) the mature polypeptide coding sequence of SEQ ID NO: 23, (ii) the cDNA sequence of the mature polypeptide coding sequence of SEQ ID NO: 23, or (iii) a full-length complementary strand of (i) or (ii).

In another second aspect, the isolated polypeptides having endoglucanase II activity are encoded by polynucleotides that hybridize under preferably medium-high stringency conditions, more preferably high stringency conditions, and most preferably very high stringency conditions with (i) the mature polypeptide coding sequence of SEQ ID NO: 25, (ii) the genomic DNA sequence of the mature polypeptide coding sequence of SEQ ID NO: 25, or (iii) a full-length complementary strand of (i) or (ii).

In another second aspect, the isolated polypeptides having endoglucanase II activity are encoded by polynucleotides that hybridize under preferably medium-high stringency conditions, more preferably high stringency conditions, and most preferably very high stringency conditions with (i) the mature polypeptide coding sequence of SEQ ID NO: 173, (ii) the cDNA sequence of the mature polypeptide coding sequence of SEQ ID NO: 173, or (iii) a full-length complementary strand of (i) or (ii).

In another second aspect, the isolated polypeptides having endoglucanase II activity are encoded by polynucleotides that hybridize under preferably medium-high stringency conditions, more preferably high stringency conditions, and most preferably very high stringency conditions with (i) the mature polypeptide coding sequence of SEQ ID NO: 175, (ii) the cDNA sequence of the mature polypeptide coding sequence of SEQ ID NO: 175, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 27, (ii) the cDNA sequence of the mature polypeptide coding sequence of SEQ ID NO: 27, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 29, (ii) the cDNA sequence of the mature polypeptide coding sequence of SEQ ID NO: 29, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 31, (ii) the cDNA sequence of the mature polypeptide coding sequence of SEQ ID NO: 31, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 177, (ii) the cDNA sequence of the mature polypeptide coding sequence of SEQ ID NO: 177, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 179, (ii) the cDNA sequence of the mature polypeptide coding sequence of SEQ ID NO: 179, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 181, (ii) the cDNA sequence of the mature polypeptide coding sequence of SEQ ID NO: 181, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 183, (ii) the cDNA sequence of the mature polypeptide coding sequence of SEQ ID NO: 183, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 185, (ii) the cDNA sequence of the mature polypeptide coding sequence of SEQ ID NO: 185, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 187, (ii) the cDNA sequence of the mature polypeptide coding sequence of SEQ ID NO: 187, or (iii) a full-length complementary strand of (i) or (ii).

In another second aspect, the isolated polypeptides having beta-glucosidase activity are encoded by polynucleotides that hybridize under preferably medium-high stringency conditions, more preferably high stringency conditions, and most preferably very high stringency conditions with (i) the mature polypeptide coding sequence of SEQ ID NO: 189, (ii) the cDNA sequence of the mature polypeptide coding sequence of SEQ ID NO: 189, or (iii) a full-length complementary strand of (i) or (ii).

In another second aspect, the isolated GH61 polypeptides having cellulolytic enhancing activity are encoded by polynucleotides that hybridize under preferably medium-high stringency conditions, more preferably high stringency conditions, and most preferably very high stringency conditions with (i) the mature polypeptide coding sequence of SEQ ID NO: 33, (ii) the cDNA sequence of the mature polypeptide coding sequence of SEQ ID NO: 33, or (iii) a full-length complementary strand of (i) or (ii).

In another second aspect, the isolated GH61 polypeptides having cellulolytic enhancing activity are encoded by polynucleotides that hybridize under preferably medium-high stringency conditions, more preferably high stringency conditions, and most preferably very high stringency conditions with (i) the mature polypeptide coding sequence of SEQ ID NO: 35, (ii) the genomic DNA sequence of the mature polypeptide coding sequence of SEQ ID NO: 35, or (iii) a full-length complementary strand of (i) or (ii).

In another second aspect, the isolated GH61 polypeptides having cellulolytic enhancing activity are encoded by polynucleotides that hybridize under preferably medium-high stringency conditions, more preferably high stringency conditions, and most preferably very high stringency conditions with (i) the mature polypeptide coding sequence of SEQ ID NO: 37, (ii) the cDNA sequence of the mature polypeptide coding sequence of SEQ ID NO: 37, or (iii) a full-length complementary strand of (i) or (ii).

In another second aspect, the isolated GH61 polypeptides having cellulolytic enhancing activity are encoded by polynucleotides that hybridize under preferably medium-high stringency conditions, more preferably high stringency conditions, and most preferably very high stringency conditions with (i) the mature polypeptide coding sequence of SEQ ID NO: 39, (ii) the cDNA sequence of the mature polypeptide coding sequence of SEQ ID NO: 39, or (iii) a full-length complementary strand of (i) or (ii).

In another second aspect, the isolated GH61 polypeptides having cellulolytic enhancing activity are encoded by polynucleotides that hybridize under preferably medium-high stringency conditions, more preferably high stringency conditions, and most preferably very high stringency conditions with (i) the mature polypeptide coding sequence of SEQ ID NO: 41, (ii) the cDNA sequence of the mature polypeptide coding sequence of SEQ ID NO: 41, or (iii) a full-length complementary strand of (i) or (ii).

In another second aspect, the isolated GH61 polypeptides having cellulolytic enhancing activity are encoded by polynucleotides that hybridize under preferably medium-high stringency conditions, more preferably high stringency conditions, and most preferably very high stringency conditions with (i) the mature polypeptide coding sequence of SEQ ID NO: 43, (ii) the cDNA sequence of the mature polypeptide coding sequence of SEQ ID NO: 43, or (iii) a full-length complementary strand of (i) or (ii).

In another second aspect, the isolated GH10 polypeptides having xylanase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 191, (ii) the cDNA sequence of the mature polypeptide coding sequence of SEQ ID NO: 191, or (iii) a full-length complementary strand of (i) or (ii).

In another second aspect, the isolated GH10 polypeptides having xylanase activity are encoded by polynucleotides that hybridize under preferably medium-high stringency conditions, more preferably high stringency conditions, and most preferably very high stringency conditions with (i) the mature polypeptide coding sequence of SEQ ID NO: 45, (ii) the genomic DNA sequence of the mature polypeptide coding sequence of SEQ ID NO: 45, or (iii) a full-length complementary strand of (i) or (ii).

In another second aspect, the isolated GH10 polypeptides having xylanase activity are encoded by polynucleotides that hybridize under preferably medium-high stringency conditions, more preferably high stringency conditions, and most preferably very high stringency conditions with (i) the mature polypeptide coding sequence of SEQ ID NO: 47, (ii) the cDNA sequence of the mature polypeptide coding sequence of SEQ ID NO: 47, or (iii) a full-length complementary strand of (i) or (ii).

In another second aspect, the isolated GH10 polypeptides having xylanase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 49, (ii) the genomic DNA sequence of the mature polypeptide coding sequence of SEQ ID NO: 49, or (iii) a full-length complementary strand of (i) or (ii).

In another second aspect, the isolated GH10 polypeptides having xylanase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 51, (ii) the cDNA sequence of the mature polypeptide coding sequence of SEQ ID NO: 51, or (iii) a full-length complementary strand of (i) or (ii).

In another second aspect, the isolated GH10 polypeptides having xylanase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 53, (ii) the genomic DNA sequence of the mature polypeptide coding sequence of SEQ ID NO: 53, or (iii) a full-length complementary strand of (i) or (ii).

In another second aspect, the isolated GH10 polypeptides having xylanase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 193, (ii) the cDNA sequence of the mature polypeptide coding sequence of SEQ ID NO: 193, or (iii) a full-length complementary strand of (i) or (ii).

In another second aspect, the isolated GH10 polypeptides having xylanase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 195, (ii) the cDNA sequence of the mature polypeptide coding sequence of SEQ ID NO: 195, or (iii) a full-length complementary strand of (i) or (ii).

In another second aspect, the isolated GH10 polypeptides having xylanase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 197, (ii) the genomic DNA sequence of the mature polypeptide coding sequence of SEQ ID NO: 197, or (iii) a full-length complementary strand of (i) or (ii).

In another second aspect, the isolated GH11 polypeptides having xylanase activity is encoded by polynucleotides that hybridize under preferably medium stringency conditions, more preferably medium-high stringency conditions, even more preferably high stringency conditions, and most preferably very high stringency conditions with the mature polypeptide coding sequence of SEQ ID NO: 55 or its full-length complementary strand.

In another second aspect, the isolated GH11 polypeptides having xylanase activity is encoded by polynucleotides that hybridize under preferably medium stringency conditions, more preferably medium-high stringency conditions, even more preferably high stringency conditions, and most preferably very high stringency conditions with the mature polypeptide coding sequence of SEQ ID NO: 199 or SEQ ID NO: 304; or its full-length complementary strand.

In another second aspect, the isolated polypeptides having beta-xylosidase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 57, (ii) the genomic DNA sequence of the mature polypeptide coding sequence of SEQ ID NO: 57, or (iii) a full-length complementary strand of (i) or (ii).

In another second aspect, the isolated polypeptides having beta-xylosidase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 59, (ii) the cDNA sequence of the mature polypeptide coding sequence of SEQ ID NO: 59, or (iii) a full-length complementary strand of (i) or (ii).

In another second aspect, the isolated polypeptides having beta-xylosidase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 201, (ii) the cDNA sequence of the mature polypeptide coding sequence of SEQ ID NO: 201, or (iii) a full-length complementary strand of (i) or (ii).

In another second aspect, the isolated polypeptides having beta-xylosidase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 203, (ii) the cDNA sequence of the mature polypeptide coding sequence of SEQ ID NO: 203, or (iii) a full-length complementary strand of (i) or (ii).

In another second aspect, the isolated polypeptides having beta-xylosidase activity is encoded by polynucleotides that hybridize under preferably medium stringency conditions, more preferably medium-high stringency conditions, even more preferably high stringency conditions, and most preferably very high stringency conditions with (i) the mature polypeptide coding sequence of SEQ ID NO: 205, (ii) the cDNA sequence of the mature polypeptide coding sequence of SEQ ID NO: 205, or (iii) a full-length complementary strand of (i) or (ii).

The nucleotide sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 157, 159, 161, 163, 165, 167, 169, 171, 173, 175, 177, 179, 181, 183, 185, 187, 189, 919, 193, 195, 197, 199, 201, 203, or 205; or a subsequence thereof; as well as the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 158, 160, 162, 164, 166, 168, 170, 172, 174, 176, 178, 180, 182, 184, 186, 188, 190, 192, 194, 196, 198, 200, 202, 204, or 206; or a fragment thereof; may be used to design nucleic acid probes to identify and clone DNA encoding polypeptides having enzyme activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having enzyme or biological activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 157, 159, 161, 163, 165, 167, 169, 171, 173, 175, 177, 179, 181, 183, 185, 187, 189, 919, 193, 195, 197, 199, 201, 203, or 205 or a subsequence thereof, the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 157, 159, 161, 163, 165, 167, 169, 171, 173, 175, 177, 179, 181, 183, 185, 187, 189, 919, 193, 195, 197, 199, 201, 203, or 205; the cDNA sequence of or the genomic DNA sequence of the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 157, 159, 161, 163, 165, 167, 169, 171, 173, 175, 177, 179, 181, 183, 185, 187, 189, 919, 193, 195, 197, 199, 201, 203, or 205; its full-length complementary strand; or a subsequence thereof; under very low to very high stringency conditions. Molecules to which the nucleic acid probe hybridizes under these conditions can be detected using, for example, X-ray film.

In one aspect, the nucleic acid probe is the mature polypeptide coding sequence of SEQ ID NO: 1. In another aspect, the nucleic acid probe is nucleotides 55 to 1590 of SEQ ID NO: 1. In another aspect, the nucleic acid probe is a polynucleotide sequence that encodes the polypeptide of SEQ ID NO: 2, or a subsequence thereof. In another aspect, the nucleic acid probe is SEQ ID NO: 1. In another aspect, the nucleic acid probe is the polynucleotide sequence contained in *Chaetomium thermophilum* CGMCC 0581, wherein the polynucleotide sequence thereof encodes a polypeptide having cellobiohydrolase I activity. In another aspect, the nucleic acid probe is the mature polypeptide coding region contained in *Chaetomium thermophilum* CGMCC 0581.

In another aspect, the nucleic acid probe is the mature polypeptide coding sequence of SEQ ID NO: 3. In another aspect, the nucleic acid probe is nucleotides 61 to 1350 of SEQ ID NO: 3. In another aspect, the nucleic acid probe is a polynucleotide sequence that encodes the polypeptide of SEQ ID NO: 4, or a subsequence thereof. In another aspect, the nucleic acid probe is SEQ ID NO: 3. In another aspect, the nucleic acid probe is the polynucleotide sequence contained in *Myceliophthora thermophila* CBS 117.65, wherein the polynucleotide sequence thereof encodes a polypeptide having cellobiohydrolase I activity. In another aspect, the nucleic acid probe is the mature polypeptide coding region contained in *Myceliophthora thermophila* CBS 117.65.

In another aspect, the nucleic acid probe is the mature polypeptide coding sequence of SEQ ID NO: 5. In another aspect, the nucleic acid probe is nucleotides 79 to 1596 of SEQ ID NO: 5. In another aspect, the nucleic acid probe is a polynucleotide sequence that encodes the polypeptide of SEQ ID NO: 6, or a subsequence thereof. In another aspect, the nucleic acid probe is SEQ ID NO: 5. In another aspect, the nucleic acid probe is the polynucleotide sequence contained in *Aspergillus fumigatus* NN055679, wherein the polynucleotide sequence thereof encodes a polypeptide having cellobiohydrolase I activity. In another aspect, the nucleic acid probe is the mature polypeptide coding region contained in *Aspergillus fumigatus* NN055679.

In another aspect, the nucleic acid probe is the mature polypeptide coding sequence of SEQ ID NO: 7. In another aspect, the nucleic acid probe is nucleotides 52 to 1374 of SEQ ID NO: 7. In another aspect, the nucleic acid probe is a polynucleotide sequence that encodes the polypeptide of SEQ ID NO: 8, or a subsequence thereof. In another aspect, the nucleic acid probe is SEQ ID NO: 7. In another aspect, the nucleic acid probe is the polynucleotide sequence contained in *Thermoascus aurantiacus* CGMCC 0583, wherein the polynucleotide sequence thereof encodes a polypeptide having cellobiohydrolase I activity. In another aspect, the nucleic acid probe is the mature polypeptide coding region contained in *Thermoascus aurantiacus* CGMCC 0583.

In another aspect, the nucleic acid probe is the mature polypeptide coding sequence of SEQ ID NO: 157. In another aspect, the nucleic acid probe is nucleotides 55 to 1428 of SEQ ID NO: 157. In another aspect, the nucleic acid probe is a polynucleotide sequence that encodes the polypeptide of SEQ ID NO: 158, or a subsequence thereof. In another aspect, the nucleic acid probe is SEQ ID NO: 157. In another aspect, the nucleic acid probe is the polynucleotide sequence contained in *Penicillium emersonii* NN051602, wherein the polynucleotide sequence thereof encodes a polypeptide having cellobiohydrolase I activity. In another aspect, the nucleic acid probe is the mature polypeptide coding region contained in *Penicillium emersonii* NN051602.

In another aspect, the nucleic acid probe is the mature polypeptide coding sequence of SEQ ID NO: 159. In another aspect, the nucleic acid probe is nucleotides 76 to 1590 of SEQ ID NO: 159. In another aspect, the nucleic acid probe is a polynucleotide sequence that encodes the polypeptide of SEQ ID NO: 160, or a subsequence thereof. In another aspect, the nucleic acid probe is SEQ ID NO: 159. In another aspect, the nucleic acid probe is the polynucleotide sequence contained in *Penicillium pinophilum* NN046877, wherein the polynucleotide sequence thereof encodes a polypeptide having cellobiohydrolase I activity. In another aspect, the nucleic acid probe is the mature polypeptide coding region contained in *Penicillium pinophilum* NN046877.

In another aspect, the nucleic acid probe is the mature polypeptide coding sequence of SEQ ID NO: 161. In another aspect, the nucleic acid probe is nucleotides 52 to 1374 of SEQ ID NO: 161. In another aspect, the nucleic acid probe is a polynucleotide sequence that encodes the polypeptide of SEQ ID NO: 162, or a subsequence thereof. In another aspect, the nucleic acid probe is SEQ ID NO: 161. In another aspect, the nucleic acid probe is the polynucleotide sequence contained in *Aspergillus terreus* ATCC 28865, wherein the polynucleotide sequence thereof encodes a polypeptide having cellobiohydrolase I activity. In another aspect, the nucleic acid probe is the mature polypeptide coding region contained in *Aspergillus terreus* ATCC 28865.

In another aspect, the nucleic acid probe is the mature polypeptide coding sequence of SEQ ID NO: 163. In another aspect, the nucleic acid probe is nucleotides 79 to 1605 of SEQ ID NO: 163. In another aspect, the nucleic acid probe is a polynucleotide sequence that encodes the polypeptide of SEQ ID NO: 164, or a subsequence thereof. In another aspect, the nucleic acid probe is SEQ ID NO: 162. In another aspect, the nucleic acid probe is the polynucleotide sequence contained in Neosartorya *fischeri* NRRL 181, wherein the polynucleotide sequence thereof encodes a polypeptide having cellobiohydrolase I activity. In another aspect, the nucleic acid probe is the mature polypeptide coding region contained in Neosartorya *fischeri* NRRL 181.

In another aspect, the nucleic acid probe is the mature polypeptide coding sequence of SEQ ID NO: 165. In another aspect, the nucleic acid probe is nucleotides 52 to 1374 of SEQ ID NO: 165. In another aspect, the nucleic acid probe is a polynucleotide sequence that encodes the polypeptide of SEQ ID NO: 166, or a subsequence thereof. In another aspect, the nucleic acid probe is SEQ ID NO: 165. In another aspect, the nucleic acid probe is the polynucleotide sequence contained in *Aspergillus nidulans* FGSCA4, wherein the polynucleotide sequence thereof encodes a polypeptide having cellobiohydrolase I activity. In another aspect, the nucleic acid probe is the mature polypeptide coding region contained in *Aspergillus nidulans* FGSCA4.

In another aspect, the nucleic acid probe is the mature polypeptide coding sequence of SEQ ID NO: 9. In another aspect, the nucleic acid probe is nucleotides 52 to 1799 of SEQ ID NO: 9. In another aspect, the nucleic acid probe is a polynucleotide sequence that encodes the polypeptide of SEQ ID NO: 10, or a subsequence thereof. In another aspect, the nucleic acid probe is SEQ ID NO: 9. In another aspect, the nucleic acid probe is the polynucleotide sequence contained in *Myceliophthora thermophila* CBS 117.65, wherein the polynucleotide sequence thereof encodes a polypeptide having cellobiohydrolase II activity. In another aspect, the nucleic acid probe is the mature polypeptide coding region contained in *Myceliophthora thermophila* CBS 117.65.

In another aspect, the nucleic acid probe is the mature polypeptide coding sequence of SEQ ID NO: 11. In another aspect, the nucleic acid probe is nucleotides 52 to 1809 of SEQ ID NO: 11. In another aspect, the nucleic acid probe is a polynucleotide sequence that encodes the polypeptide of SEQ ID NO: 12, or a subsequence thereof. In another aspect, the nucleic acid probe is SEQ ID NO: 11. In another aspect, the nucleic acid probe is the polynucleotide sequence contained in plasmid pSMai182 which is contained in *E. coli* NRRL B-50059 or contained in *Myceliophthora thermophila* CBS 202.73, wherein the polynucleotide sequence thereof encodes a polypeptide having cellobiohydrolase II activity. In another aspect, the nucleic acid probe is the mature polypeptide coding region contained in plasmid pSMai182 which is contained in *E. coli* NRRL B-50059 or contained in *Myceliophthora thermophila* CBS 202.73.

In another aspect, the nucleic acid probe is the mature polypeptide coding sequence of SEQ ID NO: 13. In another aspect, the nucleic acid probe is nucleotides 52 to 1443 of SEQ ID NO: 13. In another aspect, the nucleic acid probe is a polynucleotide sequence that encodes the polypeptide of SEQ ID NO: 14, or a subsequence thereof. In another aspect, the nucleic acid probe is SEQ ID NO: 13. In another aspect, the nucleic acid probe is the polynucleotide sequence contained in plasmid pTter6A which is contained in *E. coli* NRRL B-30802, wherein the polynucleotide sequence thereof encodes a polypeptide having cellobiohydrolase II activity. In another aspect, the nucleic acid probe is the mature polypeptide coding region contained in plasmid pTter6A which is contained in *E. coli* NRRL B-30802.

In another aspect, the nucleic acid probe is the mature polypeptide coding sequence of SEQ ID NO: 15. In another aspect, the nucleic acid probe is nucleotides 109 to 1401 of SEQ ID NO: 15. In another aspect, the nucleic acid probe is a polynucleotide sequence that encodes the polypeptide of SEQ ID NO: 16, or a subsequence thereof. In another aspect, the nucleic acid probe is SEQ ID NO: 15. In another aspect, the nucleic acid probe is the polynucleotide sequence contained in plasmid pMStr199 which is contained in *E. coli* DSM 23379, wherein the polynucleotide sequence thereof encodes a polypeptide having cellobiohydrolase II activity. In another aspect, the nucleic acid probe is the mature polypeptide coding region contained in plasmid pMStr199 which is contained in *E. coli* DSM 23379.

In another aspect, the nucleic acid probe is the mature polypeptide coding sequence of SEQ ID NO: 17. In another aspect, the nucleic acid probe is nucleotides 58 to 1700 of SEQ ID NO: 17. In another aspect, the nucleic acid probe is a polynucleotide sequence that encodes the polypeptide of SEQ ID NO: 18, or a subsequence thereof. In another aspect, the nucleic acid probe is SEQ ID NO: 17. In another aspect, the nucleic acid probe is the polynucleotide sequence contained in *Aspergillus fumigatus* NN055679, wherein the polynucleotide sequence thereof encodes a polypeptide having cellobiohydrolase II activity. In another aspect, the nucleic acid probe is the mature polypeptide coding region contained in *Aspergillus fumigatus* NN055679.

In another aspect, the nucleic acid probe is the mature polypeptide coding sequence of SEQ ID NO: 167. In another aspect, the nucleic acid probe is nucleotides 55 to 1749 of SEQ ID NO: 167. In another aspect, the nucleic acid probe is a polynucleotide sequence that encodes the polypeptide of SEQ ID NO: 168, or a subsequence thereof. In another aspect, the nucleic acid probe is SEQ ID NO: 167. In another aspect, the nucleic acid probe is the polynucleotide sequence contained in Fennellia *nivea* NN046949 or in pGEM-T-CBHI146949-2 which is contained in *E. coli* DSM 24143, wherein the polynucleotide sequence thereof encodes a polypeptide having cellobiohydrolase II activity. In another aspect, the nucleic acid probe is the mature polypeptide coding region contained in *Fennellia nivea* NN046949 or in pGEM-T-CBH1146949-2 which is contained in *E. coli* DSM 24143.

In another aspect, the nucleic acid probe is the mature polypeptide coding sequence of SEQ ID NO: 169. In another aspect, the nucleic acid probe is nucleotides 58 to 1744 of SEQ ID NO: 169. In another aspect, the nucleic acid probe is a polynucleotide sequence that encodes the polypeptide of SEQ ID NO: 170, or a subsequence thereof. In another aspect, the nucleic acid probe is SEQ ID NO: 169. In another aspect, the nucleic acid probe is the polynucleotide sequence contained in *Penicillium emersonii* NN051602, wherein the polynucleotide sequence thereof encodes a polypeptide having cellobiohydrolase II activity. In another aspect, the nucleic acid probe is the mature polypeptide coding region contained in *Penicillium emersonii* NN051602.

In another aspect, the nucleic acid probe is the mature polypeptide coding sequence of SEQ ID NO: 171. In another aspect, the nucleic acid probe is nucleotides 58 to 1701 of SEQ ID NO: 171. In another aspect, the nucleic acid probe is a polynucleotide sequence that encodes the polypeptide of SEQ ID NO: 172, or a subsequence thereof. In another aspect, the nucleic acid probe is SEQ ID NO: 171. In another aspect, the nucleic acid probe is the polynucleotide sequence contained in *Penicillium pinophilum* NN046877, wherein the polynucleotide sequence thereof encodes a polypeptide having cellobiohydrolase II activity. In another aspect, the nucleic acid probe is the mature polypeptide coding region contained in *Penicillium pinophilum* NN046877.

In another aspect, the nucleic acid probe is the mature polypeptide coding sequence of SEQ ID NO: 19. In another aspect, the nucleic acid probe is nucleotides 64 to 1502 of SEQ ID NO: 19. In another aspect, the nucleic acid probe is a polynucleotide sequence that encodes the polypeptide of SEQ ID NO: 20, or a subsequence thereof. In another aspect, the nucleic acid probe is SEQ ID NO: 19. In another aspect, the nucleic acid probe is the polynucleotide sequence contained in *Aspergillus terreus* ATCC 28865, wherein the polynucleotide sequence thereof encodes a polypeptide having endoglucanase I activity. In another aspect, the nucleic acid probe is the mature polypeptide coding region contained in *Aspergillus terreus* ATCC 28865.

In another aspect, the nucleic acid probe is the mature polypeptide coding sequence of SEQ ID NO: 21. In another aspect, the nucleic acid probe is nucleotides 64 to 1254 of SEQ ID NO: 21. In another aspect, the nucleic acid probe is a polynucleotide sequence that encodes the polypeptide of SEQ ID NO: 22, or a subsequence thereof. In another aspect, the nucleic acid probe is SEQ ID NO: 21. In another aspect, the nucleic acid probe is the polynucleotide sequence contained in *Trichoderma reesei* RutC30, wherein the polynucleotide sequence thereof encodes a polypeptide having endoglucanase II activity. In another aspect, the nucleic acid probe is the mature polypeptide coding region contained in *Trichoderma reesei* RutC30.

In another aspect, the nucleic acid probe is the mature polypeptide coding sequence of SEQ ID NO: 23. In another aspect, the nucleic acid probe is nucleotides 67 to 1185 of SEQ ID NO: 23. In another aspect, the nucleic acid probe is a polynucleotide sequence that encodes the polypeptide of SEQ ID NO: 24, or a subsequence thereof. In another aspect, the nucleic acid probe is SEQ ID NO: 23. In another aspect, the nucleic acid probe is the polynucleotide sequence contained in plasmid pC10161 which is contained in *E. coli*

NRRL B-30902, wherein the polynucleotide sequence thereof encodes a polypeptide having endoglucanase II activity. In another aspect, the nucleic acid probe is the mature polypeptide coding region contained in plasmid pC10161 which is contained in *E. coli* NRRL B-30902.

In another aspect, the nucleic acid probe is the mature polypeptide coding sequence of SEQ ID NO: 25. In another aspect, the nucleic acid probe is nucleotides 91 to 1005 of SEQ ID NO: 25. In another aspect, the nucleic acid probe is a polynucleotide sequence that encodes the polypeptide of SEQ ID NO: 26, or a subsequence thereof. In another aspect, the nucleic acid probe is SEQ ID NO: 25. In another aspect, the nucleic acid probe is the polynucleotide sequence contained in *Thermoascus aurantiacus* CGMCC 0670, wherein the polynucleotide sequence thereof encodes a polypeptide having endoglucanase II activity. In another aspect, the nucleic acid probe is the mature polypeptide coding region contained in *Thermoascus aurantiacus* CGMCC 0670.

In another aspect, the nucleic acid probe is the mature polypeptide coding sequence of SEQ ID NO: 173. In another aspect, the nucleic acid probe is nucleotides 55 to 1260 of SEQ ID NO: 173. In another aspect, the nucleic acid probe is a polynucleotide sequence that encodes the polypeptide of SEQ ID NO: 174, or a subsequence thereof. In another aspect, the nucleic acid probe is SEQ ID NO: 173. In another aspect, the nucleic acid probe is the polynucleotide sequence contained in *Aspergillus fumigatus* NN051616, wherein the polynucleotide sequence thereof encodes a polypeptide having endoglucanase II activity. In another aspect, the nucleic acid probe is the mature polypeptide coding region contained in *Aspergillus fumigatus* NN051616.

In another aspect, the nucleic acid probe is the mature polypeptide coding sequence of SEQ ID NO: 175. In another aspect, the nucleic acid probe is nucleotides 49 to 1378 of SEQ ID NO: 175. In another aspect, the nucleic acid probe is a polynucleotide sequence that encodes the polypeptide of SEQ ID NO: 176, or a subsequence thereof. In another aspect, the nucleic acid probe is SEQ ID NO: 175. In another aspect, the nucleic acid probe is the polynucleotide sequence contained in Neosartorya *fischeri* NRRL 181, wherein the polynucleotide sequence thereof encodes a polypeptide having endoglucanase II activity. In another aspect, the nucleic acid probe is the mature polypeptide coding region contained in Neosartorya *fischeri* NRRL 181.

In another aspect, the nucleic acid probe is the mature polypeptide coding sequence of SEQ ID NO: 27. In another aspect, the nucleic acid probe is nucleotides 58 to 2580 of SEQ ID NO: 27. In another aspect, the nucleic acid probe is a polynucleotide sequence that encodes the polypeptide of SEQ ID NO: 28, or a subsequence thereof. In another aspect, the nucleic acid probe is SEQ ID NO: 27. In another aspect, the nucleic acid probe is the polynucleotide sequence contained in plasmid pEJG113 which is contained in *E. coli* NRRL B-30695, wherein the polynucleotide sequence thereof encodes a polypeptide having beta-glucosidase activity. In another aspect, the nucleic acid probe is the mature polypeptide coding region contained in plasmid pEJG113 which is contained in *E. coli* NRRL B-30695.

In another aspect, the nucleic acid probe is the mature polypeptide coding sequence of SEQ ID NO: 29. In another aspect, the nucleic acid probe is nucleotides 171 to 2753 of SEQ ID NO: 29. In another aspect, the nucleic acid probe is a polynucleotide sequence that encodes the polypeptide of SEQ ID NO: 30, or a subsequence thereof. In another aspect, the nucleic acid probe is SEQ ID NO: 29. In another aspect, the nucleic acid probe is the polynucleotide sequence contained in plasmid pKKAB which is contained in *E. coli* NRRL B-30860, wherein the polynucleotide sequence thereof encodes a polypeptide having beta-glucosidase activity. In another aspect, the nucleic acid probe is the mature polypeptide coding region contained in plasmid pKKAB which is contained in *E. coli* NRRL B-30860.

In another aspect, the nucleic acid probe is the mature polypeptide coding sequence of SEQ ID NO: 31. In another aspect, the nucleic acid probe is nucleotides 58 to 2934 of SEQ ID NO: 31. In another aspect, the nucleic acid probe is a polynucleotide sequence that encodes the polypeptide of SEQ ID NO: 32, or a subsequence thereof. In another aspect, the nucleic acid probe is SEQ ID NO: 31. In another aspect, the nucleic acid probe is the polynucleotide sequence contained in *Aspergillus niger* IBT 10140, wherein the polynucleotide sequence thereof encodes a polypeptide having beta-glucosidase activity. In another aspect, the nucleic acid probe is the mature polypeptide coding region contained in *Aspergillus niger* IBT 10140.

In another aspect, the nucleic acid probe is the mature polypeptide coding sequence of SEQ ID NO: 177. In another aspect, the nucleic acid probe is nucleotides 58 to 2937 of SEQ ID NO: 177. In another aspect, the nucleic acid probe is a polynucleotide sequence that encodes the polypeptide of SEQ ID NO: 178, or a subsequence thereof. In another aspect, the nucleic acid probe is SEQ ID NO: 177. In another aspect, the nucleic acid probe is the polynucleotide sequence contained in *Aspergillus aculeatus* WDCM190, which encodes a polypeptide having beta-glucosidase activity. In another aspect, the nucleic acid probe is the mature polypeptide coding region contained in *Aspergillus aculeatus* WDCM190.

In another aspect, the nucleic acid probe is the mature polypeptide coding sequence of SEQ ID NO: 179. In another aspect, the nucleic acid probe is nucleotides 58 to 2932 of SEQ ID NO: 179. In another aspect, the nucleic acid probe is a polynucleotide sequence that encodes the polypeptide of SEQ ID NO: 180, or a subsequence thereof. In another aspect, the nucleic acid probe is SEQ ID NO: 179. In another aspect, the nucleic acid probe is the polynucleotide sequence contained in *Aspergillus kawashii* IFO4308, which encodes a polypeptide having beta-glucosidase activity. In another aspect, the nucleic acid probe is the mature polypeptide coding region contained in *Aspergillus kawashii* IFO4308.

In another aspect, the nucleic acid probe is the mature polypeptide coding sequence of SEQ ID NO: 181. In another aspect, the nucleic acid probe is nucleotides 55 to 3059 of SEQ ID NO: 181. In another aspect, the nucleic acid probe is a polynucleotide sequence that encodes the polypeptide of SEQ ID NO: 182, or a subsequence thereof. In another aspect, the nucleic acid probe is SEQ ID NO: 181. In another aspect, the nucleic acid probe is the polynucleotide sequence contained in *Aspergillus clavatus* NRRL 1, which encodes a polypeptide having beta-glucosidase activity. In another aspect, the nucleic acid probe is the mature polypeptide coding region contained in *Aspergillus clavatus* NRRL 1.

In another aspect, the nucleic acid probe is the mature polypeptide coding sequence of SEQ ID NO: 183. In another aspect, the nucleic acid probe is nucleotides 55 to 3029 of SEQ ID NO: 183. In another aspect, the nucleic acid probe is a polynucleotide sequence that encodes the polypeptide of SEQ ID NO: 184, or a subsequence thereof. In another aspect, the nucleic acid probe is SEQ ID NO: 183. In another aspect, the nucleic acid probe is the polynucleotide sequence contained in *Thielavia terrestris* NRRL 8126, which encodes a polypeptide having beta-glucosidase activity. In another aspect, the nucleic acid probe is the mature polypeptide coding region contained in *Thielavia terrestris* NRRL 8126.

In another aspect, the nucleic acid probe is the mature polypeptide coding sequence of SEQ ID NO: 185. In another aspect, the nucleic acid probe is nucleotides 64 to 2790 of SEQ ID NO: 185. In another aspect, the nucleic acid probe is a polynucleotide sequence that encodes the polypeptide of SEQ ID NO: 186, or a subsequence thereof. In another aspect, the nucleic acid probe is SEQ ID NO: 185. In another aspect, the nucleic acid probe is the polynucleotide sequence contained in pUC19 D55EX which is contained in *E. coli* NRRL B-50395, wherein the polynucleotide sequence thereof encodes a polypeptide having beta-glucosidase activity. In another aspect, the nucleic acid probe is the mature polypeptide coding region contained in in pUC19 D55EX which is contained in *E. coli* NRRL B-50395.

In another aspect, the nucleic acid probe is the mature polypeptide coding sequence of SEQ ID NO: 187. In another aspect, the nucleic acid probe is nucleotides 64 to 2790 of SEQ ID NO: 187. In another aspect, the nucleic acid probe is a polynucleotide sequence that encodes the polypeptide of SEQ ID NO: 188, or a subsequence thereof. In another aspect, the nucleic acid probe is SEQ ID NO: 187. In another aspect, the nucleic acid probe is the polynucleotide sequence contained in *Penicillium oxalicum* IBT5387, wherein the polynucleotide sequence thereof encodes a polypeptide having beta-glucosidase activity. In another aspect, the nucleic acid probe is the mature polypeptide coding region contained in *Penicillium oxalicum* IBT5387.

In another aspect, the nucleic acid probe is the mature polypeptide coding sequence of SEQ ID NO: 189. In another aspect, the nucleic acid probe is nucleotides 58 to 2961 of SEQ ID NO: 189. In another aspect, the nucleic acid probe is a polynucleotide sequence that encodes the polypeptide of SEQ ID NO: 190, or a subsequence thereof. In another aspect, the nucleic acid probe is SEQ ID NO: 189. In another aspect, the nucleic acid probe is the polynucleotide sequence contained in *Talaromyces emersonii* CBS 549.92, wherein the polynucleotide sequence thereof encodes a polypeptide having beta-glucosidase activity. In another aspect, the nucleic acid probe is the mature polypeptide coding region contained in *Talaromyces emersonii* CBS 549.92.

In another aspect, the nucleic acid probe is the mature polypeptide coding sequence of SEQ ID NO: 33. In another aspect, the nucleic acid probe is nucleotides 67 to 796 of SEQ ID NO: 33. In another aspect, the nucleic acid probe is a polynucleotide sequence that encodes the polypeptide of SEQ ID NO: 34, or a subsequence thereof. In another aspect, the nucleic acid probe is SEQ ID NO: 33. In another aspect, the nucleic acid probe is the polynucleotide sequence contained in plasmid pDZA2-7 which is contained in *E. coli* NRRL B-30704, wherein the polynucleotide sequence thereof encodes a polypeptide having cellulolytic enhancing activity. In another aspect, the nucleic acid probe is the mature polypeptide coding region contained in plasmid pDZA2-7 which is contained in *E. coli* NRRL B-30704.

In another aspect, the nucleic acid probe is the mature polypeptide coding sequence of SEQ ID NO: 35. In another aspect, the nucleic acid probe is nucleotides 58 to 900 of SEQ ID NO: 35. In another aspect, the nucleic acid probe is a polynucleotide sequence that encodes the polypeptide of SEQ ID NO: 36, or a subsequence thereof. In another aspect, the nucleic acid probe is SEQ ID NO: 35. In another aspect, the nucleic acid probe is the polynucleotide sequence contained in plasmid pTter61E which is contained in *E. coli* NRRL B-30814, wherein the polynucleotide sequence thereof encodes a polypeptide having cellulolytic enhancing activity. In another aspect, the nucleic acid probe is the mature polypeptide coding region contained in plasmid pTter61E which is contained in *E. coli* NRRL B-30814.

In another aspect, the nucleic acid probe is the mature polypeptide coding sequence of SEQ ID NO: 37. In another aspect, the nucleic acid probe is nucleotides 64 to 859 of SEQ ID NO: 37. In another aspect, the nucleic acid probe is a polynucleotide sequence that encodes the polypeptide of SEQ ID NO: 38, or a subsequence thereof. In another aspect, the nucleic acid probe is SEQ ID NO: 37. In another aspect, the nucleic acid probe is the polynucleotide sequence contained in *Aspergillus fumigatus* NN051616, wherein the polynucleotide sequence thereof encodes a polypeptide having cellulolytic enhancing activity. In another aspect, the nucleic acid probe is the mature polypeptide coding region contained in *Aspergillus fumigatus* NN051616.

In another aspect, the nucleic acid probe is the mature polypeptide coding sequence of SEQ ID NO: 39. In another aspect, the nucleic acid probe is nucleotides 64 to 1018 of SEQ ID NO: 39. In another aspect, the nucleic acid probe is a polynucleotide sequence that encodes the polypeptide of SEQ ID NO: 40, or a subsequence thereof. In another aspect, the nucleic acid probe is SEQ ID NO: 39. In another aspect, the nucleic acid probe is the polynucleotide sequence contained in *Penicillim pinophilum* NN046877, wherein the polynucleotide sequence thereof encodes a polypeptide having cellulolytic enhancing activity. In another aspect, the nucleic acid probe is the mature polypeptide coding region contained in plasmid pGEM-T-Ppin7 which is contained in *E. coli* DSM 22711.

In another aspect, the nucleic acid probe is the mature polypeptide coding sequence of SEQ ID NO: 41. In another aspect, the nucleic acid probe is nucleotides 76 to 832 of SEQ ID NO: 41. In another aspect, the nucleic acid probe is a polynucleotide sequence that encodes the polypeptide of SEQ ID NO: 42, or a subsequence thereof. In another aspect, the nucleic acid probe is SEQ ID NO: 41. In another aspect, the nucleic acid probe is the polynucleotide sequence contained in plasmid pGEM-T-GH61D23Y4 which is contained in *E. coli* DSM 22882, wherein the polynucleotide sequence thereof encodes a polypeptide having cellulolytic enhancing activity. In another aspect, the nucleic acid probe is the mature polypeptide coding region contained in plasmid pGEM-T-GH61D23Y4 which is contained in *E. coli* DSM 22882.

In another aspect, the nucleic acid probe is the mature polypeptide coding sequence of SEQ ID NO: 43. In another aspect, the nucleic acid probe is nucleotides 64 to 1104 of SEQ ID NO: 43. In another aspect, the nucleic acid probe is a polynucleotide sequence that encodes the polypeptide of SEQ ID NO: 44, or a subsequence thereof. In another aspect, the nucleic acid probe is SEQ ID NO: 43. In another aspect, the nucleic acid probe is the polynucleotide sequence contained in plasmid pAG68 which is contained in *E. coli* NRRL B-50320, wherein the polynucleotide sequence thereof encodes a polypeptide having cellulolytic enhancing activity. In another aspect, the nucleic acid probe is the mature polypeptide coding region contained in plasmid pAG68 which is contained in *E. coli* NRRL B-50320.

In another aspect, the nucleic acid probe is the mature polypeptide coding sequence of SEQ ID NO: 191. In another aspect, the nucleic acid probe is nucleotides 64 to 1104 of SEQ ID NO: 191. In another aspect, the nucleic acid probe is a polynucleotide sequence that encodes the polypeptide of SEQ ID NO: 192, or a subsequence thereof. In another aspect, the nucleic acid probe is SEQ ID NO: 191. In another aspect, the nucleic acid probe is the polynucleotide sequence contained in plasmid pGEM-T-GH61a51486 which is contained in *E. coli* DSM 22656, wherein the polynucleotide sequence thereof encodes a polypeptide having cellulolytic enhancing activity. In another aspect, the nucleic acid probe is the mature polypeptide coding region contained in plasmid pGEM-T-GH61a51486 which is contained in *E. coli* DSM 22656.

In another aspect, the nucleic acid probe is the mature polypeptide coding sequence of SEQ ID NO: 45. In another aspect, the nucleic acid probe is nucleotides 69 to 1314 of SEQ ID NO: 45. In another aspect, the nucleic acid probe is a polynucleotide sequence that encodes the polypeptide of SEQ ID NO: 46, or a subsequence thereof. In another aspect, the nucleic acid probe is SEQ ID NO: 45. In another aspect, the nucleic acid probe is the polynucleotide sequence contained in Aspergillus *aculeatus* CBS 101.43, wherein the polynucleotide sequence thereof encodes a polypeptide having xylanase activity. In another aspect, the nucleic acid probe is the mature polypeptide coding region contained in Aspergillus *aculeatus* CBS 101.43.

In another aspect, the nucleic acid probe is the mature polypeptide coding sequence of SEQ ID NO: 47. In another aspect, the nucleic acid probe is nucleotides 107 to 1415 of SEQ ID NO: 47. In another aspect, the nucleic acid probe is a polynucleotide sequence that encodes the polypeptide of SEQ ID NO: 48, or a subsequence thereof. In another aspect, the nucleic acid probe is SEQ ID NO: 47. In another aspect, the nucleic acid probe is the polynucleotide sequence contained in plasmid pHyGe001 which is contained in *E. coli* NRRL B-30703, wherein the polynucleotide sequence thereof encodes a polypeptide having xylanase activity. In another aspect, the nucleic acid probe is the mature polypeptide coding region contained in plasmid pHyGe001 which is contained in *E. coli* NRRL B-30703.

In another aspect, the nucleic acid probe is the mature polypeptide coding sequence of SEQ ID NO: 49. In another aspect, the nucleic acid probe is nucleotides 58 to 1194 of SEQ ID NO: 49. In another aspect, the nucleic acid probe is a polynucleotide sequence that encodes the polypeptide of SEQ ID NO: 50, or a subsequence thereof. In another aspect, the nucleic acid probe is SEQ ID NO: 49. In another aspect, the nucleic acid probe is the polynucleotide sequence contained in plasmid pTF12Xy1170 which is contained in *E. coli* NRRL B-50309, wherein the polynucleotide sequence thereof encodes a polypeptide having xylanase activity. In another aspect, the nucleic acid probe is the mature polypeptide coding region contained in plasmid pTF12Xy1170 which is contained in *E. coli* NRRL B-50309.

In another aspect, the nucleic acid probe is the mature polypeptide coding sequence of SEQ ID NO: 51. In another aspect, the nucleic acid probe is nucleotides 58 to 1439 of SEQ ID NO: 51. In another aspect, the nucleic acid probe is a polynucleotide sequence that encodes the polypeptide of SEQ ID NO: 52, or a subsequence thereof. In another aspect, the nucleic acid probe is SEQ ID NO: 51. In another aspect, the nucleic acid probe is the polynucleotide sequence contained in plasmid pGEM-T-Ppin3 which is contained in *E. coli* DSM 22922, wherein the polynucleotide sequence thereof encodes a polypeptide having xylanase activity. In another aspect, the nucleic acid probe is the mature polypeptide coding region contained in plasmid pGEM-T-Ppin3 which is contained in *E. coli* DSM 22922.

In another aspect, the nucleic acid probe is the mature polypeptide coding sequence of SEQ ID NO: 53. In another aspect, the nucleic acid probe is nucleotides 58 to 1185 of SEQ ID NO: 53. In another aspect, the nucleic acid probe is a polynucleotide sequence that encodes the polypeptide of SEQ ID NO: 54, or a subsequence thereof. In another aspect, the nucleic acid probe is SEQ ID NO: 53. In another aspect, the nucleic acid probe is the polynucleotide sequence contained in *Thielavia terrestris* NRRL 8126, wherein the polynucleotide sequence thereof encodes a polypeptide having xylanase activity. In another aspect, the nucleic acid probe is the mature polypeptide coding region contained in *Thielavia terrestris* NRRL 8126.

In another aspect, the nucleic acid probe is the mature polypeptide coding sequence of SEQ ID NO: 193. In another aspect, the nucleic acid probe is nucleotides 70 to 1383 of SEQ ID NO: 193. In another aspect, the nucleic acid probe is a polynucleotide sequence that encodes the polypeptide of SEQ ID NO: 194, or a subsequence thereof. In another aspect, the nucleic acid probe is SEQ ID NO: 193. In another aspect, the nucleic acid probe is the polynucleotide sequence contained in *Talaromyces emersonii* NN050022, wherein the polynucleotide sequence thereof encodes a polypeptide having xylanase activity. In another aspect, the nucleic acid probe is the mature polypeptide coding region contained in *Talaromyces emersonii* NNO50022.

In another aspect, the nucleic acid probe is the mature polypeptide coding sequence of SEQ ID NO: 195. In another aspect, the nucleic acid probe is nucleotides 70 to 1384 of SEQ ID NO: 195. In another aspect, the nucleic acid probe is a polynucleotide sequence that encodes the polypeptide of SEQ ID NO: 196, or a subsequence thereof. In another aspect, the nucleic acid probe is SEQ ID NO: 195. In another aspect, the nucleic acid probe is the polynucleotide sequence contained in pMMar26 which is contained in *E. coli* NRRL B-50266, wherein the polynucleotide sequence thereof encodes a polypeptide having xylanase activity. In another aspect, the nucleic acid probe is the mature polypeptide coding region contained in pMMar26 which is contained in *E. coli* NRRL B-50266.

In another aspect, the nucleic acid probe is the mature polypeptide coding sequence of SEQ ID NO: 197. In another aspect, the nucleic acid probe is nucleotides 58 to1188 of SEQ ID NO: 197. In another aspect, the nucleic acid probe is a polynucleotide sequence that encodes the polypeptide of SEQ ID NO: 198, or a subsequence thereof. In another aspect, the nucleic acid probe is SEQ ID NO: 197. In another aspect, the nucleic acid probe is the polynucleotide sequence contained in *E. coli* DSM 10361, wherein the polynucleotide sequence thereof encodes a polypeptide having xylanase activity. In another aspect, the nucleic acid probe is the mature polypeptide coding region contained in *E. coli* DSM 10361.

In another aspect, the nucleic acid probe is the mature polypeptide coding sequence of SEQ ID NO: 55. In another aspect, the nucleic acid probe is nucleotides 127 to 1014 of SEQ ID NO: 55. In another aspect, the nucleic acid probe is a polynucleotide sequence that encodes the polypeptide of SEQ ID NO: 56, or a subsequence thereof. In another aspect, the nucleic acid probe is SEQ ID NO: 55. In another aspect, the nucleic acid probe is the polynucleotide sequence contained in Thermobifida *fusca* DSM 22883, wherein the polynucleotide sequence thereof encodes a polypeptide having xylanase activity. In another aspect, the nucleic acid probe is the mature polypeptide coding region contained in Thermobifida *fusca* DSM 22883.

In another aspect, the nucleic acid probe is the mature polypeptide coding sequence of SEQ ID NO: 55. In another aspect, the nucleic acid probe is nucleotides 85 to 693 of SEQ ID NO: 55. In another aspect, the nucleic acid probe is a polynucleotide sequence that encodes the polypeptide of SEQ ID NO: 56, or a subsequence thereof. In another aspect, the nucleic acid probe is SEQ ID NO: 55. In another aspect, the nucleic acid probe is the polynucleotide sequence contained in *Dictyoglomus thermophilum* ATCC 35947, wherein the polynucleotide sequence thereof encodes a polypeptide having xylanase activity. In another aspect, the nucleic acid probe is the mature polypeptide coding region contained in *Dictyoglomus thermophilum* ATCC 35947.

In another aspect, the nucleic acid probe is the mature polypeptide coding sequence of SEQ ID NO: 57. In another aspect, the nucleic acid probe is nucleotides 61 to 2391 of SEQ ID NO: 57. In another aspect, the nucleic acid probe is a polynucleotide sequence that encodes the polypeptide of SEQ ID NO: 58, or a subsequence thereof. In another aspect, the nucleic acid probe is SEQ ID NO: 57. In another aspect, the nucleic acid probe is the polynucleotide sequence contained in *Trichoderma reesei* RutC30, wherein the polynucleotide sequence thereof encodes a polypeptide having beta-xylosidase activity. In another aspect, the nucleic acid probe is the mature polypeptide coding region contained in *Trichoderma reesei* RutC30.

In another aspect, the nucleic acid probe is the mature polypeptide coding sequence of SEQ ID NO: 59. In another aspect, the nucleic acid probe is nucleotides 64 to 2388 of SEQ ID NO: 59. In another aspect, the nucleic acid probe is a polynucleotide sequence that encodes the polypeptide of SEQ ID NO: 60, or a subsequence thereof. In another aspect, the nucleic acid probe is SEQ ID NO: 59. In another aspect, the nucleic acid probe is the polynucleotide sequence contained in *Talaromyces emersonii* CBS 393.64, wherein the polynucleotide sequence thereof encodes a polypeptide having beta-xylosidase activity. In another aspect, the nucleic acid probe is the mature polypeptide coding region contained in *Talaromyces emersonii* CBS 393.64.

In another aspect, the nucleic acid probe is the mature polypeptide coding sequence of SEQ ID NO: 201. In another aspect, the nucleic acid probe is nucleotides 52 to 2409 of SEQ ID NO: 201. In another aspect, the nucleic acid probe is a polynucleotide sequence that encodes the polypeptide of SEQ ID NO: 202, or a subsequence thereof. In another aspect, the nucleic acid probe is SEQ ID NO: 201. In another aspect, the nucleic acid probe is the polynucleotide sequence contained in *Aspergillus aculeatus* CBS 172.66, wherein the polynucleotide sequence thereof encodes a polypeptide having beta-xylosidase activity. In another aspect, the nucleic acid probe is the mature polypeptide coding region contained in *Aspergillus aculeatus* CBS 172.66.

In another aspect, the nucleic acid probe is the mature polypeptide coding sequence of SEQ ID NO: 203. In another aspect, the nucleic acid probe is nucleotides 52 to 2451 of SEQ ID NO: 203. In another aspect, the nucleic acid probe is a polynucleotide sequence that encodes the polypeptide of SEQ ID NO: 204, or a subsequence thereof. In another aspect, the nucleic acid probe is SEQ ID NO: 203. In another aspect, the nucleic acid probe is the polynucleotide sequence contained in *Aspergillus aculeatus* CBS 186.67, wherein the polynucleotide sequence thereof encodes a polypeptide having beta-xylosidase activity. In another aspect, the nucleic acid probe is the mature polypeptide coding region contained in *Aspergillus aculeatus* CBS 186.67.

In another aspect, the nucleic acid probe is the mature polypeptide coding sequence of SEQ ID NO: 205. In another aspect, the nucleic acid probe is nucleotides 61 to 2376 of SEQ ID NO: 205. In another aspect, the nucleic acid probe is a polynucleotide sequence that encodes the polypeptide of SEQ ID NO: 206, or a subsequence thereof. In another aspect, the nucleic acid probe is SEQ ID NO: 205. In another aspect, the nucleic acid probe is the polynucleotide sequence contained in *Aspergillus fumigatus* NN051616, wherein the polynucleotide sequence thereof encodes a polypeptide having beta-xylosidase activity. In another aspect, the nucleic acid probe is the mature polypeptide coding region contained in *Aspergillus fumigatus* NN051616.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

In a third aspect, the isolated polypeptides having cellobiohydrolase I activity are encoded by polynucleotides comprising or consisting of nucleotide sequences that have a degree of identity to the mature polypeptide coding sequence of SEQ ID NO: 1 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase I activity are encoded by polynucleotides comprising or consisting of nucleotide sequences that have a degree of identity to the mature polypeptide coding sequence of SEQ ID NO: 3 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase I activity are encoded by polynucleotides comprising or consisting of nucleotide sequences that have a degree of identity to the mature polypeptide coding sequence of SEQ ID NO: 5 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase I activity are encoded by polynucleotides comprising or consisting of nucleotide sequences that have a degree of identity to the mature polypeptide coding sequence of SEQ ID NO: 7 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase I activity are encoded by polynucleotides comprising or consisting of nucleotide sequences that have a degree of identity to the mature polypeptide coding sequence of SEQ ID NO: 157 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase I activity are encoded by polynucleotides comprising or consisting of nucleotide sequences that have a degree of identity to the mature polypeptide coding sequence of SEQ ID NO: 159 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase I activity are encoded by polynucleotides comprising or consisting of nucleotide sequences that have a degree of identity to the mature polypeptide coding sequence of SEQ ID NO: 161 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase I activity are encoded by polynucleotides comprising or consisting of nucleotide sequences that have a degree of identity to the mature polypeptide coding sequence of SEQ ID NO: 163 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase I activity are encoded by polynucleotides comprising or consisting of nucleotide sequences that have a degree of identity to the mature polypeptide coding sequence of SEQ ID NO: 165 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In another third aspect, the isolated polypeptides having cellobiohydrolase II activity are encoded by polynucleotides comprising or consisting of nucleotide sequences that have a degree of identity to the mature polypeptide coding sequence of SEQ ID NO: 9 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In another third aspect, the isolated polypeptides having cellobiohydrolase II activity are encoded by polynucleotides comprising or consisting of nucleotide sequences that have a degree of identity to the mature polypeptide coding sequence of SEQ ID NO: 11 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In another third aspect, the isolated polypeptides having cellobiohydrolase II activity are encoded by polynucleotides comprising or consisting of nucleotide sequences that have a degree of identity to the mature polypeptide coding sequence of SEQ ID NO: 13 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In another third aspect, the isolated polypeptides having cellobiohydrolase II activity are encoded by polynucleotides comprising or consisting of nucleotide sequences that have a degree of identity to the mature polypeptide coding sequence of SEQ ID NO: 15 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In another third aspect, the isolated polypeptides having cellobiohydrolase II activity are encoded by polynucleotides comprising or consisting of nucleotide sequences that have a degree of identity to the mature polypeptide coding sequence of SEQ ID NO: 17 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In another third aspect, the isolated polypeptides having cellobiohydrolase II activity are encoded by polynucleotides comprising or consisting of nucleotide sequences that have a degree of identity to the mature polypeptide coding sequence of SEQ ID NO: 167 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In another third aspect, the isolated polypeptides having cellobiohydrolase II activity are encoded by polynucleotides comprising or consisting of nucleotide sequences that have a degree of identity to the mature polypeptide coding sequence of SEQ ID NO: 169 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In another third aspect, the isolated polypeptides having cellobiohydrolase II activity are encoded by polynucleotides comprising or consisting of nucleotide sequences that have a degree of identity to the mature polypeptide coding sequence of SEQ ID NO: 171 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In another third aspect, the isolated polypeptides having endoglucanase I activity are encoded by polynucleotides comprising or consisting of nucleotide sequences that have a degree of identity to the mature polypeptide coding sequence of SEQ ID NO: 19 of preferably at least 80%, more preferably at least 85%, even more preferably at least 90%, most preferably at least 95%, and even most preferably at least 96%, at least 97%, at least 98%, or at least 99%, which encode a polypeptide having endoglucanase I activity.

In another third aspect, the isolated polypeptides having endoglucanase II activity are encoded by polynucleotides comprising or consisting of nucleotide sequences that have a degree of identity to the mature polypeptide coding sequence of SEQ ID NO: 21 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In another third aspect, the isolated polypeptides having endoglucanase II activity are encoded by polynucleotides comprising or consisting of nucleotide sequences that have a degree of identity to the mature polypeptide coding sequence of SEQ ID NO: 23 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In another third aspect, the isolated polypeptides having endoglucanase II activity are encoded by polynucleotides comprising or consisting of nucleotide sequences that have a degree of identity to the mature polypeptide coding sequence of SEQ ID NO: 25 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In another third aspect, the isolated polypeptides having endoglucanase II activity are encoded by polynucleotides comprising or consisting of nucleotide sequences that have a degree of identity to the mature polypeptide coding sequence of SEQ ID NO: 173 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In another third aspect, the isolated polypeptides having endoglucanase II activity are encoded by polynucleotides comprising or consisting of nucleotide sequences that have a degree of identity to the mature polypeptide coding sequence of SEQ ID NO: 175 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 27 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 29 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 31 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 177 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 179 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 181 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 183 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 185 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 187 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated polypeptides having beta-glucosidase activity are encoded by polynucleotides comprising or consisting of nucleotide sequences that have a degree of identity to the mature polypeptide coding sequence of SEQ ID NO: 189 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In another third aspect, the isolated GH61 polypeptides having cellulolytic enhancing activity are encoded by polynucleotides comprising or consisting of nucleotide sequences that have a degree of identity to the mature polypeptide coding sequence of SEQ ID NO: 33 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In another third aspect, the isolated GH61 polypeptides having cellulolytic enhancing activity are encoded by polynucleotides comprising or consisting of nucleotide sequences that have a degree of identity to the mature polypeptide coding sequence of SEQ ID NO: 35 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In another third aspect, the isolated GH61 polypeptides having cellulolytic enhancing activity are encoded by polynucleotides comprising or consisting of nucleotide sequences that have a degree of identity to the mature polypeptide coding sequence of SEQ ID NO: 37 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In another third aspect, the isolated GH61 polypeptides having cellulolytic enhancing activity are encoded by polynucleotides comprising or consisting of nucleotide sequences that have a degree of identity to the mature polypeptide coding sequence of SEQ ID NO: 39 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In another third aspect, the isolated GH61 polypeptides having cellulolytic enhancing activity are encoded by polynucleotides comprising or consisting of nucleotide sequences that have a degree of identity to the mature polypeptide coding sequence of SEQ ID NO: 41 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In another third aspect, the isolated GH61 polypeptides having cellulolytic enhancing activity are encoded by polynucleotides comprising or consisting of nucleotide sequences that have a degree of identity to the mature polypeptide coding sequence of SEQ ID NO: 43 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In another third aspect, the isolated GH61 polypeptides having cellulolytic enhancing activity are encoded by polynucleotides comprising or consisting of nucleotide sequences that have a degree of identity to the mature polypeptide coding sequence of SEQ ID NO: 191 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In another third aspect, the isolated polypeptides having xylanase activity are encoded by polynucleotides comprising or consisting of nucleotide sequences that have a degree of identity to the mature polypeptide coding sequence of SEQ ID NO: 45 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 47 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 49 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 51 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 53 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 193 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 195 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 197 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 55 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having xylanase activity are encoded by polynucleotides comprising or consisting of nucleotide sequences that have a degree of identity to the mature polypeptide coding sequence of SEQ ID NO: 199 or SEQ ID NO: 304 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In another third aspect, the isolated polypeptides having beta-xylosidase activity are encoded by polynucleotides comprising or consisting of nucleotide sequences that have a degree of identity to the mature polypeptide coding sequence of SEQ ID NO: 57 of preferably at least 80%, more preferably at least 85%, even more preferably at least 90%, most preferably at least 95%, and even most preferably at least 96%, at least 97%, at least 98%, or at least 99%, which encode a polypeptide having beta-xylosidase activity.

In another third aspect, the isolated polypeptides having beta-xylosidase activity are encoded by polynucleotides comprising or consisting of nucleotide sequences that have a degree of identity to the mature polypeptide coding sequence of SEQ ID NO: 59 of preferably at least 80%, more preferably at least 85%, even more preferably at least 90%, most preferably at least 95%, and even most preferably at least 96%, at least 97%, at least 98%, or at least 99%, which encode a polypeptide having beta-xylosidase activity.

In another third aspect, the isolated polypeptides having beta-xylosidase activity are encoded by polynucleotides comprising or consisting of nucleotide sequences that have a degree of identity to the mature polypeptide coding sequence of SEQ ID NO: 201 of preferably at least 80%, more preferably at least 85%, even more preferably at least 90%, most preferably at least 95%, and even most preferably at least 96%, at least 97%, at least 98%, or at least 99%, which encode a polypeptide having beta-xylosidase activity.

In another third aspect, the isolated polypeptides having beta-xylosidase activity are encoded by polynucleotides comprising or consisting of nucleotide sequences that have a degree of identity to the mature polypeptide coding sequence of SEQ ID NO: 203 of preferably at least 80%, more preferably at least 85%, even more preferably at least 90%, most preferably at least 95%, and even most preferably at least 96%, at least 97%, at least 98%, or at least 99%, which encode a polypeptide having beta-xylosidase activity.

In another third aspect, the isolated polypeptides having beta-xylosidase activity are encoded by polynucleotides comprising or consisting of nucleotide sequences that have a degree of identity to the mature polypeptide coding sequence of SEQ ID NO: 205 of preferably at least 80%, more preferably at least 85%, even more preferably at least 90%, most preferably at least 95%, and even most preferably at least 96%, at least 97%, at least 98%, or at least 99%, which encode a polypeptide having beta-xylosidase activity.

Techniques used to isolate or clone a polynucleotide encoding a polypeptide are known in the art and include isolation from genomic DNA, preparation from cDNA, or a combination thereof. The cloning of a polynucleotide from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from any strain and thus, for example, may be an allelic or species variant of the polypeptide encoding region of the nucleotide sequence.

In a fourth aspect, the isolated polynucleotides encoding polypeptides having cellobiohydrolase I activity comprise or consist of nucleotide sequences that have a degree of identity to the mature polypeptide coding sequence of SEQ ID NO: 1 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 1. In another aspect, the nucleotide sequence comprises or consists of the sequence contained in *Chaetomium thermophilum* CGMCC 0581. In another aspect, the nucleotide sequence comprises or consists of the mature polypeptide coding sequence of SEQ ID NO: 1. In another aspect, the nucleotide sequence comprises or consists of nucleotides 55 to 1590 of SEQ ID NO: 1. In another aspect, the nucleotide sequence comprises or consists of the mature polypeptide coding sequence contained in *Chaetomium thermophilum* CGMCC 0581.

In another fourth aspect, the isolated polynucleotides encoding polypeptides having cellobiohydrolase I activity comprise or consist of nucleotide sequences that have a degree of identity to the mature polypeptide coding sequence of SEQ ID NO: 3 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 3. In another aspect, the nucleotide sequence comprises or consists of the sequence contained in *Myceliophthora thermophila* CBS 117.65. In another aspect, the nucleotide sequence comprises or consists of the mature polypeptide coding sequence of SEQ ID NO: 3. In another aspect, the nucleotide sequence comprises or consists of nucleotides 61 to 1350 of SEQ ID NO: 3. In another aspect, the nucleotide sequence comprises or consists of the mature polypeptide coding sequence contained in *Myceliophthora thermophila* CBS 117.65.

In another fourth aspect, the isolated polynucleotides encoding polypeptides having cellobiohydrolase I activity comprise or consist of nucleotide sequences that have a degree of identity to the mature polypeptide coding sequence of SEQ ID NO: 5 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 5. In another aspect, the nucleotide sequence comprises or consists of the sequence contained in *Aspergillus fumigatus* NN055679. In another aspect, the nucleotide sequence comprises or consists of the mature polypeptide coding sequence of SEQ ID NO: 5. In another aspect, the nucleotide sequence comprises or consists of nucleotides 79 to 1596 of SEQ ID NO: 5. In another aspect, the nucleotide sequence comprises or consists of the mature polypeptide coding sequence contained in *Aspergillus fumigatus* NN055679.

In another fourth aspect, the isolated polynucleotides encoding polypeptides having cellobiohydrolase I activity comprise or consist of nucleotide sequences that have a degree of identity to the mature polypeptide coding sequence of SEQ ID NO: 7 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 7. In another aspect, the nucleotide sequence comprises or consists of the sequence contained in *Thermoascus aurantiacus* CGMCC 0583. In another aspect, the nucleotide sequence comprises or consists of the mature polypeptide coding sequence of SEQ ID NO: 7. In another aspect, the nucleotide sequence comprises or consists of nucleotides 52 to 1374 of SEQ ID NO: 7. In another aspect, the nucleotide sequence comprises or consists of the mature polypeptide coding sequence contained in *Thermoascus aurantiacus* CGMCC 0583.

In another fourth aspect, the isolated polynucleotides encoding polypeptides having cellobiohydrolase I activity comprise or consist of nucleotide sequences that have a degree of identity to the mature polypeptide coding sequence of SEQ ID NO: 157 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 157. In another aspect, the nucleotide sequence comprises or consists of the sequence contained in *Penicillium emersonii* NN051602. In another aspect, the nucleotide sequence comprises or consists of the mature polypeptide coding sequence of SEQ ID NO: 157. In another aspect, the nucleotide sequence comprises or consists of nucleotides 55 to 1428 of SEQ ID NO: 157. In another aspect, the nucleotide sequence comprises or consists of the mature polypeptide coding sequence contained in *Penicillium emersonii* NN051602

In another fourth aspect, the isolated polynucleotides encoding polypeptides having cellobiohydrolase I activity comprise or consist of nucleotide sequences that have a degree of identity to the mature polypeptide coding sequence of SEQ ID NO: 159 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 159. In another aspect, the nucleotide sequence comprises or consists of the sequence contained in *Penicillium pinophilum* NN046877. In another aspect, the nucleotide sequence comprises or consists of the mature polypeptide coding sequence of SEQ ID NO: 159. In another aspect, the nucleotide sequence comprises or consists of nucleotides 76 to 1590 of SEQ ID NO: 159. In another aspect, the nucleotide sequence comprises or consists of the mature polypeptide coding sequence contained in *Penicillium pinophilum* NN046877.

In another fourth aspect, the isolated polynucleotides encoding polypeptides having cellobiohydrolase I activity comprise or consist of nucleotide sequences that have a degree of identity to the mature polypeptide coding sequence of SEQ ID NO: 161 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 161. In another aspect, the nucleotide sequence comprises or consists of the sequence contained in *Aspergillus terreus* ATCC 28865. In another aspect, the nucleotide sequence comprises or consists of the mature polypeptide coding sequence of SEQ ID NO: 161. In another aspect, the nucleotide sequence comprises or consists of nucleotides 70 to 1675 of SEQ ID NO: 161. In another aspect, the nucleotide sequence comprises or consists of the mature polypeptide coding sequence contained in *Aspergillus terreus* ATCC 28865.

In another fourth aspect, the isolated polynucleotides encoding polypeptides having cellobiohydrolase I activity comprise or consist of nucleotide sequences that have a degree of identity to the mature polypeptide coding sequence of SEQ ID NO: 163 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 163. In another aspect, the nucleotide sequence comprises or consists of the sequence contained in *Neosartorya fischeri* NRRL 181. In another aspect, the nucleotide sequence comprises or consists of the mature polypeptide coding sequence of SEQ ID NO: 163. In another aspect, the nucleotide sequence comprises or consists of nucleotides 79 to 1605 of SEQ ID NO: 163. In another aspect, the nucleotide sequence comprises or consists of the mature polypeptide coding sequence contained in *Neosartorya fischeri* NRRL 181.

In another fourth aspect, the isolated polynucleotides encoding polypeptides having cellobiohydrolase I activity comprise or consist of nucleotide sequences that have a degree of identity to the mature polypeptide coding sequence of SEQ ID NO: 165 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase I activity comprises or consists of the nucleotide sequence of SEQ ID NO: 165. In another aspect, the nucleotide sequence comprises or consists of the sequence contained in *Aspergillus nidulans* strain FGSCA4. In another aspect, the nucleotide sequence comprises or consists of the mature polypeptide coding sequence of SEQ ID NO: 165. In another aspect, the nucleotide sequence comprises or consists of nucleotides 70 to 1578 of SEQ ID NO: 165. In another aspect, the nucleotide sequence comprises or consists of the mature polypeptide coding sequence contained in *Aspergillus nidulans* strain FGSCA4.

In another fourth aspect, the isolated polynucleotides encoding polypeptides having cellobiohydrolase II activity comprise or consist of nucleotide sequences that have a degree of identity to the mature polypeptide coding sequence of SEQ ID NO: 9 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In one aspect, the isolated polynucleotide encoding a polypeptide having cellobiohydrolase II activity comprises or consists of the nucleotide sequence of SEQ ID NO: 9. In another aspect, the nucleotide sequence comprises or consists of the sequence contained in *Myceliophthora thermophila* CBS 117.65. In another aspect, the nucleotide sequence comprises or consists of the mature polypeptide coding sequence of SEQ ID NO: 9. In another aspect, the nucleotide sequence comprises or consists of nucleotides 52 to 1799 of SEQ ID NO: 9. In another aspect, the nucleotide sequence comprises or consists of the mature polypeptide coding sequence contained in *Myceliophthora thermophila* CBS 117.65.

In another fourth aspect, the isolated polynucleotides encoding polypeptides having cellobiohydrolase II activity comprise or consist of nucleotide sequences that have a degree of identity to the mature polypeptide coding sequence of SEQ ID NO: 11 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In one aspect, the isolated polynucleotide encoding a polypeptide having cellobiohydrolase II activity comprises or consists of the nucleotide sequence of SEQ ID NO: 11. In another aspect, the nucleotide sequence comprises or consists of the sequence contained in plasmid pSMai182 which is contained in *E. coli* NRRL B-50059 or contained in *Myceliophthora thermophila* CBS 202.73. In another aspect, the nucleotide sequence comprises or consists of the mature polypeptide coding sequence of SEQ ID NO: 11. In another aspect, the nucleotide sequence comprises or consists of nucleotides 52 to 1809 of SEQ ID NO: 11. In another aspect, the nucleotide sequence comprises or consists of the mature polypeptide coding sequence contained in *Myceliophthora thermophila* CBS 202.73 or contained in plasmid pSMai182 which is contained in *E. coli* NRRL B-50059.

In another fourth aspect, the isolated polynucleotides encoding polypeptides having cellobiohydrolase II activity comprise or consist of nucleotide sequences that have a degree of identity to the mature polypeptide coding sequence of SEQ ID NO: 13 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In one aspect, the isolated polynucleotide encoding a polypeptide having cellobiohydrolase II activity comprises or consists of the nucleotide sequence of SEQ ID NO: 13. In another aspect, the nucleotide sequence comprises or consists of the sequence contained in plasmid pTter6A which is contained in *E. coli* NRRL B-30802. In another aspect, the nucleotide sequence comprises or consists of the mature polypeptide coding sequence of SEQ ID NO: 13. In another aspect, the nucleotide sequence comprises or consists of nucleotides 52 to 1443 of SEQ ID NO: 13. In another aspect, the nucleotide sequence comprises or consists of the mature polypeptide coding sequence contained in plasmid pTter6A which is contained in *E. coli* NRRL B-30802.

In another fourth aspect, the isolated polynucleotides encoding polypeptides having cellobiohydrolase II activity comprise or consist of nucleotide sequences that have a degree of identity to the mature polypeptide coding sequence of SEQ ID NO: 15 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In one aspect, the isolated polynucleotide encoding a polypeptide having cellobiohydrolase II activity comprises or consists of the nucleotide sequence of SEQ ID NO: 15. In another aspect, the nucleotide sequence comprises or consists of the sequence contained in plasmid pMStr199 which is contained in *E. coli* DSM 23379. In another aspect, the nucleotide sequence comprises or consists of the mature polypeptide coding sequence of SEQ ID NO: 15. In another aspect, the nucleotide sequence comprises or consists of nucleotides 109 to 1401 of SEQ ID NO: 15. In another aspect, the nucleotide sequence comprises or consists of the mature polypeptide coding sequence contained in plasmid pMStr199 which is contained in *E. coli* DSM 23379.

In another fourth aspect, the isolated polynucleotides encoding polypeptides having cellobiohydrolase II activity comprise or consist of nucleotide sequences that have a degree of identity to the mature polypeptide coding sequence of SEQ ID NO: 17 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In one aspect, the isolated polynucleotide encoding a polypeptide having cellobiohydrolase II activity comprises or consists of the nucleotide sequence of SEQ ID NO: 17. In another aspect, the nucleotide sequence comprises or consists of the sequence contained in *Aspergillus fumigatus* NN055679. In another aspect, the nucleotide sequence comprises or consists of the mature polypeptide coding sequence of SEQ ID NO: 17. In another aspect, the nucleotide sequence comprises or consists of nucleotides 58 to 1700 of SEQ ID NO: 17. In another aspect, the nucleotide sequence comprises or consists of the mature polypeptide coding sequence contained in *Aspergillus fumigatus* NN055679.

In another fourth aspect, the isolated polynucleotides encoding polypeptides having cellobiohydrolase II activity comprise or consist of nucleotide sequences that have a degree of identity to the mature polypeptide coding sequence of SEQ ID NO: 167 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In one aspect, the isolated polynucleotide encoding a polypeptide having cellobiohydrolase II activity comprises or consists of the nucleotide sequence of SEQ ID NO: 167. In another aspect, the nucleotide sequence comprises or consists of the sequence contained in pGEM-T-CBHI146949-2 which is contained in *E. coli* DSM 24143. In another aspect, the nucleotide sequence comprises or consists of the mature polypeptide coding sequence of SEQ ID NO: 167. In another aspect, the nucleotide sequence comprises or consists of nucleotides 55 to 1749 of SEQ ID NO: 167. In another aspect, the nucleotide sequence comprises or consists of the mature polypeptide coding sequence contained in pGEM-T-CBHI146949-2 which is contained in *E. coli* DSM 24143.

In another fourth aspect, the isolated polynucleotides encoding polypeptides having cellobiohydrolase II activity comprise or consist of nucleotide sequences that have a degree of identity to the mature polypeptide coding sequence of SEQ ID NO: 169 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase II activity.

In one aspect, the isolated polynucleotide encoding a polypeptide having cellobiohydrolase II activity comprises or consists of the nucleotide sequence of SEQ ID NO: 169. In another aspect, the nucleotide sequence comprises or consists of the sequence contained in *Penicillium emersonii* NN051602. In another aspect, the nucleotide sequence comprises or consists of the mature polypeptide coding sequence of SEQ ID NO: 169. In another aspect, the nucleotide sequence comprises or consists of nucleotides 58 to 1744 of SEQ ID NO: 169. In another aspect, the nucleotide sequence comprises or consists of the mature polypeptide coding sequence contained in *Penicillium emersonii* NN051602.

In another fourth aspect, the isolated polynucleotides encoding polypeptides having cellobiohydrolase II activity comprise or consist of nucleotide sequences that have a degree of identity to the mature polypeptide coding sequence of SEQ ID NO: 171 of preferably at least 80%, more preferably at least 85%, even more preferably at least 90%, most preferably at least 95%, and even most preferably at least 96%, at least 97%, at least 98%, or at least 99%, which encode a polypeptide having cellobiohydrolase I activity.

In one aspect, the isolated polynucleotide encoding a polypeptide having cellobiohydrolase II activity comprises or consists of the nucleotide sequence of SEQ ID NO: 171. In another aspect, the nucleotide sequence comprises or consists of the sequence contained in *Penicillium pinophilum* NN046877. In another aspect, the nucleotide sequence comprises or consists of the mature polypeptide coding sequence of SEQ ID NO: 171. In another aspect, the nucleotide sequence comprises or consists of nucleotides 58 to 1701 of SEQ ID NO: 171. In another aspect, the nucleotide sequence comprises or consists of the mature polypeptide coding sequence contained in *Penicillium pinophilum* NN046877.

In another fourth aspect, the isolated polynucleotides encoding polypeptides having endoglucanase I activity comprise or consist of nucleotide sequences that have a degree of identity to the mature polypeptide coding sequence of SEQ ID NO: 19 of preferably at least 80%, more preferably at least 85%, even more preferably at least 90%, most preferably at least 95%, and even most preferably at least 96%, at least 97%, at least 98%, or at least 99%, which encode a polypeptide having endoglucanase I activity.

In one aspect, the isolated polynucleotide encoding a polypeptide having endoglucanase I activity comprises or consists of the nucleotide sequence of SEQ ID NO: 19. In another aspect, the nucleotide sequence comprises or consists of the sequence contained in *Aspergillus terreus* ATCC 28865. In another aspect, the nucleotide sequence comprises or consists of the mature polypeptide coding sequence of SEQ ID NO: 19. In another aspect, the nucleotide sequence comprises or consists of nucleotides 64 to 1502 of SEQ ID NO: 19. In another aspect, the nucleotide sequence comprises or consists of the mature polypeptide coding sequence contained in *Aspergillus terreus* ATCC 28865.

In another fourth aspect, the isolated polynucleotides encoding polypeptides having endoglucanase II activity comprise or consist of nucleotide sequences that have a degree of identity to the mature polypeptide coding sequence of SEQ ID NO: 21 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In one aspect, the isolated polynucleotide encoding a polypeptide having endoglucanase II activity comprises or consists of the nucleotide sequence of SEQ ID NO: 21. In another aspect, the nucleotide sequence comprises or consists of the sequence contained in *Trichoderma reesei* RutC30. In another aspect, the nucleotide sequence comprises or consists of the mature polypeptide coding sequence of SEQ ID NO: 21. In another aspect, the nucleotide sequence comprises or consists of nucleotides 64 to 1254 of SEQ ID NO: 21. In another aspect, the nucleotide sequence comprises or consists of the mature polypeptide coding sequence contained in *Trichoderma reesei* RutC30.

In another fourth aspect, the isolated polynucleotides encoding polypeptides having endoglucanase II activity comprise or consist of nucleotide sequences that have a degree of identity to the mature polypeptide coding sequence of SEQ ID NO: 23 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In one aspect, the isolated polynucleotide encoding a polypeptide having endoglucanase II activity comprises or consists of the nucleotide sequence of SEQ ID NO: 23. In another aspect, the nucleotide sequence comprises or consists of the sequence contained in plasmid pC10161 which is contained in *E. coli* NRRL B-30902. In another aspect, the nucleotide sequence comprises or consists of the mature polypeptide coding sequence of SEQ ID NO: 23. In another aspect, the nucleotide sequence comprises or consists of nucleotides 67 to 1185 of SEQ ID NO: 23. In another aspect, the nucleotide sequence comprises or consists of the mature polypeptide coding sequence contained in plasmid pC10161 which is contained in *E. coli* NRRL B-30902.

In another fourth aspect, the isolated polynucleotides encoding polypeptides having endoglucanase II activity comprise or consist of nucleotide sequences that have a degree of identity to the mature polypeptide coding sequence of SEQ ID NO: 25 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In one aspect, the isolated polynucleotide encoding a polypeptide having endoglucanase II activity comprises or consists of the nucleotide sequence of SEQ ID NO: 25. In another aspect, the nucleotide sequence comprises or consists of the sequence contained in *Thermoascus aurantiacus* CGMCC 0670. In another aspect, the nucleotide sequence comprises or consists of the mature polypeptide coding sequence of SEQ ID NO: 25. In another aspect, the nucleotide sequence comprises or consists of nucleotides 91 to 1005 of SEQ ID NO: In another aspect, the nucleotide sequence comprises or consists of the mature polypeptide coding sequence contained in *Thermoascus aurantiacus* CGMCC 0670.

In another fourth aspect, the isolated polynucleotides encoding polypeptides having endoglucanase II activity comprise or consist of nucleotide sequences that have a degree of identity to the mature polypeptide coding sequence of SEQ ID NO: 173 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In one aspect, the isolated polynucleotide encoding a polypeptide having endoglucanase II activity comprises or consists of the nucleotide sequence of SEQ ID NO: 173. In another aspect, the nucleotide sequence comprises or consists of the sequence contained in p *Aspergillus fumigatus* NN051616. In another aspect, the nucleotide sequence comprises or consists of the mature polypeptide coding sequence of SEQ ID NO: 173. In another aspect, the nucleotide sequence comprises or consists of nucleotides 55 to 1230 of SEQ ID NO: 173. In another aspect, the nucleotide sequence comprises or consists of the mature polypeptide coding sequence contained in *Aspergillus fumigatus* NN051616.

In another fourth aspect, the isolated polynucleotides encoding polypeptides having endoglucanase II activity comprise or consist of nucleotide sequences that have a degree of identity to the mature polypeptide coding sequence of SEQ ID NO: 175 of preferably at least 80%, more preferably at least 85%, even more preferably at least 90%, most preferably at least 95%, and even most preferably at least 96%, at least 97%, at least 98%, or at least 99%, which encode a polypeptide having endoglucanase II activity.

In one aspect, the isolated polynucleotide encoding a polypeptide having endoglucanase II activity comprises or consists of the nucleotide sequence of SEQ ID NO: 175. In another aspect, the nucleotide sequence comprises or consists of the sequence contained in *Neosartorya fischeri* NRRL 181. In another aspect, the nucleotide sequence comprises or consists of the mature polypeptide coding sequence of SEQ ID NO: 175. In another aspect, the nucleotide sequence comprises or consists of nucleotides 49 to 1378 of SEQ ID NO: 175. In another aspect, the nucleotide sequence comprises or consists of the mature polypeptide coding sequence contained in *Neosartorya fischeri* NRRL 181.

In another fourth aspect, the isolated polynucleotides encoding polypeptides having beta-glucosidase activity comprise or consist of nucleotide sequences that have a degree of identity to the mature polypeptide coding sequence of SEQ ID NO: 27 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 27. In another aspect, the nucleotide sequence comprises or consists of the sequence contained in plasmid pEJG113 which is contained in *E. coli* NRRL B-30695. In another aspect, the nucleotide sequence comprises or consists of the mature polypeptide coding sequence of SEQ ID NO: 27. In another aspect, the nucleotide sequence comprises or consists of nucleotides 58 to 2580 of SEQ ID NO: 27. In another aspect, the nucleotide sequence comprises or consists of the mature polypeptide coding sequence contained in plasmid pEJG113 which is contained in *E. coli* NRRL B-30695.

In another fourth aspect, the isolated polynucleotides encoding polypeptides having beta-glucosidase activity comprise or consist of nucleotide sequences that have a degree of identity to the mature polypeptide coding sequence of SEQ ID NO: 29 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 29. In another aspect, the nucleotide sequence comprises or consists of the sequence contained in plasmid pKKAB which is contained in *E. coli* NRRL B-30860. In another aspect, the nucleotide sequence comprises or consists of the mature polypeptide coding sequence of SEQ ID NO: 29. In another aspect, the nucleotide sequence comprises or consists of nucleotides 171 to 2753 of SEQ ID NO: 29. In another aspect, the nucleotide sequence comprises or consists of the mature polypeptide coding sequence contained in plasmid pKKAB which is contained in *E. coli* NRRL B-30860.

In another fourth aspect, the isolated polynucleotides encoding polypeptides having beta-glucosidase activity comprise or consist of nucleotide sequences that have a degree of identity to the mature polypeptide coding sequence of SEQ ID NO: 31 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 31. In another aspect, the nucleotide sequence comprises or consists of the sequence contained in *Aspergillus niger* IBT 10140. In another aspect, the nucleotide sequence comprises or consists of the mature polypeptide coding sequence of SEQ ID NO: 31. In another aspect, the nucleotide sequence comprises or consists of nucleotides 58 to 2934 of SEQ ID NO: 31. In another aspect, the nucleotide sequence comprises or consists of the mature polypeptide coding sequence contained in *Aspergillus niger* IBT 10140.

In another fourth aspect, the isolated polynucleotides encoding polypeptides having beta-glucosidase activity comprise or consist of nucleotide sequences that have a degree of identity to the mature polypeptide coding sequence of SEQ ID NO: 177 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 177. In another aspect, the nucleotide sequence comprises or consists of the sequence contained in *Aspergillus aculeatus* WDCM190. In another aspect, the nucleotide sequence comprises or consists of the mature polypeptide coding sequence of SEQ ID NO: 177. In another aspect, the nucleotide sequence comprises or consists of nucleotides 58 to 2937 of SEQ ID NO: 177. In another aspect, the nucleotide sequence comprises or consists of the mature polypeptide coding sequence contained in *Aspergillus aculeatus* WDCM190.

In another fourth aspect, the isolated polynucleotides encoding polypeptides having beta-glucosidase activity comprise or consist of nucleotide sequences that have a degree of identity to the mature polypeptide coding sequence of SEQ ID NO: 179 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 179. In another aspect, the nucleotide sequence comprises or consists of the sequence contained in *Aspergillus kawashii* IFO4308. In another aspect, the nucleotide sequence comprises or consists of the mature polypeptide coding sequence of SEQ ID NO: 179. In another aspect, the nucleotide sequence comprises or consists of nucleotides 58 to 2932 of SEQ ID NO: 179. In another aspect, the nucleotide sequence comprises or consists of the mature polypeptide coding sequence contained in *Aspergillus kawashii* IFO4308.

In another fourth aspect, the isolated polynucleotides encoding polypeptides having beta-glucosidase activity comprise or consist of nucleotide sequences that have a degree of identity to the mature polypeptide coding sequence of SEQ ID NO: 181 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 181. In another aspect, the nucleotide sequence comprises or consists of the sequence contained in p *Aspergillus clavatus* NRRL 1. In another aspect, the nucleotide sequence comprises or consists of the mature polypeptide coding sequence of SEQ ID NO: 181. In another aspect, the nucleotide sequence comprises or consists of nucleotides 55 to 3059 of SEQ ID NO: 181. In another aspect, the nucleotide sequence comprises or consists of the mature polypeptide coding sequence contained in *Aspergillus clavatus* NRRL 1.

In another fourth aspect, the isolated polynucleotides encoding polypeptides having beta-glucosidase activity comprise or consist of nucleotide sequences that have a degree of identity to the mature polypeptide coding sequence of SEQ ID NO: 183 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 183. In another aspect, the nucleotide sequence comprises or consists of the sequence contained in *Thielavia terrestris* NRRL 8126. In another aspect, the nucleotide sequence comprises or consists of the mature polypeptide coding sequence of SEQ ID NO: 183. In another aspect, the nucleotide sequence comprises or consists of nucleotides 55 to 3029 of SEQ ID NO: 183. In another aspect, the nucleotide sequence comprises or consists of the mature polypeptide coding sequence contained in *Thielavia terrestris* NRRL 8126.

In another fourth aspect, the isolated polynucleotides encoding polypeptides having beta-glucosidase activity comprise or consist of nucleotide sequences that have a degree of identity to the mature polypeptide coding sequence of SEQ ID NO: 185 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 185. In another aspect, the nucleotide sequence comprises or consists of the sequence contained in pUC19 D55EX which is contained in *E. coli* NRRL B-50395. In another aspect, the nucleotide sequence comprises or consists of the mature polypeptide coding sequence of SEQ ID NO: 185. In another aspect, the nucleotide sequence comprises or consists of nucleotides 64 to 2790 of SEQ ID NO: 185. In another aspect, the nucleotide sequence comprises or consists of the mature polypeptide coding sequence contained in pUC19 D55EX which is contained in *E. coli* NRRL B-50395.

In another fourth aspect, the isolated polynucleotides encoding polypeptides having beta-glucosidase activity comprise or consist of nucleotide sequences that have a degree of identity to the mature polypeptide coding sequence of SEQ ID NO: 187 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 187. In another aspect, the nucleotide sequence comprises or consists of the sequence contained in *Penicillium oxalicum*. In another aspect, the nucleotide sequence comprises or consists of the mature polypeptide coding sequence of SEQ ID NO: 187. In another aspect, the nucleotide sequence comprises or consists of nucleotides 64 to 2790 of SEQ ID NO: 187. In another aspect, the nucleotide sequence comprises or consists of the mature polypeptide coding sequence contained in *Penicillium oxalicum*.

In another fourth aspect, the isolated polynucleotides encoding polypeptides having beta-glucosidase activity comprise or consist of nucleotide sequences that have a degree of identity to the mature polypeptide coding sequence of SEQ ID NO: 189 of preferably at least 80%, more preferably at least 85%, even more preferably at least 90%, most preferably at least 95%, and even most preferably at least 96%, at least 97%, at least 98%, or at least 99%, which encode a polypeptide having beta-glucosidase activity.

In one aspect, the isolated polynucleotide encoding a polypeptide having beta-glucosidase activity comprises or consists of the nucleotide sequence of SEQ ID NO: 189. In another aspect, the nucleotide sequence comprises or consists of the sequence contained in *Talaromyces emersonii* CBS 549.92. In another aspect, the nucleotide sequence comprises or consists of the mature polypeptide coding sequence of SEQ ID NO: 189. In another aspect, the nucleotide sequence comprises or consists of nucleotides 58 to 2961 of SEQ ID NO: 189. In another aspect, the nucleotide sequence comprises or consists of the mature polypeptide coding sequence contained in *Talaromyces emersonii* CBS 549.92.

In another fourth aspect, the isolated polynucleotides encoding GH61 polypeptides having cellulolytic enhancing activity comprise or consist of nucleotide sequences that have a degree of identity to the mature polypeptide coding sequence of SEQ ID NO: 33 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In one aspect, the isolated polynucleotide encoding a polypeptide having cellulolytic enhancing activity comprises or consists of the nucleotide sequence of SEQ ID NO: 33. In another aspect, the nucleotide sequence comprises or consists of the sequence contained in plasmid pDZA2-7 which is contained in *E. coli* NRRL B-30704. In another aspect, the nucleotide sequence comprises or consists of the mature polypeptide coding sequence of SEQ ID NO: 33. In another aspect, the nucleotide sequence comprises or consists of nucleotides 67 to 796 of SEQ ID NO: 33. In another aspect, the nucleotide sequence comprises or consists of the mature polypeptide coding sequence contained in plasmid pDZA2-7 which is contained in *E. coli* NRRL B-30704.

In another fourth aspect, the isolated polynucleotides encoding GH61 polypeptides having cellulolytic enhancing activity comprise or consist of nucleotide sequences that have a degree of identity to the mature polypeptide coding sequence of SEQ ID NO: 35 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In one aspect, the isolated polynucleotide encoding a polypeptide having cellulolytic enhancing activity comprises or consists of the nucleotide sequence of SEQ ID NO: 35. In another aspect, the nucleotide sequence comprises or consists of the sequence contained in plasmid pTter61E which is contained in *E. coli* NRRL B-30814. In another aspect, the nucleotide sequence comprises or consists of the mature polypeptide coding sequence of SEQ ID NO: 35. In another aspect, the nucleotide sequence comprises or consists of nucleotides 58 to 900 of SEQ ID NO: 35. In another aspect, the nucleotide sequence comprises or consists of the mature polypeptide coding sequence contained in plasmid pTter61E which is contained in *E. coli* NRRL B-30814.

In another fourth aspect, the isolated polynucleotides encoding GH61 polypeptides having cellulolytic enhancing activity comprise or consist of nucleotide sequences that have a degree of identity to the mature polypeptide coding sequence of SEQ ID NO: 37 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In one aspect, the isolated polynucleotide encoding a polypeptide having cellulolytic enhancing activity comprises or consists of the nucleotide sequence of SEQ ID NO: 37. In another aspect, the nucleotide sequence comprises or consists of the sequence contained in *Aspergillus fumigatus* NN051616. In another aspect, the nucleotide sequence comprises or consists of the mature polypeptide coding sequence of SEQ ID NO: 37. In another aspect, the nucleotide sequence comprises or consists of nucleotides 64 to 859 of SEQ ID NO: 37. In another aspect, the nucleotide sequence comprises or consists of the mature polypeptide coding sequence contained in *Aspergillus fumigatus* NN051616.

In another fourth aspect, the isolated polynucleotides encoding GH61 polypeptides having cellulolytic enhancing activity comprise or consist of nucleotide sequences that have a degree of identity to the mature polypeptide coding sequence of SEQ ID NO: 39 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In one aspect, the isolated polynucleotide encoding a polypeptide having cellulolytic enhancing activity comprises or consists of the nucleotide sequence of SEQ ID NO: 39. In another aspect, the nucleotide sequence comprises or consists of the sequence contained in plasmid pGEM-T-Ppin7 which is contained in *E. coli* DSM 22711. In another aspect, the nucleotide sequence comprises or consists of the mature polypeptide coding sequence of SEQ ID NO: 39. In another aspect, the nucleotide sequence comprises or consists of nucleotides 64 to 1018 of SEQ ID NO: 39. In another aspect, the nucleotide sequence comprises or consists of the mature polypeptide coding sequence contained in plasmid pGEM-T-Ppin7 which is contained in *E. coli* DSM 22711.

In another fourth aspect, the isolated polynucleotides encoding GH61 polypeptides having cellulolytic enhancing activity comprise or consist of nucleotide sequences that have a degree of identity to the mature polypeptide coding sequence of SEQ ID NO: 41 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In one aspect, the isolated polynucleotide encoding a polypeptide having cellulolytic enhancing activity comprises or consists of the nucleotide sequence of SEQ ID NO: 41. In another aspect, the nucleotide sequence comprises or consists of the sequence contained in plasmid pGEM-T-GH61D23Y4 which is contained in *E. coli* DSM 22882. In another aspect, the nucleotide sequence comprises or consists of the mature polypeptide coding sequence of SEQ ID NO: 41. In another aspect, the nucleotide sequence comprises or consists of nucleotides 76 to 832 of SEQ ID NO:

41. In another aspect, the nucleotide sequence comprises or consists of the mature polypeptide coding sequence contained in plasmid pGEM-T-GH61D23Y4 which is contained in *E. coli* DSM 22882.

In another fourth aspect, the isolated polynucleotides encoding GH61 polypeptides having cellulolytic enhancing activity comprise or consist of nucleotide sequences that have a degree of identity to the mature polypeptide coding sequence of SEQ ID NO: 43 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

In one aspect, the isolated polynucleotide encoding a polypeptide having cellulolytic enhancing activity comprises or consists of the nucleotide sequence of SEQ ID NO: 43. In another aspect, the nucleotide sequence comprises or consists of the sequence contained in plasmid pAG68 which is contained in *E. coli* NRRL B-50320. In another aspect, the nucleotide sequence comprises or consists of the mature polypeptide coding sequence of SEQ ID NO: 43. In another aspect, the nucleotide sequence comprises or consists of nucleotides 64 to 1104 of SEQ ID NO: 43. In another aspect, the nucleotide sequence comprises or consists of the mature polypeptide coding sequence contained in plasmid pAG68 which is contained in *E. coli* NRRL B-50320.

In another fourth aspect, the isolated polynucleotides encoding GH61 polypeptides having cellulolytic enhancing activity comprise or consist of nucleotide sequences that have a degree of identity to the mature polypeptide coding sequence of SEQ ID NO: 191 of preferably at least 80%, more preferably at least 85%, even more preferably at least 90%, most preferably at least 95%, and even most preferably at least 96%, at least 97%, at least 98%, or at least 99%, which encode a GH61 polypeptide having cellulolytic enhancing activity.

In one aspect, the isolated polynucleotide encoding a GH61 polypeptide having cellulolytic enhancing activity comprises or consists of the nucleotide sequence of SEQ ID NO: 191. In another aspect, the nucleotide sequence comprises or consists of the sequence contained in pGEM-T-GH61a51486 which is contained in *E. coli* DSM 22656. In another aspect, the nucleotide sequence comprises or consists of the mature polypeptide coding sequence of SEQ ID NO: 191. In another aspect, the nucleotide sequence comprises or consists of nucleotides 67 to 868 of SEQ ID NO: 191. In another aspect, the nucleotide sequence comprises or consists of the mature polypeptide coding sequence contained in pGEM-T-GH61a51486 which is contained in *E. coli* NRRL DSM 22656.

In another fourth aspect, the isolated polynucleotides encoding polypeptides having xylanase activity comprise or consist of nucleotide sequences that have a degree of identity to the mature polypeptide coding sequence of SEQ ID NO: 45 of preferably at least 80%, more preferably at least 85%, even more preferably at least 90%, most preferably at least 95%, and even most preferably at least 96%, at least 97%, at least 98%, or at least 99%, which encode an active polypeptide.

In one aspect, the isolated polynucleotide encoding a polypeptide having xylanase activity comprises or consists of the nucleotide sequence of SEQ ID NO: 45. In another aspect, the nucleotide sequence comprises or consists of the sequence contained in Aspergillus *aculeatus* CBS 101.43. In another aspect, the nucleotide sequence comprises or consists of the mature polypeptide coding sequence of SEQ ID NO: 45. In another aspect, the nucleotide sequence comprises or consists of nucleotides 69 to 1314 of SEQ ID NO: 45. In another aspect, the nucleotide sequence comprises or consists of the mature polypeptide coding sequence contained in Aspergillus *aculeatus* CBS 101.43.

In another fourth aspect, the isolated polynucleotides encoding polypeptides having xylanase activity comprise or consist of nucleotide sequences that have a degree of identity to the mature polypeptide coding sequence of SEQ ID NO: 47 of preferably at least 80%, more preferably at least 85%, even more preferably at least 90%, most preferably at least 95%, and even most preferably at least 96%, at least 97%, at least 98%, or at least 99%, which encode an active polypeptide.

In one aspect, the isolated polynucleotide encoding a polypeptide having xylanase activity comprises or consists of the nucleotide sequence of SEQ ID NO: 47. In another aspect, the nucleotide sequence comprises or consists of the sequence contained in plasmid pHyGe009 which is contained in *E. coli* NRRL B-30703. In another aspect, the nucleotide sequence comprises or consists of the mature polypeptide coding sequence of SEQ ID NO: 47. In another aspect, the nucleotide sequence comprises or consists of nucleotides 107 to 1415 of SEQ ID NO: 47. In another aspect, the nucleotide sequence comprises or consists of the mature polypeptide coding sequence contained in plasmid pHyGe009 which is contained in *E. coli* NRRL B-30703.

In another fourth aspect, the isolated polynucleotides encoding polypeptides having xylanase activity comprise or consist of nucleotide sequences that have a degree of identity to the mature polypeptide coding sequence of SEQ ID NO: 49 of preferably at least 80%, more preferably at least 85%, even more preferably at least 90%, most preferably at least 95%, and even most preferably at least 96%, at least 97%, at least 98%, or at least 99%, which encode an active polypeptide.

In one aspect, the isolated polynucleotide encoding a polypeptide having xylanase activity comprises or consists of the nucleotide sequence of SEQ ID NO: 49. In another aspect, the nucleotide sequence comprises or consists of the sequence contained in plasmid pTF12Xy1170 which is contained in *E. coli* NRRL B-50309. In another aspect, the nucleotide sequence comprises or consists of the mature polypeptide coding sequence of SEQ ID NO: 49. In another aspect, the nucleotide sequence comprises or consists of nucleotides 58 to 1194 of SEQ ID NO: 49. In another aspect, the nucleotide sequence comprises or consists of the mature polypeptide coding sequence contained in plasmid pTF12Xy1170 which is contained in *E. coli* NRRL B-50309.

In another fourth aspect, the isolated polynucleotides encoding polypeptides having xylanase activity comprise or consist of nucleotide sequences that have a degree of identity to the mature polypeptide coding sequence of SEQ ID NO: 51 of preferably at least 80%, more preferably at least 85%, even more preferably at least 90%, most preferably at least 95%, and even most preferably at least 96%, at least 97%, at least 98%, or at least 99%, which encode an active polypeptide.

In one aspect, the isolated polynucleotide encoding a polypeptide having xylanase activity comprises or consists of the nucleotide sequence of SEQ ID NO: 51. In another aspect, the nucleotide sequence comprises or consists of the sequence contained in plasmid pGEM-T-Ppin3 which is contained in *E. coli* DSM 22922. In another aspect, the nucleotide sequence comprises or consists of the mature polypeptide coding sequence of SEQ ID NO: 51. In another aspect, the nucleotide sequence comprises or consists of nucleotides 58 to 1439 of SEQ ID NO: 51. In another aspect, the nucleotide sequence comprises or consists of the mature polypeptide coding sequence contained in plasmid pGEM-T-Ppin3 which is contained in *E. coli* DSM 22922.

In another fourth aspect, the isolated polynucleotides encoding polypeptides having xylanase activity comprise or consist of nucleotide sequences that have a degree of identity to the mature polypeptide coding sequence of SEQ ID NO: 53 of preferably at least 80%, more preferably at least 85%, even more preferably at least 90%, most preferably at least 95%, and even most preferably at least 96%, at least 97%, at least 98%, or at least 99%, which encode an active polypeptide.

In one aspect, the isolated polynucleotide encoding a polypeptide having xylanase activity comprises or consists of the nucleotide sequence of SEQ ID NO: 53. In another aspect, the nucleotide sequence comprises or consists of the sequence contained in *Thielavia terrestris* NRRL 8126. In another aspect, the nucleotide sequence comprises or consists of the mature polypeptide coding sequence of SEQ ID NO: 53. In another aspect, the nucleotide sequence comprises or consists of nucleotides 58 to 1185 of SEQ ID NO: 53. In another aspect, the nucleotide sequence comprises or consists of the mature polypeptide coding sequence contained in *Thielavia terrestris* NRRL 8126.

In another fourth aspect, the isolated polynucleotides encoding polypeptides having xylanase activity comprise or consist of nucleotide sequences that have a degree of identity to the mature polypeptide coding sequence of SEQ ID NO: 193 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In one aspect, the isolated polynucleotide encoding a polypeptide having xylanase activity comprises or consists of the nucleotide sequence of SEQ ID NO: 193. In another aspect, the nucleotide sequence comprises or consists of the sequence contained in *Talaromyces emersonii* NN05002. In another aspect, the nucleotide sequence comprises or consists of the mature polypeptide coding sequence of SEQ ID NO: 193. In another aspect, the nucleotide sequence comprises or consists of nucleotides 70 to 1383 of SEQ ID NO: 193. In another aspect, the nucleotide sequence comprises or consists of the mature polypeptide coding sequence contained in *Talaromyces emersonii* NN05002.

In another fourth aspect, the isolated polynucleotides encoding polypeptides having xylanase activity comprise or consist of nucleotide sequences that have a degree of identity to the mature polypeptide coding sequence of SEQ ID NO: 195 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In one aspect, the isolated polynucleotide encoding a polypeptide having xylanase activity comprises or consists of the nucleotide sequence of SEQ ID NO: 195. In another aspect, the nucleotide sequence comprises or consists of the sequence contained in pMMar26 which is contained in *E. coli* NRRL B-50266. In another aspect, the nucleotide sequence comprises or consists of the mature polypeptide coding sequence of SEQ ID NO: 195. In another aspect, the nucleotide sequence comprises or consists of nucleotides 70 to 1384 of SEQ ID NO: 195. In another aspect, the nucleotide sequence comprises or consists of the mature polypeptide coding sequence contained in pMMar26 which is contained in *E. coli* NRRL B-50266.

In another fourth aspect, the isolated polynucleotides encoding polypeptides having xylanase activity comprise or consist of nucleotide sequences that have a degree of identity to the mature polypeptide coding sequence of SEQ ID NO: 197 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In one aspect, the isolated polynucleotide encoding a polypeptide having xylanase activity comprises or consists of the nucleotide sequence of SEQ ID NO: 197. In another aspect, the nucleotide sequence comprises or consists of the sequence contained in *E. coli* DSM 10361. In another aspect, the nucleotide sequence comprises or consists of the mature polypeptide coding sequence of SEQ ID NO: 197. In another aspect, the nucleotide sequence comprises or consists of nucleotides 58 to1188 of SEQ ID NO: 197. In another aspect, the nucleotide sequence comprises or consists of the mature polypeptide coding sequence contained in *E. coli* DSM 10361.

In another fourth aspect, the isolated polynucleotides encoding polypeptides having xylanase activity comprise or consist of nucleotide sequences that have a degree of identity to the mature polypeptide coding sequence of SEQ ID NO: 55 of preferably at least 80%, more preferably at least 85%, even more preferably at least 90%, most preferably at least 95%, and even most preferably at least 96%, at least 97%, at least 98%, or at least 99%, which encode an active polypeptide.

In one aspect, the isolated polynucleotide encoding a polypeptide having xylanase activity comprises or consists of the nucleotide sequence of SEQ ID NO: 55. In another aspect, the nucleotide sequence comprises or consists of the sequence contained in Thermobifida *fusca* DSM 22883. In another aspect, the nucleotide sequence comprises or consists of the mature polypeptide coding sequence of SEQ ID NO: 55. In another aspect, the nucleotide sequence comprises or consists of nucleotides 127 to 1014 of SEQ ID NO: 55. In another aspect, the nucleotide sequence comprises or consists of the mature polypeptide coding sequence contained in Thermobifida *fusca* DSM 22883.

In another fourth aspect, the isolated polynucleotides encoding polypeptides having xylanase activity comprise or consist of nucleotide sequences that have a degree of identity to the mature polypeptide coding sequence of SEQ ID NO: 199 or SEQ ID NO: 304 of preferably at least 80%, more preferably at least 85%, even more preferably at least 90%, most preferably at least 95%, and even most preferably at least 96%, at least 97%, at least 98%, or at least 99%, which encode a polypeptide having xylanase activity.

In one aspect, the isolated polynucleotide encoding a polypeptide having xylanase activity comprises or consists of the nucleotide sequence of SEQ ID NO: 199 or SEQ ID NO: 304. In another aspect, the nucleotide sequence comprises or consists of the sequence contained in *Dictyoglomus thermophilum* ATCC 35947. In another aspect, the nucleotide sequence comprises or consists of the mature polypeptide coding sequence of SEQ ID NO: 199 or SEQ ID NO: 304. In another aspect, the nucleotide sequence comprises or consists of nucleotides 76 to 1137 of SEQ ID NO: 199 or nucleotides 85 to 693 of SEQ ID NO: 304. In another aspect, the nucleotide sequence comprises or consists of the mature polypeptide coding sequence contained in *Dictyoglomus thermophilum* ATCC 35947.

In another fourth aspect, the isolated polynucleotides encoding polypeptides having beta-xylosidase activity comprise or consist of nucleotide sequences that have a degree of identity to the mature polypeptide coding sequence of SEQ ID NO: 57 of preferably at least 80%, more preferably at least 85%, even more preferably at least 90%, most preferably at least 95%, and even most preferably at least 96%, at least 97%, at least 98%, or at least 99%, which encode an active polypeptide.

In one aspect, the isolated polynucleotide encoding a polypeptide having beta-xylosidase activity comprises or consists of the nucleotide sequence of SEQ ID NO: 57. In another aspect, the nucleotide sequence comprises or consists of the sequence contained in *Trichoderma reesei* RutC30. In another aspect, the nucleotide sequence comprises or consists of the mature polypeptide coding sequence of SEQ ID NO: 57. In another aspect, the nucleotide sequence comprises or consists of nucleotides 61 to 2391 of SEQ ID NO: 57. In another aspect, the nucleotide sequence comprises or consists of the mature polypeptide coding sequence contained in *Trichoderma reesei* RutC30.

In another fourth aspect, the isolated polynucleotides encoding polypeptides having beta-xylosidase activity comprise or consist of nucleotide sequences that have a degree of identity to the mature polypeptide coding sequence of SEQ ID NO: 59 of preferably at least 80%, more preferably at least 85%, even more preferably at least 90%, most preferably at least 95%, and even most preferably at least 96%, at least 97%, at least 98%, or at least 99%, which encode an active polypeptide.

In one aspect, the isolated polynucleotide encoding a polypeptide having beta-xylosidase activity comprises or consists of the nucleotide sequence of SEQ ID NO: 59. In another aspect, the nucleotide sequence comprises or consists of the sequence contained in *Talaromyces emersonii* CBS 393.64. In another aspect, the nucleotide sequence comprises or consists of the mature polypeptide coding sequence of SEQ ID NO: 59. In another aspect, the nucleotide sequence comprises or consists of nucleotides 64 to 2388 of SEQ ID NO: 59. In another aspect, the nucleotide sequence comprises or consists of the mature polypeptide coding sequence contained in *Talaromyces emersonii* CBS 393.64.

In another fourth aspect, the isolated polynucleotides encoding polypeptides having beta-xylosidase activity comprise or consist of nucleotide sequences that have a degree of identity to the mature polypeptide coding sequence of SEQ ID NO: 201 of preferably at least 80%, more preferably at least 85%, even more preferably at least 90%, most preferably at least 95%, and even most preferably at least 96%, at least 97%, at least 98%, or at least 99%, which encode a polypeptide having beta-xylosidase activity.

In one aspect, the isolated polynucleotide encoding a polypeptide having beta-xylosidase activity comprises or consists of the nucleotide sequence of SEQ ID NO: 201. In another aspect, the nucleotide sequence comprises or consists of the sequence contained in *Aspergillus aculeatus* CBS 172.66. In another aspect, the nucleotide sequence comprises or consists of the mature polypeptide coding sequence of SEQ ID NO: 201. In another aspect, the nucleotide sequence comprises or consists of nucleotides 52 to 2409 of SEQ ID NO: 201. In another aspect, the nucleotide sequence comprises or consists of the mature polypeptide coding sequence contained in *Aspergillus aculeatus* CBS 172.66.

In another fourth aspect, the isolated polynucleotides encoding polypeptides having beta-xylosidase activity comprise or consist of nucleotide sequences that have a degree of identity to the mature polypeptide coding sequence of SEQ ID NO: 203 of preferably at least 80%, more preferably at least 85%, even more preferably at least 90%, most preferably at least 95%, and even most preferably at least 96%, at least 97%, at least 98%, or at least 99%, which encode a polypeptide having beta-xylosidase activity.

In one aspect, the isolated polynucleotide encoding a polypeptide having beta-xylosidase activity comprises or consists of the nucleotide sequence of SEQ ID NO: 203. In another aspect, the nucleotide sequence comprises or consists of the sequence contained in *Aspergillus aculeatus* CBS 186.67. In another aspect, the nucleotide sequence comprises or consists of the mature polypeptide coding sequence of SEQ ID NO: 203. In another aspect, the nucleotide sequence comprises or consists of nucleotides 52 to 2451 of SEQ ID NO: 203. In another aspect, the nucleotide sequence comprises or consists of the mature polypeptide coding sequence contained in *Aspergillus aculeatus* CBS 186.67.

In another fourth aspect, the isolated polynucleotides encoding polypeptides having beta-xylosidase activity comprise or consist of nucleotide sequences that have a degree of identity to the mature polypeptide coding sequence of SEQ ID NO: 205 of preferably at least 80%, more preferably at least 85%, even more preferably at least 90%, most preferably at least 95%, and even most preferably at least 96%, at least 97%, at least 98%, or at least 99%, which encode a polypeptide having beta-xylosidase activity.

In one aspect, the isolated polynucleotide encoding a polypeptide having beta-xylosidase activity comprises or consists of the nucleotide sequence of SEQ ID NO: 205. In another aspect, the nucleotide sequence comprises or consists of the sequence contained in *Aspergillus fumigatus* NN051616. In another aspect, the nucleotide sequence comprises or consists of the mature polypeptide coding sequence of SEQ ID NO: 205. In another aspect, the nucleotide sequence comprises or consists of nucleotides 61 to 2376 of SEQ ID NO: 205. In another aspect, the nucleotide sequence comprises or consists of the mature polypeptide coding sequence contained in *Aspergillus fumigatus* NN051616.

In a fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 1, (ii) the genomic DNA sequence of the mature polypeptide coding sequence of SEQ ID NO: 1, or (iii) a full-length complementary strand of (i) or (ii).

In another fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 3, (ii) the genomic DNA sequence of the mature polypeptide coding sequence of SEQ ID NO: 3, or (iii) a full-length complementary strand of (i) or (ii).

In another fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 5, (ii) the cDNA sequence of the mature polypeptide coding sequence of SEQ ID NO: 5, or (iii) a full-length complementary strand of (i) or (ii).

In another fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 7, (ii) the genomic DNA sequence of the mature polypeptide coding sequence of SEQ ID NO: 7, or (iii) a full-length complementary strand of (i) or (ii).

In another fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 157, (ii) the cDNA sequence of the mature polypeptide coding sequence of SEQ ID NO: 157, or (iii) a full-length complementary strand of (i) or (ii).

In another fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 159, (ii) the cDNA sequence of the mature polypeptide coding sequence of SEQ ID NO: 159, or (iii) a full-length complementary strand of (i) or (ii).

In another fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 161, (ii) the cDNA sequence of the mature polypeptide coding sequence of SEQ ID NO: 161, or (iii) a full-length complementary strand of (i) or (ii).

In another fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 163, (ii) the cDNA sequence of the mature polypeptide coding sequence of SEQ ID NO: 163, or (iii) a full-length complementary strand of (i) or (ii).

In another fifth aspect, the isolated polynucleotides encoding polypeptides having cellobiohydrolase I activity hybridize under preferably medium-high stringency conditions, more preferably high stringency conditions, and most preferably very high stringency conditions with (i) the mature polypeptide coding sequence of SEQ ID NO: 165, (ii) the cDNA sequence of the mature polypeptide coding sequence of SEQ ID NO: 165, or (iii) a full-length complementary strand of (i) or (ii).

In another fifth aspect, the isolated polynucleotides encoding polypeptides having cellobiohydrolase II activity hybridize under preferably medium-high stringency conditions, more preferably high stringency conditions, and most preferably very high stringency conditions with (i) the mature polypeptide coding sequence of SEQ ID NO: 9, (ii) the cDNA sequence of the mature polypeptide coding sequence of SEQ ID NO: 9, or (iii) a full-length complementary strand of (i) or (ii).

In another fifth aspect, the isolated polynucleotides encoding polypeptides having cellobiohydrolase II activity hybridize under preferably medium-high stringency conditions, more preferably high stringency conditions, and most preferably very high stringency conditions with (i) the mature polypeptide coding sequence of SEQ ID NO: 11, (ii) the cDNA sequence of the mature polypeptide coding sequence of SEQ ID NO: 11, or (iii) a full-length complementary strand of (i) or (ii).

In another fifth aspect, the isolated polynucleotides encoding polypeptides having cellobiohydrolase II activity hybridize under preferably medium-high stringency conditions, more preferably high stringency conditions, and most preferably very high stringency conditions with (i) the mature polypeptide coding sequence of SEQ ID NO: 13, (ii) the genomic DNA sequence of the mature polypeptide coding sequence of SEQ ID NO: 13, or (iii) a full-length complementary strand of (i) or (ii).

In another fifth aspect, the isolated polynucleotides encoding polypeptides having cellobiohydrolase II activity hybridize under preferably medium-high stringency conditions, more preferably high stringency conditions, and most preferably very high stringency conditions with (i) the mature polypeptide coding sequence of SEQ ID NO: 15, (ii) the genomic DNA sequence of the mature polypeptide coding sequence of SEQ ID NO: 15, or (iii) a full-length complementary strand of (i) or (ii).

In another fifth aspect, the isolated polynucleotides encoding polypeptides having cellobiohydrolase II activity hybridize under preferably medium-high stringency conditions, more preferably high stringency conditions, and most preferably very high stringency conditions with (i) the mature polypeptide coding sequence of SEQ ID NO: 17, (ii) the cDNA sequence of the mature polypeptide coding sequence of SEQ ID NO: 17, or (iii) a full-length complementary strand of (i) or (ii).

In another fifth aspect, the isolated polynucleotides encoding polypeptides having cellobiohydrolase II activity hybridize under preferably medium-high stringency conditions, more preferably high stringency conditions, and most preferably very high stringency conditions with (i) the mature polypeptide coding sequence of SEQ ID NO: 167, (ii) the cDNA sequence of the mature polypeptide coding sequence of SEQ ID NO: 167, or (iii) a full-length complementary strand of (i) or (ii).

In another fifth aspect, the isolated polynucleotides encoding polypeptides having cellobiohydrolase II activity hybridize under preferably medium-high stringency conditions, more preferably high stringency conditions, and most preferably very high stringency conditions with (i) the mature polypeptide coding sequence of SEQ ID NO: 169, (ii) the cDNA sequence of the mature polypeptide coding sequence of SEQ ID NO: 169, or (iii) a full-length complementary strand of (i) or (ii).

In another fifth aspect, the isolated polynucleotides encoding polypeptides having cellobiohydrolase II activity hybridize under preferably medium-high stringency conditions, more preferably high stringency conditions, and most preferably very high stringency conditions with (i) the mature polypeptide coding sequence of SEQ ID NO: 171, (ii) the cDNA sequence of the mature polypeptide coding sequence of SEQ ID NO: 171, or (iii) a full-length complementary strand of (i) or (ii).

In another fifth aspect, the isolated polynucleotides encoding polypeptides having endoglucanase I activity hybridize under preferably medium-high stringency conditions, more preferably high stringency conditions, and most preferably very high stringency conditions with (i) the mature polypeptide coding sequence of SEQ ID NO: 19, (ii) the cDNA sequence of the mature polypeptide coding sequence of SEQ ID NO: 19, or (iii) a full-length complementary strand of (i) or (ii).

In another fifth aspect, the isolated polynucleotides encoding polypeptides having endoglucanase II activity hybridize under preferably medium-high stringency conditions, more preferably high stringency conditions, and most preferably very high stringency conditions with (i) the mature polypeptide coding sequence of SEQ ID NO: 21, (ii) the genomic DNA sequence of the mature polypeptide coding sequence of SEQ ID NO: 21, or (iii) a full-length complementary strand of (i) or (ii).

In another fifth aspect, the isolated polynucleotides encoding polypeptides having endoglucanase II activity hybridize under preferably medium-high stringency conditions, more preferably high stringency conditions, and most preferably very high stringency conditions with (i) the mature polypeptide coding sequence of SEQ ID NO: 23, (ii) the cDNA sequence of the mature polypeptide coding sequence of SEQ ID NO: 23, or (iii) a full-length complementary strand of (i) or (ii).

In another fifth aspect, the isolated polynucleotides encoding polypeptides having endoglucanase II activity hybridize under preferably medium-high stringency conditions, more preferably high stringency conditions, and most preferably very high stringency conditions with (i) the mature polypeptide coding sequence of SEQ ID NO: 25, (ii) the genomic DNA sequence of the mature polypeptide coding sequence of SEQ ID NO: 25, or (iii) a full-length complementary strand of (i) or (ii).

In another fifth aspect, the isolated polynucleotides encoding polypeptides having endoglucanase II activity hybridize under preferably medium-high stringency conditions, more preferably high stringency conditions, and most preferably very high stringency conditions with (i) the mature polypeptide coding sequence of SEQ ID NO: 173, (ii) the cDNA sequence of the mature polypeptide coding sequence of SEQ ID NO: 173, or (iii) a full-length complementary strand of (i) or (ii).

In another fifth aspect, the isolated polynucleotides encoding polypeptides having endoglucanase II activity hybridize under preferably medium-high stringency conditions, more preferably high stringency conditions, and most preferably very high stringency conditions with (i) the mature polypeptide coding sequence of SEQ ID NO: 175, (ii) the cDNA sequence of the mature polypeptide coding sequence of SEQ ID NO: 175, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 27, (ii) the cDNA sequence of the mature polypeptide coding sequence of SEQ ID NO: 27, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 29, (ii) the cDNA sequence of the mature polypeptide coding sequence of SEQ ID NO: 29, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 31, (ii) the cDNA sequence of the mature polypeptide coding sequence of SEQ ID NO: 31, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 177, (ii) the cDNA sequence of the mature polypeptide coding sequence of SEQ ID NO: 177, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 179, (ii) the cDNA sequence of the mature polypeptide coding sequence of SEQ ID NO: 179, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 181, (ii) the cDNA sequence of the mature polypeptide coding sequence of SEQ ID NO: 181, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 183, (ii) the cDNA sequence of the mature polypeptide coding sequence of SEQ ID NO: 183, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 185, (ii) the cDNA sequence of the mature polypeptide coding sequence of SEQ ID NO: 185, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 187, (ii) the cDNA sequence of the mature polypeptide coding sequence of SEQ ID NO: 187, or (iii) a full-length complementary strand of (i) or (ii).

In another fifth aspect, the isolated polynucleotides encoding polypeptides having beta-glucosidase activity hybridize under preferably medium-high stringency conditions, more preferably high stringency conditions, and most preferably very high stringency conditions with (i) the mature polypeptide coding sequence of SEQ ID NO: 189, (ii) the cDNA sequence of the mature polypeptide coding sequence of SEQ ID NO: 189, or (iii) a full-length complementary strand of (i) or (ii).

In another fifth aspect, the isolated polynucleotides encoding GH61 polypeptides having cellulolytic enhancing activity hybridize under preferably medium-high stringency conditions, more preferably high stringency conditions, and most preferably very high stringency conditions with (i) the mature polypeptide coding sequence of SEQ ID NO: 33, (ii) the cDNA sequence of the mature polypeptide coding sequence of SEQ ID NO: 33, or (iii) a full-length complementary strand of (i) or (ii).

In another fifth aspect, the isolated polynucleotides encoding GH61 polypeptides having cellulolytic enhancing activity hybridize under preferably medium-high stringency conditions, more preferably high stringency conditions, and most preferably very high stringency conditions with (i) the mature polypeptide coding sequence of SEQ ID NO: 35, (ii) the genomic DNA sequence of the mature polypeptide coding sequence of SEQ ID NO: 35, or (iii) a full-length complementary strand of (i) or (ii).

In another fifth aspect, the isolated polynucleotides encoding GH61 polypeptides having cellulolytic enhancing activity hybridize under preferably medium-high stringency conditions, more preferably high stringency conditions, and most preferably very high stringency conditions with (i) the mature polypeptide coding sequence of SEQ ID NO: 37, (ii) the cDNA sequence of the mature polypeptide coding sequence of SEQ ID NO: 37, or (iii) a full-length complementary strand of (i) or (ii).

In another fifth aspect, the isolated polynucleotides encoding GH61 polypeptides having cellulolytic enhancing activity hybridize under preferably medium-high stringency conditions, more preferably high stringency conditions, and most preferably very high stringency conditions with (i) the mature polypeptide coding sequence of SEQ ID NO: 39, (ii) the cDNA sequence of the mature polypeptide coding sequence of SEQ ID NO: 39, or (iii) a full-length complementary strand of (i) or (ii).

In another fifth aspect, the isolated polynucleotides encoding GH61 polypeptides having cellulolytic enhancing activity hybridize under preferably medium-high stringency conditions, more preferably high stringency conditions, and most preferably very high stringency conditions with (i) the mature polypeptide coding sequence of SEQ ID NO: 41, (ii) the cDNA sequence of the mature polypeptide coding sequence of SEQ ID NO: 41, or (iii) a full-length complementary strand of (i) or (ii).

In another fifth aspect, the isolated polynucleotides encoding GH61 polypeptides having cellulolytic enhancing activity hybridize under preferably medium-high stringency conditions, more preferably high stringency conditions, and most preferably very high stringency conditions with (i) the mature polypeptide coding sequence of SEQ ID NO: 43, (ii) the cDNA sequence of the mature polypeptide coding sequence of SEQ ID NO: 43, or (iii) a full-length complementary strand of (i) or (ii).

In another fifth aspect, the isolated polynucleotides encoding GH61 polypeptides having cellulolytic enhancing activity hybridize under preferably medium-high stringency conditions, more preferably high stringency conditions, and most preferably very high stringency conditions with (i) the mature polypeptide coding sequence of SEQ ID NO: 191, (ii) the cDNA sequence of the mature polypeptide coding sequence of SEQ ID NO: 191, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 45, (ii) the genomic DNA sequence of the mature polypeptide coding sequence of SEQ ID NO: 45, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 47, (ii) the cDNA sequence of the mature polypeptide coding sequence of SEQ ID NO: 47, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 49, (ii) the genomic DNA sequence of the mature polypeptide coding sequence of SEQ ID NO: 49, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 51, (ii) the cDNA sequence of the mature polypeptide coding sequence of SEQ ID NO: 51, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 53, (ii) the genomic DNA sequence of the mature polypeptide coding sequence of SEQ ID NO: 53, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 193, (ii) the cDNA sequence of the mature polypeptide coding sequence of SEQ ID NO: 193, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 195, (ii) the cDNA sequence of the mature polypeptide coding sequence of SEQ ID NO: 195, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 197, (ii) the genomic DNA sequence of the mature polypeptide coding sequence of SEQ ID NO: 197, or (iii) a full-length complementary strand of (i) or (ii).

In another fifth aspect, the isolated polynucleotides encoding polypeptides having xylanase activity hybridize under preferably medium-high stringency conditions, more preferably high stringency conditions, and most preferably very high stringency conditions with the mature polypeptide coding sequence of SEQ ID NO: 55 or its full-length complementary strand.

In another fifth aspect, the isolated polynucleotides encoding polypeptides having xylanase activity hybridize under preferably medium-high stringency conditions, more preferably high stringency conditions, and most preferably very high stringency conditions with (i) the mature polypeptide coding sequence of SEQ ID NO: 199 or SEQ ID NO: 304, (ii) the cDNA sequence of the mature polypeptide coding sequence of SEQ ID NO: 199 or SEQ ID NO: 304, or (iii) a full-length complementary strand of (i) or (ii).

In another fifth aspect, the isolated polynucleotides encoding polypeptides having beta-xylosidase activity hybridize under preferably medium-high stringency conditions, more preferably high stringency conditions, and most preferably very high stringency conditions with (i) the mature polypeptide coding sequence of SEQ ID NO: 57, (ii) the genomic DNA sequence of the mature polypeptide coding sequence of SEQ ID NO: 57, or (iii) a full-length complementary strand of (i) or (ii).

In another fifth aspect, the isolated polynucleotides encoding polypeptides having beta-xylosidase activity hybridize under preferably medium-high stringency conditions, more preferably high stringency conditions, and most preferably very high stringency conditions with (i) the mature polypeptide coding sequence of SEQ ID NO: 59, (ii) the cDNA sequence of the mature polypeptide coding sequence of SEQ ID NO: 59, or (iii) a full-length complementary strand of (i) or (ii).

In another fifth aspect, the isolated polynucleotides encoding polypeptides having beta-xylosidase activity hybridize under preferably medium-high stringency conditions, more preferably high stringency conditions, and most preferably very high stringency conditions with (i) the mature polypeptide coding sequence of SEQ ID NO: 201, (ii) the cDNA sequence of the mature polypeptide coding sequence of SEQ ID NO: 201, or (iii) a full-length complementary strand of (i) or (ii).

In another fifth aspect, the isolated polynucleotides encoding polypeptides having beta-xylosidase activity hybridize under preferably medium-high stringency conditions, more preferably high stringency conditions, and most preferably very high stringency conditions with (i) the mature polypeptide coding sequence of SEQ ID NO: 203, (ii) the cDNA sequence of the mature polypeptide coding sequence of SEQ ID NO: 203, or (iii) a full-length complementary strand of (i) or (ii).

In another fifth aspect, the isolated polynucleotides encoding polypeptides having beta-xylosidase activity hybridize under preferably medium-high stringency conditions, more preferably high stringency conditions, and most preferably very high stringency conditions with (i) the mature polypeptide coding sequence of SEQ ID NO: 205, (ii) the cDNA sequence of the mature polypeptide coding sequence of SEQ ID NO: 205, or (iii) a full-length complementary strand of (i) or (ii).

Sources of Polypeptides Having Cellobiohydrolase I, Cellobiohydrolase II, Endoglucanase I, Endoglucanase II, Beta-Glucosidase, Cellulolytic Enhancing, Xylanase, or Beta-Xylosidase Activity A polypeptide having cellobiohydrolase I, cellobiohydrolase II, endoglucanase I, endoglucanase II, beta-glucosidase, cellulolytic enhancing, xylanase, or beta-xylosidase activity may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having cellobiohydrolase I, cellobiohydrolase II, endoglucanase I, endoglucanase II, beta-glucosidase, cellulolytic enhancing, xylanase, or beta-xylosidase activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus*, or *Oceanobacillus* polypeptide, or a Gram negative bacterial polypeptide such as an *E. coli, Pseudomonas, Salmonella, Campylobacter, Helicobacter, Flavobacterium, Fusobacterium*, llyobacter, *Neisseria*, or *Ureaplasma* polypeptide.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide.

In another preferred aspect, the polypeptide is a *Streptococcus equisimilis, Streptococcus pyogenes, Streptococcus uberis*, or *Streptococcus equi* subsp. *Zooepidemicus* polypeptide.

In another preferred aspect, the polypeptide is a *Streptomyces achromogenes, Streptomyces avermitilis, Streptomyces coelicolor, Streptomyces griseus*, or *Streptomyces lividans* polypeptide.

A polypeptide having cellobiohydrolase I, cellobiohydrolase II, endoglucanase I, endoglucanase II, beta-glucosidase, cellulolytic enhancing activity, xylanase, or beta-xylosidase may also be a fungal polypeptide, and more preferably a yeast polypeptide such as a *Candida, Kluyveromyces, Pichia, Saccharomyces, Schizosaccharomyces*, or *Yarrowia* polypeptide; or more preferably a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride* polypeptide.

In another aspect, the polypeptide having cellobiohydrolase I activity is a *Chaetomium thermophilum* CGMCC 0581 Cel7A polypeptide having cellobiohydrolase I activity, i.e., the polypeptide comprising the mature polypeptide of SEQ ID NO: 2.

In another aspect, the polypeptide having cellobiohydrolase I activity is a *Myceliophthora thermophila* CBS 117.65 Cel7A polypeptide having cellobiohydrolase I activity, i.e., the polypeptide comprising the mature polypeptide of SEQ ID NO: 4.

In another aspect, the polypeptide having cellobiohydrolase I activity is an *Aspergillus fumigatus* NN055679 Cel7A polypeptide having cellobiohydrolase I activity, i.e., the polypeptide comprising the mature polypeptide of SEQ ID NO: 6.

In another aspect, the polypeptide having cellobiohydrolase I activity is a *Thermoascus aurantiacus* CGMCC 0583 Cel7A polypeptide having cellobiohydrolase I activity, i.e., the polypeptide comprising the mature polypeptide of SEQ ID NO: 8.

In another aspect, the polypeptide having cellobiohydrolase I activity is a *Penicillium emersonii* NN051602 Cel7 polypeptide having cellobiohydrolase I activity, i.e., the polypeptide comprising the mature polypeptide of SEQ ID NO: 158.

In another aspect, the polypeptide having cellobiohydrolase I activity is a *Penicillium pinophilum* NN046877 Cel7 polypeptide having cellobiohydrolase I activity, i.e., the polypeptide comprising the mature polypeptide of SEQ ID NO: 160.

In another aspect, the polypeptide having cellobiohydrolase I activity is an *Aspergillus terreus* ATCC 28865 Cel7 polypeptide having cellobiohydrolase I activity, i.e., the polypeptide comprising the mature polypeptide of SEQ ID NO: 162.

In another aspect, the polypeptide having cellobiohydrolase I activity is a Neosartorya *fischeri* NRRL 181 Cel7 polypeptide having cellobiohydrolase I activity, i.e., the polypeptide comprising the mature polypeptide of SEQ ID NO: 164.

In another aspect, the polypeptide having cellobiohydrolase I activity is an *Aspergillus nidulans* FGSCA4 Cel7 polypeptide having cellobiohydrolase I activity, i.e., the polypeptide comprising the mature polypeptide of SEQ ID NO: 166.

In another aspect, the polypeptide having cellobiohydrolase II activity is a *Myceliophthora thermophila* CBS 117.65 Cel6A polypeptide having cellobiohydrolase II activity, i.e., the polypeptide comprising the mature polypeptide of SEQ ID NO: 10.

In another aspect, the polypeptide having cellobiohydrolase II activity is a *Myceliophthora thermophila* CBS 202.75 Cel6B polypeptide having cellobiohydrolase II activity, i.e., the polypeptide comprising the mature polypeptide of SEQ ID NO: 12.

In another aspect, the polypeptide having cellobiohydrolase II activity is a *Thielavia terrestris* NRRL 8126 Cel6A polypeptide having cellobiohydrolase II activity, i.e., the polypeptide comprising the mature polypeptide of SEQ ID NO: 14.

In another aspect, the polypeptide having cellobiohydrolase II activity is a *Trichophaea saccata* CBS 804.70 Cel6 polypeptide having cellobiohydrolase II activity, i.e., the polypeptide comprising the mature polypeptide of SEQ ID NO: 16.

In another aspect, the polypeptide having cellobiohydrolase II activity is a *Aspergillus fumigatus* NN055679 Cel6A polypeptide having cellobiohydrolase II activity, i.e., the polypeptide comprising the mature polypeptide of SEQ ID NO: 18.

In another aspect, the polypeptide having cellobiohydrolase II activity is a Fennellia *nivea* NN046949 Cel6 polypeptide having cellobiohydrolase II activity, i.e., the polypeptide comprising the mature polypeptide of SEQ ID NO: 168.

In another aspect, the polypeptide having cellobiohydrolase II activity is a *Penicillium emersonii* NN051602 Cel6A polypeptide having cellobiohydrolase II activity, i.e., the polypeptide comprising the mature polypeptide of SEQ ID NO: 170.

In another aspect, the polypeptide having cellobiohydrolase II activity is a *Penicillium pinophilum* NN046877 Cel6A polypeptide having cellobiohydrolase II activity, i.e., the polypeptide comprising the mature polypeptide of SEQ ID NO: 172.

In another aspect, the polypeptide having endoglucanase I activity is an *Aspergillus terreus* ATCC 28865 Cel6A polypeptide having endoglucanase I activity, i.e., the polypeptide comprising the mature polypeptide of SEQ ID NO: 20.

In another aspect, the polypeptide having endoglucanase II activity is a *Trichoderma reesei* RutC30 Cel5A polypeptide having endoglucanase II activity, i.e., the polypeptide comprising the mature polypeptide of SEQ ID NO: 22.

In another aspect, the polypeptide having endoglucanase II activity is a *Myceliophthora thermophila* CBS 202.75 Cel5A polypeptide having endoglucanase II activity, i.e., the polypeptide comprising the mature polypeptide of SEQ ID NO: 24.

In another aspect, the polypeptide having endoglucanase II activity is a *Thermoascus aurantiacus* CGMCC 0670 Cel5A polypeptide having endoglucanase II activity, i.e., the polypeptide comprising the mature polypeptide of SEQ ID NO: 26.

In another aspect, the polypeptide having endoglucanase II activity is an *Aspergillus fumigatus* NN051616 Cel5 polypeptide having endoglucanase II activity, i.e., the polypeptide comprising the mature polypeptide of SEQ ID NO: 174.

In another aspect, the polypeptide having endoglucanase II activity is a Neosartorya *fischeri* NRRL 181 polypeptide having endoglucanase II activity, i.e., the polypeptide comprising the mature polypeptide of SEQ ID NO: 176.

In another aspect, the polypeptide having beta-glucosidase activity is an *Aspergillus fumigatus* NN055679 Cel5A polypeptide having beta-glucosidase activity, i.e., the polypeptide comprising the mature polypeptide of SEQ ID NO: 28.

In another aspect, the polypeptide having beta-glucosidase activity is a *Penicillium brasilianum* IBT 20888 Cel5A polypeptide having beta-glucosidase activity, i.e., the polypeptide comprising the mature polypeptide of SEQ ID NO: 30.

In another aspect, the polypeptide having beta-glucosidase activity is an *Aspergillus niger* IBT 10140 GH3 polypeptide having beta-glucosidase activity, i.e., the polypeptide comprising the mature polypeptide of SEQ ID NO: 32.

In another aspect, the polypeptide having beta-glucosidase activity is an *Aspergillus aculeatus* WDCM190 Cel3 polypeptide having beta-glucosidase activity, i.e., the polypeptide comprising the mature polypeptide of SEQ ID NO: 178.

In another aspect, the polypeptide having beta-glucosidase activity is an *Aspergillus kawashii* IFO4308 Cel3 polypeptide having beta-glucosidase activity, i.e., the polypeptide comprising the mature polypeptide of SEQ ID NO: 180.

In another aspect, the polypeptide having beta-glucosidase activity is an *Aspergillus clavatus* NRRL 1 Cel3 polypeptide having beta-glucosidase activity, i.e., the polypeptide comprising the mature polypeptide of SEQ ID NO: 182.

In another aspect, the polypeptide having beta-glucosidase activity is a *Thielavia terrestris* NRRL 8126 Cel3 polypeptide having beta-glucosidase activity, i.e., the polypeptide comprising the mature polypeptide of SEQ ID NO: 184.

In another aspect, the polypeptide having beta-glucosidase activity is a *Penicillium oxalicum* IBT5387 Cel3 polypeptide having beta-glucosidase activity, i.e., the polypeptide comprising the mature polypeptide of SEQ ID NO: 186.

In another aspect, the polypeptide having beta-glucosidase activity is a *Penicillium oxalicum* IBT5387 Cel3 polypeptide having beta-glucosidase activity, i.e., the polypeptide comprising the mature polypeptide of SEQ ID NO: 188.

In another aspect, the polypeptide having beta-glucosidase activity is a *Talaromyces emersonii* CBS 549.92 Cel3 polypeptide having beta-glucosidase activity, i.e., the polypeptide comprising the mature polypeptide of SEQ ID NO: 190.

In another aspect, the polypeptide having cellulolytic enhancing activity is a *Thermoascus aurantiacus* CGMCC 0583 GH61A polypeptide having cellulolytic enhancing activity, i.e., the polypeptide comprising the mature polypeptide of SEQ ID NO: 34.

In another aspect, the polypeptide having cellulolytic enhancing activity is a *Thielavia terrestris* NRRL 8126 GH61E polypeptide having cellulolytic enhancing activity, i.e., the polypeptide comprising the mature polypeptide of SEQ ID NO: 36.

In another aspect, the polypeptide having cellulolytic enhancing activity is an *Aspergillus fumigatus* NN051616 GH61B polypeptide having cellulolytic enhancing activity, i.e., the polypeptide comprising the mature polypeptide of SEQ ID NO: 38.

In another aspect, the polypeptide having cellulolytic enhancing activity is a *Penicillium pinophilum* NN046877 GH61A polypeptide having cellulolytic enhancing activity, i.e., the polypeptide comprising the mature polypeptide of SEQ ID NO: 40.

In another aspect, the polypeptide having cellulolytic enhancing activity is a *Penicillium* sp. NN051602 GH61A polypeptide having cellulolytic enhancing activity, i.e., the polypeptide comprising the mature polypeptide of SEQ ID NO: 42.

In another aspect, the polypeptide having cellulolytic enhancing activity is a *Thielavia terrestris* NRRL 8126 GH61N polypeptide having cellulolytic enhancing activity, i.e., the polypeptide comprising the mature polypeptide of SEQ ID NO: 44.

In another aspect, the polypeptide having cellulolytic enhancing activity is a *Thermoascus crustaceus* CBS 181.67 GH61A polypeptide having cellulolytic enhancing activity, i.e., the polypeptide comprising the mature polypeptide of SEQ ID NO: 192.

In another aspect, the polypeptide having xylanase activity is an *Aspergillus aculeatus* CBS 101.43 polypeptide having xylanase activity, i.e., the polypeptide comprising the mature polypeptide of SEQ ID NO: 46.

In another aspect, the polypeptide having xylanase activity is an *Aspergillus fumigatus* NN055679 polypeptide having xylanase activity, i.e., the polypeptide comprising the mature polypeptide of SEQ ID NO: 48.

In another aspect, the polypeptide having xylanase activity is a *Trichophaea saccata* CBS 804.70 polypeptide having xylanase activity, i.e., the polypeptide comprising the mature polypeptide of SEQ ID NO: 50.

In another aspect, the polypeptide having xylanase activity is a *Penicillium pinophilum* NN046877 polypeptide having xylanase activity, i.e., the polypeptide comprising the mature polypeptide of SEQ ID NO: 52.

In another aspect, the polypeptide having xylanase activity is a *Thielavia terrestris* NRRL 8126 polypeptide having xylanase activity, i.e., the polypeptide comprising the mature polypeptide of SEQ ID NO: 54.

In another aspect, the polypeptide having xylanase activity is a *Talaromyces emersonii* NN050022 polypeptide having xylanase activity, i.e., the polypeptide comprising of the mature polypeptide of SEQ ID NO: 194.

In another aspect, the polypeptide having xylanase activity is a *Penicillium* sp. NN51602 polypeptide having xylanase activity, i.e., the polypeptide comprising of the mature polypeptide of SEQ ID NO: 196.

In another aspect, the polypeptide having xylanase activity is a *Meripilus giganteus* CBS 521.95 polypeptide having xylanase activity, i.e., the polypeptide comprising of the mature polypeptide of SEQ ID NO: 198.

In another aspect, the polypeptide having xylanase activity is a Thermobifida *fusca* DSM 22883 polypeptide having xylanase activity, i.e., the polypeptide comprising the mature polypeptide of SEQ ID NO: 56.

In another aspect, the polypeptide having xylanase activity is a *Dictyoglomus thermophilum* ATCC 35947 polypeptide having xylanase activity, i.e., the polypeptide comprising the mature polypeptide of SEQ ID NO: 200 or SEQ ID NO: 305.

In another aspect, the polypeptide having beta-xylosidase activity is a *Trichoderma reesei* RutC30 polypeptide having beta-xylosidase activity, i.e., the polypeptide comprising the mature polypeptide of SEQ ID NO: 58.

In another aspect, the polypeptide having beta-xylosidase activity is a *Talaromyces emersonii* CBS 393.64 polypeptide having beta-xylosidase activity, i.e., the polypeptide comprising the mature polypeptide of SEQ ID NO: 60.

In another aspect, the Family 3 polypeptide having beta-xylosidase activity is an *Aspergillus aculeatus* CBS 172.66 polypeptide having beta-xylosidase activity, i.e., the polypeptide comprising the mature polypeptide of SEQ ID NO: 202.

In another aspect, the Family 3 polypeptide having beta-xylosidase activity is an *Aspergillus aculeatus* CBS 186.67 polypeptide having beta-xylosidase activity, i.e., the polypeptide comprising the mature polypeptide of SEQ ID NO: 204.

In another aspect, the Family 3 polypeptide having beta-xylosidase activity is an *Aspergillus fumigatus* NN051616 polypeptide having beta-xylosidase activity, i.e., the polypeptide comprising the mature polypeptide of SEQ ID NO: 206.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Such polypeptides also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Nucleic Acid Constructs

A nucleic acid construct comprising an isolated polynucleotide encoding a polypeptide component of an enzyme composition of the present invention may be constructed by operably linking the polynucleotide to one or more (several) control sequences that direct the expression of the coding sequence in a suitable host cell under conditions compatible with the control sequences. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from a gene encoding a neutral alpha-amylase in Aspergilli in which the untranslated leader has been replaced by an untranslated leader from a gene encoding triose phosphate isomerase in Aspergilli; non-limiting examples include modified promoters from the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, Molecular Cellular Biology 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The various nucleic acids and control sequences described herein may be joined together to construct a recombinant expression vector that may include one or more (several) convenient restriction sites to allow for insertion or substitution of an isolated polynucleotide encoding a polypeptide component of the enzyme composition at such sites. Alternatively, a polynucleotide sequence may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAN/1111 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, Gene 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

Host Cells

The present invention also relates to recombinant host cells, comprising one or more isolated polynucleotides encoding polypeptide components of the enzyme composition, which are advantageously used in the recombinant production of the polypeptides. A vector is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium*, llyobacter, *Neisseria*, and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing an enzyme composition of the present invention, comprising: (a) cultivating a recombinant host cell, as described herein, under conditions conducive for production of the enzyme composition; and (b) recovering the enzyme composition.

In the production methods of the present invention, the cells are cultivated in a nutrient medium suitable for production of the enzyme composition using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the enzyme composition to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the components of the enzyme composition are secreted into the nutrient medium, the enzyme composition can be recovered directly from the medium. If the components of the enzyme composition are not secreted into the medium, the enzyme composition can be recovered from cell lysates.

The polypeptide components may be detected using methods known in the art that are specific for the polypeptides. These detection methods may include use of specific antibodies, formation of an enzyme product, or disappearance of an enzyme substrate.

The resulting enzyme composition may be recovered using methods known in the art. For example, the enzyme composition may be recovered from the nutrient medium by conventional procedures including, but not limited to, centrifugation, filtration, extraction, spray-drying, evaporation, or precipitation.

An enzyme composition of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification,* J.-C. Janson and Lars Ryden, editors, VCH Publishers, New York, 1989) to obtain substantially pure polypeptides.

Methods of Processing Cellulosic Material

The present invention also relates to methods for degrading or converting a cellulosic material, comprising: treating the cellulosic material with an enzyme composition of the present invention. In a preferred aspect, the method further comprises recovering the degraded or converted cellulosic material.

The present invention also relates to methods of producing a fermentation product, comprising: (a) saccharifying a cellulosic material with an enzyme composition of the present invention; (b) fermenting the saccharified cellulosic material with one or more fermenting microorganisms to produce the fermentation product; and (c) recovering the fermentation product from the fermentation.

The present invention also relates to methods of fermenting a cellulosic material, comprising: fermenting the cellulosic material with one or more fermenting microorganisms, wherein the cellulosic material is saccharified with an enzyme composition of the present invention. In a preferred aspect, the fermenting of the cellulosic material produces a fermentation product. In another preferred aspect, the method further comprises recovering the fermentation product from the fermentation.

The methods of the present invention can be used to saccharify a cellulosic material to fermentable sugars and convert the fermentable sugars to many useful substances, e.g., chemicals and fuels. The production of a desired fermentation product from cellulosic material typically involves pretreatment, enzymatic hydrolysis (saccharification), and fermentation.

The processing of cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and cofermentation (SSCF); hybrid hydrolysis and fermentation (HHF); separate hydrolysis and co-fermentation (SHCF), (hybrid hydrolysis and fermentation (HHCF), and direct microbial conversion (DMC). SHF uses separate process steps to first enzymatically hydrolyze lignocellulose to fermentable sugars, e.g., glucose, cellobiose, cellotriose, and pentose sugars, and then ferment the fermentable sugars to ethanol. In SSF, the enzymatic hydrolysis of lignocellulose and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, DC, 179-212). SSCF involves the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, lignocellulose hydrolysis, and fermentation) in one or more steps where the same organism is used to produce the enzymes for conversion of the lignocellulose to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment. In practicing the methods of the present invention, any pretreatment process known in the art can be used to disrupt the plant cell wall components (Chandra et al., 2007, Substrate pretreatment: The key to effective enzymatic hydrolysis of lignocellulosics? *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr* 2: 26-40).

Mechanical Pretreatment. The term "mechanical pretreatment" refers to various types of grinding or milling (e.g., dry milling, wet milling, or vibratory ball milling) to disrupt and/or reduce particle sizeplant cell wall components of the cellulosic material.

Chemical Pretreatment. In practicing the methods of the present invention, any chemical pretreatment process known in the art can be used to disrupt plant cell wall components of the cellulosic material (Chandra et al., 2007, supra; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr* 2: 26-40).

Conventional chemical pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, and gamma irradiation pretreatments.

The cellulosic material can be chemically pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, cellobiose, and/or xylose. In most cases the pretreatment step itself can result in some conversion of the cellulosic material to fermentable sugars (even in absence of enzymes).

Steam Pretreatment: In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably done at 140-230° C., more preferably 160-200° C., and most preferably 170-190° C., where the optimal temperature range depends on any addition of a chemical catalyst. Residence time for the steam pretreatment is preferably 1-15 minutes, more preferably 3-12 minutes, and most preferably 4-10 minutes, where the optimal residence time depends on temperature range and any addition of a chemical catalyst. Steam pretreatment allows for relatively high solids loadings, so that cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/11899, WO 2006/11900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). AFEX pretreatment results in the depolymerization of cellulose and partial hydrolysis of hemicellulose. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as an acid treatment, and more preferably as a continuous dilute and/or mild acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, more preferably 1-4, and most preferably 1-3. In one aspect, the acid concentration is in the range from preferably 0.01 to 20 wt % acid, more preferably 0.05 to 10 wt % acid, even more preferably 0.1 to 5 wt % acid, and most preferably 0.2 to 2.0 wt % acid. The acid is contacted with the cellulosic material and held at a temperature in the range of preferably 160-220° C., and more preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, the cellulosic material is present during pretreatment in amounts preferably between 10-80 wt %, more preferably between 20-70 wt %, and most preferably between 30-60 wt %, such as around wt %. The pretreated cellulosic material can be unwashed or washed using any method known in the art, e.g., washed with water.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, DC, 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, DC, chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Physical Pretreatment. The term "physical pretreatment" refers to any pretreatment that promotes the separation and/or release of cellulose, hemicellulose, and/or lignin from the cellulosic material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, physical pretreatment is performed in a batch-process, steam gun hydrolyzer system that uses high pressure and high temperature as defined above, e.g., a Sunds Hydrolyzer available from Sunds Defibrator AB, Sweden.

The cellulosic material can be subjected to pre-soaking, wetting, washing, or conditioning prior to pretreatment using methods known in the art.

Combined Physical and Chemical Pretreatment: The cellulosic material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, the cellulosic material is subjected to mechanical, chemical, or physical pretreatment, or any combination thereof, to promote the separation and/or release of cellulose, hemicellulose, and/or lignin.

Saccharification. In the hydrolysis step, also known as saccharification, the cellulosic material, e.g., pretreated, is hydrolyzed to break down cellulose and alternatively also hemicellulose to fermentable sugars, such as glucose, cellobiose, xylose, xylulose, arabinose, mannose, galactose, and/or soluble oligosaccharides. The hydrolysis is performed enzymatically by an enzyme composition of the present invention.

Enzymatic hydrolysis is preferably carried out in a suitable aqueous environment under conditions that can be readily determined by one skilled in the art. In a preferred aspect, hydrolysis is performed under conditions suitable for the activity of the enzyme(s), i.e., optimal for the enzyme(s). The hydrolysis can be carried out as a fed batch or continuous process where the pretreated cellulosic material (substrate) is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 96 hours, more preferably about 16 to about 72 hours, and most preferably about 24 to about 48 hours. The temperature is in the range of preferably about 25° C. to about 70° C., more preferably about 30° C. to about 65° C., and more preferably about 40° C. to 60° C., in particular about 50° C. The pH is in the range of preferably about 3 to about 8, more preferably about 3.5 to about 7, and most preferably about 4 to about 6, in particular about pH 5. The dry solids content is in the range of preferably about 5 to about 50 wt %, more preferably about 10 to about 40 wt %, and most preferably about 20 to about 30 wt %.

In a preferred aspect, an effective amount of an enzyme composition of the present invention is about 0.5 to about 50 mg, preferably at about 0.5 to about 40 mg, more preferably at about 0.5 to about 30 mg, more preferably at about 0.75 to about 20 mg, more preferably at about 0.75 to about 15 mg, even more preferably at about 1.0 to about 10 mg, and most preferably at about 2.0 to about 5 mg per g of cellulose in a cellulosic material.

Fermentation. The fermentable sugars obtained from the hydrolyzed cellulosic material can be fermented by one or more (several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be $C_6$ and/or $C_5$ fermenting organisms, or a combination thereof. Both $C_6$ and $C_5$ fermenting organisms are well known in the art.

Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment $C_6$ sugars include bacterial and fungal organisms, such as yeast. Preferred yeast includes strains of the *Saccharomyces* spp., preferably *Saccharomyces cerevisiae*.

Examples of fermenting organisms that can ferment $C_6$ sugars include bacterial and fungal organisms, such as some yeast. Preferred $C_5$ fermenting yeast include strains of *Pichia*, preferably *Pichia stipitis*, such as *Pichia stipitis* CBS 5773; strains of *Candida*, preferably *Candida boidinii*, *Candida brassicae*, *Candida sheatae*, *Candida diddensii*, *Candida pseudotropicalis*, or *Candida utilis*.

Other fermenting organisms include strains of *Zymomonas*, such as *Zymomonas mobilis*; *Hansenula*, such as *Hansenula anomala*; *Kluyveromyces*, such as *K. fragilis*; *Schizosaccharomyces*, such as *S. pombe*; *E. coli*, especially *E. coli* strains that have been genetically modified to improve the yield of ethanol; *Clostridium*, such as *Clostridium acetobutylicum*, *Chlostridium thermocellum*, and *Chlostridium phytofermentans*; *Geobacillus* sp.; *Thermoanaerobacter*, such as *Thermoanaerobacter saccharolyticum*; and *Bacillus*, such as *Bacillus coagulans*.

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida boidinii*. In another more preferred aspect, the yeast is *Candida brassicae*. In another more preferred aspect, the yeast is *Candida diddensii*. In another more preferred aspect, the yeast is *Candida pseudotropicalis*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, DC, 179-212).

Bacteria that can efficiently ferment hexose and pentose to ethanol include, for example, *Zymomonas mobilis*, *Clostridium acetobutylicum*, *Clostridium thermocellum*, *Chlostridium phytofermentans*, *Geobacillus* sp., *Thermoanaerobacter saccharolyticum*, and *Bacillus coagulans* (Philippidis, 1996, supra).

In a preferred aspect, the bacterium is a *Zymomonas*. In a more preferred aspect, the bacterium is *Zymomonas mobilis*. In another preferred aspect, the bacterium is a *Clostridium*. In another more preferred aspect, the bacterium is *Clostridium thermocellum*.

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMOSACC™ fresh yeast (available from Ethanol Technology, WI, USA), BIOFERM™ AFT and XR (available from NABC—North American Bioproducts Corporation, GA, USA), GERT STRAND™ (available from Gert Strand AB, Sweden), and FERMIOL™ (available from DSM Specialties).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TALI genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, FEMS Yeast Research 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Saccharomyces cerevisiae*. In another preferred aspect, the genetically modified fermenting microorganism is *Zymomonas mobilis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces* sp.

It is well known in the art that the organisms described above can also be used to produce other substances, as described herein.

The fermenting microorganism is typically added to the degraded lignocellulose or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In a preferred aspect, the yeast and/or another microorganism is applied to the degraded cellulosic material and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast.

Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation products: A fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); a ketone (e.g., acetone); an amino acid (e.g., aspartic acid, glutamic acid, glycine, lysine, serine, and threonine); and a gas (e.g., methane, hydrogen ($H_2$), carbon dioxide ($CO_2$), and carbon monoxide (CO)). The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, Water Science and Technology 36 (6-7): 41-47; and Gunaseelan V. N. in *Biomass and Bioenergy*, Vol.

13 (1-2), pp. 83-114, 1997, Anaerobic digestion of biomass for methane production: A review.

Recovery. The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

The present invention is further described by the following examples that should not be construed as limiting the scope of the invention.

EXAMPLES

Materials

Chemicals used as buffers and substrates were commercial products of at least reagent grade.

Media

PDA plates were composed of 39 grams of potato dextrose agar and deionized water to 1 liter.

Minimal medium plates were composed of 6 g of $NaNO_3$, 0.52 g of KCl, 1.52 g of $KH_2PO_4$, 1 ml of COVE trace elements solution, 20 g of Noble agar, 20 ml of 50% glucose, 2.5 ml of $MgSO_4 \cdot 7H_2O$, 20 ml of a 0.02% biotin solution, and deionized water to 1 liter.

COVE trace elements solution was composed of 0.04 g of $Na_2B_4O_7 \cdot 10H_2O$, 0.4 g of $CuSO_4 \cdot 5H_2O$, 1.2 g of $FeSO_4 \cdot 7H_2O$, 0.7 g of $MnSO_4 \cdot H_2O$, 0.8 g of $Na_2MoO_2 \cdot 2H_2O$, 10 g of $ZnSO_4 \cdot 7H_2O$, and deionized water to 1 liter.

MDU2BP medium was composed per liter of 45 g of maltose, 1 g of $MgSO_4 \cdot 7H_2O$, 1 g of NaCl, 2 g of $K_2SO_4$, 12 g of $KH_2PO_4$, 7 g of yeast extract, 2 g of urea, and 0.5 ml of AMG trace metals solution; pH 5.0.

AMG trace metals solution was composed per liter of 14.3 g of $ZnSO_4 \cdot 7H_2O$, 2.5 g of $CuSO_4 \cdot 5H_2O$, 0.5 g of $NiCl_2 \cdot 6H_2O$, 13.8 g of $FeSO_4 \cdot 7H_2O$, 8.5 g of $MnSO_4 \cdot 7H_2O$, and 3 g of citric acid.

NNCYP-PCS medium was composed of 5.0 g of $NaNO_3$, 3.0 g of $NH_4Cl$, 2.0 g of MES, 2.5 g of citric acid, 0.2 g of $CaCl_2 \cdot 2H_2O$, 1.0 g of Bacto Peptone, 5.0 g of yeast extract, 0.2 g of $MgSO_4 \cdot 7H_2O$, 4.0 g of $K_2HPO_4$, 1.0 ml of COVE trace elements solution, 2.5 g of glucose, 25.0 g of pretreated corn stover (PCS), and deionized water to 1 liter.

2×YT medium was composed per liter of 16 g of tryptone, 10 g of yeast extract, and 5 g of NaCl.

2×YT plates were composed per liter of 16 g of tryptone, 10 g of yeast extract, 5 g of NaCl and 15 g of Noble agar.

YG agar plates were composed per liter of 5.0 g of yeast extract, 10.0 g of glucose, and g of agar.

YEG medium was composed per liter of 20 g of dextrose and 5 g of yeast extract.

LB medium was composed per liter of 10 g of tryptone, 5 g of yeast extract, and 5 g of sodium chloride.

LB agar plates were composed of 10 g of tryptone, 5 g of yeast extract, 10 g of sodium chloride, 15 g of agar, and 1 liter of distilled water.

YP medium was composed per liter of 10 g of yeast extract and 20 g of Bacto peptone.

MEX-1 medium was composed per liter of 20 g of soya bean meal, 15 g of wheat bran, g of microcrystalline cellulose (AVICEL®; FMC, Philadelphia, PA, USA), 5 g of maltodextrin, 3 g of Bactopeptone, 0.2 g of pluronic, and 1 g of olive oil.

LB ampicillin medium was composed per liter of 10 g of tryptone, 5 g of yeast extract, 5 g of sodium chloride, and 50 mg of ampicillin (filter sterilized, added after autoclaving).

LB ampicillin plates were composed of 15 g of bacto agar per liter of LB ampicillin medium.

MY25 medium was composed per liter of 25 g of maltodextrin, 2 g of $MgSO_4 \cdot 7H_2O$, 10 g of $KH_2PO_4$, 2 g of citric acid, 2 g of $K_2SO_4$, 2 g of urea, 10 g of yeast extract, and 1.5 ml of AMG trace metals solution, adjusted to pH 6.

YPD medium was composed of 1% yeast extract, 2% peptone, and filter-sterilized 2% glucose added after autoclaving.

YPM medium was composed of 1% yeast extract, 2% peptone, and filter-sterilized 2% maltodextrin added after autoclaving.

SC-URA medium with glucose or galactose was composed of 100 ml of 10× Basal salts, ml of 20% casamino acids without vitamins, 10 ml of 1% tryptophan, 4 ml of 5% threonine (filter sterilized, added after autoclaving), and 100 ml of 20% glucose or 100 ml of 20% galactose (filter sterilized, added after autoclaving), and deionized water to 1 liter.

10× Basal salts solution was composed of 75 g of yeast nitrogen base, 113 g of succinic acid, 68 g of NaOH, and deionized water to 1 liter.

SC-agar plates were composed of 20 g of agar per liter of SC-URA medium (with glucose or galactose as indicated).

AZCL xylan SC-URA agar plates with galactose were composed of 20 g of agar per liter of SC-URA medium with galactose and 0.1% AZCL oat xylan (Megazyme, Wicklow, Ireland).

SC-URA medium with galactose was composed of 900 ml of SC-Grund Agar (autoclaved), 4 ml of 5% threonine (filter sterilized), and 100 ml of 20% galactose (filter sterilized).

SC-Grund Agar was composed of 7.5 g Yeast Nitrogen Base (without amino acids), 11.3 g of succinic acid, 6.8 g of sodium hydroxide, 5.6 g of casamino acids, 0.1 g of L-tryptophan, 20 g of agar, and deionized water to 1 liter.

COVE plates were composed per liter of 342.3 g of sucrose, 25 g of Noble agar, 20 ml of COVE salts solution, 10 mM acetamide, and 15 or 20 mM CsCl. The solution was adjusted to pH 7.0 before autoclaving.

COVE2 plates were composed per liter of 30 g of sucrose, 20 ml of COVE salts solution, ml of 1 M acetamide, and 25 g of Agar Noble.

COVE salts solution was composed per liter of 26 g of KCl, 26 g of $MgSO_4O \cdot 7H_2O$, 76 g of $KH_2PO_4$, and 50 ml of COVE trace metals.

YPG medium was composed per liter of 10 g of yeast extract, 10 g of Bacto peptone, and 20 g of glucose.

M410 medium was composed per liter of 50 g of maltose, 50 g of glucose, 2 g of $MgSO_4 \cdot 7H_2O$, 2 g of $KH_2PO_4$, 4 g of citric acid anhydrous powder, 8 g of yeast extract, 2 g of urea, 0.5 g of AMG trace metals solution, and 0.5 g of $CaCl_2$) at pH 6.0.

SOC medium was composed of 2% tryptone, 0.5% yeast extract, 10 mM NaCl, 2.5 mM KCl, 10 mM MgCl 2, and 10 mM $MgSO_4$; sterilized by autoclaving and then filter-sterilized glucose was added to 20 mM.

SY50 medium was composed per liter of 50 g of sucrose, 2 g of $MgSO_4 \cdot 7H_2O$, 10 g of $KH_2PO_4$, anhydrous, 2 g of $K_2SO_4$, 2 g of citric acid, 10 g of yeast extract, 2 g of urea, 0.5 g of $CaCl_2O \cdot 2H_2O$, and 0.5 g of 200×AMG trace metals solution, pH 6.0.

200×AMG trace metals solution was composed per liter of 3 g of citric acid, 14.3 g of $ZnSO_4 \cdot 7H_2O$, 2.5 g of $CuSO_4 \cdot 5H_2O$, 13.8 g of $FeSO_4 \cdot 7H_2O$, and 8.5 g of MnSav $H_2O$.

Cal-18 medium was composed per liter of 40 g of yeast extract, 1.3 g of magnesium sulfate, 50 g of maltodextrin, 20 g of $NaH_2PO_4$, and 0.1 g of antifoam.

Cellulase-inducing medium was composed of 20 g of cellulose, 10 g of corn steep solids, 1.45 g of $(NH_4)_2SO_4$, 2.08 g of $KH_2PO_4$, 0.28 g of $CaCl_2$, 0.42 g of $MgSO_4 \cdot 7H_2O$, 0.42 ml of Trichoderma trace metals solution, and 1-2 drops of antifoam.

Trichoderma trace metals solution was composed per liter of 216 g of $FeCl_3 \cdot 6H_2O$, 58 g of $ZnSO_4 \cdot 7H_2O$, 27 g of $MnSO_4 \cdot H_2O$, 10 g of $CuSO_4 \cdot 5H_2O$, 2.4 g of $H_3BO_3$, and 336 g of citric acid.

TE was composed of 10 mM Tris pH 7.4 and 0.1 mM EDTA.

YPM medium contained 1% yeast extract, 2% of peptone, and 2% of maltose in deionized water.

MY50 medium was composed of 50 g of Maltodextrin, 2 g of $MgSO_4 \cdot 7H_2O$, 10 g of $KH_2PO_4$, 2 g of $K_2SO_4$, 2 g of citric acid, 10 g of yeast extract, 2 g of urea, 0.5 ml of AMG trace metals solution, and distilled water to 1 liter.

AMG trace metals solution was composed per liter of 14.3 g of $ZnSO_4 \cdot 7H_2O$, 2.5 g of $CuSO_4 \cdot 5H_2O$, 0.5 g of $NiCl_2 \cdot 6H_2O$, 13.8 g of $FeSO_4 \cdot 7H_2O$, 8.5 g of $MnSO_4 \cdot 7H_2O$, 3 g of citric acid, and distilled water to 1 liter. 50× Vogels medium was composed per liter of 150 g of sodium citrate, 250 g of $KH_2PO_4$, g of $MgSO_4 \cdot 7H_2O$, 10 g of $CaCl_2O \cdot 2H_2O$, 2.5 ml of biotin stock solution, 5.0 ml of AMG trace metals solution, and distilled water to 1 liter.

COVE agar selective plates were composed of 218 g sorbitol, 20 g agar, 20 ml COVE salts solution, 10 mM acetamide, 15 mM CsCl, and deionized water to 1 liter. The solution was adjusted to pH 7.0 before autoclaving.

COVE salts solution was composed of 26 g KCl, 26 g $MgSO_4O \cdot 7H_2O$, 76 g $KH_2PO_4$, 50 ml COVE trace metals solution, and deionized water to 1 liter.

COVE trace metals solution was composed of 0.04 g $Na_2B_4O_7 \cdot 10H_2O$, 0.4 g $CuSO_4 \cdot 5H_2O$, 1.2 g $FeSO_4 \cdot 7H_2O$, 0.7 g $MnSO_4 \cdot H_2O$, 0.8 g $Na_2MoO_2 \cdot 2H_2O$, 10 g $ZnSO_4 \cdot 7H_2O$, and deionized water to 1 liter.

YP+2% glucose medium was composed of 1% yeast extract, 2% peptone and 2% glucose in deionized water.

YP+2% maltodextrin medium is composed of 2% peptone, 2% maltodextrin, and 1% yeast extract in deionized water.

DAP-2C-1 medium is composed of 3% maltodextrin, 1.1% magnesium sulfate, 0.52% tri-potassium phosphate, 0.2% citric acid, 0.1% potassium dihydrogen phosphate, 0.1% Dowfax 63N10, 0.05% yeast extract, and 0.05% of a trace element solution (1.39% ferrous sulfate, maganese sulfate, 0.68% zinc chloride, 0.3% citric acid, 0.25% copper sulfate, and 0.013% nickel chloride) in deionized water.

DAP-2C-1 medium is composed of 2% glucose, 1.1% magnesium sulfate, 1.0% maltose, tri-potassium phosphate, 0.2% citric acid, 0.1% potassium dihydrogen phosphate, 0.1% Dowfax 63N10, 0.05% yeast extract, and 0.05% of a trace element solution (1.39% ferrous sulfate, 0.845% maganese sulfate, 0.68% zinc chloride, 0.3% citric acid, 0.25% copper sulfate, and 0.013% nickel chloride) in deionized water.

Example 1: Preparation of Chaetomium thermophilum CGMCC 0581 Cel7A Cellobiohydrolase I The Chaetomium thermophilum CGMCC 0581 Cel7A cellobiohydrolase I (CBHI) gene (SEQ ID NO: 1 [DNA sequence] and SEQ ID NO: 2 [deduced amino acid sequence]) was isolated according to WO 2003/000941 and expressed in Aspergillus oryzae JaL250 (WO 99/61651).

The fungal strain Chaetomium thermophilum CGMCC 0581 was grown on agar plate composed of 0.5% yeast extract, 1% glucose and 2% agar for 3 days at 45° C. The fully grown culture was used to inoculate shake flasks containing liquid medium composed of 3% soymeal, 1.5% maltose, and 0.5% peptone. The flasks were incubated at 45° C. for 48 hours with shaking. The mycelia were harvested by centrifugation of the culture broth at 8000 rpm, 4° C. for 30 minutes, transferred into a clean plastic bag followed by immediate freezing in liquid nitrogen, and stored at −80° C. before total RNA was isolated.

The frozen mycelia were grounded into a very fine powder with a sterilized mortar and pestle baked at 200° C. for 24 hours. An RNEASY® Plant Mini Kit (QIAGEN Inc., Valencia, CA, USA) was used to isolate total RNA according to the manufacturer's instructions.

First strand cDNA synthesis from the total RNA was performed using a 3' RACE System for Rapid Amplification of cDNA Ends (Invitrogen Corporation, Carlsbad, CA, USA) according to the manufacturer's instructions. The first strand cDNA of 3' RACE was used as PCR template for PCR screening.

Two oligonucleotides shown below were used for PCR screening of cDNA of Chaetomium thermophilum CGMCC 0581. The forward primer was derived from an alignment of conserved regions of cellobiohydrolase I genes and the reverse primer was provided by the 3' RACE System.

```
Forward primer:
                                          (SEQ ID NO: 67)
5'-GGnACnGGnTA(t/c)TG(t/c)GA-3'

Reverse primer:
                                          (SEQ ID NO: 68)
5'-GGCCACGCGTCGACTAGTAC-3'
```

One hundred picomoles of the forward primer and 10 picomoles of the reverse primer were used in a PCR reaction composed of 2 µl of the first strand cDNA of 3' RACE, 5 µl of 10× Taq DNA polymerase buffer (Promega Corporation, Madison, WI, USA), 3 µl of 25 mM $MgCl_2$, 1 µl of 10 mM dNTP, and 2.5 units of Taq DNA polymerase (Promega Corporation, Madison, WI, USA) in a final volume of 50 µl. The amplification was performed in a thermocycler programmed for 1 cycle at 95° C. for 3 minutes; 30 cycles each at 95° C. for 30 seconds, 50° C. for 30 seconds, and 72° C. for 50 seconds; and 1 cycle at 72 C for 10 minutes. The heat block then went to a 4° C. soak cycle.

The reaction products were isolated by 1.0% agarose gel electrophoresis using TBE buffer where an approximately 1.3 kb product band was excised from the gel, and purified using a WIZARD® PCR Preps DNA Purification System (Promega Corporation, Madison, WI, USA) according to the manufacturer's instructions. The PCR product was sequenced using a 377 DNA Analyzer (Applied Biosystems Inc, Foster City, CA, USA). Sequencing showed that the 1.3 kb fragment was homologous to cellobiohydrolase I.

Two oligos shown below were designed for the 5' end cloning of the Chaetomium thermophilum CGMCC 0581 Cel7A cellobiohydrolase I by using a 5' RACE System for Rapid Amplification of cDNA Ends (Invitrogen Corporation, Carlsbad, CA, USA).

Primer 4310AS1:
(SEQ ID NO: 69)
5'-AGATATCCATCTCAGAGCA-3'

Primer 4310AS2:
(SEQ ID NO: 70)
5'-GTTGGCATCATTGGTCG-3'

The gene specific primer 4310AS1 was used for the first strand cDNA synthesis using a 5' RACE System according to the manufacturer's instructions. The first strand cDNA of 5' RACE (5 μl) was used as template for PCR amplification composed of 5 μl of 10× Taq DNA polymerase buffer, 3 μl of 25 mM MgCl$_2$, 1 μl of 10 mM dNTP, 1 μl of 10 μM 4310AS2 primer, 1 μl of 10 μM primer AAP (Abridged Anchor Primer, provided by the kit), and 2.5 units of Taq DNA polymerase in a final volume of 50 μl. The amplification was performed in a thermocycler programmed for 1 cycle at 94° C. for 3 minutes; 30 cycles each at 95° C. for 30 seconds, 50° C. for 30 seconds, and 72° C. for 50 seconds; and 1 cycle at 72° C. for 10 minutes. The heat block then went to a 4° C. soak cycle.

The PCR products were isolated by 1.0% agarose gel electrophoresis using TBE buffer and purified using a WIZARD® PCR Preps DNA Purification System. A dominant DNA fragment of 0.8 kb was confirmed to be the 5' end of *Chaetomium thermophilum* CGMCC 0581 Cel7A cellobiohydrolase I gene by sequencing using a 377 DNA Analyzer.

Two primers shown below were designed based on the sequence information from both and 3' end cloning. They were used for full-length cloning of the *Chaetomium thermophilum* CGMCC 0581 Cel7A cellobiohydrolase I gene.

Primer 4310S:
(SEQ ID NO: 71)
5'-ATCCTCTCCTTCCAGTTTTC-3'

Primer 4310AS:
(SEQ ID NO: 72)
5'-TATCCAAGTAGTCCACAACC-3'

Ten picomoles of the above two primers were used in a PCR reaction composed of 5 μl of first strand cDNA of 3' RACE, 5 μl of 10× Taq DNA polymerase buffer, 3 μl of 25 mM MgCl$_2$, 1 μl of 10 mM dNTP, and 2.5 units of Taq DNA polymerase in a final volume of 50 μl. The amplification was performed in a thermocycler programmed for 1 cycle at 95° C. for 3 minutes; 30 cycles each at 95° C. for 50 seconds, 55° C. for 50 seconds, and 72° C. for 90 seconds; and 1 cycle at 72° C. for 10 minutes. The heat block then went to a 4° C. soak cycle.

The reaction products were isolated by 1.0% agarose gel electrophoresis using TBE buffer where an approximately 1.5 kb product band was excised from the gel, and purified using a WIZARD® PCR Preps DNA Purification System. The PCR fragment was then ligated to pGEM-T using a pGEM-T Vector System (Promega Corporation, Madison, WI, USA). The plasmid DNA was confirmed by sequencing using a 377 DNA Analyzer. The correct clone was designated pT43-10.

Two synthetic oligonucleotide primers containing Bsp HI sites at their ends, shown below, were designed to PCR amplify the full-length open reading frame of the *Chaetomium thermophilum* CGMCC 0581 Family GH7A cellobiohydrolase I gene. A Rapid Ligation Kit (Roche Applied Science, Indianapolis, IN, USA) was used to clone the fragment into pAILo2 (WO 2004/099228).

PCR Forward primer:
(SEQ ID NO: 73)
5'-<u>TCATGA</u>TGTACAAGAAGTTCGCCG-3'

PCR Reverse primer:
(SEQ ID NO: 74)
5'-<u>TCATGA</u>TTACAGGCACTGGCTGTAC-3'

Bold letters represent coding sequence. The underlined sequence contains sequence identity to the BspHI restriction site.

Fifty picomoles of each of the primers above were used in a PCR reaction containing 50 ng of plasmid pT43-10 containing the *Chaetomium thermophilum* CGMCC 0581 cellobiohydrolase I gene, 1× Pwo Amplification Buffer with MgSO$_4$ (Boehringer Mannheim, Indianapolis, IN, USA), 4 μl of 10 mM blend of dATP, dTTP, dGTP, and dCTP, and 2.5 units of Pwo DNA Polymerase (Boehringer Mannheim, Indianapolis, IN, USA), in a final volume of 50 μl. A DNA ENGINE™ Thermal Cycler (MJ Research, Waltham, MA, USA) was used to amplify the fragment programmed for one cycle at 94° C. for 2 minutes; 35 cycles each at 94° C. for 30 seconds, 62° C. for 30 seconds, and 72° C. for 1.5 minutes. After the 35 cycles, the reaction was incubated at 72° C. for 10 minutes and then cooled at 10° C. until further processed.

A 1.6 kb PCR reaction product was isolated on a 0.8% GTG® agarose gel (Cambrex Bioproducts, East Rutherford, NJ, USA) using 40 mM Tris base-20 mM sodium acetate-1 mM disodium EDTA (TAE) buffer and 0.1 μg of ethidium bromide per ml. The DNA band was visualized with the aid of a DARKREADER™ Transilluminator (Clare Chemical Research, Dolores, CO, USA) to avoid UV-induced mutations. The 1.6 kb DNA band was excised with a disposable razor blade and purified with an ULTRAFREE® DA spin cup (Millipore, Billerica, MA, USA) according to the manufacturer's instructions.

The purified PCR fragment was cloned into pCR®4Blunt-TOPO® (Invitrogen, Carlsbad, CA, USA) using a TOPO® Blunt Cloning Kit (Invitrogen, Carlsbad, CA, USA) according to the manufacturer's instructions. PCR clones containing the coding regions of interest were sequenced to Phred Q values of at least 40 to insure that there were no PCR induced errors. All sequence alignments were performed with Consed (University of Washington). One of the clones was determined to have the expected sequence and was selected and re-named CtPCR. The CtPCR clone containing the *C. thermophilum* cellobiohydrolase I coding region was digested with Bsp HI and gel purified as described above. This DNA fragment was then ligated into the Nco I restriction site of pAILo2 with a Rapid Ligation Kit. Expression clones were confirmed by restriction digestion and sequenced to confirm that the junction vector-insert was correct. Plasmid DNA for transformation was prepared with a Midi-Prep Kit (QIAGEN Inc., Valencia, CA, USA). The final clone was re-named pAILo4.

*Aspergillus oryzae* JaL250 protoplasts were prepared according to the method of Christensen et al., 1988, Bio/Technology 6: 1419-1422. Eight micrograms of pAILo4 (as well as pAILo2 as a vector control) were used to transform *Aspergillus oryzae* JaL250 protoplasts. Twelve transformants were isolated to individual PDA plates and incubated for 5 days at 34° C. Confluent spore plates were washed with 5 ml of 0.01% TWEEN® 80 and the spore suspension was used to inoculate 25 ml of MDU2BP medium in 125 ml glass shake flasks. Transformant cultures were incubated at 34° C. with constant shaking at 200 rpm. At day five post-inoculation, cultures were centrifuged at 6000×g and their supernatants collected. Five microliters of each supernatant were mixed with an equal volume of 2× loading buffer (10% beta-mercaptoethanol) and loaded onto a 1.5 mm 8%-16% Tris-glycine SDS-PAGE gel and stained with SIMPLY BLUE™ SafeStain (Invitrogen, Carlsbad, CA, USA). SDS-PAGE profiles of the culture broths showed that twelve out of twelve transformants had a new protein band of approximately 66 kDa. Transformant number 12 was selected and designated A. oryzae Ja1250AlLo4.

Shake flask medium was composed per liter of 50 g of glucose, 2 g of $MgSO_4 \cdot 7H_2O$, 10 g of $KH_2PO_4$, 2 g of $K_2SO_4$, 0.5 g of $CaCl_2O \cdot 2H_2O$, 2 g of citric acid, 10 g of yeast extract, 0.5 g of AMG trace metals solution, and 2 g of urea. AMG trace metals solution was composed per liter of 13.8 g of $FeSO_4 \cdot 7H_2O$, 14.3 g of $ZnSO_4 \cdot 7H_2O$, 8.5 g of $MnSO_4 \cdot H_2O$, 2.5 g of $CuSO_4 \cdot 5H_2O$, g of $NiCl_2 \cdot 6H_2O$ and 3.0 g of citric acid monohydrate.

One hundred ml of shake flask medium was added to a 500 ml shake flask. The shake flask was inoculated with a glycerol spore stock of A. oryzae Ja1250AlLo4 and incubated at 34° C. on an orbital shaker at 200 rpm for 24 hours. Fifty ml of the shake flask broth was used to inoculate a fermentation vessel.

Fermentation batch medium was composed per liter of 25 g of sucrose, 2 g of $MgSO_4 \cdot 7H_2O$, 2 g of $KH_2PO_4$, 3 g of $K_2SO_4$, 5 g of $(NH_4)_2HPO_4$, 1 g of citric acid, 10 g of yeast extract, 0.5 g of AMG trace metals solution, and 0.55 g of pluronic antifoam. Fermentation feed medium was composed per liter of 320 g of maltose, 5 g of pluronic antifoam, and 1 g of citric acid monohydrate.

A total of 2 liters of the fermentation batch medium was added to a glass jacketed fermentor. The fermentation vessel was maintained at a temperature of 34° C. and the pH was controlled at 7 for 180 hours using 10% $NH_4OH$ and 10% $H_3PO_4$. Air was added to the vessel at a rate of 1 vvm and the broth was agitated by Rushton impeller rotating at 1100 rpm. Feed was started at a rate of 4 g per hour when the batch sucrose was consumed as indicated by a rise in the dissolved oxygen reading (at approximately 18-24 hours). At the end of the fermentation, whole broth was harvested from the vessel and centrifuged at 3000×g to remove the biomass. The supernatant was sterile filtered and stored at 5 to 10° C.

A 350 ml (3.15 g total protein) aliquot of the filtered A. oryzae Ja1250AlLo4 fermentation broth (AOC18-7) containing recombinant Chaetomium thermophilum Cel7A cellobiohydrolase I was concentrated and desalted, and then purified over a Q SEPHAROSE® Big Bead column (GE Healthcare, Piscataway, NJ, USA) in 20 mM Tris-HCl pH 8, over a linear 0 to 1 M NaCl gradient. Fractions were pooled based on SDS-PAGE, concentrated and buffer-exchanged to mM Tris-HCl, pH 8. The purified cellobiohydrolase I (approximately 800 mg total) was approximately 90% pure by SDS-PAGE. Protein concentration was determined using a Microplate BOA™ Protein Assay Kit (Thermo Fischer Scientific, Waltham, MA, USA) in which bovine serum albumin was used as a protein standard.

Example 2: Preparation of *Myceliophthora thermophila* CBS 117.65 Cel7A Cellobiohydrolase I The *Myceliophthora thermophila* CBS 117.65 Cel7A cellobiohydrolase I (CBHI) gene (SEQ ID NO: 3 [DNA sequence] and SEQ ID NO: 4 [deduced amino acid sequence]) was isolated according to WO 2003/000941 and expressed in *Aspergillus oryzae* JaL250.

Two synthetic oligonucleotide primers, shown below, were designed to PCR amplify the full-length open reading frame from *Myceliophthora thermophila* CBS 117.65 encoding the Family Cel7A cellobiohydrolase I.

```
PCR Forward primer:
                                   (SEQ ID NO: 75)
5'-ctcgcagtcgcagtcaag-3'

PCR Reverse primer:
                                   (SEQ ID NO: 76)
5'-cggtcaggttgcagtttag-3'
```

Thirty picomoles of each of the primers above were used in an amplification reaction containing 50 ng of DNA consisting of a pool of *Myceliophtora thermophila* CBS 117.65 cDNA prepared according to U.S. Pat. No. 6,242, 237, 1× EXPAND™ PCR Buffer (Roche Diagnostics, Mannheim, Germany), 4 µl of 2.5 mM blend of dATP, dTTP, dGTP, and dCTP, µl of EXPAND™ DNA Polymerase (Roche Diagnostics, Mannheim, Germany), in a final volume of 50 µl. The amplification of the fragment was performed in a thermocycler programmed for one cycle at 94° C. for 5 minutes; and 35 cycles each at 94° C. for 1 minute, 54° C. for 1 minute, and 72° C. for 2 minutes. After the 30 cycles, the reaction was incubated at 72° C. for minutes and then cooled at room temperature until further processed.

A 1.3 kb PCR product was isolated by 1% agarose gel electrophoresis using TBE buffer and 0.1 µg of ethidium bromide per ml. The 1.3 kb DNA band was excised with a disposable razor blade and purified using a JETSORB Gel Extraction Kit (Genomed GmbH, Lohne, Germany) according to the manufacturer's instructions.

The purified PCR fragment was cloned into pCR®4Blunt-TOPO® according to the manufacturer's instructions. PCR clones containing the coding regions of interest were sequenced. One of the clones having the expected sequence was selected and named pDAu27#15.

Two synthetic oligonucleotide primers containing a Bsp HI restriction site on the forward primer and a Pac I restriction site on the reverse primer, shown below, were designed to PCR amplify the full-length open reading frame of the *Myceliophthora thermophila* CBS 117.65 Cel7A cellobiohydrolase I from pDAu27#15. A Rapid Ligation Kit was used to clone the fragment into pAlLo2 (WO 2004/099228).

```
PCR Forward primer:
                                   (SEQ ID NO: 77)
5'-TCATGAAGCAGTACCTCCAGTA-3'

PCR Reverse primer:
                                   (SEQ ID NO: 78)
5'-TTAATTAATTAGACGTTGACAGTCGAGC-3'
```

Bold letters represent coding sequence. The underlined sequence contains sequence identity to the Bsp HI and Pac I restriction sites.

Fifty picomoles of each of the primers above were used in a PCR reaction containing 50 ng of plasmid pDAu27#15 containing the *Myceliophthora thermophila* CBS 117.65 cellobiohydrolase I I gene, 1× Pfx Amplification Buffer (Invitrogen, Carlsbad, CA, USA), 6 µl of 10 mM blend of dATP, dTTP, dGTP, and dCTP, 2.5 units of PLATINUM® Pfx DNA Polymerase (Invitrogen, Carlsbad, CA, USA), 1 µl of 50 mM $MgSO_4$, and 2.5 µl of 10× pCRx Enhancer solution (Invitrogen, Carlsbad, CA, USA) in a final volume of 50 µl. A DNA ENGINE™ Thermal Cycler was used to amplify the fragment programmed for one cycle at 98° C. for 2 minutes; and 35 cycles each at 94° C. for 30 seconds, 58° C. for 30 seconds, and 68° C. for 1.5 minutes. After the 35 cycles, the reaction was incubated at 68° C. for 10 minutes and then cooled at 10° C. until further processed.

A 1.3 kb PCR reaction product was isolated on a 0.8% GTG® agarose gel using TAE buffer and 0.1 µg of ethidium bromide per ml. The DNA band was visualized with the aid of a DARKREADER™ Transilluminator to avoid UV-induced mutations. The 1.3 kb DNA band was excised with a disposable razor blade and purified with an ULTRA-FREE® DA spin cup according to the manufacturer's instructions.

The purified PCR fragment was cloned into pCR®4Blunt-TOPO® according to the manufacturer's instructions. PCR clones containing the coding region of interest were sequenced to Phred Q values of at least 40 to insure that there were no PCR induced errors. All sequence aligments were performed with Consed (University of Washington). One of the clones that was shown to have the expected sequence was selected and re-named MtPCR. The MtPCR clone containing the M. thermophila cellobiohydrolase I coding region was double digested with Bsp HI and Bss SI and a 352 bp fragment was gel purified as described above. Another aliquot of MtPCR was also double digested with Bss SI and Pac I and a 1009 bp fragment was gel purified as described above. These DNA fragments were then ligated into pAlLo2 previously digested with Nco I and Pac I in a three-way ligation using a Rapid Ligation Kit. Expression clones were confirmed by restriction digestion and sequenced to confirm that the junction vector-insert was correct. Plasmid DNA for transformation was prepared with a Midi-Prep Kit. The final clone was re-named pAlLo10.

Aspergillus oryzae JaL250 protoplasts were prepared according to the method of Christensen et al., 1988, supra. Six micrograms of pAlLo10 (as well as pAlLo2 as a vector control) were used to transform Aspergillus oryzae JaL250 protoplasts. Eight transformants were isolated to individual PDA plates and incubated for five days at 34° C. Confluent spore plates were washed with 5 ml of 0.01% TWEEN® 80 and the spore suspension was used to inoculate 25 ml of MDU2BP medium in 125 ml glass shake flasks. Transformant cultures were incubated at 34° C. with constant shaking at 200 rpm. At day five post-inoculation, cultures were centrifuged at 6000×g and their supernatants collected. Five microliters of each supernatant were mixed with an equal volume of 2× loading buffer (10% beta-mercaptoethanol) and loaded onto a 1.5 mm 8%-16% Tris-glycine SDS-PAGE gel and stained with SIMPLY BLUE™ SafeStain. SDS-PAGE profiles of the culture broths showed that eight out of eight transformants had a new protein band of approximately 50 kDa. Transformant number 8 was selected for further studies and designated A. oryzae JaL250AlLo10.

A new fully confluent spore plate was prepared as described above. Spores were collected with 5 ml of an aqueous solution of 0.01% TWEEN® 80 and two more washes with MDU2BP medium to maximize the number of spores collected. The spore suspension was then used to inoculate 500 ml of MDU2BP medium in a two-liter Fernbach flask. The A. oryzae JaL250AlLo10 liquid culture was then incubated at 34° C. with shaking at 200 rpm. At day five post-inoculation the culture broth was collected by filtration on a 500 milliliter, 75 mm Nylon filter unit with a pore size of 0.45 µm.

The culture filtrate was desalted and buffer exchanged in 20 mM Tris, 150 mM NaCl pH 8.5, using a HIPREP® 26/10 desalting column (GE Healthcare, Piscataway, NJ, USA) according to the manufacturer's instructions Protein concentration was determined using a Microplate BCA™ Protein Assay Kit in which bovine serum albumin was used as a protein standard.

Example 3: Preparation of *Aspergillus fumigatus* NN055679 Cel7A Cellobiohydrolase I A tfasty search (Pearson et al., 1997, Genomics 46:24-36) of the *Aspergillus fumigatus* partial genome sequence (The Institute for Genomic Research, Rockville, MD) was performed using as query a Cel7 cellobiohydrolase protein sequence from *Trichoderma reesei* (Accession No. P00725). Several genes were identified as putative Family GH7 homologs based upon a high degree of similarity to the query sequence at the amino acid level. One genomic region with significant identity to the query sequence was chosen for further study, and the corresponding gene was named cel7A.

Two synthetic oligonucleotide primers shown below were designed to PCR amplify an *Aspergillus fumigatus* NN055679 cel7A cellobiohydrolase I gene (SEQ ID NO: 5 [DNA sequence] and SEQ ID NO: 6 [deduced amino acid sequence]) from genomic DNA of *Aspergillus fumigatus* prepared as described in WO 2005/047499.

```
Forward primer:
                                        (SEQ ID NO: 79)
5'-gggcATGCTGGCCTCCACCTTCTCC-3'

Reverse primer:
                                        (SEQ ID NO: 80)
5'-gggttaattaaCTACAGGCACTGAGAGTAA-3'
```

Upper case letters represent the coding sequence. The remainder of the sequence provides restriction endonuclease sites for Sph I and Pac I in the forward and reverse sequences, respectively. Using these primers, the *Aspergillus fumigatus* cel7A gene was amplified using standard PCR methods and the reaction product isolated by 1% agarose gel electrophoresis using TAE buffer and purified using a QIAQUICK® Gel Extraction Kit (QIAGEN Inc., Valencia, CA, USA) according to the manufacturer's instructions.

The fragment was digested with Sph I and Pac I and ligated into the expression vector pAlLo2 also digested with Sph I and Pac I according to standard procedures. The ligation products were transformed into E. coli XL10 SOLOPACK® cells (Stratagene, La Jolla, CA, USA) according to the manufacturer's instructions. An E. coli transformant containing a plasmid of the correct size was detected by restriction digestion and plasmid DNA was prepared using a BIOROBOT® 9600 (QIAGEN Inc., Valencia, CA, USA). DNA sequencing of the insert gene from this plasmid was performed with a Perkin-Elmer Applied Biosystems Model 377 XL Automated DNA Sequencer (Perkin-Elmer/Applied Biosystems, Inc., Foster City, CA, USA) using dye-terminator chemistry (Giesecke et al., 1992, *Journal of Virology Methods* 38: 47-60) and primer walking strategy. Nucleotide sequence data were scrutinized for quality and all sequences were compared to each other with assistance of PHRED/PHRAP software (University of Washington, Seattle, WA, USA). The nucleotide sequence was shown to match the genomic sequence determined by TIGR (SEQ ID NO: 5 [DNA sequence] and SEQ ID NO: 6 [deduced amino acid sequence]). The resulting plasmid was named pEJG93.

*Aspergillus oryzae* JaL250 protoplasts were prepared according to the method of Christensen et al., 1988, supra. Five μg of pEJG93 (as well as pAlLo2 as a vector control) was used to transform *Aspergillus oryzae* JaL250.

The transformation of *Aspergillus oryzae* JaL250 with pEJG93 yielded about 100 transformants. Ten transformants were isolated to individual PDA plates.

Confluent PDA plates of five of the ten transformants were washed with 5 ml of 0.01% TWEEN® 20 and inoculated separately into 25 ml of MDU2BP medium in 125 ml glass shake flasks and incubated at 34° C., 250 rpm. Five days after incubation, 0.5 μl of supernatant from each culture was analyzed using 8-16% Tris-Glycine SDS-PAGE gels (Invitrogen, Carlsbad, CA, USA) according to the manufacturer's instructions. SDS-PAGE profiles of the cultures showed that one of the transformants had a major band of approximately 70 kDa. This transformant was named *Aspergillus oryzae* JaL250EJG93.

Five hundred ml of shake flask medium were added to a 2800 ml shake flask. The shake flask medium was composed of 45 g of maltose, 2 g of $K_2HPO_4$, 12 g of $KH_2PO_4$, 1 g of NaCl, 1 g of $MgSO_4 \cdot 7H_2O$, 7 g of yeast extract, 2 g of urea, and 0.5 ml of trace elements solution. The trace elements solution was composed per liter of 13.8 g of $FeSO_4 \cdot 7H_2O$, 14.3 g of $ZnSO_4 \cdot 7H_2O$, 8.5 g of $MnSO_4 \cdot H_2O$, 2.5 g of $CuSO_4 \cdot 5H_2O$, 0.5 g of $NiCl_2 \cdot 6H_2O$, 3 g of citric acid, and deionized water to 1 liter. Two shake flasks were inoculated with a suspension of a PDA plate of *Aspergillus oryzae* JaL250EJG93 with 0.01% TWEEN® 80 and incubated at 34° C. on an orbital shaker at 200 rpm for 120 hours. The broth was filtered using a 0.7 μm Whatman glass filter GF/F (Whatman, Piscataway, NJ, USA) followed by a 0.22 μm EXPRESS™ Plus Membrane (Millipore, Bedford, MA, USA).

Filtered broth was concentrated and buffer exchanged using a tangential flow concentrator (Pall Filtron, Northborough, MA, USA) equipped with a 10 kDa polyethersulfone membrane (Pall Filtron, Northborough, MA, USA) with 20 mM Tris-HCl pH 8.5. Protein concentration was determined using a Microplate BCA™ Protein Assay Kit in which bovine serum albumin was used as a protein standard.

Example 4: Preparation of *Thermoascus aurantiacus* CGMCC 0583 Cel7A Cellobiohydrolase I The *Thermoascus aurantiacus* CGMCC 0583 Cel7A cellobiohydrolase I (CBHI) gene (SEQ ID NO: 7 [DNA sequence] and SEQ ID NO: 8 [deduced amino acid sequence]) was isolated according to WO 2003/000941 and expressed in *Aspergillus oryzae* JaL250. The fungal strain *Thermoascus aurantiacus* CGMCC 0583 was grown on an agar plate composed of 0.5% yeast extract, 1% glucose, and 2% agar for 3 days at 45° C. The fully grown culture was used to inoculate shake flasks containing liquid medium composed of 3% soymeal, 1.5% maltose, and 0.5% peptone. The flasks were incubated at 45° C. for 48 hours with shaking. The mycelia were harvested by centrifugation of the culture broth at 8000 rpm, 4° C. for 30 minutes, transferred into a clean plastic bag followed by immediate freezing in liquid nitrogen, and stored at −80° C. before total RNA was isolated.

The frozen mycelia were grounded into a very fine powder with a sterilized mortar and pestle baked at 200° C. for 24 hours. An RNEASY® Plant Mini Kit was used to isolate total RNA according to the manufacturer's instructions.

First strand cDNA synthesis from the total RNA was performed using a 3' RACE System for Rapid Amplification of cDNA Ends according to the manufacturer's instructions. The first strand cDNA of 3' RACE was used as PCR template for PCR screening.

Two oligonucleotides shown below were used for PCR screening of cDNA of *Thermoascus aurantiacus* CGMCC 0583. The forward primer was derived from an alignment of conserved regions of cellobiohydrolase I genes and the reverse primer was provided by the 3' RACE System.

```
Forward primer:
                                    (SEQ ID NO: 81)
5'-GGnACnGGnTA(t/c)TG(t/c)GA-3'

Reverse primer:
                                    (SEQ ID NO: 82)
5'-TCnA(a/g)CCAnA(a/g)CAT(a/g)TT-3'
```

One hundred picomoles of the above primers were used in a PCR reaction composed of 2 μl of the first strand cDNA of 3' RACE, 5 μl of 10× Taq DNA polymerase buffer, 3 μl of 25 mM $MgCl_2$, 1 μl of 10 mM dNTP, and 2.5 units of Taq DNA polymerase in a final volume of 50 μl. The amplification was performed in a thermocycler programmed for 1 cycle at 95° C. for 3 minutes; 30 cycles each at 95° C. for 30 seconds, 50° C. for 30 seconds, and 72° C. for 50 seconds; and 1 cycle at 72° C. for 10 minutes. The heat block then went to a 4° C. soak cycle.

The reaction products were isolated by 1.0% agarose gel electrophoresis using TBE buffer where an approximately 0.65 kb product band was excised from the gel, and purified using a WIZARD® PCR Preps DNA Purification System according to the manufacturer's instructions. The PCR product was sequenced using a 377 DNA Analyzer. Sequencing showed that the 0.65 kb fragment was homologous to cellobiohydrolase I.

Two oligos were designed for 5' end cloning of *Thermoascus aurantiacus* CGMCC 0583 Cel7A cellobiohydrolase I by using a 5' RACE System for Rapid Amplification of cDNA Ends.

```
Primer 025AS1:
                                    (SEQ ID NO: 83)
5'-GTAGAGATGCTGTTGGCT-3'

Primer 025AS1.5:
                                    (SEQ ID NO: 84)
5'-TCTCAGCGCAGCAGGAACCGT-3'
```

The gene specific primer 025AS1 was used for first strand cDNA synthesis using the 5' RACE System according to the manufacturer's instructions. The first strand cDNA of 5' RACE was used as template for a PCR amplification composed of 5 μl of 10× Taq DNA polymerase buffer, 3 μl of 25 mM $MgCl_2$, 1 μl of 10 mM dNTP, 2 μl of 10 μM primer 025AS1.5, 2 μl of 10 μM primer AAP (Abridged Anchor Primer, provided by the kit), and 2.5 units of Taq DNA polymerase in a final volume of 50 μl. The amplification was performed in a thermocycler programmed for 1 cycle at 94° C. for 2 minutes; 30 cycles each at 94° C. for 40 seconds, 55° C. for seconds, and 72° C. for 60 seconds; and 1 cycle at 72° C. for 10 minutes. The heat block then went to a 4° C. soak cycle.

The PCR products were isolated by 1.0% agarose gel electrophoresis using TBE buffer and purified using a WIZARD® PCR Preps DNA Purification System. A dominant DNA fragment at 0.8 kb was confirmed to be the 5' end of

*Thermoascus aurantiacus* CGMCC 0583 Cel7A cellobiohydrolase I gene by sequencing using a 377 DNA Analyzer.

One forward primer, 1F shown below, was designed based on the sequence information of the 5' end cloning. Primer 1F was used for the full-length cloning of the *Thermoascus aurantiacus* CGMCC 0583 Cel7A cellobiohydrolase I gene together with primer AUAP (provided by the kit) as the reverse primer.

```
Primer 1F:
                                    (SEQ ID NO: 85)
5'-AGCGACAGCAATAACAAT-3'
```

Ten picomoles of the above 2 primers were used in a PCR reaction composed of the 4 µl of first strand cDNA of 3' RACE, 5 µl of 10× Taq DNA polymerase buffer, 3 µl of 25 mM MgCl$_2$ 1 µl of 10 mM dNTP, and 2.5 units of Taq DNA polymerase in a final volume of 50 µl. The amplification was performed in a thermocycler programmed for 1 cycle at 95° C. for 2 minutes; 30 cycles each at 95° C. for 40 seconds, 58° C. for 40 seconds, and 72° C. for 90 seconds; and 1 cycle at 72° C. for 10 minutes. The heat block then went to a 4° C. soak cycle.

The reaction products were isolated by 1.0% agarose gel electrophoresis using TBE buffer where an approximately 1.7 kb product band was excised from the gel, and purified using a WIZARD® PCR Preps DNA Purification System. The PCR fragment was then ligated to pGEM-T using a pGEM-T Vector System. The plasmid DNA was confirmed by sequencing using a 377 DNA Analyzer. The correct clone was designated pT002-5.

Two synthetic oligonucleotide primers shown below containing Bsp LU111 sites on the forward primer and Pac 1 at the reverse primer were designed to PCR amplify the full-length open reading frame of the *Thermoascus aurantiacus* CGMCC 0583 Cel7A cellobiohydrolase I gene. A Rapid Ligation Kit was used to clone the fragment into pAlLo2.

```
PCR Forward primer:
                                    (SEQ ID NO: 86)
5'-ACATGTATCAGCGCGCTCTTCTC-3'

PCR Reverse primer:
                                    (SEQ ID NO: 87)
5'-TTAATTAATTAGTTGGCGGTGAAGGTCG-3'
```

Bold letters represent coding sequence. The underlined sequence contains sequence identity to the Bsp LU and Pac I restriction sites.

Fifty picomoles of each of the primers above were used in a PCR reaction containing 50 ng of plasmid pT002-5, 1× Pwo Amplification Buffer with MgSO$_4$, 4 µl of 10 mM blend of dATP, dTTP, dGTP, and dCTP, and 2.5 units of Pwo DNA Polymerase, in a final volume of 50 µl. A DNA ENGINE™ Thermal Cycler was used to amplify the fragment programmed for one cycle at 94° C. for 2 minutes; and 25 cycles each at 94° C. for 30 seconds, 59° C. for 30 seconds, and 72° C. for 1.5 minutes. After the 25 cycles, the reaction was incubated at 72° C. for 10 minutes and then cooled at 10° C. until further processed.

A 1.3 kb PCR reaction product was isolated on a 0.8% GTG® agarose gel using TAE buffer and 0.1 µg of ethidium bromide per ml. The DNA band was visualized with the aid of a DARKREADER™ Transilluminator to avoid UV-induced mutations. The 1.3 kb DNA band was excised with a disposable razor blade and purified with an ULTRA-FREE® DA spin cup according to the manufacturer's instructions.

The purified PCR fragment was cloned into pCR®4Blunt-TOPO® according to the manufacturer's instructions. PCR clones containing the coding region of interest were sequenced to Phred Q values of at least 40 to insure that there were no PCR induced errors. All sequence aligments were performed with Consed (University of Washington). One of the clones that was shown to have the expected sequence was selected and re-named TaPCR. The TaPCR clone containing the *T. aurantiacus* cellobiohydrolase I coding region was double digested with the restriction enzymes Bsp LU111 and Pac I and gel purified as described above. This DNA fragment was then ligated into pAlLo2 previously digested with Nco I and Pac I using a Rapid Ligation Kit. Expression clones were confirmed by restriction digestion and sequenced to confirm that the junction vector-insert was correct. Plasmid DNA for transformation was prepared with a Midi-Prep Kit. The final clone was re-named pAlLo6.

*Aspergillus oryzae* JaL250 protoplasts were prepared according to the method of Christensen et al., 1988, supra. Ten micrograms of pAlLo6 were used to transform the *Aspergillus oryzae* JaL250 protoplasts. Twelve transformants were isolated to individual PDA plates and incubated for 5 days at 34° C. Confluent spore plates were washed with 5 ml of TWEEN® 80 and the spore suspension was used to inoculate 25 ml of MDU2BP medium in 125 ml glass shake flasks. Transformant cultures were incubated at 34° C. with constant shaking at 200 rpm. At day five post-inoculation, cultures were centrifuged at 6000×g and their supernatants collected. Five microliters of each supernatant were mixed with an equal volume of 2× loading buffer (10% beta-mercaptoethanol) and analyzed by SDS-PAGE using a 1.5 mm 8%-16% Tris-glycine SDS-PAGE gel and stained with SIMPLY BLUE™ SafeStain. SDS-PAGE profiles of the culture broths showed that eleven out of twelve transformants had a new protein band of approximately 60 kDa. Transformant number 12 was selected for further studies and designated *A. oryzae* JaL250AlLo6.

A spore stock suspension was prepared from a 5 day plate culture of *A. oryzae* JaL250AlLo6 by adding 10 ml of 0.1% TWEEN® 20 to the culture plate to release the spores. A shake flask culture was started by inoculating 100 µl of the spore stock to a 250 ml baffled flask containing 50 ml of M410 medium pH 6.0. The shake flask was grown at 34° C. for 5 days with shaking a 250 rpm. The culture was filtered through a 0.2 µm pore filter device and the filtrate was recovered for protein purification.

A 50 ml volume of the filtrate was desalted and buffer exchanged in 20 mM sodium acetate pH 5.0 using an ECONO-PAC® 10-DG desalting column according to the manufacturer's instructions. Protein concentration was determined using a Microplate BCA™ Protein Assay Kit in which bovine serum albumin was used as a protein standard.

Example 5: Preparation of *Myceliophthora thermophila* CBS 117.65 Cel6A Cellobiohydrolase II The *Myceliophthora thermophila* CBS 117.65 Cel6A cellobiohydrolase II (SEQ ID NO: 9 [DNA sequence] and SEQ ID NO: 10 [deduced amino acid sequence]) was obtained according to the procedure described below.

One hundred ml of shake flask medium was added to a 500 ml shake flask. The shake flask medium was composed per liter of 15 g of glucose, 4 g of $K_2HPO_4$, 1 g of NaCl, 0.2 g of $MgSO_4·7H_2O$, 2 g of MES free acid, 1 g of Bacto Peptone, 5 g of yeast extract, 2.5 g of citric acid, 0.2 g of $CaCl_2·2H_2O$, 5 g of $NH_4NO_3$, and 1 ml of trace elements solution. The trace elements solution was composed per liter of 1.2 g of $FeSO_4·7H_2O$, 10 g of $ZnSO_4·7H_2O$, 0.7 g of $MnSO_4·H_2O$, 0.4 g of $CuSO_4·5H_2O$, 0.4 g of $Na_2B_4O_7·10H_2O$, and 0.8 g of $Na_2MoO_2·2H_2O$. The shake flask was inoculated with two plugs from a solid plate culture of *Myceliophthora thermophila* strain CBS 117.65 and incubated at 45° C. with shaking at 200 rpm for 48 hours. Fifty ml of the shake flask broth was used to inoculate a 2 liter fermentation vessel.

Fermentation batch medium was composed per liter of 5 g of yeast extract, 176 g of powdered cellulose, 2 g of glucose, 1 g of NaCl, 1 g of Bacto Peptone, 4 g of $K_2HPO_4$, 0.2 g of $CaCl_2·2H_2O$, 0.2 g of $MgSO_4·7H_2O$, 2.5 g of citric acid, 5 g of $NH_4NO_3$, 1.8 ml of anti-foam, and 1 ml of trace elements solution (above). Fermentation feed medium was composed of water and antifoam.

A total of 1.8 liters of the fermentation batch medium was added to a two liter glass jacketed fermentor (Applikon Biotechnology, Schiedam, Netherlands). Fermentation feed medium was dosed at a rate of 4 g/l/hr for a period of 72 hours. The fermentation vessel was maintained at a temperature of 45° C. and pH was controlled using an Applikon 1030 control system (Applikon Biotechnology, Schiedam, Netherlands) to a set-point of 5.6+/−0.1. Air was added to the vessel at a rate of 1 vvm and the broth was agitated by Rushton impeller rotating at 1100 to 1300 rpm. At the end of the fermentation, whole broth was harvested from the vessel and centrifuged at 3000×g to remove the biomass.

The harvested broth obtained above was centrifuged in 500 ml bottles at 13,000×g for minutes at 4° C. and then sterile filtered using a 0.22 μm polyethersulfone membrane (Millipore, Bedford, MA, USA). The filtered broth was concentrated and buffer exchanged with mM Tris-HCl pH 8.5 using a tangential flow concentrator equipped with a 10 kDa polyethersulfone membrane at approximately 20 psi. To decrease the amount of pigment, the concentrate was applied to a 60 ml Q SEPHAROSE™ Big Bead column equilibrated with 20 mM Tris-HCl pH 8.5, and step eluted with equilibration buffer containing 600 mM NaCl. Flow-through and eluate fractions were examined on 8-16% CRITERION® SDS-PAGE gels (Bio-Rad Laboratories, Inc., Hercules, CA, USA) stained with GELCODE® Blue Stain Reagent (Bio-Rad Laboratories, Inc., Hercules, CA, USA). The flow-through fraction contained the *Myceliophthora thermophila* Cel6A cellobiohydrolase as judged by the presence of a band corresponding to the apparent molecular weight of the protein by SDS-PAGE (approximately 75 kDa).

The flow-through fraction was concentrated using an ultrafiltration device (Millipore, Bedford, MA, USA) equipped with a 10 kDa polyethersulfone membrane at 40 psi, 4° C. and mixed with an equal volume of 20 mM Tris-HCl pH 7.5 containing 3.4 M ammonium sulfate for a final concentration of 1.7 M ammonium sulfate. The sample was filtered (0.2 μM syringe filter, polyethersulfone membrane, Whatman, Maidstone, United Kingdom) to remove particulate matter prior to loading onto a PHENYL SUPEROSE™ column (HR 16/10, GE Healthcare, Piscataway, NJ, USA) equilibrated with 1.7 M ammonium sulfate in 20 mM Tris-HCl pH 7.5. Bound proteins were eluted with a 12 column volume decreasing salt gradient of 1.7 M ammonium sulfate to 0 M ammonium sulfate in 20 mM Tris-HCl pH 7.5. Fractions were analyzed by 8-16% SDS-PAGE gel electrophoresis as described above, which revealed that the *Myceliophthora thermophila* Cel6A cellobiohydrolase eluted at the very end of the gradient (approximately 20 mM ammonium sulfate).

Fractions containing the Cel6A cellobiohydrolase II were pooled and diluted 10-fold in 20 mM Tris-HCl pH 9.0 (to lower the salt and raise the pH) and then applied to a 1 ml RESOURCE™ Q column (GE Healthcare, Piscataway, NJ, USA) equilibrated with 20 mM Tris-HCl pH 9.0. Bound proteins were eluted with a 20 column volume salt gradient from 0 mM to 550 mM NaCl in 20 mM Tris-HCl pH 9.0. *M. thermophila* Cel6A cellobiohydrolase II eluted as a single peak early in the gradient (~25 mM NaCl). The cellobiohydrolase II was >90% pure as judged by SDS-PAGE. Protein concentrations were determined using a BCA Protein Assay Kit (Pierce, Rockford, IL, USA) in which bovine serum albumin was used as a protein standard.

Example 6: Preparation of Recombinant
*Myceliophthora thermophila* CBS 202.75 Cel6A
Cellobiohydrolase II

*Myceliophthora thermophila* CBS 202.75 was grown in 100 ml of YEG medium in a baffled shake flask at 45° C. for 2 days with shaking at 200 rpm. Mycelia were harvested by filtration using MIRACLOTH® (Calbiochem, La Jolla, CA, USA), washed twice in deionized water, and frozen under liquid nitrogen. Frozen mycelia were ground, by mortar and pestle, to a fine powder, and total DNA was isolated using a DNEASY® Plant Maxi Kit (QIAGEN Inc., Valencia, CA, USA).

A full-length Family 6 cellobiohydrolase gene (Cel6A) was isolated from *Myceliophthora thermophila* CBS 202.75 using a GENOMEWALKER™ Universal Kit (Clontech Laboratories, Inc., Mountain View, CA, USA) according to the manufacturer's instructions. Briefly, total genomic DNA from *Myceliophthora thermophila* CBS 202.75 was digested separately with four different restriction enzymes (Dra I, Eco RV, Pvu II, and Stu I) that leave blunt ends. Each batch of digested genomic DNA was then ligated separately to the GENOMEWALKER™ Adaptor (Clontech Laboratories, Inc., Mountain View, CA, USA) to create four libraries. These libraries were then employed as templates in PCR reactions using two gene-specific primers shown below, one for primary PCR and one for secondary PCR. The primers were designed based on a partial Family 6 cellobiohydrolase gene (Cel6A) sequence from *Myceliophthora thermophila* (WO 2004/056981).

```
Primer MtCel6A-R4:
                                (SEQ ID NO: 88)
5'-ATTGGCAGCCCGGATCTGGGACAGAGTCTG-3'

Primer MtCel6A-R5:
                                (SEQ ID NO: 89)
5'-CCGGTCATGCTAGGAATGGCGAGATTGTGG-3'
```

The primary amplifications were composed of 1 μl (approximately 6 ng) of each library as template, 0.4 mM each of dATP, dTTP, dGTP, and dCTP, 10 pmol of Adaptor Primer 1 (Clontech Laboratories, Inc., Mountain View, CA, USA), 10 pmol of primer MtCel6A-R4, 1× ADVANTAGE® GC-Melt LA Buffer (Clontech Laboratories, Inc., Mountain View, CA, USA), and 1.25 units of ADVANTAGE® GC Genomic Polymerase Mix (Clontech Laboratories, Inc., Mountain View, CA, USA) in a final volume of 25 μl. The amplification reactions were incubated in an EPPENDORF® MASTERCYCLER® 5333 (Eppendorf Scientific, Inc., Westbury, NY, USA) programmed for pre-denaturing at 94° C. for 1 minute; 7 cycles each at a denaturing temperature of 94° C. for 30 seconds; annealing and elongation at 72° C. for 5 minutes; and 32 cycles each at 67° C. for 5 minutes.

The secondary amplifications were composed of 1 µl of each primary PCR product as template, 0.4 mM each of dATP, dTTP, dGTP, and dCTP, 10 pmol of Adaptor Primer 2 (Clontech Laboratories, Inc., Mountain View, CA, USA), 10 pmol of primer MtCel6A-R5, 1× ADVANTAGE® GC-Melt LA Buffer, and 1.25 units of ADVANTAGE® GC Genomic Polymerase Mix in a final volume of 25 µl. The amplifications were incubated in an EPPENDORF® MASTERCYCLER® 5333 programmed for pre-denaturing at 94° C. for 1 minute; 5 cycles each at a denaturing temperature of 94° C. for 30 seconds; annealing and elongation at 72° C. for 5 minutes; and 20 cycles at 67° C. for 5 minutes.

The reaction products were isolated by 1.0% agarose gel electrophoresis using TAE buffer where a 3.5 kb product band from the Eco RV library was excised from the gel, purified using a QIAQUICK® Gel Extraction Kit according to the manufacturer's instructions, and sequenced.

DNA sequencing of the 3.5 kb PCR fragment was performed with a Perkin-Elmer Applied Biosystems Model 377 XL Automated DNA Sequencer (Perkin-Elmer/Applied Biosystems, Inc., Foster City, CA, USA) using dye-terminator chemistry (Giesecke et al., 1992, *Journal of Virology Methods* 38: 47-60) and primer walking strategy. The following gene specific primers were used for sequencing:

```
MtCel6A-F2:
                                    (SEQ ID NO: 90)
5'-GCTGTAAACTGCGAATGGGTTCAG-3'

MtCel6A-F3:
                                    (SEQ ID NO: 91)
5'-GGGTCCCACATGCTGCGCCT-3'

MtCel6A-R8:
                                    (SEQ ID NO: 92)
5'-AAAATTCACGAGACGCCGGG-3'
```

Nucleotide sequence data were scrutinized for quality and all sequences were compared to each other with assistance of PHRED/PHRAP software (University of Washington, Seattle, WA, USA). The 3.5 kb sequence was compared and aligned with a partial Family 6 cellobiohydrolase gene (Cel6A) sequence from *Myceliophthora thermophila* (WO 2004/056981).

A gene model for the *Myceliophthora thermophila* sequence was constructed based on similarity of the encoded protein to homologous glycoside hydrolase Family 6 proteins from *Thielavia terrestris, Chaetomium thermophilum, Humicola insolens*, and *Trichoderma reesei*. The nucleotide sequence and deduced amino acid sequence of the *Myceliophthora thermophila* CBS 202.75 Cel6A cellobiohydrolase II gene are shown in SEQ ID NO: 11 and SEQ ID NO: 12, respectively. The genomic fragment encodes a polypeptide of 482 amino acids, interrupted by 3 introns of 96, 87, and 180 bp. The % G+C content of the gene and the mature coding sequence are 61.6% and 64%, respectively. Using the SignalP software program (Nielsen et al., 1997, *Protein Engineering* 10: 1-6), a signal peptide of 17 residues was predicted. The predicted mature protein contains 465 amino acids with a molecular mass of 49.3 kDa.

Two synthetic oligonucleotide primers shown below were designed to PCR amplify the *Myceliophthora thermophila* cellobiohydrolase gene from the genomic DNA prepared above for construction of an *Aspergillus oryzae* expression vector. An IN-FUSION™ Cloning Kit (BD Biosciences, Palo Alto, CA, USA) was used to clone the fragment directly into the expression vector pAlLo2, without the need for restriction digestion and ligation.

```
MtCel6A-F4:
                                    (SEQ ID NO: 93)
5'-ACTGGATTTACCATGGCCAAGAAGCTTTTCATCACC-3'

MtCel6A-R9:
                                    (SEQ ID NO: 94)
5'-TCACCTCTAGTTAATTAATTAGAAGGGCGGGTTGGCGT-3'
```

Bold letters represent coding sequence. The remaining sequence is homologous to the insertion sites of pAlLo2.

Fifty picomoles of each of the primers above were used in a PCR reaction composed of 100 ng of *Myceliophthora thermophila* genomic DNA, 1× ADVANTAGE® GC-Melt LA Buffer, 0.4 mM each of dATP, dTTP, dGTP, and dCTP, and 1.25 units of ADVANTAGE® GC Genomic Polymerase Mix in a final volume of 25 µl. The amplification reaction was incubated in an EPPENDORF® MASTERCYCLER® 5333 programmed for 1 cycle at 94° C. for 1 minutes; and cycles each at 94° C. for 30 seconds, 62° C. for 30 seconds, and 72° C. for 2 minutes. The heat block then went to a 4° C. soak cycle.

The reaction products were isolated by 1.0% agarose gel electrophoresis using TAE buffer where a 1842 bp product band was excised from the gel, and purified using a QIAQUICK® Gel Extraction Kit according to the manufacturer's instructions.

Plasmid pAlLo2 was digested with Nco I and Pac I, isolated by 1.0% agarose gel electrophoresis using TAE buffer, and purified using a QIAQUICK® Gel Extraction Kit according to the manufacturer's instructions.

The gene fragment and the digested vector were ligated together using an IN-FUSION™ Cloning Kit resulting in pSMai180 in which transcription of the cellobiohydrolase gene was under the control of a NA2-tpi promoter (a modified promoter from the gene encoding neutral alpha-amylase in *Aspergillus niger* in which the untranslated leader has been replaced by an untranslated leader from the gene encoding triose phosphate isomerase in *Aspergillus nidulans*). The ligation reaction (50 µl) was composed of 1× IN-FUSION™ Buffer (BD Biosciences, Palo Alto, CA, USA), 1×BSA (BD Biosciences, Palo Alto, CA, USA), 1 µl of IN-FUSION™ enzyme (diluted 1:10) (BD Biosciences, Palo Alto, CA, USA), 100 ng of pAlLo2 digested with Nco I and Pac I, and 50 ng of the *Myceliophthora thermophila* Cel6A purified PCR product. The reaction was incubated at room temperature for 30 minutes. One µl of the reaction was used to transform *E. coli* XL10 SOLOPACK® Gold cells. An *E. coli* transformant containing pSMai180 was detected by restriction digestion and plasmid DNA was prepared using a BIOROBOT® 9600. The *Myceliophthora thermophila* Cel6A insert in pSMai180 was confirmed by DNA sequencing.

The same 1842 bp PCR fragment was cloned into pCR®2.1-TOPO® (Invitrogen, Carlsbad, CA, USA) using a TOPO® TA CLONING® Kit to generate pSMai182. The *Myceliophthora thermophila* cel6A gene insert in pSMai182 was confirmed by DNA sequencing. *E. coli* pSMai182 was deposited with the Agricultural Research Service Patent Culture Collection, Northern Regional Research Center, 1815 University Street, Peoria, Ill., 61604, on Sep. 6, 2007.

The *Myceliophthora thermophila* Family 6 cellobiohydrolase Cel6A gene was expressed in *Aspergillus oryzae* JaL355. *A. oryzae* JaL355 (WO 2002/40694) protoplasts were prepared according to the method of Christensen et al., 1988, supra. Three μg of pSMai180 were used to transform *Aspergillus oryzae* JaL355.

The transformation of *Aspergillus oryzae* JaL355 with pSMai180 yielded about 50 transformants. Twenty transformants were isolated to individual Minimal medium plates.

Confluent Minimal Medium plates of the 20 transformants were washed with 5 ml of 0.01% TWEEN® 20 and inoculated separately into 25 ml of MDU2BP medium in 125 ml glass shake flasks and incubated at 34° C., 250 rpm. After 5 days incubation, 5 μl of supernatant from each culture were analyzed using 8-16% CRITERION® SDS-PAGE gels and a CRITERION® Cell (Bio-Rad Laboratories, Inc., Hercules, CA, USA), according to the manufacturer's instructions. The resulting gel was stained with BIO-SAFE™ Coomassie Stain (Bio-Rad Laboratories, Inc., Hercules, CA, USA). SDS-PAGE profiles of the cultures showed that the majority of the transformants had a major band of approximately 70 kDa.

A confluent plate of one transformant, designated transformant 14, was washed with 10 ml of 0.01% TWEEN® 20 and inoculated into a 2 liter Fernbach flask containing 500 ml of MDU2BP medium to generate broth for characterization of the enzyme. The culture was harvested on day 5 and filtered using a 0.22 μm EXPRESS™ Plus Membrane.

The filtered broth was concentrated and buffer exchanged using a tangential flow concentrator equipped with a 10 kDa polyethersulfone membrane with 20 mM Tris-HCl pH 8.0. The concentrated and buffer exchanged broth was adjusted to 20 mM Tris-HCl pH 8.0-1.2 M $(NH_4)_2SO_4$ and applied to a Phenyl SUPEROSE™ column (HR 16/10) equilibrated with 20 mM Tris-HCl pH 8.0-1.2 M $(NH_4)_2SO_4$. Bound proteins were eluted with a linear gradient over 10 column volumes from 300 to 0 mM $(NH_4)_2SO_4$ in 20 mM Tris-HCl pH 8.0. SDS-PAGE of eluate fractions showed a major band at approximately 70 kDa. These fractions were then concentrated and buffer exchanged by centrifugal concentration using a VIVASPIN™ centrifugal concentrator (10 kDa polyethersulfone membrane, Sartorius, Gottingen, Germany) into 20 mM Tris-HCl pH 8.0. Protein concentration was determined using a Microplate BCA™ Protein Assay Kit in which bovine serum albumin was used as a protein standard.

Example 7: Preparation of *Thielavia terrestris* NRRL 8126 Cel6A Cellobiohydrolase II (CBHII)

*Thielavia terrestris* NRRL 8126 Cel6A cellobiohydrolase II (SEQ ID NO: 13 [DNA sequence] and SEQ ID NO: 14 [deduced amino acid sequence]) was recombinantly prepared according to WO 2006/074435 using *Trichoderma reesei* as a host.

Culture filtrate was desalted and buffer exchanged in 20 mM Tris-150 mM sodium chloride pH 8.5 using an ECONO-PAC® 10-DG desalting column according to the manufacturer's instructions. Protein concentration was determined using a Microplate BCA™ Protein Assay Kit in which bovine serum albumin was used as a protein standard.

Example 8: Preparation of *Trichophaea saccata* CBS 804.70 Cellobiohydrolase II (CBHII)

The *Trichophaea saccata* CBS 804.70 cellobiohydrolase II (CBHII) (SEQ ID NO: 15 [DNA sequence] and SEQ ID NO: 16 [deduced amino acid sequence]) was prepared as described below.

*Trichophaea saccata* CBS 804.70 was inoculated onto a PDA plate and incubated for 7 days at 28° C. Several mycelia-PDA agar plugs were inoculated into 750 ml shake flasks containing 100 ml of MEX-1 medium. The flasks were incubated at 37° C. for 9 days with shaking at 150 rpm. The fungal mycelia were harvested by filtration through MIRACLOTH® (Calbiochem, San Diego, CA, USA) before being frozen in liquid nitrogen. The mycelia were then pulverized into a powder by milling the frozen mycelia together with an equal volume of dry ice in a coffee grinder precooled with liquid nitrogen. The powder was transferred into a liquid nitrogen prechilled mortar and pestle and ground to a fine powder with a small amount of baked quartz sand. The powdered mycelial material was kept at −80° C. until use.

Total RNA was prepared from the frozen, powdered mycelia of *Trichophaea saccata* CBS 804.70 by extraction with guanidium thiocyanate followed by ultracentrifugation through a M CsCl cushion according to Chirgwin et al., 1979, *Biochemistry* 18: 5294-5299. The polyA enriched RNA was isolated by oligo (dT)-cellulose affinity chromatography according to Aviv et al., 1972, *Proc. Natl. Acad. Sci. USA* 69: 1408-1412.

Double stranded cDNA was synthesized according to the general methods of Gubler and Hoffman, 1983, *Gene* 25: 263-269; Sambrook, J., Fritsch, E. F., and Maniantis, T. *Molecular cloning: A Laboratory Manual*, $2^{nd}$ ed., 1989, Cold Spring Harbor Laboratory, Cold Spring Harbor, New York; and Kofod et al., 1994, *J. Biol. Chem.* 269: 29182-29189, using a polyA-Not I primer (Promega Corp., Madison, Wisconsin, USA). After synthesis, the cDNA was treated with mung bean nuclease, blunt ended with T4 DNA polymerase, and ligated to a 50-fold molar excess of Eco RI adaptors (Invitrogen Corp., Carlsbad, CA, USA). The cDNA was cleaved with Not I and the cDNA was size fractionated by 0.8% agarose gel electrophoresis using in 44 mM Tris base, 44 mM boric acid, 0.5 mM EDTA (TBE) buffer. The fraction of cDNA of 700 bp and larger was excised from the gel and purified using a GFX® PCR DNA and Gel Band Purification Kit (GE Healthcare Life Sciences, Piscataway, NJ, USA) according to the manufacturer's instructions.

The prepared cDNA was then directionally cloned by ligation into Eco RI-Not I cleaved pMHas5 (WO 03/044049) using a Rapid Ligation Kit (Roche Diagnostics GmbH, Penzberg, Germany) according to the manufacturer's instructions. The ligation mixture was electroporated into *E. coli* DH10B cells (Invitrogen Corp., Carlsbad, CA, USA) using a GENE PULSER® and Pulse Controller (Bio-Rad Laboratories, Inc., Hercules, CA, USA) at 50 μF, 25 mAmp, 1.8 kV with a 2 mm gap cuvette according to the manufacturer's procedure.

The electroporated cells were spread onto LB plates supplemented with 50 μg of kanamycin per ml. A cDNA plasmid pool was prepared from approximately 30,000 total transformants of the original cDNA-pMHas5 vector ligation. Plasmid DNA was prepared directly from the pool of colonies using a QIAPREP® Spin Midi/Maxiprep Kit (QIAGEN GmbH Corporation, Hilden, Germany). The cDNA library was designated SBL521-2.

A transposon containing plasmid designated pSigA4 was constructed from the pSigA2 transposon containing plasmid described in WO 01/77315 in order to create an improved version of the signal trapping transposon of pSigA2 with decreased selection background. The pSigA2 transposon contains a signal less beta-lactamase construct encoded on the transposon itself. PCR was used to create a deletion of the intact beta-lactamase gene found on the plasmid backbone using a proofreading PROOFSTART® DNA polymerase (QIAGEN GmbH Corporation, Hilden, Germany) and the following 5' phosphorylated primers (TAG Copenhagen, Denmark):

```
SigA2NotU-P:
                                    (SEQ ID NO: 95)
5'-TCGCGATCCGTTTTCGCATTTATCGTGAAACGCT-3'

SigA2NotD-P:
                                    (SEQ ID NO: 96)
5'-CCGCAAACGCTGGTGAAAGTAAAAGATGCTGAA-3'
```

The amplification reaction was composed of 1 µl of pSigA2 (10 ng/µl), 5 µl of 10× ProofStart Buffer (QIAGEN GmbH Corporation, Hilden, Germany), 2.5 µl of dNTP mix (20 mM), 0.5 µl of SigA2NotU-P (10 mM), 0.5 µl of SigA2NotD-P (10 mM), 10 µl of Q solution (QIAGEN GmbH Corporation, Hilden, Germany), and 31.25 µl of deionized water. A DNA ENGINE™ Thermal Cycler (MJ Research Inc., Waltham, MA, USA) was used for the amplification programmed for 1 cycle at 95° C. for 5 minutes; and 20 cycles each at 94° C. for 30 seconds, 62° C. for 30 seconds, and 72° C. for 4 minutes.

A 3.9 kb PCR reaction product was isolated by 0.8% agarose gel electrophoresis using TAE buffer and 0.1 µg of ethidium bromide per ml. The DNA band was visualized with the aid of an Eagle Eye Imaging System (Stratagene, La Jolla, CA, USA) at 360 nm. The 3.9 kb DNA band was excised from the gel and purified by using a GFX® PCR DNA and Gel Band Purification Kit according to the manufacturer's instructions.

The 3.9 kb fragment was self-ligated at 16° C. overnight with 10 units of T4 DNA ligase (New England Biolabs, Inc., Beverly, MA, USA), 9 µl of the 3.9 kb PCR fragment, and 1 µl of ligation buffer (New England Biolabs, Inc., Beverly, MA, USA). The ligation was heat inactivated for 10 minutes at 65° C. and then digested with Dpn I at 37° C. for 2 hours. After incubation, the digestion was purified using a GFX® PCR DNA and Gel Band Purification Kit.

The purified material was then transformed into E. coli TOP10 competent cells (Invitrogen Corp., Carlsbad, CA, USA) according to the manufacturer's instructions. The transformation mixture was plated onto LB plates supplemented with 25 µg of chloramphenicol per ml. Plasmid minipreps were prepared from several transformants and digested with Bgl II. One plasmid with the correct construction was chosen. The plasmid was designated pSigA4. Plasmid pSigA4 contains the Bgl II flanked transposon SigA2 identical to that disclosed in WO 01/77315.

A 60 µl sample of plasmid pSigA4 DNA (0.3 µg/µl) was digested with Bgl II and separated by 0.8% agarose gel electrophoresis using TAE buffer. A SigA2 transposon DNA band of 2 kb was eluted with 200 µl of EB buffer (QIAGEN GmbH Corporation, Hilden, Germany) and purified using a GFX® PCR DNA and Gel Band Purification Kit according to the manufacturer's instructions and eluted in 200 µl of EB buffer. SigA2 was used for transposon assisted signal trapping.

A complete description of transposon assisted signal trapping can be found in WO 01/77315. A cDNA plasmid pool was prepared from 30,000 total transformants of the original cDNA-pMHas5 vector ligation. Plasmid DNA was prepared directly from a pool of colonies recovered from solid LB selective medium using a QIAPREP® Spin Midi/Maxiprep Kit. The plasmid pool was treated with transposon SigA2 and MuA transposase (Finnzymes OY, Espoo, Finland) according to the manufacturer's instructions.

For in vitro transposon tagging of the Trichophaea saccata CBS 804.70 cDNA library, 4 or 8 µl of SigA2 transposon containing approximately 2.6 µg of DNA were mixed with 1 µl of the plasmid DNA pool of the Trichophaea saccata CBS 804.70 cDNA library containing 2 µg of DNA, 2 µl of MuA transposase (0.22 µg/µl), and 5 µl of 5× buffer (Finnzymes OY, Espoo, Finland) in a total volume of 50 µl and incubated at 30° C. for 3.5 hours followed by heat inactivation at 75° C. for 10 minutes. The DNA was precipitated by addition of 5 µl of 3 M sodium acetate pH 5 and 110 µl of 96% ethanol and centrifuged for 30 minutes at 10,000×g. The pellet was washed in 70% ethanol, air dried at room temperature, and resuspended in 10 µl of 10 mM Tris, pH 8, 1 mM EDTA (TE) buffer.

A 1.5 µl volume of the transposon tagged plasmid pool was electroporated into 20 µl of E. coli DH10B ultracompetent cells (Gibco-BRL, Gaithersburg MD, USA) according to the manufacturer's instructions using a GENE PULSER® and Pulse Controller (Bio-Rad Laboratories, Inc., Hercules, CA, USA) at 50 uF, 25 mAmp, 1.8 kV with a 2 mm gap cuvette according to the manufacturer's procedure.

The electroporated cells were incubated in SOC medium with shaking at 250 rpm for 2 hours at 28° C. before being plated on the following selective media: LB medium supplemented with 50 µg of kanamycin per ml; LB medium supplemented with 50 µg of kanamycin per ml and 15 µg of chloramphencol per ml; and/or LB medium supplemented with 50 µg of kanamycin per ml, 15 µg of chloramphencol per ml, and 12.5 µg of ampicillin per ml.

From dilution plating of the electroporation onto LB medium supplemented with kanamycin and chloramphencol medium, it was determined that approximately 72,000 colonies were present containing a cDNA library plasmid with a SigA2 transposition per electroporation and that approximately 69 colonies were recovered under triple selection (LB, kanamycin, chorlamphenicol, ampicillin). Further electroporation and plating experiments were performed until 445 total colonies were recovered under triple selection. The colonies were miniprepped using a QIAPREP® 96 Turbo Miniprep Kit (QIAGEN GmbH Corporation, Hilden, Germany). Plasmids were sequenced with the transposon forward and reverse primers (primers A and B), shown below, according to the procedure disclosed in WO 2001/77315 (page 28)

```
Primer A:
                                    (SEQ ID NO: 97)
5'-AGCGTTTGCGGCCGCGATCC-3'

Primer B:
                                    (SEQ ID NO: 98)
5'-TTATTCGGTCGAAAAGGATCC-3'
```

The Trichophaea saccata Family GH6 cDNA encoding cellobiohydrolase was subcloned into the Aspergillus expression vector pMStr57 (WO 2004/032648) by PCR amplifying the protein coding sequence from the cDNA library SBL0521, described above, with the two synthetic oligonucleotide primers shown below.

```
Primer 848:
                                    (SEQ ID NO: 99)
5'-ACACAACTGGGGATCCTCATCATGAAGAACTTCCTTCTGG-3'
```

-continued

Primer 849:
(SEQ ID NO: 100)
5'-CCCTCTAGATCTCGAGTTACGTGAAGCTAGGATTAGCATT-3'

The amplification was performed using IPROOF™ High Fidelity 2× Master Mix (Bio-Rad Laboratories, Inc., Hercules, CA, USA) following the manufacturer's instructions. The amplification reaction was composed of SBL0521 pool DNA as template, 25 pmol each of primers 848 and 849, and 25 µl of IPROOF™ High Fidelity 2× Master Mix in a final volume of 50 µl. The amplification was performed by pre-denaturing at 98° C. for 2 minutes; 5 cycles each with denaturing at 98° C. for 10 seconds, annealing at 65° C. for 10 seconds, and elongation at 72° C. for 1 minute; and 25 cycles each with denaturing at 98° C. for 10 seconds, and combined annealing extension at 72° C. for 1 minute. A final elongation was made at 72° C. for 10 minutes.

A PCR product of 1.4 kb was separated from residual reaction components using a GFX® PCR DNA and Gel Band Purification Kit according to the manufacturer's instructions.

The PCR fragment was cloned into Bam HI and Xho I digested pMStr57 using an IN-FUSION™ Dry-Down PCR Cloning Kit (Clontech Laboratories, Inc., Mountain View, CA, USA). Approximately 50 ng of PCR product and 200 ng of vector in a total volume of 10 µl were added to the IN-FUSION™ Dry-Down pellet. The reaction was performed according to the manufacturer's instructions. The Trichophaea saccata Family GH6 cellobiohydrolase encoding DNA of the resulting Aspergillus expression construct, pMStr179, was sequenced and the sequence agreed completely with the cellobiohydrolase coding sequence of SEQ ID NO: 16.

The same PCR fragment was cloned into the pCR®-BluntII-TOPO vector (Invitrogen, Life Technologies, Carlsbad, CA, USA) using a Zero Blunt TOPO PCR Cloning Kit, to generate pMStr199. The Trichophaea saccata Family GH6 cellobiohydrolase encoding DNA of pMStr199 was sequenced and the sequence agreed completely with the cellobiohydrolase coding sequence of SEQ ID NO: 1. E. coli strain NN059165, containing pMStr199, was deposited with the Deutsche Sammlung von Mikroorganismen und Zellkulturen GmbH (DSM), Braunschweig, Germany, on Feb. 24, 2010 and assigned the accession number DSM 23379.

The nucleotide sequence and deduced amino acid sequence of the Trichophaea saccata cellobiohydrolase cDNA are shown in SEQ ID NO: 1 and SEQ ID NO: 2, respectively. The coding sequence is 1344 bp including the stop codon. The encoded predicted protein is 447 amino acids. Using the SignalP program (Nielsen et al., 1997, Protein Engineering 10: 1-6), a signal peptide of 16 residues was predicted. The predicted mature protein contains 431 amino acids with a predicted molecular mass of 45.3 kDa and an isoelectric pH of 5.06.

A comparative pairwise global alignment of amino acid sequences was determined using the Needleman-Wunsch algorithm (Needleman and Wunsch, 1970, J. Mol. Biol. 48: 443-453) as implemented in the Needle program of EMBOSS with gap open penalty of 10, gap extension penalty of 0.5, and the EBLOSUM62 matrix. The alignment showed that the deduced amino acid sequence of the Trichophaea saccata cDNA encoding a Family GH6 polypeptide having cellobiohydrolase activity shares 64% identity (excluding gaps) to the deduced amino acid sequence of a cellobiohydrolase from Aspergillus fumigatus (GENESEQP:ABB80166).

The Aspergillus oryzae strain BECh2 (WO 2000/39322) was transformed with pMStr179 according to Christensen et al., 1988, Biotechnology 6, 1419-1422 and WO 2004/032648. Ten transformants were cultured for 4 days at 30° C. in 750 µl of DAP2C-1 medium (WO 2004/032648), in which 2% glucose was substituted for maltodextrin. Samples were monitored by SDS-PAGE using a CRITERION™ XT Precast 12% Bis-Tris gel (Bio-Rad Laboratories, Inc., Hercules, CA, USA) according to the manufacturer's instructions. LMW standards from an Amersham Low Molecular Weight Calibration Kit for SDS Electrophoresis (GE Healthcare UK Limited, Buckinghamshire, UK) were used as molecular weight markers. The gel was stained with INSTANTBLUE™ (Expedeon Protein Solutions, Cambridge, UK). Eight transformants produced a novel protein doublet in the range of 55-60 kDa.

Two of these transformants, designated Aspergillus oryzae MStr335 and MStr336, were isolated twice by dilution streaking conidia on selective medium (amdS) containing 0.01% TRITON® X-100 to limit colony size.

Spores from four confluent COVE N slants of Aspergillus oryzae MStr335 spores were collected with a solution of 0.01% TWEEN® 20 and used to inoculate 21 shake flasks each containing 150 ml of DAP2C-1 medium (WO 2004/032648) in which 2% glucose was substituted for maltodextrin. The flasks were incubated at 30° C. with constant shaking at 200 rpm for 3 days. Fungal mycelia and spores were removed at harvesting by first filtering the fermentation broth through a sandwich of 3 glass microfiber filters with increasing particle retention sizes of 1.6 µm, 1.2 µm and 0.7 µm, and then filtering through a 0.45 µm filter. Protein concentration was determined using a Microplate BCA™ Protein Assay Kit in which bovine serum albumin was used as a protein standard.

Example 9: Preparation of Aspergillus fumigatus Cellobiohydrolase II

Aspergillus fumigatus NN055679 cellobiohydrolase II (CBHII) (SEQ ID NO: 17 [DNA sequence] and SEQ ID NO: 18 [deduced amino acid sequence]) was prepared according to the following procedure.

Two synthetic oligonucleotide primers, shown below, were designed to PCR amplify the full-length open reading frame of the Aspergillus fumigatus Family 6A glycosyl hydrolase from genomic DNA. A TOPO Cloning kit was used to clone the PCR product. An IN-FUSION™ Cloning Kit was used to clone the fragment into pAl Lo2.

Forward primer:
(SEQ ID NO: 101)
5'-ACTGGATTTACCATGAAGCACCTTGCATCTTCCATCG-3'

Reverse primer:
(SEQ ID NO: 102)
5'-TCACCTCTAGTTAATTAAAAGGACGGGTTAGCGT-3'

Bold letters represent coding sequence. The remaining sequence contains sequence identity compared with the insertion sites of pAlLo2.

Fifty picomoles of each of the primers above were used in a PCR reaction containing 500 ng of Aspergillus fumigatus genomic DNA, 1× ThermoPol Taq reaction buffer (New England Biolabs, Ipswich, MA, USA), 6 µl of 10 mM blend of dATP, dTTP, dGTP, and dCTP, 0.1 unit of Taq DNA Polymerase (New England Biolabs, Ipswich, MA, USA), in a final volume of 50 µl. An EPPENDORF® MASTERCY- CLER® 5333 was used to amplify the fragment programmed for one cycle at 98° C. for 2 minutes; and 35 cycles each at 96° C. for 30 seconds, 61° C. for 30 seconds, and 72° C. for 2 minutes. After the 35 cycles, the reaction was incubated at 72° C. for 10 minutes and then cooled at 10° C. until further processed. To remove the A-tails produced by Taq the reaction was incubated for 10 minutes at 68° C. in the presence of 1 unit of Pfx DNA polymerase (Invitrogen, Carlsbad, CA, USA).

A 1.3 kb PCR reaction product was isolated on a 0.8% GTG-agarose gel (Cambrex Bioproducts, East Rutherford, NJ, USA) using TAE buffer and 0.1 µg of ethidium bromide per ml. The DNA band was visualized with the aid of a DARK READER™ (Clare Chemical Research, Dolores, CO) to avoid UV-induced mutations. The 1.3 kb DNA band was excised with a disposable razor blade and purified with an Ultrafree-DA spin cup (Millipore, Billerica, MA) according to the manufacturer's instructions.

The purified 1.3 kb PCR product was cloned into the PCR4Blunt-TOPO vector (Invitrogen). Two microliters of the purified PCR product were mixed with one microliter of a 2M Sodium chloride solution and one microliter of the Topo vector. The reaction was incubated at room temperature for 15 minutes and then two microliters of the Topo reaction were used to transform *E. coli* TOP10 competent cells according to the manufacturer's instructions. Two aliquots of 100 microliters each of the transformation reaction were spreaded onto two 150 mm 2×YT-Amp plates and incubated overnight at 37° C.

Eight recombinant colonies were used to inoculate liquid cultures containing three milliliters of LB supplemented with 100 µg of ampicillin per milliliter of media. Plasmid DNA was prepared from these cultures using a BIOROBOT® 9600. Clones were analyzed by restriction digest. Plasmid DNA from each clone was digested with the enzyme Eco RI according to the manufacturer instructions (NEB, Ipswich, MA, USA) and analyzed by agarose gel electrophoresis as above. Six out of eight clones had the expected restriction digest pattern from these, clones 2, 4, 5, 6, 7 and 8 were selected to be sequenced to confirm that there were no mutations in the cloned insert. Sequence analysis of their 5-prime and 3-prime ends indicated that clones 2, 6 and 7 had the correct sequence. These three clones were selected for re-cloning into pAlLo2. One microliter aliquot of each clone was mixed with 17 µl of diluted TE (1:10 dilution) and 1 µl of this mix was used to re-amplify the *Aspergillus fumigatus* glycosyl hydrolase 6A coding region.

Fifty picomoles of each of the primers above were used in a PCR reaction containing 1 µl of the diluted mix of clones 2, 6 and 7, 1× Pfx Amplification Buffer (Invitrogen, Carlsbad, CA, USA), 6 µl of 10 mM blend of dATP, dTTP, dGTP, and dCTP, 2.5 units of PLATINUM® Pfx DNA Polymerase, 1 µl of 50 mM MgSO 4, in a final volume of 50 µl. An EPPENDORF® MASTERCYCLER® 5333 was used to amplify the fragment programmed for one cycle at 98° C. for 2 minutes; and 35 cycles each at 94° C. for 30 seconds, 61° C. for 30 seconds, and 68° C. for 1.5 minutes. After the 35 cycles, the reaction was incubated at 68° C. for 10 minutes and then cooled at 10° C. until further processed. A 1.3 kb PCR reaction product was isolated on a 0.8% GTG-agarose gel using TAE buffer and 0.1 µg of ethidium bromide per ml. The DNA band was visualized with the aid of a DARK-READER™ Transilluminator to avoid UV-induced mutations. The 1.0 kb DNA band was excised with a disposable razor blade and purified with an Ultrafree-DA spin cup (Millipore, Billerica, MA) according to the manufacturer's instructions.

The vector pAlLo2 was linearized by digestion with Nco I and Pac I (using conditions specified by the manufacturer). The fragment was purified by gel electrophoresis and ultrafiltration as described above. Cloning of the purified PCR fragment into the linearized and purified pAlLo2 vector was performed with an IN-FUSION™ Cloning Kit. The reaction (20 µl) contained 1× IN-FUSION™ Buffer, 1×BSA, 1 µl of IN-FUSION™ enzyme (diluted 1:10), 100 ng of pAlLo2 digested with Nco I and Pac I, and 50 ng of the *Aspergillus fumigatus* GH6A purified PCR product. The reaction was incubated at room temperature for 30 minutes. A 2 µl sample of the reaction was used to transform transform *E. coli* TOP10 competent cells according to the manufacturer's instructions. After the recovery period, two 100 µl aliquots from the transformation reaction were plated onto 150 mm 2×YT plates supplemented with 100 µg of ampicillin per ml. The plates were incubated overnight at 37° C. A set of eight putative recombinant clones was selected at random from the selection plates and plasmid DNA was prepared from each one using a BIOROBOT® 9600. Clones were analyzed by Pst I restriction digest. Seven out of eight clones had the expected restriction digest pattern. Clones 1, 2 and 3 were then sequenced to confirm that there were no mutations in the cloned insert. Clone #2 was selected and designated pAlLo33.

*Aspergillus fumigatus* cel6A (JaL355 ALLO33 Exp03191) was grown to obtain culture broth for the purification of a cellobiosehydrolase II.

Seven hundred and fifty ml of shake flask medium were added to a 2800 ml shake flask. The shake flask medium was composed per liter of 45 g of maltose, 2 g of $K_2HPO_4$, 12 g of $KH_2PO_4$, 1 g of NaCl, 1 g of $MgSO_4·7H_2O$, 7 g of yeast extract, 2 g of urea, and 0.5 ml of trace elements solution. The trace elements solution was composed per liter of 13.8 g of $FeSO_4·7H_2O$, 14.3 g of $ZnSO_4·7H_2O$, 8.5 g of $MnSO_4·H_2O$, 2.5 g of $CuSO_4·5H_2O$, 0.5 g of $NiCl_2·6H_2O$, and 3 g of citric acid. Two shake flasks were inoculated by suspension of a PDA plate of *Aspergillus fumigatus* cel6A with 0.01% TWEEN® 20 and incubated at 34° C. on an orbital shaker at 200 rpm for 120 hours.

The broth was filtered using 0.7 µm glass filter GF/F (Whatman, Piscataway, NJ, USA) and then using a 0.22 µm EXPRESS™ Plus Membrane (Millipore, Bedford, MA, USA).

The filtered broth was concentrated and buffer exchanged using a tangential flow concentrator (Pall Filtron, Northborough, MA, USA) equipped with a 10 kDa polyethersulfone membrane (Pall Filtron, Northborough, MA, USA) with 20 mM Tris-HCl pH 8.0. Protein concentration was determined using a Microplate BCA™ Protein Assay Kit in which bovine serum albumin was used as a protein standard.

Example 10: Preparation of *Aspergillus terreus* ATCC 28865 Cel7 Endoglucanase I The *Aspergillus terreus* ATCC 28865 Cel7 endoglucanase I gene (SEQ ID NO: 19 [DNA sequence] and SEQ ID NO: 20 [deduced amino acid sequence]) was cloned and expressed in *Aspergillus oryzae* as described below.

Two synthetic oligonucleotide primers, shown below, were designed to PCR amplify the endoglucanase I gene from *Aspergillus terreus* ATCC 28865 genomic DNA. Genomic DNA was isolated using a FASTDNA® Spin Kit for Soil (MP Biomedicals, Solon, OH, USA).

Primer #226:
(SEQ ID NO: 103)
5'-TAACAATTGTCACCATGAATTCTCTTACAAAAAGCAT-3'

Primer #227:
(SEQ ID NO: 104)
5'-TATGCGGCCGCAGTCTGCATGTGTTACGCACCT-3'

The amplification reaction was composed of 1 µl of *Aspergillus terreus* ATCC 28865 genomic DNA, 12.5 µl of 2× REDDYMIX™ PCR Buffer (Thermo Fisher Scientific Inc., Waltham, MA, USA), 1 µl of primer #226 (5 µM), 1 µl of #227 (5 µM), and 9.5 µl of $H_2O$. The amplification reaction was incubated in a PTC-200 DNA ENGINE™ Thermal Cycler (MJ Research Inc., Waltham, MA, USA) programmed for 1 cycle at 94° C. for 2 minutes; and 35 cycles each at 94° C. for 15 seconds and 60° C. for 1.5 minutes.

A 1.44 kb PCR reaction product was isolated by 1% agarose gel electrophoresis using TAE buffer and staining with SYBR® Safe DNA gel stain (Invitrogen Corp., Carlsbad, CA, USA). The DNA band was visualized with the aid of an EAGLE EYE® Imaging System (Stratagene, La Jolla, CA, USA) and a DARKREADER® Transilluminator. The 1.44 kb DNA band was excised from the gel and purified using a GFX® PCR DNA and Gel Band Purification Kit according to the manufacturer's instructions.

The 1.44 kb fragment was cleaved with Mfe I and Not I and purified using a GFX® PCR DNA and Gel Band Purification Kit according to the manufacturer's instructions.

The cleaved 1.44 kb fragment was then directionally cloned by ligation into Eco RI-Not I cleaved pXYG1051 (WO 2005/080559) using T4 ligase (Promega, Madison, WI, USA) according to the manufacturer's instructions. The ligation mixture was transformed into *E. coli* TOP10F competent cells (Invitrogen Corp., Carlsbad, CA, USA) according to the manufacturer's instructions. The transformation mixture was plated onto LB plates supplemented with 100 µg of ampicillin per ml. Plasmid minipreps were prepared from several transformants and sequenced. One plasmid with the correct *Aspergillus terreus* GH7 coding sequence (SEQ ID NO: 13) was chosen. The plasmid was designated pXYG1051-NP003857. The expression vector pXYG1051 contains the same neutral amylase II (NA2) promoter derived from *Aspergillus niger*, and terminator elements as pCaHj483 (disclosed in Example 4 of WO 98/00529). Furthermore pXYG1051 has pUC18 derived sequences for selection and propagation in *E. coli*, and pDSY82 (disclosed in Example 4 of U.S. Pat. No. 5,958,727) derived sequences for selection and expression in *Aspergillus* facilitated by the pyrG gene of *Aspergillus oryzae*, which encodes orotidine decarboxylase and is used to complement a pyrG mutant *Aspergillus* strain.

The expression plasmid pXYG1051-NP003857 was transformed into *Aspergillus oryzae* JaL355 as described in WO 98/00529. Transformants were purified on selection plates through single conidia prior to sporulating them on PDA plates. Production of the *Aspergillus terreus* GH7 polypeptide by the transformants was analyzed from culture supernatants of 1 ml 96 deep well stationary cultivations at 26° C. in YP medium with 2% maltodextrin. Expression was verified by SDS-PAGE using a NUPAGE® NOVEX® 4-12% Bis-Tris Gel with 50 mM 2-(N-morpholino)ethanesulfonic acid (MES) buffer (Invitrogen Corporation, Carlsbad, CA, USA) by Coomassie blue staining. One transformant was selected for further work and designated *Aspergillus oryzae* 28.4.

For larger scale production, *Aspergillus oryzae* 28.4 spores were spread onto a PDA plate and incubated for five days at 37° C. The confluent spore plate was washed twice with 5 ml of 0.01% TWEEN® 20 to maximize the number of spores collected. The spore suspension was then used to inoculate twenty-five 500 ml flasks containing 100 ml of YPM medium. The culture was incubated at 30° C. with constant shaking at 85 rpm. At day four post-inoculation, the culture broth was collected by filtration through a triple layer of glass microfiber filters of 1.6 µm, 1.2 µm, and 0.7 µm (Whatman, Piscataway, NJ, USA). Fresh culture broth from this transformant produced a band of GH7 protein of approximately 64 kDa. The identity of this band as the *Aspergillus terreus* GH7 polypeptide was verified by peptide sequencing using standard techniques.

Two liters of the filtered broth was concentrated to 400 ml and washed with 50 mM HEPES pH 7.0 using a SARTOFLOVVO Alpha Plus Crossflow System with a 10 kDa cut-off (Sartorius Stedim Biotech S.A., Aubagne Cedex, France). Ammonium sulphate was added to a final concentration of 1 M and dissolved in the ultrafiltrate. The solution was loaded onto a Source 15 Phenyl XK 26/20 50 ml column (GE Healthcare, HiHerod, Denmark). After loading the column was washed with 150 ml of 1 M ammonium sulphate and eluted with 1 column volume of 50% ethanol in a 0% to 100% gradient followed by 5 column volumes of 50% ethanol at a flow rate of 10 ml per minute. Fractions of 10 ml were collected and analyzed by SDS-PAGE. Fractions 3 to 8 were pooled and diluted to 1000 ml with 50 mM HEPES pH 7.0 before loading onto a Q SEPHAROSE® Fast Flow XK26/20 60 ml column (GE Healthcare, HiHerod, Denmark). After loading the column was washed 3 times with 60 ml of 50 mM HEPES pH 7.0 and eluded with 100 ml of 50 mM HEPES pH 7.0, 1 M NaCl at a flow rate of 10 ml per minute. Fractions of ml were collected and analyzed by SDS-PAGE. The flow through and first wash were pooled and concentrated to 400 ml and washed with 50 mM HEPES pH 7.0 using a SARTOFLOVVO Alpha plus Crossflow System with a 10 kDa cut-off. Further concentration was conducted using a VIVASPIN™ centrifugal concentrator according to the manufacturer's instructions to a final volume of 80 ml. The protein concentration was determined by A 280/A 260 absorbance.

Example 11: Preparation of *Trichoderma reesei* RutC30 Cel5A Endoglucanase II

The *Trichoderma reesei* RutC30 Cel5A endoglucanase II gene (SEQ ID NO: 21 [DNA sequence] and SEQ ID NO: 22 [deduced amino acid sequence]) was cloned and expressed in *Aspergillus oryzae* as described below.

Two synthetic oligonucleotide primers, shown below, were designed to PCR amplify the endoglucanase II gene from *Trichoderma reesei* RutC30 genomic DNA. Genomic DNA was isolated using a DNEASY® Plant Maxi Kit. An IN-FUSION™ PCR Cloning Kit was used to clone the fragment directly into pAl Lo2 (WO 2004/099228).

Forward primer:
(SEQ ID NO: 105)
5'-ACTGGATTTACCATGAACAAGTCCGTGGCTCCATTGCT-3'

```
Reverse primer:
                                      (SEQ ID NO: 106)
5'-TCACCTCTAGTTAATTAACTACTTTCTTGCGAGACACG-3'
```

Bold letters represent coding sequence. The remaining sequence contains sequence identity to insertion sites of pAlLo2.

Fifty picomoles of each of the primers above were used in a PCR reaction containing 200 ng of *Trichoderma reesei* genomic DNA, 1× Pfx Amplification Buffer (Invitrogen, Carlsbad, CA, USA), 6 µl of 10 mM blend of dATP, dTTP, dGTP, and dCTP, 2.5 units of PLATINUM® Pfx DNA polymerase, and 1 µl of 50 mM $MgSO_4$ in a final volume of 50 µl. The amplification reaction was incubated in an EPPENDORF® MASTERCYCLER® 5333 programmed for one cycle at 98° C. for 2 minutes; and 35 cycles each at 94° C. for 30 seconds, 61° C. for 30 seconds, and 68° C. for 1.5 minutes. After the 35 cycles, the reaction was incubated at 68° C. for 10 minutes and then cooled at 10° C. A 1.5 kb PCR reaction product was isolated on a 0.8% GTG® agarose gel using TAE buffer and 0.1 µg of ethidium bromide per ml. The DNA band was visualized with the aid of a DARKREADER™ Transilluminator. The 1.5 kb DNA band was excised with a disposable razor blade and purified using an ULTRAFREE® DA spin cup according to the manufacturer's instructions.

Plasmid pAlLo2 was linearized by digestion with Nco I and Pac I. The plasmid fragment was purified by gel electrophoresis and ultrafiltration as described above. Cloning of the purified PCR fragment into the linearized and purified pAlLo2 vector was performed using an IN-FUSION™ PCR Cloning Kit. The reaction (20 µl) contained 1× IN-FUSION™ Buffer, 1×BSA, 1 µl of IN-FUSION™ enzyme (diluted 1:10), 100 ng of pAlLo2 digested with Nco I and Pac I, and 100 ng of the *Trichoderma reesei* Cel5A endoglucanase II PCR product. The reaction was incubated at room temperature for 30 minutes. A 2 µl sample of the reaction was used to transform *E. coli* XL10 SOLOPACK® Gold cells according to the manufacturer's instructions. After a recovery period, two 100 µl aliquots from the transformation reaction were plated onto 150 mm 2×YT plates supplemented with 100 µg of ampicillin per ml. The plates were incubated overnight at 37° C. A set of 3 putative recombinant clones was recovered the selection plates and plasmid DNA was prepared from each one using a BIOROBOT® 9600. Clones were analyzed by Pci I/Bsp LU11 I restriction digestion. One clone with the expected restriction digestion pattern was then sequenced to confirm that there were no mutations in the cloned insert. Clone #3 was selected and designated pAlLo27.

*Aspergillus oryzae* JaL250 protoplasts were prepared according to the method of Christensen et al., 1988, supra. Five micrograms of pAlLo27 (as well as pAlLo2 as a control) were used to transform *Aspergillus oryzae* JaL250 protoplasts.

The transformation of *Aspergillus oryzae* JaL250 with pAlLo27 yielded about 50 transformants. Eleven transformants were isolated to individual PDA plates and incubated for five days at 34° C.

Confluent spore plates were washed with 3 ml of 0.01% TWEEN® 80 and the spore suspension was used to inoculate 25 ml of MDU2BP medium in 125 ml glass shake flasks. Transformant cultures were incubated at 34° C. with constant shaking at 200 rpm. At day five post-inoculation, cultures were centrifuged at 6000×g and their supernatants collected. Five microliters of each supernatant were mixed with an equal volume of 2× loading buffer (10% beta-mercaptoethanol) and loaded onto a 1.5 mm 8%-16% Tris-glycine SDS-PAGE gel and stained with SIMPLYBLUE™ SafeStain (Invitrogen Corp., Carlsbad, CA, USA). SDS-PAGE profiles of the culture broths showed that ten out of eleven transformants produced a new protein band of approximately 45 kDa. Transformant number 1, designated *Aspergillus oryzae* JaL250AlLo27, was cultivated in a fermentor.

One hundred ml of shake flask medium were added to a 500 ml shake flask. The shake flask medium was composed per liter of 50 g of sucrose, 10 g of $KH_2PO_4$, 0.5 g of $CaCl_2$, 2 g of $MgSO_4 \cdot 7H_2O$, 2 g of $K_2SO_4$, 2 g of urea, 10 g of yeast extract, 2 g of citric acid, and 0.5 ml of trace metals solution. The trace metals solution was composed per liter of 13.8 g of $FeSO_4 \cdot 7H_2O$, 14.3 g of $ZnSO_4 \cdot 7H_2O$, 8.5 g of $MnSO_4 \cdot H_2O$, 2.5 g of $CuSO_4 \cdot 5H_2O$, and 3 g of citric acid. The shake flask was inoculated with two plugs of *Aspergillus oryzae* JaL250AlLo27 from a PDA plate and incubated at 34° C. on an orbital shaker at 200 rpm for 24 hours. Fifty ml of the shake flask broth was used to inoculate a 3 liter fermentation vessel.

A total of 1.8 liters of the fermentation batch medium was added to a three liter glass jacketed fermentor (Applikon Biotechnology, Schiedam, Netherlands). The fermentation batch medium was composed per liter of 10 g of yeast extract, 24 g of sucrose, 5 g of $(NH_4)_2SO_4$, 2 g of $KH_2PO_4$, 0.5 g of $CaCl_2O \cdot 2H_2O$, 2 g of $MgSO_4 \cdot 7H_2O$, 1 g of citric acid, 2 g of $K_2SO_4$, 0.5 ml of anti-foam, and 0.5 ml of trace metals solution. Trace metals solution was composed per liter of 13.8 g of $FeSO_4 \cdot 7H_2O$, 14.3 g of $ZnSO_4 \cdot 7H_2O$, 8.5 g of $MnSO_4 \cdot H_2O$, 2.5 g of $CuSO_4 \cdot 5H_2O$, and 3 g of citric acid. Fermentation feed medium was composed of maltose. Fermentation feed medium was dosed at a rate of 0 to 4.4 g/l/hr for a period of 185 hours. The fermentation vessel was maintained at a temperature of 34° C. and pH was controlled using an Applikon 1030 control system (Applikon Biotechnology, Schiedam, Netherlands) to a set-point of 6.1+/−0.1. Air was added to the vessel at a rate of 1 vvm and the broth was agitated by a Rushton impeller rotating at 1100 to 1300 rpm. At the end of the fermentation, whole broth was harvested from the vessel and centrifuged at 3000×g to remove the biomass. The supernatant was sterile filtered and stored at 5 to 10° C.

The supernatant was desalted and buffer-exchanged in 20 mM Bis-Tris pH 6.0 using a HIPREP® 26/10 desalting column according to the manufacturer's instructions. The buffer exchanged sample was loaded onto a MonoQ® column (GE Healthcare, Piscataway, NJ, USA) equilibrated with 20 mM Bis-Tris pH 6.0, and the bound protein was eluted with a linear gradient from 0 to 1000 mM sodium chloride. Protein fractions were pooled and buffer exchanged into 1.2 M $(NH_4)_2SO_4$–20 mM Tris-HCl pH 8.5. The sample was loaded onto a Phenyl SUPEROSE™ column (HR 16/10) equilibrated with 1.2 M $(NH_4)_2SO_4$–20 mM Tris-HCl pH 8.0. Bound proteins were eluted with a linear gradient over 20 column volumes from 1.2 to 0 M $(NH_4)_2SO_4$ in 20 mM Tris-HCl pH 8.5. The fractions were pooled, concentrated, and loaded onto a SUPERDEX® 75 HR 26/60 column (GE Healthcare, Piscataway, NJ, USA) equilibrated with 20 mM Tris-150 mM sodium chloride pH 8.5. Fractions were pooled and concentrated in 20 mM Tris-150 mM sodium chloride pH 8.5. Protein concentration was determined using a Microplate BCA™ Protein Assay Kit in which bovine serum albumin was used as a protein standard.

Example 12: Preparation of *Myceliophthora thermophila* CBS 202.75 Cel5A Endoglucanase II

*Myceliophthora thermophila* CBS 202.75 Cel5A endoglucanase II (EGII) (SEQ ID NO: 23 [DNA sequence] and SEQ ID NO: 24 [deduced amino acid sequence]) was prepared recombinantly according to WO 2007/109441 using *Aspergillus oryzae* HowB104 as a host. The culture filtrate was desalted and buffer-exchanged in 20 mM Tris pH 8.0 using a HIPREP® 26/10 desalting column according to the manufacturer's instructions. The buffer exchanged sample was applied to a MonoQ® column equilibrated with 20 mM Tris pH 8.0, and the bound protein was eluted with a gradient from 0 to 500 mM sodium chloride. Fractions were pooled and concentrated in 20 mM Tris pH 8.0. Protein concentration was determined using a Microplate BCA™ Protein Assay Kit in which bovine serum albumin was used as a protein standard.

Example 13: Preparation of *Thermoascus aurantiacus* CGMCC 0670 Cel5A Endoglucanase II

*Thermoascus aurantiacus* CGMCC 0670 cDNA encoding a Cel5A endoglucanase II (SEQ ID NO: 25 [DNA sequence] and SEQ ID NO: 26 [deduced amino acid sequence]) was cloned according to the following procedure. The *T. aurantiacus* strain was grown in 80 ml of CBH1 medium (2.5% AVICEL®, 0.5% glucose, 0.14% $(NH_4)_2SO_4$) in 500 ml Erlenmeyer baffled flasks at 45° C. for 3 days with shaking at 165 rpm. Mycelia were harvested by centrifugation at 7000 rpm for 30 minutes and stored at −80C before use for RNA extraction. RNA was isolated from 100 mg of mycelia using a RNEASY® Plant Mini Kit.

The cDNA for the *Thermoascus aurantiacus* endoglucanase was isolated by RT PCR using a 3' RACE system and a 5' RACE system and primers BG025-1, BG025-2, BG025-3, and BG025-4 shown below to the N-terminal amino acids.

```
Primer BG025-1:
                                    (SEQ ID NO: 107)
5'-AA(T/C)GA(A/G)TC(T/C/A/G)GG(T/C/A/G)GC(T/C/A/G)
GAATT-3'

Primer BG025-2:
                                    (SEQ ID NO: 108)
5'-AA(T/C)GA(A/G)TC(T/C/A/G)GG(T/C/A/G)GC(T/C/A/G)
GAGTT-3'

Primer BG025-3:
                                    (SEQ ID NO: 109)
5'-AA(T/C)GA(A/G)AG(T/C)GG(T/C/A/G)GC(T/C/A/G)GAAT
T-3'

Primer BG025-4:
                                    (SEQ ID NO: 110)
5'-AA(T/C)GA(A/G)AG(T/C)GG(T/C/A/G)GC(T/C/A/G)GAGT
T-3'
```

The RT PCR products were ligated into plasmid pGEM-T using a pGEM-T Vector System and transformed into *E. coli* strain JM109. A single clone harboring a plasmid named pBGC1009 containing the endoglucanase cDNA was isolated.

PCR primers were designed to amplify the cDNA encoding the *T. aurantiacus* endoglucanase from plasmid pBGC1009. Restriction enzyme sites Bsp HI and Pac I were incorporated for in-frame cloning into *Aspergillus oryzae* expression plasmid pBM120a (WO 2006/039541).

```
Primer 996261:
                                    (SEQ ID NO: 111)
5'-GATCTCATGAAGCTCGGCTCTCTCGT-3'
   BspHI Primer 996167:
                                    (SEQ ID NO: 112)
5'-TTAATTAATCAAAGATACGGAGTCAAAATAGG-3'
   PacI
```

The fragment of interest was amplified by PCR using an EXPAND™ High Fidelity PCR System. The PCR amplification reaction mixture contained 1 μl of 0.09 μg/μl pBGC1009, 1 μl of primer 996261 (50 μmol/μl), 1 μl of primer 996167 (50 μmol/μl), 5 μl of 10×PCR buffer with 15 mM $MgCl_2$, 1 μl of dNTP mix (10 mM each), 37.25 μl of water, and 0.75 μl (3.5 U/μl) of DNA polymerase mix. An EPPENDORF® MASTERCYCLER® thermocycler was used to amplify the fragment programmed for 1 cycle at 94° C. for 2 minutes; 10 cycles each at 94° C. for 15 seconds, 55° C. for 30 seconds, 72° C. for 1.5 minutes; 15 cycles each at 94° C. for 15 seconds, 55° C. for 30 seconds, and 72° C. for 1.5 minutes plus 5 second elongation at each successive cycle; 1 cycle at 72° C. for 7 minutes; and a 4° C. hold.

The 1008 bp PCR product was purified by 1% agarose gel electrophoresis using TAE buffer, excised from the gel, and purified using a QIAQUICK® Gel Purification Kit (QIAGEN Inc., Valencia, CA, USA). The purified product was ligated directly into pCR®2.1-TOPO® according to the manufacturer's instructions. The resulting plasmid was named pBM124a.

Plasmid pBM124a was digested with Bsp HI and Pac I, purified by 1% agarose gel electrophoresis using TAE buffer, excised from the gel, and purified using a QIAQUICK® Gel Purification Kit. The plasmid fragment was ligated to the vector pBM120a, which was digested with Nco I and Pac I. The resulting expression plasmid was designated pBM123a. Plasmid pBM123a contains a duplicate NA2-TPI promoter driving expression of the *Thermoascus aurantiacus* endoglucanase cDNA clone, the AMG terminator, and amdS as a selectable marker.

*Aspergillus oryzae* BECh2 (WO 2000/139322) protoplasts were prepared according to the method of Christensen et al., 1988, supra. Six μg of pBM123a were used to transform *Aspergillus oryzae* BECh2. Primary transformants were selected on COVE plates for 5 days. Transformants were spore purified twice prior to shake flask analysis.

Spores of the transformants were inoculated into 25 ml of MY25 medium in 125 ml shake flasks. The cultures were incubated at 34° C., 200 rpm on a platform shaker for five days. On day 3 and day 5, culture supernatants were harvested and clarified by centrifugation to remove mycelia. Twenty microliters of supernatant from three transformants were analyzed using a CRITERION® stain-free, 10-20% gradient SDS-PAGE gel (Bio-Rad Laboratories, Inc., Hercules, CA, USA) according to the manufacturer's instructions. SDS-PAGE profiles of the cultures showed that all transformants had a new major band of approximately 32 kDa. One transformant was chosen and named EXP00858.

Plastic, non-baffled 500 ml shake flasks containing 100 ml of SY50 medium were inoculated with 0.1 ml of a spore stock of EXP00858, and incubated at 34° C., 200 rpm for 24 hours to produce a seed culture. Fifty ml of the seed culture was inoculated into a 2 liter fermentation tank containing 2 liters of medium composed per liter of 0.5 g of pluronic acid, 30 g of sucrose, 2 g of MgSO$_4$·7H$_2$O, 2 g of anhydrous KH$_2$PO$_4$, 1 g of citric acid, 2 g of (NH$_4$)$_2$SO$_4$, 1 g of K$_2$SO$_4$, 20 g of yeast extract, and 0.5 g of 200×AMG trace metals solution, pH 5.0. The fermentation was fed with a maltose feed. The pH was controlled using 5N H$_3$PO$_4$ and 15% NH$_4$OH and maintained at 5.0 and then raised to 5.25. Temperature was maintained 34.0° C.+/−1.0° C. Agitation was 1000 rpm. Airflow was 1.0 vvm.

A 200 ml volume of cell-free supernatant was diluted to 1 liter with deionized water. The pH was adjusted to 8 and the sample filter sterilized using a 0.22 μm polyethersulphone (PES) filter. The filter sterilized sample was loaded onto a 250 ml Q SEPHAROSE™ Fast Flow column (GE Healthcare, Piscataway, NJ, USA) pre-equilibrated with 25 mM Tris pH 8. The enzyme was eluted from the column with a 0 to 1 M NaOH gradient in the same buffer. The fractions containing beta-glucosidase activity were pooled (400 ml) and the enzyme concentration calculated from the theoretic extinction coefficient and the absorbance of the sample at 280 nm.

Example 14: Preparation of *Aspergillus fumigatus* NN055679 Cel3A Beta-Glucosidase

*Aspergillus fumigatus* NN055679 Cel3A beta-glucosidase (SEQ ID NO: 27 [DNA sequence] and SEQ ID NO: 28 [deduced amino acid sequence]) was recombinantly prepared according to WO 2005/047499 using *Trichoderma reesei* RutC30 as a host.

Filtered broth was concentrated and buffer exchanged using a tangential flow concentrator equipped with a 10 kDa polyethersulfone membrane with 20 mM Tris-HCl pH 8.5. The sample was loaded onto a Q SEPHAROSE® High Performance column (GE Healthcare, Piscataway, NJ, USA) equilibrated in 20 mM Tris pH 8.5, and bound proteins were eluted with a linear gradient from 0-600 mM sodium chloride. The fractions were concentrated and loaded onto a SUPERDEX® 75 HR 26/60 column equilibrated with 20 mM Tris-150 mM sodium chloride pH 8.5. Protein concentration was determined using a Microplate BCA™ Protein Assay Kit in which bovine serum albumin was used as a protein standard.

Example 15: Preparation of *Penicillium brasilianum* IBT 20888 Cel3A Beta-Glucosidase

*Penicillium brasilianum* IBT 20888 Cel3A beta-glucosidase (SEQ ID NO: 29 [DNA sequence] and SEQ ID NO: 30 [deduced amino acid sequence]) was recombinantly prepared according to WO 2007/019442 using *Aspergillus oryzae* as a host.

Filtered broth was concentrated and buffer exchanged using a tangential flow concentrator equipped with a 10 kDa polyethersulfone membrane with 20 mM Tris-HCl pH 8.0. The sample was loaded onto a Q SEPHAROSE® High Performance column (GE Healthcare, Piscataway, NJ, USA) equilibrated in 20 mM Tris pH 8.0, and bound proteins were eluted with a linear gradient from 0-600 mM sodium chloride. The fractions were concentrated into 20 mM Tris pH 8.0. Protein concentration was determined using a Microplate BCA™ Protein Assay Kit in which bovine serum albumin was used as a protein standard.

Example 16: Preparation of *Aspergillus niger* IBT 10140 Cel3 Beta-Glucosidase

The *Aspergillus niger* IBT 10140 Cel3 beta-glucosidase gene (SEQ ID NO: 31 [DNA sequence] and SEQ ID NO: 32 [deduced amino acid sequence]) was isolated by PCR using two cloning primers GH3-9.1f and GH3-9.1r shown below, which were designed based on the publicly available *Aspergillus niger* Cel3 sequence (CAK48740.1) for direct cloning using an IN-FUSION™ Cloning Kit.

```
Primer GH3-9.1f:
                                       (SEQ ID NO: 113)
    acacaactggggatccaccatgaggttcacttcgatcgagg Primer GH3-9.1r:
                                       (SEQ ID NO: 114)
    agatctcgagaagcttaGTGAACAGTAGGCAGAGACGCCCG
```

A PCR reaction was performed with genomic DNA prepared from *Aspergillus niger* strain NN005810 in order to amplify the full-length gene. The genomic DNA was isolated using a FASTDNA® Spin Kit (MP Biomedicals, Santa Ana, CA, USA). The PCR reaction was composed of 1 μl of genomic DNA, 0.75 μl of primer GH3-9.1f (10 μM), 0.75 μl of primer GH3-9.1r (10 μM), 3 μl of 5× HF buffer (Finnzymes Oy, Finland), 0.25 μl of 50 mM MgCl$_2$, 0.3 μl of 10 mM dNTP, μl of PHUSION® DNA polymerase (Finnzymes Oy, Finland), and PCR-grade water up to 15 μl. The PCR reaction was performed using a DYAD® PCR machine (Bio-Rad Laboratories, Inc., Hercules, CA, USA) programmed for 2 minutes at 98° C. followed by 10 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds; and 5 minutes at 72° C.

The reaction products were isolated by 1.0% agarose gel electrophoresis using TAE buffer where an approximately 2.6 kb PCR product band was excised from the gel and purified using a GFX® PCR DNA and Gel Band Purification Kit according to manufacturer's instructions. DNA corresponding to the *A. niger* Cel3 beta-glucosidase gene was cloned into the expression vector pDAu109 (WO 2005/042735) linearized with Bam HI and Hind III, using an IN-FUSION™ Dry-Down PCR Cloning Kit according to the manufacturer's instructions.

A 2.5 μl volume of the diluted ligation mixture was used to transform *E. coli* TOP10 chemically competent cells. Three colonies were selected on LB agar plates containing 100 μg of ampicillin per ml and cultivated overnight in 3 ml of LB medium supplemented with 100 μg of ampicillin per ml. Plasmid DNA was purified using an E.Z.N.A.® Plasmid Mini Kit (Omega Bio-Tek, Inc., Norcross, GA, USA) according to the manufacturer's instructions. The *A. niger* Cel3 beta-glucosidase gene sequence was verified by Sanger sequencing before heterologous expression.

Protoplasts of *Aspergillus oryzae* BECh2 (WO 2000/39322) were prepared as described in WO 95/02043. One hundred microliters of protoplast suspension were mixed with 2.5-15 μg of the *Aspergillus* expression vector and 250 μl of 10 mM CaCl$_2$-10 mM Tris-HCl pH 7.5-60% PEG 4000 (PEG 4000; Applichem, Omaha, NE, USA) (polyethylene glycol, molecular weight 4,000) were added and gently mixed. The mixture was incubated at 37° C. for 30 minutes and the protoplasts were spread on COVE plates for transformant selection. After incubation for 4-7 days at 37° C., spores of sixteen transformants were picked up and inoculated into YPM medium. After 4 days cultivation at 30° C. culture broth was analyzed in order to identified the best transformants based on their ability to produce *A. niger* Cel3 beta-glucosidase. The screening was based on intensity of the band corresponding to the heterologous expressed protein determined by SDS-PAGE and activity of the enzyme on 4-nitrophenyl-beta-D-glucopyranoside (pNPG) using an assay was modified from Hagerdal et al., 1979, *Biotechnology and Bioengineering* 21: 345-355: 10 µl of culture broth was mixed with 90 µl of assay reagent containing 10 µl of 0.1% TWEEN®, 10 µl of 1 M sodium citrate pH 5, 4 µl of 100 mM pNPG substrate (Sigma Aldrich) solubilized in DMSO (0.4% final volume in stock solution), and filtered water. The assay was incubated for 30 minutes at 37° C. and the absorbance was analyzed at 405 nm before and after addition of 100 µl of 1 M sodium carbonate pH 10. The highest absorbance values at 405 nm were correlated to the SDS-PAGE data for selection of the best transformant.

Spores of the best transformant were spread on COVE plates containing 0.01% TRITON® X-100 in order to isolate single colonies. The spreading was repeated twice in total on COVE sucrose medium (Cove, 1996, *Biochim. Biophys. Acta* 133: 51-56) containing 1 M sucrose and 10 mM sodium nitrate, supplemented with 10 mM acetamide and 15 mM CsCl. Fermentation was then performed in 250 ml shake flasks using YP medium containing 2% maltodextrin for 4 days at 30° C. with shaking at 100 rpm.

A 2 liter volume of culture supernatant (EXP02895) was filtered with a 0.7 µm glass fiber filter and then sterile filtered using a 0.22 µm PES membrane (Nalgene Thermo Fisher Scientific, Rochester, NY, USA). The filtered supernatant was concentrated and diafiltered using cross-flow Sartocon Slice Cassettes (non Cellulose) with 10 kDa cut-off (Sartorius Stedim Biotech S.A., Aubagne Cedex, France). The final volume was adjusted to 500 ml and pH adjusted to 4.5 by slowly adding dilute 10% acetic acid. The final ionic strength was under 4 MSi.

A 50 ml XK26 column (GE Healthcare, HiHerod, Denmark) was packed with Xpressline ProA (UpFront Chromatography A/S, Copenhagen, Denmark) equilibrated with 50 mM sodium acetate pH 4.5 buffer. The filtered supernatant was loaded onto the column using a P500 Pump (GE Health Care, HiHerod, Denmark) at a flow of 45 ml per minute and washed with 50 mM sodium acetate pH 4.5 buffer until all unbound material was eluted. The bound protein was eluted with 50 mM Tris pH 8 buffer using an ÄKTAexplorer System (GE Healthcare, HiHerod, Denmark). Fractions were collected and monitored by UV absorbance at 280 nm. The eluted protein were pooled and adjusted to pH 7 by slowly adding 0.5 M Tris base with a final ionic strength under 4 MSi.

A 50 ml Q SEPHAROSE® Fast Flow column was equilibrated with 50 mM HEPES pH 7 buffer (buffer A). The column was then washed to remove unbound material by washing with 50 mM HEPES pH 7 buffer until the UV absorbance of the wash was below 0.05 at 280 nm. The bound protein was eluted using a linear salt gradient of 0 to 1 M NaCl in 50 mM HEPES pH 7 buffer as buffer B (10 column volume) using an ÄKTAexplorer System. Purity of protein fractions was determined by SDS-PAGE analysis using a 4-20% Tris-Glycine Gel (Invitrogen Carlsbad, CA, USA) according to the manufacturer's instructions. Staining after electrophoresis was performed using INSTANT BLUE™ (Expedeon Ltd., Cambridgeshire, UK) according to the manufacturer's instructions. Fractions showing expected protein bands were pooled. Identification of the protein was determined by MS-Edman degradation using standard methods.

Example 17: Preparation of *Thermoascus aurantiacus* CGMCC 0583 GH61A Polypeptide Having Cellulolytic Enhancing Activity

*Thermoascus aurantiacus* CGMCC 0583 GH61A polypeptide having cellulolytic enhancing activity (SEQ ID NO: 33 [DNA sequence] and SEQ ID NO: 34 [deduced amino acid sequence]) was recombinantly prepared according to WO 2005/074656 using *Aspergillus oryzae* JaL250 as a host. The recombinantly produced *Thermoascus aurantiacus* GH61A polypeptide was first concentrated by ultrafiltration using a 10 kDa membrane, buffer exchanged into 20 mM Tris-HCl pH 8.0, and then purified using a 100 ml Q SEPHAROSE® Big Beads column (GE Healthcare, Piscataway, NJ, USA) with 600 ml of a 0-600 mM NaCl linear gradient in the same buffer. Fractions of 10 ml were collected and pooled based on SDS-PAGE.

The pooled fractions (90 ml) were then further purified using a 20 ml MONO Q® column (GE Healthcare, Piscataway, NJ, USA) with 500 ml of a 0-500 mM NaCl linear gradient in the same buffer. Fractions of 6 ml were collected and pooled based on SDS-PAGE. The pooled fractions (24 ml) were concentrated by ultrafiltration using a 10 kDa membrane, and chromatographed using a 320 ml SUPERDEX® 75 SEC column (GE Healthcare, Piscataway, NJ, USA) with isocratic elution of approximately 1.3 liters of 150 mM NaCl-20 mM Tris-HCl pH 8.0. Fractions of 20 ml were collected and pooled based on SDS-PAGE. Protein concentration was determined using a Microplate BCA™ Protein Assay Kit in which bovine serum albumin was used as a protein standard.

Example 18: Preparation of *Thielavia terrestris* NRRL 8126 GH61E Polypeptide Having Cellulolytic Enhancing Activity

*Thielavia terrestris* NRRL 8126 GH61E polypeptide having cellulolytic enhancing activity (SEQ ID NO: 35 [DNA sequence] and SEQ ID NO: 36 [deduced amino acid sequence]) was recombinantly prepared according to U.S. Pat. No. 7,361,495 using *Aspergillus oryzae* JaL250 as a host.

Filtered culture broth was desalted and buffer-exchanged into 20 mM sodium acetate-150 mM NaCl pH 5.0 using a HIPREP® 26/10 Desalting Column according to the manufacturer's instructions. Protein concentration was determined using a Microplate BCA™ Protein Assay Kit in which bovine serum albumin was used as a protein standard.

Example 19: Preparation of *Aspergillus fumigatus* NN051616 GH61B Polypeptide Having Cellulolytic Enhancing Activity A tblastn search (Altschul et al., 1997, *Nucleic Acids Res.* 25: 3389-3402) of the *Aspergillus fumigatus* partial genome sequence (The Institute for Genomic Research, Rockville, MD) was performed using as query several known GH61 proteins including GH61A from *Thermoascus aurantiacus* (GeneSeqP Accession Number AEC05922). Several genes were identified as putative Family GH61 homologs based upon a high degree of similarity to the query sequences at the amino acid level. One genomic region of approximately 850 bp with greater than 70% identity to the *Thermoascus aurantiacus* GH61A sequence at the amino acid level was chosen for further study.

*Aspergillus fumigatus* NN051616 was grown and harvested as described in U.S. Pat. No. 7,244,605. Frozen mycelia were ground, by mortar and pestle, to a fine powder and genomic DNA was isolated using a DNEASY® Plant Kit according to manufacturer's instructions.

Two synthetic oligonucleotide primers shown below were designed to PCR amplify the *Aspergillus fumigatus* Family GH61B protein gene from the genomic DNA. An IN- FUSION® Cloning Kit was used to clone the fragment directly into the expression vector pAlLo2, without the need for restriction digestion and ligation.

```
Forward primer:
                                         (SEQ ID NO: 115)
5'-ACTGGATTTACCATGACTTTGTCCAAGATCACTTCCA-3'

Reverse primer:
                                         (SEQ ID NO: 116)
5'-TCACCTCTAGTTAATTAAGCGTTGAACAGTGCAGGACCAG-3'
```

Bold letters represent coding sequence. The remaining sequence is homologous to the insertion sites of pAlLo2.

Fifty picomoles of each of the primers above were used in a PCR reaction containing 204 ng of *Aspergillus fumigatus* genomic DNA, 1× Pfx Amplification Buffer (Invitrogen, Carlsbad, CA, USA), 1.5 µl of 10 mM blend of dATP, dTTP, dGTP, and dCTP, 2.5 units of PLATINUM® Pfx DNA Polymerase, and 1 µl of 50 mM MgSO$_4$ in a final volume of 50 µl. The amplification was performed using an EPPENDORF® MASTERCYCLER® 5333 epgradient S (Eppendorf Scientific, Inc., Westbury, NY, USA) programmed for one cycle at 94° C. for 3 minutes; and 30 cycles each at 94° C. for 30 seconds, 56° C. for 30 seconds, and 72° C. for 1 minutes. The heat block was then held at 72° C. for 15 minutes followed by a 4° C. soak cycle.

The reaction products were isolated by 1.0% agarose gel electrophoresis using TAE buffer where an approximately 850 bp product band was excised from the gel and purified using a MINELUTE® Gel Extraction Kit (QIAGEN Inc., Valencia, CA, USA) according to the manufacturer's instructions.

The fragment was then cloned into pAlLo2 using an IN-FUSION® Cloning Kit. The vector was digested with Nco I and Pac I. The fragment was purified by gel electrophoresis as above and a QIAQUICK® Gel Purification Kit. The gene fragment and the digested vector were combined together in a reaction resulting in the expression plasmid pAG43 in which transcription of the Family GH61B protein gene was under the control of the NA2-tpi promoter. The recombination reaction (20 µl) was composed of 1× IN-FUSION® Buffer, 1×BSA, 1 µl of IN-FUSION® enzyme (diluted 1:10), 166 ng of pAlLo2 digested with Nco I and Pac I, and 110 ng of the *Aspergillus fumigatus* GH61B protein purified PCR product. The reaction was incubated at 37° C. for 15 minutes followed by 15 minutes at 50° C. The reaction was diluted with 40 µl of 10 mM Tris-0.1 M EDTA buffer and 2.5 µl the diluted reaction was used to transform *E. coli* SOLOPACK® Gold cells. An *E. coli* transformant containing pAG43 (GH61B protein gene) was identified by restriction enzyme digestion and plasmid DNA was prepared using a BIOROBOT® 9600.

DNA sequencing of the 862 bp PCR fragment was performed with a Perkin-Elmer Applied Biosystems Model 377 XL Automated DNA Sequencer using dye-terminator chemistry (Giesecke et al., 1992, supra) and primer walking strategy. The following vector specific primers were used for sequencing:

```
pAllo2 5 Seq:
                                         (SEQ ID NO: 117)
5' TGTCCCTTGTCGATGCG 3' pAllo2 3 Seq:
                                         (SEQ ID NO: 118)
5' CACATGACTTGGCTTCC 3'
```

Nucleotide sequence data were scrutinized for quality and all sequences were compared to each other with assistance of PHRED/PHRAP software (University of Washington, Seattle, WA, USA).

A gene model for the *Aspergillus fumigatus* sequence was constructed based on similarity of the encoded protein to the *Thermoascus aurantiacus* GH61A protein (GeneSeqP Accession Number AEC05922). The nucleotide sequence and deduced amino acid sequence, are shown in SEQ ID NO: 37 and SEQ ID NO: 38, respectively. The genomic fragment encodes a polypeptide of 250 amino acids, interrupted by 2 introns of 53 and 56 bp. The % G+C content of the gene and the mature coding sequence are 53.9% and 57%, respectively. Using the SignalP software program (Nielsen et al., 1997, *Protein Engineering* 10: 1-6), a signal peptide of 21 residues was predicted. The predicted mature protein contains 221 amino acids with a predicted molecular mass of 23.39 kDa.

*Aspergillus oryzae* JaL355 protoplasts were prepared according to the method of Christensen et al., 1988, supra. Six µg of pAG43 were used to transform *Aspergillus oryzae* JaL355. Twenty-six transformants were isolated to individual PDA plates.

Confluent PDA plates of 24 transformants were each washed with 5 ml of 0.01% TWEEN® 20 and the spores were each collected. Eight µl of each spore stock was added to 1 ml of YPG, YPM, and M410 media separately in 24 well plates and incubated at 34° C. After 3 days of incubation, 7.5 µl of supernatant from four transformants were analyzed using a CRITERION® stain-free, 8-16% gradient SDS-PAGE gel according to the manufacturer's instructions. Based on this gel, M410 was chosen as the best medium. Five days after incubation, 7.5 µl of supernatant from each M410 culture was analyzed using a CRITERION® stain-free, 8-16% gradient SDS-PAGE gel. SDS-PAGE profiles of the cultures showed that several transformants had a new major band of approximately 25 kDa.

A confluent plate of one transformant (grown on PDA) was washed with 5 ml of 0.01% TWEEN® 20 and inoculated into four 500 ml Erlenmeyer flasks containing 100 ml of M410 medium to generate broth for characterization of the enzyme. The flasks were harvested on day 5 (300 ml), filtered using a 0.22 µm EXPRESS™ Plus Membrane, and stored at 4° C.

The filtered shake flask broth containing *Aspergillus fumigatus* GH61B polypeptide having cellulolytic enhancing activity was concentrated using a 10 kDa MWCO Amicon Ultra centrifuge concentrator (Millipore, Bedford, MA, USA) to approximately 10-fold smaller volume. The concentrated filtrate was buffer-exchanged and desalted using a BIO-GEL® P6 desalting column (Bio-Rad Laboratories, Inc., Hercules, CA, USA) pre-equilibrated in 20 mM Tris-(hydroxymethyl)aminomethane (Sigma, St. Louis, MO, USA), pH 8.0, according to the manufacturer's instructions with the following exception: 3 ml of sample was loaded and eluted with 3 ml of buffer. Concentrated, desalted GH61B protein was quantified using a BCA protein assay using bovine serum albumin as a protein concentration standard. Quantification was performed in triplicate. Enzyme purity was confirmed using 8-16% gradient SDS-PAGE at 200 volts for 1 hour and staining with BIO-SAFE™ Coomassie Stain.

Example 20: Preparation of *Penicillium pinophilum* GH61 Polypeptide Having Cellulolytic Enhancing Activity

*Penicillium pinophilum* GH61 polypeptide having cellulolytic enhancing activity SEQ ID NO: 39 [DNA sequence] and SEQ ID NO: 40 [deduced amino acid sequence]) was prepared according to the procedure described below.

Compost samples were collected from Yunnan, China on Dec. 12, 2000. *Penicillium pinophilum* NN046877 was isolated using single spore isolation techniques on PDA plates at 45° C. *Penicillium pinophilum* strain NN046877 was inoculated onto a PDA plate and incubated for 4 days at 37° C. in the darkness. Several mycelia-PDA plugs were inoculated into 500 ml shake flasks containing 100 ml of NNCYP-PCS medium. The flasks were incubated for 5 days at 37° C. with shaking at 160 rpm. The mycelia were collected at day 4 and day 5. The mycelia from each day were frozen in liquid nitrogen and stored in a −80° C. freezer until use.

The frozen mycelia were transferred into a liquid nitrogen prechilled mortar and pestle and ground to a fine powder. Total RNA was prepared from the powdered mycelia of each day by extraction with TRIZOL™ reagent (Invitrogen Corporation, Carlsbad, CA, USA). The polyA enriched RNA was isolated using a mTRAP™ Total Kit (Active Motif, Carlsbad, CA, USA).

Double stranded cDNA from each day was synthesized with a SMART™ cDNA library Construction Kit (Clontech Laboratories, Inc., Mountain View, CA, USA). The cDNA was cleaved with Sfi I and the cDNA was size fractionated by 0.8% agarose gel electrophoresis using TBE buffer. The fraction of cDNA of 500 bp and larger was excised from the gel and purified using a GFX® PCR DNA and Gel Band Purification Kit according to the manufacturer's instructions. Then equal amounts of cDNA from day 4 and day 5 were pooled for library construction.

The pooled cDNA was then directionally cloned by ligation into Sfi I cleaved pMHas7 (WO 2009/037253) using T4 ligase (New England Biolabs, Inc., Beverly, MA, USA) according to the manufacturer's instructions. The ligation mixture was electroporated into *E. coli* ELECTROMAX™ DH10B™ cells (Invitrogen Corp., Carlsbad, CA, USA) using a GENE PULSER® and Pulse Controller (Bio-Rad Laboratories, Inc., Hercules, CA, USA) at 25 uF, 25 mAmp, 1.8 kV with a 1 mm gap cuvette according to the manufacturer's procedure.

The electroporated cells were plated onto LB plates supplemented with 50 mg of kanamycin per liter. A cDNA plasmid pool was prepared from 60,000 total transformants of the original pMHas7 vector ligation. Plasmid DNA was prepared directly from the pool of colonies using a QIAGEN® Plasmid Kit (QIAGEN Inc., Valencia, CA, USA).

A transposon containing plasmid designated pSigA4 was constructed from the pSigA2 transposon containing plasmid described WO 2001/77315 in order to create an improved version of the signal trapping transposon of pSigA2 with decreased selection background. The pSigA2 transposon contains a signal less beta-lactamase construct encoded on the transposon itself. PCR was used to create a deletion of the intact beta lactamase gene found on the plasmid backbone using a proofreading Pfu Turbo polymerase PROOFSTART™ (QIAGEN GmbH Corporation, Hilden, Germany) and the following 5' phosphorylated primers (TAG Copenhagen, Denmark):

SigA2NotU-P:
(SEQ ID NO: 119)
5'-TCGCGATCCGTTTTCGCATTTATCGTGAAACGCT-3'

SigA2NotD-P:
(SEQ ID NO: 120)
5'-CCGCAAACGCTGGTGAAAGTAAAAGATGCTGAA-3'

The amplification reaction was composed of 1 µl of pSigA2 (10 ng/µl), 5 µl of 10× PROOFSTART™ Buffer (QIAGEN GmbH Corporation, Hilden, Germany), 2.5 µl of dNTP mix (20 mM), 0.5 µl of SigA2NotU-P (10 mM), 0.5 µl of SigA2NotD-P (10 mM), 10 µl of Q solution (QIAGEN GmbH Corporation, Hilden, Germany), and 31.25 µl of deionized water. A DNA ENGINE™ Thermal Cycler (MJ Research Inc., Waltham, MA, USA) was used for amplification programmed for one cycle at 95° C. for 5 minutes; and 20 cycles each at 94° C. for 30 seconds, 62° C. for 30 seconds, and 72° C. for 4 minutes.

A 3.9 kb PCR reaction product was isolated by 0.8% agarose gel electrophoresis using TAE buffer and 0.1 µg of ethidium bromide per ml. The DNA band was visualized with the aid of an EAGLE EYE® Imaging System (Stratagene, La Jolla, CA, USA) at 360 nm. The 3.9 kb DNA band was excised from the gel and purified using a GFX® PCR DNA and Gel Band Purification Kit according to the manufacturer's instructions.

The 3.9 kb fragment was self-ligated at 16° C. overnight with 10 units of T4 DNA ligase (New England Biolabs, Inc., Beverly, MA, USA), 9 µl of the 3.9 kb PCR fragment, and 1 µl of ligation buffer (New England Biolabs, Inc., Beverly, MA, USA). The ligation was heat inactivated for 10 minutes at 65° C. and then digested with Dpn I at 37° C. for 2 hours. After incubation, the digestion was purified using a GFX® PCR DNA and Gel Band Purification Kit.

The purified material was then transformed into *E. coli* TOP10 competent cells according to the manufacturer's instructions. The transformation mixture was plated onto LB plates supplemented with 25 µg of chloramphenicol per ml. Plasmid minipreps were prepared from several transformants and digested with Bgl II. One plasmid with the correct construction was chosen. The plasmid was designated pSigA4. Plasmid pSigA4 contains the Bgl II flanked transposon SigA2 identical to that disclosed in WO 2001/77315.

A 60 µl sample of plasmid pSigA4 DNA (0.3 µg/µl) was digested with Bgl II and separated by 0.8% agarose gel electrophoresis using TBE buffer. A SigA2 transposon DNA band of 2 kb was eluted with 200 µl of EB buffer (QIAGEN GmbH Corporation, Hilden, Germany) and purified using a GFX® PCR DNA and Gel Band Purification Kit according to the manufacturer's instructions and eluted in 200 µl of EB buffer. SigA2 was used for transposon assisted signal trapping.

A complete description of transposon assisted signal trapping is described in WO 2001/77315. The plasmid pool was treated with transposon SigA2 and HYPERMU™ transposase (EPICENTRE Biotechnologies, Madison, WI, USA) according to the manufacturer's instructions.

For in vitro transposon tagging of the *Penicillium pinophilum* cDNA library, 2 µl of SigA2 transposon containing approximately 100 ng of DNA were mixed with 1 µl of the plasmid DNA pool of the *Penicillium pinophilum* cDNA library containing 1 µg of DNA, 1 µl of HYPERMU™ transposase, and 2 µl of 10× buffer (EPICENTRE Biotechnologies, Madison, WI, USA) in a total volume of 20 µl and incubated at 30° C. for 3 hours followed by adding 2 µl of stop buffer (EPICENTRE Biotechnologies, Madison, WI, USA) and heat inactivation at 75° C. for 10 minutes. The DNA was precipitated by addition of 2 µl of 3 M sodium acetate pH 5 and 55 µl of 96% ethanol and centrifuged for 30 minutes at 10,000×g, 4° C. The pellet was washed in 70% ethanol, air dried at room temperature, and resuspended in 10 µl of deionized water.

A 2 µl volume of the transposon tagged plasmid pool was electroporated into 50 µl of *E. coli* ELECTROMAX™ DH10B™ cells (Invitrogen Corp., Carlsbad, CA, USA) according to the manufacturer's instructions using a GENE PULSER® and Pulse Controller at 25 uF, 25 mAmp, 1.8 kV with a 1 mm gap cuvette according to the manufacturer's procedure.

The electroporated cells were incubated in SOC medium with shaking at 225 rpm for 1 hour at 37° C. before being plated onto the following selective media: LB medium supplemented with 50 µg of kanamycin per ml; LB medium supplemented with 50 µg of kanamycin per ml and 15 µg of chloramphencol per ml; and LB medium supplemented with 50 µg of kanamycin per ml, 15 µg of chloramphencol per ml, and 30 µg of ampicillin per ml.

From plating of the electroporation onto LB medium supplemented with kanamycin, chloramphencol and ampicillin, approximately 200 colonies per 50 µl were observed after 3 days at 30° C. All colonies were replica plated onto LB kanamycin, chloramphenicol, and ampicillin medium described above. Five hundred colonies were recovered under this selection condition. The DNA from each colony was sequenced with the transposon forward and reverse primers (primers A and B), shown below, according to the procedure disclosed in WO 2001/77315 (page 28).

```
Primer A:
                                       (SEQ ID NO: 121)
5'-agcgtttgcggccgcgatcc-3'

Primer B:
                                       (SEQ ID NO: 122)
5'-ttattcggtcgaaaaggatcc-3'
```

DNA sequences were obtained from SinoGenoMax Co., Ltd (Beijing, China). Primer A and primer B sequence reads for each plasmid were trimmed to remove vector and transposon sequence. The assembled sequences were grouped into contigs by using the program PhredPhrap (Ewing et al., 1998, *Genome Research* 8: 175-185; Ewing and Green, 1998, *Genome Research* 8: 186-194). All contigs were subsequently compared to sequences available in standard public DNA and protein sequences databases (TrEMBL, SWALL, PDB, EnsemblPep, GeneSeqP) using the program BLASTX 2.0a19MP-WashU [14 Jul. 1998] [Build linux-x86 18:51:44 30 Jul. 1998] (Gish et al., 1993, *Nat. Genet.* 3: 266-72). The family GH10 xylanase candidate was identified directly by analysis of the BlastX results.

*Penicillium pinophilum* NN046877 was grown on a PDA agar plate at 37° C. for 4-5 days. Mycelia were collected directly from the agar plate into a sterilized mortar and frozen under liquid nitrogen. Frozen mycelia were ground, by mortar and pestle, to a fine powder, and genomic DNA was isolated using a DNEASY® Plant Mini Kit (QIAGEN Inc., Valencia, CA, USA).

Based on the *Penicillium pinophilum* GH10 xylanase gene information obtained as described above, oligonucleotide primers, shown below, were designed to amplify the GH61 gene from genomic DNA of *Penicillium pinophilum* GH10 NN046877. An IN-FUSION® CF Dry-down Cloning Kit was used to clone the fragment directly into the expression vector pPFJO355, without the need for restriction digestion and ligation.

```
Sense primer:
                                       (SEQ ID NO: 123)
5'-ACACAACTGGGGATCCACCATGACTCTAGTAAAGGCTATTCTTTTAG
C-3'

Antisense primer:
                                       (SEQ ID NO: 124)
5'-GTCACCCTCTAGATCTTCACAAACATTGGGAGTAGTATGG-3'
```

Bold letters represented the coding sequence and the remaining sequence was homologous to insertion sites of pPFJO355.

The expression vector pPFJO355 contains the *Aspergillus oryzae* TAKA-amylase promoter, *Aspergillus niger* glucoamylase terminator elements, pUC19 derived sequences for selection and propagation in *E. coli*, and an *Aspergillus nidulans* pyrG gene, which encodes an orotidine decarboxylase for selection of a transformant of a pyrG mutant *Aspergillus* strain. Twenty picomoles of each of the primers above were used in a PCR reaction composed of *Penicillium* sp. NN051602 genomic DNA, 10 µl of 5× GC Buffer (Finnzymes Oy, Espoo, Finland), 1.5 µl of DMSO, 2.5 mM each of dATP, dTTP, dGTP, and dCTP, and 0.6 unit of PHUSION™ High-Fidelity DNA Polymerase (Finnzymes Oy, Espoo, Finland), in a final volume of 50 µl. The amplification was performed using a Peltier Thermal Cycler (MJ Research Inc., South San Francisco, CA, USA) programmed for denaturing at 98° C. for 1 minutes; 5 cycles of denaturing at 98° C. for 15 seconds, annealing at 56° C. for 30 seconds, with a 1° C. increase per cycle and elongation at 72° C. for 75 seconds; and 25 cycles each at 98° C. for 15 seconds, 65C for 30 seconds and 72° C. for 75 seconds; and a final extension at 72° C. for 10 minutes. The heat block then went to a 4° C. soak cycle.

The reaction products were isolated by 1.0% agarose gel electrophoresis using TBE buffer where an approximately 1.4 kb product band was excised from the gel, and purified using an ILLUSTRA® GFX® PCR DNA and Gel Band Purification Kit according to the manufacturer's instructions.

Plasmid pPFJO355 was digested with Bam I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION® CF Dry-down PCR Cloning Kit resulting in pPpin3 in which transcription of the *Penicillium pinophilum* GH10 xylanase gene was under the control of a promoter from the gene for *Aspergillus oryzae* alpha-amylase. In brief, 30 ng of pPFJO355 digested with Bam I and Bgl II, and 60 ng of the *Penicillium pinophilum* GH10 xylanase gene purified PCR product were added to a reaction vial and resuspended in a final volume of 10 µl with addition of deionized water. The reaction was incubated at 37° C. for 15 minutes and then 50° C. for 15 minutes. Three µl of the reaction were used to transform *E. coli* TOP10 competent cells. An *E. coli* transformant containing pPpin3 was detected by colony PCR and plasmid DNA was prepared using a QIAprep Spin Miniprep Kit (QIAGEN Inc., Valencia, CA, USA). The *Penicillium pinophilum* GH10 xylanase gene insert in pPpin3 was confirmed by DNA sequencing using a 3730XL DNA Analyzer (Applied Biosystems Inc, Foster City, CA, USA).

The same PCR fragment was cloned into vector pGEM-T using a pGEM-T Vector System to generate pGEM-T-Ppin3. The *Penicillium pinophilum* GH10 xylanase gene contained in pGEM-T-Ppin3 was confirmed by DNA sequencing using a 3730XL DNA Analyzer. *E. coli* strain T-Ppin3, containing pGEM-T-Ppin3, was deposited with the Deutsche Sammlung von Mikroorganismen and Zellkulturen GmbH (DSM), D-38124 Braunschweig, Germany on Sep. 7, 2009, and assigned accession number DSM 22922.

DNA sequencing of the *Penicillium pinophilum* genomic clone encoding a GH10 polypeptide having xylanase activity was performed with an Applied Biosystems Model 3700 Automated DNA Sequencer using version 3.1 BIG-DYE™ terminator chemistry (Applied Biosystems, Inc., Foster City, CA, USA) and dGTP chemistry (Applied Biosystems, Inc., Foster City, CA, USA) and primer walking strategy. Nucleotide sequence data were scrutinized for quality and all sequences were compared to each other with assistance of PHRED/PHRAP software (University of Washington, Seattle, WA, USA).

The nucleotide sequence and deduced amino acid sequence of the *Penicillium pinophilum* gh10 gene are shown in SEQ ID NO: 39 and SEQ ID NO: 40, respectively. The coding sequence is 1442 bp including the stop codon and is interrupted by three introns of 51 bp (199-249), 73 bp (383-455), and 94 bp (570-663). The encoded predicted protein is 407 amino acids. The % G+C of the coding sequence of the gene (including introns) is 47.99% G+C and the mature polypeptide coding sequence is 49.22%. Using the SignalP program (Nielsen et al., 1997, *Protein Engineering* 10: 1-6), a signal peptide of 19 residues was predicted. The predicted mature protein contains 388 amino acids with a predicted molecular mass of 41.5 kDa and an isoelectric pH of 5.03.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Penicillium pinophilum* gene encoding the GH10 polypeptide having xylanase activity shares 76% and 87% identity (excluding gaps) to the deduced amino acid sequence of a predicted GH10 family protein from *Talaromyces emersonii* (AAU99346) and *Penicillium* mameffei (B6QN64), respectively.

*Aspergillus oryzae* HowB101 (WO 95/35385 Example 1) protoplasts were prepared according to the method of Christensen et al., 1988, *Bio/Technology* 6: 1419-1422. Three µg of pPpin3 were transformed into *Aspergillus oryzae* HowB101.

The transformation of *Aspergillus oryzae* HowB101 with pPpin3 yielded about 50 transformants. Twelve transformants were isolated to individual Minimal medium plates.

Four transformants were inoculated separately into 3 ml of YPM medium in a 24-well plate and incubated at 30° C. with shaking at 150 rpm. After 3 days incubation, 20 µl of supernatant from each culture were analyzed by SDS-PAGE using a NUPAGE® NOVEX® 4-12% Bis-Tris Gel with MES buffer according to the manufacturer's instructions. The resulting gel was stained with INSTANT® Blue (Expedeon Ltd., Babraham Cambridge, UK). SDS-PAGE profiles of the cultures showed that the majority of the transformants had a major band of approximately 55 kDa. The expression strain was designated *Aspergillus oryzae* EXP02765.

A slant of one transformant, designated transformant 2, was washed with 10 ml of YPM and inoculated into a 2 liter flask containing 400 ml of YPM medium to generate broth for characterization of the enzyme. The culture was harvested on day 3 and filtered using a 0.45 µm DURAPORE® Membrane (Millipore, Bedford, MA, USA).

A 1 liter volume of supernatant of the recombinant *Aspergillus oryzae* strain EXP02765 was precipitated with ammonium sulfate (80% saturation) and redissolved in 50 ml of 25 mM sodium acetate pH 4.3, and then dialyzed against the same buffer and filtered through a 0.45 µm filter. The solution was applied to a 40 ml Q SEPHAROSE™ Fast Flow column column equilibrated in 25 mM sodium acetate pH 4.3. The recombinant GH10 protein did not bind to the column. The fractions with xylanase activity were collected and evaluated by SDS-PAGE as described above. Fractions containing a band of approximately 55 kDa were pooled. The pooled solution was concentrated by ultrafiltration.

Example 21: Preparation of *Penicillium* sp. GH61 Polypeptide Having Cellulolytic Enhancing Activity

*Penicillium* sp. GH61 polypeptide having cellulolytic enhancing activity SEQ ID NO: 41 [DNA sequence] and SEQ ID NO: 42 [deduced amino acid sequence]) according to the following procedure.

A compost sample was collected from Yunnan, China. *Penicillium* sp. NN051602 was isolated using single spore isolation techniques on PDA plates at 45° C. The *Penicillium* sp. strain was inoculated onto a PDA plate and incubated for 4 days at 45° C. in the darkness. Several mycelia-PDA plugs were inoculated into 500 ml shake flasks containing 100 ml of NNCYP-PCS medium. The flasks were incubated for 6 days at 45° C. with shaking at 160 rpm. The mycelia were collected at day 4, day 5, and day 6. Then the mycelia from each day were combined and frozen in liquid nitrogen, and then stored in a −80° C. freezer until use.

The frozen mycelia were transferred into a liquid nitrogen prechilled mortar and pestle and ground to a fine powder. Total RNA was prepared from the powdered mycelia by extraction with TRIZOL® reagent and purified using a RNEASY® Mini Kit according to the manufacturer's protocol. Fifty micrograms of total RNA was submitted to sequencing as described above.

Total RNA enriched for polyA sequences with the mRNASeq protocol was sequenced using an ILLUMINA® GA2 system (Illumina, Inc., San Diego, CA, USA). The raw 36 base pair reads were assembled with an in-house developed assembler. The assembled sequences were analyzed using standard bioinformatics methods for gene finding and functional prediction. ESTscan 2.0 was used for gene prediction. NCBI blastall version 2.2.10 and HMMER version 2.1.1 were used to predict function based on structural homology. The Family GH61 candidate was identified directly by analysis of the Blast results.

*Penicillium* sp. NN051602 was grown on a PDA agar plate at 45° C. for 3 days. Mycelia were collected directly from the agar plate into a sterilized mortar and frozen under liquid nitrogen. Frozen mycelia were ground, by mortar and pestle, to a fine powder, and genomic DNA was isolated using a DNEASY® Plant Mini Kit (QIAGEN Inc., Valencia, CA, USA).

Based on the ILLUMINA® sequencing information of the *Penicillium* sp. GH61 gene obtained as described above, oligonucleotide primers, shown below, were designed to amplify the GH61 gene from genomic DNA of *Penicillium* sp. NN051602. An IN-FUSION® CF Dry-down Cloning Kit (Clontech Laboratories, Inc., Mountain View, CA, USA) was used to clone the fragment directly into the expression vector pPFJO355, without the need for restriction digestion and ligation.

Sense primer:
(SEQ ID NO: 125)
5'-ACACAACTGGGGATCCACCATGCTGTCTTCGACGACTCGCA-3'

Antisense primer:
(SEQ ID NO: 126)
5'-GTCACCCTCTAGATCTCGACTTCTTCTAGAACGTCGGCTCA-3'

Bold letters represented the coding sequence and the remaining sequence was homologous to insertion sites of pPFJO355.

Twenty picomoles of each of the primers above were used in a PCR reaction composed of *Penicillium* sp. NN051602 genomic DNA, 10 µl of 5× GC Buffer, 1.5 µl of DMSO, 2.5 mM each of dATP, dTTP, dGTP, and dCTP, and 0.6 unit of PHUSION™ High-Fidelity DNA Polymerase (Finnzymes Oy, Espoo, Finland) in a final volume of 50 µl. The amplification was performed using a Peltier Thermal Cycler programmed for denaturing at 98° C. for 1 minutes; 5 cycles of denaturing at 98° C. for 15 seconds, annealing at 63° C. for 30 seconds, with a 1° C. increase per cycle and elongation at 72° C. for 60 seconds; and 25 cycles each at 98° C. for 15 seconds and 72° C. for 60 seconds; and a final extension at 72° C. for 5 minutes. The heat block then went to a 4° C. soak cycle.

The reaction products were isolated by 1.0% agarose gel electrophoresis using TBE buffer where an approximately 0.9 kb product band was excised from the gel, and purified using an ILLUSTRA® GFX® PCR DNA and Gel Band Purification Kit according to the manufacturer's instructions.

Plasmid pPFJO355 was digested with Bam I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION® CF Dry-down PCR Cloning Kit resulting in pGH61D23Y4 in which transcription of the *Penicillium* sp. GH61 gene was under the control of a promoter from the gene for *Aspergillus oryzae* alpha-amylase. In brief, 30 ng of pPFJO355 digested with Bam I and Bgl II, and 60 ng of the *Penicillium* sp. GH61 gene purified PCR product were added to a reaction vial and resuspended in a final volume of 10 µl with addition of deionized water. The reaction was incubated at 37° C. for 15 minutes and then 50° C. for 15 minutes. Three µl of the reaction were used to transform *E. coli* TOP10 competent cells. An *E. coli* transformant containing pGH61D23Y4 was detected by colony PCR and plasmid DNA was prepared using a QIAprep Spin Miniprep Kit (QIAGEN Inc., Valencia, CA, USA). The *Penicillium* sp. GH61 gene insert in pGH61D23Y4 was confirmed by DNA sequencing using a 3730XL DNA Analyzer.

The same PCR fragment was cloned into vector pGEM-T using a pGEM-T Vector System to generate pGEM-T-GH61D23Y4. The *Penicillium* sp. GH61 gene insert in pGEM-T-GH61D23Y4 was confirmed by DNA sequencing using a 3730XL DNA Analyzer. *E. coli* strain T-51602, containing pGEM-T-GH61D23Y4, was deposited with the Deutsche Sammlung von Mikroorganismen and Zellkulturen GmbH (DSM), Mascheroder Weg 1 B, D-38124 Braunschweig, Germany on Aug. 26, 2009 and assigned accession number DSM 22882.

DNA sequencing of the *Penicillium* sp. genomic clone encoding a GH61A polypeptide having cellulolytic-enhancing activity was performed with an Applied Biosystems Model 3700 Automated DNA Sequencer using version 3.1 BIG-DYE™ terminator chemistry (Applied Biosystems, Inc., Foster City, CA, USA) and dGTP chemistry (Applied Biosystems, Inc., Foster City, CA, USA) and primer walking strategy. Nucleotide sequence data were scrutinized for quality and all sequences were compared to each other with assistance of PHRED/PHRAP software (University of Washington, Seattle, WA, USA).

The nucleotide sequence and deduced amino acid sequence of the *Penicillium* sp. gh61a gene are shown in SEQ ID NO: 45 and SEQ ID NO: 46, respectvely. The coding sequence is 835 bp including the stop codon and is interrupted by one intron of 73 bp (114-186). The encoded predicted protein is 253 amino acids. The % G+C of the coding sequence of the gene (including introns) is 63.35% G+C and the mature polypeptide coding sequence is 64.62%. Using the SignalP program (Nielsen et al., 1997, *Protein Engineering* 10: 1-6), a signal peptide of 25 residues was predicted. The predicted mature protein contains 228 amino acids with a predicted molecular mass of 24.33 kDa and an isoelectric pH of 4.17.

A comparative pairwise global alignment of amino acid sequences was determined using the Needleman-Wunsch algorithm (Needleman and Wunsch, 1970, J. Mol. Biol. 48: 443-453) as implemented in the Needle program of EMBOSS with gap open penalty of 10, gap extension penalty of 0.5, and the EBLOSUM62 matrix. The alignment showed that the deduced amino acid sequence of the *Penicillium* gene encoding the GH61A polypeptide having cellulolytic-enhancing activity shares 74% identity (excluding gaps) to the deduced amino acid sequence of a predicted GH61 family protein from *Thermoascus aurantiacus* (GENESEQP:AUM17198).

*Aspergillus oryzae* HowB101 (WO 95/35385 Example 1) protoplasts were prepared according to the method of Christensen et al., 1988, Bio/Technology 6: 1419-1422. Three µg of pGH61D23Y4 were used to transform *Aspergillus oryzae* HowB101.

The transformation of *Aspergillus oryzae* HowB101 with pGH61D23Y4 yielded about 50 transformants. Twelve transformants were isolated to individual Minimal medium plates.

Six transformants were inoculated separately into 3 ml of YPM medium in a 24-well plate and incubated at 30° C., 150 rpm. After 3 days incubation, 20 µl of supernatant from each culture were analyzed on a NUPAGE® NOVEX® 4-12% Bis-Tris Gel with MES buffer according to the manufacturer's instructions. The resulting gel was stained with INSTANT® Blue (Expedeon Ltd., Babraham Cambridge, UK). SDS-PAGE profiles of the cultures showed that the majority of the transformants had a major band of approximately 45 kDa. The expression strain was designated as *Aspergillus oryzae* EXP03089.

A slant of one transformant, designated transformant 1, was washed with 10 ml of YPM medium and inoculated into a 2 liter flask containing 400 ml of YPM medium to generate broth for characterization of the enzyme. The culture was harvested on day 3 and filtered using a 0.45 µm DURAPORE Membrane (Millipore, Bedford, MA, USA).

A 400 ml volume of the filtered broth of the recombinant strain *Aspergillus oryzae* EXP03089 was precipitated with ammonium sulfate (80% saturation) and redissolved in 20 ml of 25 mM sodium acetate pH 5.0 buffer, and then dialyzed against the same buffer and filtered through a 0.45 µm filter. The solution was applied to a 30 ml Q SEPHAROSE® Fast Flow column (GE Healthcare, Buckinghamshire, UK) equilibrated in 25 mM sodium acetate pH 5.0.

The recombinant GH61 protein was eluted with a linear NaCl gradient (0-0.4 M). Fractions eluted with 0.1-0.2 M NaCl were collected and dialyzed against the same equilibration buffer. The sample was further purified on a MONO Q® column (GE Healthcare, Buckinghamshire, UK) with a linear NaCl gradient (0-0.3 M). Fractions were evaluated by SDS-PAGE. Fractions containing a band of approximately 45 kDa were pooled. The pooled solution was concentrated by ultrafiltration.

Example 22: Preparation of *Thielavia terrestris* GH61N Polypeptide Having Cellulolytic Enhancing Activity

*Thielavia terrestris* NRRL 8126 (SEQ ID NO: 43 [DNA sequence] and SEQ ID NO: 44 [deduced amino acid sequence]) was prepared according to the following procedure.

Genomic sequence information was generated by the U.S. Department of Energy Joint Genome Institute (JGI). A preliminary assembly of the genome was downloaded from JGI and analyzed using the Pedant-Pro™ Sequence Analysis Suite (Biomax Informatics AG, Martinsried, Germany). Gene models constructed by the software were used as a starting point for detecting GH61 homologues in the genome. More precise gene models were constructed manually using multiple known GH61 protein sequences as a guide.

To generate genomic DNA for PCR amplification, *Thielavia terrestris* NRRL 8126 was grown in 50 ml of NNCYP medium supplemented with 1% glucose in a baffled shake flask at 42° C. and 200 rpm for 24 hours. Mycelia were harvested by filtration, washed twice in TE (10 mM Tris-1 mM EDTA), and frozen under liquid nitrogen. A pea-size piece of frozen mycelia was suspended in 0.7 ml of 1% lithium dodecyl sulfate in TE and disrupted by agitation with an equal volume of 0.1 mm zirconia/silica beads (Biospec Products, Inc., Bartlesville, OK, USA) for 45 seconds in a FastPrep FP120 (ThermoSavant, Holbrook, NY, USA). Debris was removed by centrifugation at 13,000×g for 10 minutes and the cleared supernatant was brought to 2.5 M ammonium acetate and incubated on ice for 20 minutes. After the incubation period, the nucleic acids were precipitated by addition of 2 volumes of ethanol. After centrifugation for 15 minutes in a microfuge at 4° C., the pellet was washed in 70% ethanol and air dried. The DNA was resuspended in 120 µl of 0.1×TE and incubated with 1 µl of DNase-free RNase A at 37° C. for minutes. Ammonium acetate was added to 2.5 M and the DNA was precipitated with 2 volumes of ethanol. The pellet was washed in 70% ethanol, air dried, and resuspended in TE buffer.

Two synthetic oligonucleotide primers shown below were designed to PCR amplify the *Thielavia terrestris* Family GH61N gene from the genomic DNA. An IN-FUSION™ Cloning Kit was used to clone the fragment directly into the expression vector, pAlLo2 (WO 2005/074647), without the need for restriction digests and ligation.

```
Forward primer:
                                             (SEQ ID NO: 127)
5'-ACTGGATTTACCATGCCTTCTTTCGCCTCCAA-3'

Reverse primer:
                                             (SEQ ID NO: 128)
5'-TCACCTCTAGTTAATTAATCAGTTTGCCTCCTCAGCCC-3'
```

Bold letters represent coding sequence. The remaining sequence is homologous to the insertion sites of pAlLo2.

Fifty picomoles of each of the primers above were used in a PCR reaction containing 1 µg of *Thielavia terrestris* genomic DNA, 1× ADVANTAGE® GC-Melt LA Buffer (BD Biosciences, Palo Alto, CA, USA), 1 µl of 10 mM blend of dATP, dTTP, dGTP, and dCTP, 1.25 units of ADVANTAGE® GC Genomic LA Polymerase Mix (BD Biosciences, Palo Alto, CA, USA), in a final volume of 25 µl. The amplification conditions were one cycle at 94° C. for 1 minute; and 30 cycles each at 94° C. for 30 seconds, 60.5° C. for 30 seconds, and 72° C. for 1 minute. The heat block was then held at 72° C. for 5 minutes followed by a 4° C. soak cycle.

The reaction products were isolated by 1.0% agarose gel electrophoresis using TAE buffer where an approximately 1.1 kb product band was excised from the gel and purified using a MINELUTE® Gel Extraction Kit (QIAGEN Inc., Valencia, CA, USA) according to the manufacturer's instructions.

The fragment was then cloned into pAlLo2 using an IN-FUSION™ Cloning Kit. The vector was digested with Nco I and Pac I. The fragment was purified by 1.0% agarose gel electrophoresis using TAE buffer, excised from the gel, and purified using a QIAQUICK® Gel Extraction Kit (QIAGEN Inc., Valencia, CA, USA). The gene fragment and the digested vector were combined together in a reaction resulting in the expression plasmid pAG66, in which transcription of the Family GH61N gene was under the control of the NA2-tpi promoter (a modified promoter from the gene encoding neutral alpha-amylase in *Aspergillus niger* in which the untranslated leader has been replaced by an untranslated leader from the gene encoding triose phosphate isomerase in *Aspergillus nidulans*). The recombination reaction (20 µl) was composed of 1× IN-FUSION™ Buffer (BD Biosciences, Palo Alto, CA, USA), 1×BSA (BD Biosciences, Palo Alto, CA, USA), 1 µl of IN-FUSION™ enzyme (diluted 1:10) (BD Biosciences, Palo Alto, CA, USA), 186 ng of pAlLo2 digested with Nco I and Pac I, and 96.6 ng of the *Thielavia terrestris* GH61N purified PCR product. The reaction was incubated at 37° C. for 15 minutes followed by 15 minutes at 50° C. The reaction was diluted with 40 µl of TE buffer and 2.5 µl the diluted reaction was used to transform *E. coli* TOP10 Competent cells. An *E. coli* transformant containing pAG66 (GH61N gene) was identified by restriction enzyme digestion and plasmid DNA was prepared using a BIOROBOT® 9600.

*Aspergillus oryzae* JaL355 protoplasts were prepared according to the method of Christensen et al., 1988, Bio/Technology 6: 1419-1422. Five lig of pAG43 was used to transform *Aspergillus oryzae* JaL355. Three transformants were isolated to individual PDA plates.

Plugs were taken from the original transformation plate of each of the three transformants and added separately to 1 ml of M410 medium in 24 well plates, which were incubated at 34° C. Five days after incubation, 7.5 µl of supernatant from each culture was analyzed using CRITERION® stain-free, 8-16% gradient SDS-PAGE, (Bio-Rad Laboratories, Inc., Hercules, CA, USA) according to the manufacturer's instructions. SDS-PAGE profiles of the cultures showed that several transformants had new major bands of approximately 70 kDa and 35 kDa.

Confluent PDA plates of two of the transformants were washed with 5 ml of 0.01% TWEEN® 20 and inoculated into five 500 ml Erlenmeyer flask containing 100 ml of M410 medium and incubated to generate broth for characterization of the enzyme. The flasks were harvested on days 3 and 5 and filtered using a 0.22 µm stericup suction filter (Millipore, Bedford, MA).

Example 23: Preparation of *Aspergillus aculeatus* CBS 101.43 GH10 Xylanase 11

*Aspergillus aculeatus* CBS 101.43 GH10 xylanase II (SEQ ID NO: 45 [DNA sequence] and SEQ ID NO: 46 [deduced amino acid sequence]) was purified from SHEARZYME® 2X-CDN01013. The sample was desalted and buffer-exchanged in 20 mM Bis-Tris pH 6.0 using a HIPREP® 26/10 desalting column according to the manufacturer's instructions. The buffer exchanged sample was applied to a Q SEPHAROSE® Big Beads column (64 ml) equilibrated with 20 mM Bis-Tris pH 6.0, and the bound protein was eluted with a gradient from 0 to 500 mM sodium chloride over 10 column volumes. Fractions were pooled and concentrated into 200 mM sodium chloride-20 mM Bis-Tris pH 6.0. Protein concentration was determined using a Microplate BCA™ Protein Assay Kit with bovine serum albumin as a protein standard.

Example 24: Preparation of *Aspergillus fumigatus* NN055679 GH10 Xylanase

*Aspergillus fumigatus* NN055679 GH10 xylanase (xyn3) (SEQ ID NO: 47 [DNA sequence] and SEQ ID NO: 48 [deduced amino acid sequence]) was prepared recombinantly according to WO 2006/078256 using *Aspergillus oryzae* BECh2 (WO 2000/39322) as a host.

The filtered broth was desalted and buffer-exchanged into 20 mM Tris-150 mM NaCl pH 8.5 using a HIPREP® 26/10 Desalting Column according to the manufacturer's instructions. Protein concentration was determined using a Microplate BCA™ Protein Assay Kit with bovine serum albumin as a protein standard.

Example 25: Preparation of *Trichophaea saccata* CBS 804.70 GH10 Xylanase

*Trichophaea saccata* CBS 804.70 was inoculated onto a PDA plate and incubated for 7 days at 28° C. Several mycelia-PDA agar plugs were inoculated into 750 ml shake flasks containing 100 ml of MEX-1 medium. The flasks were agitated at 150 rpm for 9 days at 37° C. The fungal mycelia were harvested by filtration through MIRA-CLOTH® (Calbiochem, San Diego, CA, USA) before being frozen in liquid nitrogen. The mycelia were then pulverized into a powder by milling the frozen mycelia together with an equal volume of dry ice in a coffee grinder precooled with liquid nitrogen. The powder was transferred into a liquid nitrogen prechilled mortar and pestle and ground to a fine powder with a small amount of baked quartz sand. The powdered mycelial material was kept at −80° C. until use.

Total RNA was prepared from the frozen, powdered mycelium of *Trichophaea saccata CBS* 804.70 by extraction with guanidium thiocyanate followed by ultracentrifugation through a M CsCl cushion according to Chirgwin et al., 1979, *Biochemistry* 18: 5294-5299. The polyA enriched RNA was isolated by oligo (dT)-cellulose affinity chromatography according to Aviv et al., 1972, *Proc. Natl. Acad. Sci. USA* 69: 1408-1412.

Double stranded cDNA was synthesized according to the general methods of Gubler and Hoffman, 1983, Gene 25: 263-269; Sambrook, J., Fritsch, E. F., and Maniatis, T. Molecular cloning: A Laboratory Manual, 2nd ed., 1989, Cold Spring Harbor Laboratory, Cold Spring Harbor, New York; and Kofod et al., 1994, *J. Biol. Chem.* 269: 29182-29189, using a polyA-Not I primer (Promega Corp., Madison, Wisconsin, USA). After synthesis, the cDNA was treated with mung bean nuclease, blunt ended with T4 DNA polymerase, and ligated to a 50-fold molar excess of Eco RI adaptors (Invitrogen Corp., Carlsbad, CA, USA). The cDNA was cleaved with Not I and the cDNA was size fractionated by 0.8% agarose gel electrophoresis using TBE buffer. The fraction of cDNA of 700 bp and larger was excised from the gel and purified using a GFX® PCR DNA and Gel Band Purification Kit according to the manufacturer's instructions.

The directional, size-fractioned cDNA was ligated into Eco RI-Not I cleaved pYES 2.0 (Invitrogen, Carlsbad, CA, USA). The ligation reactions were performed by incubation at 16° C. for 12 hours, then heating at 70° C. for 20 minutes, and finally addition of 10 µl of water to each tube. One µl of each ligation mixture was electroporated into 40 µl of electrocompetent *E. coli* DH10B cells (Invitrogen Corp., Carlsbad, CA, USA) as described by Sambrook et al., 1989, supra.

The *Trichophaea saccata* CBS 804.70 library was established in *E. coli* consisting of pools. Each pool was made by spreading transformed *E. coli* on LB ampicillin plates, yielding colonies/plate after incubation at 37° C. for 24 hours. Twenty ml of LB medium was added to the plate and the cells were suspended therein. The cell suspension was shaken in a 50 ml tube for 1 hour at 37° C.

Plasmid DNA from several of the library pools of *T. saccata* CBS 804.70 was isolated using a Midi Plasmid Kit (QIAGEN Inc., Valencia, CA, USA), according to the manufacturer's instructions, and stored at −20° C.

One µl aliquots of purified plasmid DNA from several of the library pools were transformed into *S. cerevisiae* W3124 by electroporation (Becker and Guarante, 1991, Methods Enzymol. 194: 182-187) and the transformants were plated onto SC-agar plates containing 2% glucose and incubated at 30° C. In total, 50-100 plates containing 250-400 yeast colonies were obtained from each pool. After 3-5 days of incubation, the SC agar plates were replica plated onto a set of 0.1% AZCL xylan (oat) SC-URA agar plates with galactose. The plates were incubated for 2-4 days at 30° C. and xylanase positive colonies were identified as colonies surrounded by a blue halo. The positive clones were streak-purified and obtai strain CBS 521.95 ned as single colonies.

Xylanase-expressing yeast colonies were inoculated into 5 ml of YPD medium in 25 ml tubes. The tubes were shaken overnight at 30° C. One ml of the culture was centrifugated to pellet the yeast cells.

DNA was isolated according to WO 94/14953 and dissolved in 50 µl of water. The DNA was transformed into *E. coli* DH10B using standard procedures (Sambrook et al., 1989, supra).

Plasmid DNA was isolated from the *E. coli* transformants using standard procedures (Sambrook et al., 1989, supra). Plasmids were sequenced using both pYES primers as sequencing primers. One specific plasmid clone of 1283 bp designated TF12Xy1170 was found to encode a Family 10 glycoside hydrolase protein and was further characterized. More reliable sequence was obtained by further sequencing of the fragment using the specific primers shown below designed based on the initial sequence:

TF12Xy1170F1:

```
                                             (SEQ ID NO: 129)
5'-TGAAATGGGATGCTACTGA-3'

TF12Xyl170F2:
                                             (SEQ ID NO: 130)
5'-CAACGACTACAACATCGAGG-3'

TF12Xyl170R1:
                                             (SEQ ID NO: 131)
5'-ATTTGCTGTCCACCAGTGAA-3'
```

One plasmid matching the original cDNA sequence was designated pTF12Xy1170 and the *E. coli* strain containing this clone was designated *E. coli* pTF12Xy1170 and deposited on Jul. 28, 2009, with the Agricultural Research Service Patent Culture Collection, Northern Regional Research Center, Peoria, IL, USA, and given the accession number NRRL B-50309.

The nucleotide sequence and deduced amino acid sequence of the *Trichophaea saccata* gh10a gene are shown in SEQ ID NO: 49 and SEQ ID NO: 50, respectively. The coding sequence is 1197 bp including the stop codon. The encoded predicted protein contains 398 amino acids. The % G+C of the coding region of the gene is 53.6% and the mature polypeptide coding region is also 53.6%. Using the SignalP program, version 3 (Nielsen et al., 1997, *Protein Engineering* 10: 1-6), a signal peptide of 19 residues was predicted. The predicted mature protein contains 379 amino acids with a molecular mass of 40.4 kDa.

Analysis of the deduced amino acid sequence of the gh10a gene with the Interproscan program (Zdobnov and Apweiler, 2001, *Bioinformatics* 17: 847-848) showed that the GH10A protein contained the core sequence typical of a Family 10 glycoside hydrolase, extending from approximately amino acid residue 65 to residue 377 of the predicted mature polypeptide. The GH10A protein also contained the sequence signature of a type 1 fungal cellulose binding domain (CBMI). This sequence signature known as Prosite Entry PS00562 (Sigrist et al., 2002, *Brief Bioinform.* 3: 265-274) was present from amino acid residue 8 to residue 35 of the predicted mature polypeptide.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Trichophaea saccata* gene encoding the GH10A mature polypeptide shared 62.6% and 62.0% identity (excluding gaps) to the deduced amino acid sequences of Family 10 glycoside hydrolase proteins from *Phanerochaete chrysosporium* and *Meripilus giganteus*, respectively (accession numbers UNIPROT:B7SIW2 and GENESEQP:AAW23327, respectively).

The *Trichophaea saccata* CBS 804.70 gh10a gene was excised from the pTF12xyl170 using Bam HI and Xho 1, and ligated into the *Aspergillus* expression vector pDAu109 (WO 2005/042735), also digested with Bam HI and Xho 1, using standard methods (Sambrook et al., 1989, supra). The ligation reaction was transformed into *E. coli* TOP10 chemically competent cells according to the manufacturer's instructions. Eight colonies were grown overnight in LB ampicillin medium and plasmid DNA was isolated using a QIAprep Spin Miniprep Kit (QIAGEN Inc., Valencia, CA, USA) according to the manufacturer's directions. Plasmids containing the correct size inserts were sequenced to determine integrity and orientation of the insert. Plasmid pDAu81#5 was found to be error free and was therefore chosen for scale-up.

Protoplasts of *Aspergillus oryzae* BECH2 (WO 2000/39322) were prepared as described in WO 95/02043. *A. oryzae* BECh2 was constructed as described in WO 00139322. One hundred microliters of protoplast suspension were mixed with 5-25 µg of the *Aspergillus* expression vector pDAu81#5 in 10 µl of STC composed of 1.2 M sorbitol, 10 mM Tris-HCl, pH 7.5, 10 mM CaCl 2 (Christensen et al., 1988, Bio/Technology 6: 1419-1422). The mixture was left at room temperature for 25 minutes. Two hundred microliters of 60% PEG 4000 (BDH, Poole, England) (polyethylene glycol, molecular weight 4,000), 10 mM $CaCl_2$, and 10 mM Tris-HCl pH 7.5 were added and gently mixed and finally 0.85 ml of the same solution was added and gently mixed. The mixture was left at room temperature for 25 minutes, centrifuged at 2,500×g for 15 minutes, and the pellet was resuspended in 2 ml of 1.2 M sorbitol. This sedimentation process was repeated, and the protoplasts were spread on COVE plates. After incubation for 4-7 days at 37° C. spores were picked and spread on COVE plates containing 0.01% TRITON® X-100 in order to isolate single colonies. The spreading was repeated twice more on COVE sucrose medium (Cove, 1996, *Biochim. Biophys. Acta* 133: 51-56) containing 1 M sucrose and 10 mM sodium nitrate.

Ten of the transformants were inoculated in 10 ml of YPG medium. After 3-4 days of incubation at 30° C., 200 rpm, the supernatant was removed and analyzed by SDS-PAGE 10% Bis-Tris gels (Invitrogen, Carlsbad, CA, USA) as recommended by the manufacturer. Gels were stained with Coomassie blue and all isolates displayed a diffuse band between 35 and 45 kDa. These transformants were analyzed further for xylanase activity at pH 6.0 using a modified AZCL-arabinoxylan as substrate isolated from wheat (Megazyme, Wicklow, Ireland) in 0.2 M sodium phosphate pH 6.0 buffer containing 0.01% TRITON® X-100 according to the manufacturer's instructions. The transformant producing the highest level of activity was chosen for production of the xylanase.

The transformant producing the highest level of activity was grown using standard methods. The broth was filtered using Whatmann glass filters GF/D, GF/A, GF/C, GF/F (2.7 µm, 1.6 µm, 1.2 µm and 0.7 µm, respectively) (Whatman, Piscataway, NJ, USA) followed by filtration using a NALGENE® bottle top 0.45 µm filter (Thermo Fisher Scientific, Rochester, NY, USA).

Ammonia sulfate was added to the filtered broth to a final concentration of 3 M and the precipitate was collected after centrifugation at 10,000×g for 30 minutes. The precipitate was dissolved in 10 mM Tris/HCl pH 8.0 and dialyzed against 10 mM Tris/HCl pH 8.0 overnight. The dialyzed preparation was applied to a 150 ml Q SEPHAROSE® Fast Flow column equilibrated with 10 mM Tris/HCl pH 8.0 and the enzyme was eluted with a 1050 ml (7 column volumes) linear salt gradient from 0 to 1 M NaCl in 10 mM Tris/HCl pH 8.0. Elution was followed at 280 nm and fractions were collected and assayed for xylanase activity using 0.2% AZCL-Arabinoxylan from wheat in 0.2 M sodium phosphate buffer pH 6.0 containing 0.01% TRITON® X-100. Fractions containing xylanase activity were pooled and stored at −20° C.

Example 26: Preparation of *Penicillium pinophilum* GH10 Xylanase

*Penicillium pinophilum* GH10 xylanase (SEQ ID NO: 51 [DNA sequence] and SEQ ID NO: 52 [deduced amino acid sequence]) was prepared according to the following procedure.

Compost samples were collected from Yunnan, China on Dec. 12, 2000. *Penicillium pinophilum* NN046877 was isolated using single spore isolation techniques on PDA plates at 45° C. *Penicillium pinophilum* strain NN046877 was inoculated onto a PDA plate and incubated for 4 days at 37° C. in the darkness. Several mycelia-PDA plugs were inoculated into 500 ml shake flasks containing 100 ml of NNCYP-PCS medium. The flasks were incubated for 5 days at 37° C. with shaking at 160 rpm. The mycelia were collected at day 4 and day 5. The mycelia from each day were frozen in liquid nitrogen and stored in a −80° C. freezer until use.

The frozen mycelia were transferred into a liquid nitrogen prechilled mortar and pestle and ground to a fine powder. Total RNA was prepared from the powdered mycelia of each day by extraction with TRIZOL™ reagent. The polyA enriched RNA was isolated using a mTRAP™ Total Kit.

Double stranded cDNA from each day was synthesized with a SMART™ cDNA library Construction Kit (Clontech Laboratories, Inc., Mountain View, CA, USA). The cDNA was cleaved with Sfi I and the cDNA was size fractionated by 0.8% agarose gel electrophoresis using TBE buffer. The fraction of cDNA of 500 bp and larger was excised from the gel and purified using a GFX® PCR DNA and Gel Band Purification Kit according to the manufacturer's instructions. Then equal amounts of cDNA from day 4 and day 5 were pooled for library construction.

The pooled cDNA was then directionally cloned by ligation into Sfi I cleaved pMHas7 (WO 2009/037253) using T4 ligase (New England Biolabs, Inc., Beverly, MA, USA) according to the manufacturer's instructions. The ligation mixture was electroporated into *E. coli* ELECTROMAX™ DH10B™ cells (Invitrogen Corp., Carlsbad, CA, USA) using a GENE PULSER® and Pulse Controller (Bio-Rad Laboratories, Inc., Hercules, CA, USA) at 25 uF, 25 mAmp, 1.8 kV with a 1 mm gap cuvette according to the manufacturer's procedure.

The electroporated cells were plated onto LB plates supplemented with 50 mg of kanamycin per liter. A cDNA plasmid pool was prepared from 60,000 total transformants of the original pMHas7 vector ligation. Plasmid DNA was prepared directly from the pool of colonies using a QIAGEN® Plasmid Kit (QIAGEN Inc., Valencia, CA, USA).

A transposon containing plasmid designated pSigA4 was constructed from the pSigA2 transposon containing plasmid described WO 2001/77315 in order to create an improved version of the signal trapping transposon of pSigA2 with decreased selection background. The pSigA2 transposon contains a signal less beta-lactamase construct encoded on the transposon itself. PCR was used to create a deletion of the intact beta lactamase gene found on the plasmid backbone using a proofreading Pfu Turbo polymerase PROOFSTART™ (QIAGEN GmbH Corporation, Hilden, Germany) and the following 5' phosphorylated primers (TAG Copenhagen, Denmark):

SigA2NotU-P:
(SEQ ID NO: 132)
5'-TCGCGATCCGTTTTCGCATTTATCGTGAAACGCT-3'

SigA2NotD-P:
(SEQ ID NO: 133)
5'-CCGCAAACGCTGGTGAAAGTAAAAGATGCTGAA-3'

The amplification reaction was composed of 1 µl of pSigA2 (10 ng/µl), 5 µl of 10× PROOFSTART™ Buffer (QIAGEN GmbH Corporation, Hilden, Germany), 2.5 µl of dNTP mix (20 mM), 0.5 µl of SigA2NotU-P (10 mM), 0.5 µl of SigA2NotD-P (10 mM), 10 µl of Q solution (QIAGEN GmbH Corporation, Hilden, Germany), and 31.25 µl of deionized water. A DNA ENGINE™ Thermal Cycler (MJ Research Inc., Waltham, MA, USA) was used for amplification programmed for one cycle at 95° C. for 5 minutes; and 20 cycles each at 94° C. for 30 seconds, 62° C. for 30 seconds, and 72° C. for 4 minutes.

A 3.9 kb PCR reaction product was isolated by 0.8% agarose gel electrophoresis using TAE buffer and 0.1 µg of ethidium bromide per ml. The DNA band was visualized with the aid of an EAGLE EYE® Imaging System (Stratagene, La Jolla, CA, USA) at 360 nm. The 3.9 kb DNA band was excised from the gel and purified using a GFX® PCR DNA and Gel Band Purification Kit according to the manufacturer's instructions.

The 3.9 kb fragment was self-ligated at 16° C. overnight with 10 units of T4 DNA ligase (New England Biolabs, Inc., Beverly, MA, USA), 9 µl of the 3.9 kb PCR fragment, and 1 µl of ligation buffer (New England Biolabs, Inc., Beverly, MA, USA). The ligation was heat inactivated for 10 minutes at 65° C. and then digested with Dpn I at 37° C. for 2 hours. After incubation, the digestion was purified using a GFX® PCR DNA and Gel Band Purification Kit.

The purified material was then transformed into *E. coli* TOP10 competent cells according to the manufacturer's instructions. The transformation mixture was plated onto LB plates supplemented with 25 µg of chloramphenicol per ml. Plasmid minipreps were prepared from several transformants and digested with Bgl II. One plasmid with the correct construction was chosen. The plasmid was designated pSigA4. Plasmid pSigA4 contains the Bgl II flanked transposon SigA2 identical to that disclosed in WO 2001/77315.

A 60 µl sample of plasmid pSigA4 DNA (0.3 µg/µl) was digested with Bgl II and separated by 0.8% agarose gel electrophoresis using TBE buffer. A SigA2 transposon DNA band of 2 kb was eluted with 200 µl of EB buffer (QIAGEN GmbH Corporation, Hilden, Germany) and purified using a GFX® PCR DNA and Gel Band Purification Kit according to the manufacturer's instructions and eluted in 200 µl of EB buffer. SigA2 was used for transposon assisted signal trapping.

A complete description of transposon assisted signal trapping is described in WO 2001/77315. The plasmid pool was treated with transposon SigA2 and HYPERMU™ transposase (EPICENTRE Biotechnologies. Madison, WI, USA) according to the manufacturer's instructions.

For in vitro transposon tagging of the *Penicillium pinophilum* cDNA library, 2 µl of SigA2 transposon containing approximately 100 ng of DNA were mixed with 1 µl of the plasmid DNA pool of the *Penicillium pinophilum* cDNA library containing 1 µg of DNA, 1 µl of HYPERMU™ transposase, and 2 µl of 10× buffer (EPICENTRE Biotechnologies, Madison, WI, USA) in a total volume of 20 µl and incubated at 30° C. for 3 hours followed by adding 2 µl of stop buffer (EPICENTRE Biotechnologies, Madison, WI, USA) and heat inactivation at 75° C. for 10 minutes. The DNA was precipitated by addition of 2 µl of 3 M sodium acetate pH 5 and 55 µl of 96% ethanol and centrifuged for 30 minutes at 10,000×g, 4° C. The pellet was washed in 70% ethanol, air dried at room temperature, and resuspended in 10 µl of deionized water.

A 2 µl volume of the transposon tagged plasmid pool was electroporated into 50 µl of *E. coli* ELECTROMAX™ DH10B™ cells (Invitrogen Corp., Carlsbad, CA, USA) according to the manufacturer's instructions using a GENE PULSER® and Pulse Controller at 25 uF, 25 mAmp, 1.8 kV with a 1 mm gap cuvette according to the manufacturer's procedure.

The electroporated cells were incubated in SOC medium with shaking at 225 rpm for 1 hour at 37° C. before being plated onto the following selective media: LB medium supplemented with 50 µg of kanamycin per ml; LB medium supplemented with 50 µg of kanamycin per ml and 15 µg of chloramphencol per ml; and LB medium supplemented with 50 µg of kanamycin per ml, 15 µg of chloramphencol per ml, and 30 µg of ampicillin per ml.

From plating of the electroporation onto LB medium supplemented with kanamycin, chloramphencol and ampicillin, approximately 200 colonies per 50 µl were observed after 3 days at 30° C. All colonies were replica plated onto LB kanamycin, chloramphenicol, and ampicillin medium described above. Five hundred colonies were recovered under this selection condition. The DNA from each colony was sequenced with the transposon forward and reverse primers (primers A and B), shown below, according to the procedure disclosed in WO 2001/77315 (page 28).

Primer A:
(SEQ ID NO: 134)
5'-agcgtttgcggccgcgatcc-3'

Primer B:
(SEQ ID NO: 135)
5'-ttattcggtcgaaaaggatcc-3'

DNA sequences were obtained from SinoGenoMax Co., Ltd (Beijing, China). Primer A and primer B sequence reads for each plasmid were trimmed to remove vector and transposon sequence. The assembled sequences were grouped into contigs by using the program PhredPhrap (Ewing et al., 1998, *Genome Research* 8: 175-185; Ewing and Green, 1998, *Genome Research* 8: 186-194). All contigs were subsequently compared to sequences available in standard public DNA and protein sequences databases (TrEMBL, SWALL, PDB, EnsemblPep, GeneSeqP) using the program BLASTX 2.0a19MP-WashU [14 Jul. 1998] [Build linux-x86 18:51:44 30 Jul. 1998] (Gish et al., 1993, *Nat. Genet.* 3: 266-72). The family GH10 xylanase candidate was identified directly by analysis of the BlastX results.

*Penicillium pinophilum* NN046877 was grown on a PDA agar plate at 37° C. for 4-5 days. Mycelia were collected directly from the agar plate into a sterilized mortar and frozen under liquid nitrogen. Frozen mycelia were ground, by mortar and pestle, to a fine powder, and genomic DNA was isolated using a DNEASY® Plant Mini Kit (QIAGEN Inc., Valencia, CA, USA).

Based on the *Penicillium pinophilum* GH10 xylanase gene information obtained as described above, oligonucleotide primers, shown below, were designed to amplify the GH61 gene from genomic DNA of *Penicillium pinophilum* GH10 NN046877. An IN-FUSION® CF Dry-down Cloning Kit (Clontech Laboratories, Inc., Mountain View, CA, USA) was used to clone the fragment directly into the expression vector pPFJO355, without the need for restriction digestion and ligation.

Sense primer:
(SEQ ID NO: 136)
5'-ACACAACTGGGGATCCACCATGACTCTAGTAAAGGCTATTCTTTTAG
C-3'

Antisense primer:
(SEQ ID NO: 137)
5'-GTCACCCTCTAGATCTTCACAAACATTGGGAGTAGTATGG-3'

Bold letters represented the coding sequence and the remaining sequence was homologous to insertion sites of pPFJO355.

Twenty picomoles of each of the primers above were used in a PCR reaction composed of *Penicillium* sp. NN051602 genomic DNA, 10 µl of 5× GC Buffer, 1.5 µl of DMSO, 2.5 mM each of dATP, dTTP, dGTP, and dCTP, and 0.6 unit of PHUSION™ High-Fidelity DNA Polymerase, in a final volume of 50 µl. The amplification was performed using a Peltier Thermal Cycler programmed for denaturing at 98° C. for 1 minutes; 5 cycles of denaturing at 98° C. for 15 seconds, annealing at 56° C. for 30 seconds, with a 1° C. increase per cycle and elongation at 72° C. for 75 seconds; and 25 cycles each at 98° C. for 15 seconds, 65C for 30 seconds and 72° C. for 75 seconds; and a final extension at 72° C. for 10 minutes. The heat block then went to a 4° C. soak cycle.

The reaction products were isolated by 1.0% agarose gel electrophoresis using TBE buffer where an approximately 1.4 kb product band was excised from the gel, and purified using an ILLUSTRA® GFX® PCR DNA and Gel Band Purification Kit according to the manufacturer's instructions.

Plasmid pPFJO355 was digested with Bam I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION® CF Dry-down PCR Cloning Kit resulting in pPpin3 in which transcription of the *Penicillium pinophilum* GH10 xylanase gene was under the control of a promoter from the gene for *Aspergillus oryzae* alpha-amylase. In brief, 30 ng of pPFJO355 digested with Bam I and Bgl II, and 60 ng of the *Penicillium pinophilum* GH10 xylanase gene purified PCR product were added to a reaction vial and resuspended in a final volume of 10 µl with addition of deionized water. The reaction was incubated at 37° C. for 15 minutes and then 50° C. for 15 minutes. Three µl of the reaction were used to transform *E. coli* TOP10 competent cells. An *E. coli* transformant containing pPpin3 was detected by colony PCR and plasmid DNA was prepared using a QIAprep Spin Miniprep Kit (QIAGEN Inc., Valencia, CA, USA). The *Penicillium pinophilum* GH10 xylanase gene insert in pPpin3 was confirmed by DNA sequencing using a 3730XL DNA Analyzer.

The same PCR fragment was cloned into vector pGEM-T using a pGEM-T Vector System to generate pGEM-T-Ppin3. The *Penicillium pinophilum* GH10 xylanase gene contained in pGEM-T-Ppin3 was confirmed by DNA sequencing using a 3730XL DNA Analyzer. *E. coli* strain T-Ppin3, containing pGEM-T-Ppin3, was deposited with the Deutsche Sammlung von Mikroorganismen and Zellkulturen GmbH (DSM), D-38124 Braunschweig, Germany on Sep. 7, 2009, and assigned accession number DSM 22922.

DNA sequencing of the *Penicillium pinophilum* genomic clone encoding a GH10 polypeptide having xylanase activity was performed with an Applied Biosystems Model 3700 Automated DNA Sequencer using version 3.1 BIG-DYE™ terminator chemistry (Applied Biosystems, Inc., Foster City, CA, USA) and dGTP chemistry (Applied Biosystems, Inc., Foster City, CA, USA) and primer walking strategy. Nucleotide sequence data were scrutinized for quality and all sequences were compared to each other with assistance of PHRED/PHRAP software (University of Washington, Seattle, WA, USA).

The nucleotide sequence and deduced amino acid sequence of the *Penicillium pinophilum* gh10 gene are shown in SEQ ID NO: 51 and SEQ ID NO: 52, respectively. The coding sequence is 1442 bp including the stop codon and is interrupted by three introns of 51 bp (199-249), 73 bp (383-455), and 94 bp (570-663). The encoded predicted protein is 407 amino acids. The % G+C of the coding sequence of the gene (including introns) is 47.99% G+C and the mature polypeptide coding sequence is 49.22%. Using the SignalP program (Nielsen et al., 1997, *Protein Engineering* 10: 1-6), a signal peptide of 19 residues was predicted. The predicted mature protein contains 388 amino acids with a predicted molecular mass of 41.5 kDa and an isoelectric pH of 5.03.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Penicillium pinophilum* gene encoding the GH10 polypeptide having xylanase activity shares 76% and 87% identity (excluding gaps) to the deduced amino acid sequence of a predicted GH10 family protein from *Talaromyces emersonii* (AAU99346) and *Penicillium mameffei* (B6QN64), respectively.

*Aspergillus oryzae* HowB101 (WO 95/35385 Example 1) protoplasts were prepared according to the method of Christensen et al., 1988, *Bio/Technology* 6: 1419-1422. Three µg of pPpin3 were transformed into *Aspergillus oryzae* HowB101.

The transformation of *Aspergillus oryzae* HowB101 with pPpin3 yielded about 50 transformants. Twelve transformants were isolated to individual Minimal medium plates. Four transformants were inoculated separately into 3 ml of YPM medium in a 24-well plate and incubated at 30° C. with shaking at 150 rpm. After 3 days incubation, 20 µl of supernatant from each culture were analyzed by SDS-PAGE using a NUPAGE® NOVEX® 4-12% Bis-Tris Gel with MES buffer according to the manufacturer's instructions. The resulting gel was stained with INSTANT® Blue (Expedeon Ltd., Babraham Cambridge, UK). SDS-PAGE profiles of the cultures showed that the majority of the transformants had a major band of approximately 55 kDa. The expression strain was designated *Aspergillus oryzae* EXP02765.

A slant of one transformant, designated transformant 2, was washed with 10 ml of YPM and inoculated into a 2 liter flask containing 400 ml of YPM medium to generate broth for characterization of the enzyme. The culture was harvested on day 3 and filtered using a 0.45 µm DURAPORE® Membrane (Millipore, Bedford, MA, USA).

A 1 liter volume of supernatant of the recombinant *Aspergillus oryzae* strain EXP02765 was precipitated with ammonium sulfate (80% saturation) and redissolved in 50 ml of 25 mM sodium acetate pH 4.3, and then dialyzed against the same buffer and filtered through a 0.45 µm filter. The solution was applied to a 40 ml Q SEPHAROSE™ Fast Flow column column equilibrated in 25 mM sodium acetate pH 4.3. The recombinant GH10 protein did not bind to the column. The fractions with xylanase activity were collected and evaluated by SDS-PAGE as described above. Fractions containing a band of approximately 55 kDa were pooled. The pooled solution was concentrated by ultrafiltration.

Example 27: Preparation of *Thielavia terrestris* GH10E Xylanase

*Thielavia terrestris* NRRL 8126 GH10E xylanase (SEQ ID NO: 53 [DNA sequence] and SEQ ID NO: 54 [deduced amino acid sequence]) was prepared according to the following procedure.

Two synthetic oligonucleotide primers shown below were designed to PCR amplify the *Thielavia terrestris* gh10e gene from genomic DNA. An InFusion Cloning Kit (Clontech, Mountain View, CA) was used to clone the fragment directly into the expression vector, pAl Lo2 (WO 2005/074647).

Forward primer:
(SEQ ID NO: 138)
5'-ACTGGATTTACCATGGCCCTCAAATCGCTCCTGTTG-3'

Reverse primer:
(SEQ ID NO: 139)
5'-TCACCTCTAGTTAATTAATTACAAGCACTGAGAGTA-3'

Bold letters represent coding sequence. The remaining sequence is homologous to the insertion sites of pAlLo2.

Fifty picomoles of each of the primers above were used in a PCR reaction containing 2 µg of *Thielavia terrestris* genomic DNA, 1× Pfx Amplification Buffer (Invitrogen, Carlsbad, CA, USA), 2×PCR, Enhancer solution (Invitrogen, Carlsbad, CA, USA), 1.5 µl of 10 mM blend of dATP, dTTP, dGTP, and dCTP, 2.5 units of PLATINUM® Pfx DNA Polymerase, and 1 µl of 50 mM $MgSO_4$ in a final volume of 50 µl. The amplification conditions were one cycle at 94° C. for 2 minutes; and 30 cycles each at 94° C. for 15 seconds, 59.5° C. for 30 seconds, and 68° C. for 150 seconds. The heat block was then held at 68° C. for 7 minutes followed by a 4° C. soak cycle.

The reaction products were isolated on a 1.0% agarose gel using TAE buffer and an approximately 1.2 kb product band was excised from the gel and purified using a MINELUTE® Gel Extraction Kit (QIAGEN Inc., Valencia, CA, USA) according to the manufacturer's instructions.

The fragment was then cloned into pAlLo2 using an IN-FUSION™ Cloning Kit. The vector was digested with Nco I and Pac I (using conditions specified by the manufacturer). The fragment was purified by gel electrophoresis as above and a QIAQUICK® Gel Extraction Kit. The gene fragment and the digested vector were combined together in a reaction resulting in the expression plasmid pAG29, in which transcription of the gh10e gene was under the control of the NA2-tpi promoter (a hybrid of the promoters from the genes for *Aspergillus niger* neutral alpha-amylase and *Aspergillus nidulans* triose phosphate isomerase). The recombination reaction (10 µl) was composed of 1× InFusion Buffer (Clontech, Mountain View, CA, USA), 1×BSA (Clontech, Mountain View, CA, USA), 0.5 µl of InFusion enzyme (diluted 1:10) (Clontech, Mountain View, CA, USA), 93 ng of pAlLo2 digested with Nco I and Pac I, and 1 µl of the *Thielavia terrestris* gh10e purified PCR product. The reaction was incubated at 37° C. for 15 minutes followed by 15 minutes at 50° C. The reaction was diluted with 40 µl of TE buffer and 2.5 µl the diluted reaction was used to transform *E. coli* SOLOPACK® Gold cells.

Plasmid DNA was prepared using a BIOROBOT® 9600 and a restriction enzyme digest performed. Putative pAG29 clones were digested with Pst I. The plasmid DNA from these clones was then sequenced to identify clones without PCR induced errors. Sequencing reactions contained 1.5 µl of plasmid DNA, 4.5 µl of water, and 4 µl of sequencing master-mix containing 1 µl of 5× sequencing buffer (Millipore, Billerica, MA, USA), 1 µl of BIGDYE™ terminator (Applied Biosystems, Inc., Foster City, CA, USA), 1 µl of water and one of the following primers at 3.2 µmoles per reaction.

pAlLo2 5'
(SEQ ID NO: 140)
5'-TGTCCCTTGTCGATGCG-3' pAlLo2 3'
(SEQ ID NO: 141)
5'-CACATGACTTGGCTTCC-3'

Aspergillus oryzae JaL355 protoplasts were prepared according to the method of Christensen et al., 1988, Bio/Technology 6: 1419-1422. Five lig of pAG29 was used to transform Aspergillus oryzae JaL355. Twenty-four transformants were isolated to individual PDA plates.

Confluent PDA plates of 24 transformants were washed with 5 ml of 0.01% TWEEN® 20 and spores collected. Eight µl of each spore stock was added to 1 ml of YPG, YPM, and M410 separately in 24 well plates and incubated at 34° C. Three days after incubation, 7.5 µl of supernatant from selected culture was analyzed using Criterion stain-free, 8-16% gradient SDS-PAGE, (BioRad, Hercules, CA) according to the manufacturer's instructions. SDS-PAGE profiles of the cultures showed that several transformants had a new major band of approximately 50 kDa and the best expression in M410. After a total of six days of incubation, all M410 cultures were sampled as described above and analyzed using Criterion stain-free, 8-16% gradient SDS-PAGE gel, (BioRad, Hercules, CA) at which point the transformant exhibiting the best expression was selected.

A confluent PDA plate of the top transformant was washed with 5 ml of 0.01% TWEEN® 20 and inoculated into five 500 ml Erlenmeyer flask containing 100 ml of M410 medium to generate broth for characterization of the enzyme. The flasks were harvested on day 5. Broths were filtered using a 0.22 µm stericup suction filter (Millipore, Bedford, MA).

Example 28: Preparation of Thermobifida *Fusca* GH11 Xylanase

A linear integration vector-system was used for the expression cloning of a Thermobifida *fusca* DSM 22883 GH11 xylanase gene (SEQ ID NO: 55 [DNA sequence] and SEQ ID NO: 56 [deduced amino acid sequence]). The linear integration construct was a PCR fusion product made by fusion of each gene between two *Bacillus* subtils homologous chromosomal regions along with a strong promoter and a chloramphenicol resistance marker. The fusion was made by SOE PCR (Horton et al., 1989, *Gene* 77: 61-68). The SOE PCR method is also described in WO 2003/095658. Each gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* crylllA promoter including stabilizing sequence. The gene coding for chloramphenicol acetyl-transferase was used as marker (Diderichsen et al., 1993, *Plasmid* 30: 312). The final gene construct was integrated into the *Bacillus* chromosome by homologous recombination into the pectate lyase locus.

The GH11 xylanase gene (SEQ ID NO: 55 [DNA sequence] and SEQ ID NO: 56 [deduced amino acid sequence]) was isolated from Thermobifida *fusca* DSM 22883 (NN018438) by a polymerase chain reaction (PCR1) using the primers shown in the table below. The primers are based on the protein sequence UNIPROT:Q5RZ98. Thermobifida *fusca* DSM 22883 was isolated from a soil sample obtained from Oahu, Hawaii in 2001. The xylanase gene was cloned as a full-length gene and as a truncated gene. The genes were designed to contain a C-terminal HQHQHQH tag to ease purification but the His-tag was not used for the purification. The forward primer Ocs3 was designed so the gene was amplified from the start codon (ATG) and has 24 bases overhang (shown in italic in the table below). This overhang is complementary to part of one of the two linear vector fragments and is used when the PCR fragment and the vector fragments are assembled (described below). The reverse primer Ocs1 was designed to amplify the truncated version of the gene while the reverse primer Ocs2 was designed to amplify the full-length gene. Both Ocs1 and Ocs2 carry an overhang consisting of 24 bp encoding a HQHQHQH-tag and a stop codon (the overhang is shown in italic in the table below). This overhang is complementary to part of one of the two linear vector fragments and is used when the PCR fragment and the vector fragments are assembled (described below).

A PCR fragment was isolated containing the full-length xylanase gene and the short 24 bp flanking DNA sequences included in the primers as overhang. Another PCR fragment was isolated containing the truncated xylanase gene and the same short 24 bp flanking DNA sequences.

For each gene construct 3 fragments were PCR amplified: the gene fragment from genomic DNA from the Thermobifida *fusca* (NN018438), the upstream flanking fragment was amplified with primers 260558 and iMB1361Uni1, and the downstream flanking fragment was amplified with primers 260559 and oth432 from genomic DNA of the strain iMB1361 (described in patent application WO 2003095658). All primers used are listed in Table below.

| Amplification of | SPECIFIC PRIMER FORWARD | SPECIFIC PRIMER REVERSE |
|---|---|---|
| Full-length gene | OCS3:<br>5'-*CTGAAAAAAAGGAGAGGAT AAAGA*ATGAACCATGCCCCCG CCA-3' (SEQ ID NO: 142) | OCS2:<br>5'-*CTAATGCTGGTGTTGGTGC TGATG*GTTGGCGCTGCAGGA CACCGT-3' (SEQ ID NO: 143) |
| Truncated gene | OCS3:<br>5'-*CTGAAAAAAAGGAGAGGAT AAAGA*ATGAACCATGCCCCCG CCA 3' (SEQ ID NO: 142) | OCS1:<br>5'-*CTAATGCTGGTGTTGGTGC TGATG*GGGGTTGTCACCGCC GCT-3' (SEQ ID NO: 144) |

-continued

| Amplification of | SPECIFIC PRIMER FORWARD | SPECIFIC PRIMER REVERSE |
|---|---|---|
| Upstream flanking fragment | 260558:<br>5'-GAGTATCGCCAGTAAGGGG<br>CG 3' (SEQ ID NO: 145) | iMB1361Uni1:<br>5'-TCTTTATCCTCTCCTTTTTTT<br>CAGAGCTC 3' (SEQ ID NO: 146) |
| Downstream flanking fragment | oth432:<br>5'-CATCAGCACCAACACCAGCA<br>TCCGTAATCGCATGTTCAATCC<br>GCTCCATA 3' (SEQ ID NO: 147) | 260559:<br>5'-GCAGCCCTAAAATCGCATAA<br>AGC-3' (SEQ ID NO: 148) |

The gene fragment was amplified using a proofreading polymerase PHUSION™ DNA Polymerase according to the manufacturer's instructions with the addition of 2% DMSO. The two flanking DNA fragments were amplified with an EXPAND™ High Fidelity PCR System according to the manufacturer's recommendations. The PCR conditions were as follows: one cycle at 94° C. for 2 minutes; 10 cycles each at 94° C. for 15 seconds, 50° C. for 45 seconds, 68° C. for 4 minutes; 20 cycles each at 94° C. for 15 seconds, 50° C. for 45 seconds, and 68° C. for 4 minutes (+20 seconds extension pr cycle); and one cycle at 68° C. for 10 minutes The 3 PCR fragments were subjected to a subsequent splicing by overlap extension (SOE) PCR reaction to assemble the 3 fragments into one linear vector construct. This was performed by mixing the 3 fragments in equal molar ratios and a new PCR reaction was run under the following conditions: one cycle at 94° C. for 2 minutes; 10 cycles each at 94° C. for 15 seconds, 50° C. for 45 seconds, and 68° C. for 5 minutes; 10 cycles each at 94° C. for 15 seconds, 50° C. for 45 seconds, and 68° C. for 8 minutes; 15 cycles each at 94° C. for 15 seconds, 50° C. for 45 seconds, and 68° C. for 8 minutes (in addition 20 seconds extra per cycle). After the first cycle the two end primers 260558 and 260559 were added (20 µMol of each). Two µl of the PCR product was transformed into Bacillus subtilis. Transformants were selected on LB plates supplemented with 6 µg of chloramphenicol per ml. The full-length xylanase coding sequence was integrated by homologous recombination into the genome of the Bacillus subtilis host TH1 (amy-, spo-, apr-, npr-; WO 2005/038024). The truncated xylanase coding sequence was integrated by homologous recombination into the genome of the Bacillus subtilis host PL2317 (amy-, spo-, apr-, npr-, xyl-).

Transformants were then screened for their ability to produce large amounts of active xylanase. The screening was based on intensity of the band corresponding to the heterologous expressed protein by SDS-PAGE analysis and activity of the enzyme on LB agar plates containing AZCL-xylan (Megazyme International Ireland, Ltd., Wicklow, Ireland).

One transformant, Bacillus subtilis EXP01687, was isolated which contained the full-length xylanase gene expressed in the host strain Bacillus subtilis TH1. The full-length xylanase gene sequence of Bacillus subtilis EXP01687 was confirmed by Sanger sequencing. The protein sequence differs by 2 amino acids from UNIPROT: Q5RZ98.

Another transformant, Bacillus subtilis EXP01672, was isolated which contains the truncated xylanase gene expressed in the host strain Bacillus subtilis PL2317. The truncated xylanase gene sequence of Bacillus subtilis EXP01672 was confirmed by Sanger sequencing to encode the secretion signal and mature amino acid sequence to proline at position 236 of SEQ ID NO: 56. The protein sequence differs by 2 amino acids from UNIPROT:Q5RZ98.

Bacillus subtilis EXP01687 was grown in 500 ml baffled Erlenmeyer flasks containing Cal-18 medium supplemented with 34 mg of chloramphenicol per liter for 2 days at 37° C. with shaking at 200 rpm. The enzyme was purified from the culture supernatant according to the protocol described below.

In step 1, the whole culture (800 ml) was centrifuged at 17,600×g for 30 minutes and then filtered through a SEITZ-EKS filter (Pall Seitzschenk Filtersystems GmbH, Bad Kreuznach, Germany). Sodium chloride was added to the filtered sample to 50 mM NaCl and the pH was adjusted to pH 7.5. The sample (750 ml) was applied to a 20 ml Ni SEPHAROSE® 6 Fast Flow column (GE Healthcare, Piscataway, NJ, USA) equilibrated with 50 mM $Na_2HPO_4$, 50 mM NaCl pH 7.5, and the bound protein was eluted with a 5 column volume gradient to 100% 50 mM $Na_2HPO_4$, 500 mM imidazol pH 7.5. The enzyme was found in the effluent by SDS-PAGE analysis revealing a protein of the correct size in the effluent and nothing of the correct size in the eluent. This result was confirmed by activity measurement using AZCL-arabinoxylan (wheat) as substrate as described above.

In step 2, ammonium sulfate was added to the effluent (of step 1) to 1 M and the pH adjusted to 7.5. The sample (800 ml) was applied to a 60 ml TOYOPEARL® Phenyl-650M column (TOSOH Corporation, Tokyo, Japan) equilibrated with 1 M ammonium sulfate pH 7.5. The bound protein was eluted with Milli-Q® ultrapure water (Millipore, Billerica, MA, USA). Fractions with $A_{280}$ were pooled (55 ml). The pooled fractions were desalted and buffer-exchanged with 25 mM acetic acid pH 4.5 using a HIPREP® 26/10 desalting column according to the manufacturer's instructions.

In step 3, the buffer exchanged sample of step 2 (110 ml) was diluted 2.5-fold with Milli-Q® ultrapure water and applied to a 10 ml SP SEPHAROSE® Fast Flow column (GE Healthcare, Piscataway, NJ, USA) equilibrated with 25 mM acetic acid pH 4.5. The bound protein was eluted with a five column volume gradient from 0 to 500 mM sodium chloride in 25 mM acetic acid pH 4.5. Based on SDS-PAGE analysis and $A_{280}$ and $A_{260}$. Also fractions were pooled (10 ml).

In step 4, the pooled fractions of step 3 were diluted 25-fold with Milli-Q® ultrapure water and the pH was adjusted to pH 6.0 and applied to 10 ml SP SEPHAROSE® Fast Flow column equilibrated with 5 mM succinic acid pH 6.0. The bound protein was eluted with a ten column volume gradient from 0 to 500 mM sodium chloride in 5 mM succinic acid pH 6.0. Based on SDS-PAGE analysis and $A_{280}$ and $A_{260}$ fractions were pooled (12 ml). Separate portions of the pooled fractions were then subjected to three different steps (steps 5(a), 5(b), and 5(c)) described below.

In step 5(a), 6 ml of the pooled fractions of step 4 were diluted to 25 ml with Milli-Q® ultrapure water and the pH was adjusted to pH 9.0 and applied to a 1 ml RESOURCE™ Q column (GE Healthcare, Piscataway, NJ, USA) equilibrated with 25 mM boric acid pH 9.0. The bound protein was eluted with a ten column volume gradient from 0 to 500 mM sodium chloride in 25 mM boric acid pH 9.0. Based on $A_{280}$ and $A_{260}$, the protein was in the effluent (35 ml). This sample was concentrated using an AMICON® ultrafiltration cell equipped with a 5 kDa cut-off membrane (Millipore, Billerica, MA, USA).

In step 5(b), 3 ml of the pool of step 4 were diluted to 30 ml with Milli-Q® ultrapure water and pH was adjusted to pH 9.6 and applied to a 1 ml RESOURCE™ Q column equilibrated with 12.5 mM boric acid pH 9.7. The bound protein was eluted with a ten column volume gradient from 0 to 500 mM sodium chloride in 12.5 mM boric acid pH 9.7. Based on $A_{280}$ and $A_{260}$ and SDS-PAGE analysis, the protein was in the effluent (36 ml).

In step 5(c), one quarter of the pool of step 4 was diluted with Milli-Q® ultrapure water and the pH was adjusted to pH 8.0 and applied to a 1 ml RESOURCE™ Q column equilibrated with 25 mM borate pH 8.0. The bound protein was eluted with a ten column volume gradient from 0 to 500 mM sodium chloride in 25 mM borate pH 8.0. Based on $A_{280}$ and $A_{260}$ and SDS-PAGE analysis, the protein was in the effluent (25 ml).

In step 6, the sample from step 5(a), the effluent from step 5(b), and the effluent from step 5(c) were pooled and diluted with 25 mM acetic acid pH 4.5, and the pH was adjusted to pH 4.58. The pooled sample (100 ml) was applied to a 1 ml HITRAP® SP Fast Flow column (GE Healthcare, Piscataway, NJ, USA) equilibrated with 25 mM acetic acid pH 4.5. The bound protein was eluted with one column volume gradient from 0 to 500 mM sodium chloride in 25 mM acetic acid pH 4.5. Based on SDS-PAGE analysis and $A_{280}$ and $A_{280}$ fractions were pooled (3.5 ml). The MW of the purified xylanase was 20-25 kDa based on SDS-PAGE analysis.

Example 29: Preparation of *Trichoderma reesei* RutC30 GH3 Beta-Xylosidase

A *Trichoderma reesei* RutC30 beta-xylosidase gene (SEQ ID NO: 57 [DNA sequence] and SEQ ID NO: 58 [deduced amino acid sequence]) was isolated by screening a Lambda ZAP®-CMR XR Library prepared from *T. reesei* RutC30 genomic DNA using a Lambda ZAP®-CMR XR Library Construction Kit (Stratagene, La Jolla, CA, USA) according to the manufacturer's instructions. *T. reesei* RutC30 genomic DNA was prepared using standard methods. A DNA segment encoding 2300 bp of the *T. reesei* beta-xylosidase was amplified using the PCR primers shown below.

```
Forward Primer:
                                  (SEQ ID NO: 149)
5'-gtgaataacgcagctcttctcg-3'

Reverse Primer:
                                  (SEQ ID NO: 150)
5'-ccttaattaattatgcgtcaggtgt-3'
```

Primer 994768 was designed to amplify from the first base after the beta-xylosidase start site and primer 994769 was designed with a Pac I site at the 5' end.

Fifty picomoles of each of the primers above were used in a PCR reaction consisting of 50 ng of plasmid DNA from the lamda zap library, 1 μl of 10 mM blend of dATP, dTTP, dGTP, and dCTP, 5 μl of 10× PLATINUM® Pfx DNA Polymerase Buffer, and 1 unit of PLATINUM® Pfx DNA Polymerase, in a final volume of 50 μl. An EPPENDORF® MASTERCYCLER® 5333 was used to amplify the DNA fragment programmed for one cycle at 95° C. for 3 minutes; and 30 cycles each at 94° C. for 45 seconds, 55° C. for 60 seconds, and 72° C. for 1 minute 30 seconds. After the 30 cycles, the reaction was incubated at 72° C. for 10 minutes and then cooled to 4° C. until further processing.

A 2.3 kb PCR product was purified by 1% agarose gel electrophoresis using TAE buffer, excised from the gel, and purified using a QIAQUICK® Gel Extraction Kit. The 2.3 kb PCR product was then digested with Pac I to facilitate insertion into pAlLo1 (WO 2004/099228).

The pAlLo1 vector was digested with Nco I and then filled in using T4 polymerase (Roche, Nutley, NJ, USA) according to manufacturer's instructions. A second enzyme, Pac I, was then used to digest the 5' end of pAlLo1 and the reaction was purified by agarose gel electrophoresis as described above to isolate a 6.9 kb vector fragment.

The 2.3 kb beta-xylosidase fragment was then ligated into the 6.9 kb vector fragment and transformed into *E. coli* XL1-Blue Subcloning Competent Cells (Invitrogen, Carlsbad, CA, USA) according to manufacturer's instructions. Transformants were screened using restriction digest analysis in order to identify those with the correct insert. A new expression vector, pSaMe04, was confirmed by sequencing using an ABI3700 (Applied Biosystems, Foster City, CA) and dye terminator chemistry (Giesecke et al., 1992, *Journal of Virology Methods* 38: 47-60).

Two synthetic oligonucleotide primers shown below were designed to PCR amplify the *Trichoderma reesei* beta-xylosidase gene from pSaMe04 to construct a *Trichoderma* expression vector. An IN-FUSION™ Cloning Kit was used to clone the fragment directly into the expression vector pMJ09 (WO 2005/056772), without the need for restriction digestion and ligation.

```
TrBXYL-F (ID 064491):
                                  (SEQ ID NO: 151)
5'-CGGACTGCGCACCATGGTGAATAACGCAGCTCT-3'

TrBXYL-R (ID 064492):
                                  (SEQ ID NO: 152)
5'-TCGCCACGGAGCTTATTATGCGTCAGGTGTAGCAT-3'
```

Bold letters represent coding sequence. The remaining sequence is homologous to the insertion sites of pMJ09.

Fifty picomoles of each of the primers above were used in a PCR reaction composed of ng of pSaMe04, 1 μl of 10 mM blend of dATP, dTTP, dGTP, and dCTP, 5 μl of 10× ACCUTAQ™ DNA Polymerase Buffer (Sigma-Aldrich, St. Louis, MO, USA), and 5 units of ACCUTAQ™ DNA Polymerase (Sigma-Aldrich, St. Louis, MO, USA), in a final volume of 50 μl. An EPPENDORF® MASTERCYCLER® 5333 was used to amplify the DNA fragment programmed for one cycle at 95° C. for 3 minutes; and 30 cycles each at 94° C. for 45 seconds, for 60 seconds, and 72° C. for 1 minute 30 seconds. After the 30 cycles, the reaction was incubated at 72° C. for 10 minutes and then cooled to 4° C. until further processing.

The reaction products were isolated by 1.0% agarose gel electrophoresis using TAE buffer where a 1.2 kb product band was excised from the gel and purified using a QIAQUICK® Gel Extraction Kit according to the manufacturer's instructions.

The 1.2 kb fragment was then cloned into pMJ09 using an IN-FUSION™ Cloning Kit. The vector was digested with Nco I and Pac I and purified by agarose gel electrophoresis as described above. The gene fragment and the digested vector were ligated together in a reaction resulting in the expression plasmid pSaMe-TrBXYL in which transcription of the beta-xylosidase gene was under the control of the *T. reesei* cbh1 gene promoter. The ligation reaction (50 µl) was composed of 1× IN-FUSION™ Buffer, 1×BSA, 1 µl of IN-FUSION™ enzyme (diluted 1:10), 100 ng of pMJ09 digested with Nco I and Pac I, and 100 ng of the *Trichoderma reesei* beta-xylosidase purified PCR product. The reaction was incubated at room temperature for 30 minutes. One µl of the reaction was used to transform *E. coli* XL10 SOLOPACK® Gold cells. An *E. coli* transformant containing pSaMe-TrBXYL was detected by restriction enzyme digestion and plasmid DNA was prepared using a BIORO-BOT® 9600. DNA sequencing of the *Trichoderma reesei* beta-xylosidase gene from pSaMe-TrBXYL was performed using dye-terminator chemistry (Giesecke et al., 1992, supra) and primer walking strategy.

Plasmid pSaMe-AaXYL was constructed to comprise the *Trichoderma reesei* cellobiohydrolase I gene promoter and terminator and the *Aspergillus aculeatus* GH10 xylanase coding sequence.

Cloning of the *Aspergillus aculeatus* xylanase followed the overall expression cloning protocol as outlined in H. Dalbrage et al., 1994, *Mol. Gen. Genet.* 243: 253-260.

RNA was isolated from *Aspergillus aculeatus* CBS 101.43 mycelium. Poly(A)⁺ RNA was isolated from total RNA by chromatography on oligo(dT)-cellulose. Double-stranded cDNA was synthesized as described by Maniatis et al. (Molecular cloning: a laboratory manual. Cold Spring Harbor Laboratory Press, 1982). After synthesis the cDNA was treated with mung bean nuclease, blunt-ended with T4 DNA polymerase, and ligated to non-palindromic Bst XI adaptors (Invitrogen, Carlsbad, CA, USA). The cDNA was size fractionated by 1% agarose gel electrophoresis using TAE buffer where fragments ranging from 600 bp to 4000 bp were used in the library construction. The DNA was ligated into Bst XI-digested pYES 2.0 between the GAL1 promoter and the iso-1-cytochrome c terminator and transformed into *Escherichia coli* MC1061 cells (Stratagene, La Jolla, CA, USA. The library was plated onto LB plates and incubated overnight at 37° C. The colonies were scraped from the plates and resuspended in LB medium supplemented with 100 µg of ampicillin per ml. Plasmid DNA was isolated using a Plasmid Midi Kit (QIAGEN Inc., Valenicia, CA, USA). The purified plasmid DNA was pooled.

The purified plasmid DNA mixture was transformed into *Saccharomyces cerevisiae* W3124 cells (MATe; Lira 3-52; leu 2-3, 112; his 3-D200; pep 4-1137; prci::HIS3; prb1:: LEU2; circ-; van den Hazel et al., 1992, *Eur. J. Biochem.* 207: 277-283). Cultivation, transformation and media were as described by Guthrie et al., 1991, *Meth. Enzymol.* Vol 194, Academic Press. The transformed cells were plated onto synthetic complete agar containing 2% glucose for 3 days at 30° C. After 3 days the colonies were replica plated to SC medium with 2% galactose and incubated for 4 days at 30° C. Xylanase expressing colonies were identified by 1% agarose overlay with 0.1% AZCL-Birch-Xylan at pH 4.5 (Dalbrage, 2006, FEMS Microbiology Reviews 21: 29-42). Colonies expressing xylanase activity were surrounded by a blue zone. Plasmid DNA, rescued from the positive colonies, contained a DNA insert of approximately 1.3 kb. Sequencing of the isolated gene fragment revealed a 1218 bp open reading frame encoding a polypeptide with a theoretical molecular weight of 43.0 kDa. The cDNA fragment was subcloned into the *Aspergillus* expression vector pHD464 (Dalbrage and Heldt-Hansen, 1994, *Mol. Gen. Genet.* 243, 253-260) digested with Bam Hi and Xho I by cutting the done with Barn H and Xho I and isolating the 1.2 kb cDNA insert (Christgau et al., 1996, *Biochem. J.* 319: 705-712) to generate plasmid pA2X2.

The *Aspergillus aculeatus* GH10 xylanase coding sequence was PCR amplified using plasmid pA2x2 as template and primers 153505 and 153506 shown below using standard methods to yield an approximately 1.2 kb fragment. The 1.2 kb fragment was digested with Bam HI and Xho I (introduced in the PCR primers) and cloned into vector pCaHj527 (WO 2004/099228). The resulting plasmid was designated pMT2155 in which the cDNA was under transcriptional control of the neutral amylase II (NA2) promoter from *A. niger* and the AMG terminator from *A. niger*.

Primer 153505:
(SEQ ID NO: 153)
5'-TCTTGGATCCACCATGGTCGGACTGCTTTCAATCACC-3'

Primer 153506:
(SEQ ID NO: 154)
5'-TTAACTCGAGTCACAGACACTGCGAGTAATAGTC-3'

Two synthetic oligonucleotide primers shown below were designed to PCR amplify the *Aspergillus aculeatus* GH10 gene from plasmid pMT2155 and introduce flanking regions for insertion into expression vector pMJ09 (WO 2005/056772). Bold letters represent coding sequence and the remaining sequence is homologous to the insertion sites of pMJ09.

Forward Primer:
(SEQ ID NO: 155)
5'-cggactgcgcaccatggtcggactgctttcaat-3'

Reverse Primer:
(SEQ ID NO: 156)
5'-tcgccacggagcttatcacagacactgcgagtaat-3'

Fifty picomoles of each of the primers above were used in a PCR reaction consisting of 50 ng of pMT2155, 1 µl of 10 mM blend of dATP, dTTP, dGTP, and dCTP, 5 µl of 10× ACCUTAQ™ DNA Polymerase Buffer, and 5 units of ACCUTAQ™ DNA Polymerase, in a final volume of 50 µl. An EPPENDORF® MASTERCYCLER® 5333 was used to amplify the DNA fragment programmed for one cycle at 95° C. for 3 minutes; and 30 cycles each at 94° C. for 45 seconds, 55° C. for 60 seconds, and 72° C. for 1 minute 30 seconds. After the 30 cycles, the reaction was incubated at 72° C. for 10 minutes and then cooled to 4° C. until further processing.

The reaction products were isolated on a 1.0% agarose gel using TAE buffer where a 1.2 kb product band was excised from the gel and purified using a QIAquick Gel Extraction Kit according to the manufacturer's instructions.

The fragment was then cloned into pMJ09 using an IN-FUSION™ Cloning Kit. The vector was digested with Nco I and Pac I and purified by agarose gel electrophoresis as described above. The 1.2 kb gene fragment and the digested vector were ligated together in a reaction resulting in the expression plasmid pSaMe-AaXYL in which transcription of the Family GH10 gene was under the control of the *T. reesei* cbh1 promoter. The ligation reaction (50 ul) was composed of 1× IN-FUSION™ Buffer, 1×BSA, 1 µl of IN-FUSION™ enzyme (diluted 1:10), 100 ng of pAlLo2 digested with Nco I and Pac I, and 100 ng of the *Aspergillus aculeatus* GH10 xylanase purified PCR product. The reaction was incubated at room temperature for 30 minutes. One µl of the reaction was used to transform *E. coli* XL10 SOLOPACK® Gold cells according to the manufacturer. An *E. coli* transformant containing pSaMe-AaGH10 was detected by restriction enzyme digestion and plasmid DNA was prepared using a BIOROBOT® 9600. DNA sequencing of the *Aspergillus aculeatus* GH10 gene from pSaMe-AaXYL was performed using dye-terminator chemistry (Giesecke et al., 1992, supra) and primer walking strategy.

Plasmids pSaMe-AaXYL encoding the *Aspergillus aculeatus* GH10 endoglucanase and pSaMe-TrBXYL encoding the *Trichoderma reesei* beta-xylosidase were co-transformed into *Trichoderma reesei* RutC30 by PEG-mediated transformation (Penttila et al., 1987, Gene 61 155-164) to generate *T. reesei* strain SaMe-BXX13. Each plasmid contained the *Aspergillus nidulans* amdS gene to enable transformants to grow on acetamide as the sole nitrogen source.

*Trichoderma reesei* RutC30 was cultivated at 27° C. and 90 rpm in 25 ml of YP medium supplemented with 2% (w/v) glucose and 10 mM uridine for 17 hours. Mycelia were collected by filtration using a Vacuum Driven Disposable Filtration System (Millipore, Bedford, MA, USA) and washed twice with deionized water and twice with 1.2 M sorbitol. Protoplasts were generated by suspending the washed mycelia in 20 ml of 1.2 M sorbitol containing 15 mg of GLUCANEX™ (Novozymes A/S, Bagsvaerd, Denmark) per ml and 0.36 units of chitinase (Sigma Chemical Co., St. Louis, MO, USA) per ml and incubating for 15-25 minutes at 34° C. with gentle shaking at rpm. Protoplasts were collected by centrifuging for 7 minutes at 400×g and washed twice with cold 1.2 M sorbitol. The protoplasts were counted using a haemacytometer and resuspended in STC to a final concentration of $1\times10^8$ protoplasts per ml. Excess protoplasts were stored in a Cryo 1° C. Freezing Container (Nalgene, Rochester, NY, USA) at −80° C.

Approximately 4 µg of plasmids pSaMe-AaXYL and pSaMe-TRBXYL were digested with Pme I and added to 100 µl of protoplast solution and mixed gently, followed by 250 µl of 10 mM $CaCl_2$-10 mM Tris-HCl pH 7.5-60% PEG 4000, mixed, and incubated at room temperature for 30 minutes. STC (3 ml) was then added and mixed and the transformation solution was plated onto COVE plates using *Aspergillus nidulans* amdS selection. The plates were incubated at 28° C. for 5-7 days. Transformants were sub-cultured onto COVE2 plates and grown at 28° C.

Over 40 transformants were subcultured onto fresh plates containing acetamide and allowed to sporulate for 7 days at 28° C.

The *Trichoderma reesei* transformants were cultivated in 125 ml baffled shake flasks containing 25 ml of cellulase-inducing medium at pH 6.0 by inoculating spores of the transformants and incubating at 28° C. and 200 rpm for 7 days. *Trichoderma reesei* RutC30 was run as a control. Culture broth samples were removed at day 5. One ml of each culture broth was centrifuged at 15,700×g for 5 minutes in a micro-centrifuge and the supernatants transferred to new tubes.

SDS-PAGE was performed using CRITERION® Tris-HCl (5% resolving) gels (Bio-Rad Laboratories, Inc.) with a CRITERION® System. Five ill of day 7 supernatants (see above) were suspended in 2× concentration of Laemmli Sample Buffer (Bio-Rad Laboratories, Inc., Hercules, CA, USA) and boiled in the presence of 5% beta-mercaptoethanol for 3 minutes. The supernatant samples were loaded onto a polyacrylamide gel and subjected to electrophoresis with 1× Tris/Glycine/SDS as running buffer (Bio-Rad Laboratories, Inc., Hercules, CA, USA). The resulting gel was stained with BIO-SAFE™ Coomassie Stain. The transformant showing the highest expression of both the *A. aculeatus* GH10 xylanase and the *T. reesei* beta-xylosidase based on the protein gel was designated *T. reesei* SaMe-BXX13.

*Trichoderma reesei* SaMe-BXX13 was cultivated in 500 ml baffled shake flasks containing 250 ml of cellulase-inducing medium at pH 6.0 inoculated with spores of *T. reesei* SaMe-BXX13. Shake flasks were incubated at 28° C. at 200 rpm for five days. The culture broth was then filtered using an 0.22 µm EXPRESS™ Plus Membrane.

The filtered broth was concentrated and buffer exchanged using a tangential flow concentrator equipped with a 10 kDa polyethersulfone membrane to pH 4.0 with acetic acid. Sample was loaded onto a SP SEPHAROSE® column equilibrated in 50 mM sodium acetate pH 4.0, eluting bound proteins with a gradient of 0-1000 mM sodium chloride. Fractions were buffer exchanged into 20 mM sodium phosphate pH 7.0 using a tangential flow concentrator and applied to a Phenyl SUPEROSE™ column (HR 16/10) equilibrated with 1.5 M $(NH_4)_2SO_4$-20 mM sodium phosphate pH 7.0. Bound proteins were eluted with a linear gradient over 20 column volumes from 1.5 to 0 M $(NH_4)_2SO_4$ in 20 mM Tris-HCl pH 7.0. The protein fractions were buffer exchanged into 20 mM TEA HCl pH 7.5 using a tangential flow concentrator. Sample was applied to a MonoQ® column, equilibrated in 20 mM TEA HCl pH 7.5, eluting bound proteins with a gradient from 0-300 mM sodium chloride. Buffer of final protein fractions was 20 mM TEA-100 mM sodium chloride pH 7.5. Protein concentration was determined using a Microplate BCA™ Protein Assay Kit in which bovine serum albumin was used as a protein standard.

Example 30: Preparation of *Talaromyces emersonii* CBS 393.64 GH3 Beta-Xylosidase

*Talaromyces emersonii* CBS 393.64 (NN005049) beta-xylosidase (SEQ ID NO: 59 [DNA sequence] and SEQ ID NO: 60 [deduced amino acid sequence]) was prepared recombinantly according to Rasmussen et al., 2006, *Biotechnology and Bioengineering* 94: 869-876 using *Aspergillus oryzae* JaL355 as a host (WO 2003/070956).

The *Talaromyces emersonii* beta-xylosidase was purified according to Rasmussen et al., 2006, supra.

Example 31: Preparation of *Trichoderma reesei* RutC30 Cel7B Endoglucanase I

*Trichoderma reesei* RutC30 Cel7B endoglucanase I (EGI) (SEQ ID NO: 61 [DNA sequence] and SEQ ID NO: 62 [deduced amino acid sequence]) was prepared recombinantly according to WO 2005/067531 using *Aspergillus oryzae* JaL250 as a host.

The harvested broth was centrifuged in 500 ml bottles at 13,000×g for 20 minutes at 4° C. and then sterile filtered using a 0.22 µm polyethersulfone membrane (Millipore, Bedford, MA, USA). The filtered broth was concentrated and buffer exchanged with 20 mM Tris-HCl pH 8.5 using a tangential flow concentrator equipped with a 10 kDa polyethersulfone membrane. The sample was loaded onto a Q SEPHAROSE® High Performance column equilibrated with 20 mM Tris-HCl pH 8.5, and step eluted with equilibration buffer containing 600 mM NaCl. Flow-through and eluate fractions were analyzed by SGS-PAGE gel analysis using a CRITERION™ stain-free imaging system (Bio-Rad Laboratories, Inc., Hercules, CA, USA). The eluate fractions containing *Trichoderma reesei* Cel7B EGI were pooled, concentrated and buffer exchanged into 20 mM Tris-HCl pH 8.5. Protein concentration was determined using a Microplate BCA™ Protein Assay Kit in which bovine serum albumin was used as a protein standard.

Example 32: Preparation of *Trichoderma reesei* RutC30 Cel7A Cellobiohydrolase I

*Trichoderma reesei* RutC30 Cel7A cellobiohydrolase I (CBHI) (SEQ ID NO: 63 [DNA sequence] and SEQ ID NO: 64 [deduced amino acid sequence]) was prepared as described by Ding and Xu, 2004, "Productive cellulase adsorption on cellulose" in Lignocellulose Biodegradation (Saha, B. C. ed.), Symposium Series 889, pp. 154-169, American Chemical Society, Washington, DC. Protein concentration was determined using a Microplate BCA™ Protein Assay Kit in which bovine serum albumin was used as a protein standard.

Example 33: Preparation of *Trichoderma reesei* RutC30 Cel6A Cellobiohydrolase II The *Trichoderma reesei* RutC30 Cel6A cellobiohydrolase II gene (SEQ ID NO: 65 [DNA sequence] and SEQ ID NO: 66 [deduced amino acid sequence]) was isolated from *Trichoderma reesei* RutC30 as described in WO 2005/056772.

The *Trichoderma reesei* Cel6A cellobiohydrolase II gene was expressed in *Fusarium venenatum* using pEJG61 as an expression vector according to the procedures described in U.S. Published Application No. 20060156437. Fermentation was performed as described in U.S. Published Application No. 20060156437.

Filtered broth was desalted and buffer-exchanged into 20 mM sodium acetate-150 mM NaCl pH 5.0 using a HIPREP® 26/10 Desalting Column according to the manufacturer's instructions. Protein concentration was determined using a Microplate BCA™ Protein Assay Kit in which bovine serum albumin was used as a protein standard.

Example 34: Pretreated Corn Stover Hydrolysis Assay

Corn stover was pretreated at the U.S. Department of Energy National Renewable Energy Laboratory (NREL) using 1.4 wt % sulfuric acid at 165° C. and 107 psi for 8 minutes. The water-insoluble solids in the pretreated corn stover (PCS) contained 56.5% cellulose, 4.6% hemicellulose and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003.

Unmilled, unwashed PCS (whole slurry PCS) was prepared by adjusting the pH of PCS to 5.0 by addition of 10 M NaOH with extensive mixing, and then autoclaving for 20 minutes at 120° C. The dry weight of the whole slurry PCS was 29%. The PCS was used unwashed or washed with water. Milled unwashed PCS (dry weight 32.35%) was prepared by milling whole slurry PCS in a Cosmos ICMG 40 wet multi-utility grinder (EssEmm Corporation, Tamil Nadu, India). Milled washed PCS (dry weight 32.35%) was prepared in the same manner, with subsequent washing with deionized water and decanting off the supernatant fraction repeatedly.

The hydrolysis of PCS was conducted using 2.2 ml deep-well plates (Axygen, Union City, CA, USA) in a total reaction volume of 1.0 ml. The hydrolysis was performed with 50 mg of PCS (insoluble solids in case of unwashed PCS and total solids in case of washed PCS) per ml of 50 mM sodium acetate pH 5.0 buffer containing 1 mM manganese sulfate and various protein loadings of various enzyme compositions (expressed as mg protein per gram of cellulose). Enzyme compositions were prepared and then added simultaneously to all wells in a volume ranging from 50 µl to 200 µl, for a final volume of 1 ml in each reaction. The plate was then sealed using an ALPS-300™ plate heat sealer (Abgene, Epsom, United Kingdom), mixed thoroughly, and incubated at a specific temperature for 72 hours. All experiments reported were performed in triplicate.

Following hydrolysis, samples were filtered using a 0.45 µm MULTISCREEN® 96-well filter plate (Millipore, Bedford, MA, USA) and filtrates analyzed for sugar content as described below. When not used immediately, filtered aliquots were frozen at −20° C. The sugar concentrations of samples diluted in 0.005 M $H_2SO_4$ were measured using a 4.6×250 mm AMINEX® HPX-87H column (Bio-Rad Laboratories, Inc., Hercules, CA, USA) by elution with w/w benzoic acid-0.005 M $H_2SO_4$ at 65° C. at a flow rate of 0.6 ml per minute, and quantitation by integration of the glucose, cellobiose, and xylose signals from refractive index detection (CHEMSTATION®, AGILENT® 1100 HPLC, Agilent Technologies, Santa Clara, CA, USA) calibrated by pure sugar samples. The resultant glucose and cellobiose equivalents were used to calculate the percentage of cellulose conversion for each reaction.

Glucose, cellobiose, and xylose were measured individually. Measured sugar concentrations were adjusted for the appropriate dilution factor. In case of unwashed PCS, the net concentrations of enzymatically-produced sugars were determined by adjusting the measured sugar concentrations for corresponding background sugar concentrations in unwashed PCS at zero time point. All HPLC data processing was performed using MICROSOFT EXCEL™ software (Microsoft, Richland, WA, USA).

The degree of cellulose conversion to glucose was calculated using the following equation:% conversion=glucose concentration/glucose concentration in a limit digest. To calculate total conversion the glucose and cellobiose values were combined. Cellobiose concentration was multiplied by 1.053 in order to convert to glucose equivalents and added to the glucose concentration. The degree of total cellulose conversion was calculated using the following equation:

% conversion=[glucose concentration+1.053×(cellobiose concentration)]/[(glucose concentration+ 1.053×(cellobiose concentration) in a limit digest].

The 1.053 factor for cellobiose takes into account the increase in mass when cellobiose is converted to glucose. In order to calculate % conversion, a 100% conversion point was set based on a cellulase control (50-100 mg of *Trichoderma reesei* cellulase per gram cellulose), and all values were divided by this number and then multiplied by 100. Triplicate data points were averaged and standard deviation was calculated.

Example 35: Evaluation of Several Cellulolytic
Proteins Replacing CBHI, CBHII, and EGII
Components in a Reconstituted *Trichoderma
reesei*-Based Enzyme Composition for Improved
Performance at 50° C., 55° C., and 60° C.

Several cellulolytic proteins were tested in various combinations at 50° C., 55° C., and against a reconstituted *Trichoderma reesei*-based enzyme composition that included four major *Trichoderma reesei* cellulases (45% *Trichoderma reesei* Cel7A CBHI, 25% *Trichoderma reesei* Cel6A CBHII, 5% *Trichoderma reesei* Cel7B EGI, 5% *Trichoderma reesei* Cel5A EGII), a beta-glucosidase (10% *Aspergillus fumigatus* Cel3A beta-glucosidase), and a Family 61 polypeptide having cellulolytic enhancing activity (10% *Thermoascus aurantiacus* GH61A polypeptide).

The evaluated enzymes included *Chaetomium thermophilum* Cel7A CBHI, *Myceliophthora thermophila* Cel7A CBHI, *Myceliophthora thermophila* Cel6A CBHII, and *Myceliophthora thermophila* Cel5A EGII. All enzyme compositions contained 45% CBHI, 25% CBHII, 5% *Trichoderma reesei* Cel7B EGI, 5% EGII, 10% *Aspergillus fumigatus* beta-glucosidase, and 10% *Thermoascus aurantiacus* GH61A polypeptide having cellulolytic enhancing activity. All enzyme compositions, including the *Trichoderma reesei*-based composition, were applied at the same dosage of 5 mg protein per g cellulose.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

Figure 1:
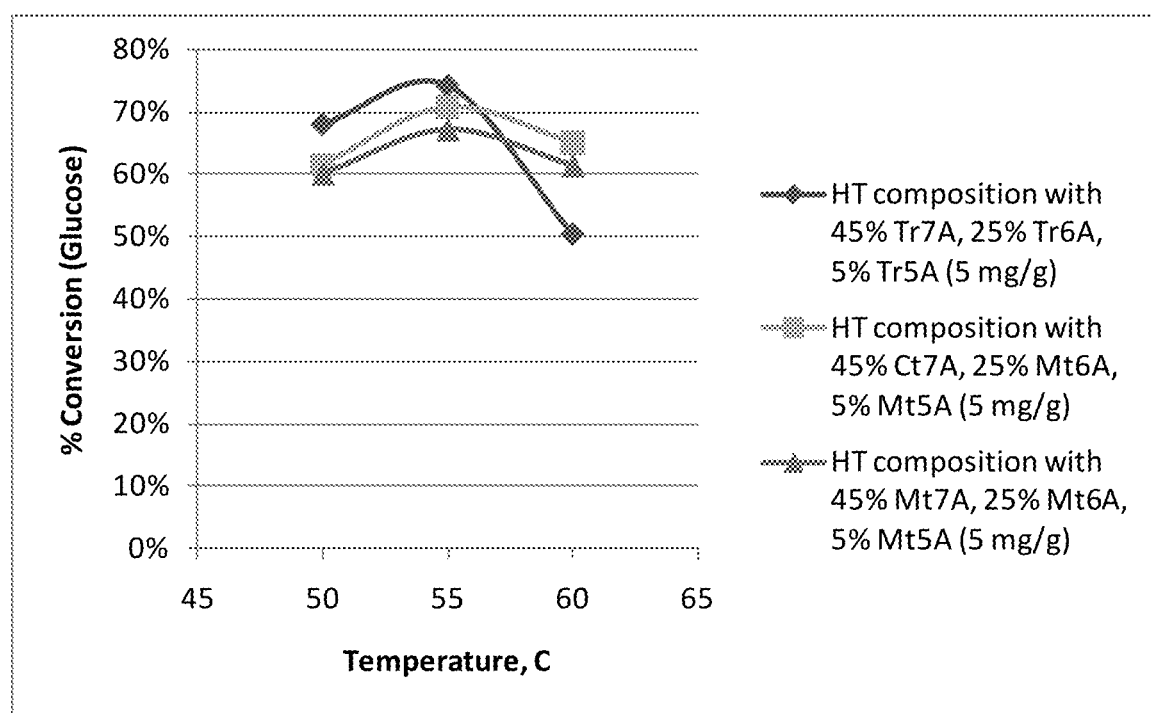
FIG. 1 shows a comparison of two enzyme compositions with a *Trichoderma reesei*— based composition in hydrolysis of milled washed PCS at 50° C., 55° C., and 60° C.

The results as shown in FIG. 1 demonstrated that the best enzyme composition for cellulose hydrolysis included *Chaetomium thermophilum* Cel7A CBHI, *Myceliophthora thermophila* Cel6A CBHII, *Trichoderma reesei* Cel7B EGI, *Myceliophthora thermophila* Cel5A EGII, *Aspergillus fumigatus* beta-glucosidase, and *Thermoascus aurantiacus* GH61A polypeptide having cellulolytic enhancing activity. Replacement of the *Trichoderma reesei* Cel7A CBHI, Cel6A CBHII, and Cel5A EGII with *Chaetomium thermophilum* Cel7A CBHI, *Myceliophthora thermophila* Cel6A CBHII, and *Myceliophthora thermophila* Cel5A EGII significantly improved the degree of cellulose conversion to glucose at 60° C. (from 50% to 65%). The improved composition hydrolyzed milled washed PCS almost as efficiently at 60° C. (65% cellulose conversion to glucose) as the *Trichoderma reesei*-based composition at 50° C. (68%).

Example 36: Evaluation of GH61 Polypeptides
Having Cellulolytic Enhancing Activity for the
Ability to Enhance PCS-Hydrolyzing Activity of a
High-Temperature Enzyme Composition at 50° C.,
55° C., and 60° C.

*Thermoascus aurantiacus* GH61A polypeptide having cellulolytic enhancing activity and *Thielavia terrestris* GH61E polypeptide having cellulolytic enhancing activity, prepared as described herein, were tested at 10% total protein addition for the ability to stimulate a high-temperature cellulase composition at 50° C., 55° C., and 60° C. using milled washed PCS. The compositions consisting of 45% *Chaetomium thermophilum* Cel7A CBHI, 25% *Myceliophthora thermophila* Cel6A CBHII, 5% *Trichoderma reesei* Cel7B EGI, 5% *Myceliophthora thermophila* Cel5A EGII, 10% *Aspergillus fumigatus* beta-glucosidase, and 10% GH61 polypeptide having cellulolytic enhancing activity were used for hydrolysis of milled washed PCS at 5 mg protein per g cellulose, and the results were compared with the results for a high-temperature enzyme composition without a GH61 polypeptide, which was used at 4.5 mg protein per g cellulose. The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

Figure 2:
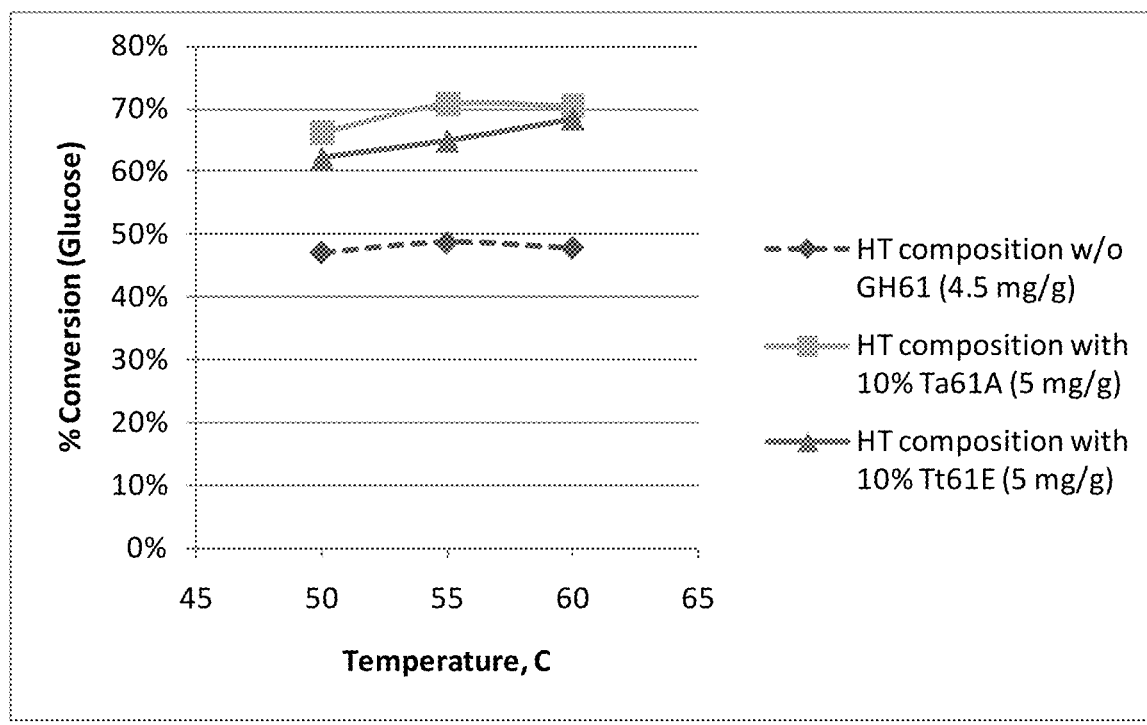
FIG. 2 shows the effect of *Thermoascus aurantiacus* GH61A or *Thielavia terrestris* GH61E GH61 polypeptides having cellulolytic enhancing activity on PCS-hydrolysing activity of a high-temperature enzyme composition at 50° C., 55° C., and 60° C.

The results shown in FIG. 2 demonstrated that the *Thermoascus aurantiacus* GH61A and *Thielavia terrestris* GH61E polypeptides were able to significanty enhance PCS-hydrolyzing activity of the high-temperature enzyme composition at all temperatures from 50° C. to 60° C., and that the stimulating effect was more pronounced at higher temperatures. At 60° C., a composition without a GH61 polypeptide showed 48% conversion of cellulose to glucose. For comparison, compositions that included *Thermoascus aurantiacus* GH61A or *Thielavia terrestris* GH61E polypeptides showed 70% and 68% conversion of cellulose to glucose, respectively.

Example 37: Evaluation of a Binary Composition
of *Thermoascus aurantiacus* GH61A and *Thielavia
terrestris* GH61E GH61 Polypeptides Having
Cellulolytic Enhancing Activity for the Ability to
Enhance PCS-Hydrolyzing Activity of a
High-Temperature Enzyme Composition at 50° C.,
55° C., and 60° C.

The boosting performance of a binary composition comprising equal amounts (on a protein basis) of *Thermoascus aurantiacus* GH61A and *Thielavia terrestris* GH61E GH61 polypeptides having cellulolytic enhancing activity was compared with the boosting performance of the individual GH61 proteins alone at equivalent total protein loading at 50° C., 55° C., and 60° C. The high-temperature enzyme compositions included 45% *Chaetomium thermophilum* Cel7A CBHI, 25% *Myceliophthora thermophila* Cel6A CBHII, 5% *Trichoderma reesei* Cel7B EGI, 5% *Myceliophthora thermophila* Cel5A EGII, 10% *Aspergillus fumigatus* beta-glucosidase, and 10% GH61 component (either an individual polypeptide or a binary composition). The total protein loading in hydrolysis reactions was 5 mg protein per g cellulose.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

Figure 3:
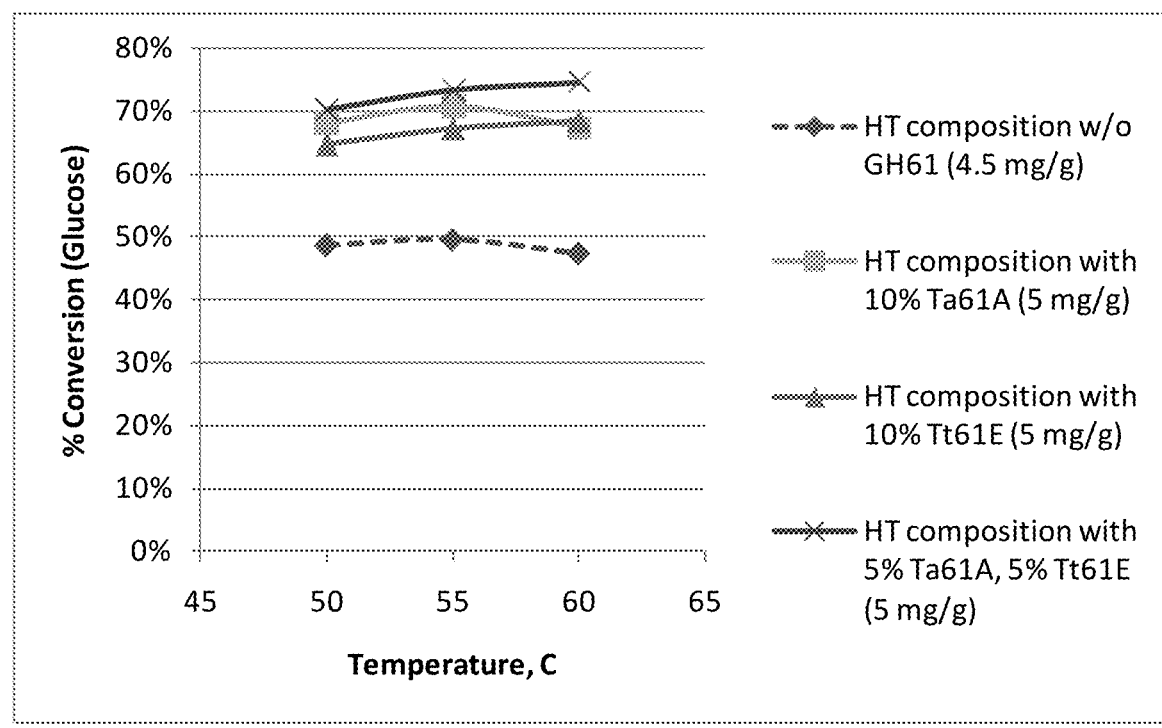
FIG. 3 shows the boosting performance of a binary composition comprising equal amounts of *Thermoascus aurantiacus* GH61A and *Thielavia terrestris* GH61E GH61 polypeptides having cellulolytic enhancing activity in comparison with the boosting performance of the individual GH61 polypeptides in hydrolysis of milled washed PCS at 50° C., 55° C.

The results shown in FIG. 3 demonstrated that the binary combination of the two GH61 polypeptides having cellulolytic enhancing activity, *Thermoascus aurantiacus* GH61A and *Thielavia terrestris* GH61E, provided greater enhancement than either of the GH61 proteins alone. The effect was especially pronounced at 60° C.

Example 38: Evaluation of Binary Compositions
Containing Different Ratios of *Thermoascus
aurantiacus* GH61A and *Thielavia terrestris*
GH61E GH61 Polypeptides Having Cellulolytic
Enhancing Activity for the Ability to Enhance
PCS-Hydrolyzing Activity of a High-Temperature
Enzyme Composition at 60° C.

After determining that a 1:1 composition of *Thermoascus aurantiacus* GH61A and *Thielavia terrestris* GH61E GH61 polypeptides having cellulolytic enhancing activity performed better in enhancing the PCS-hydrolyzing activity of a high-temperature enzyme composition than either protein alone, the effect was analyzed in more detail by examining different ratios of the *Thermoascus aurantiacus* GH61A and *Thielavia terrestris* GH61E polypeptides. The various binary compositions of the GH61 polypeptides were added at 0.5 mg protein per g cellulose to a high-temperature enzyme composition (4.5 mg protein per g cellulose) so that the final mixture consisted of 45% *Chaetomium thermophilum* Cel7A CBHI, 25% *Myceliophthora thermophila* Cel6A CBHII, 5% *Trichoderma reesei* Cel7B EGI, 5% *Myceliophthora thermophila* Cel5A EGII, 10% *Penicillium brasilianum* beta-glucosidase, and 10% GH61 component (either an individual GH61 polypeptide or a binary composition).

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

Figure 4:
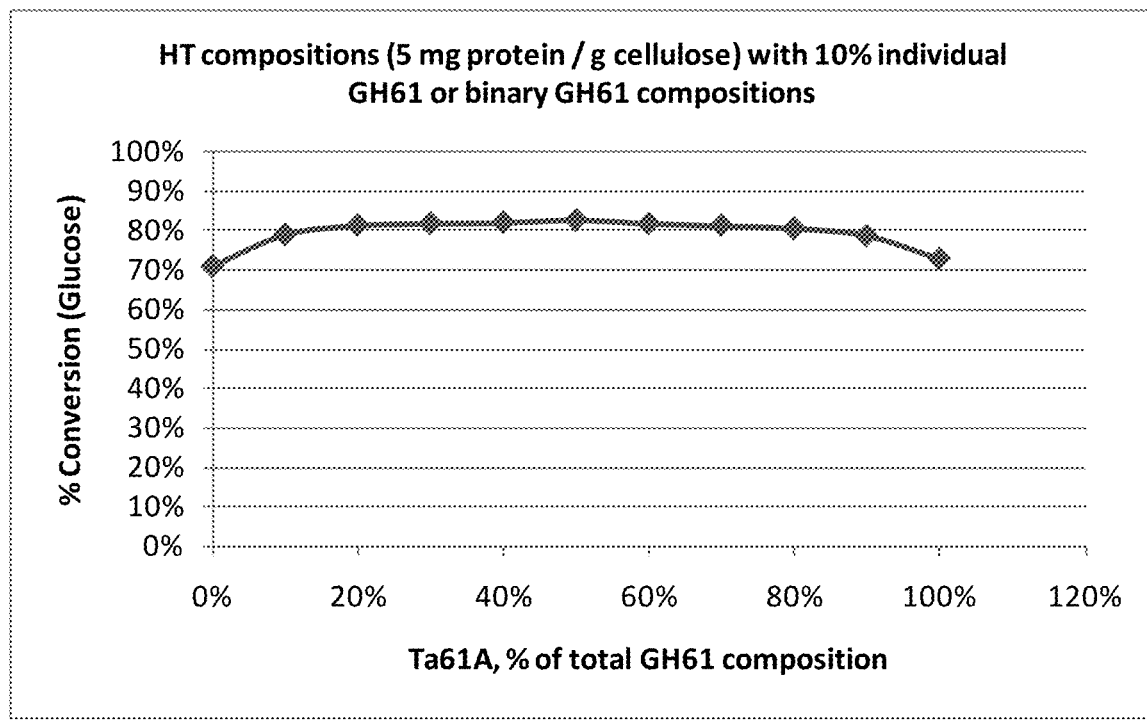
FIG. 4 shows the effect of compositions containing different ratios of *Thermoascus aurantiacus* GH61A and *Thielavia terrestris* GH61E polypeptides on PCS-hydrolysing activity of a high-temperature enzyme composition at 60° C.

The results are shown in Table 1 and FIG. 4. All binary compositions of *Thermoascus aurantiacus* GH61A and *Thielavia terrestris* GH61E GH61 polypeptides having cellulolytic enhancing activity provided significantly better enhancement of PCS hydrolysis by the high-temperature enzyme composition than either protein alone. The best performance was obtained for binary GH61 compositions that included at least 20% of either *Thermoascus aurantiacus* GH61A or *Thielavia terrestris* GH61E polypeptide having cellulolytic enhancing activity.

TABLE 1

Addition of binary GH61 polypeptide compositions (0.5 mg protein per g cellulose) to a high-temperature enzyme composition (4.5 mg protein per g cellulose) at 60° C.

| mg protein per g cellulose | | % of total GH61 addition | | |
|---|---|---|---|---|
| *Thermoascus aurantiacus* GH61A | *Thielavia terrestris* GH61E | *Thermoascus aurantiacus* GH61A | *Thielavia terrestris* GH61E | % Conversion |
| 0.00 | 0.00 | 0 | 0 | 47.9 |
| 0.00 | 0.50 | 0 | 100 | 71.0 |
| 0.05 | 0.45 | 10 | 90 | 79.0 |
| 0.10 | 0.40 | 20 | 80 | 81.3 |
| 0.15 | 0.35 | 30 | 70 | 81.8 |
| 0.20 | 0.30 | 40 | 60 | 82.0 |
| 0.25 | 0.25 | 50 | 50 | 82.7 |
| 0.30 | 0.20 | 60 | 40 | 81.8 |
| 0.35 | 0.15 | 70 | 30 | 81.2 |
| 0.40 | 0.10 | 80 | 20 | 80.6 |
| 0.45 | 0.05 | 90 | 10 | 78.8 |
| 0.50 | 0.00 | 100 | 0 | 72.8 |

Example 39: Evaluation of Different Levels of a Binary 1:1 Composition Comprising *Thermoascus aurantiacus* GH61A and *Thielavia terrestris* GH61E GH61 Polypeptides Having Cellulolytic Enhancing Activity for the Ability to Enhance PCS-Hydrolyzing Activity of a High-Temperature Enzyme Composition at 60° C.

The ability of *Thermoascus aurantiacus* GH61A polypeptide having cellulolytic enhancing activity, *Thielavia terrestris* GH61E polypeptide having cellulolytic enhancing activity, or their binary 1:1 composition (on a protein basis) to stimulate a high-temperature enzyme composition was examined by adding different GH61 protein loadings (0.125, 0.25, 0.5, 1.0, 1.5 mg protein per g cellulose) to a constant loading of the high-temperature enzyme composition (4.5 mg per g cellulose) at 60° C. The high-temperature enzyme composition contained 45% *Chaetomium thermophilum* Cel7A CBHI, 25% *Myceliophthora thermophila* Cel6A CBHII, 5% *Trichoderma reesei* Cel7B EGI, 5% *Myceliophthora thermophila* Cel5A EGII, and 10% *Penicillium brasilianum* Cel3A beta-glucosidase.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

Figure 5:
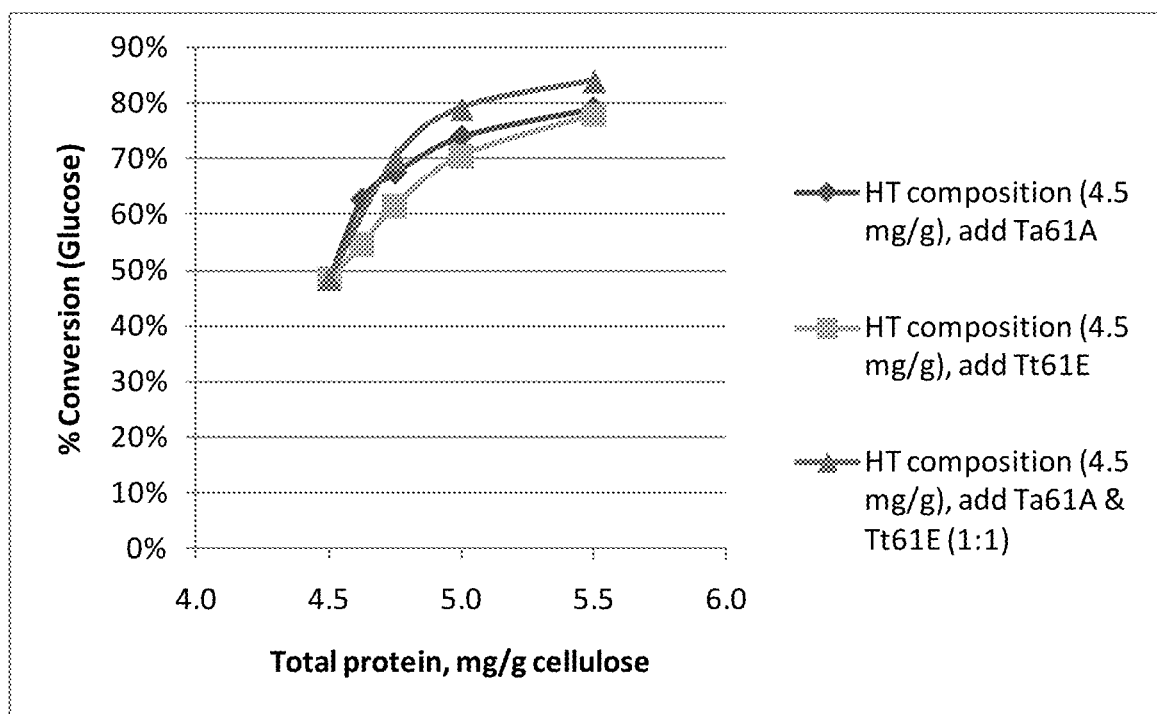
FIG. 5 shows the effect of different levels of individual *Thermoascus aurantiacus* GH61A and *Thielavia terrestris*

The results shown in FIG. 5 demonstrated that at equivalent protein loadings, the 1:1 compositions of *Thermoascus aurantiacus* GH61A and *Thielavia terrestris* GH61E GH61 polypeptides having cellulolytic enhancing activity provided greater PCS hydrolysis enhancement than either of the GH61 proteins alone. The effect was especially pronounced at relatively high additions of the GH61 proteins. The effect saturated when the level of the GH61 binary composition reached approximately 20% of the total protein loading.

Example 40: Effect of Thermobifida *Fusca* GH11 Xylanase on Saccharification of Milled Washed PCS by a High-Temperature Enzyme Composition at 50-65° C.

The ability of Thermobifida *fusca* GH11 xylanase (0.5 mg protein per g cellulose) to stimulate saccharification of milled washed PCS by a high-temperature enzyme composition (5 mg protein per g cellulose) was examined at 50° C., 55° C., 60° C., and 65° C. For comparison, the high-temperature enzyme composition without a supplemental xylanase was tested at 5.0, 5.5, and 6.0 mg protein per g cellulose. The high-temperature enzyme composition included 45% *Chaetomium thermophilum* Cel7A CBHI, 25% *Myceliophthora thermophila* Cel6A CBHII, 5% *Trichoderma reesei* Cel7B EGI, 5% *Myceliophthora thermophila* Cel5A EGII, 10% *Penicillium brasilianum* Cel3A beta-glucosidase, and 10% *Thermoascus aurantiacus* GH61A polypeptide having cellulolytic enhancing activity.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

The results shown in FIG. 6 demonstrated that addition of Thermobifida *fusca* GH11 xylanase significantly improved performance of the high-temperature enzyme composition at all temperatures from 50° C. to 65° C., increasing the cellulose conversion to glucose by 4-7% after 72 hours of hydrolysis.

Example 41: Replacement of *Chaetomium thermophilum* Cel7A Cellobiohydrolase I in a High-Temperature Enzyme Composition with Various Thermostable CBHI Proteins at 50-65° C.

The ability of several thermostable CBHI proteins to replace *Chaetomium thermophilum* Cel7A CBHI in a high-temperature enzyme composition (4 mg total protein per g cellulose) was tested at 50° C., 55° C., 60° C., and 65° C. The high-temperature enzyme composition included 45%

*Chaetomium thermophilum* Cel7A CBHI, 25% *Myceliophthora thermophila* Cel6A CBHII, 10% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, and 10% *Penicillium brasilianum* Cel3A beta-glucosidase.

The following recombinant CBHI cellulases from an *Aspergillus oryzae* expression host were tested as a replacement for *Chaetomium thermophilum* Cel7A CBHI: *Myceliophthora thermophila* Cel7A, *Aspergillus fumigatus* Cel7A, and *Thermoascus aurantiacus* Cel7A.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

As shown in FIG. 7, the replacement of *Chaetomium thermophilum* Cel7A CBHI with *Aspergillus fumigatus* Cel7A CBHI gave the best hydrolysis results, providing an almost 6% improvement of the final hydrolysis yield at 60° C. Surprisingly, a native *Thermoascus aurantiacus* Cel7A CBHI, which contained no CBM, also showed a remarkably good performance at elevated temperatures.

Example 42: Comparison of High-Temperature Enzyme Compositions Containing *Aspergillus fumigatus* Cel7A CBHI or *Chaetomium thermophilum* Cel7A CBHI with *Trichoderma reesei*-Based Cellulase SaMe-MF268 (XCL-533) at 50° C. and 60° C.

Two high-temperature enzyme compositions that included either *Aspergillus fumigatus* Cel7A CBHI or *Chaetomium thermophilum* Cel7A CBHI were tested in comparison with *Trichoderma reesei*-based cellulase composition SaMe-MF268 (XCL-533) at four protein loadings (3.5, 4.0, 4.5, and 5.0 mg protein per g cellulose) and two temperatures (50° C. and using milled washed PCS as a substrate The high-temperature enzyme compositions included 45% Cel7A CBHI, 25% *Myceliophthora thermophila* Cel6A CBHII, 5% *Trichoderma reesei* Cel7B EGI, 5% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, 7.5% *Penicillium brasilianum* GH3A beta-glucosidase, and 2.5% *Thermobifida fusca* GH11 xylanase. The *Trichoderma reesei*-based enzyme composition SaMe-MF268 (XCL-533) was obtained as described in WO 2008/151079. The composition comprises a *Thermoascus aurantiacus* GH61A polypeptide having cellulolytic enhancing activity, a beta-glucosidase fusion protein comprising the *Humicola insolens* endoglucanase V core polypeptide fused to the wild-type *Aspergillus oryzae* beta-glucosidase, a *Trichoderma reesei* Cel7A cellobiohydrolase I, a *Trichoderma reesei* Cel6A cellobiohydrolase II, a *Trichoderma reesei* Cel7B endoglucanase I, a *Trichoderma reesei* Cel5A endoglucanase II, a *Trichoderma reesei* Cel45A endoglucanase V, and a *Trichoderma reesei* Cel12A endoglucanase III.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

Protein dose profiles for the *Aspergillus fumigatus* Cel7A CBHI-based composition in comparison with the *Chaetomium thermophilum* Cel7A CBHI-based composition and the *Trichoderma reesei*-based cellulase composition XCL-533 are shown in FIG. 8. The *Trichoderma reesei*-based cellulase composition XCL-533 showed poor performance at 60° C., while both high-temperature enzyme compositions were significantly activated by the temperature increase from 50° C. to 60° C. The high-temperature enzyme composition that included *Aspergillus fumigatus* Cel7A CBHI performed at 60° C. as well as the *Trichoderma reesei*-based cellulase composition XCL-533 performed at its optimum temperature of 50° C., requiring approximately 3.5 mg protein per g cellulose to achieve 80% conversion of cellulose to glucose in 72 hours. For the *Chaetomium thermophilum* Cel7A CBHI-based composition, the protein loading required to achieve the same degree of cellulose conversion at 60° C. was 4.5 mg protein per g cellulose.

Example 43: Hydrolysis Time-Course for *Aspergillus fumigatus* Cel7A CBHI-Based High-Temperature Enzyme Composition in Comparison with *Trichoderma reesei*-Based Cellulase Composition SaMe-MF268 at 50° C. and 60° C.

Hydrolysis performance of the *Aspergillus fumigatus* Cel7A CBHI-based high-temperature enzyme composition and the *Trichoderma reesei*-based cellulase composition SaMe-MF268 (XCL-533) was compared over a longer incubation time (five days) at 50° C. and using milled washed PCS as a substrate. The *Aspergillus fumigatus* Cel7A CBHI-based enzyme composition included 45% *Aspergillus fumigatus* Cel7A CBHI, 25% *Myceliophthora thermophila* Cel6A CBHII, 5% *Trichoderma reesei* Cel7B EGI, 5% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, 7.5% *Penicillium brasilianum* GH3A beta-glucosidase, and 2.5% *Thermobifida fusca* GH11 xylanase. The *Aspergillus fumigatus* Cel7A CBHI-based enzyme composition and the *Trichoderma reesei*-based cellulase composition XCL-533 were tested at four different protein loadings, 2.0, 3.0, 3.5, and 4.0 mg protein per g cellulose.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

The time-course hydrolysis results for one of the four tested protein loadings (2 mg protein per g cellulose) are shown in FIG. 9. Similar trends were obtained for the three other protein loadings (data not shown). The *Trichoderma reesei*-based cellulase composition XCL-533 showed significantly reduced performance at 60° C., while the *Aspergillus fumigatus* Cel7A CBHI-based enzyme composition was significantly activated by the temperature increase from 50° C. to 60° C.

Comparison of the *Aspergillus fumigatus* Cel7A CBHI-based enzyme composition at and the *Trichoderma reesei*-based cellulase composition XCL-533 at 50° C. showed that the high-temperature composition performed better than the *Trichoderma reesei*-based cellulase composition XCL-533 during the initial three days, and similarly to the *Trichoderma reesei*-based cellulase composition XCL-533 during the last two days of hydrolysis. Comparison of the *Aspergillus fumigatus* Cel7A CBHI-based enzyme composition and the *Trichoderma reesei*-based cellulase composition XCL-533 at the same temperature of 50° C. showed slower but steadier rates of glucose accumulation for the high-temperature composition in comparison with the *Trichoderma reesei*-based cellulase composition XCL-533, resulting in a better performance of the high-temperature composition in a long-term hydrolysis at 50° C. (5 days).

Example 44: Evaluation of Four Xylanases for Synergy with the *Aspergillus fumigatus Cel*7A CBH I-Based High-Temperature Enzyme Composition at 50° C., 55° C., and 60° C.

*Aspergillus aculeatus* GH10 xylanase II, *Aspergillus fumigatus* GH10 xyn3 xylanase, *Trichophaea saccata* GH10 xylanase, and Thermobifida *fusca* GH11 xylanase were assayed for synergy with a high-temperature enzyme composition containing Cel7A CBHI from *Aspergillus fumigatus* at 50° C., 55° C., and 60° C. using milled washed PCS as a substrate. The xylanases were added at 10% (0.35 mg protein per g cellulose) to a constant loading of the high-temperature enzyme composition (3.5 mg protein per g cellulose). The high-temperature enzyme composition included 45% *Aspergillus fumigatus* Cel7A CBHI, 25% *Myceliophthora thermophila* Cel6A CBHII, 5% *Trichoderma reesei* Cel7B EGI, 5% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, and 10% *Penicillium brasilianum* Cel3A beta-glucosidase.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis.

The results shown in FIG. 10 demonstrated a considerable synergy between the xylanases and the high-temperature enzyme composition. At an equivalent protein loading (3.85 mg protein per g cellulose), all enzyme compositions that included xylanases achieved a significantly higher degree of cellulose conversion compared to the non-supplemented high-temperature enzyme composition. GH10 xylanases from *Aspergillus fumigatus* (xyn3) and *Trichophaea saccata* showed better performance than *Aspergillus aculeatus* GH10 xylanase II and Thermobifida *fusca* GH11 xylanase. The addition of the top two xylanases to the high-temperature enzyme composition resulted in an additional 11-16% conversion of cellulose to glucose in 72 hours compared to the non-supplemented enzyme composition (3.85 mg protein per g cellulose).

Example 45: Evaluation of *Aspergillus fumigatus* GH10 Xylanase Xyn3, *Trichophaea Saccata* GH10 Xylanase, and Thermobifida *Fusca* GH11 Xylanase for Synergy with a High-Temperature Enzyme Composition at 60° C.

The ability of *Aspergillus fumigatus* GH10 xyn3 xylanase, *Trichophaea saccata* GH10 xylanase, and Thermobifida *fusca* GH11 xylanase to synergize with a high-temperature enzyme composition containing *Aspergillus fumigatus* Cel7A CBHI was further examined by adding different levels of each xylanase (1.25%, 2.5%, 5%, 10%, and 20%) to a constant loading of the high-temperature enzyme composition (3 mg protein per g cellulose) at 60° C. using washed milled PCS as a substrate. The high-temperature enzyme composition included 45% *Aspergillus fumigatus* Cel7A CBHI, 25% *Myceliophthora thermophila* Cel6A CBHII, 5% *Trichoderma reesei* Cel7B EGI, 5% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, and 10% *Penicillium brasilianum* Cel3A beta-glucosidase.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis. The results are shown in FIG. 11.

*Aspergillus fumigatus* GH10 xyn3 and *Trichophaea saccata* GH10 xylanases performed similarly and showed better enhancement of PCS hydrolysis than Thermobifida *fusca* GH11 xylanase. The high-temperature enzyme composition supplemented with the GH10 xylanase from *Aspergillus fumigatus* or *Trichophaea saccata* significantly outperformed the *Trichoderma reesei*-based cellulase composition SaMe-MF268 (XCL-533) after 72 hours of incubation with milled washed PCS. The optimal addition level was about 5% for the *Aspergillus fumigatus* GH10 xyn3 and *Trichophaea saccata* GH10 xylanases and about 10% for the Thermobifida *fusca* GH11 xylanase. As shown in FIG. 11, the addition of either *Aspergillus fumigatus* GH10 xyn3 or *Trichophaea saccata* GH10 xylanase to the high-temperature composition at a level of only 5% at 60° C. enhanced the cellulose conversion to glucose from 65% to 83%. An equivalent loading of the *Trichoderma reesei*-based cellulase composition XCL-533 (3.15 mg protein per g cellulose) yielded 73% conversion of cellulose to glucose at 50° C.

Example 46: Comparison of *Aspergillus fumigatus* Cel7A-Based High-Temperature Enzyme Composition Containing *Aspergillus fumigatus* GH10 Xyn3 Xylanase with *Trichoderma reesei*-Based Cellulase SaMe-MF268

A high-temperature enzyme composition containing *Aspergillus fumigatus* GH10 xyn3 xylanase and the *Trichoderma reesei*-based cellulase composition SaMe-MF268 (XCL-533) were tested at three different protein loadings, 2.0, 3.0, and 4.0 mg protein per g cellulose, and the protein loading profile of the high-temperature enzyme composition at 60° C. was compared with the protein loading profile of the *Trichoderma reesei*-based cellulase composition XCL-533 at 50° C. The high-temperature enzyme composition contained 45% *Aspergillus fumigatus* Cel7A CBHI, 25% *Myceliophthora thermophila* Cel6A CBHII, 5% *Trichoderma reesei* Cel7B EGI, 5% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, 5% *Penicillium brasilianum* Cel3A beta-glucosidase, and 5% *Aspergillus fumigatus* GH10 xyn3.

The assay was performed as described in Example 34. The 1 ml reactions with 5% milled washed PCS were conducted for 72 hours in 50 mM sodium acetate pH 5.0 buffer containing 1 mM manganese sulfate. All reactions were performed in triplicate and involved single mixing at the beginning of hydrolysis. The results are shown in FIG. 12.

The experiment confirmed that the improved high-temperature enzyme composition containing *Aspergillus fumigatus* GH10 xyn3 xylanase significantly surpassed the performance of the *Trichoderma reesei*-based cellulase composition XCL-533. At 60° C., the high-temperature enzyme composition required a significantly lower protein loading (2.75 mg protein per g cellulose) than the *Trichoderma reesei*-based cellulase composition XCL-533 at 50° C. (3.80 mg protein per g cellulose) to hydrolyze 80% of cellulose to glucose in 72 hours.

Example 47: Comparison of High-Temperature Enzyme Compositions Containing *Aspergillus fumigatus* GH10 Xyn3 or *Trichophaea saccata* GH10 Xylanase with *Trichoderma reesei*-Based Cellulase SaMe-MF268 in Hydrolysis of Washed and Unwashed PCS Protein loading profiles of the improved high-temperature enzyme compositions containing either GH10 xylanase from *Aspergillus fumigatus* (xyn 3) or GH10 xylanase from *Trichophaea saccata* were compared with protein loading profiles of the *Trichoderma reesei*-based cellulase composition SaMe-MF268 (XCL-533) using milled washed and milled unwashed PCS. The high-temperature enzyme compositions included 45% *Aspergillus fumigatus* Cel7A CBHI, 25% *Myceliophthora thermophila* Cel6A CBHII, 5% *Trichoderma reesei* Cel7B EGI, 5% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, 5% *Penicillium brasilianum* Cel3A beta-glucosidase, and 5% GH10 xylanase. The high-temperature enzyme compositions and the *Trichoderma reesei*-based cellulase composition XCL-533 were tested at five different protein loadings, 2.0, 3.0, 4.0, and 6.0 mg protein per g cellulose. All reactions with the high-temperature enzyme compositions were performed at 60° C., while all reactions with the *Trichoderma reesei*-based cellulase composition XCL-533 were performed at 50° C.

The assay was performed as described in Example 34. The 1 ml reactions with milled washed or milled unwashed PCS were conducted for 72 hours in 50 mM sodium acetate pH 5.0 buffer containing 1 mM manganese sulfate. Washed PCS was used at 5% total solids, whereas unwashed PCS was used at 5% insoluble solids. All reactions were performed in triplicate and involved single mixing at the beginning of hydrolysis.

The results are shown in Table 2 and FIGS. 13A and 13B. The high-temperature enzyme compositions containing *Aspergillus fumigatus* GH10 xyn 3 xylanase or *Trichophaea saccata* GH10 xylanase showed similar performance, requiring similar protein loadings to achieve the same levels of cellulose conversion to glucose. The improved high-temperature enzyme compositions containing *Aspergillus fumigatus* GH10 xyn 3 xylanase or *Trichophaea saccata* GH10 xylanase outperformed the *Trichoderma reesei*-based cellulase composition XCL-533 on both washed (A) and unwashed (B) PCS.

TABLE 2

Protein loadings required for reaching 80% cellulose conversion of washed and unwashed PCS (mg protein per g cellulose). Temperature: 60° C. for high-temperature enzyme compositions, 50° C. for XCL-533.

| Composition | Washed PCS | Unwashed PCS |
|---|---|---|
| XCL-533 | 3.6 | 4.9 |
| High-temperature composition with *Aspergillus fumigatus* GH10 xyn3 xylanase | 2.6 | 4.2 |
| High-temperature composition with *Trichophaea saccata* GH10 xylanase | 2.5 | 4.2 |

Example 48: Effect of *Trichoderma reesei* GH3 and *Talaromyces emersonii* GH3 Beta-Xylosidases on Saccharification of Milled Unwashed PCS by a High-Temperature Enzyme Composition at 60° C.

The ability of two beta-xylosidases, *Trichoderma reesei* GH3 beta-xylosidase and *Talaromyces emersonii* GH3 beta-xylosidase, to enhance hydrolysis of milled unwashed PCS by a high-temperature enzyme composition was evaluated at 60° C. as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis. The results are shown in FIGS. 14A and 14B.

The high-temperature enzyme composition included 45% *Aspergillus fumigatus* Cel7A CBHI, 25% *Myceliophthora thermophila* Cel6A CBHII, 5% *Trichoderma reesei* Cel7B EGI, 5% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, 5% *Aspergillus fumigatus* GH10 xyn3 xylanase, and 5% *Penicillium brasilianum* Cel3A beta glucosidase. The high-temperature enzyme composition (3 mg total protein per g cellulose) was supplemented with *Trichoderma reesei* GH3 beta-xylosidase and *Talaromyces emersonii* GH3 beta-xylosidase at 1%, 2%, 3.5%, 5%, and 10% replacement levels, and the hydrolysis results were compared with the results for the high-temperature enzyme composition containing no beta-xylosidase (0% replacement level).

As shown in FIG. 14A, the inclusion of *Trichoderma reesei* GH3 beta-xylosidase and *Talaromyces emersonii* GH3 beta-xylosidase in the high-temperature enzyme composition increased the level of enzymatically-produced monomeric xylose from approximately 0.5 g/L (0% beta-xylosidase replacement) to approximately 2 g/L. The optimal replacement levels were 3.5% for *Trichoderma reesei* GH3 beta-xylosidase and 1-2% for *Talaromyces emersonii* GH3 beta-xylosidase. As shown in FIG. 14B, the combined yield of glucose and cellobiose was increased by an additional 1.5% for a mixture containing 3.5% *Trichoderma reesei* GH3 beta-xylosidase and by an additional 2.5% for a mixture containing 2% *Talaromyces emersonii* GH3 beta-xylosidase.

These results demonstrated that both beta-xylosidases provided a small but significant benefit by increasing the degree of cellulose and hemicellulose conversion of milled unwashed PCS to soluble sugars (glucose, cellobiose and xylose). *Talaromyces emersonii* GH3 beta-xylosidase appeared to be slightly more active than *Trichoderma reesei* GH3 beta-xylosidase at increasing the monomeric xylose level by approximately 1.5 g/L (FIG. 14A) and the cellulose

Example 49: Evaluation of Four Cellobiohydrolases I Replacing a CBHI Component in a High-Temperature Enzyme Composition in Saccharification of Milled Unwashed PCS at 50-65° C.

The ability of four cellobiohydrolase I proteins to replace a CBHI component in a high-temperature enzyme composition (3 mg total protein per g cellulose) was tested at 50° C., 55° C., and 65° C. using milled unwashed PCS as a substrate. The high-temperature enzyme composition included 35% CBHI, 25% *Myceliophthora thermophila* Cel6A CBHII, 15% *Thermoascus aurantiacus* Cel5A EGII, 15% *Thermoascus aurantiacus* GH61A polypeptide having cellulolytic enhancing activity, 5% *Aspergillus fumigatus* Cel3A beta-glucosidase, and 5% *Aspergillus fumigatus* GH10 xyn3 xylanase.

The following CBHI cellulases were tested in the high-temperature enzyme composition: *Trichoderma reesei* Cel7A CBHI, *Chaetomium thermophilum* Cel7A CBHI, *Aspergillus fumigatus* Cel7A CBHI, and *Thermoascus aurantiacus* Cel7A CBHI.

The assay was performed as described in Example 34. The 1 ml reactions with milled unwashed PCS (5% insoluble solids) were conducted for 72 hours in 50 mM sodium acetate pH buffer containing 1 mM manganese sulfate. All reactions were performed in triplicate and involved single mixing at the beginning of hydrolysis.

As shown in FIG. 15, *Aspergillus fumigatus* Cel7A performed better than other cellobiohydrolases I at all temperatures from 50° C. to 65° C. *Chaetomium thermophilum* Cel7A also performed well in the entire range of temperatures, but the degree of cellulose conversion to glucose was lower compared to *Aspergillus fumigatus* Cel7A. *Trichoderma reesei* Cel7A did not perform well at temperatures above 55° C. *Thermoascus aurantiacus* Cel7A, which contained no CBM, showed a remarkably good performance at 60° C. and 65° C., but was less efficient in hydrolyzing the cellulose in unwashed PCS at lower temperatures (50° C. and 55° C.).

Example 50: Evaluation of Four Cellobiohydrolases II Replacing a CBHII Component in a High-Temperature Enzyme Composition in Saccharification of Milled Unwashed PCS at 50-65° C.

The ability of several cellobiohydrolase II proteins to replace a CBHII component in a high-temperature enzyme composition (3 mg total protein per g cellulose) was tested at 50° C., 60° C., and 65° C. using milled unwashed PCS as a substrate. The high-temperature enzyme composition included 35% *Aspergillus fumigatus* Cel7A CBHI, 25% CBHII, 15% *Thermoascus aurantiacus* Cel5A EGII, 15% *Thermoascus aurantiacus* GH61A polypeptide having cellulolytic enhancing activity, 5% *Aspergillus fumigatus* Cel3A beta-glucosidase, and 5% *Aspergillus fumigatus* GH10 xyn3 xylanase.

The following CBHII cellulases were tested in the high-temperature enzyme composition: *Myceliophthora thermophila* Cel6A CBHII, *Thielavia terrestris* Cel6A CBHII, *Aspergillus fumigatus* Cel6A CBHII, and *Trichophaea saccata* Cel6A CBHII.

The assay was performed as described in Example 34. The 1 ml reactions with milled unwashed PCS (5% insoluble solids) were conducted for 72 hours in 50 mM sodium acetate pH buffer containing 1 mM manganese sulfate. All reactions were performed in triplicate and involved single mixing at the beginning of hydrolysis.

As shown in FIG. 16, CBHII from *Aspergillus fumigatus* performed about the same as CBHII from *Myceliophthora thermophila* at all temperatures, showing only a slightly lower hydrolysis at 60-65° C. *Thielavia terrestris* Cel6A CBHII had high thermostability and performed well in the entire range of temperatures, but the degree of cellulose conversion to glucose was lower compared to *Myceliophthora thermophila* Cel6A CBHII. *Trichophaea saccata* Cel6A CBHII had high activity at 50-55° C., but did not perform well at higher temperatures.

Example 51: Evaluation of Two Endoglucanases I Replacing an Endoglucanase Component in a High-Temperature Enzyme Composition in Saccharification of Milled Unwashed PCS at 50-65° C.

The ability of two endoglucanase I proteins to replace an endoglucanase component in a high-temperature enzyme composition (3 mg total protein per g cellulose) was tested at 50° C., 55° C., 60° C., and 65° C. using milled unwashed PCS as a substrate. The high-temperature enzyme composition included 35% *Aspergillus fumigatus* Cel7A CBHI, 25% *Myceliophthora thermophila* Cel6A CBHII, 15% EG cellulase, 15% *Thermoascus aurantiacus* GH61A polypeptide having cellulolytic enhancing activity, 5% *Aspergillus fumigatus* Cel3A beta-glucosidase, and 5% *Aspergillus fumigatus* GH10 xyn3 xylanase.

The following EGIs were tested in the high-temperature enzyme composition: *Trichoderma reesei* Cel7B EGI and *Aspergillus terreus* Cel7 EGI.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

As shown in FIG. 17, the high-temperature enzyme composition containing *Aspergillus terreus* Cel7 EGI performed significantly better than the high-temperature enzyme composition containing *Trichoderma reesei* Cel7B EGI within this temperature range.

Example 52: Evaluation of Three Endoglucanases II Replacing an Endoglucanase Component in a High-Temperature Enzyme Composition in Saccharification of Milled Unwashed PCS at 50-65° C.

The ability of three endoglucanase II proteins to replace an endoglucanase component in a high-temperature enzyme composition (3 mg total protein per g cellulose) was tested at 50° C., 55° C., 60° C., and 65° C. using milled unwashed PCS as a substrate. The high-temperature enzyme composition included 35% *Aspergillus fumigatus* Cel7A CBHI, 25% *Myceliophthora thermophila* Cel6A CBHII, 15% EG cellulase, 15% *Thermoascus aurantiacus* GH61A polypeptide having cellulolytic enhancing activity, 5% *Aspergillus fumigatus* Cel3A beta-glucosidase, and 5% *Aspergillus fumigatus* GH10 xyn3 xylanase.

The following EGIIs were tested in the high-temperature enzyme composition: *Trichoderma reesei* Cel5A EGII, *Myceliophthora thermophila* Cel5A EGII, and *Thermoascus aurantiacus* Cel5A EGII.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

As shown in FIG. 18, all endoglucanase II proteins performed similarly within this temperature range, with *Myceliophthora thermophila* Cel5A EGII slightly outperforming *Trichoderma reesei* Cel5A EGII and *Thermoascus aurantiacus* Cel5A EGII.

Example 53: Evaluation of Three Beta-Glucosidases Replacing a Beta-Glucosidase Component in a High-Temperature Enzyme Composition in Saccharification of Milled Unwashed PCS at 50-65° C.

In a first experiment, three beta-glucosidases, including *Aspergillus fumigatus* Cel3A beta-glucosidase, *Penicillium brasilianum* Cel3A beta-glucosidase, and *Aspergillus niger* Cel3 beta-glucosidase, were evaluated in a high-temperature enzyme composition at 50° C., 55° C., and 60° C. using milled unwashed PCS as a substrate. The high-temperature enzyme composition included 45% *Aspergillus fumigatus* Cel7A CBHI, 25% *Thielavia terrestris* Cel6A CBHII, 5% *Trichoderma reesei* Cel7B EGI, 5% *Thermoascus aurantiacus* Cel5A EGII, 5% *Thermoascus aurantiacus* GH61A polypeptide having cellulolytic enhancing activity, 5% *Thielavia terrestris* GH61E polypeptide having cellulolytic enhancing activity, 5% *Aspergillus fumigatus* GH10 xyn3 xylanase, and 5% beta-glucosidase. The high-temperature enzyme composition was used at 3.0 mg total protein per g cellulose.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

The results shown in FIG. 19 demonstrated that all three beta-glucosidases performed about the same at 50° C. and 55° C., whereas *Aspergillus niger* Cel3 beta-glucosidase showed slightly lower hydrolysis at 60° C. than the other two beta-glucosidases.

In a second experiment, *Aspergillus fumigatus* Cel3A beta-glucosidase and *Penicillium brasilianum* Cel3A beta-glucosidase were compared in a high-temperature enzyme composition at four temperatures, 50° C., 55° C., 60° C., and 65° C., using milled unwashed PCS as a substrate. The high-temperature enzyme composition included 35% *Aspergillus fumigatus* Cel7A CBHI, 25% *Myceliophthora thermophila* Cel6A CBHII, 15% *Thermoascus aurantiacus* Cel5A EGII, 15% *Thermoascus aurantiacus* GH61A polypeptide having cellulolytic enhancing activity, 5% beta-glucosidase, and 5% *Aspergillus fumigatus* GH10 xyn3 xylanase. The high-temperature enzyme composition was used at 3.0 mg total protein per g cellulose.

The assay was performed as described in Example 34. The 1 ml reactions with milled unwashed PCS (5% insoluble solids) were conducted for 72 hours in 50 mM sodium acetate pH buffer containing 1 mM manganese sulfate. All reactions were performed in triplicate and involved single mixing at the beginning of hydrolysis.

The results shown in FIG. 20 demonstrated that Cel3A beta-glucosidases from *Aspergillus fumigatus* and *Penicillium brasilianum* performed about the same within this temperature range.

Example 54: Evaluation of Six Xylanases Replacing a Xylanase Component in a High-Temperature Enzyme Composition in Saccharification of Milled Unwashed PCS at 50-65° C.

The ability of six xylanases to replace a xylanase component in a high-temperature enzyme composition (3 mg total protein per g cellulose) was tested at 50° C., 55° C., 60° C., and using milled unwashed PCS as a substrate. The high-temperature enzyme composition included 35% *Aspergillus fumigatus* Cel7A CBHI, 25% *Myceliophthora thermophila* Cel6A CBHII, 15% *Thermoascus aurantiacus* Cel5A EGII, 15% *Thermoascus aurantiacus* GH61A polypeptide having cellulolytic enhancing activity, 5% *Aspergillus fumigatus* Cel3A beta-glucosidase, and 5% xylanase.

The following xylanases were tested in the high-temperature enzyme composition: *Aspergillus aculeatus* GH10 xyn II xylanase, *Aspergillus fumigatus* GH10 xyn3, *Trichophaea saccata* GH10 xylanase, *Thermobifida fusca* GH11 xylanase, *Penicillium pinophilum* GH10 xylanase, and *Thielavia terrestris* GH10E xylanase.

The assay was performed as described in Example 34. The 1 ml reactions with milled unwashed PCS (5% insoluble solids) were conducted for 72 hours in 50 mM sodium acetate pH buffer containing 1 mM manganese sulfate. All reactions were performed in triplicate and involved single mixing at the beginning of hydrolysis.

As shown in FIG. 21, GH10 xylanase from *Penicillium pinophilum* was superior to GH10 xylanases from *Aspergillus fumigatus* and *Trichophaea saccata* at all temperatures from to 65° C. The *Aspergillus aculeatus* GH10 and *Thielavia terrestris* GH10E xylanases performed about the same as the *Aspergillus fumigatus* GH10 and *Trichophaea saccata* GH10 xylanases at 50° C. and 55° C., but did not perform well at higher temperatures (60° C. and 65° C.).

The *Thermobifida fusca* GH11 performed relatively well at 60° C. and 65° C., but overall the degree of cellulose conversion to glucose was lower compared to other xylanases.

Example 55: Evaluation of the Ability of Four GH61 Polypeptides Having Cellulolytic Enhancing Activity to Enhance PCS-Hydrolyzing Activity of a High-Temperature Enzyme Composition at 50-65° C. Using Milled Unwashed PCS The ability of four GH61 polypeptides having cellulolytic enhancing activity, *Thermoascus aurantiacus* GH61A, *Thielavia terrestris* GH61E, *Penicillium pinophilum* GH61, and *Aspergillus fumigatus* GH61B, to enhance the PCS-hydrolyzing activity of a high-temperature enzyme composition was evaluated using milled unwashed PCS at 50° C., 55° C., and 65° C. The high-temperature enzyme composition included 35% *Aspergillus fumigatus* Cel7A CBHI, 25% *Myceliophthora thermophila* Cel6A CBHII, 15% *Thermoascus aurantiacus* Cel5A EGII, 15% GH61 polypeptide having cellulolytic enhancing activity, 5% *Aspergillus fumigatus* Cel3A beta-glucosidase, and 5% *Aspergillus fumigatus*

GH10 xyn3 xylanase. The high-temperature enzyme composition was used at 3 mg total protein per g cellulose.

The assay was performed as described in Example 34. The 1 ml reactions with milled unwashed PCS (5% insoluble solids) were conducted for 72 hours in 50 mM sodium acetate pH buffer containing 1 mM manganese sulfate. All reactions were performed in triplicate and involved single mixing at the beginning of hydrolysis.

As shown in FIG. 22, all four GH61 polypeptides showed a significant cellulase-enhancing activity, with *Thermoascus aurantiacus* GH61A polypeptide being the most efficient enhancer among the four within this temperature range. High-temperature enzyme compositions containing *Thermoascus aurantiacus* GH61A and *Thielavia terrestris* GH61E polypeptides performed better at higher temperatures (60° C. and 65° C.) than high-temperature enzyme compositions containing *Penicillium pinophilum* GH61 and *Aspergillus fumigatus* GH61B polypeptides.

Example 56: Evaluation of the Ability of Three GH61 Polypeptides Having Cellulolytic Enhancing Activity to Enhance PCS-Hydrolyzing Activity of a High-Temperature Enzyme Composition at 50-65° C. Using Milled Unwashed PCS The ability of three GH61 polypeptides having cellulolytic enhancing activity, *Thermoascus aurantiacus* GH61A, *Thielavia terrestris* GH61N, and *Penicillium* sp GH61A, to enhance the PCS-hydrolyzing activity of a high-temperature enzyme composition was evaluated using milled unwashed PCS at 50° C., 55° C., 60° C., and 65° C. The high-temperature enzyme composition included 45% *Aspergillus fumigatus* Cel7A CBHI, 25% *Myceliophthora thermophila* Cel6A CBHII, 10% *Myceliophthora thermophila* Cel5A EGII, 10% GH61 polypeptide, 5% *Aspergillus fumigatus* Cel3A beta-glucosidase, and 5% *Aspergillus fumigatus* GH10 xyn3 xylanase. The results for the enzyme compositions containing GH61 polypeptides (3 mg total protein per g cellulose) were compared with the results for a similar enzyme composition to which no GH61 polypeptide was added (2.7 mg total protein per g cellulose).

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

As shown in FIG. 23, all three GH61 polypeptides showed a significant cellulase-enhancing activity, with *Thermoascus aurantiacus* GH61A polypeptide being the most efficient enhancer at 55-65° C., and *Thielavia terrestris* GH61N polypeptide slightly outperforming *Thermoascus aurantiacus* GH61A polypeptide at 50° C. The high-temperature enzyme composition containing *Penicillium* sp. GH61A polypeptide performed almost as well as the high-temperature enzyme composition containing *Thermoascus aurantiacus* GH61A polypeptide at all four temperatures (50-65° C.). *Thielavia terrestris* GH61N polypeptide performed well at 50° C. and 55° C., but showed a significant decline in performance at higher temperatures (60° C. and 65° C.).

Example 57: Hydrolysis of Milled Unwashed PCS by *Trichoderma reesei*-Based XCL-602 Cellulase at Different Replacement Levels by *Aspergillus fumigatus* Cel7A Cellobiohydrolase I, *Myceliophthora thermophila* Cel6A Cellobiohydrolase II, or their Binary Compositions at 50-60° C.

A *Trichoderma reesei* strain 981-08-D4-based cellulase containing *Aspergillus fumigatus* beta-glucosidase and *Thermoascus aurantiacus* GH61A polypeptide, designated *Trichoderma reesei*-based XCL-602 cellulase, was tested in 1-ml hydrolysis reactions at 50° C., 55° C., and using milled unwashed PCS as a substrate. The *Trichoderma reesei*-based XCL-602 cellulase was used alone or in mixtures with *Aspergillus fumigatus* Cel7A CBHI (10%, 20%, 30% or 40% of total protein), *Myceliophthora thermophila* Cel6A CBHII (10% or 20% of total protein), or both *Aspergillus fumigatus* Cel7A CBHI and *Myceliophthora thermophila* Cel6A CBHII (10%/10%, 10%/20%, 20%/10%, 20%/20%, 30%/10%, 30%/20%, 40%/20% of total protein). The level of *Thermoascus aurantiacus* GH61A polypeptide in all *Trichoderma reesei* XCL-602 compositions was maintained constant at 8% of total protein. *Trichoderma reesei*-based enzyme composition SaMe-MF268 (XCL-533) was also included in the experiment. The non-replaced *Trichoderma reesei*-based XCL-602 cellulase and *Trichoderma reesei*-based XCL-533 cellulase and various *Trichoderma reesei* XCL-602 compositions containing *Aspergillus fumigatus* Cel7A CBHI and/or *Myceliophthora thermophila* Cel6A CBHII were used at 3 mg total protein per g cellulose.

The assay was performed as described in Example 34. The 1 ml reactions with 50 mg of insoluble PCS solids per ml were conducted for 72 hours in 50 mM sodium acetate pH 5.0 buffer containing 1 mM manganese sulfate. All reactions were performed in triplicate and involved single mixing at the beginning of hydrolysis.

The results shown in FIG. 24 demonstrated that non-replaced *Trichoderma reesei*-based XCL-602 cellulase performed about the same as non-replaced *Trichoderma reesei*-based XCL-533 cellulase at all three temperatures. At 50° C. and 55° C., the replacement of 10%, 20%, or 30% protein in XCL-602 cellulase by *Aspergillus fumigatus* Cel7A CBHI or the replacement of 10% or 20% protein in XCL-602 cellulase by *Myceliophthora thermophila* Cel6A CBHII did not have a significant effect on the degree of cellulose conversion to glucose after 72 hours of hydrolysis. The replacement of 40% protein in the *Trichoderma reesei*-based XCL-602 cellulase by *Aspergillus fumigatus* Cel7A CBHI had a negative effect on the degree of cellulose conversion to glucose at 50° C. and 55° C. At 60° C., the replacement of protein in the *Trichoderma reesei*-based XCL-602 cellulase by *Aspergillus fumigatus* Cel7A CBHI (10-40% of total protein) or *Myceliophthora thermophila* Cel6A CBHII (10-20% of total protein) significantly improved the hydrolysis over non-replaced *Trichoderma reesei*-based XCL-602 cellulase at an equivalent protein loading (3 mg protein per g cellulose). Higher replacement levels by *Aspergillus fumigatus* Cel7A CBHI or *Myceliophthora thermophila* Cel6A CBHII provided a greater hydrolysis enhancement over non-replaced XCL-602 cellulase at 60° C.

For the *Trichoderma reesei*-based XCL-602 cellulase compositions that included both *Aspergillus fumigatus* Cel7A CBHI and *Myceliophthora thermophila* Cel6A CBHII, the optimal replacement levels were 10-20% *Aspergillus fumigatus* Cel7A CBHI/10-20% *Myceliophthora thermophila* Cel6A CBHII at 50° C. and 55° C., and 40%

*Aspergillus fumigatus* Cel7A CBHI/20% *Myceliophthora thermophila* Cel6A CBHII at 60° C.

Example 58: Hydrolysis of Milled Unwashed PCS by *Trichoderma reesei*-Based XCL-602 Cellulase Containing *Aspergillus fumigatus* Cel7A Cellobiohydrolase I and *Myceliophthora thermophila* Cel6A Cellobiohydrolase II, and Additionally Supplemented by *Aspergillus fumigatus* GH10 Xyn 3 and/or *Thielavia terrestris* GH61E at 50-60° C.

The *Trichoderma reesei*-based XCL-602 cellulase containing *Aspergillus fumigatus* Cel7A cellobiohydrolase I and *Myceliophthora thermophila* Cel6A cellobiohydrolase II was tested in 1-ml hydrolysis reactions at 50° C., 55° C. and 60° C. using milled unwashed PCS as a substrate. The *Trichoderma reesei*-based XCL-602 cellulase was used alone (3.0 mg protein per g cellulose) or with replacement by different binary compositions consisting of *Aspergillus fumigatus* Cel7A CBHI and *Myceliophthora thermophila* Cel6A CBHII (10%/10% or 40%/20% of total protein) to a total protein loading of 3 mg protein per g cellulose. The level of *Thermoascus aurantiacus* GH61A polypeptide in all *Trichoderma reesei* XCL-602-based compositions containing *Aspergillus fumigatus* Cel7A CBHI and *Myceliophthora thermophila* Cel6A CBHII was maintained constant at 8% of total protein. The *Trichoderma reesei* XCL-602-based compositions containing *Aspergillus fumigatus* Cel7A CBHI and *Myceliophthora thermophila* Cel6A CBHII (3 mg protein per g cellulose) were additionally supplemented with 5% *Aspergillus fumigatus* GH10 xyn 3 xylanase (0.15 mg protein per g cellulose), 5% *Thielavia terrestris* GH61E polypeptide (0.15 mg protein per g cellulose), or with a binary composition consisting of 5% *Aspergillus fumigatus* GH10 xyn 3 xylanase and 5% *Thielavia terrestris* GH61E polypeptide (0.30 mg protein per g cellulose). For comparison, the non-replaced *Trichoderma reesei*-based XCL-602 cellulase was used alone at 3.15 mg protein per g cellulose and 3.3 mg protein per g cellulose.

The assay was performed as described in Example 34. The 1 ml reactions with 50 mg of insoluble PCS solids per ml were conducted for 72 hours in 50 mM sodium acetate pH 5.0 buffer containing 1 mM manganese sulfate. All reactions were performed in triplicate and involved single mixing at the beginning of hydrolysis.

The results shown in FIGS. 25A and 25B demonstrated that the addition of 5% *Aspergillus fumigatus* GH10 xyn3 xylanase and/or 5% *Thielavia terrestris* GH61E polypeptide to the *Trichoderma reesei* XCL-602-based compositions containing *Aspergillus fumigatus* Cel7A CBHI and *Myceliophthora thermophila* Cel6A CBHII significantly improved the hydrolysis performance at all three temperatures, with a very large improvement obtained when both the *Aspergillus fumigatus* GH10 xyn3 xylanase and the *Thielavia terrestris* GH61E polypeptide were added together. The best XCL-602-based composition in this experiment (XCL-602 with 10% replacement by *Aspergillus fumigatus* Cel7A CBHI and 10% replacement by *Myceliophthora thermophila* Cel6A CBHII, and with additional supplementation by 5% *Aspergillus fumigatus* GH10 xyn3 xylanase and 5% *Thielavia terrestris* GH61E polypeptide) required 3.3 mg protein per g cellulose to achieve 82% conversion of cellulose to glucose in milled unwashed PCS after 72 hours of hydrolysis at 55° C. This represents a 1.5× reduction in protein loading compared to *Trichoderma reesei* XCL-533 (SaMe-MF268), which required 4.9 mg protein per g cellulose to achieve 80% conversion of cellulose to glucose in milled unwashed PCS after 72 hours of hydrolysis at 50° C. (Table 2).

Example 59: Hydrolysis of Milled Unwashed PCS by *Trichoderma reesei*-Based XCL-602 Cellulase Compositions Containing Different Replacement Levels of *Trichoderma reesei*-Based XCL-592 Cellulase at 50-60° C.

The *Trichoderma reesei*-based XCL-602 cellulase was tested alone (3.0 mg protein per g cellulose) or in mixtures with *Trichoderma reesei* RutC30-based cellulase containing *Aspergillus aculeatus* GH10 xylanase, designated as *Trichoderma reesei*-based XCL-592 cellulase. The *Trichoderma reesei*-based XCL-592 cellulase replaced 5%, 10%, 15%, 20%, or 25% of protein in the *Trichoderma reesei*-based XCL-602 cellulase to a total protein loading of 3 mg protein per g cellulose. The non-replaced *Trichoderma reesei*-based XCL-602 cellulase and XCL-602-based enzyme compositions were tested in 1-ml hydrolysis reactions at 50° C., 55° C. and 60° C. using milled unwashed PCS as a substrate. For comparison, *Trichoderma reesei*-based XCL-533 cellulase was tested at 4.5 mg protein per g cellulose.

The assay was performed as described in Example 34. The 1 ml reactions with 50 mg of insoluble PCS solids per ml were conducted for 72 hours in 50 mM sodium acetate pH 5.0 buffer containing 1 mM manganese sulfate. All reactions were performed in triplicate and involved single mixing at the beginning of hydrolysis.

The results shown in FIG. 26 demonstrated that the optimal replacement level of *Trichoderma reesei*-based XCL-602 cellulase by *Trichoderma reesei*-based XCL-592 cellulase at 50° C. and 55° C. was between 10% and 15% of total protein. At 50° C. and 55° C., the best *Trichoderma reesei*-based XCL-602 cellulase compositions performed significantly better than *Trichoderma reesei*-based XCL-602 cellulase alone at an equivalent protein loading (3 mg protein per g cellulose), but were not able to reach the performance level obtained with *Trichoderma reesei*-based XCL-533 cellulase at 4.5 mg protein per g cellulose.

Example 60: Comparison of *Thermoascus aurantiacus* GH61A and *Thielavia terrestris* GH61E GH61 Polypeptides Having Cellulolytic Enhancing Activity Replacing 5% of Protein in *Trichoderma reesei*-Based XCL-602 Cellulase or XCL-602-Based Enzyme Composition in Hydrolysis of Milled Unwashed PCS at 50-60° C.

The *Trichoderma reesei*-based XCL-602 cellulase was tested alone and with 5% replacement by *Thermoascus aurantiacus* GH61A polypeptide having cellulolytic enhancing activity or *Thielavia terrestris* GH61E polypeptide having cellulolytic enhancing activity at 50-60° C. using milled unwashed PCS as a substrate. In addition, the *Trichoderma reesei*-based XCL-602 cellulase composition containing 30% *Aspergillus fumigatus* Cel7A CBHI, 20% *Myceliophthora thermophila* Cel6A CBHI,I and 5% *Thermoascus aurantiacus* GH61A polypeptide was tested in comparison with a similar composition containing *Thielavia terrestris* GH61E polypeptide instead of *Thermoascus aurantiacus* GH61A polypeptide. All compositions were tested at 3 mg protein per g cellulose.

The assay was performed as described in Example 34. The 1 ml reactions with 50 mg of insoluble PCS solids per ml were conducted for 72 hours in 50 mM sodium acetate pH 5.0 buffer containing 1 mM manganese sulfate. All reactions were performed in triplicate and involved single mixing at the beginning of hydrolysis.

As shown in FIG. 27A, replacement of 5% protein in *Trichoderma reesei*-based XCL-602 cellulase by *Thielavia terrestris* GH61E polypeptide did not provide an advantage over the equivalent replacement by *Thermoascus aurantiacus* GH61A polypeptide. Similarly, as shown in FIG. 27B, the replacement of 5% protein in *Trichoderma reesei*-based XCL-602 cellulase by *Thielavia terrestris* GH61E polypeptide along with the 30% replacement by *Aspergillus fumigatus* Cel7A CBHI and 20% replacement by *Myceliophthora thermophila* Cel6A CBHII, did not provide an advantage over the equivalent replacement by *Thermoascus aurantiacus* GH61A polypeptide. Each GH61 polypeptide was tested at six different replacement levels ranging from 5% to 20%, and the conclusion was consistent for all replacement levels (data not shown). The results indicated that the *Thielavia terrestris* GH61E polypeptide did not synergize with the *Thermoascus aurantiacus* GH61A polypeptide under these conditions.

Example 61: Comparison of XCL-602-Based Enzyme Compositions Containing Different Replacement Levels of *Thermoascus aurantiacus* GH61A or *Thielavia terrestris* GH61E GH61 Polypeptides Having Cellulolytic Enhancing Activity in Hydrolysis of Milled Unwashed PCS at 50-60° C.

*Thermoascus aurantiacus* GH61A and *Thielavia terrestris* GH61E GH61 polypeptides having cellulolytic enhancing activity were tested separately at six different replacement levels (5%, 7.5%, 10%, 12.5%, 15%, and 20%) in different *Trichoderma reesei*-based XCL-602 cellulase compositions at 50-60° C. using milled unwashed PCS as a substrate. In one case, the *Trichoderma reesei*-based XCL-602 cellulase compositions comprised different replacement levels of a GH61 polypeptide along with a 5% replacement by *Aspergillus fumigatus* GH10 xyn3 xylanase. In another case, *Trichoderma reesei*-based XCL-602 cellulase compositions comprised different replacement levels of a GH61 polypeptide along with a 30% replacement by *Aspergillus fumigatus* Cel7A CBHI, a 20% replacement by *Myceliophthora thermophila* Cel6A CBHII, and a 5% replacement by *Aspergillus fumigatus* GH10 xyn3 xylanase. All enzyme compositions were tested at 3 mg total protein per g cellulose. For comparison, *Trichoderma reesei*-based XCL-533 cellulase was tested at 4.5 mg protein per g cellulose.

The assay was performed as described in Example 34. The 1 ml reactions with 50 mg of insoluble PCS solids per ml were conducted for 72 hours in 50 mM sodium acetate pH 5.0 buffer containing 1 mM manganese sulfate. All reactions were performed in triplicate and involved single mixing at the beginning of hydrolysis.

The results shown in Table 3 demonstrated that the optimal replacement level for both GH61 polypeptides at 50° C. and 55° C. was 10-12.5% of the total protein in the *Trichoderma reesei*-based XCL-602 cellulase compositions. At 60° C., the optimal replacement level for both GH61 polypeptides was 20% of the total protein in the *Trichoderma reesei*-based XCL-602 cellulase compositions. The equivalent replacement levels of the *Thermoascus aurantiacus* GH61A and *Thielavia terrestris* GH61E polypeptides in similar *Trichoderma reesei*-based XCL-602 cellulase compositions provided a similar enhancement of the cellulose hydrolysis in milled unwashed PCS at 50-60° C.

TABLE 3

Comparison of *Trichoderma reesei*-based XCL-602 cellulase compositions containing different replacement levels of *Thermoascus aurantiacus* GH61A or *Thielavia terrestris* GH61E polypeptides in hydrolysis of milled unwashed PCS at 50-60° C.

| GH61 replacement level | 50° C. | 55° C. | 60° C. |
|---|---|---|---|
| XCL-602 with 5% replacement by *Aspergillus fumigatus* GH10 xyn3 xylanase and 0-20% replacement by a GH61 polypeptide (3 mg total protein per g cellulose) | | | |
| 0% *T. aurantiacus* GH61A | 67% | 66% | 42% |
| 5% *T. aurantiacus* GH61A | 69% | 69% | 46% |
| 7.5% *T. aurantiacus* GH61A | 69% | 69% | 47% |
| 10% *T. aurantiacus* GH61A | 69% | 69% | 49% |
| 12.5% *T. aurantiacus* GH61A | 69% | 69% | 49% |
| 15% *T. aurantiacus* GH61A | 69% | 69% | 49% |
| 20% *T. aurantiacus* GH61A | 66% | 69% | 51% |
| 0% *T. terrestris* GH61E | 67% | 66% | 42% |
| 5% *T. terrestris* GH61E | 68% | 69% | 45% |
| 7.5% *T. terrestris* GH61E | 68% | 68% | 46% |
| 10% *T. terrestris* GH61E | 68% | 68% | 47% |
| 12.5% *T. terrestris* GH61E | 65% | 68% | 48% |
| 15% *T. terrestris* GH61E | 64% | 67% | 48% |
| 20% *T. terrestris* GH61E | 62% | 65% | 49% |
| XCL-602 with 30% replacement by *Aspergillus fumigatus* Cel7A CBHI, 20% replacement by *Myceliophthora thermophila* Cel6A CBHII, 5% replacement by *Aspergillus fumigatus* GH10 xyn3 xylanase and 0-20% replacement by a GH61 polypeptide (3 mg total protein per g cellulose) | | | |
| 0% *T. aurantiacus* GH61A | 64% | 68% | 58% |
| 5% *T. aurantiacus* GH61A | 70% | 75% | 66% |
| 7.5% *T. aurantiacus* GH61A | 72% | 75% | 67% |
| 10% *T. aurantiacus* GH61A | 72% | 76% | 68% |
| 12.5% *T. aurantiacus* GH61A | 71% | 76% | 70% |
| 15% *T. aurantiacus* GH61A | 71% | 76% | 69% |
| 20% *T. aurantiacus* GH61A | 68% | 72% | 71% |
| 0% *T. terrestris* GH61E | 64% | 68% | 58% |
| 5% *T. terrestris* GH61E | 68% | 72% | 65% |
| 7.5% *T. terrestris* GH61E | 69% | 73% | 65% |
| 10% *T. terrestris* GH61E | 69% | 74% | 69% |
| 12.5% *T. terrestris* GH61E | 67% | 73% | 68% |
| 15% *T. terrestris* GH61E | 66% | 74% | 69% |
| 20% *T. terrestris* GH61E | 65% | 72% | 69% |

Example 62: Hydrolysis of Milled Unwashed PCS by Non-Replaced XCL-602 and Various XCL-602-Based Enzyme Compositions (3 mg Protein Per g Cellulose) in Comparison with *Trichoderma reesei*-Based XCL-533 Cellulase (4.5 mg Protein Per g Cellulose) at 50-60° C.

Example 61 was repeated using the same *Trichoderma reesei*-based XCL-602 cellulase compositions except that only one GH61 polypeptide (*Thermoascus aurantiacus* GH61A) was tested at a single replacement level (10% of total protein). The *Trichoderma reesei*-based XCL-602 cellulase and all *Trichoderma reesei*-based XCL-602 cellulase compositions were used at 3 mg total protein per g cellulose.

The assay was performed as described in Example 34. The 1 ml reactions with 50 mg of insoluble PCS solids per ml were conducted for 72 hours in 50 mM sodium acetate pH 5.0 buffer containing 1 mM manganese sulfate. All reactions were performed in triplicate and involved single mixing at the beginning of hydrolysis.

The results shown in FIG. 28A demonstrated that the replacement of *Trichoderma reesei*-based XCL-602 cellulase with a composition comprising 5% *Aspergillus fumigatus* GH10 xyn3 xylanase and 10% *Thermoascus aurantiacus* GH61A polypeptide to a total protein loading of 3 mg protein per g cellulose has significantly improved the hydrolysis yield over the non-replaced *Trichoderma reesei*-based XCL-602 cellulase at all three temperatures. As shown in FIG. 27B, the enhancement was even more pronounced when the *Trichoderma reesei*-based XCL-602 cellulase was additionally replaced with 30% *Aspergillus fumigatus* Cel7A CBHI and 20% *Myceliophthora thermophila* Cel6A CBHII. The results shown in FIG. 28B demonstrated that the replacement of *Trichoderma reesei*-based XCL-602 cellulase with 30% *Aspergillus fumigatus* Cel7A CBHI and 20% *Myceliophthora thermophila* Cel6A CBHII increased the degree of cellulose conversion to glucose after 72 hours of hydrolysis at 60° C. from 37% to 48%. Additional 5% replacement by *Aspergillus fumigatus* GH10 xyn3 xylanase increased the degree of cellulose conversion to glucose to 58%, and additional 10% replacement by *Thermoascus aurantiacus* GH61A polypeptide increased the degree of cellulose conversion to glucose to 68% compared to 37% obtained with non-replaced *Trichoderma reesei*-based XCL-602 cellulase. At 3 mg protein per g cellulose, the best XCL-602-based enzyme composition comprising the XCL-602 cellulase with 30% replacement by *Aspergillus fumigatus* Cel7A CBHI, 20% replacement by *Myceliophthora thermophila* Cel6A CBHII, 5% replacement by *Aspergillus fumigatus* GH10 xyn3 xylanase and 10% replacement by *Thermoascus aurantiacus* GH61A polypeptide, was capable of achieving the same cellulose conversion of milled unwashed PCS at 55° C. (76%) as non-replaced *Trichoderma reesei*-based XCL-602 cellulase at 4.5 mg protein per g cellulose and 50° C.—a 1.5-fold reduction in protein loading.

Example 63: Preparation of *Penicillium emersonii* Strain NN051602 GH7 Cellobiohydrolase I The *Penicillium emersonii* strain NN051602 Cel7 cellobiohydrolase I (SEQ ID NO: 157 [DNA sequence] and SEQ ID NO: 158 [deduced amino acid sequence]) was obtained according to the procedure described below.

*Penicillium emersonii* was grown on a PDA agar plate at 45° C. for 3 days. Mycelia were collected directly from the agar plate into a sterilized mortar and frozen under liquid nitrogen. Frozen mycelia were ground, by mortar and pestle, to a fine powder, and genomic DNA was isolated using a DNeasy® Plant Mini Kit (QIAGEN Inc., Valencia, CA, USA).

Oligonucleotide primers, shown below, were designed to amplify the GH7 cellobiohydrolase I gene from genomic DNA of *Penicillium emersonii*. An IN-FUSION™ CF Dry-down Cloning Kit (Clontech Laboratories, Inc., Mountain View, CA, USA) was used to clone the fragment directly into the expression vector pPFJO355, without the need for restriction digestion and ligation.

```
Sense primer:
                                       (SEQ ID NO: 207)
5'-ACACAACTGGGGATCCACC atgcttcgacgggctcttc-3'

Antisense primer:
                                       (SEQ ID NO: 208)
5'-GTCACCCTCTAGATCT CGCAGAGCAACTTCCGTCTACTTC-3'
```

Bold letters represented the coding sequence (for the sense primer) or the downstream sequence of the coding region (for the antisense primer). The remaining sequence was homologous to the insertion sites of pPFJO355.

Twenty picomoles of each of the primers above were used in a PCR reaction composed of *Penicillium emersonii* genomic DNA, 10 µl of 5× GC Buffer, 1.5 µl of DMSO, 2.5 mM each of dATP, dTTP, dGTP, and dCTP, and 0.6 unit of Phusion™ High-Fidelity DNA Polymerase in a final volume of 50 µl. The amplification was performed using a Peltier Thermal Cycler programmed for denaturing at 98° C. for 1 minute; 8 cycles of denaturing at 98° C. for 15 seconds, annealing at 65° C. for 30 seconds, with 1° C. decrease per cycle and elongation at 72° C. for 80 seconds; and another 23 cycles each at 98° C. for 15 seconds, 66° C. for 30 seconds and 72 C for 75 seconds; final extension at 72° C. for 7 minutes. The heat block then went to a 4° C. soak cycle.

The reaction products were isolated by 1.0% agarose gel electrophoresis using 90 mM Tris-borate and 1 mM EDTA (TBE) buffer where an approximately 1.4 kb product band was excised from the gel, and purified using an ILLUSTRA® GFX® PCR DNA and Gel Band Purification Kit according to the manufacturer's instructions.

Plasmid pPFJO355 was digested with Bam I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION™ CF Dry-down PCR Cloning resulting in pGH7_ZY209383 in which transcription of the *Penicillium emersonii* GH7 cellobiohydrolase I gene was under the control of the *Aspergillus oryzae* TAKA amylase promoter from the gene for *Aspergillus oryzae* alpha-amylase. The cloning operation was according to the manufacturer's instruction. In brief, 30 ng of pPFJO355 digested with Bam I and Bgl II, and 60 ng of the *Penicillium emersonii* GH7 cellobiohydrolase I gene purified PCR product were added to the reaction vial and resuspended the powder in a final volume of 10 ul with addition of deionized water. The reaction was incubated at 37° C. for 15 minutes and then 50° C. for 15 minutes. Five µl of the reaction were used to transform *E. coli* TOP10 competent cells. An *E. coli* transformant containing pGH7_ZY209383 was detected by colony PCR and plasmid DNA was prepared using a QIAprep Spin Miniprep Kit (QIAGEN Inc., Valencia, CA, USA). The *Penicillium emersonii* GH7 cellobiohydrolase I gene insert in pGH7_ZY209383 was confirmed by DNA sequencing using a 3730XL DNA Analyzer.

*Aspergillus oryzae* HowB101 (WO 95/35385) protoplasts were prepared according to the method of Christensen et al., 1988, Bio/Technology 6: 1419-1422 and transformed with 3 µg of pGH7_ZY209383. The transformation yielded about 50 transformants. Twelve transformants were isolated to individual Minimal medium plates.

Four transformants were inoculated separately into 3 ml of YPM medium in a 24-well plate and incubated at 30° C., 150 rpm. After 3 days incubation, 20 µl of supernatant from each culture were analyzed by SDS-PAGE using a NUPAGE® NOVEX® 4-12% Bis-Tris Gel with MES buffer according to the manufacturer's instructions. The resulting gel was stained with INSTANT® Blue. SDS-PAGE profiles of the cultures showed that the majority of the transformants had a major smeary band of approximately 50 kDa. The expression strain was designated as *A. oryzae* EXP03477.

A slant of *A. oryzae* EXP03477 was washed with 10 ml of YPM medium and inoculated into a 2 liter flask containing 400 ml of YPM medium to generate broth for characterization of the enzyme. The culture was harvested on day 3 and filtered using a 0.45 µm DURAPORE Membrane (Millipore, Bedford, MA, USA).

A 1600 ml volume of filtered broth of *A. oryzae* EXP03477 was precipitated with ammonium sulfate (80% saturation), re-dissolved in 100 ml of 25 mM Bis-Tris pH 6.5 buffer, dialyzed against the same buffer, and filtered through a 0.45 μm filter; the final volume was 200 ml. The solution was applied to a 40 ml Q Sepharose® Fast Flow column equilibrated with 25 mM Bis-Tris pH 6.5, and the proteins were eluted with a linear NaCl gradient (0-0.4 M). Fractions with activity against PASO were collected and applied to a 40 ml Phenyl Sepharose™ HIC column (GE Healthcare, Piscataway, NJ, USA) equilibrated in 20 mM PBS with 1.8 M $(NH_4)_2SO_4$ pH 7 buffer, and the proteins were eluted with 20 mM PBS pH 7. Fractions from the column with activity toward phosphoric acid swollen cellulose (PASO) as substrate were analyzed by SDS-PAGE using a NUPAGE® NOVEX® 4-12% Bis-Tris Gel with MES buffer. Fractions with the correct molecular weight were pooled. Then the pooled solution was concentrated by ultrafiltration. Protein concentration was determined using a Microplate BCA™ Protein Assay Kit in which bovine serum albumin was used as a protein standard.

Example 64: Preparation of *Penicillium Pinophilium* Strain NN046877 GH7 Cellobiohydrolase I The *Penicillium* pinophilium strain NN046877 Cel7 cellobiohydrolase II (SEQ ID NO: 159 [DNA sequence] and SEQ ID NO: 160 [deduced amino acid sequence]) was obtained according to the procedure described below.

*Penicillium pinophilum* was grown on a PDA agar plate at 37° C. for 4-5 days. Mycelia were collected directly from the agar plate into a sterilized mortar and frozen under liquid nitrogen. Frozen mycelia were ground, by mortar and pestle, to a fine powder, and genomic DNA was isolated using a DNeasy® Plant Mini Kit.

Oligonucleotide primers, shown below, were designed to amplify the GH7 cellobiohydrolase I gene from the genomic DNA of *Penicillium pinophilum*. An 1N-FUSION™ CF Dry-down Cloning Kit (Clontech Laboratories, Inc., Mountain View, CA, USA) was used to clone the fragment directly into the expression vector pPFJO355, without the need for restriction digestion and ligation.

```
Sense primer:
                                    (SEQ ID NO: 209)
5'-ACACAACTGGGGATCCACCATGTCTGCCTTGAACTCTTTC-3'

Antisense primer:
                                    (SEQ ID NO: 210)
5'-GTCACCCTCTAGATCTTCACAAACATTGAGAGTAGTAAGGGTT-3'
```

Bold letters represented the coding sequence and the remaining sequence was homologous to the insertion sites of pPFJO355.

Twenty picomoles of each of the primers above were used in a PCR reaction composed of *Penicillium pinophilum* genomic DNA, 10 μl of 5× GC Buffer, 1.5 μl of DMSO, 2.5 mM each of dATP, dTTP, dGTP, and dCTP, and 0.6 unit of Phusion™ High-Fidelity DNA Polymerase in a final volume of 50 μl. The amplification was performed using a Peltier Thermal Cycler programmed for denaturing at 98° C. for 1 minute; 5 cycles of denaturing at 98° C. for 15 seconds, annealing at 56° C. for 30 seconds, with 1° C. increasing per cycle and elongation at 72° C. for 75 seconds; and another 25 cycles each at 98° C. for 15 seconds, 65C for 30 seconds and 72° C. for seconds; final extension at 72° C. for 10 minutes. The heat block then went to a 4° C. soak cycle.

The reaction products were isolated by 1.0% agarose gel electrophoresis using 90 mM Tris-borate and 1 mM EDTA (TBE) buffer where an approximately 1.6 kb product band was excised from the gel, and purified using an ILLUSTRA® GFX® PCR DNA and Gel Band Purification Kit according to the manufacturer's instructions.

Plasmid pPFJO355 was digested with Barn I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION™ CF Dry-down PCR Cloning resulting in pPpin6 in which transcription of the *Penicillium pinophilum* GH7 cellobiohydrolase I gene was under the control of the *Aspergillus oryzae* TAKA amylase promoter. In brief, 30 ng of pPFJO355 digested with Barn I and Bgl II, and 100 ng of the *Penicillium pinophilum* GH7 cellobiohydrolase I gene purified PCR product were added to a reaction vial and resuspended in a final volume of 10 μl with addition of deionized water. The reaction was incubated at 37° C. for 15 minutes and then 50° C. for 15 minutes. Three μl of the reaction were used to transform *E. coli* TOP10 competent cells. An *E. coli* transformant containing pPpin6 was detected by colony PCR and plasmid DNA was prepared using a QlAprep Spin Miniprep Kit (QIAGEN Inc., Valencia, CA, USA). The *Penicillium pinophilum* GH7 cellobiohydrolase I gene insert in pPpin6 was confirmed by DNA sequencing using a 3730XL DNA Analyzer.

*Aspergillus oryzae* HowB101 (WO 95/35385) protoplasts were prepared according to the method of Christensen et al., 1988, Bio/Technology 6: 1419-1422 and transformed with 3 μg of pPpin6. The transformation yielded about 50 transformants. Four transformants were isolated to individual Minimal medium plates.

Four transformants were inoculated separately into 3 ml of YPM medium in a 24-well plate and incubated at 30° C., 150 rpm. After 3 days incubation, 20 μl of supernatant from each culture were analyzed by SDS-PAGE using a NUPAGE® NOVEX® 4-12% Bis-Tris Gel with MES buffer according to the manufacturer's instructions. The resulting gel was stained with INSTANT® Blue. SDS-PAGE profiles of the cultures showed that the majority of the transformants had a major smear band of approximately 60-90 kDa. The expression strain was designated as *A. oryzae* EXP02768.

A slant of *A. oryzae* EXP02768 was washed with 10 ml of YPM medium and inoculated into a 2 liter flask containing 400 ml of YPM medium to generate broth for characterization of the enzyme. The culture was harvested on day 3 and filtered using a 0.45 μm DURAPORE Membrane (Millipore, Bedford, MA, USA).

A 1600 ml volume of the filtered broth of *A. oryzae* EXP02768 was precipitated with ammonium sulfate (80% saturation), re-dissolved in 100 ml of 25 mM Bis-Tris pH 6.0, dialyzed against the same buffer, and filtered through a 0.45 μm filter; the final volume was 200 ml. The solution was applied to a 40 ml Q Sepharose® Fast Flow column equilibrated in 25 mM Bis-Tris pH 6.0, and the proteins were eluted with a linear NaCl gradient (0-0.4 M). Fractions from the column with activity against pNP-β-D-lactopyranoside were analyzed by SDS-PAGE using a NUPAGE® NOVEX® 4-12% Bis-Tris Gel with MES buffer. Fractions with the correct molecular weight were pooled and concentrated by ultrafiltration. Protein concentration was determined using a Microplate BCA™ Protein Assay Kit in which bovine serum albumin was used as a protein standard.

Example 65: Preparation of *Aspergillus terreus* ATCC 28865 GH7 Cellobiohydrolase I The *Aspergillus terreus* ATCC 28865 GH7 cellobiohydrolase I (SEQ ID NO: 161 [DNA sequence] and SEQ ID NO: 162 [deduced amino acid sequence]) was obtained according to the procedure described below.

Two synthetic oligonucleotide primers, shown below, were designed to PCR amplify the cellobiohydrolase I gene from *Aspergillus terreus* ATCC 28865 genomic DNA. Genomic DNA was isolated using a FastDNA spin for Soil Kit (MP Biomedicals, OH, USA).

```
Primer #222:
                                       (SEQ ID NO: 211)
5'-TAAGAATTCACCATGCCTTCCACCTACGA-3'

Primer #302:
                                       (SEQ ID NO: 212)
5'-TATGCGGCCGCATTCTCCTAGACACCCCGCAT-3'
```

The amplification reaction was composed of 1 µl of *Aspergillus terreus* genomic DNA, 12.5 µl of 2× REDDY-MIX™ PCR Buffer (Thermo Fisher Scientific Inc., Waltham, MA, USA), 1 µl of 5 µM primer #222, 1 µl of 5 µM primer #302, and 9.5 µl of H$_2$O. The amplification reaction was incubated in a PTC-200 DNA ENGINE™ Thermal Cycler programmed for 1 cycle at 94° C. for 2 minutes; and 35 cycles each at 94° C. for 15 seconds and 60° C. for 1.5 minutes.

A 1.7 kb PCR reaction product was isolated by 1% agarose gel electrophoresis using TAE buffer and staining with SYBR Safe DNA gel stain (Invitrogen Corp., Carlsbad, CA, USA). The DNA band was visualized with the aid of an Eagle Eye Imaging System and a DarkReader Transilluminator (Clare Chemical Research, Dolores, CO, USA). The 1.7 kb DNA band was excised from the gel and purified using a GFX® PCR DNA and Gel Band Purification Kit according to the manufacturer's instructions.

The 1.7 kb fragment was cleaved with EcoR I and Not I and purified using a GFX® PCR DNA and Gel Band Purification Kit according to the manufacturer's instructions.

The cleaved 1.7 kb fragment was then directionally cloned by ligation into Eco RI-Not I cleaved pXYG1051 (WO 2005/080559) using T4 ligase (Promega, Madison, WI, USA) according to the manufacturer's instructions. The ligation mixture was transformed into *E. coli* TOP10F competent cells according to the manufacturer's instructions. The transformation mixture was plated onto LB plates supplemented with 100 µg of ampicillin per ml. Plasmid minipreps were prepared from several transformants and sequenced. One plasmid with the correct *Aspergillus terreus* GH7 coding sequence was chosen. The plasmid was designated pXYG1051-NP003568.

The expression plasmid pXYG1051-NP003568 was transformed into *Aspergillus oryzae* JaL355 as described in WO 98/00529. Transformants were purified on selection plates through single conidia prior to sporulating them on PDA plates. Production of the *Aspergillus terreus* GH7 polypeptide by the transformants was analyzed from culture supernatants of 1 ml 96 deep well stationary cultivations at 26° C. in YP medium with 2% maltodextrin. Expression was verified by SDS-PAGE using a NUPAGE® NOVEX® 4-12% Bis-Tris Gel with MES buffer and Coomassie blue staining. One transformant was selected for further work and designated *Aspergillus oryzae* 64.1.

For larger scale production, *Aspergillus oryzae* 64.1 spores were spread onto a PDA plate and incubated for five days at 37° C. The confluent spore plate was washed twice with 5 ml of 0.01% TWEEN® 20 to maximize the number of spores collected. The spore suspension was then used to inoculate twenty-five 500 ml flasks containing 100 ml of YPG medium. The culture was incubated at 30° C. with constant shaking at 120 rpm. At day four post-inoculation, the culture broth was collected by filtration through a triple layer of Whatman glass microfiber filters of 1.6 µm, 1.2 µm, and 0.7 µm. Fresh culture broth from this transformant produced a band of GH7 protein of approximately 55 kDa. The identity of this band as the *Aspergillus terreus* GH7 polypeptide was verified by peptide sequencing.

Two liters of the filtered broth were concentrated to 400 ml and washed with 50 mM HEPES pH 7.0 using a SARTOFLOW® Alpha ultrafiltration system with a 10 kDa MW-CO (Sartorius Stedim Biotech S.A., Aubagne Cedex, France). Ammonium sulphate was added to a final concentration of 1 M and dissolved in the ultrafiltrate. The solution was applied on a Source Phenyl XK 26/20 50 ml column (GE Healthcare, HiHerod, Denmark). After application the column was washed with 150 ml of 1 M ammonium sulphate and eluted with 1 column volume of 50% ethanol in a 0% to 100% gradient followed by 5 column volumes of 50% ethanol at a flow rate of 10 ml/minute. Fractions of 10 ml were collected and analyzed by SDS-PAGE. Fraction 3 to 8 were pooled and diluted to 1000 ml with 50 mM HEPES pH 7.0 before application on a Q Sepharose® Fast Flow column XK26/20 60 ml column (GE Healthcare, HiHerod, Denmark). After application the column was washed 3 times with 60 ml of 50 mM HEPES pH 7.0 and eluted with 100 ml of 50 mM HEPES pH 7.0, 1 M NaCl at a flow rate of 10 ml/minute. Fractions of 10 ml were collected and analyzed by SDS-PAGE. The flow-through and first wash were pooled and concentrated to 400 ml and washed with 50 mM HEPES pH 7.0 using the ultrafiltration system described above. Further concentration was conducted using a VIVAS-PIN™ centrifugal concentrator according to the manufacturer's instructions to a final volume of 80 ml. The protein concentration was determined by A280/A260 absorbance. Protein concentration was also determined using a Microplate BCA™ Protein Assay Kit in which bovine serum albumin was used as a protein standard.

Example 66: Preparation of Neosartorya *Fischeri* Strain NRRL 181 GH7 Cellobiohydrolase I The Neosartorya *fischeri* NRRL 181 GH7 cellobiohydrolase I (SEQ ID NO: 163 [DNA sequence] and SEQ ID NO: 164 [deduced amino acid sequence]) was obtained according to the procedure described below.

Two synthetic oligonucleotide primers, shown below, were designed to PCR amplify the cellobiohydrolase I gene from Neosartorya *fischeri* genomic DNA. Genomic DNA was isolated using a FastDNA Spin for Soil Kit.

```
Primer #374:
                                       (SEQ ID NO: 213)
5'-TAAGAATTCACCATGCCTTCCACCTACGA-3'
```

-continued

```
Primer #375:
                                         (SEQ ID NO: 214)
5'-TATGCGGCCGCATTCTCCTAGACACCCCGCAT-3'
```

The amplification reaction was composed of 1 µl of Neosartorya fischeri genomic DNA, 12.5 µl of 2× REDDY-MIX™ PCR Buffer, 1 µl of 5 µM primer #374, 1 µl of 5 µM primer #375, and 9.5 µl of H₂O. The amplification reaction was incubated in a PTC-200 DNA ENGINE™ Thermal Cycler programmed for 1 cycle at 94° C. for 2 minutes; and 35 cycles each at 94° C. for 15 seconds and 60° C. for 1.5 minutes.

A 1.6 kb PCR reaction product was isolated by 1% agarose gel electrophoresis using TAE buffer and staining with SYBR Safe DNA gel stain. The DNA band was visualized with the aid of an Eagle Eye Imaging System and a DarkReader Transilluminator. The 1.6 kb DNA band was excised from the gel and purified using a GFX® PCR DNA and Gel Band Purification Kit according to the manufacturer's instructions.

The 1.6 kb fragment was cleaved with EcoR I and Not I and purified using a GFX® PCR DNA and Gel Band Purification Kit according to the manufacturer's instructions.

The cleaved 1.6 kb fragment was then directionally cloned by ligation into Eco RI-Not I cleaved pXYG1051 (WO 2005/080559) using T4 ligase according to the manufacturer's instructions. The ligation mixture was transformed into E. coli TOP10F competent cells according to the manufacturer's instructions. The transformation mixture was plated onto LB plates supplemented with 100 µg of ampicillin per ml. Plasmid minipreps were prepared from several transformants and sequenced. One plasmid with the correct Neosartorya fischeri GH7 cellobiohydrolase coding sequence was chosen. The plasmid was designated pXYG1051-N P003786.

The expression plasmid pXYG1051-NP003786 was transformed into Aspergillus oryzae JaL355 as described in WO 98/00529. Transformants were purified on selection plates to single conidia prior to sporulating them on PDA plates. Production of the Neosartorya fischeri GH7 cellobiohydrolase by the transformants was analyzed from culture supernatants of 1 ml 96 deep well stationary cultivations at 26° C. in YP medium with 2% maltodextrin. Expression was verified by SDS-PAGE using a NUPAGE® NOVEX® 4-12% Bis-Tris Gel with MES buffer and Coomassie blue staining. One transformant was selected for further work and designated Aspergillus oryzae 92.7.

For larger scale production, Aspergillus oryzae 92.7 spores were spread onto a PDA plate and incubated for five days at 37° C. The confluent spore plate was washed twice with 5 ml of 0.01% TWEEN® 20 to maximize the number of spores collected. The spore suspension was then used to inoculate twenty-five 500 ml flasks containing 100 ml of YPM medium. The culture was incubated at 26° C. with constant shaking at 120 rpm. At day five post-inoculation, the culture broth was collected by filtration through a triple layer of Whatman glass microfiber filters of 1.6 µm, 1.2 µm, and 0.7 µm. Fresh culture broth from this transformant produced a band of GH7 protein of approximately 70 kDa. The identity of this band as the Neosartorya fischeri GH7 cellobiohydrolase was verified by peptide sequencing.

Two liters of the filtered broth were concentrated to 400 ml and washed with 50 mM HEPES pH 7.0 using a SARTOFLOW® Alpha ultrafiltration system with a 10 kDa MW-CO. Ammonium sulphate was added to a final concentration of 1 M and dissolved in the ultrafiltrate. The solution was applied to a Source 15 Phenyl XK 26/20 50 ml column. After application the column was washed with 150 ml of 1 M ammonium sulphate and eluded with 1 column volume of 50% ethanol in a 0% to 100% gradient followed by 5 column volumes of 50% ethanol at a flow rate of 10 ml/minute. Fractions of 10 ml were collected and analyzed by SDS-PAGE. Fraction 3 to 8 were pooled and diluted to 1000 ml with 50 mM HEPES pH 7.0 before application to a Q Sepharose® Fast Flow XK26/20 60 ml column. After application the column was washed 3 times with 60 ml of 50 mM HEPES pH 7.0 and eluded with 100 ml of 50 mM HEPES pH 7.0, 1 M NaCl at a flow rate of 10 ml/minute. Fractions of 10 ml were collected and analyzed by SDS-PAGE. The flow-through and first wash were pooled and concentrated to 400 ml and washed with 50 mM HEPES pH 7.0 using a SARTOFLOVVO Alpha ultrafiltration system with a 10 kDa MW-CO. Further concentration was conducted using a VIVASPIN™ centrifugal concentrator according to the manufacturer's instructions to a final volume of 80 ml. The protein concentration determined by A280/A260 absorbance. Protein concentration was also determined using a Microplate BCA™ Protein Assay Kit in which bovine serum albumin was used as a protein standard.

Example 67: Preparation of Aspergillus nidulans Strain FGSCA4 GH7 Cellobiohydrolase I The Aspergillus nidulans strain FGSCA4 GH7 cellobiohydrolase I (SEQ ID NO: 165 [DNA sequence] and SEQ ID NO: 166 [deduced amino acid sequence]) was obtained according to the procedure described below.

Two synthetic oligonucleotide primers, shown below, were designed to PCR amplify the cellobiohydrolase I gene from Aspergillus nidulans genomic DNA. Genomic DNA was isolated using a FastDNA Spin for Soil Kit.

```
Primer #376:
                                         (SEQ ID NO: 215)
5'-TAACAATTGACCATGGCATCTTCATTCCAGTTGTA-3'

Primer #377:
                                         (SEQ ID NO: 216)
5'-TATGCGGCCGCGTCTCCCATTTACGACCCACCA-3'
```

The amplification reaction was composed of 1 µl of Aspergillus nidulans genomic DNA, 12.5 µl of 2× REDDY-MIX™ PCR Buffer, 1 µl of 5 µM primer #374, 1 µl of 5 µM primer #375, and 9.5 µl of H₂O. The amplification reaction was incubated in a PTC-200 DNA ENGINE™ Thermal Cycler programmed for 1 cycle at 94° C. for 2 minutes; and 35 cycles each at 94° C. for 15 seconds and 60° C. for 1.5 minutes.

A 1.6 kb PCR reaction product was isolated by 1% agarose gel electrophoresis using TAE buffer and staining with SYBR Safe DNA gel stain. The DNA band was visualized with the aid of an Eagle Eye Imaging System and a DarkReader Transilluminator. The 1.6 kb DNA band was excised from the gel and purified using a GFX® PCR DNA and Gel Band Purification Kit according to the manufacturer's instructions.

The 1.6 kb fragment was cleaved with Mfe I and Not I and purified using a GFX® PCR DNA and Gel Band Purification Kit according to the manufacturer's instructions.

The cleaved 1.6 kb fragment was then directionally cloned by ligation into Eco RI-Not I cleaved pXYG1051 (WO 2005/080559) using T4 ligase according to the manufacturer's instructions. The ligation mixture was transformed into *E. coli* TOP10F competent cells according to the manufacturer's instructions. The transformation mixture was plated onto LB plates supplemented with 100 µg of ampicillin per ml. Plasmid minipreps were prepared from several transformants and sequenced. One plasmid with the *Aspergillus nidulans* GH7 coding sequence was chosen. Two mutations introduced during PCR were identified which result in a change of Leu 7 to Trp and of Glu 436 to Gly relative to the public sequence Q8NK02. The plasmid was designated pXYG1051-NP003787.

The expression plasmid pXYG1051-NP003787 was transformed into *Aspergillus oryzae* JaL355 as described in WO 98/00529. Transformants were purified on selection plates to single conidia prior to sporulating them on PDA plates. Production of the *Aspergillus nidulans* GH7 cellobiohydrolase by the transformants was analyzed from culture supernatants of 1 ml 96 deep well stationary cultivations at 26° C. in YP medium with 2% maltodextrin. Expression was verified by SDS-PAGE using a NUPAGE® NOVEX® 4-12% Bis-Tris Gel with MES buffer and Coomassie blue staining. One transformant was selected for further work and designated *Aspergillus oryzae* 70.5.

For larger scale production, *Aspergillus oryzae* 70.5 spores were spread onto a PDA plate and incubated for five days at 37° C. The confluent spore plate was washed twice with 5 ml of 0.01% TWEEN® 20 to maximize the number of spores collected. The spore suspension was then used to inoculate twenty-five 500 ml flasks containing 100 ml of YPM medium. The culture was incubated at 26° C. with constant shaking at 120 rpm. At day six post-inoculation, the culture broth was collected by filtration through a triple layer of Whatman glass microfiber filters of 1.6 µm, 1.2 µm, and 0.7 µm. Fresh culture broth from this transformant produced a band of GH7 protein of approximately 54 kDa. The identity of this band as the *Aspergillus nidulans* GH7 cellobiohydrolase was verified by peptide sequencing.

Two liters of the filtered broth were concentrated to 400 ml and washed with 50 mM HEPES pH 7.0 using a SARTOFLOW® Alpha ultrafiltration system with a 10 kDa MW-CO. Ammonium sulphate was added to a final concentration of 1 M and dissolved in the ultrafiltrate. The solution was applied on a Source 15 Phenyl XK 26/20 50 ml column. After application the column was washed with 150 ml of 1 M ammonium sulphate and eluded with 1 column volume of 50% ethanol in a 0% to 100% gradient followed by 5 column volumes of 50% ethanol at a flow rate of 10 ml/minute. Fractions of 10 ml were collected and analyzed by SDS-PAGE. Fraction 3 to 8 were pooled and diluted to 1000 ml with 50 mM HEPES pH 7.0 before application on a Q Sepharose® Fast Flow XK26/20 60 ml column. After application the column was washed 3 times with 60 ml of 50 mM HEPES pH 7.0 and eluded with 100 ml of 50 mM HEPES pH 7.0, 1 M NaCl at a flow rate of 10 ml/minute. Fractions of 10 ml were collected and analyzed by SDS-PAGE. The flow-through and first wash were pooled and concentrated to 400 ml and washed with 50 mM HEPES pH 7.0 using a SARTOFLOVVO Alpha ultrafiltration system with a 10 kDa MW-CO. Further concentration was conducted using a VIVASPIN™ centrifugal concentrator according to the manufacturer's instructions to a final volume of 80 ml. The protein concentration determined by A280/A260 absorbance. Protein concentration was also determined using a Microplate BCA™ Protein Assay Kit in which bovine serum albumin was used as a protein standard.

Example 68: Preparation of a *Fennellia nivea* Strain NN046949 GH6 Cellobiohydrolase II The *Fennellia nivea* strain NN046949 GH6 cellobiohydrolase II (SEQ ID NO: 167 [DNA sequence] and SEQ ID NO: 168 [deduced amino acid sequence]) was obtained according to the procedure described below.

*Fennellia nivea* strain NN046949 was isolated from a soil from Yunnan, China by directly plating the soil sample onto a PDA plate followed by incubation at 37° C. for 5 days. The strain was then purified by transferring the mycelia onto a YG agar plate. The *Fennellia nivea* strain NN046949 was identified as *Fennellia nivea* based on both morphological and molecular (ITS sequencing) characterization.

*Fennellia nivea* strain NN046949 was inoculated onto a PDA plate and incubated for 4 days at 37° C. in the darkness. Several mycelia-PDA plugs were inoculated into 500 ml shake flasks containing 100 ml of NNCYP-PCS medium. The flasks were incubated for 6 days at 37° C. with shaking at 160 rpm. The mycelia were collected at 4, 5, and 6 days, and each frozen in liquid nitrogen and stored in a −80° C. freezer until use.

The frozen *F. nivea* mycelia were mixed and transferred into a liquid nitrogen prechilled mortar and pestle and ground to a fine powder. Total RNA was prepared from the powdered mycelia of each day by extraction with TRIZOL® reagent and purified using a RNEASY® Plant Mini Kit according to the manufacturer's protocol. The polyA enriched RNA was isolated using a mTRAP™ Total Kit. Eighty-seven µgs of total RNA was submitted for sequencing as described in Example 3.

Total RNA enriched for polyA sequences with the mRNASeq protocol were sequenced using an ILLUMINA® GA2 System (Illumina, Inc., San Diego, CA, USA). The raw 75 base pair reads were assembled and the assembled sequences were analyzed using standard bioinformatics methods for gene finding and functional prediction. Briefly, ESTscan 2.0 was used for gene prediction. NCBI blastall version 2.2.10 and HMMER version 2.1.1 were used to predict function based on structural homology. The Family GH6 cellobiohydrolase was identified directly by analysis of the Blast results.

*Fennellia nivea* strain NN046949 was grown on PDA agar plate at 37° C. for 3 days. Mycelia were collected directly from the agar plate into a sterilized motar and frozen under liquid nitrogen. Frozen mycelia were ground, by mortar and pestle, to a fine powder, and genomic DNA was isolated using a DNEASY® Plant Mini Kit (QIAGEN Inc., Valencia, CA, USA).

Based on the *F. nivea* GH6 cellobiohydrolase gene sequence obtained in Example 3, oligonucleotide primers, shown below, were designed to amplify the gene from genomic DNA of *Fennellia nivea*. An IN-FUSION™ CF Dry-down PCR Cloning Kit was used to clone the fragment directly into the expression vector pPFJO355, without the need for restriction digestion and ligation.

Sense primer:
(SEQ ID NO: 217)
5'-ACACAACTGGGGATCCACCATGGGACGGGTTTCTTCTCTTG-3'

Antisense primer:
(SEQ ID NO: 218)
5'-GTCACCCTCTAGATCTAAGAACACCCCGCAAAGAAAGTC-3'

Bold letters represent the coding sequence for the sense primer or the reverse compliment sequence downstream of the stop codon for the antisense primer. The remaining sequence is homologous to the insertion sites of pPFJO355.

Twenty picomoles of each of the primers above were used in a PCR reaction composed of *Fennellia nivea* genomic DNA, 10 µl of 5× GC Buffer, 1.5 µl of DMSO, 2 µl of 2.5 mM each of dATP, dTTP, dGTP, and dCTP, and 1 unit of Phusion™ High-Fidelity DNA Polymerase in a final volume of 50 µl. The amplification was performed using an Peltier Thermal Cycler programmed for denaturing at 98° C. for 1 minutes; 5 cycles of denaturing at 98° C. for 15 seconds, annealing at 70° C. for 30 seconds, with 1° C. decreasing per cycle and elongation at 72° C. for 30 seconds; 25 cycles each at 98° C. for 15 seconds and 72° C. for 90 seconds; and a final extension at 72° C. for 10 minutes. The heat block then went to a 4° C. soak cycle.

The reaction products were isolated by 1.0% agarose gel electrophoresis using TBE buffer where an approximately 1.8 kb product band was excised from the gel, and purified using an ILLUSTRA™ GFX™ PCR DNA and Gel Band Purification Kit (GE Healthcare, Buckinghamshire, UK) according to the manufacturer's instructions.

Plasmid pPFJO355 was digested with Bam I and Bgl II, isolated by 1.0% agarose gel electrophoresis using TBE buffer, and purified using an ILLUSTRA™ GFX™ PCR DNA and Gel Band Purification Kit according to the manufacturer's instructions. The gene fragment and the digested vector were ligated together using an IN-FUSION™ Dry Down PCR Cloning Kit resulting in pCBHI146949-2 in which transcription of the *Fennellia nivea* GH6 cellobiohydrolase gene was under the control of the *Aspergillus oryzae* TAKA alpha-amylase promoter. In brief, 30 ng of pPFJO355 digested with Bam 1 and Bgl 11, and 50 ng of the *F. nivea* GH6 cellobiohydrolase gene purified PCR product were added to a reaction vial and resuspended in a final volume of 10 µl with addition of deionized water. The reaction was incubated at 37° C. for minutes and then 50° C. for 15 minutes. Three µl of the reaction were used to transform *E. coli* TOP10 competent cells. An *E. coli* transformant containing pCBHI146949-2 was detected by colony PCR and plasmid DNA was prepared using a QIAprep Spin Miniprep Kit (QIAGEN Inc., Valencia, CA, USA). The *F. nivea* GH6 cellobiohydrolase gene insert in pCBHI146949-2 was confirmed by DNA sequencing using a 3730XL DNA Analyzer.

The same gene fragment was then incubated in 10× Taq DNA polymerase mix (TIANGEN Biotech (Beijing) Co. Ltd., Beijing, China) at 72° C. for 20 minutes to add adenine to the 3' end of each nucleotide strand. Then the gene fragment was ligated to pGEM-T vector using a pGEM-T Vector System to generate pGEM-T-CBH1146949-2. The Fennellia nivea cellobiohydrolase gene insert in pGEM-T-CBH1146949-2 was confirmed by DNA sequencing using a 3730XL DNA Analyzer. *E. coli* strain T-CBH1146949-2, containing pGEM-T-CBH1146949-2, was deposited on Oct. 28, 2010 with the Deutsche Sammlung von Mikroorganismen and Zellkulturen GmbH (DSMZ), Mascheroder Weg 1 B, D-38124 Braunschweig, Germany assigned the accession number DSM 24143.

Nucleotide sequence data were scrutinized for quality and all sequences were compared to each other with assistance of PHRED/PHRAP software (University of Washington, Seattle, WA, USA).

The nucleotide sequence and deduced amino acid sequence of the *F. nivea* cellobiohydrolase gene are shown in SEQ ID NO: 167 and SEQ ID NO: 168, respectively. The genomic fragment encodes a polypeptide of 469 amino acids, interrupted by 7 predicted introns of 49 bp (nucleotides 77-125), 247 bp (nucleotides 195-241), 46 bp (nucleotides 570-615), 55 bp (nucleotides 870-924), 50 bp (nucleotides 1063-1112), 46 bp (nucleotides 1371-1416), and 49 bp (nucleotides 1659-1707). The % G+C content of the full-length coding sequence and the mature coding sequence are 57.65% and 60.24%, respectively. Using the SignalP software program (Nielsen et al., 1997, *Protein Engineering* 10: 1-6), a signal peptide of 18 residues was predicted. The predicted mature protein contains 451 amino acids with a predicted molecular mass of 48.77 kDa and an isoelectric point of 5.17. Amino acids 112 to 469 are indicative of a Family 6 glycosyl hydrolase. Based on the deduced amino acid sequence, the cellobiohydrolase appears to fall into the cellobiohydrolase Family GH6 according to Coutinho and Henrissat, 1999, supra. Amino acids 22 to 50 are indicative of a CBM domain and amino acids 58 to 111 a linker region.

*Aspergillus oryzae* HowB101 (WO 95/35385) protoplasts were prepared according to the method of Christensen et al., 1988, Bio/Technology 6: 1419-1422 and transformed with 3 µg of pCBHII46949-2. The transformation yielded about 50 transformants. Four transformants were isolated to individual Minimal medium plates.

Four transformants were inoculated separately into 3 ml of YPM medium in 24-well plate and incubated at 30° C., 150 rpm. After 3 days incubation, 20 µl of supernatant from each culture were analyzed by SDS-PAGE using a NUPAGE® NOVEX® 4-12% Bis-Tris Gel with MES buffer according to the manufacturer's instructions. The resulting gel was stained with INSTANTBLUE™ (Expedeon Ltd., Babraham Cambridge, UK). SDS-PAGE profiles of the cultures showed that the majority of the transformants had a band of approximately 60 kDa. One transformant was chosen as the expression strain and designated *Aspergillus oryzae* EXP03324.

A slant of *Aspergillus oryzae* EXP03324 was washed with 10 ml of YPM medium and inoculated into 4 2-liter flasks, containing 400 ml of YPM medium for each, to generate broth for characterization of the enzyme. The culture was harvested on day 3 by filtering the culture against MIRACLOTH® (CALBIOCHEM, Inc. La Jolla, CA, USA). The filtered culture broth was then again filtered using a 0.45 µm DURAPORE Membrane (Millipore, Bedford, MA, USA).

A 1600 ml volume of the *Aspergillus oryzae* EXP03324 filtered broth was precipitated with ammonium sulfate (80% saturation), re-dissolved in 100 ml 25 mM Bis-Tris pH 6.5 buffer, dialyzed against the same buffer, and filtered through a 0.45 µm filter; the final volume was 200 ml. The solution was applied to a 40 ml Q Sepharose® Fast Flow column equilibrated in 25 mM Bis-Tris pH 6.5 buffer and the proteins were eluted with a linear 0-0.4 M NaCl gradient. Fractions from the column were analyzed by SDS-PAGE using a NUPAGE® NOVEX® 4-12% Bis-Tris Gel with MES buffer. Fractions with a molecular weight of 60 kDa were pooled. Then the pooled solution was concentrated by ultrafiltration and assayed for cellobiohydrolase activity using phosphoric acid swollen cellulose (PASO) as substrate. Protein concentration was determined using a Microplate BOAT™ Protein Assay Kit in which bovine serum albumin was used as a protein standard.

A PASO stock slurry solution was prepared by moistening 5 g of AVICEL® (JRS Pharma GmbH & Co., Rosenberg, Germany) with water, followed by the addition of 150 ml of ice cold 85% o-phosphoric acid. The suspension was slowly stirred in an ice-bath for 1 hour. Then 500 ml of ice cold acetone were added while stirring. The slurry was filtered using MIRACLOTH® and then washed three times with 100 ml of ice-cold acetone (drained as dry as possible after each wash). Finally, the filtered slurry was washed twice with 500 ml of water, and again drained as dry as possible after each wash. The PASO was mixed with deionized water to a total volume of 500 ml to a concentration of 10 g/liter, blended to homogeneity using an ULTRA-TURRAX® Homogenizer (Cole-Parmer, Vernon Hills, IL, USA), and stored in a refrigerator for up to one month.

The PASO stock solution was diluted with 50 mM sodium acetate pH 5.0 buffer to a concentration of 2 g/liter, and used as the substrate. To 150 µl of PASO stock solution, 20 µl of enzyme sample were added and the reaction mixture was incubated for 60 minutes with shaking at 850 rpm. At the end of the incubation, 50 µl of 2% NaOH were added to stop the reaction. The reaction mixture was centrifuged at 1,000×g. The released sugars were measured by first mixing 10 µl of the reaction mixture with 90 µl of 0.4% NaOH, followed by 50 µl of 1.5% p-hydroxybenzoic acid hydrazide in 2% NaOH (PHBAH, Sigma Chemical Co., St. Loius, MO, USA). The mixture was boiled at 100° C. for 5 minutes, and then 100 µl were transferred to a microtiter plate for an absorbance reading at 410 nm using a Spectra Max M2 (Molecular Devices, Sunnyvale, CA, USA). Blanks were made by omitting PASO in the hydrolysis step, and by replacing the hydrolysate with buffer in the sugar determination step. The assay results demonstrated that the purified enzyme possessed cellobiohydrolase activity.

Example 69: Preparation of *Penicillium emersonii* Strain NN051602 GH6A Cellobiohydrolase II

*Penicillium emersonii* strain NN051602 GH6A cellobiohydrolase II (SEQ ID NO: 169 [DNA sequence] and SEQ ID NO: 170 [deduced amino acid sequence]) was obtained according to the procedure described below.

*Penicillium emersonii* was grown on a PDA agar plate at 45° C. for 3 days. Mycelia were collected directly from the agar plate into a sterilized mortar and frozen under liquid nitrogen. Frozen mycelia were ground, by mortar and pestle, to a fine powder, and genomic DNA was isolated using a DNeasy® Plant Mini Kit (QIAGEN Inc., Valencia, CA, USA).

Oligonucleotide primers, shown below, were designed to amplify the GH6 cellobiohydrolase II gene from genomic DNA of *Penicillium emersonii*. An IN-FUSION™ CF Dry-down Cloning Kit was used to clone the fragment directly into the expression vector pPFJO355, without the need for restriction digestion and ligation.

```
Sense primer:
                               (SEQ ID NO: 219)
5'-ACACAACTGGGGATCCACCATGCGGAATCTTCTTGCTCTTGC-3'

Antisense primer:
                               (SEQ ID NO: 220)
5'-GTCACCCTCTAGATCTCTAGAACAGCGGGTTAGCATTCGTG-3'
```

Bold letters represented the coding sequence. The remaining sequence was homologous to the insertion sites of pPFJO355.

Twenty picomoles of each of the primers above were used in a PCR reaction composed of *Penicillium emersonii* genomic DNA, 10 µl of 5× HF Buffer, 1.5 µl of DMSO, 5 mM each of dATP, dTTP, dGTP, and dCTP, and 0.6 unit of Phusion™ High-Fidelity DNA Polymerase in a final volume of 50 µl. The amplification was performed using a Peltier Thermal Cycler programmed for denaturing at 98° C. for 1 minutes; 8 cycles of denaturing at 98° C. for 15 seconds, annealing at 66° C. for 30 seconds, with a 1° C. decrease per cycle and elongation at 72° C. for 70 seconds; and another 25 cycles each at 98° C. for 15 seconds, 62° C. for 30 seconds and 72° C. for 80 seconds; final extension at 72° C. for 5 minutes. The heat block then went to a 4° C. soak cycle.

The reaction products were isolated by 1.0% agarose gel electrophoresis using TBE buffer where an approximately 1.8 kb product band was excised from the gel, and purified using an ILLUSTRA® GFX® PCR DNA and Gel Band Purification Kit according to the manufacturer's instructions.

Plasmid pPFJO355 was digested with Bam I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION™ CF Dry-down PCR Cloning resulting in pCBHII51602 in which transcription of the *Penicillium emersonii* GH6 cellobiohydrolase II gene was under the control of the *Aspergillus oryzae* TAKA amylase promoter. In brief, 30 ng of pPFJO355, digested with Bam I and Bgl II, and 60 ng of the *Penicillium emersonii* GH6 cellobiohydrolase II gene purified PCR product were added to a reaction vial and resuspended in a final volume of 10 µl with addition of deionized water. The reaction was incubated at 37° C. for 15 minutes and then 50° C. for 15 minutes. Three µl of the reaction were used to transform *E. coli* TOP10 competent cells. An *E. coli* transformant containing pCBHII51602 was detected by colony PCR and plasmid DNA was prepared using a QIAprep Spin Miniprep Kit (QIAGEN Inc., Valencia, CA, USA). The *Penicillium emersonii* GH6 cellobiohydrolase II gene insert in pCBHII51602 was confirmed by DNA sequencing using a 3730XL DNA Analyzer.

*Aspergillus oryzae* HowB101 (WO 95/35385) protoplasts were prepared according to the method of Christensen et al., 1988, Bio/Technology 6: 1419-1422 and transformed with 3 µg of pCBHII51602. The transformation yielded about 50 transformants. Twelve transformants were isolated to individual Minimal medium plates.

Six transformants were inoculated separately into 3 ml of YPM medium in 24-well plate and incubated at 30° C., 150 rpm. After 3 days incubation, 20 µl of supernatant from each culture were analyzed by SDS-PAGE using a NUPAGE® NOVEX® 4-12% Bis-Tris Gel with MES buffer according to the manufacturer's instructions. The resulting gel was stained with INSTANT® Blue. SDS-PAGE profiles of the cultures showed that the majority of the transformants had a major smeary band of approximately 62 kDa. The expression strain was designated as *A. oryzae* EXP03259.

A slant of *A. oryzae* EXP03259 was washed with 10 ml of YPM medium and inoculated into a 2 liter flask containing 400 ml of YPM medium to generate broth for characterization of the enzyme. The culture was harvested on day 3 and filtered using a 0.45 µm DURAPORE Membrane.

A 1600 ml volume of filtered broth of *A. oryzae* EXP03259 was precipitated with ammonium sulfate (80% saturation), re-dissolved in 100 ml 2 of 5 mM Bis-Tris pH 6.0, dialyzed against the same buffer, and filtered through a 0.45 µm filter; the final volume was 200 ml. The solution was applied to a 40 ml Q Sepharose® Fast Flow column equilibrated with 25 mM Bis-Tris pH 6.0, and the proteins were eluted with a linear NaCl gradient (0-0.4 M). Fractions from the column with activity against PASC were analyzed by SDS-PAGE using a NUPAGE® NOVEX® 4-12% Bis-Tris Gel with MES buffer. Fractions with the correct molecular weight were pooled and concentrated by ultrafiltration.

Example 70: Preparation of *Penicillium pinophilum* Strain NN046877 GH6A Cellobiohydrolase II The *Penicillium pinophilum* strain NN046877 GH6A cellobiohydrolase II (SEQ ID NO: 171 [DNA sequence] and SEQ ID NO: 172 [deduced amino acid sequence]) was obtained according to the procedure described below.

*Penicillium pinophilum* was grown on a PDA agar plate at 37° C. for 4-5 days. Mycelia were collected directly from the agar plate into a sterilized mortar and frozen under liquid nitrogen. Frozen mycelia were ground, by mortar and pestle, to a fine powder, and genomic DNA was isolated using a DNeasy® Plant Mini Kit (QIAGEN Inc., Valencia, CA, USA).

Oligonucleotide primers, shown below, were designed to amplify the GH6 cellobiohydrolase II gene from genomic DNA of *Penicillium pinophilum*. An IN-FUSION™ CF Dry-down Cloning Kit was used to clone the fragment directly into the expression vector pPFJO355, without the need for restriction digestion and ligation.

```
Sense primer:
                                    (SEQ ID NO: 221)
5'-ACACAACTGGGGATCCACCATGTTGCGATATCTTTCCACC-3'

Antisense primer:
                                    (SEQ ID NO: 222)
5'-GTCACCCTCTAGATCTTCATCTAGACCAAAGCTGGGTTG-3'
```

Bold letters represented the coding sequence and the remaining sequence was homologous to the insertion sites of pPFJO355.

Twenty picomoles of each of the primers above were used in a PCR reaction composed of *Penicillium pinophilum* genomic DNA, 10 μl of 5× GC Buffer, 1.5 μl of DMSO, 2.5 mM each of dATP, dTTP, dGTP, and dCTP, and 0.6 unit of Phusion™ High-Fidelity DNA Polymerase in a final volume of 50 μl. The amplification was performed using a Peltier Thermal Cycler programmed for denaturing at 98° C. for 1 minutes; 5 cycles of denaturing at 98° C. for 15 seconds, annealing at 56° C. for 30 seconds, with a 1° C. increase per cycle and elongation at 72° C. for 75 seconds; and another 25 cycles each at 98° C. for 15 seconds, 65C for 30 seconds and 72° C. for 75 seconds; final extension at 72° C. for 10 minutes. The heat block then went to a 4° C. soak cycle.

The reaction products were isolated by 1.0% agarose gel electrophoresis using TBE buffer where an approximately 1.7 kb product band was excised from the gel, and purified using an ILLUSTRA® GFX® PCR DNA and Gel Band Purification Kit according to the manufacturer's instructions.

Plasmid pPFJO355 was digested with Bam I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION™ CF Dry-down PCR Cloning resulting in pPpin12 in which transcription of the *Penicillium pinophilum* GH6 cellobiohydrolase II gene was under the control of the *Aspergillus oryzae* TAKA amylase promoter. In brief, 30 ng of pPFJO355, digested with Bam I and Bgl II, and 60 ng of the *Penicillium pinophilum* GH6 cellobiohydrolase II gene purified PCR product were added to a reaction vial and resuspended in a final volume of 10 ul with addition of deionized water. The reaction was incubated at 37° C. for 15 minutes and then 50° C. for 15 minutes. Three μl of the reaction were used to transform *E. coli* TOP10 competent cells. An *E. coli* transformant containing pPpin12 was detected by colony PCR and plasmid DNA was prepared using a QIAprep Spin Miniprep Kit. The *Penicillium pinophilum* GH6 cellobiohydrolase II gene insert in pPpin12 was confirmed by DNA sequencing using a 3730XL DNA Analyzer.

*Aspergillus oryzae* HowB101 (WO9535385) protoplasts were prepared according to the method of Christensen et al., 1988, Bio/Technology 6: 1419-1422 and transformed with 3 μg of pPpin12. The transformation yielded about 50 transformants. Four transformants were isolated to individual Minimal medium plates.

Four transformants were inoculated separately into 3 ml of YPM medium in 24-well plate and incubated at 30° C., 150 rpm. After 3 days incubation, 20 μl of supernatant from each culture were analyzed by SDS-PAGE using a NUPAGE® NOVEX® 4-12% Bis-Tris Gel with MES buffer according to the manufacturer's instructions. The resulting gel was stained with INSTANT® Blue. SDS-PAGE profiles of the cultures showed that the majority of the transformants had a major band of approximately 65 kDa. The expression strain was designated *A. oryzae* EXP02774.

A slant of *A. oryzae* EXP02774 was washed with 10 ml of YPM mediumand inoculated into a 2 liter flask containing 400 ml of YPM medium to generate broth for characterization of the enzyme. The culture was harvested on day 3 and filtered using a 0.45 μm DURAPORE Membrane.

A 1600 ml volume of the filtered broth of *A. oryzae* EXP02774 was precipitated with ammonium sulfate (80% saturation), re-dissolved in 100 ml 25 mM Bis-Tris pH 6.0, dialyzed against the same buffer, and filtered through a 0.45 μm filter; the final volume was 200 ml. The solution was applied to a 40 ml Q Sepharose® Fast Flow column equilibrated in 25 mM Bis-Tris pH 6.0, and the proteins were eluted with a linear NaCl gradient (0-0.4 M). Fractions from the column with activity against PASC were collected and applied to a 40 ml HITRAP® SP Fast Flow column equilibrated in 25 mM Bis-Tris pH 6.0, and the proteins were eluted with a linear NaCl gradient (0-0.4 M). Fractions from the column with activity against PASC were analyzed by SDS-PAGE using a NUPAGE® NOVEX® 4-12% Bis-Tris Gel with MES buffer. Fractions with the correct molecular weight were pooled and concentrated by ultrafiltration. Protein concentration was determined using a Microplate BCA™ Protein Assay Kit in which bovine serum albumin was used as a protein standard.

Example 71: Preparation of *Aspergillus fumigatus* Strain NN051616 GH5 Endoglucanase II The *Aspergillus fumigatus* strain NN051616 GH5 endoglucanase II (SEQ ID NO: 173 [DNA sequence] and SEQ ID NO: 174 [deduced amino acid sequence]) was obtained according to the procedure described below.

Two synthetic oligonucleotide primers shown below were designed to PCR amplify the *Aspergillus fumigatus* Family GH5 gene from the genomic DNA. An IN-FUSION™ Cloning Kit was used to clone the fragment directly into the expression vector, pAlLo2 (WO 2005/074647), without the need for restriction digests and ligation.

Forward primer:
(SEQ ID NO: 223)
5'-ACTGGATTTACCATGAAATTCGGTAGCATTGTGCTC-3'

Reverse primer:
(SEQ ID NO: 224)
5'-TCACCTCTAGTTAATTAATCAACCCAGGTAGGGCTCCAAGATG-3'

Bold letters represent coding sequence. The remaining sequence is homologous to the insertion sites of pAlLo2.

Fifteen picomoles of each of the primers above were used in a PCR reaction containing 200 ng of *Aspergillus fumigatus* genomic DNA, 1× Pfx Amplification Buffer (Invitrogen, Carlsbad, CA, USA), 1 mM MgSO$_4$, 1.5 µl of 10 mM blend of dATP, dTTP, dGTP, and dCTP, 2.5 units of Pfx DNA polymerase (Invitrogen, Carlsbad, CA, USA), in a final volume of 50 µl. The amplification conditions were one cycle at 98° C. for 3 minutes; and 30 cycles each at 98° C. for 30 seconds, 57° C. for 30 seconds, and 72° C. for 75 seconds. The heat block was then held at 72° C. for 15 minutes followed by a 4° C. soak cycle.

The reaction products were isolated on a 1.0% agarose gel using TAE buffer and a 2.4 kb product band was excised from the gel and purified using a MinElute® Gel Extraction Kit (QIAGEN Inc., Valencia, CA) according to the manufacturer's instructions.

The fragment was then cloned into pAlLo2 using an IN-FUSION™ Cloning Kit. The vector was digested with Nco I and Pac I. The fragment was purified by gel electrophoresis and a QIAquick Kit (QIAGEN Inc., Valencia, CA, USA). The gene fragment and the digested vector were combined together in a reaction resulting in the expression plasmid pAG10, in which transcription of the *Aspergillus fumigatus* Family GH5 gene was under the control of the NA2-tpi promoter (a hybrid of the promoters from the genes for *Aspergillus niger* neutral alpha-amylase and *Aspergillus oryzae* triose phosphate isomerase). The recombination reaction (20 µl) was composed of 1× I IN-FUSION™ Buffer (Clontech, Mountain View, CA), 1×BSA (Clontech, Mountain View, CA), 1 µl of IN-FUSION™ enzyme (diluted 1:10) (Clontech, Mountain View, CA), 180 ng of pAlLo2 digested with Nco I and Pac 1, and 80 ng of the *Aspergillus fumigatus* beta-xylosidase purified PCR product. The reaction was incubated at ambient temperature for minutes. The reaction was diluted with 40 µl of TE buffer and 2.5 µl the diluted reaction was used to transform *E. coli* SOLOPACK® Gold cells. An *E. coli* transformant containing pAG10 (*Aspergillus fumigatus* Family GH5 gene) was identified by restriction enzyme digestion and plasmid DNA was prepared using a QIAGEN BioRobot 9600. The pAG10 plasmid construct was sequenced using an Applied Biosystems 3130xl Genetic Analyzer (Applied Biosystems, Foster City, CA, USA) to verify the sequence.

*Aspergillus oryzae* JaL355 protoplasts were prepared according to the method of Christensen et al., 1988, Bio/Technology 6: 1419-1422 and transformed with 5 µg of pAG10. Three transformants were isolated to individual PDA plates.

Plugs taken from the original transformation plate of each of the three transformants were added to 1 ml of M410 medium separately in 24 well plates, which were incubated at 34° C. After five days of incubation, 7.5 µl of supernatant from each culture was analyzed using CRITERION® stain-free, 8-16% gradient SDS-PAGE, (Bio-Rad Laboratories, Inc., Hercules, CA, USA) according to the manufacturer's instructions. SDS-PAGE profiles of the cultures showed that the transformants had a new major band of approximately 35 kDa.

Confluent PDA plate of the highest expressing transformant was washed with 5 ml of TWEEN® 20 and inoculated into three 500 ml Erlenmeyer flasks, each containing 100 ml of M410 medium. Inoculated flasks were incubated with shaking for 3 days at 34° C. The broths were pooled and filtered through a 0.22 µm stericup suction filter (Millipore, Bedford, MA, USA). A 35 ml volume of filtered broth was buffer exchanged into 50 mM sodium acetate pH using a 400 ml Sephadex G-25 column (GE Healthcare, United Kingdom) according to the manufacturer's instructions. Protein concentration was determined using a Microplate BCA™ Protein Assay Kit in which bovine serum albumin was used as a protein standard.

Example 72: Preparation of Neosartorya *Fischeri* Strain NRRL 181 GH5 Endoglucanase II The Neosartorya *fischeri* NRRL 181 GH5 endoglucanase II (SEQ ID NO: 175 [DNA sequence] and SEQ ID NO: 176 [deduced amino acid sequence]) was obtained according to the procedure described below.

Two synthetic oligonucleotide primers, shown below, were designed to PCR amplify the endoglucanase gene from Neosartorya *fischeri* NRRL 181 genomic DNA. Genomic DNA was isolated using a FastDNA spin for Soil Kit.

Primer #350:
(SEQ ID NO: 225)
5'-TAAGAATTCACCATGAAGGCTTCGACTATTATCTGTGCA-3'

Primer #358:
(SEQ ID NO: 226)
5'-TATGCGGCCGCACGGCAATCCAAGTCATTCAA-3'

The amplification reaction was composed of 1 µl of Neosartorya *fischeri* genomic DNA, 12.5 µl of 2× REDDY-MIX™ PCR Buffer, 1 µl of 5 µM primer #374, 1 µl of 5 µM primer #375, and 9.5 µl of H$_2$O. The amplification reaction was incubated in a PTC-200 DNA ENGINE™ Thermal Cycler programmed for 1 cycle at 94° C. for 2 minutes; and 35 cycles each at 94° C. for 15 seconds and 60° C. for 1.5 minutes.

A 1.4 kb PCR reaction product was isolated by 1% agarose gel electrophoresis using TAE buffer and staining with SYBR Safe DNA gel stain. The DNA band was visualized with the aid of an Eagle Eye Imaging System and a DarkReader Transilluminator. The 1.4 kb DNA band was excised from the gel and purified using a GFX® PCR DNA and Gel Band Purification Kit according to the manufacturer's instructions.

The 1.4 kb fragment was cleaved with EcoR I and Not I and purified using a GFX® PCR DNA and Gel Band Purification Kit according to the manufacturer's instructions.

The cleaved 1.4 kb fragment was then directionally cloned by ligation into Eco RI-Not I cleaved pXYG1051 (WO 2005/080559) using T4 ligase according to the manufacturer's instructions. The ligation mixture was transformed into *E. coli* TOP10F competent cells according to the manufacturer's instructions. The transformation mixture was plated onto LB plates supplemented with 100 µg of ampicillin per ml. Plasmid minipreps were prepared from several transformants and sequenced. One plasmid with the correct Neosartorya *fischeri* GH5 coding sequence was chosen.

The expression plasmid pXYG1051-NP003772 was transformed into *Aspergillus oryzae* JaL355 as described in WO 98/00529. Transformants were purified on selection plates to single conidia prior to sporulating them on PDA plates. Production of the *Neosartorya fischeri* GH5 polypeptide by the transformants was analyzed from culture supernatants of 1 ml 96 deep well stationary cultivations at 26° C. in YP medium with 2% maltodextrin. Expression was verified SDS-PAGE using a NUPAGE® NOVEX® 4-12% Bis-Tris Gel with MES buffer and Coomassie blue staining. One transformant was selected for further work and designated *Aspergillus oryzae* 83.3.

For larger scale production, *Aspergillus oryzae* 83.3 spores were spread onto a PDA plate and incubated for five days at 37° C. The confluent spore plate was washed twice with 5 ml of 0.01% TWEEN® 20 to maximize the number of spores collected. The spore suspension was then used to inoculate twenty-five 500 ml flasks containing 100 ml of YPG medium. The culture was incubated at 26° C. with constant shaking at 120 rpm. At day five post-inoculation, the culture broth was collected by filtration through a triple layer of Whatman glass microfiber filters of 1.6 µm, 1.2 µm, and 0.7 µm. Fresh culture broth from this transformant produced a band of GH7 protein of approximately 46 kDa. The identity of this band as the *Neosartorya fischeri* GH5 polypeptide was verified by peptide sequencing.

Two liters of the filtered broth were concentrated to 400 ml and washed with 50 mM HEPES pH 7.0 using a SARTOFLOW® Alpha ultrafiltration system with a 10 kDa MW-CO. Ammonium sulphate was added to a final concentration of 1 M and dissolved in the ultrafiltrate. The solution was applied on a Source 15 Phenyl XK 26/20 50 ml column. After application the column was washed with 150 ml of 1 M ammonium sulphate and eluded with 1 column volume of 50% ethanol in a 0% to 100% gradient followed by 5 column volumes of 50% ethanol at a flow rate of 10 ml/minute. Fractions of 10 ml were collected and analyzed by SDS-PAGE. Fraction 3 to 8 were pooled and diluted to 1000 ml with 50 mM HEPES pH 7.0 before application on a Q Sepharose® Fast Flow column XK26/20 60 ml column. After application the column was washed 3 times with 60 ml of 50 mM HEPES pH 7.0 and eluded with 100 ml of 50 mM HEPES pH 7.0, 1 M NaCl at a flow rate of 10 ml/minute. Fractions of 10 ml were collected and analyzed by SDS-PAGE. The flow-through and first wash were pooled and concentrated to 400 ml and washed with 50 mM HEPES pH 7.0 using the ultrafiltration system described above. Further concentration was conducted using a VIVASPIN™ centrifugal concentrator according to the manufacturer's instructions to a final volume of 80 ml. The protein concentration was determined by A280/A260 absorbance. Protein concentration was also determined using a Microplate BCA™ Protein Assay Kit in which bovine serum albumin was used as a protein standard.

Example 73: Preparation of *Aspergillus aculeatus* Strain WDCM190 GH3 Beta-Glucosidase The *Aspergillus aculeatus* strain WDCM190 GH3 beta-glucosidase (SEQ ID NO: 177 [DNA sequence] and SEQ ID NO: 178 [deduced amino acid sequence]) was obtained according to the procedure described below.

To generate genomic DNA for PCR amplification, *Aspergillus aculeatus* WDCM190 was propagated on PDA agar plates by growing at 26° C. for 7 days. Spores harvested from the PDA plates were inoculated into 25 ml of YP+2% glucose medium in a baffled shake flask and incubated at 26° C. for 48 hours with agitation at 200 rpm.

Genomic DNA was isolated according to a modified FastDNA® SPIN protocol (Qbiogene, Inc., Carlsbad, CA, USA). Briefly, a FastDNA® SPIN Kit for Soil (Qbiogene, Inc., Carlsbad, CA, USA) was used in a FastPrep® 24 Homogenization System (MP Biosciences, Santa Ana, CA, USA). Two ml of fungal material were harvested by centrifugation at 14,000×g for 2 minutes. The supernatant was removed and the pellet resuspended in 500 µl of deionized water. The suspension was transferred to a Lysing Matrix E FastPrep® tube (Qbiogene, Inc., Carlsbad, CA, USA) and 790 µl of sodium phosphate buffer and 100 µl of MT buffer from the FastDNA® SPIN Kit were added to the tube. The sample was then secured in a FastPrep® Instrument (Qbiogene, Inc., Carlsbad, CA, USA) and processed for 60 seconds at a speed of m/sec. The sample was then centrifuged at 14000×g for two minutes and the supernatant transferred to a clean EPPENDORF® tube. A 250 µl volume of PPS reagent from the FastDNA® SPIN Kit was added and then the sample was mixed gently by inversion. The sample was again centrifuged at 14000×g for 5 minutes. The supernatant was transferred to a ml tube followed by 1 ml of Binding Matrix suspension from the FastDNA® SPIN Kit and then mixed by inversion for two minutes. The sample was placed in a stationary tube rack and the silica matrix was allowed to settle for 3 minutes. A 500 µl volume of the supernatant was removed and discarded and then the remaining sample was resuspended in the matrix. The sample was then transferred to a SPIN filter tube from the FastDNA® SPIN Kit and centrifuged at 14000×g for 1 minute. The catch tube was emptied and the remaining matrix suspension added to the SPIN filter tube. The sample was again centrifuged (14000×g, 1 minute). A 500 µl volume of SEWS-M solution from the FastDNA® SPIN Kit was added to the SPIN filter tube and the sample was centrifuged at the same speed for 1 minute. The catch tube was emptied and the SPIN filter replaced in the catch tube. The unit was centrifuged at 14000×g for 2 minutes to "dry" the matrix of residual SEWS-M wash solution. The SPIN filter was placed in a fresh catch tube and allowed to air dry for 5 minutes at room temperature. The matrix was gently resuspended in 100 µl of DES (DNase/Pyrogen free water) with a pipette tip. The unit was centrifuged (14000×g, 1 minute) to elute the genomic DNA followed by elution with 100 µl of 10 mM Tris, 0.1 mM EDTA, pH 8.0 by renewed centrifugation at 14000×g for 1 minute and the eluates were combined. The concentration of the DNA harvested from the catch tube was measured by a UV spectrophotometer at 260 nm.

The *Aspergillus aculeatus* Cel3 beta-glucosidase gene was isolated by PCR using two cloning primers GH3-8f and GH3-8r shown below, which were designed based on the publicly available *Aspergillus aculeatus* Cel3 mRNA sequence (Genbank D64088.1) for direct cloning by IN-FUSION™ strategy.

```
Primer GH3-8f:
                                    (SEQ ID NO: 227)
5'-acacaactggggatccaccatgaagctcagttggcttgaggcgg-3'

Primer GH3-8r:
                                    (SEQ ID NO: 228)
5'-agatctcgagaagcttattgcaccttcgggagcgccgcgtgaag-3'
```

A PCR reaction was performed with genomic DNA prepared from *Aspergillus aculeatus* strain (IAM2445; WDCM190) in order to amplify the full-length gene. The PCR reaction was composed of 1 µl of genomic DNA, 0.75 µl of primer GH3-8f (10 µM), 0.75 µl of primer GH3-8r (10 µM), 3 µl of 5× HF buffer, 0.25 µl of 50 mM MgCl$_2$, 0.3 µl of 10 mM dNTP, 0.15 µl of PHUSION® DNA polymerase, and PCR-grade water up to 15 µl. The PCR reaction was performed using a DYAD® PCR machine programmed for 2 minutes at 98° C. followed by 10 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds, and 5 minutes at 72° C.

The reaction products were isolated by 1.0% agarose gel electrophoresis using TAE buffer where an approximately 2.9 kb PCR product band was excised from the gel and purified using a GFX® PCR DNA and Gel Band Purification Kit according to manufacturer's instructions. DNA corresponding to the *Aspergillus aculeatus* Cel3 beta-glucosidase gene was cloned into the expression vector pDAu109 (WO 2005042735) linearized with Bam HI and Hind III, using an IN-FUSION™ Dry-Down PCR Cloning Kit according to the manufacturer's instructions.

A 2.5 µl volume of the diluted ligation mixture was used to transform *E. coli* TOP10 chemically competent cells. Three colonies were selected on LB agar plates containing 100 µg of ampicillin per ml and cultivated overnight in 3 ml of LB medium supplemented with 100 µg of ampicillin per ml. Plasmid DNA was purified using an E.Z.N.A.® Plasmid Mini Kit according to the manufacturer's instructions. The *Aspergillus aculeatus* Cel3 beta-glucosidase gene sequence was verified by Sanger sequencing before heterologous expression.

The coding sequence is 2940 bp including the stop codon and is interrupted by 6 introns of 73 bp (nucleotides 58 to 130), 52 bp (nucleotides 274 to 325), 57 bp (nucleotides 371 to 427), 61 bp (nucleotides 481 to 541), 64 bp (nucleotides 1734 to 1797), and 50 bp (nucleotides 2657 to 2706). The encoded predicted protein is 860 amino acids. Using the SignalP program (Nielsen et al., 1997, *Protein Engineering* 10: 1-6), a signal peptide of 19 residues was predicted. The predicted mature protein contains 841 amino acids.

Protoplasts of *Aspergillus oryzae* BECh2 (WO 2000/39322) were prepared as described in WO 95/02043. One hundred microliters of protoplast suspension were mixed with 2.5-15 µg of the *Aspergillus* expression vector and 250 µl of 60% PEG 4000 (Applichem Inc. Omaha, NE, USA) (polyethylene glycol, molecular weight 4,000), 10 mM CaCl$_2$, and 10 mM Tris-HCl pH 7.5 were added and gently mixed. The mixture was incubated at 37° C. for 30 minutes and the protoplasts were spread on COVE sucrose (1 M) plates supplemented with 10 mM acetamide and 15 mM CsCl for transformant selection. After incubation for 4-7 days at 37° C. spores of several transformants were seeded on YP-2% maltodextrin medium. After 4 days cultivation at culture broth was analyzed in order to identify the best transformants based on their ability to produce a large amount of active *Aspergillus aculeatus* Cel3 beta-glucosidase. The screening was based on intensity of the band corresponding to the heterologous expressed protein determined by SDS-PAGE and activity of the enzyme on 4-nitrophenyl-beta-D-glucopyranoside (pNPG) as described in Example 16 herein.

Spores of the best transformant designated were spread on COVE plates containing 0.01% TRITON® X-100 in order to isolate single colonies. The spreading was repeated twice in total on COVE sucrose medium (Cove, 1996, *Biochim. Biophys. Acta* 133: 51-56) containing 1 M sucrose and 10 mM sodium nitrate, supplemented with 10 mM acetamide and 15 mM CsCl. Fermentation was then carried out in 250 ml shake flasks using YP-2% maltodextrin medium for 4 days at 30° C. with shaking at 100 rpm. The broth was filtered using standard methods. Protein concentration was determined using a Microplate BCA™ Protein Assay Kit in which bovine serum albumin was used as a protein standard.

Example 74: Preparation of *Aspergillus kawashii* Strain IFO 4308 GH3 Beta-Glucosidase The *Aspergillus kawashii* strain IFO 4308 GH3 beta-glucosidase (SEQ ID NO: 179 [DNA sequence] and SEQ ID NO: 180 [deduced amino acid sequence]) was obtained according to the procedure described below.

To generate genomic DNA for PCR amplification, the fungi were propagated on PDA agar plates by growing at 26° C. for 7 days. Spores harvested from the PDA plates were used to inoculate 25 ml of YP+2% glucose medium in a baffled shake flask and incubated at 26° C. for 48 hours with agitation at 200 rpm.

Genomic DNA was isolated according to the procedure described in Example 73.

The Aspergiiius kawachii beta-glucosidase gene was isolated by PCR using two cloning primers GH3-33f and GH3-33r shown below, which were designed based on the publicly available *Aspergillus kawachii* full-length sequence (GenBank AB003470.1) for direct cloning by IN-FUSION™ strategy.

```
Primer GH3-33f:
                                   (SEQ ID NO: 229)
acacaactggggatccaccatgaggttcactttgattgaggcgg Primer GH3-33r:
                                   (SEQ ID NO: 230)
agatctcgagaagcttaGTGAACAGTAGGCAGAGACGCCCGGAGC
```

A PCR reaction was performed with the genomic DNA prepared from *Aspergillus kawachii* IFO 4308 in order to amplify the full-length gene. The PCR reaction was composed of 1 µl of genomic DNA, 0.75 µl of primer GH3-33f (10 µM), 0.75 µl of primer GH3-33r (10 µM), 3 µl of 5× HF buffer, 0.25 µl of 50 mM MgCl$_2$, 0.3 µl of 10 mM dNTP, 0.15 µl of PHUSION® DNA polymerase, and PCR-grade water up to 15 µl. The PCR reaction was performed using a DYAD® PCR machine programmed for 2 minutes at 98° C. followed by 10 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds, and 5 minutes at 72° C.

The reaction products were isolated by 1.0% agarose gel electrophoresis using TAE buffer where an approximately 2.9 kb PCR product band was excised from the gel and purified using a GFX® PCR DNA and Gel Band Purification Kit according to manufacturer's instructions. DNA corresponding to the *Aspergillus kawachii* beta-glucosidase gene was cloned into the expression vector pDAu109 (WO 2005042735) linearized with Bam HI and Hind III, using an IN-FUSION™ Dry-Down PCR Cloning Kit according to the manufacturer's instructions.

A 2.5 µl volume of the diluted ligation mixture was used to transform *E. coli* TOP10 chemically competent cells. Three colonies were selected on LB agar plates containing 100 µg of ampicillin per ml and cultivated overnight in 3 ml of LB medium supplemented with 100 µg of ampicillin per ml. Plasmid DNA was purified using an E.Z.N.A.® Plasmid Mini Kit according to the manufacturer's instructions. The *Aspergillus kawachii* beta-glucosidase gene sequence was verified by Sanger sequencing before heterologous expression.

The coding sequence is 2935 bp including the stop codon and is interrupted by 6 introns of 92 bp (nucleotides 58 to 149), 48 bp (nucleotides 293 to 340), 54 bp (nucleotides 386 to 439), 51 bp (nucleotides 493 to 543), 57 bp (nucleotides 1736 to 1792), and 50 bp (nucleotides 2652 to 2701). The encoded predicted protein is 860 amino acids. Using the SignalP program (Nielsen et al., 1997, *Protein Engineering* 10: 1-6), a signal peptide of 19 residues was predicted. The predicted mature protein contains 841 amino acids.

Protoplasts of *Aspergillus oryzae* BECh2 (WO 2000/39322) were prepared as described in WO 95/02043. One hundred microliters of protoplast suspension were mixed with 2.5-15 µg of the *Aspergillus* expression vector and 250 µl of 60% PEG 4000, 10 mM CaCl$_2$, and 10 mM Tris-HCl pH 7.5 were added and gently mixed. The mixture was incubated at 37° C. for 30 minutes and the protoplasts were spread on COVE sucrose (1 M) plates supplemented with 10 mM acetamide and 15 mM CsCl for transformant selection. After incubation for 4-7 days at 37° C. spores of several transformants were seeded on YP-2% maltodextrin medium. After 4 days cultivation at 30° C. culture broth was analyzed in order to identify the best transformants based on their ability to produce a large amount of active *Aspergillus kawachii* beta-glucosidase. The screening was based on intensity of the band corresponding to the heterologous expressed protein determined by SDS-PAGE and activity of the enzyme on 4-nitrophenyl-beta-D-glucopyranoside (pNPG) as described in Example 16 herein.

Spores of the best transformant were spread on COVE plates containing 0.01% TRITON® X-100 in order to isolate single colonies. The spreading was repeated twice in total on COVE sucrose medium (Cove, 1996, *Biochim. Biophys. Acta* 133: 51-56) containing 1 M sucrose and 10 mM sodium nitrate, supplemented with 10 mM acetamide and 15 mM CsCl. Fermentation was then carried out in 250 ml shake flasks using YP-2% maltodextrin medium for 4 days at 30° C. with shaking at 100 rpm. The broth was filtered using standard methods. Protein concentration was determined using a Microplate BCA™ Protein Assay Kit in which bovine serum albumin was used as a protein standard.

Example 75: Preparation of *Aspergillus clavatus* Strain NRRL 1 GH3 Beta-Glucosidase The *Aspergillus clavatus* strain NRRL 1 GH3 beta-glucosidase (SEQ ID NO: 181 [DNA sequence] and SEQ ID NO: 182 [deduced amino acid sequence]) was obtained according to the procedure described below.

Genomic DNA was isolated according to the procedure described in Example 73.

The *Aspergillus clavatus* beta-glucosidase gene was isolated by PCR using two cloning primers, GH3-10f and GH3-10r, shown below, which were designed based on the publicly available *Aspergillus clavatus* partial mRNA sequence (XM_001269581) for direct cloning by IN-FUSION™ strategy.

Primer GH3-10f:
(SEQ ID NO: 231)
acacaactggggatccaccATGAGGTTCAGCTGGCTTGAGGTCG

Primer GH3-10r:
(SEQ ID NO: 232)
agatctcgagaagcttaCTGTACCCGGGGCAGAGGTGCTCTC

A PCR reaction was performed with the genomic DNA prepared from *Aspergillus clavatus* NRRL1 in order to amplify the full-length gene. The PCR reaction was composed of 1 µl of genomic DNA, 0.75 µl of primer GH3-10f (10 µM), 0.75 µl of primer GH3-10r (10 µM), 3 µl of 5× HF buffer, 0.25 µl of 50 mM MgCl$_2$, 0.3 µl of 10 mM dNTP, 0.15 µl of PHUSION® DNA polymerase, and PCR-grade water up to 15 µl. The PCR reaction was performed using a DYAD® PCR machine programmed for 2 minutes at 98° C. followed by 10 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds, and 5 minutes at 72° C.

The reaction products were isolated by 1.0% agarose gel electrophoresis using TAE buffer where an approximately 3.0 kb PCR product band was excised from the gel and purified using a GFX® PCR DNA and Gel Band Purification Kit according to manufacturer's instructions. DNA corresponding to the *Aspergillus clavatus* beta-glucosidase gene was cloned into the expression vector pDAu109 (WO 2005042735) linearized with Bam HI and Hind III, using an IN-FUSION™ Dry-Down PCR Cloning Kit according to the manufacturer's instructions.

A 2.5 µl volume of the diluted ligation mixture was used to transform *E. coli* TOP10 chemically competent cells. Three colonies were selected on LB agar plates containing 100 µg of ampicillin per ml and cultivated overnight in 3 ml of LB medium supplemented with 100 µg of ampicillin per ml. Plasmid DNA was purified using an E.Z.N.A.® Plasmid Mini Kit according to the manufacturer's instructions. The *Aspergillus clavatus* beta-glucosidase gene sequence was verified by Sanger sequencing before heterologous expression.

The coding sequence is 3062 bp including the stop codon and is interrupted by 8 introns of 67 bp (nucleotides 58 to 124), 61 bp (nucleotides 265 to 325), 62 bp (nucleotides 371 to 432), bp (nucleotides 489 to 553), 50 bp (nucleotides 948 to 997), 53 bp (nucleotides 1021 to 1073), 61 bp (nucleotides 1849 to 1909), and 60 bp (nucleotides 2769 to 2828). The encoded predicted protein is 860 amino acids. Using the SignalP program (Nielsen et al., 1997, *Protein Engineering* 10: 1-6), a signal peptide of 18 residues was predicted. The predicted mature protein contains 842 amino acids.

Protoplasts of *Aspergillus oryzae* BECh2 (WO 2000/39322) were prepared as described in WO 95/02043. One hundred microliters of protoplast suspension were mixed with 2.5-15 µg of the *Aspergillus* expression vector and 250 µl of 60% PEG 4000, 10 mM CaCl$_2$, and 10 mM Tris-HCl pH 7.5 were added and gently mixed. The mixture was incubated at 37° C. for 30 minutes and the protoplasts were spread on COVE sucrose (1 M) plates supplemented with 10 mM acetamide and 15 mM CsCl for transformant selection. After incubation for 4-7 days at 37° C. spores of several transformants were seeded on YP-2% maltodextrin medium. After 4 days cultivation at 30° C. culture broth was analyzed in order to identify the best transformants based on their ability to produce a large amount of active *Aspergillus clavatus* beta-glycosidase. The screening was based on intensity of the band corresponding to the heterologous expressed protein determined by SDS-PAGE and activity of the enzyme on 4-nitrophenyl-beta-D-glucopyranoside (pNPG) as described in Example 16.

Spores of the best transformant were spread on COVE plates containing 0.01% TRITON® X-100 in order to isolate single colonies. The spreading was repeated twice in total on COVE sucrose medium (Cove, 1996, *Biochim. Biophys. Acta* 133: 51-56) containing 1 M sucrose and 10 mM sodium nitrate, supplemented with 10 mM acetamide and 15 mM CsCl. Fermentation was then carried out in 250 ml shake flasks using YP-2% maltodextrin medium for 4 days at 30° C. with shaking at 100 rpm. The broth was filtered using standard methods. Protein concentration was determined using a Microplate BCA™ Protein Assay Kit in which bovine serum albumin was used as a protein standard.

Example 76: Preparation of *Thielavia terrestris* NRRL 8126 GH3 Beta-Glucosidase The *Thielavia terrestris* GH3 beta-glucosidase (SEQ ID NO: 183 [DNA sequence] and SEQ ID NO: 184 [deduced amino acid sequence]) was obtained according to the procedure described below.

Three agarose plugs from culture of *Thielavia terrestris* NRRL 8126 grown on a PDA plate were inoculated into 100 ml of NNCYP medium supplemented with 1.5% glucose and incubated for 25 hours at 42° C. and 200 rpm on an orbital shaker. Fifty ml of this culture was used to inoculate a 1.8 liter of NNCYP medium supplemented with 0.4% glucose and 52 g of powdered cellulose per liter and was incubated at 42° C. The pH was controlled at 5.0 by the addition of 15% ammonium hydroxide or 5 N phosphoric acid, as needed.

The fermentations were run at 42° C. with minimum dissolved oxygen at 25% at a 1.0 VVM air flow and an agitation at 1100 rpm. Feed medium was delivered into a 2 liter fermentation vessel at 0 hours with a feed rate of 6.0-8.0 g/hour for 120 hours. Pooled cultures were centrifuged at 3000×g for 10 minutes and the supernatant was filtered through a disposable filtering unit with a glass fiber prefilter (Nalgene, Rochester NY, USA). The filtrate was cooled to 4° C. for storage.

A 0.3 ml aliquot of the filtrate was precipitated with 10% trichloroacetic acid (TCA)-80% acetone for 20 minutes on ice. The suspension was centrifuged for 10 minutes at 13,000×g. The supernatant was removed and the protein pellet remaining was rinsed with cold acetone. The protein pellet was dissolved in 30 μl of 1× lithium dodecyl sulfate (LDS) SDS-PAGE loading buffer with 50 mM dithiothreitol (DTT) and heated at 80° C. for 10 minutes. A 15 μl sample was separated by SDS-PAGE using a 7 cm 4-12% NuPAGE Bis-Tris SDS-PAGE gradient gel and 2-(N-morpholino) ethanesulfonic acid (MES) running buffer. The SDS-PAGE was run under reducing conditions according to the manufacturer's recommended protocol (Invitrogen, Carlsbad, CA, USA). The gel was removed from the cassette and rinsed 3 times with deionized water for at least 5 minutes each and stained with Bio-Safe Coomassie Stain (Bio-Rad Laboratories, Inc., Hercules, CA, USA) for 1 hour followed by destaining with doubly-distilled water for more than 30 minutes. Protein bands observed at approximately 95 kD was excised and reduced with 50 μl of 10 mM DTT in 100 mM ammonium bicarbonate for 30 minutes. Following reduction, the gel pieces were alkylated with 50 μl of 55 mM iodoacetamide in 100 mM ammonium bicarbonate for 20 minutes. The dried gel pieces were allowed to re-hydrate in a trypsin digestion solution (6 ng/μl sequencing grade trypsin in 50 mM ammonium bicarbonate) for 30 minutes at room temperature, followed by an 8 hour digestion at 40° C. Each of the reaction steps described was followed by numerous washes and pre-washes with the desired solutions. Fifty μl of acetonitrile was used to de-hydrate the gel pieces between reactions and they were air-dried between steps. Peptides were extracted twice with 1% formic acid/2% acetonitrile in HPLC grade water for 30 minutes. Peptide extraction solutions were transferred to a 96 well PCR type microtiter plate that had been cooled to 10-15° C. Microtiter plates containing the recovered peptide solutions were sealed to prevent evaporation and stored at 4° C. until mass spectrometry analysis could be performed.

For de-novo peptide sequencing by tandem mass spectrometry, a Q-Tof Micro™, a hybrid orthogonal quadrupole time-of-flight mass spectrometer (Waters Micromass® MS Technologies, Milford, MA, USA) was used for LC/MS/MS analysis. The Q-Tof Micro™ was fitted with an Ultimate™ capillary and nano-flow HPLC system which had been coupled with a FAMOS micro autosampler and a Switchos II column switching device (LCPackings, San Francisco, CA, USA) for concentrating and desalting samples. Samples were loaded onto a guard column (300 μm ID×5 cm, C18 pepmap) fitted in the injection loop and washed with formic acid in water at 40 μl/minute for 2 minutes using the Switchos II pump. Peptides were separated on a 75 μm ID×15 cm, C18, 3 μm, 100 Å PepMap™ (LC Packings, San Francisco, CA, USA) nanoflow fused capillary column at a flow rate of 175 nl/minute from a split flow of 175 μl/minute using a NAN-75 calibrator (Dionex, Sunnyvale, CA, USA). A step elution gradient of 5% to 80% acetonitrile in 0.1% formic acid was applied over a 45 minute interval. The column eluent was monitored at 215 nm and introduced into the Q-Tof Micro™ through an electrospray ion source fitted with the nanospray interface. The Q-Tof Micro™ is fully microprocessor controlled using Masslynx™ software version 3.5 (Waters Micromass® MS Technologies, Milford, MA, USA). Data was acquired in survey scan mode and from a mass range of m/z 400 to 1990 with the switching criteria for MS to MS/MS to include an ion intensity of greater than 10.0 counts per second and charge states of +2, +3, and +4. Analysis spectra of up to 4 co-eluting species with a scan time of 1.9 seconds and inter-scan time of 0.1 seconds could be obtained. A cone voltage of 65 volts was typically used and the collision energy was programmed to be varied according to the mass and charge state of the eluting peptide and in the range of 10-60 volts. The acquired spectra were combined, smoothed and centered in an automated fashion and a peak list generated. This peak list was searched against selected public and private databases using ProteinLynx™ Global Server 1.1 software (Waters Micromass® MS Technologies, Milford, MA). Results from the ProteinLynx™ searches were evaluated and un-identified proteins were analyzed further by evaluating the MS/MS spectrums of each ion of interest and de-novo sequence was determined by identifying the y and b ion series and matching mass differences to the appropriate amino acid.

Peptide sequences obtained from de novo sequencing by mass spectrometry were obtained from several multiply charged ions for the approximately 95 kDa polypeptide gel band.

A doubly charged tryptic peptide ion of 524.76 m/z sequence was determined to be Ser-Pro-Phe-Thr-Trp-Gly-Pro-Thr-Arg (amino acids 607 to 615 of SEQ ID NO: 184). A second doubly charged tryptic peptide ion of 709.91 partial sequence was determined to be Gly-Val-Asn-Val-[Ile/Leu]-[Ile-Leu]-Gly-[Ile/Leu]-Gly-Pro (amino acids 148 to 155 of SEQ ID NO: 184). A second doubly charged tryptic peptide ion of 745.38 partial sequence was determined to be Pro-Pro-His-Ala-Thr-Asp (amino acids 747 to 752 of SEQ ID NO: 184). A third doubly charged tryptic peptide ion of 808.92 m/z sequence was determined to be Tyr-Glu-Ser-[Ile/Leu]-[Ile/Leu]-Ser-Asn-Tyr-Ala-Thr-Ser-Q1n-[Ile/Leu]-Lys (amino acids 487 to 499 of SEQ ID NO: 184). A fourth doubly charged tryptic peptide ion of 1023.96 a partial sequence was determined to be Phe-Asn-Ser-Gly-Phe-Pro-Ser-Gly-Gln-Thr-Ala-Ala-Ala-Thr-Phe-Asp-Arg (amino acids 114 to 130 of SEQ ID NO: 184).

To generate genomic DNA for PCR amplification, *Thielavia terrestris* NRRL 8126 was grown in 50 ml of NNCYP medium supplemented with 1% glucose in a baffled shake flask at 42° C. and 200 rpm for 24 hours. Mycelia were harvested by filtration, washed twice in TE (10 mM Tris-1 mM EDTA), and frozen under liquid nitrogen. A pea-size piece of frozen mycelia was suspended in 0.7 ml of 1% lithium dodecyl sulfate in TE and disrupted by agitation with an equal volume of 0.1 mm zirconia/silica beads (Biospec Products, Inc., Bartlesville, OK, USA) for 45 seconds in a FastPrep FP120 (ThermoSavant, Holbrook, NY, USA). Debris was removed by centrifugation at 13,000×g for 10 minutes and the cleared supernatant was brought to 2.5 M ammonium acetate and incubated on ice for 20 minutes. After the incubation period, the nucleic acids were precipitated by addition of 2 volumes of ethanol. After centrifugation for 15 minutes in a microfuge at 4° C., the pellet was washed in 70% ethanol and air dried. The DNA was resuspended in 120 µl of 0.1×TE and incubated with 1 µl of DNase-free RNase A at 37° C. for minutes. Ammonium acetate was added to 2.5 M and the DNA was precipitated with 2 volumes of ethanol. The pellet was washed in 70% ethanol, air dried, and resuspended in TE buffer.

A low redundancy draft sequence of the *Thielavia terrestris* NRRL 8126 genome was generated by the Joint Genome Center (JGI), Walnut Creek, CA, USA, using the whole genome shotgun method according to Martinez et al., 2008, *Nature Biotechnol.* 26: 553-560. Shotgun sequencing reads (approximately 18307) were assembled into contigs using the Phrap assembler (Ewing and Green, 1998, *Genome Res.* 8: 186-194).

A tblastn search (Altschul et al., 1997, *Nucleic Acids Res.* 25: 3389-3402) of the assembled contigs was carried out using as query a beta-glucosidase protein sequence from *Neurospora crassa* (UniProt accession number q7rwp2). A translated amino acid sequence with greater than 73.8% identity to the query sequence was identified.

The sequence was searched against public databases using blastp (Altschul et al., 1997, supra) and was found to be 80.1% identical to a beta-glucosidase from *Podospora anserina* (UniProt accession number B2AVE8).

The nucleotide sequence and deduced amino acid sequence of the *Thielavia terrestris* beta-glucosidase gene are shown in SEQ ID NO: 183 and SEQ ID NO: 184, respectively. The coding sequence is 3032 bp including the stop codon and is interrupted by three introns of 295 bp, 57 bp, and 61 bp. The encoded predicted protein is 872 amino acids. Using the SignalP program (Nielsen et al., 1997, *Protein Engineering* 10: 1-6), a signal peptide of 18 residues was predicted. The predicted mature protein contains 854 amino acids with a predicted molecular mass of 93 kDa and an isoelectric point of 5.57.

*Thielavia terrestris* NRRL 8126 was grown for 3 days on PDA plates at 45° C. Mycelia were scraped from the plates and approximately 100 mg of mycelia (wet weight) were used to inoculate 500 ml shake flasks containing 100 ml of either MY50 medium or 1× Vogel's medium supplemented with 2% microcrystalline cellulose (AVICEL®). Cultures were grown for 2, 3, 4 and 5 days at 45° C. with vigorous shaking. The mycelia were harvested by filtration through MIRACLOTH® (EMD Chemicals Inc., Gibbstown, NJ, USA), and quick frozen in liquid nitrogen.

To isolate total RNA frozen mycelia of *Thielavia terrestris* NRRL 8126 were ground in an electric coffee grinder. The ground material was mixed 1:1 v/v with 20 ml of FENAZOL™ (Ambion, Inc., Austin, TX, USA) in a 50 ml tube. Once the mycelia were suspended, they were extracted with chloroform and three times with a mixture of phenol-chloroform-isoamyl alcohol 25:24:1 v/v/v. From the resulting aqueous phase, the RNA was precipitated by adding 1/10 volume of 3 M sodium acetate pH 5.2 and 1.25 volumes of isopropanol. The precipitated RNA was recovered by centrifugation at 12,000×g for 30 minutes at 4° C. The final pellet was washed with cold 70% ethanol, air dried, and resuspended in 500 ml of diethylpyrocarbonate treated water (DEPC-water).

RNA samples were pooled and the quality and quantity of the purified RNA was assessed with an AGILENT® 2100 Bioanalyzer (Agilent Technologies, Inc., Palo Alto, CA, USA). A total of 630 µg of RNA was isolated.

Poly A+ RNA was isolated from total RNA using an Absolutely mRNA™ Purification Kit (Stratagene, La Jolla, CA, USA) according to the manufacturer's instructions. cDNA synthesis and cloning was performed according to a procedure based on the SuperScript™ Plasmid System with Gateway® Technology for cDNA Synthesis and Cloning (Invitrogen, Carsbad, CA, USA). 1-2 µg of poly A+ RNA, reverse transcriptase SuperScript II (Invitrogen, Carsbad, CA, USA), and oligo dT-Not I primer 5'-GACTAGTTCTA-GATCGCGAGCGGCCGCCCTTTTTTTTTTTTTTVN-3' (SEQ ID NO: 233) were used to synthesize first strand cDNA. Second strand synthesis was performed with *E. coli* DNA ligase, polymerase I, and RNase H followed by end repair using T4 DNA polymerase. The Sal I adaptor (5'-TCGACCCACGCGTCCG-3' [SEQ ID NO: 234] and 5'-CGGACGCGTGGG-3' [SEQ ID NO: 235]) was ligated to the cDNA, digested with Not I, and subsequently size selected (>2 kb) by 1.1% agarose gel electrophoresis using TAE buffer. The cDNA inserts were directionally ligated into Sal I and Not I digested vector pCMVsport6 (Invitrogen, Carsbad, CA, USA). The ligation was transformed into ElectroMAX™ DH10B™ T1 cells (Invitrogen, Carsbad, CA, USA).

Library quality was first assessed by randomly selecting 24 clones and PCR amplifying the cDNA inserts with the primers M13-F and M13-R shown below to determine the fraction of insertless clones.

```
Primer M13-F:
                                (SEQ ID NO: 236)
5'-GTAAAACGACGGCCAGT-3'

Primer M13-R:
                                (SEQ ID NO: 237)
5'-AGGAAACAGCTATGACCAT-3'
```

Colonies from each library were plated onto LB plates at a density of approximately 1000 colonies per plate. Plates were grown at 37° C. for 18 hours and then individual colonies were picked and each used to inoculate a well containing LB medium supplemented with 100 µg of ampicillin per ml in a 384 well plate (Nunc, Rochester, NY, USA). Clones were grown at 37° C. for 18 hours. Plasmid DNA for sequencing was produced by rolling circle amplification using a Templiphi™ Kit (GE Healthcare, Piscataway, NJ, USA). Subclone inserts were sequenced from both ends using primers complimentary to the flanking vector sequence as shown below and BigDye® terminator chemistry using a 3730 DNA Analyzer (Applied Biosystems, Foster City, CA, USA).

```
Forward primer:
                                    (SEQ ID NO: 238)
5'-ATTTAGGTGACACTATAGAA-3'

Reverse primer:
                                    (SEQ ID NO: 239)
5'-TAATACGACTCACTATAGGG-3'
```

A clone showing 67.4% identity at the nucleotide level to a beta-glucosidase from *Aspergillus oryzae* (U.S. Published Application No. 2005233423) was identified.

Two synthetic oligonucleotide primers shown below were designed to PCR amplify the *Thielavia terrestris* Family GH3B beta-glucosidase gene from the cDNA clone. An IN-FUSION® Cloning Kit (BD Biosciences, Palo Alto, CA, USA) was used to clone the fragment directly into the expression vector pAlLo2 (WO 2005/074647), without the need for restriction digestion and ligation.

```
Forward primer:
                                    (SEQ ID NO: 240)
5'-ACTGGATTTACCATGAAGCCTGCCATTGTGCT-3'

Reverse primer:
                                    (SEQ ID NO: 241)
5'-TCACCTCTAGTTAATTAATCACGGCAACTCAATGCTCA-3'
```

Bold letters represent coding sequence. The remaining sequence is homologous to the insertion sites of pAlLo2.

Fifty picomoles of each of the primers above were used in a PCR reaction containing 200 ng of plasmid cDNA, 1×2× Advantage GC-Melt LA Buffer (Clonetech Laboratories, Inc., Mountain View, CA, USA), 1 µl of 10 mM blend of dATP, dTTP, dGTP, and dCTP, and 1.25 units of Advantage GC Genomic LA Polymerase Mix (Clonetech Laboratories, Inc., Mountain View, CA, USA) in a final volume of 50 µl. The amplification was performed using an EPPENDORF® MASTERCYCLER® 5333 epgradient S (Eppendorf Scientific, Inc., Westbury, NY, USA) programmed for one cycle at 94° C. for 1 minute; and 30 cycles each at 94° C. for 30 seconds, 60.5° C. for 30 seconds, and 72° C. for 3 minutes. The heat block was then held at 72° C. for 15 minutes followed by a 4° C. soak cycle.

The reaction products were isolated by 1.0% agarose gel electrophoresis using TAE buffer where an approximately 2.6 kb product band was excised from the gel and purified using a MINELUTE® Gel Extraction Kit (QIAGEN Inc., Valencia, CA, USA) according to the manufacturer's instructions.

The fragment was then cloned into pAlLo2 using an IN-FUSION® Cloning Kit. The vector was digested with Nco I and Pac I. The fragment was purified by gel electrophoresis as above and a QIAQUICK® Gel Purification Kit (QIAGEN Inc., Valencia, CA, USA). The gene fragment and the digested vector were combined together in a reaction resulting in the expression plasmid pAG81, in which transcription of the Family GH3B protein gene was under the control of the NA2-tpi promoter (a hybrid of the promoters from the genes for *Aspergillus niger* neutral alpha-amylase and *Aspergillus nidulans* triose phosphate isomerase). The recombination reaction (10 µl) was composed of 1× IN-FUSION® Buffer (BD Biosciences, Palo Alto, CA, USA), 1×BSA (BD Biosciences, Palo Alto, CA, USA), 1 µl of IN-FUSION® enzyme (diluted 1:10) (BD Biosciences, Palo Alto, CA, USA), 108 ng of pAlLo2 digested with Nco I and Pac 1, and 94 ng of the *Thielavia terrestris* GH3B protein purified PCR product. The reaction was incubated at 37° C. for 15 minutes followed by 15 minutes at 50° C. The reaction was diluted with 40 µl of 10 mM Tris-0.1 M EDTA buffer and 2.5 µl the diluted reaction was used to transform *E. coli* TOP10 Competent cells. An *E. coli* transformant containing pAG81 (GH3B protein gene) was identified by restriction enzyme digestion and plasmid DNA was prepared using a BIOROBOT® 9600. The plasmid construct was sequenced using an Applied Biosystems 3130xl Genetic Analyzer (Applied Biosystems, Foster City, CA, USA) to verify the gene sequence.

*Aspergillus oryzae* JaL355 protoplasts were prepared according to the method of Christensen et al., 1988, Bio/Technology 6: 1419-1422, which were transformed with 5 µg of pAG81. Twenty-six transformants were isolated to individual PDA plates. A small plug from each transformant was used to inoculate 1 ml of M410 media in a 24 well plate and incubated at 34° C. After 5 days of incubation, 7.5 µl of supernatant from four transformants was analyzed using a CRITERION® stain-free, 8-16% gradient SDS-PAGE gel (Bio-Rad Laboratories, Inc., Hercules, CA, USA) according to the manufacturer's instructions. SDS-PAGE profiles of the cultures showed that several transformants had a new major band of approximately 150 kDa.

A confluent PDA plate of the top transformant (was washed with 5 ml of 0.01% TWEEN® 20 and inoculated into 500 ml flasks each containing 100 ml of M410 medium to generate broth for characterization of the enzyme. The flasks were harvested on day 5, filtered using a 0.22 µm stericup suction filter (Millipore, Bedford, MA, USA), and stored at 4° C.

A 45 ml aliquot of shake flask broth prepared was concentrated ten-fold using a VIVASPIN™ centrifugal concentrator with a molecular weight cut-off of 10 kDa and buffer-exchanged into 50 mM sodium acetate of pH 5. A 4 ml aliquot of the buffer-exchanged, concentrated broth was then diluted to a 10 ml volume with 1 M Tris-HCl pH 8 and water to a concentration of 20 mM Tris-HCl, and the pH adjusted to a final value of 8 using 2 N sodium hydroxide. The resulting material was then purified using a MONO Q™ 5/5 column (GE Healthcare, Piscataway, NJ, USA) equilibrated with 20 mM Tris-HCl buffer pH 7.8. Unbound material was washed from the column with 2 ml equilibration buffer, and then the column was eluted with a linear gradient from 0-500 mM sodium chloride in the equilibration buffer. Fractions of 0.3 ml were collected. Unbound material collected during column loading and unbound material washed from the column were pooled for a total volume of 12 ml. Five µl of the fractions, including the pooled unbound material, showing UV absorbance at 280 nm were analyzed using a CRITERION STAIN FREE™ 8-16% Tris-HCl SDS-PAGE gel (Bio-Rad Laboratories, Inc., Hercules, CA, USA) according to the manufacturer's instructions. Precision Plus Protein™ unstained standards (Bio-Rad Laboratories, Inc., Hercules, CA, USA) were used as molecular weight markers. The gel was removed from the cassette and imaged using a CRITERION STAIN FREE™ IMAGER (Bio-Rad Laboratories, Inc., Hercules, CA, USA). The beta-glucosidase was identified in the pooled unbound material as a band at 150 kDa by SDS-PAGE. The 12 ml of pooled unbound material was concentrated as described above to a final volume of 2 ml. The concentrated material was purified using a HI LOAD™ 16/60 SUPERDEX™ PREP GRADE column (GE Healthcare, Piscataway, NJ, USA) equilibrated with 20 mM Tris.HCl buffer of pH 7.8 containing 150 mM sodium chloride, and eluted with the equilibration buffer. Fractions of 3 ml were collected. Column fractions were analyzed by SDS-PAGE as described above. Fractions containing the purified beta-glucosidase, identified by a band at 150 kDa by SDS-PAGE, were pooled for a total volume of 6 ml. The pooled material was concentrated using a VIVASPIN™ centrifugal concentrator with a molecular weight cut-off of 5 kDa (GE Healthcare, Piscataway, NJ, USA) to a final volume of 0.4 ml. Protein concentration was determined using the Bio-Rad Protein Assay (Bio-Rad Laboratories, Inc., Hercules, CA, USA).

The enzyme activity of the purified beta-glucosidase was measured using p-nitrophenyl-beta-D-glucopyranoside as substrate. A p-nitrophenyl-beta-D-glucopyranoside stock solution was made by dissolving p-nitrophenyl-beta-D-glucopyranoside in dimethylsulfoxide (DMSO) to constitute a 0.1 M solution. Before assay, a sample of the stock solution was diluted 100-fold in 100 mM sodium acetate pH 5 containing 0.01% TWEEN® 20 to a 1 mM solution. A 100 µl volume of 1 mM p-nitrophenyl-beta-D-glucopyranoside was mixed with each dilution of the enzyme for a 120 µl total volume, and then incubated at 40° C. for 20 minutes. Substrate alone, enzyme alone, and buffer alone were run as controls. p-Nitrophenol standard solutions of 0.40, 0.25, 0.20, 0.10, 0.05, and 0.02 mM were prepared by diluting a 10 mM stock solution in 100 mM sodium acetate pH 5 containing 0.01% TWEEN® 20. At 20 minutes, 50 µl of 1.0 M sodium carbonate buffer pH 10 was added to each well (including samples, substrate control, enzyme control, reagent control, and standards), mixed, and the absorbance at 405 nm immediately measured on a SPECTRAMAX™ 340 PC plate reader (Molecular Devices, Sunnyvale, CA, USA). The activity measured was 84 units per mg of protein. One unit of activity was defined as the amount of enzyme capable of releasing 1 µmole of p-nitrophenolate anion per minute at pH 40° C.

The enzyme activity of the purified beta-glucosidase was also measured with cellobiose. A 2 mg/ml stock solution of cellobiose was prepared in 50 mM sodium acetate pH 5 containing 0.01% TWEEN® 20, and 100 µl were combined with each enzyme dilution for a total volume of 150 µl and incubated at 50° C. for 30 minutes. Substrate alone, enzyme alone, and buffer alone were run as controls. Glucose standard solutions of 1.0, 0.50, 0.25, 0.125, 0.063, and 0.031 mg/ml were prepared in 50 mM sodium acetate pH 5. containing 0.01% TWEEN® 20. At 30 minutes, 50 µl of 0.5 M sodium hydroxide solution was added to each well (including samples, substrate control, enzyme control, reagent control, and standards), mixed, and then 20 µl of the mixture was transferred to a Costar@ EIA/RIA 96-well plate (Corning Incorporated, Corning, NY, USA) and combined with 200 µl of GLUCOSE OXIDASE REAGENT (Pointe Scientific, Inc., Canton, MI, USA), and allowed to stand at 25° C. for 20 minutes and then the absorbance at 500 nm was measured on a SPECTRAMAX™ 340 PC plate reader (Molecular Devices, Sunnyvale, CA, USA). The activity measured was 264 units per mg of protein. One unit of activity was defined as the amount of enzyme capable of releasing 1 µmole of glucose per minute at pH 5, 50° C.

Example 77: Preparation of *Penicillium oxalicum* Strain IBT5387 GH3 Beta-Glucosidase The *Penicillium oxalicum* strain IBT5387 (Technical University of Denmark; NN005786) GH3 beta-glucosidase (SEQ ID NO: 185 [DNA sequence] and SEQ ID NO: 186 [deduced amino acid sequence]) was obtained according to the procedure described below.

*Aspergillus oryzae* BECh2 (WO 2000/39322) was used as a host cell for expressing the *P. oxalicum* strain IBT5387 Family GH3 beta-glucosidase gene.

A set of degenerate primers shown below were designed according to the strategy described by Rose et al., 1998, *Nucleic Acids Research* 26: 1628-1635, for cloning a gene encoding a beta-glucosidase (EC 3.2.1.21) belonging to Family GH3.

```
GH3scree.f1:
                            (SEQ ID NO: 242)
atgaccctggccgaaaaagtcaacytnacnacngg GH3scree.f2:
                            (SEQ ID NO: 243)
ggtggccggaactgggaaggcttctsnccngaycc GH3scree.f5:
                            (SEQ ID NO: 244)
gagctgggcttccagggctttgtnatgwsngaytgg GH3scree.f6:
                            (SEQ ID NO: 245)
agcgctttggccggcctcgayatgwsnatgcc GH3scree.r1:
                            (SEQ ID NO: 246)
atcccagttgctcaggtcccknckngt GH3scree.r2:
                            (SEQ ID NO: 247)
aaaggttgtgtagctcagnccrtgnccraaytc GH3scree.r3:
                            (SEQ ID NO: 248)
gtcaaagtggcggtagtcgatraanacnccytc GH3scree.r4:
                            (SEQ ID NO: 249)
ggtgggcgagttgccgacggggttgactctgccrtanar GH3scree.r5:
                            (SEQ ID NO: 250)
gccgggcagaccggcccagaggatggcngtnacrttngg GH3scree.r6:
                            (SEQ ID NO: 251)
caggacgggccaaccgagtgaatgacnacdatngtrtt
```

PCR screening of *Penicillium oxalicum* strain IBT5387 was performed using two successive PCRs. The forward primers (GH3scree.f1, GH3scree.f2, GH3scree.f5, or GH3scree.f6) (0.33 µl of a 10 mM stock) were combined with the reverse primers (GH3scree.r1, GH3scree.r2, GH3scree.r3, GH3scree.r4, GH3scree.r5, or GH3scree.r6) (0.33 µl of a 10 mM stock) in a 10 µl mixture containing 0.33 µl of *P. oxalicum* genomic DNA and 5 µl of REDDYMIX™ Extensor PCR Master Mix 1 (ABgene Ltd., Surrey, United Kingdom). *P. oxalicum* genomic DNA was obtained according to the procedure described in the FastDNA® SPIN Kit (Q-BIOgene, Carlsbad, CA, USA). The PCR reaction was performed using a DYAD® Thermal Cycler (Bio-Rad Laboratories, Inc., Hercules, CA, USA) programmed for one cycle at 94° C. for 2 minutes; 9 cycles each at 94° C. for 15 seconds, 63° C. for 30 seconds with a decrease of 1° C. for each cycle, and 68° C. for 1 minutes 45 seconds; 24 cycles each at 94° C. for 15 seconds, 55° C. for 30 seconds, and 68° C. for 1 minutes 45 seconds; and extension at 68° C. for 7 minutes.

PCR products obtained during the first PCR were re-amplified with their corresponding primers by transferring 0.5 µl of the first PCR reaction to a second 20 µl mixture containing the same concentration of primers, dNTPs, DNA polymerase, and buffer as the first PCR reaction. The second PCR was performed using a DYAD® Thermal Cycler programmed for one cycle at 94° C. for 2 minutes; 24 cycles each at 94° C. for 15 seconds, 58° C. for 30 seconds, and 68° C. for 1 minutes 45 seconds; and an extension at 68° C. for 7 minutes.

PCR products obtained during the second amplification were analyzed by 1% agarose gel electrophoresis using TAE buffer. Single bands ranging from 2000 to 800 nucleotides in size were excised from the gel and purified using a GFX® PCR DNA and Gel Band Purification Kit according to the manufacturer's instructions. Purified DNA samples were directly sequenced with primers used for amplification. Sequences were assembled in SeqMan v7.2.1 (DNA star, Madison, WI, USA) into a contig that was used for designing primers shown below, based on recommendations of length and temperature described in a GENE WALKING SPEEDUP™ Kit (Seegene, Inc., Seoul, Korea).

```
5786GH3-51TSP1f:
                                  (SEQ ID NO: 252)
CACCAACACCGGCAATCTAGC

5786GH3-51TSP2f:
                                  (SEQ ID NO: 253)
GGTGACGAGGTTGTCCAACTGTACG

5786GH3-51TSP1r:
                                  (SEQ ID NO: 254)
CTTGAAGCCAAGGCGAGG

5786GH3-51TSP2r:
                                  (SEQ ID NO: 255)
TCCGGTATTTCCTACACATGGTCC
```

GeneWalking was based on the protocol from the GENE WALKING SPEEDUP™ Kit with some minor differences. Only two PCR amplifications were carried out and in both cases, the REDDYMIX™ Extensor PCR Master Mix 1 was used in place of the enzyme mix present in the Kit. GeneWalking PCR 1 was performed in a total volume of 15 μl by mixing 1.2 μl of primer 1 to 4 (2.5 mM) from the GENE WALKING SPEEDUP™ Kit with 0.3 μl of primer 5786GH3-51TSP1f or primer 5786GH3-51TSP1r (10 mM) in the presence of 7.5 μl of REDDYMIX™ Extensor PCR Master Mix 1, and 0.5 μl of P. oxalicum genomic DNA. The PCR was performed using a DYAD® Thermal Cycler programmed for one cycle at 94° C. for 3 minutes followed by 1 minute at 42° C. and 2 minutes at 68° C.; 30 cycles each at 94° C. for 30 seconds, 58° C. for 30 seconds, and 68° C. for 1 minute and 40 seconds; and elongation at 68° C. for 7 minutes. A 0.5 μl aliquot of the amplification reaction was transferred to a second PCR tube containing a 20 μl mixture composed of 10 μl of REDDYMIX™ Extensor PCR Master Mix 1, 1 μl of primer 5 (10 mM) from the Kit, 1 μl of primers T5786GH3-51SP2f or 5786GH3-51TSP2r (10 mM). The amplification was performed in a DYAD® Thermal Cycler programmed for denaturation at 94° C. for 3 minutes; 35 cycles each at 94° C. for 30 seconds, 58° C. for 30 seconds, and 68° C. for 1 minute and 40 seconds; and elongation at 68° C. for 7 minutes.

The PCR products were analyzed by 1% agarose gel electrophoresis in TAE buffer. Single bands ranging from 700 to 1200 nucleotides in size were excised from the gel and purified using a GFX® PCR DNA and Gel Band Purification Kit according to manufacturer's instructions. Purified DNA samples were directly sequenced with the primers used for amplification.

Based on blastx analyses, the start and the stop codons of the gene were identified and the primers shown below were designed for cloning the gene into the expression vector pDAu109 (WO 2005042735) using an IN-FUSION™ Dry-Down PCR Cloning Kit.

```
5786GH3-51r1:
                                  (SEQ ID NO: 256)
agatctcgagaagcttaCCATGACTCCAATCGCGCGCTCAAGG 5786GH3-51f1:
                                  (SEQ ID NO: 257)
acacaactggggatccaccATGAGGAGCTCAACGACGGTTCTGGCC
```

The P. oxalicum beta-glucosidase gene was amplified by PCR using the two cloning primers described above with P. oxalicum strain IBT5387 genomic DNA. The PCR was composed of 1 μl of P. oxalicum genomic DNA, 0.75 μl of primer 5786GH3-51f1 (10 μM), 0.75 μl of primer 5786GH3-51r1 (10 μM), 3 μl of 5× HF buffer, 0.25 μl of 50 mM MgCl$_2$, 0.3 μl of 10 mM dNTP, 0.15 μl of PHUSION® DNA polymerase, and PCR-grade water to 15 μl. The amplification reaction was performed using a DYAD® Thermal Cycler programmed for 2 minutes at 98° C. followed by 10 touchdown cycles each at 98° C. for 15 seconds, 70° C. (−1° C./cycle) for 30 seconds, and 72° C. for 2 minutes and 30 seconds; and 25 cycles each at 98° C. for 15 seconds, 60° C. for 30 seconds, 72° C. for 2 minutes and 30 seconds, and 5 minutes at 72° C.

The reaction product was isolated by 1.0% agarose gel electrophoresis using TAE buffer where an approximately 2.8 kb PCR product band was excised from the gel and purified using a GFX® PCR DNA and Gel Band Purification Kit according to manufacturer's instructions. DNA corresponding to the Penicillium oxalicum beta-glucosidase gene was cloned into the expression vector pDAu109 (WO 2005042735) linearized with Bam HI and Hind III, using an IN-FUSION™ Dry-Down PCR Cloning Kit according to the manufacturer's instructions.

A 2.5 μl volume of the diluted ligation mixture was used to transform E. coli TOP10 chemically competent cells. Three colonies were selected on LB agar plates containing 100 μg of ampicillin per ml and cultivated overnight in 3 ml of LB medium supplemented with 100 μg of ampicillin per ml. Plasmid DNA was purified using an E.Z.N.A.® Plasmid Mini Kit according to the manufacturer's instructions. The Penicillium oxalicum beta-glucosidase gene sequence was verified by Sanger sequencing before heterologous expression. One plasmid designated pIF113#1 was selected for expressing the P. oxalicum beta-glucosidase in an Aspergillus oryzae host cell.

The coding sequence is 2793 bp including the stop codon with 2 predicted introns of 82 bp (nucleotides 85 to 116) and 59 bp (nucleotides 346 to 404). The encoded predicted protein is 883 amino acids. Using the SignalP program (Nielsen et al., 1997, Protein Engineering 10: 1-6), a signal peptide of 21 residues was predicted. The predicted mature protein contains 862 amino acids with a predicted molecular mass of 94.7 kDa and an isoelectric point of 5.04.

Protoplasts of Aspergillus oryzae BECh2 (WO 2000/39322) were prepared according to WO 95/002043. One hundred μl of protoplasts were mixed with 2.5-15 μg of the Aspergillus expression vector and 250 μl of 60% PEG 4000 (Applichem, Darmstadt, Germany) (polyethylene glycol, molecular weight 4,000), 10 mM CaCl$_2$, and 10 mM Tris-HCl pH 7.5 and gently mixed. The mixture was incubated at 37° C. for 30 minutes and the protoplasts were spread onto COVE plates for selection. After incubation for 4-7 days at 37° C. spores of sixteen transformants were inoculated into 0.5 ml of YP medium supplemented with 2% maltodextrin in 96 deep-well plates. After 4 days cultivation at 30° C., the culture broths were analyzed to identify the best transformants producing large amounts of active *P. oxalicum* beta-glucosidase. The analysis was based on SDS-PAGE and activity of the enzyme on 4-nitrophenyl-beta-D-glucopyranoside (pNPG) as described in Example 16.

Spores of the best transformant were spread on COVE plates containing 0.01% TRITON® X-100 in order to isolate single colonies. The spreading was repeated twice in total on COVE plates containing 10 mM sodium nitrate. Spores were then inoculated into 100 ml of YP medium supplemented with 2% maltodextrin in 250 ml shake flasks and incubated for 4 days at 30° C. with shaking at 100 rpm.

Combined supernatants of the shake flask cultures were first filtered using a glass micro fiber filter with a 0.7 µm pore size, and then sterile filtered using a filtration unit equipped with a PES (Polyether sulfone) with a 0.22 µm pore size (Nalge Nunc International, New York, NY USA). The sterile filtered supernatant was then adjusted to a concentration of 2 M ammonium sulfate by slowly adding solid ammonium sulfate, dissolving by gentle stirring, and then filtering using a glass micro fiber filter with a 0.7 µm pore size. If there was any precipitate, it was discarded.

The filtered supernatant was applied to a 50 ml Toyopearl Phenyl-650M column (TOSOH Bioscience GmbH, Germany) equilibrated with 2 M ammonium sulfate in water and unbound material was eluted with 2 M ammonium sulfate until the UV absorbance at 280 nm was below 0.05. Bound protein was eluted with 50% ethanol as solution B using a step gradient. Ten ml fractions were collected and monitored by UV absorbance at 280 nm. The fractions were analyzed by SDS-PAGE and pooled the fractions containing protein with the expected molecular weight. The pooled fractions were dialyzed using 50 mM HEPES pH 7.5 buffer, so the ionic strength was below 4 MSi and the pH was 7.5.

The pooled protein was applied to a 50 ml Q Sepharose® Fast Flow column equilibrated with 50 mM HEPES pH 7.5 buffer and unbound material was eluted with 50 mM HEPES buffer pH 7.5. The bound protein was then eluted with a linear 20 column volume salt gradient in 50 mM HEPES buffer pH 7.5 containing 1 M NaCl as buffer B. Ten ml fractions of the eluate were collected and each were analyzed for purity of the protein by SDS-PAGE. The fractions with highest purity were pooled. Identity of the beta-glucosidase was confirmed by mass spectroscopy and protein identification was carried out by in gel digestion. Protein concentration was determined using a Microplate BCA™ Protein Assay Kit in which bovine serum albumin was used as a protein standard.

Example 78: Preparation of *Penicillium oxalicum* Strain IBT5387 GH3 Beta-Glucosidase The *Penicillium oxalicum* strain IBT5387 (Technical University of Denmark; NN005786) GH3 beta-glucosidase (SEQ ID NO: 187 [DNA sequence] and SEQ ID NO: 188 [deduced amino acid sequence]) was obtained according to the procedure described below.

Genomic DNA was isolated according to the procedure described in Example 73.

A set of degenerate primers (shown below) was hand-designed according to the strategy described by Rose et al., 1998, *Nucleic Acids Res.* 26: 1628-1635, for targeting beta-glucosidases (EC 3.2.1.21) belonging to Family GH3.

```
GH3scree.f1
                                      (SEQ ID NO: 258)
atgaccctggccgaaaaagtcaacytnacnacngg GH3scree.f2
                                      (SEQ ID NO: 259)
ggtggccggaactgggaaggcttctsnccngaycc GH3scree.f5
                                      (SEQ ID NO: 260)
gagctgggcttccagggctttgtnatgwsngaytgg GH3scree.f6
                                      (SEQ ID NO: 261)
agcgctttggccggcctcgayatgwsnatgcc GH3scree.r1
                                      (SEQ ID NO: 262)
atcccagttgctcaggtccckncknqt GH3scree.r2
                                      (SEQ ID NO: 263)
aaaggttgtgtagctcagnccrtgnccraaytc GH3scree.r3
                                      (SEQ ID NO: 264)
gtcaaagtggcggtagtcgatraanacnccytc GH3scree.r4
                                      (SEQ ID NO: 265)
ggtgggcgagttgccgacggggttgactctgccrtanar GH3scree.r5
                                      (SEQ ID NO: 266)
gccgggcagaccggcccagaggatggcngtnacrttngg GH3scree.r6
                                      (SEQ ID NO: 267)
caggacggggccaaccgagtgaatgacnacdatngtrtt
```

PCR screening of *Penicillium oxalicum* strain IBT5387 genomic DNA was performed with two successive PCRs. Each forward primers (f1, f2, f5, and f6) (0.33 µl of a 10 mM stock) was combined with each reverse primers (r1, r2, r3, r4, r5, and r6) (0.33 µl of a 10 mM stock) in a 10 µl mix containing 0.33 µl genomic DNA, 5 µl of Reddy Mix Extensor PCR Master Mix 1 (Cat #AB-0794/A, ABgene UK, commercialized by Thermo Fisher Scientific). A hot-start PCR reaction was carried out in a DYAD® PCR machine for 2 minutes at 94° C. followed by 9 cycles each at 94° C. for 15 seconds, 63° C. for 30 seconds with a 1° C. decrease for each cycle, 68° C. for 1 minute 45 seconds, and followed by 24 cycles each at 94° C. for 15 seconds, 55° C. for 30 seconds, 68° C. for 1 minute 45 seconds, supplemented by a 7 minutes extension at 68° C. PCR-products produced during this first PCR were re-amplified with their corresponding primers by transferring 0.5 µl of the first PCR reaction to a second 20 µl mix containing the same concentration of primers, dNTPs, polymerase, and buffer than in the first PCR reaction. The second PCR was carried out on the same PCR block at 94° C. for 2 minutes followed by 24 cycles each at 94° C. for 15 seconds, 58° C. for 30 seconds, 68° C. for 1 minute 45 seconds and completed by a 7 minutes extension at 68° C. PCR products produced during the second amplification were analyzed on 1% agarose gel electrophoresis in TAE buffer. Single bands ranging from 2000 to 800 nts in size were collected and eluted using the GFX® PCR DNA and Gel Band Purification Kit according to manufacturer's instructions. Purified DNA samples were directly sequenced with primers used for amplification.

Sequences were assembled in SeqMan v7.2.1 (DNA star, Madison, WI, USA) into a contig that was used for nblast searches (Altschul et al., 1997, *Nucleic Acids Res.* 25: 3389-3402) on publicly available sequences. Results of the search indicated that the sequence GenBank EU700488.1 was nearly identical to the contig identified. Therefore, the cloning primers 5786GH3-50f and 5786GH3-50r were designed based on the sequence information of the cds from GenBank EU700488.1 for IN-FUSION™ cloning according to the manufacturer instructions for cloning in the expression vector pDAu109 (WO 2005/042735).

```
5786GH3-50f1:
                                    (SEQ ID NO: 268)
5'-acacaactggggatccaccATGAAGCTCGAGTGGCTGGAAGC-3'

5786GH3-50r1
                                    (SEQ ID NO: 269)
5'-agatctcgagaagcttaCTGCACCTTGGGCAGATCGGCTG-3'
```

The *Penicillium oxalicum* beta-glucosidase gene was amplified by PCR using the two cloning primers described previously in a PCR reaction that was performed with genomic DNA prepared from the strain IBT5387 (from DTU received in 1992). The PCR reaction was composed of 1 µl of genomic DNA, 0.75 µl of primer 5786GH3-51f1 (10 µM); 0.75 µl of primer 5786GH3-51r1 (10 µM); 3 µl of 5× HF buffer, 0.25 µl of 50 mM MgCl$_2$, 0.3 µl of 10 mM dNTP; 0.15 µl of PHUSION® DNA polymerase, and PCR-grade water up to 15 µl. The PCR reaction was performed using a DYAD® PCR machine programmed for 2 minutes at 98° C. followed by touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds, and 5 minutes at 72° C.

The reaction product was isolated by 1.0% agarose gel electrophoresis using TAE buffer where an approximately 2.8 kb PCR product band was excised from the gel and purified using a GFX® PCR DNA and Gel Band Purification Kit according to manufacturer's instructions. DNA corresponding to the *Penicillium oxalicum* beta-glucosidase gene was cloned into the expression vector pDAu109 (WO 2005042735) linearized with Bam HI and Hind III, using an IN-FUSION™ Dry-Down PCR Cloning Kit according to the manufacturer's instructions.

A 2.5 µl volume of the diluted ligation mixture was used to transform *E. coli* TOP10 chemically competent cells. Three colonies were selected on LB agar plates containing 100 µg of ampicillin per ml and cultivated overnight in 3 ml of LB medium supplemented with 100 µg of ampicillin per ml. Plasmid DNA was purified using an E.Z.N.A.® Plasmid Mini Kit according to the manufacturer's instructions. The *Penicillium oxalicum* beta-glucosidase gene sequence was verified by Sanger sequencing before heterologous expression.

The coding sequence is 2964 bp including the stop codon and is interrupted by 5 introns of 101 bp (nucleotides 61 to 161), 64 bp (nucleotides 302 to 365), 79 bp (nucleotides 411 to 489), 63 bp (nucleotides 543 to 605), and 71 bp (nucleotides 2660 to 2730). The encoded predicted protein is 861 amino acids. Using the SignalP program (Nielsen et al., 1997, *Protein Engineering* 10: 1-6), a signal peptide of 19 residues was predicted. The predicted mature protein contains 842 amino acids.

Protoplasts of *Aspergillus oryzae* BECh2 (WO 2000/39322) were prepared as described in WO 95/02043. One hundred microliters of protoplast suspension were mixed with 2.5-15 µg of the *Aspergillus* expression vector and 250 µl of 60% PEG 4000, 10 mM CaCl$_2$, and 10 mM Tris-HCl pH 7.5 were added and gently mixed. The mixture was incubated at 37° C. for 30 minutes and the protoplasts were spread on COVE sucrose (1 M) plates supplemented with 10 mM acetamide and 15 mM CsCl for transformant selection. After incubation for 4-7 days at 37° C. spores of several transformants were seeded on YP-2% maltodextrin medium. After 4 days cultivation at 30° C. culture broth was analyzed in order to identify the best transformants based on their ability to produce a large amount of active *Penicillium oxalicum* beta-glucosidase. The screening was based on intensity of the band corresponding to the heterologous expressed protein determined by SDS-PAGE and activity of the enzyme on 4-nitrophenyl-beta-D-glucopyranoside (pNPG) as described in Example 16.

Spores of the best transformant were spread on COVE plates containing 0.01% TRITON® X-100 in order to isolate single colonies. The spreading was repeated twice in total on COVE sucrose medium (Cove, 1996, *Biochim. Biophys. Acta* 133: 51-56) containing 1 M sucrose and 10 mM sodium nitrate, supplemented with 10 mM acetamide and 15 mM CsCl. Fermentation was then carried out in 250 ml shake flasks using DAP-2C-1 medium for 4 days at with shaking at 100 rpm.

Filtered broth was concentrated and washed with deionized water using a tangential flow concentrator equipped with a Sartocon® Slice cassette with a 10 kDa MW-CO polyethersulfone membrane (Sartorius Stedim Biotech GmbH, Goettingen, Germany). The concentrate was added to M ammonium sulphate and loaded onto a Phenyl Toyopearl (650M) column (Tosoh Corporation, 3-8-2 Shiba, Minato-ku, Tokyo, Japan) equilibrated in 2 M ammonium sulphate, and bound proteins were eluted with 1 M ammonium sulphate. The eluted protein was buffer exchanged with 25 mM HEPES pH 7.5 with sodium chloride by ultrafiltration with a 10 kDa polyethersulfone membrane using Vivaspin 20 (Sartorius Stedim Biotech GmbH, Goettingen, Germany). Protein concentration was determined using a Microplate BCA™ Protein Assay Kit in which bovine serum albumin was used as a protein standard.

Example 79: Preparation of *Talaromyces emersonii* Strain CBS 549.92 GH3 Beta-Glucosidase The *Talaromyces emersonii* strain CBS 549.92 GH3 beta-glucosidase (SEQ ID NO: 189 [DNA sequence] and SEQ ID NO: 190 [deduced amino acid sequence]) was obtained according to the procedure described below.

Genomic DNA was isolated according to the procedure described in Example 73.

The *Talaromyces emersonii* beta-glucosidase gene was isolated by PCR using two cloning primers GH3-11f and GH3-11r shown below, which were designed based on the publicly available *Talaromyces emersonii* full-length sequence (Genbank AY072918.4) for direct cloning using the IN-FUSION™ strategy.

```
Primer GH3-11f:
                                    (SEQ ID NO: 270)
acacaactggggatccaccatgaggaacgggttgctcaaggtcg Primer GH3-11r:
                                    (SEQ ID NO: 271)
agatctcgagaagcttaaattccagggtatggcttaaggggc
```

A PCR reaction was performed with genomic DNA prepared from *Talaromyces emersonii* strain CBS 549.92 in order to amplify the full-length gene. The PCR reaction was composed of 1 µl of genomic DNA, 0.75 µl of primer GH3-11f (10 µM); 0.75 µl of primer GH3-11r (10 µM); 3 µl of 5× HF buffer, 0.25 µl of 50 mM MgCl$_2$, 0.3 µl of 10 mM dNTP; 0.15 µl of PHUSION® DNA polymerase, and PCR-grade water up to 15 µl. The PCR reaction was performed using a DYAD® PCR machine programmed for 2 minutes at 98° C. followed by 10 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds, and 5 minutes at 72° C.

The reaction product was isolated by 1.0% agarose gel electrophoresis using TAE buffer where an approximately 2.9 kb PCR product band was excised from the gel and purified using a GFX® PCR DNA and Gel Band Purification Kit according to manufacturer's instructions. DNA corresponding to the *Talaromyces emersonii* beta-glucosidase gene was cloned into the expression vector pDAu109 (WO 2005042735) linearized with Bam HI and Hind III, using an IN-FUSION™ Dry-Down PCR Cloning Kit according to the manufacturer's instructions.

A 2.5 µl volume of the diluted ligation mixture was used to transform *E. coli* TOP10 chemically competent cells. Three colonies were selected on LB agar plates containing 100 µg of ampicillin per ml and cultivated overnight in 3 ml of LB medium supplemented with 100 µg of ampicillin per ml. Plasmid DNA was purified using an E.Z.N.A.® Plasmid Mini Kit according to the manufacturer's instructions. The *Talaromyces emersonii* beta-glucosidase gene sequence was verified by Sanger sequencing before heterologous expression.

The coding sequence is 2925 bp including the stop codon and is interrupted by 6 introns of 60 bp (nucleotides 61 to 120), 61 bp (nucleotides 261 to 321), 60 bp (nucleotides 367 to 426), 57 bp (nucleotides 480 to 536), 56 bp (nucleotides 1717 to 1772), and 54 bp (nucleotides 2632 to 2685). The encoded predicted protein is 858 amino acids. Using the SignalP program (Nielsen et al., 1997, *Protein Engineering* 10: 1-6), a signal peptide of 19 residues was predicted. The predicted mature protein contains 839 amino acids.

Protoplasts of *Aspergillus oryzae* BECh2 (WO 2000/39322) were prepared as described in WO 95/02043. One hundred microliters of protoplast suspension were mixed with 2.5-15 µg of the *Aspergillus* expression vector and 250 µl of 60% PEG 4000, 10 mM CaCl$_2$, and 10 mM Tris-HCl pH 7.5 were added and gently mixed. The mixture was incubated at 37° C. for 30 minutes and the protoplasts were spread on COVE sucrose (1 M) plates supplemented with 10 mM acetamide and 15 mM CsCl for transformant selection. After incubation for 4-7 days at 37° C. spores of several transformants were seeded on YP-2% maltodextrin medium. After 4 days cultivation at 30° C. culture broth was analyzed in order to identify the best transformants based on their ability to produce a large amount of active *Talaromyces emersonii* beta-glucosidase. The screening was based on intensity of the band corresponding to the heterologous expressed protein determined by SDS-PAGE and activity of the enzyme on 4-nitrophenyl-beta-D-glucopyranoside (pNPG) as described in Example 16.

Spores of the best transformant were spread on COVE plates containing 0.01% TRITON® X-100 in order to isolate single colonies. The spreading was repeated twice in total on COVE sucrose medium (Cove, 1996, *Biochim. Biophys. Acta* 133: 51-56) containing 1 M sucrose and 10 mM sodium nitrate, supplemented with 10 mM acetamide and 15 mM CsCl. Fermentation was then carried out in 250 ml shake flasks using YP-2% maltodextrin medium for 4 days at 30° C. with shaking at 100 rpm. The broth was filtered using standard methods. Protein concentration was determined using a Microplate BCA™ Protein Assay Kit in which bovine serum albumin was used as a protein standard.

Example 80: Preparation of *Thermoascus crustaceus* Strain CBS 181.67 GH61A Polypeptide The *Thermoascus crustaceus* strain CBS 181.67 GH61A polypeptide having cellulolytic enhancing activity (SEQ ID NO: 191 [DNA sequence] and SEQ ID NO: 192 [deduced amino acid sequence]) was obtained according to the procedure described below.

*Aspergillus oryzae* strain HowB101 (WO 95/35385) was used as a host for recombinantly expressing the *Thermoascus crustaceus* GH61 polypeptides having cellulolytic enhancing activity.

*Thermoascus crustaceus* strain CBS 181.67 was inoculated onto a PDA plate and incubated for 3-4 days at 45° C. in the darkness. Several mycelia-PDA plugs were inoculated into 500 ml shake flasks containing 100 ml of NNCYP-PCS medium. The flasks were incubated for 6 days at 45° C. with shaking at 160 rpm. The mycelia were collected at day 3, day 4, day 5, and day 6. Then the mycelia from each day were combined and frozen in liquid nitrogen, and then stored in a −80° C. freezer until use.

Genomic DNA was extracted using a DNEASY® Plant Mini Kit (QIAGEN Inc., Valencia, CA, USA). Total RNA was isolated by using a RNEASY® Plant Mini Kit. cDNA was synthesized by following the instructions of the 3' Rapid Amplification of cDNA End System (3' RACE) (Invitrogen Corporation, Carlsbad, CA, USA).

Four degenerate primers shown below were designed based on conserved regions of known GH61 sequences.

```
GH61A scF1:
                                 (SEQ ID NO: 272)
5'-GCNACNGAYCTNGGNTTTG-3'

GH61A scF2:
                                 (SEQ ID NO: 273)
5'-GCNACNGAYCTNGGNTTCG-3'

GH61A scF3:
                                 (SEQ ID NO: 274)
5'-GCNACNGAYTTRGGNTTYG-3'

GH61A scR1:
                                 (SEQ ID NO: 275)
5'-CAYTGNGGRTARTTYTGNGC-3'
```

PCR was performed by using a combination of forward primers GH61A scF1, GH61 scF2, and GH61A scF3, and reverse primer GH61A scR1 and cDNA as template. The amplification reaction was composed of 5 µl of 10×PCR buffer (Invitrogen Corporation, Carlsbad, CA, USA), 2 µl of 25 mM MgCl$_2$, 1 µl of 10 mM dNTP, 1 µl of 100 µM forward primer, 1 µl of 100 µM reverse primer, 2 µl of cDNA, 0.5 µl of Taq DNA polymerase High Fidelity (Invitrogen Corporation, Carlsbad, CA, USA), and 37.5 µl of H$_2$O. The amplification was performed using an Peltier Thermal Cycler programmed for denaturing at 94° C. for 2 minutes; 30 cycles each at 94° C. for 40 seconds, 50° C. for 40 seconds, and 72° C. for 1 minute; and a final extension at 72° C. for 10 minutes.

A PCR product of approximately 500 base pairs was detected by 1% agarose gel electrophoresis using TBE buffer. The PCR fragment was excised from the gel and purified using an ILLUSTRA® GFX® PCR DNA and Gel Band Purification Kit according to the manufacturer's instructions, directly sequenced, and confirmed to be a GH61A partial gene by blast. Based on this partial sequence, new primers shown below were designed for 5' and 3' end cloning using a Genome Walking Kit (Takara Bio Inc., Otsu, Shiga, Japan):

```
61ASPR1:
                                   (SEQ ID NO: 276)
5'-TGCAAGGAGCAAGGTAGTTGA-3'

61ASPR2:
                                   (SEQ ID NO: 277)
5'-GAGTCCATTCCAGCTTGACGGT-3'

61ASPF1:
                                   (SEQ ID NO: 278)
5'-TCAGACAATCTGATAGCGGC-3'

61ASPF2:
                                   (SEQ ID NO: 279)
5'-ATCCCAACCACAACTGCACCT-3'
```

For 5' end and 3' end cloning, the primary amplifications were composed of 2 µl of genomic DNA as template, 2.5 mM each of dATP, dTTP, dGTP, and dCTP, 100 µmol of AP2 (provided by the Genome Walking Kit) and 10 µmol of primer 61ASPR1 for 5' end cloning or 100 µmol of AP3 (provided by the Genome Walking Kit), and 10 µmol of primer 61ASPF1 for 3' end cloning, 5 µl of 10× LA PCR Buffer II (provided by the Genome Walking Kit), and 2.5 units of TakaRa LA Taq DNA polymerase (provided by the Genome Walking Kit) in a final volume of µl. The amplifications were performed using an Peltier Thermal Cycler programmed for pre-denaturing at 94° C. for 1 minute and 98° C. for 1 minute; five cycles each at a denaturing temperature of 94° C. for 30 seconds; annealing at 60° C. for 1 minute and elongation at 72° C. for 2 minutes; 1 cycle of denaturing at 94° C. for 30 seconds; annealing at 25° C. for 3 minutes and elongation at 72° C. for 2 minutes; fifteen repeats of 2 cycles at 94° C. for 30 seconds, 62° C. for 1 minutes, and 72° C. for 2 minutes; followed by 1 cycle at 94° C. for 30 seconds, 44° C. for 1 minutes, and 72° C. for 2 minutes; and a final extension at 72° C. for 10 minutes. The heat block then went to a 4° C. soak cycle.

The secondary amplifications were composed of 2 µl of 20× diluted primary PCR product as templates, 2.5 mM each of dATP, dTTP, dGTP, and dCTP, 100 µmol of AP2, and 10 pmol of primer 61ASPR2 for 5' end cloning or 100 µmol of AP3 and 10 µmol of primer 61ASPF2 for 3' end cloning, 5 µl of 10× LA PCR Buffer II, and 2.5 units of TakaRa LA Taq DNA polymerase in a final volume of 50 µl. The amplifications were performed using an Peltier Thermal Cycler programmed for fifteen repeats of 2 cycles of 94° C. for 30 seconds; 62° C. for 1 minutes; 72° C. for 2 minutes; followed by 1 cycle at 94° C. for 30 seconds, 44° C. for 1 minutes, and 72° C. for 2 minutes; and a final extension at 72° C. for 10 minutes. The heat block then went to a 4° C. soak cycle.

The PCR products from the 5' and 3' end PCR were recovered and sequenced. They were identified as the 5' end and 3' end of the GH61A polypeptide gene. Then the three sequences including the partial gene, 5' end, and 3' end were assembled to generate the full-length GH61A.

The obtained full-length gene showed that the sequence contains a coding region of 871 nucleotides including 1 intron and stop codon, and encodes 251 amino acids with a predicted signal peptide of 22 amino acids.

Based on the full-length *Thermoascus crustaceus* GH61A gene sequence, oligonucleotide primers, shown below, were designed to amplify the GH61A gene from genomic DNA of *Thermoascus crustaceus* CBS 181.67. An IN-FUSION® CF Dry-Down Cloning Kit (Clontech Laboratories, Inc., Mountain View, CA, USA) was used to clone the fragment directly into the expression vector pPFJO355, without the need for restriction digestion and ligation.

```
Sense primer:
                                   (SEQ ID NO: 280)
5'-ACACAACTGGGGATCCACCATGGCCTTTTCCCAGATAATGGCTA-3'

Antisense primer:
                                   (SEQ ID NO: 281)
5'-GTCACCCTCTAGATCTGGATCGCAGGAGCGTTCAGA-3'
```

Bold letters represent the coding sequence for the sense primer and the downstream sequence of the stop codon for the antisense primer. The remaining sequence is homologous to the insertion sites of pPFJO355.

Twenty picomoles of each of the primers above were used in a PCR reaction composed of *Thermoascus crustaceus* genomic DNA, 10 µl of 5× GC Buffer, 1.5 µl of DMSO, 2 µl of 2.5 mM each of dATP, dTTP, dGTP, and dCTP, and 1 unit of PHUSION™ High-Fidelity DNA Polymerase in a final volume of 50 µl. The amplification was performed using a Peltier Thermal Cycler programmed for denaturing at 98° C. for 1 minute; 5 cycles of denaturing at 98° C. for 15 seconds, annealing at 70° C. for 30 seconds, with a 1° C. decrease per cycle, and elongation at 72° C. for 30 seconds; 25 cycles each at 98° C. for 15 seconds and 72° C. for 90 seconds; and a final extension at 72° C. for 10 minutes. The heat block then went to a 4° C. soak cycle.

The reaction products were isolated by 1.0% agarose gel electrophoresis using TBE buffer where an approximately 1.0 kb product band was excised from the gel, and purified using an ILLUSTRA® GFX® PCR DNA and Gel Band Purification Kit according to the manufacturer's instructions.

Plasmid pPFJO355 was digested with Bam HI and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION® CF Dry-Down PCR Cloning Kit resulting in pGH61a51486 in which transcription of the *Thermoascus crustaceus* GH61A gene was under the control of the *Aspergillus oryzae* TAKA-alpha-amylase promoter. In brief, 30 ng of pPFJO355 digested with Bam HI and Bgl II and 50 ng of the *Thermoascus crustaceus* GH61A gene purified PCR product were added to a reaction vial and resuspended in a final volume of 10 µl with deionized water. The reaction was incubated at 37° C. for 15 minutes and then 50° C. for 15 minutes. Three µl of the reaction were used to transform *E. coli* TOP10 competent cells according to the manufacturer's instructions.

The transformation was spread on LB plates supplemented with 100 µg of ampicillin per ml and incubated at 37° C. for 1 day. An *E. coli* transformant containing a plasmid designated pGH61a51486 was detected by colony PCR and plasmid DNA was prepared using a QIAprep Spin Miniprep Kit (QIAGEN Inc., Valencia, CA, USA). The *Thermoascus crustaceus* GH61A gene insert in pGH61a51486 was confirmed by DNA sequencing using a 3730XL DNA Analyzer.

The same PCR fragment was cloned into pGEM-T vector using a pGEM-T Vector System to generate pGEM-T-

GH61a51486. The *Thermoascus crustaceus* GH61A gene insert in pGEM-T-GH61a51486 was confirmed by DNA sequencing using a 3730XL DNA Analyzer. *E. coli* strain T-51486A, designated NN059126, containing pGEM-T-GH61a51486, was deposited at the Deutsche Sammlung von Mikroorganismen and Zellkulturen GmbH (DSM), Mascheroder Braunschweig, Germany, on Jun. 10, 2009, and assigned accession number DSM 22656.

Nucleotide sequence data were scrutinized for quality and all sequences were compared to each other with assistance of PHRED/PHRAP software (University of Washington, Seattle, WA, USA).

The nucleotide sequence and deduced amino acid sequence of the *Thermoascus crustaceus* gh61a gene are shown in SEQ ID NO: 191 and SEQ ID NO: 192, respectively. The coding sequence is 871 bp including the stop codon and is interrupted by one intron of 115 base pairs (nucleotides 105-219). The encoded predicted protein is 251 amino acids. The % G+C content of the full-length coding sequence and the mature coding sequence are 50.23% and 52.55%, respectively. Using the SignalP software program (Nielsen et al., 1997, *Protein Engineering* 10: 1-6), a signal peptide of 22 residues was predicted. The predicted mature protein contains 229 amino acids with a predicted molecular mass of 26.35 kDa.

*Aspergillus oryzae* HowB101 protoplasts were prepared according to the method of Christensen et al., 1988, Bio/Technology 6: 1419-1422 and transformed with 3 µg of pGH61a51486. The transformation yielded about 50 transformants. Twelve transformants were isolated to individual Minimal medium plates.

Four transformants were inoculated separately into 3 ml of YPM medium in a 24-well plate and incubated at 30° C. with shaking at 150 rpm. After 3 days incubation, 20 µl of supernatant from each culture were analyzed by SDS-PAGE using a NUPAGE® NOVEX® 4-12% Bis-Tris Gel with MES buffer according to the manufacturer's instructions. The resulting gel was stained with INSTANT BLUE™ (Expedeon Ltd., Babraham Cambridge, UK). SDS-PAGE profiles of the cultures showed that the majority of the transformants had a major band of approximately 30 kDa. The expression strain was designated *Aspergillus oryzae* EXP03151.

A slant of *Aspergillus oryzae* EXP03151 was washed with 10 ml of YPM medium and inoculated into a 2 liter flask containing 400 ml of YPM medium to generate broth for characterization of the enzyme. The culture was harvested on day 3 and filtered using a 0.45 µm DURAPORE® Membrane (Millipore, Bedford, MA, USA).

The filtered broth was concentrated and buffer exchanged using a tangential flow concentrator equipped with a Sartocon® Slice cassette with a 10 kDa cut-off polyethersulfone membrane (Sartorius Stedim Biotech GmbH, Goettingen, Germany) with 25 mM HEPES, pH 7.0. The protein was applied to a Q Sepharose™ Fast Flow column (GE Healthcare, Piscataway, NJ, USA) equilibrated in 25 mM HEPES pH 7.0. The protein was recovered in the eluate. Protein concentration was determined using a Microplate BCA™ Protein Assay Kit in which bovine serum albumin was used as a protein standard.

Example 81: Preparation of *Talaromyces emersonii* Strain NN05002 GH10 Xylanase

The *Talaromyces emersonii* strain NN05002 GH10 xylanase (SEQ ID NO: 193 [DNA sequence] and SEQ ID NO: 194 [deduced amino acid sequence]) was obtained according to the procedure described below.

*Talaromyces emersonii* was grown on a PDA agar plate at 45° C. for 3 days. Mycelia were collected directly from the agar plate into a sterilized mortar and frozen under liquid nitrogen. Frozen mycelia were ground, by mortar and pestle, to a fine powder, and genomic DNA was isolated using a DNeasy® Plant Mini Kit.

Oligonucleotide primers, shown below, were designed to amplify the GH10 xylanase gene from genomic DNA of *Talaromyces emersonii*. An IN-FUSION™ CF Dry-down Cloning Kit was used to clone the fragment directly into the expression vector pPFJO355, without the need for restriction digestion and ligation.

Sense primer:
(SEQ ID NO: 282)
5'-ACACAACTGGGGATCCACCATGGTTCGCCTCAGTCCAG-3'

Antisense primer:
(SEQ ID NO: 283)
5'-GTCACCCTCTAGATCTTTACAGACACTGCGAGTAATACTCATTG-3'

Bold letters represented the coding sequence. The remaining sequence was homologous to the insertion sites of pPFJO355.

Twenty picomoles of each of the primers above were used in a PCR reaction composed of *Talaromyces emersonii* genomic DNA, 10 µl of 5× GC Buffer, 1.5 µl of DMSO, 5 mM each of dATP, dTTP, dGTP, and dCTP, and 0.6 unit of Phusion™ High-Fidelity DNA Polymerase in a final volume of 50 µl. The amplification was performed using a Peltier Thermal Cycler programmed for denaturing at 98° C. for 40 seconds; 8 cycles of denaturing at 98° C. for 15 seconds, annealing at 65° C. for 30 seconds, with a 1° C. decrease per cycle and elongation at 72° C. for 80 seconds; and another 23 cycles each at 98° C. for 15 seconds, 58° C. for 30 seconds and 72° C. for 80 seconds; final extension at 72° C. for 7 minutes. The heat block then went to a soak cycle.

The reaction products were isolated by 1.0% agarose gel electrophoresis using TBE buffer where an approximately 1.4 kb product band was excised from the gel, and purified using an ILLUSTRA® GFX® PCR DNA and Gel Band Purification Kit according to the manufacturer's instructions.

Plasmid pPFJO355 was digested with Bam I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION™ CF Dry-down PCR Cloning resulting in pxynTe50022 in which transcription of the *Talaromyces emersonii* GH10 xylanase gene was under the control of the *Aspergillus oryzae* TAKA amylase promoter. In brief, 20 ng of pPFJO355 digested with Bam I and Bgl II, and 60 ng of the *Talaromyces emersonii* GH10 xylanase gene purified PCR product were added to a reaction vial and resuspended in a final volume of 10 µl with addition of deionized water. The reaction was incubated at 37° C. for 15 minutes and then 50° C. for 15 minutes. Three µl of the reaction were used to transform *E. coli* TOP10 competent cells. An *E. coli* transformant containing pxynTe50022 was detected by colony PCR and plasmid DNA was prepared using a QIAprep Spin Miniprep Kit. The *Talaromyces emersonii* GH10 xylanase gene insert in pxynTe50022 was confirmed by DNA sequencing using a 3730XL DNA Analyzer.

*Aspergillus oryzae* HowB101 (WO 95/35385) protoplasts were prepared according to the method of Christensen et al., 1988, Bio/Technology 6: 1419-1422 and transformed with 3 μg of pxynTe50022. The transformation yielded about 50 transformants. Twelve transformants were isolated to individual Minimal medium plates.

Four transformants were inoculated separately into 3 ml of YPM medium in a 24-well plate and incubated at 30° C., 150 rpm. After 3 days incubation, 20 μl of supernatant from each culture were analyzed by SDS-PAGE using a NUPAGE® NOVEX® 4-12% Bis-Tris Gel with MES buffer according to the manufacturer's instructions. The resulting gel was stained with INSTANT® Blue. SDS-PAGE profiles of the cultures showed that the majority of the transformants had a major smeary band of approximately 55 kDa. The expression strain was designated as *A. oryzae* EXP03373.

A slant of *A. oryzae* EXP03373 was washed with 10 ml of YPM medium and inoculated into six 2 liter flasks, each containing 400 ml of YPM medium, to generate broth for characterization of the enzyme. The culture was harvested on day 3 by filtering the culture through MIRACLOTH® (CALBIOCHEM, Inc. La Jolla, CA, USA). The filtered culture broth was then again filtered using a 0.45 μm DURAPORE Membrane. Protein concentration was determined using a Microplate BCA™ Protein Assay Kit in which bovine serum albumin was used as a protein standard.

A 1600 ml volume of filtered broth supernatant of *A. oryzae* EXP03373 was precipitated with ammonium sulfate (80% saturation), re-dissolved in 100 ml of 25 mM Bis-Tris pH 6.0, dialyzed against the same buffer, and filtered through a 0.45 μm filter; the final volume was 200 ml. The solution was applied to a 40 ml Q Sepharose® Fast Flow column equilibrated with 25 mM Bis-Tris pH 6.0, and the proteins were eluted with a linear NaCl gradient (0-0.4 M). Fractions with activity against AZCL-xylan were analyzed by SDS-PAGE using a NUPAGE® NOVEX® 4-12% Bis-Tris Gel with MES buffer. Fractions with the correct molecular weight were pooled and concentrated by ultra filtration.

The supernatants were tested for endocellulase activity by microtiter plate assay as described below. A solution of 0.2% of the blue substrate AZCL-Xylan (Megazyme) was suspended in a 0.1 M sodium acetate buffer (pH 5.5) under stirring. The solution was distributed under stirring to a microtiter plate (200 μl to each well). Twenty μl of enzyme sample was added and incubated in an EPPENDORF® Thermomixer for 20 minutes at 50° C. and 650 rpm. A denatured enzyme sample (100° C. boiling for 20 minutes) was used as blank. After incubation the colored solution was separated from the solid by centrifugation at 3000 rpm for 5 minutes at 4° C. Then 150 μl of supernatant was transferred to a microtiter plate and the absorbance was measured using a Spectra Max M2 at 595 nm.

Example 82: Preparation of *Penicillium* sp. Strain NN51602 GH10 Xylanase

The *Penicillium* sp. strain NN51602 GH10 xylanase (SEQ ID NO: 195 [DNA sequence] and SEQ ID NO: 196 [deduced amino acid sequence]) was obtained according to PCT/US10/032034. Protein concentration was determined using a Microplate BCA™ Protein Assay Kit in which bovine serum albumin was used as a protein standard.

Example 83: Preparation of *Meripilus giganteus* Strain CBS 521.95 GH10 Xylanase The *Meripilus giganteus* strain CBS 521.95 GH10 xylanase (SEQ ID NO: 197 [DNA sequence] and SEQ ID NO: 198 [deduced amino acid sequence]) was recombinantly prepared according to WO 97/27290 except *Aspergillus oryzae* Bech2 (WO 2000/39322) was used as a host and pDAu75 as the expression vector. Vector pDAu75 is a derivative of pJa1721 (WO 03/008575). Plasmid pDAu75 mainly differs from pJa1721 in that the selection marker URA3 of *E. coli* has been disrupted by the insertion of the ampicillin resistance gene *E. coli* beta lactamase, which allows for rapid selection of positive recombinant *E. coli* clones using commercially available and highly competent strains on commonly used LB ampicillin plates. The ampicillin resistance gene is entirely removable using the two flanking Not I sites restoring a functional selection marker URA3. The techniques used for making pDAu75 from pJa1721 are common molecular biology techniques for DNA cloning. Cloning of the cDNA sequence of the *Meripilus giganteus* GH10 xylanase gene into pDAu75 was performed by a restriction/ligation cloning procedure from the xylanase producing yeast colony as described in WO 97/27290.

The broth was filtered using Whatmann glass filter GF/D, GF/A, GF/C, GF/F (2.7 μm, 1.6 μm, 1.2 μm and 0.7 μm, respectively) followed by filtration through a 0.45 μm filter.

Ammonia sulfate was added to the filtered broth to a final concentration of 3 M and the precipitate was collected after centrifugation at 10,000×g for 30 minutes. The precipitate was dissolved in 10 mM Tris/HCl pH 8.0 and dialyzed against 10 mM Tris/HCl pH 8.0 overnight. The dialyzed preparation was applied to a 150 ml Q SEPHAROSE® Fast Flow column equilibrated with 10 mM Tris/HCl pH 8.0 and the enzyme was eluted with a 1050 ml (7 column volumes) linear salt gradient from 0 to 1 M NaCl in 10 mM Tris/HCl pH 8.0. Elution was followed with A280 nm detection and fractions were collected and assayed for xylanase activity using 0.2% AZCL-Arabinoxylan from wheat (Megazyme) in 0.2 M sodium phosphate pH 6.0 μlus 0.01% TRITON® X100. Fractions containing xylanase activity were pooled and stored at −20° C. Protein concentration was determined using a Microplate BCA™ Protein Assay Kit in which bovine serum albumin was used as a protein standard.

Example 84: Preparation of *Dictyoglomus Thermophilum* Strain ATCC 35947 GH11 Xylanase The *Dictyoglomus thermophilum* GH11 xylanase (SEQ ID NO: 199 [DNA sequence] and SEQ ID NO: 200 [deduced amino acid sequence]) was recombinantly prepared according to the following procedure.

*Bacillus subtilis* strains were made competent using the method described by Anagnostopoulos and Spizizen, 1961, *Journal of Bacteriology* 81: 741-746. DNA sequencing was conducted with an ABI 3700 Sequencing (Applied Biosystems, Inc., Foster City, CA, USA).

*Bacillus subtilis* strain SM025 was constructed as described below to delete an intracellular serine protease (ispA) gene in *Bacillus subtilis* strain A164Δ10 (Bindel-Connelly et al., 2004, *J. Bacteriol.* 186: 4159-4167).

A deletion plasmid, pNNB194-ispAΔ, was constructed by splicing by overlap extension (SOE) (Horton et al., 1989, Gene 77: 61-8). Flanking DNA sequences 5' and 3' of the ispA gene were obtained by PCR amplification from chromosomal DNA derived from *Bacillus subtilis* strain 164Δ5 (U.S. Pat. No. 5,891,701) using primer pairs 994525/994526 and 994527/994528, respectively, shown below. Chromosomal DNA was obtained according to the procedure of Pitcher et al., 1989, *Lett. Appl. Microbiol.* 8: 151-156.

```
Primer 994525:
                               (SEQ ID NO: 284)
5'-GGATCCATTATGTAGGGCGTAAAGC-3'

Primer 994526:
                               (SEQ ID NO: 285)
5'-TTAGCAAGCTTAATCACTTTAATGCCCTCAG-3'

Primer 994527:
                               (SEQ ID NO: 286)
5'-TGATTAAGCTTGCTAATCCGCAGGACACTTC-3'

Primer 994528:
                               (SEQ ID NO: 287)
5'-GGTACCAACACTGCCTCTCTCATCTC-3'
```

PCR amplifications were conducted in 50 μl reactions composed of 10 ng of *Bacillus subtilis* strain 164Δ5 chromosomal DNA, 0.4 μM of each primer, 200 μM each of dATP, dCTP, dGTP, and dTTP, 1×PCR Buffer II (Applied Biosystems, Inc., Foster City, CA, USA) with 2.5 mM MgCl 2, and 2.5 units of AmpliTaq GOLD® DNA Polymerase (Applied Biosystems, Inc., Foster City, CA, USA). The reactions were performed in a ROBOCYCLER® 40 Temperature Cycler (Stratagene, Corp., La Jolla, CA, USA) programmed for 1 cycle at 95° C. for 10 minutes; 25 cycles each at 95° C. for 1 minute, 50° C. for 1 minute, and 72° C. for 1 minute; and 1 cycle at 72° C. for 7 minutes.

The PCR products were resolved by 0.8% agarose gel electrophoresis using 0.5×TBE buffer (50 mM Tris base-50 mM boric acid-1 mM disodium EDTA). A band of approximately 400 bp obtained using the primer pair 994525/994526 for the 5' flanking DNA sequence of the ispA gene was excised from the gel and extracted using a QIAQUICK® Gel Extraction Kit (QIAGEN Inc., Valencia, CA, USA). A band of approximately 400 bp obtained using the primer pair 994527/994528 for the 3' flanking DNA sequence of the ispA gene was excised from the gel and extracted using a QIAQUICK® Gel Extraction Kit.

The final SOE fragment was amplified using the same procedure above with the 400 bp fragments as templates and primers 994525 and 994528, shown above, to produce an ispA deletion fragment. The PCR product of approximately 800 kb was resolved by 0.8% agarose gel electrophoresis using 0.5×TBE buffer.

The final 800 kb SOE fragment was cloned into pCR02.1 (Invitrogen, Carlsbad, CA, USA) using a TA-TOPO® Cloning Kit (Invitrogen, Carlsbad, CA, USA) and transformed into ONE SHOT® TOP10 Chemically Competent *E. coli* cells (Invitrogen, Carlsbad, CA, USA) according to the manufacturer's instructions. Transformants were selected on 2×YT agar plates supplemented with 100 μg of ampicillin per ml and incubated at 37° C. for 16 hours. The DNA sequence of the cloned fragment was verified by DNA sequencing with M13 forward and reverse primers (Invitrogen, Inc, Carlsbad, CA, USA). The plasmid was designated pCR®2.1-ispAΔ.

Plasmid pCR2.1-ispAΔ was digested with Bam HI and Asp718 and subjected to 0.8% agarose gel electrophoresis using 0.5×TBE buffer to isolate the ispA deletion fragment. A 800 bp fragment corresponding to the ispA deletion fragment was excised from the gel and extracted using a QIAQUICK® Gel Extraction Kit.

The temperature sensitive plasmid pNNB194 (pSK+/pE194; U.S. Pat. No. 5,958,728) was digested with Bam HI and Asp718 and resolved by 0.8% agarose gel electrophoresis using TBE buffer to isolate the vector fragment. A 6600 bp vector fragment of pNNB194 was excised from the gel and extracted using a QIAQUICK® Gel Extraction Kit.

The ispA deletion fragment and the pNNB194 fragment were ligated together using a Rapid DNA Ligation Kit (Roche Applied Science, Indianapolis, IN, USA) and the ligation mix was transformed into *E. coli* SURE® cells (Stratagene Corp., La Jolla, CA, USA) selecting for ampicillin resistance according to the manufacturer's instructions. Plasmid DNA was isolated from eight transformants using a BIOROBOT® 9600, digested with Bam HI and Asp718, and analyzed by agarose electrophoresis as described above to identify plasmids which harbored the ispAΔ fragment. One transformant was identified and designated pNNB194-ispAΔ.

Plasmid pNNB194-ispAΔ was introduced into *Bacillus subtilis* A164Δ10 (Bindel-Connelly et al., 2004, *J. Bacteriol.* 186: 4159-4167) and integrated at the ispA locus by selective growth at 45° C. on Tryptose blood agar base (TBAB) plates supplemented with 1 μg of erythromycin and 25 μg of lincomycin per ml. The integrated plasmid was then excised by non-selective growth on LB medium at 34° C. Chromosomal DNA was isolated from several erythromycin sensitive clones according to the method of Pitcher et al., 1989, supra, and analyzed by PCR using primers 994525 and 994528 using the same method above to confirm the presence of the ispA deletion. One such clone was designated *Bacillus subtilis* SM025.

A linear integration vector-system was used for the expression cloning of a synthetic *Dictyoglomus thermophilum* Family 11 xylanase gene without a binding domain and without a signal peptide. The synthetic gene sequence was based on the public gene sequence UNIPROT: P77853. The synthetic gene was codon optimized for expression in *Bacillus subtilis* following recommendations by Gustafsson et al., 2004, *Trends in Biotechnology* 22: 346-353. The synthetic gene was generated by DNA2.0 (Menlo Park, CA, USA) and delivered as a cloned fragment in their standard cloning vector (kanamycin resistant). The xylanase gene was cloned as a truncated gene without binding domain and with the signal peptide from *Bacillus clausii* serine protease gene (aprH, SAVINASE™, Novo Nordisk A/S, Bagsvrd, Denmark) (included in the flanking region). The gene was designed to contain a C-terminal HQHQHQHQP tag to ease purification. The forward primer was designed so the gene was amplified from the signal peptide cleavage site and it had 26 bases overhang (shown in italic in the table below). This overhang was complementary to part of one of the two linear vector fragments and was used when the PCR fragment and the vector fragments were assembled (described below). The reverse primer was designed to amplify the truncated version of the gene and contained an overhang consisting of 30 bp encoding a HQHQHQHQP-tag and a stop codon (the overhang is shown in italic in the table below). This overhang was complementary to part of one of the two linear vector fragments and was used when the PCR fragment and the vector fragments were assembled (described below).

The linear integration construct was a PCR fusion product made by fusion of each gene between two *Bacillus* subtils homologous chromosomal regions along with a strong promoter and a chloramphenicol resistance marker. The fusion was made by splicing by overlap extension (SOE) (Horton et al., 1989, supra). The SOE PCR method is also described in WO 2003/095658. Each gene was expressed under the control of a triple promoter system (described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* crylllA promoter including the mRNA stabilizing sequence. The gene coding for chloramphenicol acetyl-transferase was used as marker (described, for example, by Diderichsen et al., 1993, *Plasmid* 30: 312). The final gene construct was integrated by homologous recombination into the pectate lyase locus of the *Bacillus* chromosome.

The GH11 xylanase gene was amplified from plasmid 7587 by PCR using the primers shown in the Table below 1 below. The plasmid 7587 contains the synthetic *Dictyoglomus thermophilum* GH11 xylanase gene (SEQ ID NO: 304 for the DNA sequence and SEQ ID NO: 305 for the deduced amino acid sequence) without a binding domain and without a signal peptide.

Three fragments were PCR amplified to make the construct: the gene fragment containing the truncated xylanase gene and the 26 bp and 30 bp flanking DNA sequences included in the primers as overhang, the upstream flanking fragment (including a signal peptide from Savinase and amplified with the primers 260558 and iMB1361Uni2) and the downstream flanking fragment (amplified with the primers 260559 and HQHQHQHQP-f). The flanking fragments were amplified from genomic DNA of the strain iMB1361 (described in patent application WO 2003/095658). All primers used are listed in the Table 1 below.

The gene fragment was amplified using a proofreading polymerase PHUSION™ DNA Polymerase according to the manufacturer's instructions. The two flanking DNA fragments were amplified with "Expand High Fidelity PCR System" (Roche-Applied-Science) according to standard procedures (following the manufacturer's recommendations). The PCR conditions were as follows: 94° C. for 2 minutes followed by 10 cycles of (94° C. for 15 seconds, 50° C. for 45 seconds, 68° C. for 4 minutes) followed by 20 cycles of (94° C. for 15 seconds, 50° C. for 45 seconds, 68° C. for 4 minutes (+20 seconds extension per cycle)) and ending with one cycle at 68° C. for 10 min. The 3 PCR fragments were subjected to a subsequent Splicing by Overlap Extension (SOE) PCR reaction to assemble the 3 fragments into one linear vector construct. This was performed by mixing the 3 fragments in equal molar ratios and a new PCR reaction were run under the following conditions: initial 2 minutes. at 94° C., followed by 10 cycles of (94° C. for 15 seconds, 50° C. for 45 seconds, 68° C. for 5 minutes), 10 cycles of (94° C. for 15 seconds, 50° C. for 45 seconds, 68° C. for 8 minutes), 15 cycles of (94° C. for 15 seconds, 50° C. for seconds, 68° C. for 8 minutes in addition 20 seconds extra per cycle). After the $1^{st}$ cycle the two end primers 260558 and 260559 were added (20 μMol of each). Two μl of the PCR product were transformed into *Bacillus subtilis*. Transformants were selected on LB plates supplemented with 6 μg of chloramphenicol per ml. The truncated xylanase construct was integrated by homologous recombination into the genome of the *Bacillus subtilis* host PL4250 (AprE−, NprE−, SrfC−, SpoIIAC−, AmyE−, comS+). One transformant, EXP01955, was selected for further work. The xylanase coding region was sequenced in this transformant. It contained one mutation leading to a change of the HQHQHQHQP-tag to a HQHQHQHQQ-tag) but no other mutations were observed.

TABLE 1

Primers used

| Amplification of | SPECIFIC PRIMER FORWARD | SPECIFIC PRIMER REVERSE |
|---|---|---|
| Truncated gene | FORWARD (SEQ ID NO: 288) 5'-CTTTTAGTTCATCGATCGCATCGG CTGCTCAGACATCAATCACACTTA-3' | REVERSE (SEQ ID NO: 289) 5'-CTAGGGTTGATGCTGGTGTTGGTGC TGATGGCTGCCCTGAGAGAAAGTG-3' |
| Upstream flanking fragment | 260558: (SEQ ID NO: 290) 5'-GAGTATCGCCAGTAAGGGGCG-3' | iMB1361Uni2 (SEQ ID NO: 291) 5' AGCCGATGCGATCGATGAACTA 3' |
| Downstream flanking fragment | HQHQHQHQP-f (SEQ ID NO: 292) 5'-CATCAGCACCAACACCAGCACCAG CCATAATCGCATGTTCAATCCGCTCCA TA-3' | 260559: (SEQ ID NO: 293) 5'-GCAGCCCTAAAATCGCATAAAGC-3' |

Chromosomal DNA from *Bacillus subtilis* strain EXP01955 was used as a template to PCR clone the *Bacillus clausii* serine protease gene (aprH, SAVINASE™, Novo Nordisk A/S, Bagsvrd, Denmark) signal sequence/mature *D. thermophilum* xylanase gene (CBM-deleted) into pCR2.1-TOPO using the following primers which introduce a Sac I site at the 5' end (just upstream of the aprH ribosome binding site) and a Mlu I site at the 3' end (just after the translation stop codon which was introduced after the Ser codon at position 691-693, thereby avoiding the incorporation of the HQHQHQHQQ-tag). Chromosomal DNA was obtained according to the procedure of Pitcher et al., 1989, supra.

Primer 062405:
(SEQ ID NO: 294)
5'-GAGCTCTATAAAAATGAGGAGGGAACCGAATGAAGAAACC-3'

Primer 062406:
(SEQ ID NO: 295)
5'-ACGCGTTTAGCTGCCCTGAGAGAAAGTG-3'

The PCR amplifications were conducted in 50 μl reactions composed of 10 ng of *B. subtilis* EXP01955 chromosomal DNA, 0.4 μM of each primer, 200 μM each of dATP, dCTP, dGTP, and dTTP, 1×PCR Buffer II with 2.5 mM MgCl 2, and 2.5 units of AmpliTaq GOLD® DNA Polymerase. The reactions were performed in a ROBOCYCLER® 40 Temperature Cycler programmed for 1 cycle at 95° C. for 10 minutes; 25 cycles each at 95° C. for 1 minute, 50° C. for 1 minute, and 72° C. for 1 minute; and 1 cycle at 72° C. for 7 minutes. A PCR product of approximately 740 kb of the truncated xylanase gene was resolved by 0.8% agarose gel electrophoresis using 0.5×TBE buffer, excised from the gel, and extracted using a QIAQUICK® Gel Extraction Kit.

The 740 kb fragment was cloned into pCR®2.1 using a TA-TOPO® Cloning Kit according to the manufacturer's instructions and transformed into ONE SHOT® TOP10 Chemically Competent *E. coli* cells according to the manufacturer's instructions. Transformants were selected on 2×YT agar plates supplemented with 100 μg of ampicillin per ml and incubated at 37° C. for 16 hours. The DNA sequence of the cloned fragment was verified by DNA sequencing with M13 forward and reverse primers. The plasmid was designated pCR2.1-Dt xyl.

DNA sequencing revealed that there was an extra G at position 19 of the sequence encoding the aprH signal sequence. A QUIKCHANGE® XL Site-Directed Mutagenesis Kit (Stratagene Corp., La Jolla, CA, USA) was utilized to correct the mistake in plasmid pCR2.1-Dt xyl using the following primers to delete the extra G residue:

```
Primer 062535:
                              (SEQ ID NO: 296)
5'-CCGTTGGGGAAAATTGTCGC-3'

Primer 062536:
                              (SEQ ID NO: 297)
5'-GCGACAATTTTCCCCAACGG-3'
```

The kit was used according to the manufacturer's instructions and the change was successfully made resulting in plasmid pCR2.1-Dt xyl2.

Plasmid pCR2.1-Dt xyl2 and pMDT100 WO 2008/140615 were digested with Sac I and Mlu I. The digestions were each resolved by 0.8% agarose gel electrophoresis using 0.5×TBE buffer. A vector fragment of approximately 8.0 kb from pMDT100 and a xylanase gene fragment of approximately 700 bp from pCR2.1-Dt xyl2 were excised from the gels and extracted using a QIAQUICK® Gel Extraction Kit. The two purified fragments were ligated together using a Rapid DNA Ligation Kit.

Competent cells of *Bacillus subtilis* 168Δ4 were transformed with the ligation products according to the method of Young and Spizizen, 1961, *Journal of Bacteriology* 81: 823-829, or Dubnau and Davidoff-Abelson, 1971, *Journal of Molecular Biology* 56: 209-221. *Bacillus subtilis* 168Δ4 is derived from the *Bacillus subtilis* type strain 168 (BGSC 1A1, *Bacillus* Genetic Stock Center, Columbus, OH, USA) and has deletions in the spoIIAC, aprE, nprE, and amyE genes. The deletion of the four genes was performed essentially as described for *Bacillus subtilis* A164Δ5 (U.S. Pat. No. 5,891,701).

*Bacillus subtilis* transformants were selected at 37° C. after 16 hours of growth on TBAB plates supplemented with 5 μg of chloramphenicol per ml. To screen for integration of the plasmid by double cross-over at the amyE locus, *Bacillus subtilis* primary transformants were patched onto TBAB plates supplemented with 6 μg of neomycin per ml and onto TBAB plates supplemented with 5 μg of chloramphenicol per ml. Integration of the plasmid by double cross-over at the amyE locus does not incorporate the neomycin resistance gene and therefore renders the strain neomycin sensitive. A chloramphenicol resistant, neomycin sensitive transformant was identified, which harbored the *Dictyoglomus thermophilum* xylanase expression cassette in the amyE locus, and designated *Bacillus subtilis* 168 with pSMO271.

Genomic DNA was isolated from *Bacillus subtilis* 168 with pSMO271 (Pitcher et al., 1989, supra) and 0.1 μg was transformed into competent *Bacillus subtilis* SM025. Transformants were selected on TBAB plates supplemented with 5 μg of chloramphenicol per ml at 37° C. A chloramphenicol resistant transformant was single colony purified and designated *Bacillus subtilis* SM047.

The *Bacillus subtilis* strain designated SMO7 was streaked on agar slants and incubated for about 24 hours at 37° C. The agar medium was composed per liter of 10 g of soy peptone, 10 g of sucrose, 2 g of trisodium citrate dihydrate, 4 g of $KH_2PO_4$, 5 g of $Na_2HPO_4$, 15 g of Bacto agar, 0.15 mg of biotin, 2 ml of trace metals, and deionized water to 1 liter. The trace metals solution was composed of 1.59 g of $ZnSO_4 \cdot 7 H_2O$, 0.76 g of $CuSO_4 \cdot 5 H_2O$, 7.52 g of $FeSO_4 \cdot 7 H_2O$, 1.88 g of $MnSO_4 \cdot H_2O$, 20 g of citric acid, and deionized water to 1 liter. Approximately 15 ml of sterile buffer (7.0 g of $Na_2HPO_4$, 3.0 g of $KH_2PO_4$, 4.0 g of NaCl, 0.2 g of $MgSO_4 \cdot 7 H_2O$, and deionized water to 1 liter) was used to gently wash off some of the cells from the agar surface. The bacterial suspension was then used for inoculation of baffled shake flasks containing 100 ml of growth medium composed of 11 g of soy bean meal, 0.4 g of $Na_2HPO_4$, 5 drops of antifoam, and deionized water to 100 ml. The inoculated shake flasks were incubated at 37° C. for about 20 hours with shaking at 300 rpm, after which 100 ml (obtained by combining the media from two independent shake flasks with the same strain) were used for inoculation of a 3 liter fermentor with 900 ml of medium composed of 40 g of hydrolyzed potato protein, 6 g of $K_2SO_4$, 4 g of $Na_2HPO_4$, 12 g of $K_2HPO_4$, 4 g of $(NH_4)_2SO_4$, 0.5 g of $CaCO_3$, 2 g of citric acid; 4 g of $MgSO_4$, 40 ml of trace metals solution (described above), 1 mg of biotin (biotin was added as 1 ml of a 1 g per liter biotin solution in the buffer described above), 1.3 ml of antifoam, and deionized water to 1 liter. The medium was adjusted to pH 5.25 with phosphoric acid prior to being autoclaved.

The fermentation was carried out as a fed-batch fermentation with sucrose solution being the feed. The fermentation temperature was held constant at 37° C. The tanks were aerated with 3 liter air per minute, and the agitation rate was held in the range of 1,500-1,800 rpm. The fermentation time was around 60-70 hours. The pH was maintained in the range of pH 6.5-7.3.

The fermentation was assayed for xylanase activity according to the following procedure. Culture supernatants were diluted appropriately in 0.1 M sodium acetate pH 5.0. A purified *Dictyoglomus thermophilum* xylanase was diluted using 2-fold steps starting with a 1.71 μg/ml concentration and ending with a 0.03 μg/ml concentration in the sample buffer. A total of 40 μl of each dilution including standard was transferred to a 96-well flat bottom plate. Using a Biomek NX (Beckman Coulter, Fullerton CA, USA), a 96-well pipetting workstation, 40 μl an Azo-Wheat arabinoxylan (Megazyme International, Ireland) substrate solution (1% w/v) was added to each well then incubated at 50° C. for 30 minutes. Upon completion of the incubation the reaction was stopped with 200 μl of ethanol (95% v/v). The samples were then incubated at ambient temperatures for 5 minutes followed by centrifugation at 3,000 rpm for 10 minutes. One hundred-fifty microliters of the supernatant was removed and dispensed into a new 96-well flat bottom plate. An optical density of 590 nm was obtained for the 96-well plate using a SPECTRAMAX® 250 μlate reader (Molecular Devices, Sunnvale CA, USA). Sample concentrations were determined by extrapolation from the generated standard curve.

Filtrated broth was added to 2% v/v GC-850 (Gulbrandsen, SC, USA) followed by centrifugation at 20,000×g for 20 minutes. The supernatant was again added 2% v/v GC-850 followed by centrifugation at 20,000×g for 20 minutes. The supernatant was concentrated using a tangential flow concentrator equipped with a Sartocon® Slice cassette with a 10 kDa MW-CO polyethersulfone membrane. The concentrate was 80° C. treated for 30 minutes and filtrated through a 1.2 μm glass microfibre filter (Whatman, International Ltd, Maidstone, England). The pH was adjusted to pH 8.0 and loaded onto a MEP HyperCel™ (Pall Corporation, East Hills, NY USA) column. The bound proteins were eluted with 50 mM acetic acid pH 4.5. The eluted proteins were stirred with activated carbon 1% w/v (Picatif FGV 120, Pica, France) for 15 minutes and filtrated on 0.2 μm PES filter (Nalge Nunc International, New York, NY USA). The pH was adjusted to pH 5.0 using 3 M Tris. Protein concentration was determined using a Microplate BCA™ Protein Assay Kit in which bovine serum albumin was used as a protein standard.

Example 85: Preparation of *Aspergillus aculeatus* Strain CBS 172.66 GH3 Beta-Xylosidase The *Aspergillus aculeatus* strain CBS 172.66 GH beta-xylosidase (SEQ ID NO: 201 [DNA sequence] and SEQ ID NO: 202 [deduced amino acid sequence]) was recombinantly prepared according to the following procedure. *Aspergillus aculeatus* CBS 172.66 was used as the source of the polypeptide having beta-xylosidase activity.

Genomic sequence information was generated by the U.S. Department of Energy Joint Genome Institute (JGI). A preliminary assembly of the genome was downloaded from JGI and analyzed using the Pedant-Pro™ Sequence Analysis Suite (Biomax Informatics AG, Martinsried, Germany). Gene models constructed by the software were used as a starting point for detecting GH3 homologues in the genome. More precise gene models were constructed manually using multiple known GH3 protein sequences as a guide.

To generate genomic DNA for PCR amplification, *Aspergillus aculeatus* CBS 172.66 was propagated on PDA agar plates by growing at 26° C. for 7 days. Spores harvested from the PDA plates were used to inoculate 25 ml of YP+2% glucose medium in a baffled shake flask and incubated at 26° C. for 48 hours with agitation at 200 rpm.

Genomic DNA was isolated according to a modified FastDNA® SPIN protocol (Qbiogene, Inc., Carlsbad, CA, USA). Briefly a FastDNA® SPIN Kit for Soil (Qbiogene, Inc., Carlsbad, CA, USA) was used in a FastPrep® 24 Homogenization System (MP Biosciences, Santa Ana, CA, USA). Two ml of fungal material from the above cultures were harvested by centrifugation at 14,000×g for 2 minutes. The supernatant was removed and the pellet resuspended in 500 μl of deionized water. The suspension was transferred to a Lysing Matrix E FastPrep® tube (Qbiogene, Inc., Carlsbad, CA, USA) and 790 μl of sodium phosphate buffer and 100 μl of MT buffer from the FastDNA® SPIN Kit were added to the tube. The sample was then secured in the FastPrep® Instrument (Qbiogene, Inc., Carlsbad, CA, USA) and processed for 60 seconds at a speed of 5.5 m/sec. The sample was then centrifuged at 14,000×g for two minutes and the supernatant transferred to a clean EPPENDORF® tube. A 250 μl volume of PPS reagent from the FastDNA® SPIN Kit was added and then the sample was mixed gently by inversion. The sample was again centrifuged at 14,000×g for 5 minutes. The supernatant was transferred to a 15 ml tube followed by 1 ml of Binding Matrix suspension from the FastDNA® SPIN Kit and then mixed by inversion for two minutes. The sample was placed in a stationary tube rack and the silica matrix was allowed to settle for 3 minutes. A 500 μl volume of the supernatant was removed and discarded and then the remaining sample was resuspended in the matrix. The sample was then transferred to a SPIN filter tube from the FastDNA® SPIN Kit and centrifuged at 14,000×g for 1 minute. The catch tube was emptied and the remaining matrix suspension added to the SPIN filter tube. The sample was again centrifuged (14,000×g, 1 minute). A 500 μl volume of SEWS-M solution from the FastDNA® SPIN Kit was added to the SPIN filter tube and the sample was centrifuged at the same speed for 1 minute. The catch tube was emptied and the SPIN filter replaced in the catch tube. The unit was centrifuged at 14,000×g for 2 minutes to "dry" the matrix of residual SEWS-M wash solution. The SPIN filter was placed in a fresh catch tube and allowed to air dry for 5 minutes at room temperature. The matrix was gently resuspended in 100 μl of DES (DNase/Pyrogen free water) with a pipette tip. The unit was centrifuged (14,000× g, 1 minute) to elute the genomic DNA followed by elution with 100 μl of 10 mM Tris, 0.1 mM EDTA, pH 8.0 by renewed centrifugation at 14,000×g for 1 minute and the eluates were combined. The concentration of the DNA harvested from the catch tube was measured by a UV spectrophotometer at 260 nm.

Synthetic oligonucleotide primers shown below are designed to PCR amplify *Aspergillus aculeatus* CBS 172.66 GH3 genes from the genomic DNA prepared in Example 2. An IN-FUSION™ Cloning Kit (Clontech, Mountain View, CA, USA) is used to clone the fragments directly into the expression vector pDau109 (WO 2005/042735).

Primer GH3-114f:
(SEQ ID NO: 298)
5'-ACACAACTGGGGATCCACCATGGCTGTGGCGGCTCTT-3'

Primer GH3-114r:
(SEQ ID NO: 299)
5'-AGATCTCGAGAAGCTTACTACTCATCCCCCTGCAC-3'

PCR reactions are carried out with genomic DNA prepared from Example 2 for amplification of the genes identified in Example 1. The PCR reaction is composed of 1 μl of genomic DNA, 1 μl of primer forward (f) (50 μM); 1 μl of primer reverse (r) (50 μM); 10 μl of 5×HF buffer, 2 μl of 10 mM dNTP; 1 μl of PHUSION® DNA polymerase, and PCR-grade water up to 50 μl. Primers GH3-114f and GH3-114r are used simultaneously.

The PCR reactions are performed using a DYAD® PCR machine programmed for 2 minutes at 98° C. followed by 20 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds; and 5 minutes at 72° C.

The reaction products are isolated by 1.0% agarose gel electrophoresis using 40 mM Tris base, 20 mM sodium acetate, 1 mM disodium EDTA (TAE) buffer where approximately 2.5 to 3.0 kb PCR product bands are excised from the gels and purified using a GFX® PCR DNA and Gel Band Purification Kit according to manufacturer's instructions. DNA corresponding to the *A. aculeatus* GH3 genes are cloned into the expression vector pDAu109 (WO 2005042735) linearized with Bam HI and Hind III, using an IN-FUSION™ Dry-Down PCR Cloning Kit according to the manufacturer's instructions.

A 2.5 μl volume of the five times diluted ligation mixture is used to transform *E. coli* TOP10 chemically competent cells. Five colonies are selected on LB agar plates containing 100 μg of ampicillin per ml and cultivated overnight in 3 ml of LB medium supplemented with 100 μg of ampicillin per ml. Plasmid DNA is purified using an E.Z.N.A.® Plasmid Mini Kit according to the manufacturer's instructions. The *Aspergillus aculeatus* GH3 gene sequences were verified by Sanger sequencing with an Applied Biosystems Model 3700 Automated DNA Sequencer using version 3.1 BIG-DYE™ terminator chemistry (Applied Biosystems, Inc., Foster City, CA, USA) (Applied Biosystems, Inc., Foster City, CA, USA). Nucleotide sequence data are scrutinized for quality and all sequences are compared to each other with assistance of PHRED/PHRAP software (University of Washington, Seattle, WA, USA).

The coding sequence is 2412 bp including the stop codon and contains no introns. The encoded predicted protein is 803 amino acids. Using the SignalP program (Nielsen et al., 1997, supra), a signal peptide of 17 residues was predicted. The predicted mature protein contains 786 amino acids.

Spores of the best transformant were spread on COVE plates containing 0.01% TRITON® X-100 in order to isolate single colonies. The spreading was repeated twice in total on COVE sucrose medium (Cove, 1996, *Biochim. Biophys. Acta* 133: 51-56) containing 1 M sucrose and 10 mM sodium nitrate, supplemented with 10 mM acetamide and 15 mM CsCl. Fermentation was then carried out in 250 ml shake flasks using DAP-2C-1 medium for 4 days at with shaking at 100 rpm. The fermentation broth was filtered using standard methods.

Ammonium sulphate was added to the filtrated broth to a concentration of 2 M. After filtration using a 0.2 µm PES filter (Thermo Fisher Scientific, Roskilde, Denmark), the filtrate was loaded onto a Phenyl Sepharose™ 6 Fast Flow column (high sub) (GE Healthcare, Piscataway, NJ, USA) equilibrated in 25 mM HEPES pH 7.0 with 2 M ammonium sulphate, and bound proteins were eluted with 25 mM HEPES pH 7.0 with no ammonium sulphate. The fractions were pooled and applied to a Sephadex™ G-25 (medium) (GE Healthcare, Piscataway, NJ, USA) column equilibrated in 25 mM HEPES pH 7.0. The fractions were pooled and then applied to a SOURCE™ 15Q (GE Healthcare, Piscataway, NJ, USA) column equilibrated in 25 mM HEPES pH 7.0, and bound proteins were eluted with a linear gradient from 0-1000 mM sodium chloride. Protein concentration was determined using a Microplate BCA™ Protein Assay Kit in which bovine serum albumin was used as a protein standard.

Example 86: Preparation of *Aspergillus aculeatus* Strain CBS 186.67 GH3 Beta-Xylosidase The *Aspergillus aculeatus* strain CBS 186.67 GH3 beta-xylosidase (SEQ ID NO: 203 [DNA sequence] and SEQ ID NO: 204 [deduced amino acid sequence]) was recombinantly prepared according to the following procedure.

Genomic DNA was isolated according to the procedure described in Example 73.

The *Aspergillus aculeatus* beta-xylosidase gene was isolated by PCR using two cloning primers GH3-101f and GH3-101r, shown below, which were designed based on the publicly available *Aspergillus aculeatus* xyl2 full-length sequence (GenBank AB462375.1) for direct cloning using the IN-FUSION™ strategy.

```
Primer GH3-101f:
                                          (SEQ ID NO: 300)
5'-acacaactggggatccaccatggctgtggcggctcttgctctgctg g-3'

Primer GH3-101r:
                                          (SEQ ID NO: 301)
5'-agatctcgagaagcttaCTCATCCCCCGCCACCCCTGCACCTC

C-3'
```

A PCR reaction was performed with genomic DNA prepared from *Aspergillus aculeatus* CBS 186.67 in order to amplify the full-length gene. The PCR reaction was composed of 1 µl of genomic DNA, 0.75 µl of primer GH3-101.1f (10 µM), 0.75 µl of primer GH3-101.1r (10 µM), 3 µl of 5× HF buffer, 0.25 µl of 50 mM MgCl$_2$, 0.3 µl of 10 mM dNTP, 0.15 µl of PHUSION® DNA polymerase, and PCR-grade water up to 15 µl. The PCR reaction was performed using a DYAD® PCR machine programmed for 2 minutes at 98° C. followed by 10 touchdown cycles at 98° C. for 15 seconds, 70° C. (−1° C./cycle) for 30 seconds, and 72° C. for 2 minutes 30 seconds; and 25 cycles each at 98° C. for 15 seconds, 60° C. for 30 seconds, 72° C. for 2 minutes 30 seconds, and 5 minutes at 72° C.

The reaction products were isolated by 1.0% agarose gel electrophoresis using TAE buffer where an approximately 2.4 kb PCR product band was excised from the gel and purified using a GFX® PCR DNA and Gel Band Purification Kit according to manufacturer's instructions. DNA corresponding to the *Aapergillus aculeatus* beta-xylosidase gene was cloned into the expression vector pDAu109 (WO 2005042735) linearized with Bam HI and Hind III, using an IN-FUSION™ Dry-Down PCR Cloning Kit according to the manufacturer's instructions.

A 2.5 µl volume of the diluted ligation mixture was used to transform *E. coli* TOP10 chemically competent cells. Three colonies were selected on LB agar plates containing 100 µg of ampicillin per ml and cultivated overnight in 3 ml of LB medium supplemented with 100 µg of ampicillin per ml. Plasmid DNA was purified using an E.Z.N.A.® Plasmid Mini Kit according to the manufacturer's instructions. The *Aspergillus aculeatus* beta-xylosidase gene sequence was verified by Sanger sequencing before heterologous expression.

The coding sequence is 2454 bp including the stop codon. The gene does not contain introns. The encoded predicted protein is 817 amino acids. Using the SignalP program (Nielsen et al., 1997, *Protein Engineering* 10: 1-6), a signal peptide of 17 residues was predicted. The predicted mature protein contains 800 amino acids.

Protoplasts of *Aspergillus oryzae* MT3568 were prepared as described in WO 95/02043. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene with the pyrG gene. One hundred microliters of protoplast suspension were mixed with 2.5-15 µg of the *Aspergillus* expression vector and 250 µl of 60% PEG 4000, 10 mM CaCl$_2$, and 10 mM Tris-HCl pH 7.5 were added and gently mixed. The mixture was incubated at 37° C. for 30 minutes and the protoplasts were spread on COVE sucrose (1 M) plates supplemented with 10 mM acetamide and 15 mM CsCl for transformant selection. After incubation for 4-7 days at 37° C. spores of several transformants were seeded on YP-2% maltodextrin medium. After 4 days cultivation at 30° C. culture broth was analyzed in order to identify the best transformants based on their ability to produce a large amount of active *Aculeatus aculeatus* beta-xylosidase. The screening was based on intensity of the band corresponding to the heterologous expressed protein determined by SDS-PAGE and activity of the enzyme on 4-nitrophenyl-beta-D-xylopyranoside (pNPX) as follows. Ten µl of culture broth was mixed with 90 µl of assay reagent containing 10 µl of 0.1% TWEEN® 20, 10 µl of 1 M sodium citrate pH 5, 4 µl of 100 mM of pNPX substrate (Sigma Aldrich) solubilized in DMSO (0.4% final volume in stock solution), and filtered water. The assay was performed for 30 minutes at 37° C. and absorbance determined at 405 nm before and after addition of 100 µl of 1 M sodium carbonate pH 10. The highest absorbance values at 405 nm were correlated to the SDS-PAGE data for selection of the best transformant.

Spores of the best transformant designated *A. oryzae* EXP3611 were spread on COVE plates containing 0.01% TRITON® X-100 in order to isolate single colonies. The spreading was repeated twice in total on COVE sucrose medium (Cove, 1996, *Biochim. Biophys. Acta* 133: 51-56) containing 1 M sucrose and 10 mM sodium nitrate, supplemented with 10 mM acetamide and 15 mM CsCl. Fermentation was then carried out in 250 ml shake flasks using DAP-4C-1 medium for 4 days at 30° C. with shaking at 100 rpm. The fermentation broth was filtered using standard methods. Protein concentration was determined using a Microplate BCA™ Protein Assay Kit in which bovine serum albumin was used as a protein standard.

Example 87: Preparation of *Aspergillus fumigatus* Strain NN051616 GH3 Beta-Xylosidase Q0H905

The *Aspergillus fumigatus* strain NN051616 GH3 beta-xylosidase (SEQ ID NO: 205 [DNA sequence] and SEQ ID NO: 206 [deduced amino acid sequence]) was recombinantly prepared according to the following procedure.

Two synthetic oligonucleotide primers shown below were designed to PCR amplify the *Aspergillus fumigatus* beta xylosidase gene from the genomic DNA. An InFusion Cloning Kit (Clontech, Mountain View, CA) was used to clone the fragment directly into the expression vector, pAlLo2 (WO 2005/074647), without the need for restriction digests and ligation.

```
Forward primer:
                                  (SEQ ID NO: 302)
5'-ACTGGATTTACCATGGCGGTTGCCAAATCTATTGCT-3'

Reverse primer:
                                  (SEQ ID NO: 303)
5'-TCACCTCTAGTTAATTAATCACGCAGACGAAATCTGCT-3'
```

Bold letters represent coding sequence. The remaining sequence is homologous to the insertion sites of pAlLo2.

Fifteen picomoles of each of the primers above were used in a PCR reaction containing 250 ng of *Aspergillus fumigatus* genomic DNA, 1× Expand High Fidelity Buffer with MgCl 2 (Roche Applied Science, Indianapolis, IN), 1 µl of 10 mM blend of dATP, dTTP, dGTP, and dCTP, 0.75 units of Expand High fidelity Enzyme Mix (Roche Applied Science, Indianapolis, IN), in a final volume of 50 µl. The amplification conditions were one cycle at 94° C. for 2 minutes; 10 cycles each at 94° C. for 15 seconds, 56.5° C. for 30 seconds, and 72° C. for 2 minutes; and 20 cycles each at 94° C. for 15 seconds, 56.5° C. for 30 seconds, and 72° C. for 2 minutes plus 5 seconds per successive cycle. The heat block was then held at 72° C. for 7 minutes followed by a 4° C. soak cycle.

The reaction products were isolated on a 1.0% agarose gel using TAE buffer and a 2.4 kb product band was excised from the gel and purified using a MinElute® Gel Extraction Kit (QIAGEN Inc., Valencia, CA) according to the manufacturer's instructions.

The fragment was then cloned into pAlLo2 using an InFusion Cloning Kit. The vector was digested with Nco I and Pac I (using conditions specified by the manufacturer). The fragment was purified by gel electrophoresis and QIAquick kit (QIAGEN Inc., Valencia, CA) gel purification. The gene fragment and the digested vector were combined together in a reaction resulting in the expression plasmid pAG57, in which transcription of the *Aspergillus fumigatus* beta-xylosidase gene was under the control of the NA2-tpi promoter (a hybrid of the promoters from the genes for *Aspergillus niger* neutral alpha-amylase and *Aspergillus oryzae* triose phosphate isomerase). The recombination reaction (20 µl) was composed of 1× InFusion Buffer (Clontech, Mountain View, CA), 1×BSA (Clontech, Mountain View, CA), 1 µl of InFusion enzyme (diluted 1:10) (Clontech, Mountain View, CA), 182 ng of pAlLo2 digested with Nco I and Pac 1, and 97.7 ng of the *Aspergillus fumigatus* beta-xylosidase purified PCR product. The reaction was incubated at 37° C. for 15 minutes followed by 15 minutes at 50° C. The reaction was diluted with 40 µl of TE buffer and 2.5 µl the diluted reaction was used to transform *E. coli* Top10 Competent cells. An *E. coli* transformant containing pAG57 (*Aspergillus fumigatus* beta-xylosidase gene) was identified by restriction enzyme digestion and plasmid DNA was prepared using a BIOROBOT® 9600. The pAG57 plasmid construct was sequenced using an Applied Biosystems 3130xl Genetic Analyzer (Applied Biosystems, Foster City, CA, USA) to verify the sequence.

*Aspergillus oryzae* JaL355 protoplasts were prepared according to the method of Christensen et al., 1988, Bio/Technology 6: 1419-1422 and transformed with 5 µg of pAG57. Twenty-four transformants were isolated to individual PDA plates.

Plugs taken from the original transformation plate of each of the twenty-four transformants were added to 1 ml of M410 separately in 24 well plates, which were incubated at 34° C. After three days of incubation, 7.5 µl of supernatant from each culture was analyzed using Criterion stain-free, 8-16% gradient SDS-PAGE, (BioRad, Hercules, CA) according to the manufacturer's instructions. SDS-PAGE profiles of the cultures showed that several transformants had a new major band of approximately 130 kDa.

Confluent PDA plate of the highest expressing transformant was washed with 5 ml of TWEEN® 20 and inoculated into a 500 ml Erlenmeyer flask containing 100 ml of M410 medium. Inoculated flask was incubated with shaking for 3 days at 34° C. The broth was filtered through a 0.22 µm stericup suction filter (Millipore, Bedford, MA).

Filtered broth was concentrated and buffer exchanged using a tangential flow concentrator (Pall Filtron, Northborough, MA, USA) equipped with a 10 kDa polyethersulfone membrane (Pall Filtron, Northborough, MA, USA) with 50 mM sodium acetate pH 5.0. Protein concentration was determined using a Microplate BCA™ Protein Assay Kit in which bovine serum albumin was used as a protein standard.

Example 88: Evaluation of Two Cellobiohydrolases I Replacing a CBHI Component in a High-Temperature Enzyme Composition in Saccharification of Milled Unwashed PCS at 50-65° C.

The ability of two cellobiohydrolase I proteins to replace a CBHI component in a high-temperature enzyme composition (3 mg total protein per g cellulose) was tested at 50° C., 55° C., 60° C., and 65° C. using milled unwashed PCS as a substrate. The high-temperature enzyme composition included 37% CBHI, 25% *Aspergillus fumigatus* Cel6A CBHII, 10% *Myceliophthora thermophila* Cel5A EGII, 15% *Penicillium* sp. GH61A polypeptide having cellulolytic enhancing activity, 5% *Aspergillus fumigatus* Cel3A beta-glucosidase, 5% *Aspergillus fumigatus* GH10 xyn3 xylanase, and 3% *Trichoderma reesei* GH3 beta-xylosidase.

The following CBHIs were each tested in the high-temperature enzyme composition: *Aspergillus fumigatus* Cel7A CBHI and *Penicillium emersonii* Cel7A CBHI.

The assay was performed as described in Example 34. The 1 ml reactions with milled unwashed PCS (5% insoluble solids) were conducted for 72 hours in 50 mM sodium acetate pH buffer containing 1 mM manganese sulfate. All reactions were performed in triplicate and involved single mixing at the beginning of hydrolysis.

As shown in FIG. 29, *Penicillium emersonii* Cel7A CBHI performed the same as *Aspergillus fumigatus* Cel7A CBHI at 50° C. and performed better than *Aspergillus fumigatus* Cel7A CBHI at 55-65° C. (as the degree of cellulose conversion to glucose was higher for *Penicillium emersonii* Cel7A CBHI than *Aspergillus fumigatus* Cel7A CBHI at 55-65° C.).

Example 89: Evaluation of Two Cellobiohydrolases I Replacing a CBHI Component in a High-Temperature Enzyme Composition in Saccharification of Milled Unwashed PCS at 50-65° C.

The ability of two cellobiohydrolase I proteins to replace a CBHI component in a high-temperature enzyme composition (3 mg total protein per g cellulose) was tested at 50° C., 55° C., and 65° C. using milled unwashed PCS as a substrate. The high-temperature enzyme composition included 40% CBHI, 25% *Aspergillus fumigatus* Cel6A CBHII, 10% *Myceliophthora thermophila* Cel5A EGII, 15% *Thermoascus aurantiacus* GH61A polypeptide having cellulolytic enhancing activity, 5% *Aspergillus fumigatus* GH10 xylanase, and 5% *Aspergillus fumigatus* Cel3A beta-glucosidase.

The following CBHIs were each tested in the high-temperature enzyme composition: *Aspergillus fumigatus* Cel7A CBHI and *Penicillium pinophilum* Cel7A CBHI. The high-temperature composition including *Aspergillus fumigatus* Cel7A CBHI was loaded at 3.3 mg total protein per gram cellulose instead of 3 mg total protein per gram cellulose, in which *Penicillium pinophilum* Cel7A CBHI was loaded.

The assay was performed as described in Example 34. The 1 ml reactions with 5% milled unwashed PCS were conducted for 72 hours in 50 mM sodium acetate pH 5.0 buffer containing 1 mM manganese sulfate. All reactions were performed in triplicate and involved single mixing at the beginning of hydrolysis.

As shown in FIG. 30, *Penicillium pinophilum* Cel7A CBHI performed well in the entire range of temperatures. *Penicillium pinophilum* Cel7A CBHI performed about the same as *Aspergillus fumigatus* Cel7A CBHI at 50° C. and 55° C., but the performance was slightly lower compared to *Aspergillus fumigatus* Cel7A CBHI at 60° C. and 65° C.

Example 90: Evaluation of Two Cellobiohydrolases I Replacing a CBHI Component in a High-Temperature Enzyme Composition in Saccharification of Milled Unwashed PCS at 50-65° C.

The ability of two cellobiohydrolase I proteins to replace a CBHI component in a high-temperature enzyme composition (3 mg total protein per g cellulose) was tested at 50° C., 55° C., and 65° C. using milled unwashed PCS as a substrate. The high-temperature enzyme composition included 37% CBHI, 25% *Aspergillus fumigatus* Cel6A CBHII, 10% *Myceliophthora thermophila* Cel5A EGII, 15% *Thermoascus aurantiacus* GH61A polypeptide having cellulolytic enhancing activity, 5% *Aspergillus fumigatus* Cel3A beta-glucosidase, 5% *Aspergillus fumigatus* GH10 xyn3 xylanase, and 3% *Trichoderma reesei* GH3 beta-xylosidase.

The following CBHIs were each tested in the high-temperature enzyme composition: *Aspergillus fumigatus* Cel7A CBHI and *Aspergillus terreus* Cel7A CBHI.

The assay was performed as described in Example 34. The 1 ml reactions with milled unwashed PCS (5% insoluble solids) were conducted for 72 hours in 50 mM sodium acetate pH buffer containing 1 mM manganese sulfate. All reactions were performed in triplicate and involved single mixing at the beginning of hydrolysis.

As shown in FIG. 31, the performance of *Aspergillus terreus* Cel7A CBHI was the same as the performance of *Aspergillus fumigatus* Cel7A CBHI at 55° C. and lower at 60-65° C.; however, at 50° C., the degree of cellulose conversion to glucose was much higher for *Aspergillus terreus* Cel7A CBHI than *Aspergillus fumigatus* Cel7A CBHI at 50° C.

Example 91: Evaluation of Three Cellobiohydrolases I Replacing a CBHI Component in a High-Temperature Enzyme Composition in Saccharification of Milled Unwashed PCS at 50-60° C.

The ability of three cellobiohydrolase I proteins to replace a CBHI component in a high-temperature enzyme composition (3 mg total protein per g cellulose) was tested at 50° C., 55° C., and 60° C. using milled unwashed PCS as a substrate. The high-temperature enzyme composition included 45% CBHI, 25% *Thielavia terrestris* Cel6A CBHII, 5% *Trichoderma reesei* Cel7B EGI, 5% *Thermoascus aurantiacus* Cel5A EGII, 5% *Thermoascus aurantiacus* GH61A polypeptide having cellulolytic enhancing activity, 5% *Thielavia terrestris* GH61E polypeptide having cellulolytic enhancing activity, 5% *Aspergillus fumigatus* Cel3A beta-glucosidase, and 5% *Aspergillus fumigatus* GH10 xyn3 xylanase.

The following CBHIs were each tested in the high-temperature enzyme composition: *Aspergillus fumigatus* Cel7A CBHI, *Neosartorya fischeri* Cel7A CBHI, and *Aspergillus nidulans* Cel7A CBHI.

The assay was performed as described in Example 34. The 1 ml reactions with milled unwashed PCS (5% insoluble solids) were conducted for 72 hours in 50 mM sodium acetate pH buffer containing 1 mM manganese sulfate. All reactions were performed in triplicate and involved single mixing at the beginning of hydrolysis.

As shown in FIG. 32, the performance of *Neosartorya fischeri* Cel7A CBHI was lower than the performance of *Aspergillus fumigatus* Cel7A CBHI at 50° C. and 55° C., but performance was the same at 60° C. *Aspergillus nidulans* Cel7A CBHI performed almost the same as *Aspergillus fumigatus* Cel7A CBHI at 50° C., but showed lower hydrolysis at 55° C. and 60° C.

Example 92: Evaluation of Two Cellobiohydrolases II Replacing a CBHII Component in a High-Temperature Enzyme Composition in Saccharification of Milled Unwashed PCS at 50-65° C.

The ability of two cellobiohydrolase II proteins to replace a CBHII component in a high-temperature enzyme composition (3 mg total protein per g cellulose) was tested at 50° C., 55° C., and 65° C. using milled unwashed PCS as a substrate. The high-temperature enzyme composition included 37% *Aspergillus fumigatus* Cel7A CBHI, 25% CBHII, 10% *Myceliophthora thermophila* Cel5A EGII, 15% *Thermoascus aurantiacus* GH61A polypeptide having cellulolytic enhancing activity, 5% *Aspergillus fumigatus* Cel3A beta-glucosidase, 5% *Aspergillus fumigatus* GH10 xyn3 xylanase, and 3% *Trichoderma reesei* GH3 beta-xylosidase.

The following CBHIIs were each tested in the high-temperature enzyme composition: *Aspergillus fumigatus* Cel6A CBHII and Finnellia *nivea* Cel6A CBHII.

The assay was performed as described in Example 34. The 1 ml reactions with milled unwashed PCS (5% insoluble solids) were conducted for 72 hours in 50 mM sodium acetate pH buffer containing 1 mM manganese sulfate. All reactions were performed in triplicate and involved single mixing at the beginning of hydrolysis.

As shown in FIG. 33, Finnellia *nivea* Cel6A CBHII performed well at 50-55° C. as it showed hydrolysis levels similar to *Aspergillus fumigatus* Cel6A CBHII at 50-55° C., but the performance declined at 60-65° C.

Example 93: Evaluation of Three Cellobiohydrolases II Replacing a CBHII Component in a High-Temperature Enzyme Composition in Saccharification of Milled Unwashed PCS at 50-65° C.

The ability of three cellobiohydrolase II proteins to replace a CBHII component in a high-temperature enzyme composition (3 mg total protein per g cellulose) was tested at 50° C., 55° C., and 65° C. using milled unwashed PCS as a substrate. The high-temperature enzyme composition included 37% *Aspergillus fumigatus* Cel7A CBHI, 25% CBHII, 10% *Trichoderma reesei* Cel5A EGII, 15% *Penicillium* sp. GH61A polypeptide having cellulolytic enhancing activity, 5% *Aspergillus fumigatus* Cel3A beta-glucosidase, 5% *Aspergillus fumigatus* GH10 xyn3 xylanase, and 3% *Trichoderma reesei* GH3 beta-xylosidase.

The following CBHIIs were each tested in the high-temperature enzyme composition: *Aspergillus fumigatus* Cel6A CBHII, *Penicillium emersonii* Cel6A CBHII, and *Penicillium pinophilum* Cel6A CBHII.

The assay was performed as described in Example 34. The 1 ml reactions with milled unwashed PCS (5% insoluble solids) were conducted for 72 hours in 50 mM sodium acetate pH buffer containing 1 mM manganese sulfate. All reactions were performed in triplicate and involved single mixing at the beginning of hydrolysis.

As shown in FIG. 34, *Penicillium emersonii* Cel6A CBHII performed well in the entire range of temperatures. *Penicillium emersonii* Cel6A CBHII performed almost as well as *Aspergillus fumigatus* Cel6A CBHII at 50° C., but performed slightly lower than *Aspergillus fumigatus* Cel6A CBHII at 55-65° C. The performance of *Penicillium pinophilum* Cel6A CBHII was comparable to that of *Aspergillus fumigatus* Cel6A CBHII at 50° C. and 55° C.; however, performance declined at 60° C. and 65° C.

Example 94: Evaluation of Three Endoglucanases II Replacing an Endoglucanase Component in a High-Temperature Enzyme Composition in Saccharification of Milled Unwashed PCS at 50-65° C.

The ability of three endoglucanase II proteins to replace an endoglucanase component in a high-temperature enzyme composition (3 mg total protein per g cellulose) was tested at 55° C., 60° C., and 65° C. using milled unwashed PCS as a substrate. The high-temperature enzyme composition included 40% *Aspergillus fumigatus* Cel7A CBHI, 25% *Aspergillus fumigatus* Cel6A CBHII, 10% EG cellulase, 15% *Thermoascus aurantiacus* GH61A polypeptide having cellulolytic enhancing activity, 5% *Aspergillus fumigatus* Cel3A beta-glucosidase, and 5% *Aspergillus fumigatus* GH10 xyn3 xylanase.

The following EGIIs were each tested in the high-temperature enzyme composition: *Aspergillus fumigatus* Cel5A EGII, Neosartorya *fischeri* Cel5A EGII, and *Myceliophthora thermophila* Cel5A EGII.

The assay was performed as described in Example 34. The 1 ml reactions with milled unwashed PCS (5% insoluble solids) were conducted for 72 hours in 50 mM sodium acetate pH buffer containing 1 mM manganese sulfate. All reactions were performed in triplicate and involved single mixing at the beginning of hydrolysis.

As shown in FIG. 35, all endoglucanase II proteins performed similarly within this temperature range, with Neosartorya *fischeri* Cel5A EGII and *Myceliophthora thermophila* Cel5A EGII having similar activity at 50° C. and 55° C. and *Aspergillus fumigatus* Cel5A EGII having comparable activity to Neosartorya *fischeri* Cel5A EGII and *Myceliophthora thermophila* Cel5A EGII at 60° C. and 65° C.

Example 95: Evaluation of Two Beta-Glucosidases Replacing a Beta-Glucosidase Component in a High-Temperature Enzyme Composition in Saccharification of Milled Unwashed PCS at 50-65° C.

The ability of three beta-glucosidase proteins to replace a beta-glucosidase component in a high-temperature enzyme composition (3 mg total protein per g cellulose) was tested at 55° C., 60° C., and 65° C. using milled unwashed PCS as a substrate. The high-temperature enzyme composition included 37% *Aspergillus fumigatus* Cel7A CBHI, 25% *Aspergillus fumigatus* Cel6A CBHII, 10% *Myceliophthora thermophila* Cel5A EGII, 15% *Thermoascus aurantiacus* GH61A polypeptide having cellulolytic enhancing activity, 5% beta-glucosidase, 5% *Aspergillus fumigatus* GH10 xyn3 xylanase, and 3% *Trichoderma reesei* GH3 beta-xylosidase.

The following beta-glucosidases were each tested in the high-temperature enzyme composition: *Aspergillus fumigatus* Cel3A beta-glucosidase and *Aspergillus aculeatus* beta-glucosidases.

The assay was performed as described in Example 34, with the exception of glucose background, in which 40 g per liter of glucose was included in the reactions. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

As shown in FIG. 36, *Aspergillus aculeatus* Cel3A beta-glucosidase had slightly higher or similar performance as *Aspergillus fumigatus* Cel3A beta-glucosidase at all temperatures

Example 96: Evaluation of Four Beta-Glucosidases Replacing a Beta-Glucosidase Component in a High-Temperature Enzyme Composition in Saccharification of Milled Unwashed PCS at 50-60° C.

Four beta-glucosidases, including *Aspergillus fumigatus* Cel3A beta-glucosidase, *Aspergillus kawashii* Cel3A beta-glucosidase, *Aspergillus clavatus* Cel3 beta-glucosidase, and *Talaromyces emersonii* Cel3A beta-glucosidase were each evaluated in a high-temperature enzyme composition at 50° C., 55° C., and 60° C. using milled unwashed PCS as a substrate. The high-temperature enzyme composition included 45% *Aspergillus fumigatus* Cel7A CBHI, 25% *Thielavia terrestris* Cel6A CBHII, 5% *Trichoderma reesei* Cel7B EGI, 5% *Thermoascus aurantiacus* Cel5A EGII, 5% *Thermoascus aurantiacus* GH61A polypeptide having cellulolytic enhancing activity, 5% *Thielavia terrestris* GH61E polypeptide having cellulolytic enhancing activity, 5% *Aspergillus fumigatus* GH10 xyn3 xylanase, and 5% beta-glucosidase. The high-temperature enzyme composition was used at 3.0 mg total protein per g cellulose.

The assay was performed as described in Example 34. The 1 ml reactions with milled unwashed PCS (5% insoluble solids) were conducted for 72 hours in 50 mM sodium acetate pH buffer containing 1 mM manganese sulfate. All reactions were performed in triplicate and involved single mixing at the beginning of hydrolysis.

The results shown in FIG. 37 demonstrated that all beta-glucosidases except *Talaromyces emersonii* Cel3A beta-glucosidase had similar performance all three temperatures. *Talaromyces emersonii* Cel3A beta-glucosidase had lower activity at 50° C. and 55° C. but had equivalent activity at 60° C.

Example 97: Evaluation of Three Beta-Glucosidases Replacing a Beta-Glucosidase Component in a High-Temperature Enzyme Composition in Saccharification of Milled Unwashed PCS at 50-65° C.

Three beta-glucosidases, including *Aspergillus fumigatus* Cel3A beta-glucosidase, *Penicillium oxalicum* Cel3A beta-glucosidase (Example 77), and *Penicillium oxalicum* Cel3A beta-glucosidase (Example 78) were each evaluated in a high-temperature enzyme composition at 50° C., 55° C., 60° C., and 65° C. using milled unwashed PCS as a substrate. The high-temperature enzyme composition included 40% *Aspergillus fumigatus* Cel7A CBHI, 25% *Aspergillus fumigatus* Cel6A CBHII, 10% *Myceliophthora thermophila* Cel5A EGII, 15% *Thermoascus aurantiacus* GH61A polypeptide having cellulolytic enhancing activity, 5% *Aspergillus fumigatus* GH10 xyn3 xylanase, and 5% beta-glucosidase. The high-temperature enzyme composition was used at 3.0 mg total protein per g cellulose.

The assay was performed as described in Example 34. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

The results shown in FIG. 38 demonstrated that the beta-glucosidases had similar activity at all temperatures.

Example 98: Evaluation of the Ability of Three GH61 Polypeptides Having Cellulolytic Enhancing Activity to Enhance PCS-Hydrolyzing Activity of a High-Temperature Enzyme Composition at 50-65° C. Using Milled Washed PCS The ability of three GH61 polypeptides having cellulolytic enhancing activity, *Thermoascus aurantiacus* GH61A, Penicffium sp GH61A, and *Thermoascus crustaceus* GH61A, were each evaluated for their ability to enhance the PCS-hydrolyzing activity of a high-temperature enzyme composition using milled washed PCS at 50° C., 55° C., 60° C., and 65° C. Each GH61 polypeptide was separately added at 11.6% enzyme to a high temperature enzyme mixture. The high-temperature enzyme composition included 43.5% *Aspergillus fumigatus* Cel7A CBHI, 29% *Aspergillus fumigatus* Cel6A CBHII, 12% *Myceliophthora thermophila* Cel5A EGII, 6% *Aspergillus fumigatus* Cel3A beta-glucosidase, 6% *Aspergillus fumigatus* GH10 xyn3 xylanase, and 4% *Trichoderma reesei* GH3 beta-xylosidase. The results for the enzyme compositions containing GH61 polypeptides (2.3725 mg total protein per g cellulose) were compared with the results for a similar enzyme composition to which no GH61 polypeptide was added (2.125 mg total protein per g cellulose).

The assay was performed as described in Example 34. The 1 ml reactions with milled washed PCS (5% insoluble solids) were conducted for 72 hours in 50 mM sodium acetate pH buffer containing 1 mM manganese sulfate. All reactions were performed in triplicate and involved single mixing at the beginning of hydrolysis.

As shown in FIG. 39, all three GH61 polypeptides showed significant cellulase-enhancing activity, with *Thermoascus aurantiacus* GH61A polypeptide, Penicffium sp GH61A polypeptide, and *Thermoascus crustaceus* GH61A polypeptide having similar enhancement at and 55° C. while *Thermoascus aurantiacus* GH61A polypeptide had higher activity than Penicffium sp GH61A polypeptide and *Thermoascus crustaceus* GH61A polypeptide at 60° C. and 65° C.

Example 99: Evaluation of Three Xylanases Replacing a Xylanase Component in a High-Temperature Enzyme Composition in Saccharification of Milled Unwashed PCS at 50-65° C.

The ability of three xylanases to replace an xylanase component in a high-temperature enzyme composition (3 mg total protein per g cellulose) was tested at 50° C., 55° C., 60° C., and using milled unwashed PCS as a substrate. The high-temperature enzyme composition included 37% *Aspergillus fumigatus* Cel7A CBHI, 25% *Aspergillus fumigatus* Cel6A CBHII, 10% *Myceliophthora thermophila* Cel5A EGII, 15% *Thermoascus aurantiacus* GH61A polypeptide having cellulolytic enhancing activity, 5% *Aspergillus fumigatus* Cel3A beta-glucosidase, 3% *Trichoderma reesei* GH3 beta-xylosidase and 5% xylanase.

The following xylanases were each tested in the high-temperature enzyme composition: *Aspergillus fumigatus* GH10 xylanase 3, *Talaromyces emersonii* GH10 xylanase, and *Penicillium emersonii* GH10 xylanase.

The assay was performed as described in Example 34. The 1 ml reactions with milled unwashed PCS (5% insoluble solids) were conducted for 72 hours in 50 mM sodium acetate pH buffer containing 1 mM manganese sulfate. All reactions were performed in triplicate and involved single mixing at the beginning of hydrolysis.

As shown in FIG. 40, *Talaromyces emersonii* GH10 xylanase and *Penicillium emersonii* GH10 xylanase had similar activity as *Aspergillus fumigatus* GH10 xylanase 3 at all three temperatures.

Example 100: Evaluation of Three Xylanases by Adding a Xylanase Component to a High-Temperature Enzyme Composition in Saccharification of Milled Unwashed PCS at 50-60° C.

Three xylanases were each evaluated as a 10% addition to a high-temperature enzyme composition (3.5 mg total protein per g cellulose) at 50° C., 55° C., and 60° C. using milled unwashed PCS as a substrate. The high-temperature enzyme composition included 45% *Aspergillus fumigatus* Cel7A CBHI, 25% *Myceliophthora thermophila* Cel6A CBHII, 10% *Myceliophthora thermophila* Cel5A EGII, 5% *Thermoascus aurantiacus* GH61A polypeptide having cellulolytic enhancing activity, 5% *Thielavia terrestris* GH61E polypeptide having cellulolytic enhancing activity, and 5% *Penicillium brasilianum* Cel3A beta-glucosidase.

The following xylanases were each tested in the high-temperature enzyme composition: *Aspergillus fumigatus* GH10 xylanase (xyl3), *Meripilus giganteus* GH10 xylanase, and *Dictyoglomus thermophilum* GH11 xylanase.

The assay was performed as described in Example 34. The 1 ml reactions with milled unwashed PCS (5% insoluble solids) were conducted for 72 hours in 50 mM sodium acetate pH buffer containing 1 mM manganese sulfate. All reactions were performed in triplicate and involved single mixing at the beginning of hydrolysis.

As shown in FIG. 41, all three xylanase increased hydrolysis of the high-temperature enzyme composition. *Aspergillus fumigatus* GH10 xylanase and *Meripilus giganteus* GH10 xylanase had the same activity at 50° C. and 55° C. but *Aspergillus fumigatus* GH10 xylanase 3 had significantly higher activity at 60° C. than *Meripilus giganteus* GH10 xylanase. *Dictyoglomus thermophilum* GH11 xylanase had lower activity than *Aspergillus fumigatus* GH10 xylanase 3 at all three temperatures but *Dictyoglomus thermophilum* GH11 xylanase had increasing activity as temperature increases to 60° C.

Example 101: Comparison of XCL-602-Based Enzyme Compositions Containing Different Cellobiohydrolases and Xylanases in Hydrolysis of Milled Unwashed PCS at 50-60° C.

Four XCL-602 based enzyme compositions containing a different cellobiohydrolase and xylanase were tested at 50° C., 55° C., and 60° C. using milled unwashed PCS as a substrate. The cellobiohydrolases tested in the XCL-602 based enzyme compositions were *Aspergillus fumigatus* Cel7A CBHI and *Penicillium emersonii* Cel7 CBHI. The xylanases tested were *Aspergillus fumigatus* GH10 xylanase 3 and *Trichophaea saccata* GH10 xylanase. The XCL-602 based enzyme compositions included 40% XCL-602, 20% CBHI, 20% *Aspergillus fumigatus* Cel6A CBHII, 12.5% *Penicillium* species GH61A, 5% xylanase, and 2.5% *Talaromyces emersonii* GH3 beta-xylosidase. XCL-602 based enzyme compositions containing *Aspergillus fumigatus* Cel7A CBHI were tested at 3.0, 5.0, and 7.0 mg protein per g cellulose while XCL-602 based enzyme compositions containing *Penicillium emersonii* Cel7 CBHI were tested at 3.0 mg protein per g cellulose. For comparison, *Trichoderma reesei*-based XCL-602 cellulase was tested at 3.0, 5.0, and 7.0 mg protein per g cellulose.

The assay was performed as described in Example 34. The 1 ml reactions with milled unwashed PCS (5% insoluble solids) were conducted for 72 hours in 50 mM sodium acetate pH buffer containing 1 mM manganese sulfate. All reactions were performed in triplicate and involved single mixing at the beginning of hydrolysis.

The results for 3 mg protein per g cellulose are shown in FIG. 42. The two xylanases, *Aspergillus fumigatus* GH10 xylanase 3 and *Trichophaea saccata* GH10 xylanase showed similar performance in the XCL-602 based enzyme compositions with either *Aspergillus fumigatus* Cel7A CBHI or *Penicillium emersonii* Cel7 CBHI. For the CBHIs in the XCL-602 based enzyme compositions with either xylanase, *Penicillium emersonii* Cel7 CBHI had slightly higher performance than *Aspergillus fumigatus* Cel7A CBHI at all three temperatures. Finally, all XCL-602 based enzyme compositions replaced with CBHI, CBHII, GH61, xylanase, and beta-xylosidase had significantly higher hydrolysis over the non-replaced *Trichoderma reesei*-based XCL-602 cellulase at all three temperatures. At 80% glucose conversion, the XCL-602 based enzyme compositions containing *Aspergillus fumigatus* Cel7A CBHI and either xylanase at 55° C. required 4.3 mg protein per g cellulose while XCL-602 at 50° C. required 6.5 mg protein per g cellulose, a 1.5-fold reduction in protein loading.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An isolated recombinant host cell encoding an enzyme composition comprising:

(I) a polypeptide having cellobiohydrolase I activity selected from the group consisting of: (a) a polypeptide comprising an amino acid sequence having at least 85% sequence identity to the mature polypeptide of SEQ ID NO: 158; (b) a polypeptide encoded by a polynucleotide that hybridizes under at least high stringency conditions with (i) the mature polypeptide coding sequence of SEQ ID NO: 157, (ii) the genomic DNA sequence of the mature polypeptide coding sequence of SEQ ID NO: 157, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 85% sequence identity to the mature polypeptide coding sequence of SEQ ID NO: 5; and (d) a polypeptide comprising the mature polypeptide of SEQ ID NO: 6;

(II) a polypeptide having beta-glucosidase activity; and (III) a polypeptide having endoglucanase I activity is selected from the group consisting of: (a) a polypeptide comprising an amino acid sequence having at least 85% sequence identity to the mature polypeptide of SEQ ID NO: 62; (b) a polypeptide encoded by a polynucleotide that hybridizes under at least high stringency conditions with (i) the mature polypeptide coding sequence of SEQ ID NO: 61, (ii) the genomic DNA sequence of the mature polypeptide coding sequence of SEQ ID NO: 61, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 85% sequence identity to the mature polypeptide coding sequence of SEQ ID NO: 61; and (d) a polypeptide comprising the mature polypeptide of SEQ ID NO: 62.

2. The isolated recombinant host cell of claim 1, wherein the polypeptide having cellobiohydrolase I activity is selected from the group consisting of: (a) a polypeptide comprising an amino acid sequence having at least 90% sequence identity to the mature polypeptide of SEQ ID NO: 158; (b) a polypeptide encoded by a polynucleotide that hybridizes under at least high stringency conditions with (i) the mature polypeptide coding sequence of SEQ ID NO: 157, (ii) the genomic DNA sequence of the mature polypeptide coding sequence of SEQ ID NO: 157, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 90% sequence identity to the mature polypeptide coding sequence of SEQ ID NO: 5; and (d) a polypeptide comprising the mature polypeptide of SEQ ID NO: 6.

3. The isolated recombinant host cell of claim 1, wherein the polypeptide having cellobiohydrolase I activity is selected from the group consisting of: (a) a polypeptide comprising an amino acid sequence having at least 95% sequence identity to the mature polypeptide of SEQ ID NO: 158; (b) a polypeptide encoded by a polynucleotide that hybridizes under at least high stringency conditions with (i) the mature polypeptide coding sequence of SEQ ID NO: 157, (ii) the genomic DNA sequence of the mature polypeptide coding sequence of SEQ ID NO: 157, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 5; and (d) a polypeptide comprising the mature polypeptide of SEQ ID NO: 6.

4. The isolated recombinant host cell of claim 1, wherein the enzyme composition further comprises a polypeptide having cellobiohydrolase II activity.

5. The isolated recombinant host cell of claim 4, wherein the polypeptide having cellobiohydrolase II activity is from *Talaromyces*.

6. The isolated recombinant host cell of claim 1, wherein the polypeptide having beta-glucosidase activity is from *Talaromyces*.

7. The isolated recombinant host cell of claim 1, wherein the polypeptide having endoglucanase I activity is selected from the group consisting of: (a) a polypeptide comprising an amino acid sequence having at least 90% sequence identity to the mature polypeptide of SEQ ID NO: 62; (b) a polypeptide encoded by a polynucleotide that hybridizes under at least high stringency conditions with (i) the mature polypeptide coding sequence of SEQ ID NO: 61, (ii) the genomic DNA sequence of the mature polypeptide coding sequence of SEQ ID NO: 61, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 90% sequence identity to the mature polypeptide coding sequence of SEQ ID NO: 61; and (d) a polypeptide comprising the mature polypeptide of SEQ ID NO: 62.

8. The isolated recombinant host cell of claim 1, wherein the polypeptide having endoglucanase I activity is selected from the group consisting of: (a) a polypeptide comprising an amino acid sequence having at least 95% sequence identity to the mature polypeptide of SEQ ID NO: 62; (b) a polypeptide encoded by a polynucleotide that hybridizes under at least high stringency conditions with (i) the mature polypeptide coding sequence of SEQ ID NO: 61, (ii) the genomic DNA sequence of the mature polypeptide coding sequence of SEQ ID NO: 61, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 61; and (d) a polypeptide comprising the mature polypeptide of SEQ ID NO: 62.

9. The isolated recombinant host cell of claim 1, wherein the enzyme composition further comprises a polypeptide having endoglucanase II activity.

10. The isolated recombinant host cell of claim 1, wherein the enzyme composition further comprises a GH61 polypeptide having cellulolytic enhancing activity.

11. The isolated recombinant host cell of claim 1, wherein the enzyme composition further comprises a polypeptide having xylanase activity.

12. The isolated recombinant host cell of claim 11, wherein the enzyme composition further comprises a Family 10 polypeptide having xylanase activity or a Family 11 polypeptide having xylanase activity.

13. The isolated recombinant host cell of claim 1, wherein the enzyme composition further comprises a polypeptide having beta-xylosidase activity.

14. The isolated recombinant host cell of claim 13, wherein the polypeptide having beta-xylosidase activity is a GH3 beta-xylosidase.

15. The isolated recombinant host cell of claim 13, wherein the polypeptide having beta-xylosidase activity is selected from the group consisting of: (a) a polypeptide comprising an amino acid sequence having at least 85% sequence identity to the mature polypeptide of SEQ ID NO: 206; (b) a polypeptide encoded by a polynucleotide that hybridizes under at least high stringency conditions with (i) the mature polypeptide coding sequence of SEQ ID NO: 205, (ii) the genomic DNA sequence of the mature polypeptide coding sequence of SEQ ID NO: 205, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 85% sequence identity to the mature polypeptide coding sequence of SEQ ID NO: 205; and (d) a polypeptide comprising the mature polypeptide of SEQ ID NO: 206.

16. The isolated recombinant host cell of claim 13, wherein the polypeptide having beta-xylosidase activity is selected from the group consisting of: (a) a polypeptide comprising an amino acid sequence having at least 90% sequence identity to the mature polypeptide of SEQ ID NO: 206; (b) a polypeptide encoded by a polynucleotide that hybridizes under at least high stringency conditions with (i) the mature polypeptide coding sequence of SEQ ID NO: 205, (ii) the genomic DNA sequence of the mature polypeptide coding sequence of SEQ ID NO: 205, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 90% sequence identity to the mature polypeptide coding sequence of SEQ ID NO: 205; and (d) a polypeptide comprising the mature polypeptide of SEQ ID NO: 206.

17. The isolated recombinant host cell of claim 13, wherein the polypeptide having beta-xylosidase activity is selected from the group consisting of: (a) a polypeptide comprising an amino acid sequence having at least 95% sequence identity to the mature polypeptide of SEQ ID NO: 206; (b) a polypeptide encoded by a polynucleotide that hybridizes under at least high stringency conditions with (i) the mature polypeptide coding sequence of SEQ ID NO: 205, (ii) the genomic DNA sequence of the mature polypeptide coding sequence of SEQ ID NO: 205, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 205; and (d) a polypeptide comprising the mature polypeptide of SEQ ID NO: 206.

18. A method of producing an enzyme composition, comprising: (a) cultivating the recombinant host cell of claim 1 under conditions conducive for production of the enzyme composition; and (b) recovering the enzyme composition.

19. A method for degrading or converting a cellulosic material, comprising: treating the cellulosic material with an enzyme composition comprising:
(I) a polypeptide having cellobiohydrolase I activity selected from the group consisting of: (a) a polypeptide comprising an amino acid sequence having at least 85% sequence identity to the mature polypeptide of SEQ ID NO: 158; (b) a polypeptide encoded by a polynucleotide that hybridizes under at least high stringency conditions with (i) the mature polypeptide coding sequence of SEQ ID NO: 157, (ii) the genomic DNA sequence of the mature polypeptide coding sequence of SEQ ID NO: 157, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 85% sequence identity to the mature polypeptide coding sequence of SEQ ID NO: 5; and (d) a polypeptide comprising the mature polypeptide of SEQ ID NO: 6;
(II) a polypeptide having beta-glucosidase activity; and
(III) a polypeptide having endoglucanase I activity is selected from the group consisting of: (a) a polypeptide comprising an amino acid sequence having at least 85% sequence identity to the mature polypeptide of SEQ ID NO: 62; (b) a polypeptide encoded by a polynucleotide that hybridizes under at least high stringency conditions with (i) the mature polypeptide coding sequence of SEQ ID NO: 61, (ii) the genomic DNA sequence of the mature polypeptide coding sequence of SEQ ID NO: 61, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 85% sequence identity to the mature polypeptide coding sequence of SEQ ID NO: 61; and (d) a polypeptide comprising the mature polypeptide of SEQ ID NO: 62;

wherein the degrading or converting of the cellulosic material is performed with the enzyme composition at a temperature in the range of about 40° C. to about 70° C.

20. The method of claim 19, wherein saccharification of the cellulosic material is performed with the enzyme composition at a temperature in the range of about 50° C. to about 65° C.

21. The method of claim 19, wherein the polypeptide having cellobiohydrolase I activity is selected from the group consisting of: (a) a polypeptide comprising an amino acid sequence having at least 90% sequence identity to the mature polypeptide of SEQ ID NO: 158; (b) a polypeptide encoded by a polynucleotide that hybridizes under at least high stringency conditions with (i) the mature polypeptide coding sequence of SEQ ID NO: 157, (ii) the genomic DNA sequence of the mature polypeptide coding sequence of SEQ ID NO: 157, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 90% sequence identity to the mature polypeptide coding sequence of SEQ ID NO: 5; and (d) a polypeptide comprising the mature polypeptide of SEQ ID NO: 6.

22. The method of claim 19, wherein the polypeptide having cellobiohydrolase I activity is selected from the group consisting of: (a) a polypeptide comprising an amino acid sequence having at least 95% sequence identity to the mature polypeptide of SEQ ID NO: 158; (b) a polypeptide encoded by a polynucleotide that hybridizes under at least high stringency conditions with (i) the mature polypeptide coding sequence of SEQ ID NO: 157, (ii) the genomic DNA sequence of the mature polypeptide coding sequence of SEQ ID NO: 157, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 5; and (d) a polypeptide comprising the mature polypeptide of SEQ ID NO: 6.

23. The method of claim 19, wherein the enzyme composition further comprises a polypeptide having cellobiohydrolase II activity.

24. The method of claim 23, wherein the polypeptide having cellobiohydrolase II activity is from *Talaromyces*.

25. The method of claim 19, wherein the polypeptide having beta-glucosidase activity is from *Talaromyces*.

26. The method of claim 19, wherein the polypeptide having endoglucanase I activity is selected from the group consisting of: (a) a polypeptide comprising an amino acid sequence having at least 90% sequence identity to the mature polypeptide of SEQ ID NO: 62; (b) a polypeptide encoded by a polynucleotide that hybridizes under at least high stringency conditions with (i) the mature polypeptide coding sequence of SEQ ID NO: 61, (ii) the genomic DNA sequence of the mature polypeptide coding sequence of SEQ ID NO: 61, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 90% sequence identity to the mature polypeptide coding sequence of SEQ ID NO: 61; and (d) a polypeptide comprising the mature polypeptide of SEQ ID NO: 62.

27. The method of claim 19, wherein the polypeptide having endoglucanase I activity is selected from the group consisting of: (a) a polypeptide comprising an amino acid sequence having at least 95% sequence identity to the mature polypeptide of SEQ ID NO: 62; (b) a polypeptide encoded by a polynucleotide that hybridizes under at least high stringency conditions with (i) the mature polypeptide coding sequence of SEQ ID NO: 61, (ii) the genomic DNA sequence of the mature polypeptide coding sequence of SEQ ID NO: 61, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 61; and (d) a polypeptide comprising the mature polypeptide of SEQ ID NO: 62.

28. The method of claim 19, wherein the enzyme composition further comprises a polypeptide having endoglucanase II activity.

29. The method of claim 19, wherein the enzyme composition further comprises a GH61 polypeptide having cellulolytic enhancing activity.

30. The method of claim 19, wherein the enzyme composition further comprises a polypeptide having xylanase activity.

31. The method of claim 19, wherein the enzyme composition further comprises a Family 10 polypeptide having xylanase activity or a Family 11 polypeptide having xylanase activity.

32. The method of claim 19, wherein the enzyme composition further comprises a polypeptide having beta-xylosidase activity.

33. The method of claim 32, wherein the polypeptide having beta-xylosidase activity is a GH3 beta-xylosidase.

34. The method of claim 32, wherein the polypeptide having beta-xylosidase activity is selected from the group consisting of: (a) a polypeptide comprising an amino acid sequence having at least 85% sequence identity to the mature polypeptide of SEQ ID NO: 206; (b) a polypeptide encoded by a polynucleotide that hybridizes under at least high stringency conditions with (i) the mature polypeptide coding sequence of SEQ ID NO: 205, (ii) the genomic DNA sequence of the mature polypeptide coding sequence of SEQ ID NO: 205, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 85% sequence identity to the mature polypeptide coding sequence of SEQ ID NO: 205; and (d) a polypeptide comprising the mature polypeptide of SEQ ID NO: 206.

35. The method of claim 32, wherein the polypeptide having beta-xylosidase activity is selected from the group consisting of: (a) a polypeptide comprising an amino acid sequence having at least 90% sequence identity to the mature polypeptide of SEQ ID NO: 206; (b) a polypeptide encoded by a polynucleotide that hybridizes under at least high stringency conditions with (i) the mature polypeptide coding sequence of SEQ ID NO: 205, (ii) the genomic DNA sequence of the mature polypeptide coding sequence of SEQ ID NO: 205, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 90% sequence identity to the mature polypeptide coding sequence of SEQ ID NO: 205; and (d) a polypeptide comprising the mature polypeptide of SEQ ID NO: 206.

36. The method of claim 32, wherein the polypeptide having beta-xylosidase activity is selected from the group consisting of: (a) a polypeptide comprising an amino acid sequence having at least 95% sequence identity to the mature polypeptide of SEQ ID NO: 206; (b) a polypeptide encoded by a polynucleotide that hybridizes under at least high stringency conditions with (i) the mature polypeptide coding sequence of SEQ ID NO: 205, (ii) the genomic DNA sequence of the mature polypeptide coding sequence of SEQ ID NO: 205, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 205; and (d) a polypeptide comprising the mature polypeptide of SEQ ID NO: 206.

37. A method for producing a fermentation product, comprising:
(a) saccharifying a cellulosic material with an enzyme composition comprising:
(I) a polypeptide having cellobiohydrolase I activity selected from the group consisting of: (a) a polypeptide comprising an amino acid sequence having at least 85% sequence identity to the mature polypeptide of SEQ ID NO: 158; (b) a polypeptide encoded by a polynucleotide that hybridizes under at least high stringency conditions with (i) the mature polypeptide coding sequence of SEQ ID NO: 157, (ii) the genomic DNA sequence of the mature polypeptide coding sequence of SEQ ID NO: 157, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 85% sequence identity to the mature polypeptide coding sequence of SEQ ID NO: 5; and (d) a polypeptide comprising the mature polypeptide of SEQ ID NO: 6;

(II) a polypeptide having beta-glucosidase activity; and
(III) a polypeptide having endoglucanase I activity is selected from the group consisting of: (a) a polypeptide comprising an amino acid sequence having at least 85% sequence identity to the mature polypeptide of SEQ ID NO: 62; (b) a polypeptide encoded by a polynucleotide that hybridizes under at least high stringency conditions with (i) the mature polypeptide coding sequence of SEQ ID NO: 61, (ii) the genomic DNA sequence of the mature polypeptide coding sequence of SEQ ID NO: 61, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 85% sequence identity to the mature polypeptide coding sequence of SEQ ID NO: 61; and (d) a polypeptide comprising the mature polypeptide of SEQ ID NO: 62;
wherein the saccharification of the cellulosic material is performed with the enzyme composition at a temperature in the range of about 40° C. to about 70° C.;
(b) fermenting the saccharified cellulosic material with one or more fermenting microorganisms to produce the fermentation product; and
(c) recovering the fermentation product from the fermentation.

38. The method of claim 37, wherein saccharification of the cellulosic material is performed with the enzyme composition at a temperature in the range of about 50° C. to about 65° C.

39. The method of claim 37, wherein saccharification of the cellulosic material is performed with the enzyme composition at a temperature in the range of about 50° C. to about 65° C.

40. The method of claim 37, wherein the polypeptide having cellobiohydrolase I activity is selected from the group consisting of: (a) a polypeptide comprising an amino acid sequence having at least 90% sequence identity to the mature polypeptide of SEQ ID NO: 158; (b) a polypeptide encoded by a polynucleotide that hybridizes under at least high stringency conditions with (i) the mature polypeptide coding sequence of SEQ ID NO: 157, (ii) the genomic DNA sequence of the mature polypeptide coding sequence of SEQ ID NO: 157, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 90% sequence identity to the mature polypeptide coding sequence of SEQ ID NO: 5; and (d) a polypeptide comprising the mature polypeptide of SEQ ID NO: 6.

41. The method of claim 37, wherein the polypeptide having cellobiohydrolase I activity is selected from the group consisting of: (a) a polypeptide comprising an amino acid sequence having at least 95% sequence identity to the mature polypeptide of SEQ ID NO: 158; (b) a polypeptide encoded by a polynucleotide that hybridizes under at least high stringency conditions with (i) the mature polypeptide coding sequence of SEQ ID NO: 157, (ii) the genomic DNA sequence of the mature polypeptide coding sequence of SEQ ID NO: 157, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 5; and (d) a polypeptide comprising the mature polypeptide of SEQ ID NO: 6.

42. The method of claim 37, wherein the composition further comprises a polypeptide having cellobiohydrolase II activity.

43. The method of claim 42, wherein the polypeptide having cellobiohydrolase II activity is from *Talaromyces*.

44. The method of claim 37, wherein the polypeptide having beta-glucosidase activity is from *Talaromyces*.

45. The method of claim 37, wherein the polypeptide having endoglucanase I activity is selected from the group consisting of: (a) a polypeptide comprising an amino acid sequence having at least 90% sequence identity to the mature polypeptide of SEQ ID NO: 62; (b) a polypeptide encoded by a polynucleotide that hybridizes under at least high stringency conditions with (i) the mature polypeptide coding sequence of SEQ ID NO: 61, (ii) the genomic DNA sequence of the mature polypeptide coding sequence of SEQ ID NO: 61, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 90% sequence identity to the mature polypeptide coding sequence of SEQ ID NO: 61; and (d) a polypeptide comprising the mature polypeptide of SEQ ID NO: 62.

46. The method of claim 37, wherein the polypeptide having endoglucanase I activity is selected from the group consisting of: (a) a polypeptide comprising an amino acid sequence having at least 95% sequence identity to the mature polypeptide of SEQ ID NO: 62; (b) a polypeptide encoded by a polynucleotide that hybridizes under at least high stringency conditions with (i) the mature polypeptide coding sequence of SEQ ID NO: 61, (ii) the genomic DNA sequence of the mature polypeptide coding sequence of SEQ ID NO: 61, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 61; and (d) a polypeptide comprising the mature polypeptide of SEQ ID NO: 62.

47. The method of claim 37, wherein the enzyme composition further comprises a polypeptide having endoglucanase II activity.

48. The method of claim 37, wherein the enzyme composition further comprises a GH61 polypeptide having cellulolytic enhancing activity.

49. The method of claim 37, wherein the enzyme composition further comprises a polypeptide having xylanase activity.

50. The method of claim 37, wherein the enzyme composition further comprises a Family 10 polypeptide having xylanase activity or a Family 11 polypeptide having xylanase activity.

51. The method of claim 37, wherein the enzyme composition further comprises a polypeptide having beta-xylosidase activity.

52. The method of claim 51, wherein the polypeptide having beta-xylosidase activity is a GH3 beta-xylosidase.

53. The method of claim 51, wherein the polypeptide having beta-xylosidase activity is selected from the group consisting of: (a) a polypeptide comprising an amino acid sequence having at least 85% sequence identity to the mature polypeptide of SEQ ID NO: 206; (b) a polypeptide encoded by a polynucleotide that hybridizes under at least high stringency conditions with (i) the mature polypeptide coding sequence of SEQ ID NO: 205, (ii) the genomic DNA sequence of the mature polypeptide coding sequence of SEQ ID NO: 205, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 85% sequence identity to the mature polypeptide coding sequence of SEQ ID NO: 205; and (d) a polypeptide comprising the mature polypeptide of SEQ ID NO: 206.

54. The method of claim 51, wherein the polypeptide having beta-xylosidase activity is selected from the group consisting of: (a) a polypeptide comprising an amino acid sequence having at least 90% sequence identity to the mature polypeptide of SEQ ID NO: 206; (b) a polypeptide encoded by a polynucleotide that hybridizes under at least high stringency conditions with (i) the mature polypeptide coding sequence of SEQ ID NO: 205, (ii) the genomic DNA sequence of the mature polypeptide coding sequence of SEQ ID NO: 205, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 90% sequence identity to the mature polypeptide coding sequence of SEQ ID NO: 205; and (d) a polypeptide comprising the mature polypeptide of SEQ ID NO: 206.

55. The method of claim 51, wherein the polypeptide having beta-xylosidase activity is selected from the group consisting of: (a) a polypeptide comprising an amino acid sequence having at least 95% sequence identity to the mature polypeptide of SEQ ID NO: 206; (b) a polypeptide encoded by a polynucleotide that hybridizes under at least high stringency conditions with (i) the mature polypeptide coding sequence of SEQ ID NO: 205, (ii) the genomic DNA sequence of the mature polypeptide coding sequence of SEQ ID NO: 205, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide and washing three times each for 15 minutes using 2×SSC, 0.2% SDS at 65° C.; (c) a polypeptide encoded by a polynucleotide comprising a nucleotide sequence having at least 95% sequence identity to the mature polypeptide coding sequence of SEQ ID NO: 205; and (d) a polypeptide comprising the mature polypeptide of SEQ ID NO: 206.

* * * * *